(12) United States Patent
Cartledge et al.

(10) Patent No.: US 9,827,093 B2
(45) Date of Patent: Nov. 28, 2017

(54) ACTIVELY CONTROLLABLE STENT, STENT GRAFT, HEART VALVE AND METHOD OF CONTROLLING SAME

(71) Applicant: Edwards Lifesciences CardiAQ LLC, Irvine, CA (US)

(72) Inventors: Richard George Cartledge, Boca Raton, FL (US); Kevin W. Smith, Coral Gables, FL (US); Thomas O. Bales, Jr., Miami, FL (US); Derek Dee Deville, Coral Gables, FL (US); Korey Kline, Miami, FL (US); Max Pierre Mendez, Miami, FL (US); Matthew A. Palmer, Miami, FL (US); Michael Walter Kirk, Miami, FL (US); Carlos Rivera, Cooper City, FL (US); Eric Petersen, Homestead, FL (US); M. Sean McBrayer, Miami, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 766 days.

(21) Appl. No.: 14/278,594

(22) Filed: May 15, 2014

(65) Prior Publication Data
US 2014/0296962 A1    Oct. 2, 2014

Related U.S. Application Data

(63) Continuation-in-part of application No. 13/772,203, filed on Feb. 20, 2013, and a continuation-in-part of
(Continued)

(51) Int. Cl.
*A61F 2/06* (2013.01)
*A61F 2/24* (2006.01)
(Continued)

(52) U.S. Cl.
CPC ............ *A61F 2/2418* (2013.01); *A61F 2/243* (2013.01); *A61F 2/2436* (2013.01);
(Continued)

(58) Field of Classification Search
CPC ...... A61F 2002/9505; A61F 2002/9511; A61F 2002/9517; A61F 2/2427; A61F 2/243; A61F 2/2433; A61F 2/2436; A61F 2/2439
See application file for complete search history.

(56) References Cited

U.S. PATENT DOCUMENTS

| 2,684,069 A | 7/1954 | Donaldson et al. |
| 3,490,975 A | 1/1970 | Lightwood et al. |

(Continued)

FOREIGN PATENT DOCUMENTS

| CA | 2557657 A1 | 9/2005 |
| CN | 1684644 A | 10/2005 |

(Continued)

OTHER PUBLICATIONS

International Search Report & Written Opinion (PCT/US07/17061) International Searching Authority.
(Continued)

*Primary Examiner* — Diane Yabut
(74) *Attorney, Agent, or Firm* — Klarquist Sparkman, LLP; AnneMarie Kaiser

(57) ABSTRACT

A method for implanting a stent includes contracting a self-expanding/forcibly-expanding stent of a shape-memory material set to a given shape to a reduced implantation size with a delivery system having drive wires. The stent has a selectively adjustable assembly with adjustable elements operatively connected to the drive wires such that, when the adjustable elements are adjusted by the drive wires, a configuration change in at least a portion of the self-expanding stent occurs. The contracted stent is inserted into
(Continued)

a native annulus in which the stent is to be implanted. The drive wires are rotated with the delivery system to forcibly expand the stent into the native annulus. While rotating the drive wires, a torque applied to the drive wires is determined with the delivery system. Rotation of the drive wires is stopped based upon a value of the determined torque.

25 Claims, 217 Drawing Sheets

Related U.S. Application Data application No. 13/656,717, filed on Oct. 21, 2012, now Pat. No. 9,566,178.

(60) Provisional application No. 61/824,264, filed on May 16, 2013, provisional application No. 61/717,037, filed on Oct. 22, 2012, provisional application No. 61/550,004, filed on Oct. 21, 2011, provisional application No. 61/585,937, filed on Jan. 12, 2012, provisional application No. 61/591,753, filed on Jan. 27, 2012, provisional application No. 61/601,961, filed on Feb. 22, 2012, provisional application No. 61/682,558, filed on Aug. 13, 2012, provisional application No. 61/739,711, filed on Dec. 19, 2012.

(51) Int. Cl.
*A61F 2/95* (2013.01)
*A61F 2/966* (2013.01)

(52) U.S. Cl.
CPC .......... *A61F 2/2439* (2013.01); *A61F 2/2427* (2013.01); *A61F 2002/9505* (2013.01); *A61F 2002/9511* (2013.01); *A61F 2002/9517* (2013.01); *A61F 2002/9534* (2013.01); *A61F 2002/9665* (2013.01); *A61F 2220/0041* (2013.01); *A61F 2220/0075* (2013.01); *A61F 2220/0091* (2013.01); *A61F 2250/001* (2013.01); *A61F 2250/0006* (2013.01); *A61F 2250/006* (2013.01); *A61F 2250/0018* (2013.01); *A61F 2250/0039* (2013.01); *A61F 2250/0065* (2013.01); *A61F 2250/0069* (2013.01)

(56) References Cited

U.S. PATENT DOCUMENTS

| | | | |
|---|---|---|---|
| 3,657,744 A | 4/1972 | Ersek |
| 3,667,474 A | 6/1972 | Lapkin et al. |
| 4,056,854 A | 11/1977 | Boretos et al. |
| 4,323,525 A | 4/1982 | Bornat |
| 4,459,252 A | 7/1984 | MacGregor et al. |
| 4,475,972 A | 10/1984 | Wong et al. |
| 4,585,000 A | 4/1986 | Hershenson et al. |
| 4,602,911 A | 7/1986 | Ahmadi |
| 4,655,771 A | 4/1987 | Wallsten |
| 4,800,882 A | 1/1989 | Gianturco et al. |
| 4,851,009 A | 7/1989 | Pinchuk et al. |
| 4,906,244 A | 3/1990 | Pinchuk et al. |
| 4,921,484 A | 5/1990 | Hillstead |
| 4,954,126 A | 9/1990 | Wallsten et al. |
| 4,990,151 A | 2/1991 | Wallsten et al. |
| 5,019,090 A | 5/1991 | Pinchuk |
| 5,061,275 A | 10/1991 | Wallsten et al. |
| 5,092,877 A | 3/1992 | Pinchuk |
| 5,133,742 A | 7/1992 | Pinchuk et al. |
| 5,163,951 A | 11/1992 | Pinchuk et al. |
| 5,180,368 A | 1/1993 | Garrison et al. |
| 5,211,658 A | 5/1993 | Clouse et al. |
| 5,229,431 A | 7/1993 | Pinchuk et al. |
| 5,411,552 A | 5/1995 | Andersen et al. |
| 5,425,705 A | 6/1995 | Evard et al. |
| 5,441,516 A | 8/1995 | Wang et al. |
| 5,443,477 A | 8/1995 | Marin et al. |
| 5,449,372 A | 9/1995 | Schmaltz et al. |
| 5,456,667 A | 10/1995 | Ham et al. |
| 5,456,694 A | 10/1995 | Marin |
| 5,484,565 A | 1/1996 | Larsen et al. |
| 5,531,785 A | 7/1996 | Love et al. |
| 5,536,251 A | 7/1996 | Evard et al. |
| 5,554,183 A | 9/1996 | Nazari |
| 5,562,725 A | 10/1996 | Schmitt et al. |
| 5,569,296 A | 10/1996 | Marin et al. |
| 5,575,818 A | 11/1996 | Pinchuk et al. |
| 5,591,196 A | 1/1997 | Marin et al. |
| 5,593,417 A | 1/1997 | Rhodes et al. |
| 5,617,878 A | 4/1997 | Taheri |
| 5,618,300 A | 4/1997 | Marin et al. |
| 5,628,788 A | 5/1997 | Pinchuk et al. |
| 5,632,772 A | 5/1997 | Alcime et al. |
| 5,639,278 A | 6/1997 | Dereume et al. |
| 5,641,373 A | 6/1997 | Shannon et al. |
| 5,693,088 A | 12/1997 | Lazarus et al. |
| 5,697,948 A | 12/1997 | Marin et al. |
| 5,700,269 A | 12/1997 | Pinchuk et al. |
| 5,700,285 A | 12/1997 | Myers et al. |
| 5,713,907 A | 2/1998 | Hogendijk et al. |
| 5,713,948 A | 2/1998 | Uflacker |
| 5,718,159 A | 2/1998 | Thompson et al. |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,735,892 A | 4/1998 | Myers et al. |
| 5,776,186 A | 7/1998 | Uflacker |
| 5,797,951 A | 8/1998 | Mueller |
| 5,810,870 A | 9/1998 | Myers et al. |
| 5,824,034 A | 10/1998 | Schmitt et al. |
| 5,824,037 A | 10/1998 | Fogarty et al. |
| 5,824,040 A | 10/1998 | Cox et al. |
| 5,840,081 A | 11/1998 | Andersen et al. |
| 5,843,173 A | 12/1998 | Shannon et al. |
| 5,855,565 A | 1/1999 | Bar-Cohen |
| 5,855,598 A | 1/1999 | Pinchuk et al. |
| 5,871,536 A | 2/1999 | Lazarus et al. |
| 5,925,075 A | 7/1999 | Myers et al. |
| 5,928,258 A | 7/1999 | Khan et al. |
| 5,948,018 A | 9/1999 | Dereume et al. |
| 5,957,949 A | 9/1999 | Leonhardt et al. |
| 5,968,091 A | 10/1999 | Pinchuk et al. |
| 5,972,029 A | 10/1999 | Fuisz |
| 5,976,650 A | 11/1999 | Campbell et al. |
| 5,993,482 A | 11/1999 | Chuter |
| 5,993,489 A | 11/1999 | Lewis et al. |
| 6,015,431 A | 1/2000 | Thornton et al. |
| 6,027,529 A | 2/2000 | Roychowdhury et al. |
| 6,027,811 A | 2/2000 | Campbell et al. |
| 6,036,716 A | 3/2000 | Kruchinin et al. |
| 6,110,198 A | 8/2000 | Fogarty et al. |
| 6,120,534 A | 9/2000 | Ruiz et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,159,565 A | 12/2000 | Campbell et al. |
| 6,165,212 A | 12/2000 | Dereume et al. |
| 6,168,614 B1 | 1/2001 | Andersen et al. |
| 6,168,616 B1 | 1/2001 | Brown, III |
| 6,168,621 B1 | 1/2001 | Vrba |
| 6,193,745 B1 | 2/2001 | Fogarty et al. |
| 6,217,585 B1 | 4/2001 | Houser et al. |
| 6,221,102 B1 | 4/2001 | Baker et al. |
| 6,224,626 B1 | 5/2001 | Steinke |
| 6,267,783 B1 | 7/2001 | Letendre et al. |
| 6,267,834 B1 | 7/2001 | Shannon et al. |
| 6,273,895 B1 | 8/2001 | Pinchuk et al. |
| 6,276,661 B1 | 8/2001 | Laird |
| 6,283,991 B1 | 9/2001 | Cox et al. |
| 6,295,940 B1 | 10/2001 | Shonteff |

(56) References Cited

U.S. PATENT DOCUMENTS

| | | |
|---|---|---|
| 6,296,661 B1 | 10/2001 | Davila et al. |
| 6,299,636 B1 | 10/2001 | Schmitt et al. |
| 6,299,637 B1 | 10/2001 | Shaolian et al. |
| 6,309,413 B1 | 10/2001 | Dereume et al. |
| 6,312,458 B1 | 11/2001 | Golds |
| 6,312,460 B2 | 11/2001 | Drasler et al. |
| 6,312,465 B1 | 11/2001 | Griffin et al. |
| 6,319,276 B1 | 11/2001 | Holman et al. |
| 6,327,772 B1 | 12/2001 | Zadno-Azizi |
| 6,344,052 B1 | 2/2002 | Greenan et al. |
| 6,348,061 B1 | 2/2002 | Whitman |
| 6,348,066 B1 | 2/2002 | Pinchuk et al. |
| 6,355,030 B1 | 3/2002 | Aldrich et al. |
| 6,355,055 B1 | 3/2002 | Waksman et al. |
| 6,357,104 B1 | 3/2002 | Myers |
| 6,402,779 B1 | 6/2002 | Colone et al. |
| 6,425,916 B1 | 7/2002 | Garrison et al. |
| 6,451,052 B1 | 9/2002 | Burmeister et al. |
| 6,454,795 B1 | 9/2002 | Chuter |
| 6,458,092 B1 | 10/2002 | Gambale et al. |
| 6,461,327 B1 | 10/2002 | Addis et al. |
| 6,464,720 B2 | 10/2002 | Boatman et al. |
| 6,488,705 B2 | 12/2002 | Schmitt et al. |
| 6,497,724 B1 | 12/2002 | Stevens et al. |
| 6,520,988 B1 | 2/2003 | Colombo et al. |
| 6,530,952 B2 | 3/2003 | Vesely |
| 6,540,782 B1 | 4/2003 | Snyders |
| 6,547,815 B2 | 4/2003 | Myers |
| 6,558,396 B1 | 5/2003 | Inoue |
| 6,569,191 B1 | 5/2003 | Hogan |
| 6,569,196 B1 | 5/2003 | Vesely |
| 6,575,994 B1 | 6/2003 | Marin et al. |
| 6,579,297 B2 | 6/2003 | Bicek et al. |
| 6,582,458 B1 | 6/2003 | White et al. |
| 6,582,462 B1 | 6/2003 | Andersen et al. |
| 6,648,913 B1 | 11/2003 | Yee et al. |
| 6,656,215 B1 | 12/2003 | Yanez et al. |
| 6,669,720 B1 | 12/2003 | Pierce |
| 6,673,103 B1 | 1/2004 | Golds et al. |
| 6,682,558 B2 | 1/2004 | Tu et al. |
| 6,695,813 B1 | 2/2004 | Boyle et al. |
| 6,716,230 B2 | 4/2004 | Whitman |
| 6,719,782 B1 | 4/2004 | Chuter |
| 6,730,118 B2 | 5/2004 | Spenser et al. |
| 6,730,121 B2 | 5/2004 | Ortiz et al. |
| 6,733,521 B2 | 5/2004 | Chobotov et al. |
| 6,733,525 B2 | 5/2004 | Yang et al. |
| 6,740,105 B2 | 5/2004 | Yodfat et al. |
| 6,761,733 B2 | 7/2004 | Chobotov et al. |
| 6,773,456 B1 | 8/2004 | Gordon et al. |
| 6,814,748 B1 | 11/2004 | Baker et al. |
| 6,837,893 B2 | 1/2005 | Miller |
| 6,860,900 B2 | 3/2005 | Clerc et al. |
| 6,860,901 B1 | 3/2005 | Baker et al. |
| 6,863,686 B2 | 3/2005 | Shannon |
| 6,875,231 B2 | 4/2005 | Anduiza et al. |
| 6,881,221 B2 | 4/2005 | Golds |
| 6,890,350 B1 | 5/2005 | Walak |
| 6,893,459 B1 | 5/2005 | Macoviak |
| 6,893,460 B2 | 5/2005 | Spenser et al. |
| 6,908,478 B2 | 6/2005 | Alferness et al. |
| 6,918,926 B2 | 7/2005 | Letort |
| 6,929,659 B2 | 8/2005 | Pinchuk |
| 6,945,994 B2 | 9/2005 | Austin et al. |
| 6,949,119 B2 | 9/2005 | Myers |
| 6,951,571 B1 | 10/2005 | Srivastava |
| 6,994,722 B2 | 2/2006 | DiCarlo |
| 7,004,176 B2 | 2/2006 | Lau |
| 7,007,396 B2 | 3/2006 | Rudko et al. |
| 7,011,681 B2 | 3/2006 | Vesely |
| 7,018,400 B2 | 3/2006 | Lashinski et al. |
| 7,033,389 B2 | 4/2006 | Sherry |
| 7,041,132 B2 | 5/2006 | Quijano et al. |
| 7,052,511 B2 | 5/2006 | Weldon et al. |
| 7,090,688 B2 | 8/2006 | Nishtala et al. |
| 7,097,658 B2 | 8/2006 | Oktay |
| 7,112,217 B1 | 9/2006 | Kugler et al. |
| 7,122,051 B1 | 10/2006 | Dallara et al. |
| 7,137,993 B2 | 11/2006 | Acosta et al. |
| 7,141,063 B2 | 11/2006 | White et al. |
| 7,152,605 B2 | 12/2006 | Khairkhahan et al. |
| 7,160,318 B2 | 1/2007 | Greenberg et al. |
| 7,166,125 B1 | 1/2007 | Baker et al. |
| 7,169,172 B2 | 1/2007 | Levine et al. |
| 7,175,656 B2 | 2/2007 | Khairkhahan |
| 7,217,287 B2 | 5/2007 | Wilson et al. |
| 7,235,093 B2 | 6/2007 | Gregorich |
| 7,250,028 B2 | 7/2007 | Julian et al. |
| 7,258,696 B2 | 8/2007 | Rabkin et al. |
| 7,297,150 B2 | 11/2007 | Cartledge et al. |
| 7,326,236 B2 | 2/2008 | Andreas et al. |
| 7,329,279 B2 | 2/2008 | Haug et al. |
| 7,331,991 B2 | 2/2008 | Kheradvar et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,399,315 B2 | 7/2008 | Iobbi |
| 7,435,257 B2 | 10/2008 | Lashinski et al. |
| 7,445,630 B2 | 11/2008 | Lashinski et al. |
| 7,452,371 B2 | 11/2008 | Pavcnik et al. |
| 7,455,690 B2 | 11/2008 | Cartledge et al. |
| 7,481,836 B2 | 1/2009 | Greenan |
| 7,507,252 B2 | 3/2009 | Lashinski et al. |
| 7,510,572 B2 | 3/2009 | Gabbay |
| 7,524,331 B2 | 4/2009 | Birdsall |
| 7,544,206 B2 | 6/2009 | Cohn |
| 7,556,646 B2 | 7/2009 | Yang et al. |
| 7,591,848 B2 | 9/2009 | Allen |
| 7,597,704 B2 | 10/2009 | Frazier et al. |
| 7,625,403 B2 | 12/2009 | Krivoruchko |
| 7,637,935 B2 | 12/2009 | Pappas et al. |
| 7,674,296 B2 | 3/2010 | Rhoda et al. |
| 7,682,390 B2 | 3/2010 | Seguin |
| 7,691,141 B2 | 4/2010 | Lewis et al. |
| 7,708,773 B2 | 5/2010 | Pinchuk et al. |
| 7,713,282 B2 | 5/2010 | Frazier et al. |
| 7,722,662 B2 | 5/2010 | Steinke et al. |
| 7,727,270 B2 | 6/2010 | Rucker |
| 7,763,065 B2 | 7/2010 | Schmid |
| 7,780,724 B2 | 8/2010 | Kheradvar et al. |
| 7,785,341 B2 | 8/2010 | Forster et al. |
| 7,803,185 B2 | 9/2010 | Gabbay |
| 7,806,917 B2 | 10/2010 | Xiao |
| 7,828,839 B2 | 11/2010 | Cook et al. |
| 7,862,577 B2 | 1/2011 | Gray et al. |
| 7,862,609 B2 | 1/2011 | Butaric et al. |
| 7,887,583 B2 | 2/2011 | Macoviak |
| 7,896,913 B2 | 3/2011 | Damm et al. |
| 7,914,574 B2 | 3/2011 | Schmid |
| 7,935,141 B2 | 5/2011 | Randall et al. |
| 7,947,071 B2 | 5/2011 | Schmid |
| 7,959,666 B2 | 6/2011 | Salahieh et al. |
| 7,972,370 B2 | 7/2011 | Douk et al. |
| 7,988,724 B2 | 8/2011 | Salahieh et al. |
| 7,998,189 B2 | 8/2011 | Kölbel et al. |
| 8,012,197 B2 | 9/2011 | Bashiri et al. |
| 8,016,873 B1 | 9/2011 | Drasler et al. |
| 8,021,421 B2 | 9/2011 | Fogarty et al. |
| 8,043,356 B2 | 10/2011 | Kölbel et al. |
| 8,043,357 B2 | 10/2011 | Hartley |
| 8,048,153 B2 | 11/2011 | Salahieh et al. |
| 8,052,732 B2 | 11/2011 | Mitchell et al. |
| 8,052,749 B2 | 11/2011 | Salahieh et al. |
| 8,052,750 B2 | 11/2011 | Tuval et al. |
| 8,062,344 B2 | 11/2011 | Dorn et al. |
| 8,062,345 B2 | 11/2011 | Ouellette et al. |
| 8,128,681 B2 | 3/2012 | Shoemaker et al. |
| 8,157,853 B2 | 4/2012 | Laske et al. |
| 8,157,860 B2 | 4/2012 | McNamara et al. |
| 8,226,707 B2 | 7/2012 | White |
| 8,252,036 B2 | 8/2012 | Cartledge et al. |
| 8,500,790 B2 | 8/2013 | Khairkhahan |
| 8,523,936 B2 | 9/2013 | Schmid |
| 8,540,762 B2 | 9/2013 | Schmid |

(56) References Cited

U.S. PATENT DOCUMENTS

| | | | |
|---|---|---|---|
| 8,647,378 B2 | 2/2014 | Mews | |
| 8,673,001 B2 | 3/2014 | Cartledge | |
| 8,685,080 B2 | 4/2014 | White | |
| 8,852,261 B2 | 10/2014 | White | |
| 8,858,620 B2 | 10/2014 | Salahieh | |
| 8,894,703 B2 | 11/2014 | Salahieh | |
| 8,998,976 B2 | 4/2015 | Gregg | |
| 2001/0023369 A1 | 9/2001 | Chobotov | |
| 2001/0025161 A1 | 9/2001 | Martinez | |
| 2001/0053931 A1 | 12/2001 | Hess et al. | |
| 2002/0032481 A1 | 3/2002 | Gabbay | |
| 2002/0055768 A1 | 5/2002 | Hess et al. | |
| 2002/0077695 A1 | 6/2002 | Swanson et al. | |
| 2002/0120327 A1 | 8/2002 | Cox et al. | |
| 2003/0004560 A1 | 1/2003 | Chobotov et al. | |
| 2003/0009211 A1 | 1/2003 | DiCarlo | |
| 2003/0040791 A1* | 2/2003 | Oktay | A61F 2/82 623/1.17 |
| 2003/0050694 A1 | 3/2003 | Yang et al. | |
| 2003/0055495 A1 | 3/2003 | Pease | |
| 2003/0074048 A1 | 4/2003 | Sherry | |
| 2003/0105516 A1 | 6/2003 | Austin | |
| 2003/0120331 A1 | 6/2003 | Chobotov | |
| 2003/0135268 A1 | 7/2003 | Desai | |
| 2003/0176911 A1 | 9/2003 | Iancea | |
| 2003/0191518 A1 | 10/2003 | Spiridigliozzi et al. | |
| 2003/0199967 A1 | 10/2003 | Hartley et al. | |
| 2003/0204249 A1 | 10/2003 | Letort | |
| 2003/0216770 A1 | 11/2003 | Persidsky et al. | |
| 2003/0229389 A1 | 12/2003 | Escano | |
| 2004/0049266 A1 | 3/2004 | Anduiza et al. | |
| 2004/0138734 A1 | 7/2004 | Chobotov et al. | |
| 2004/0148021 A1 | 7/2004 | Cartledge | |
| 2004/0162603 A1 | 8/2004 | Golds et al. | |
| 2004/0230289 A1 | 11/2004 | DiMatteo et al. | |
| 2004/0243221 A1 | 12/2004 | Fawzi | |
| 2005/0002981 A1 | 1/2005 | Lahtinen et al. | |
| 2005/0038497 A1 | 2/2005 | Neuendorf et al. | |
| 2005/0055089 A1 | 3/2005 | Macoviak et al. | |
| 2005/0075712 A1 | 4/2005 | Biancucci et al. | |
| 2005/0075725 A1 | 4/2005 | Rowe | |
| 2005/0096737 A1 | 5/2005 | Shannon et al. | |
| 2005/0137686 A1 | 6/2005 | Salahieh et al. | |
| 2005/0137699 A1 | 6/2005 | Salahieh | |
| 2005/0171599 A1 | 8/2005 | White | |
| 2005/0228484 A1 | 10/2005 | Stephens et al. | |
| 2006/0009833 A1 | 1/2006 | Chobotov | |
| 2006/0030927 A1 | 2/2006 | Hess | |
| 2006/0064151 A1 | 3/2006 | Guterman | |
| 2006/0074482 A1 | 4/2006 | Lewis et al. | |
| 2006/0089708 A1 | 4/2006 | Osse et al. | |
| 2006/0135984 A1 | 6/2006 | Kramer et al. | |
| 2006/0149350 A1 | 7/2006 | Patel et al. | |
| 2006/0161247 A1 | 7/2006 | Sherry | |
| 2006/0173527 A1 | 8/2006 | Scherrible | |
| 2006/0212113 A1 | 9/2006 | Shaolian et al. | |
| 2006/0217796 A1 | 9/2006 | DiMatteo et al. | |
| 2006/0253190 A1 | 11/2006 | Kuo | |
| 2007/0010876 A1 | 1/2007 | Salahieh | |
| 2007/0010877 A1 | 1/2007 | Salahieh | |
| 2007/0073389 A1* | 3/2007 | Bolduc | A61B 17/064 623/1.36 |
| 2007/0088431 A1 | 4/2007 | Bourang et al. | |
| 2007/0088436 A1 | 4/2007 | Parsons et al. | |
| 2007/0100427 A1 | 5/2007 | Perouse | |
| 2007/0106364 A1 | 5/2007 | Buzzard et al. | |
| 2007/0123972 A1 | 5/2007 | Greenberg et al. | |
| 2007/0142906 A1 | 6/2007 | Figulla | |
| 2007/0142907 A1 | 6/2007 | Moaddeb et al. | |
| 2007/0179591 A1 | 8/2007 | Baker et al. | |
| 2007/0208223 A1 | 9/2007 | Julian et al. | |
| 2007/0225797 A1 | 9/2007 | Krivoruhko | |
| 2007/0276462 A1 | 11/2007 | Iancea et al. | |
| 2007/0288089 A1 | 12/2007 | Gurskis | |
| 2008/0004398 A1 | 1/2008 | Durrieu et al. | |
| 2008/0004696 A1 | 1/2008 | Vesely | |
| 2008/0009746 A1 | 1/2008 | Forster | |
| 2008/0015687 A1 | 1/2008 | Lashinski et al. | |
| 2008/0027483 A1 | 1/2008 | Cartledge et al. | |
| 2008/0065011 A1 | 3/2008 | Marchand et al. | |
| 2008/0208213 A1 | 8/2008 | Benjamin et al. | |
| 2008/0249534 A1 | 10/2008 | Gruber et al. | |
| 2008/0255652 A1 | 10/2008 | Thomas | |
| 2008/0306586 A1 | 12/2008 | Cartledge et al. | |
| 2009/0005760 A1 | 1/2009 | Cartledge et al. | |
| 2009/0030501 A1 | 1/2009 | Morris | |
| 2009/0099638 A1 | 4/2009 | Grewe | |
| 2009/0099649 A1 | 4/2009 | Chobotov et al. | |
| 2009/0125098 A1 | 5/2009 | Chuter | |
| 2009/0132035 A1 | 5/2009 | Roth et al. | |
| 2009/0216314 A1 | 8/2009 | Quadri | |
| 2009/0228093 A1 | 9/2009 | Taylor et al. | |
| 2009/0234443 A1 | 9/2009 | Ottma et al. | |
| 2009/0254165 A1 | 10/2009 | Tabor et al. | |
| 2009/0299463 A1 | 12/2009 | Fawzi et al. | |
| 2009/0306768 A1 | 12/2009 | Quadri | |
| 2010/0030255 A1 | 2/2010 | Berra et al. | |
| 2010/0049313 A1 | 2/2010 | Alon et al. | |
| 2010/0280495 A1 | 11/2010 | Paul et al. | |
| 2010/0331972 A1 | 12/2010 | Pintor et al. | |
| 2011/0054519 A1 | 3/2011 | Neuss | |
| 2011/0066224 A1* | 3/2011 | White | A61F 2/2412 623/1.15 |
| 2011/0093060 A1 | 4/2011 | Cartledge | |
| 2011/0098802 A1 | 4/2011 | Braido et al. | |
| 2011/0098804 A1* | 4/2011 | Yeung | A61F 2/2412 623/2.1 |
| 2011/0218619 A1 | 9/2011 | Benichou et al. | |
| 2011/0219603 A1 | 9/2011 | White | |
| 2011/0224781 A1 | 9/2011 | White | |
| 2011/0230956 A1 | 9/2011 | White | |
| 2011/0245918 A1 | 10/2011 | White | |
| 2011/0251670 A1 | 10/2011 | Kheradvar et al. | |
| 2011/0251674 A1 | 10/2011 | Schmid | |
| 2011/0288622 A1 | 11/2011 | Chan et al. | |
| 2011/0288629 A1 | 11/2011 | White | |
| 2012/0035710 A1 | 2/2012 | Hartley | |
| 2012/0065723 A1 | 3/2012 | Drasler et al. | |
| 2012/0089217 A1 | 4/2012 | Mews et al. | |
| 2012/0323316 A1 | 12/2012 | Chau | |
| 2013/0046373 A1 | 2/2013 | Cartledge | |
| 2013/0158656 A1 | 6/2013 | Sutton | |
| 2013/0166017 A1 | 6/2013 | Cartledge | |
| 2013/0310923 A1 | 11/2013 | Kheradvar | |
| 2014/0018911 A1 | 1/2014 | Zhou | |

FOREIGN PATENT DOCUMENTS

| | | |
|---|---|---|
| EP | 836451 A1 | 4/1998 |
| EP | 855883 A1 | 8/1998 |
| EP | 0937439 A3 | 10/1999 |
| EP | 1095634 A2 | 5/2001 |
| EP | 1283027 A2 | 2/2003 |
| EP | 1556116 A2 | 7/2005 |
| EP | 2537487 A1 | 12/2012 |
| JP | 2001129001 A | 5/2001 |
| WO | 9308767 A1 | 5/1993 |
| WO | 9406372 A1 | 3/1994 |
| WO | 9505131 A1 | 2/1995 |
| WO | 9505132 A1 | 2/1995 |
| WO | 9633066 A1 | 10/1996 |
| WO | 9603999 A1 | 12/1996 |
| WO | 9712562 A1 | 4/1997 |
| WO | 9717899 A1 | 5/1997 |
| WO | 9721403 A1 | 6/1997 |
| WO | 97/26829 | 7/1997 |
| WO | 9725000 A1 | 7/1997 |
| WO | 9727959 A1 | 8/1997 |
| WO | 9733532 A2 | 9/1997 |
| WO | 9841167 A1 | 9/1998 |
| WO | 98/49974 | 11/1998 |
| WO | 9915108 A2 | 4/1999 |
| WO | 9943379 A1 | 9/1999 |
| WO | 9947071 A1 | 9/1999 |

(56) References Cited

FOREIGN PATENT DOCUMENTS

| | | | |
|---|---|---|---|
| WO | 0033770 | A2 | 6/2000 |
| WO | 0071057 | A1 | 11/2000 |
| WO | 0074598 | A1 | 12/2000 |
| WO | 0101886 | A1 | 1/2001 |
| WO | 0106953 | A1 | 2/2001 |
| WO | 0115633 | A1 | 3/2001 |
| WO | 0126582 | A1 | 4/2001 |
| WO | 0137892 | A1 | 5/2001 |
| WO | 0138373 | A1 | 5/2001 |
| WO | 0152771 | A1 | 7/2001 |
| WO | 02/41789 | A2 | 5/2002 |
| WO | 0239925 | A2 | 5/2002 |
| WO | 02078569 | A2 | 10/2002 |
| WO | 02102234 | A2 | 10/2002 |
| WO | 03003945 | A2 | 1/2003 |
| WO | 03/018100 | | 3/2003 |
| WO | 03/028558 | A2 | 4/2003 |
| WO | 03043539 | A1 | 5/2003 |
| WO | 03047460 | A2 | 6/2003 |
| WO | 03053283 | A1 | 7/2003 |
| WO | 03075798 | A1 | 9/2003 |
| WO | 03082153 | A2 | 10/2003 |
| WO | 03084440 | A1 | 10/2003 |
| WO | 2004016193 | A2 | 2/2004 |
| WO | 2004016201 | A2 | 2/2004 |
| WO | 2004058047 | A2 | 7/2004 |
| WO | 2004093746 | A1 | 11/2004 |
| WO | 2004103219 | A2 | 12/2004 |
| WO | 2004105636 | A2 | 12/2004 |
| WO | 2005039445 | A2 | 5/2005 |
| WO | 2005086942 | A2 | 9/2005 |
| WO | 2005115118 | A2 | 12/2005 |
| WO | 2006014347 | A1 | 2/2006 |
| WO | 2006076325 | A1 | 7/2006 |
| WO | 2006076326 | A2 | 7/2006 |
| WO | 2006076328 | A1 | 7/2006 |
| WO | 2006104859 | A1 | 10/2006 |
| WO | 2006107562 | A2 | 10/2006 |
| WO | 2006128017 | A2 | 11/2006 |
| WO | 2007088549 | A2 | 8/2007 |
| WO | 2007133809 | A2 | 11/2007 |
| WO | 2008016578 | A2 | 2/2008 |
| WO | 2008042266 | A2 | 4/2008 |
| WO | 2008016578 | A3 | 7/2008 |
| WO | 2008/140796 | | 11/2008 |
| WO | 2009046372 | A2 | 4/2009 |
| WO | 2009046372 | A3 | 4/2009 |
| WO | 2009073767 | A1 | 6/2009 |
| WO | 2010/011699 | | 1/2010 |
| WO | 2010011699 | A2 | 1/2010 |

OTHER PUBLICATIONS

International Search Report of PCT/US11/67695.
European Search Report of European Patent App. No. 12 84 1445 dated Mar. 11, 2015.
Office action of China Patent App. No. 201180068672.0 dated Jan. 23, 2015.
International Search Report and Written Opinion of PCT/US2014/038305 dated Oct. 10, 2014.
International Search Report and Written Opinion of the International Searching Authority for International Application No. PCT/US2012/061292 dated Jan. 7, 2013.
Extended European Search Report & Search Opinion (PCT/US2007/017061) of the European Patent Office dated Apr. 3, 2013.
International Search Report and Written Opinion of the International Searching Authority for International App. No. PCT/US2007/017061 dated Aug. 6, 2008.
Office Action of the Australian Patent office for Application No. 2013260693 dated Dec. 1, 2014.
International Search Report of PCT/US11/67695 dated Apr. 25, 2012.
International Search Report of PCT/US2013/027072 dated Apr. 29, 2013.
Official Communication From the European Patent Office for European Pat. App. No. 12841445.5 dated Feb. 18, 2016.

\* cited by examiner

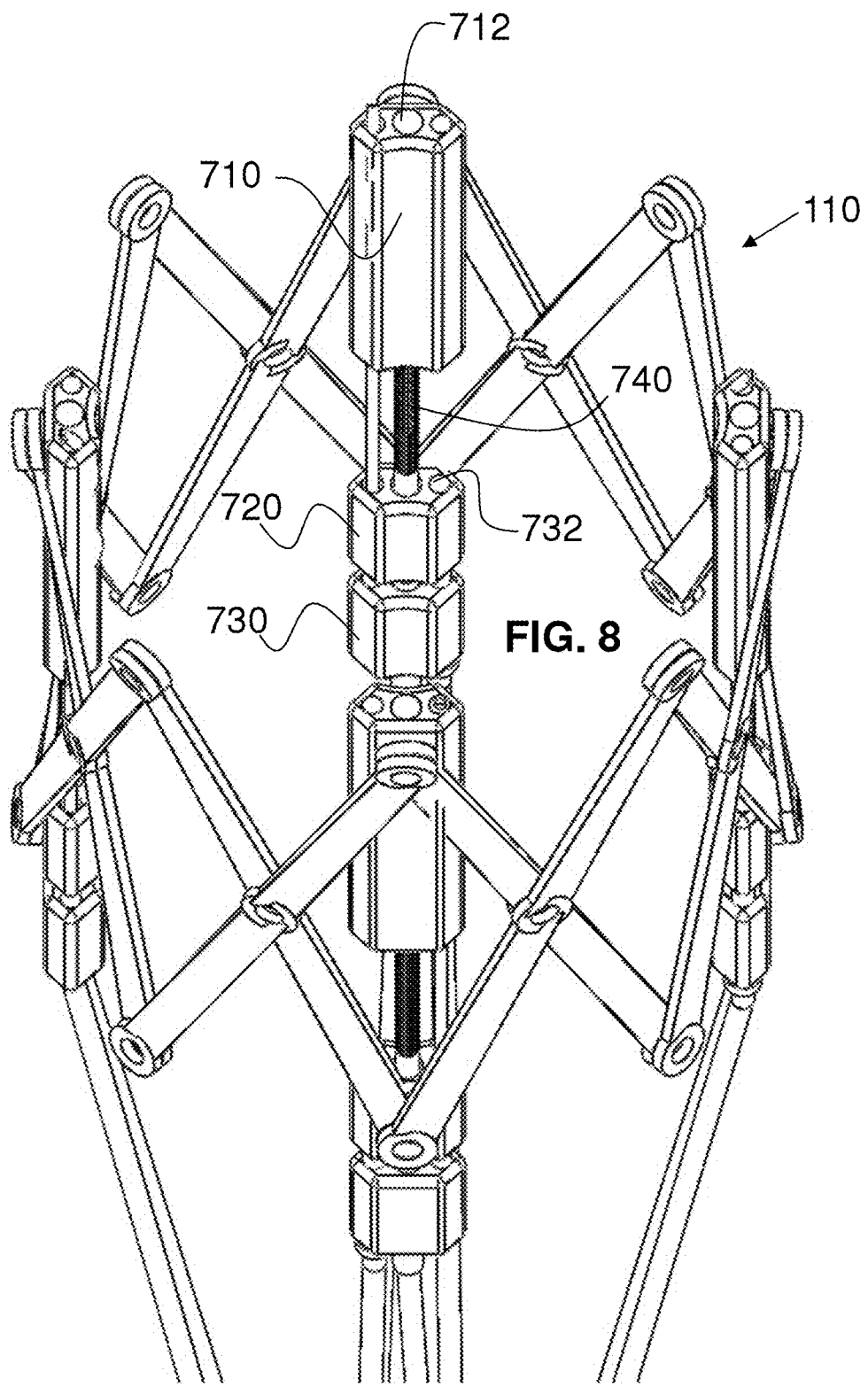

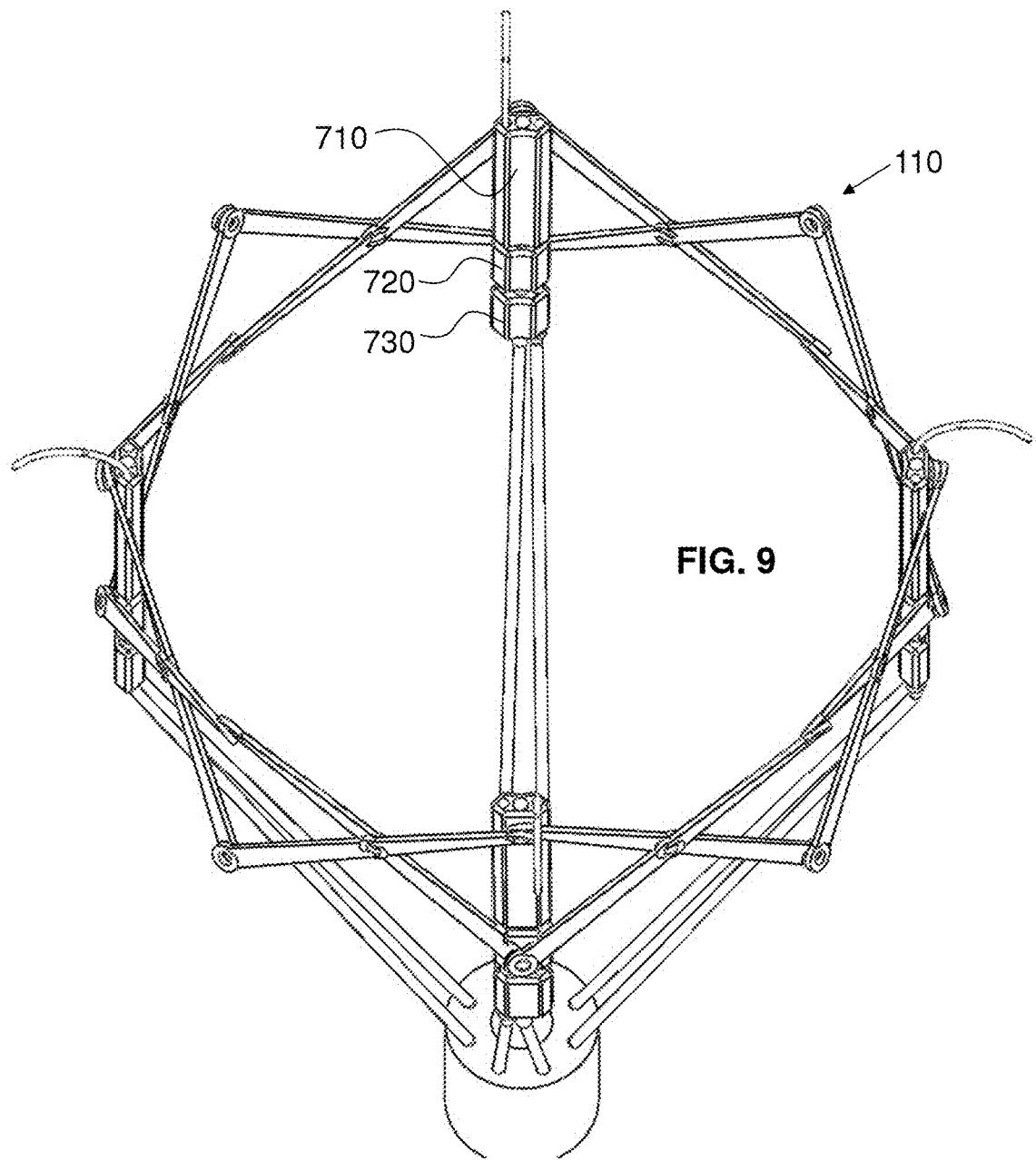

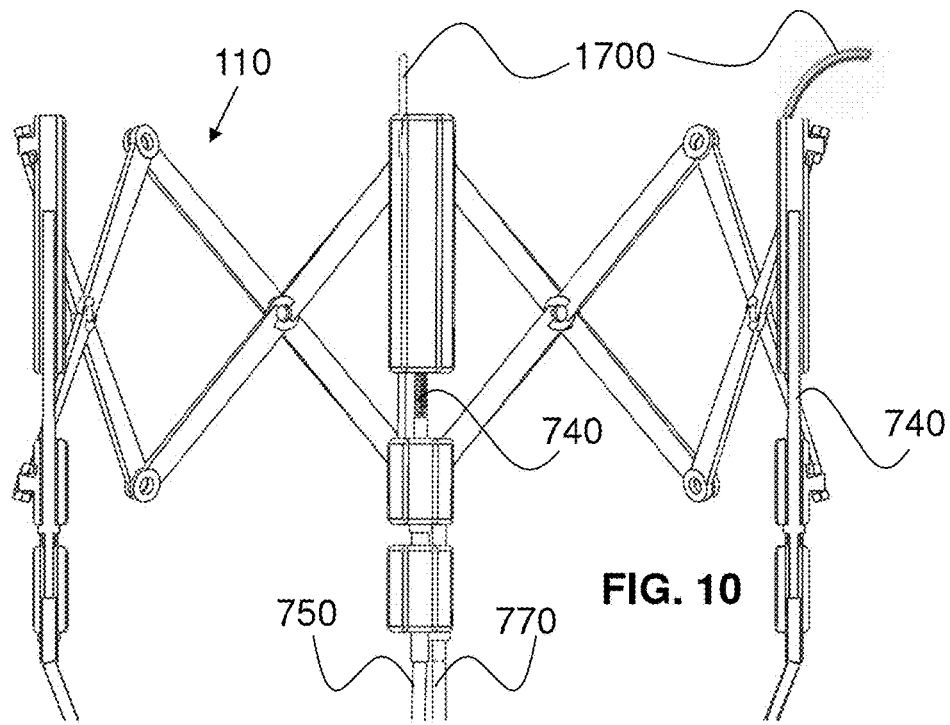
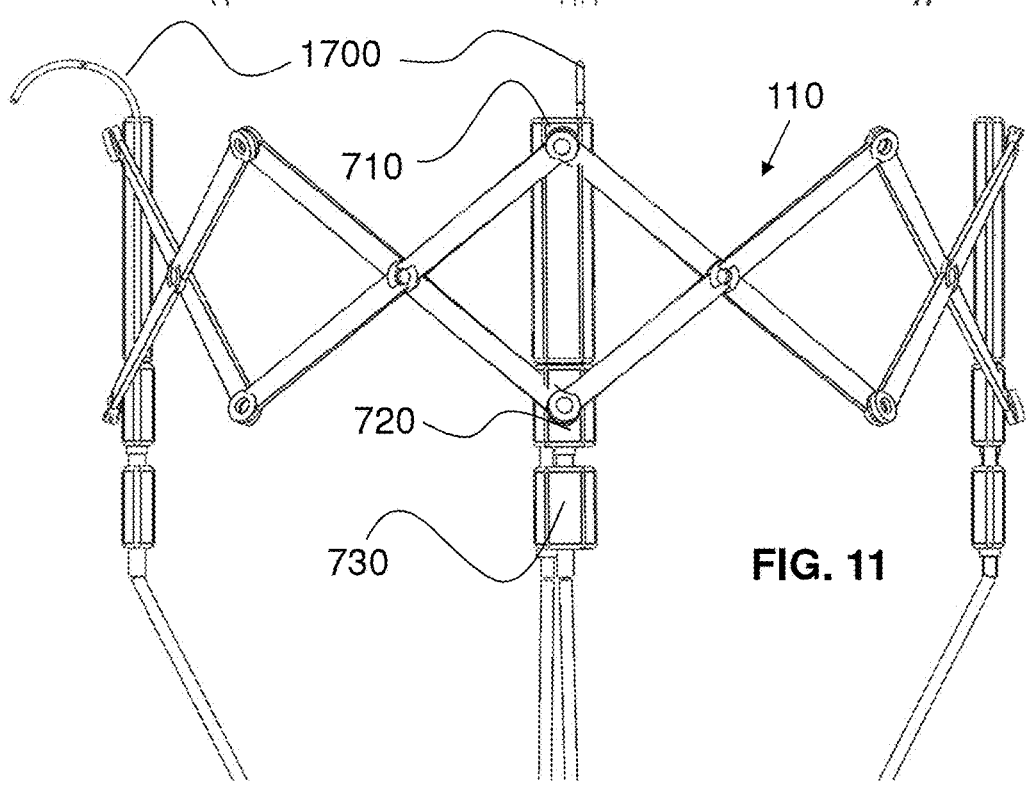

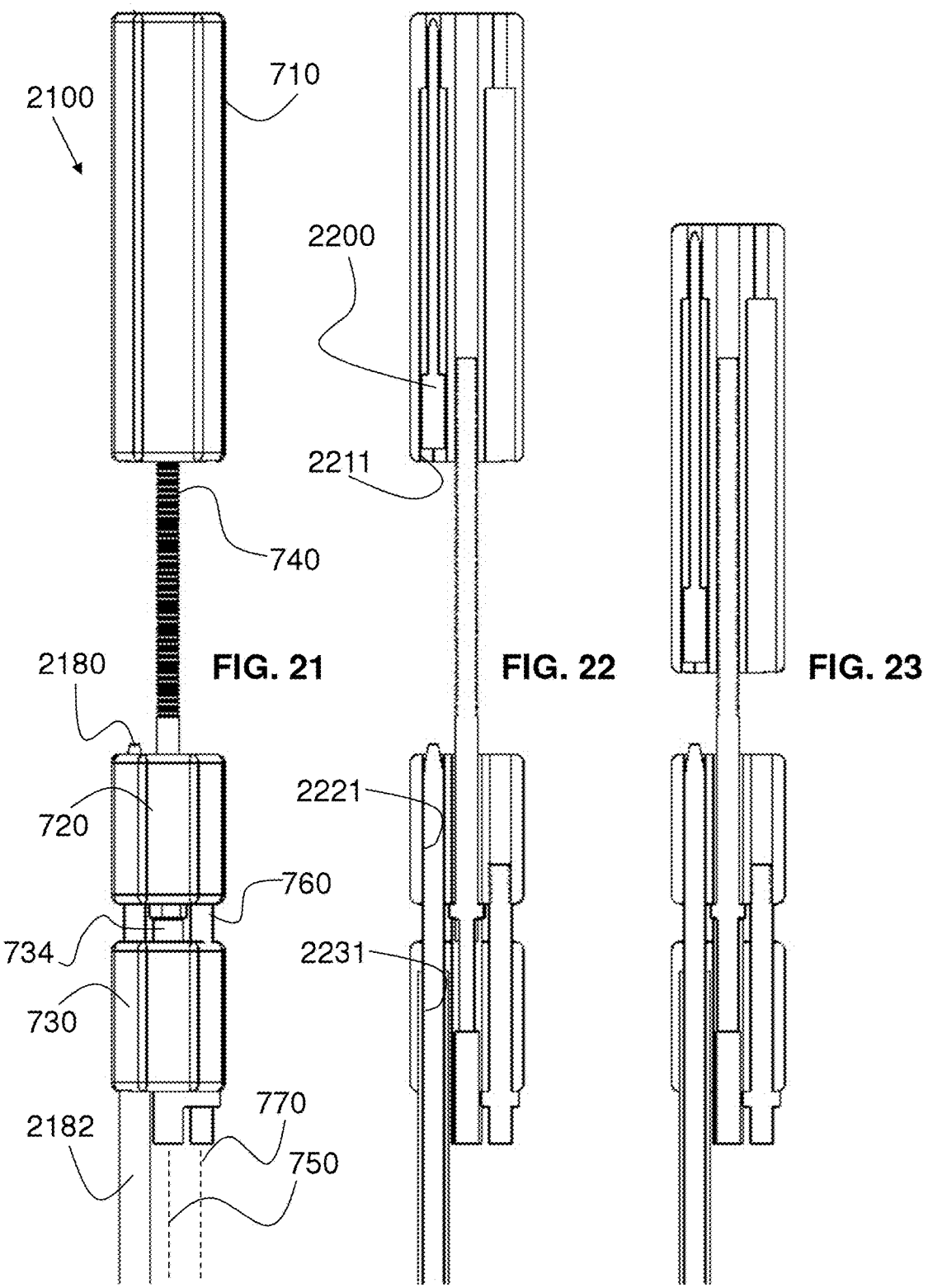

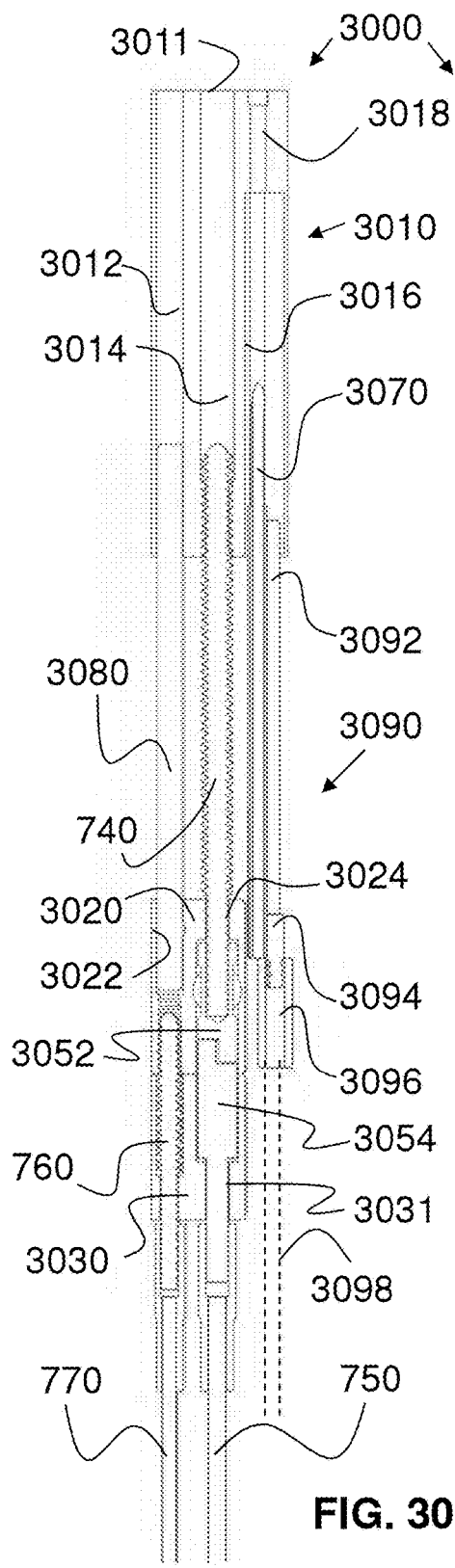
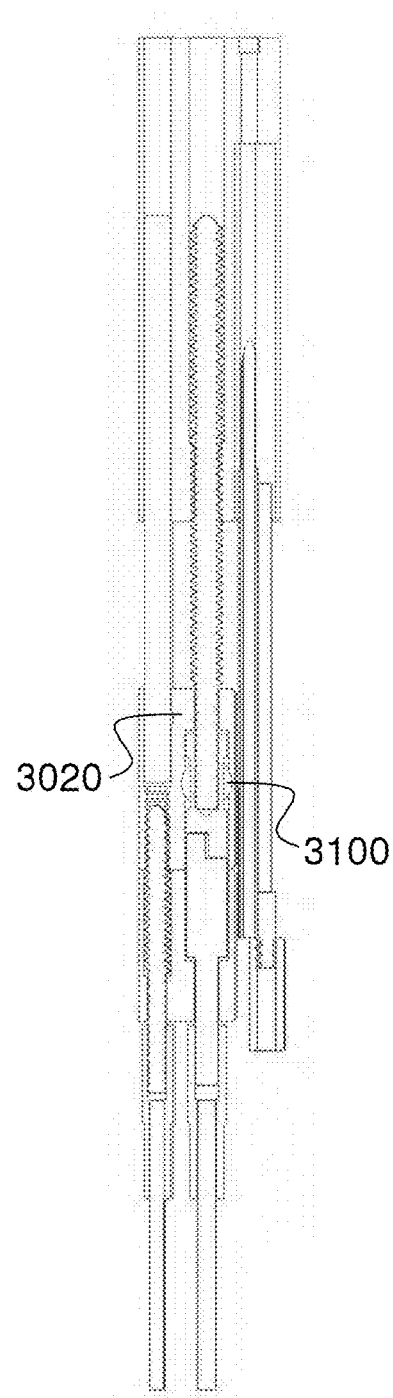
FIG. 30
FIG. 31

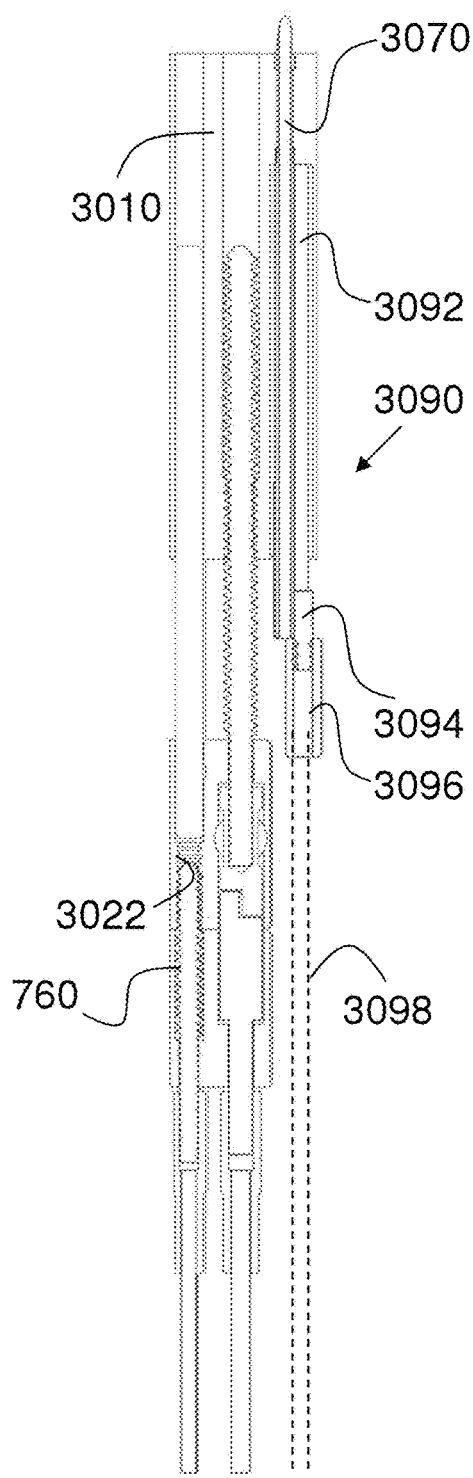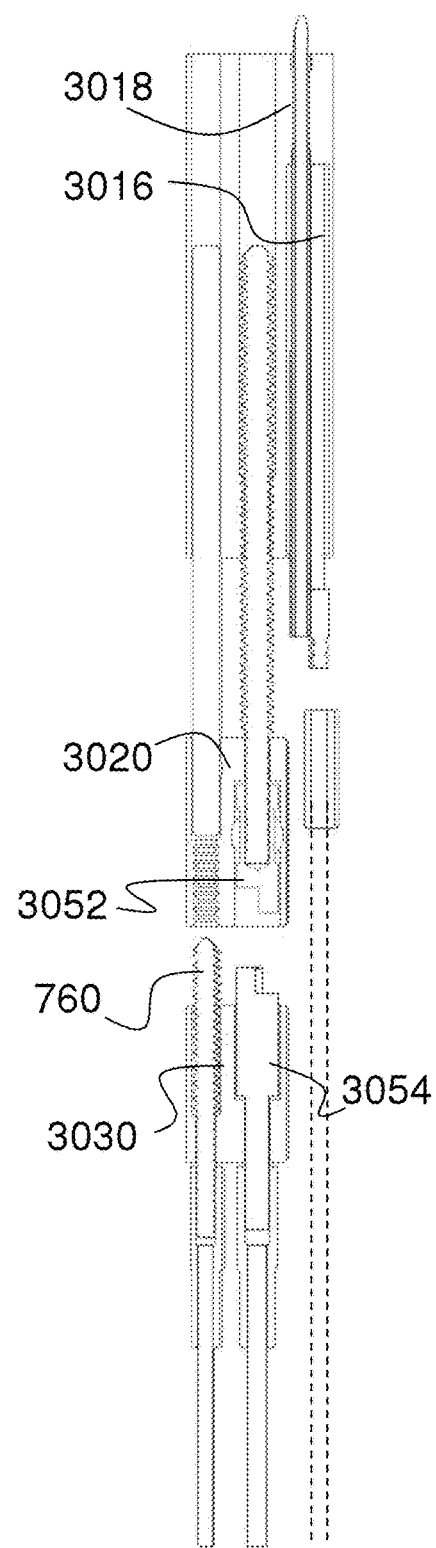
FIG. 32  FIG. 33

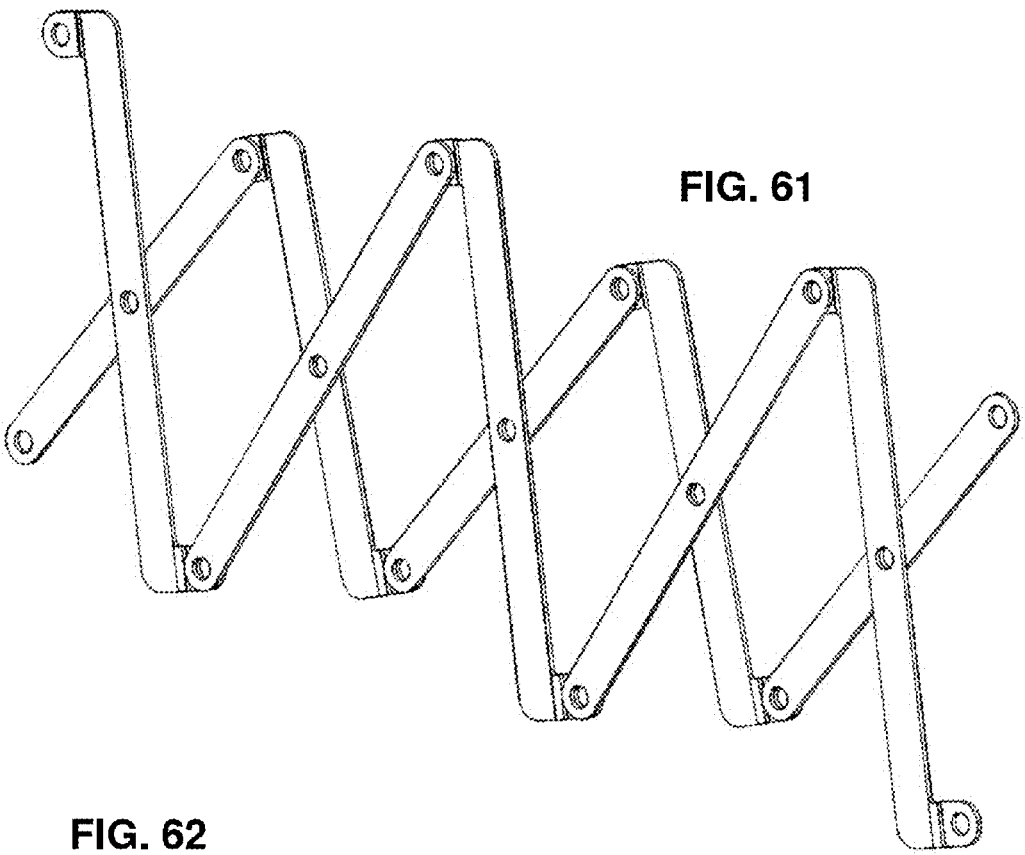
FIG. 61
FIG. 62
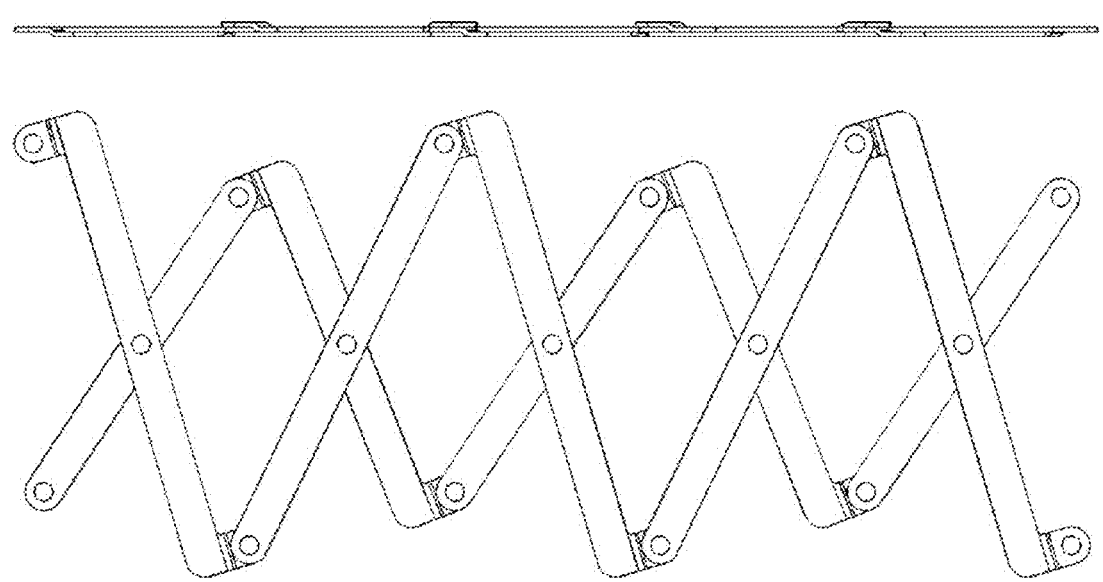
FIG. 63

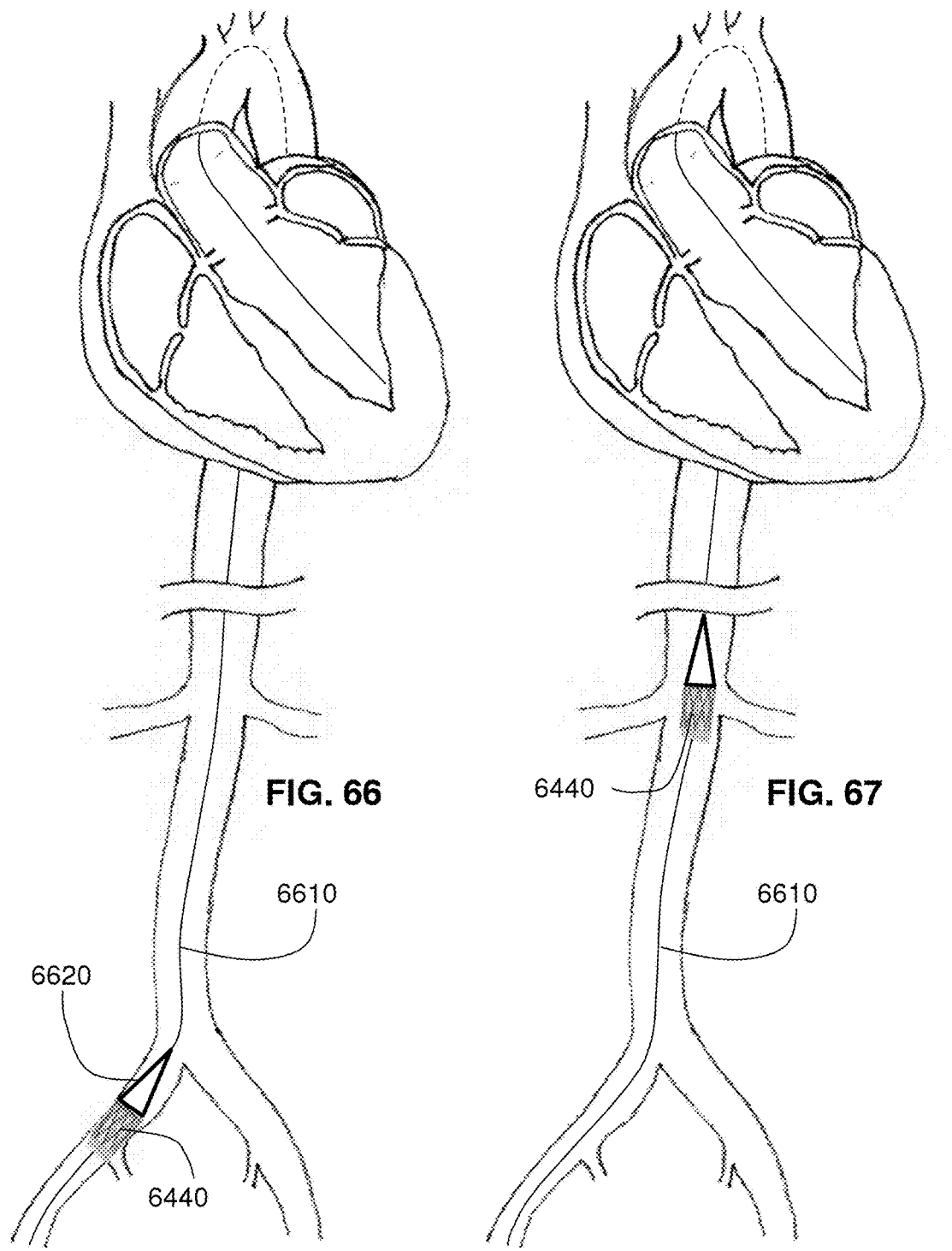

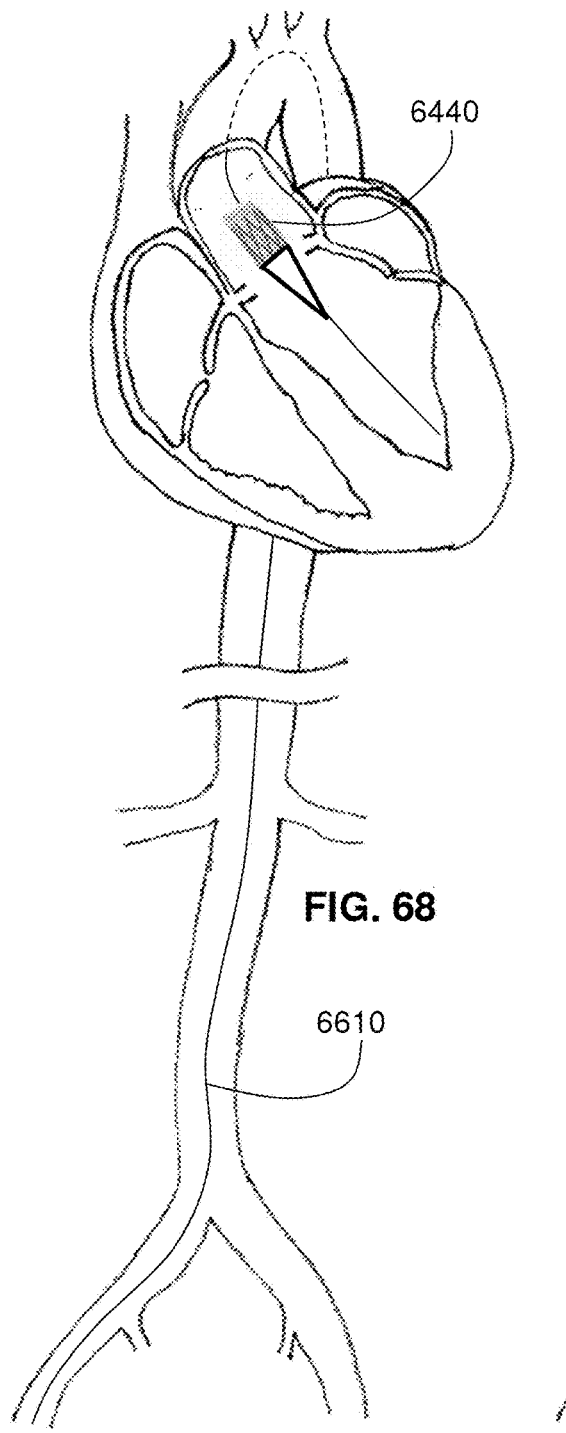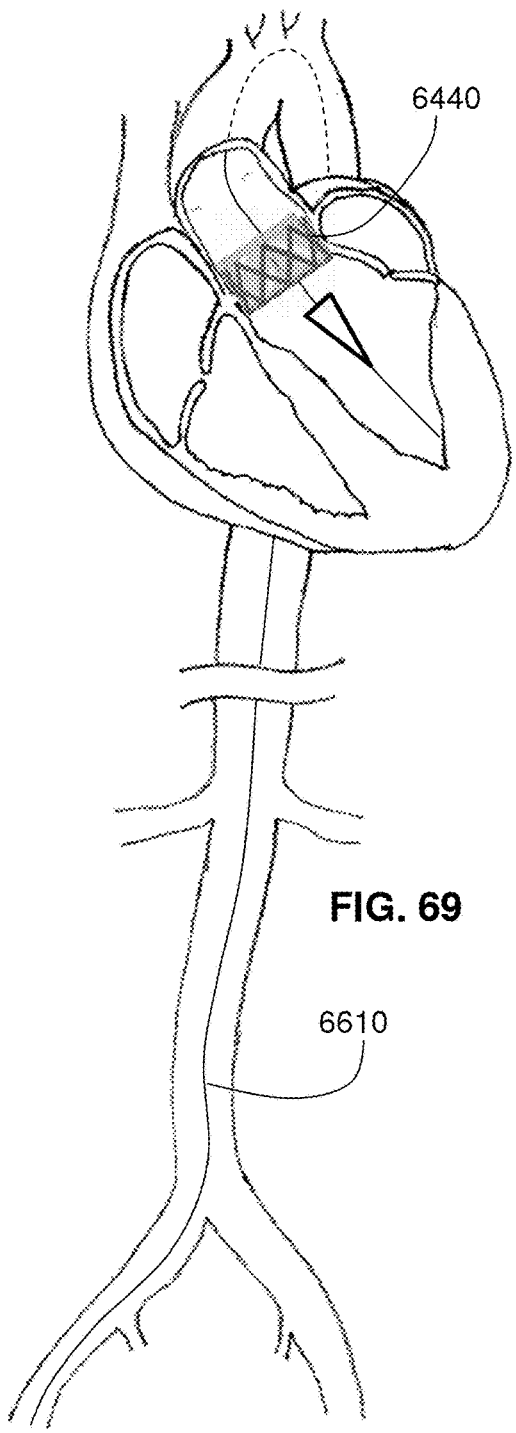

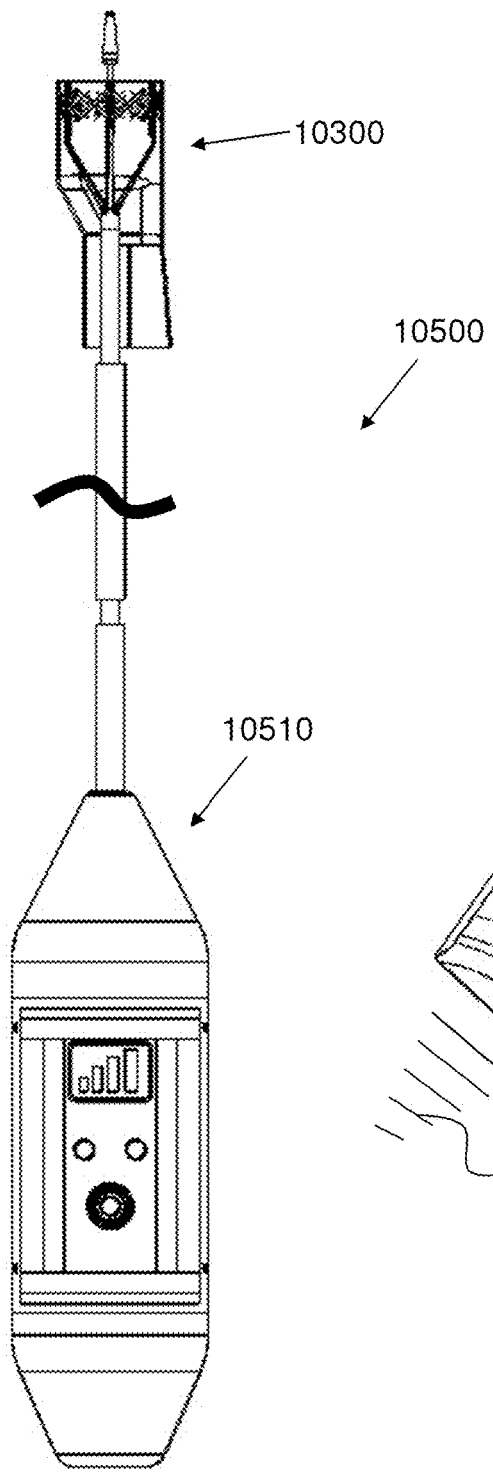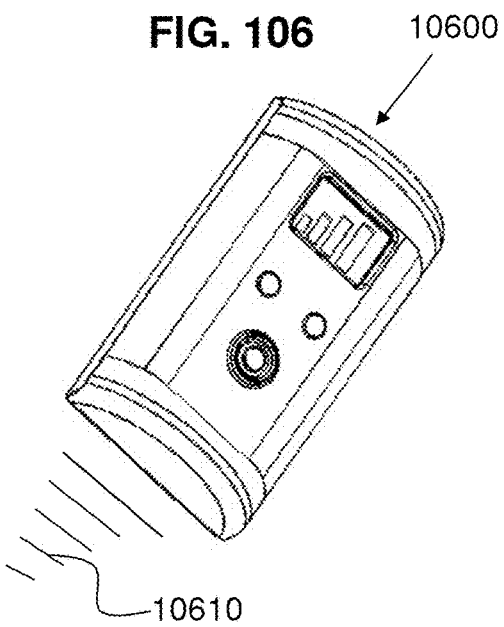
FIG. 105
FIG. 106

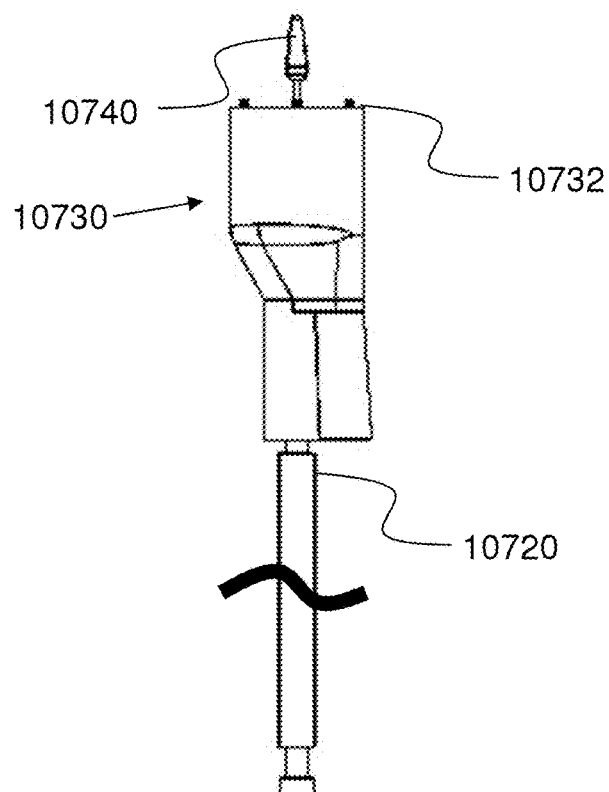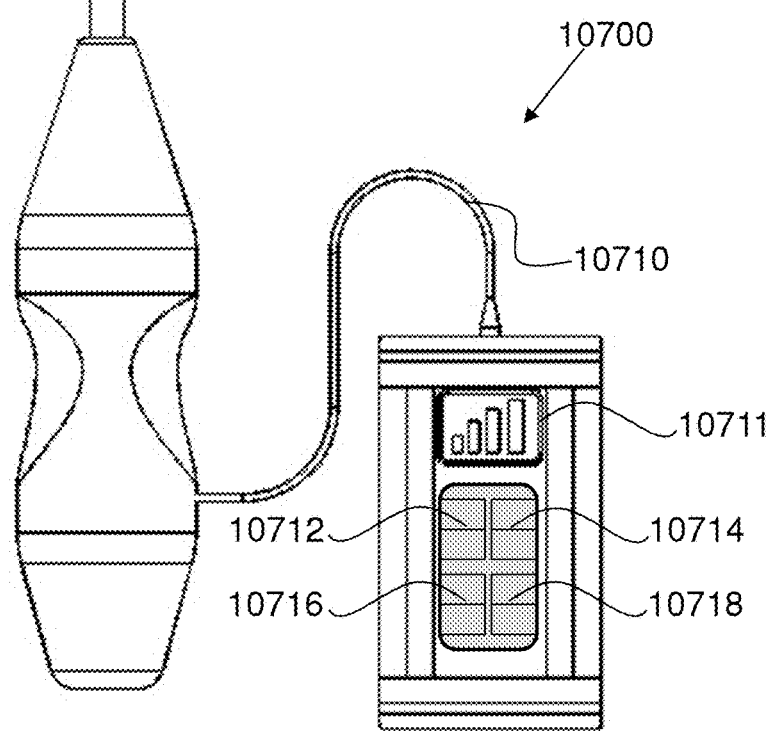
FIG. 107

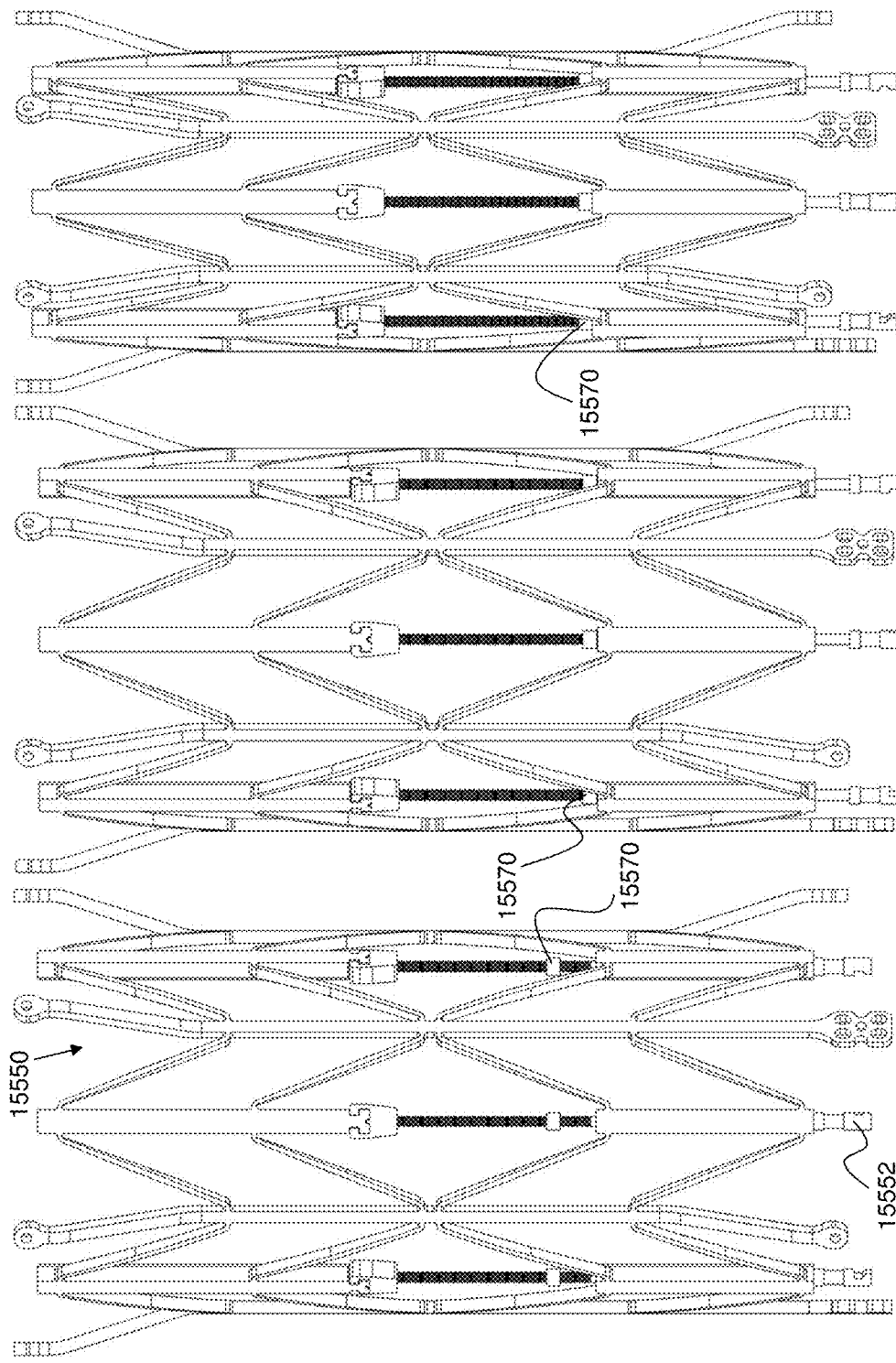

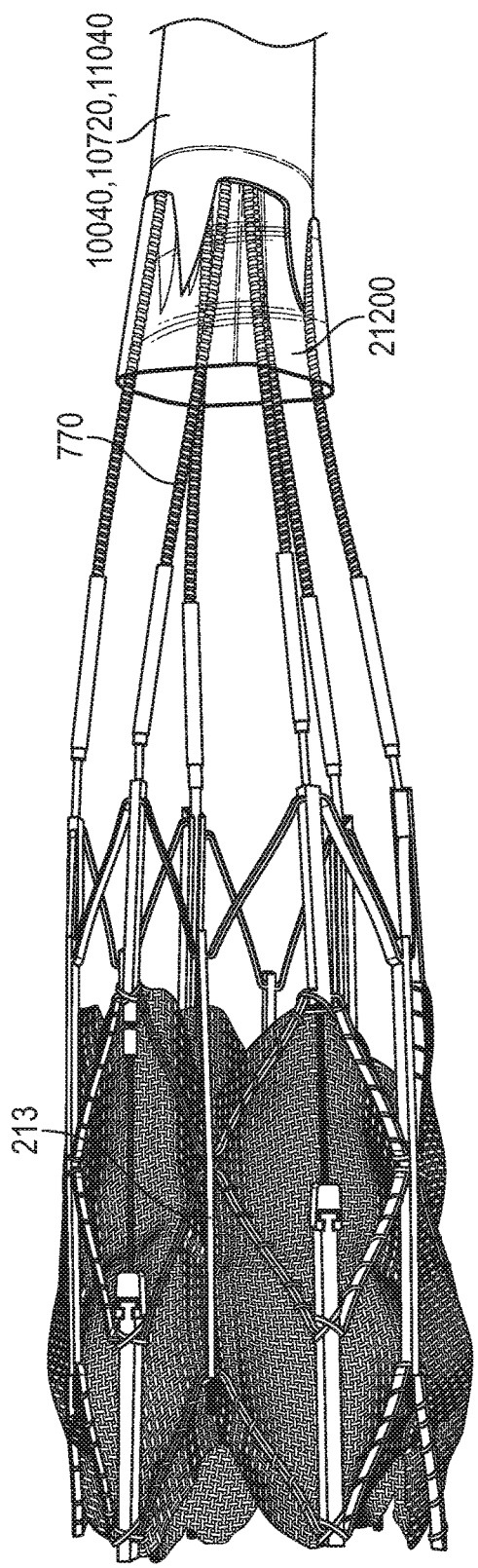
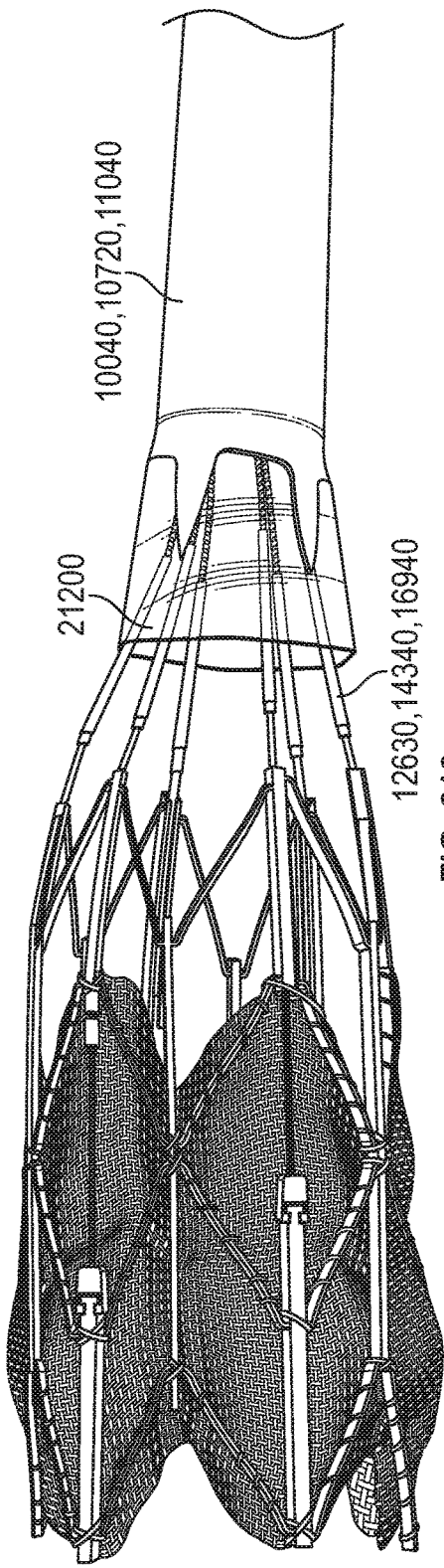

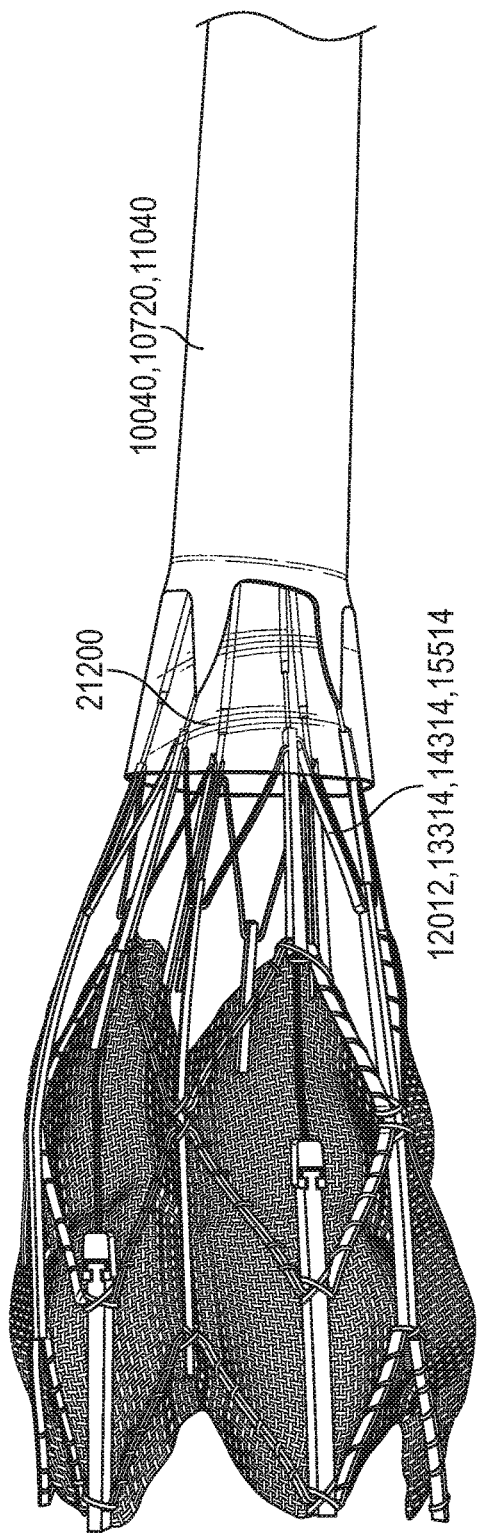
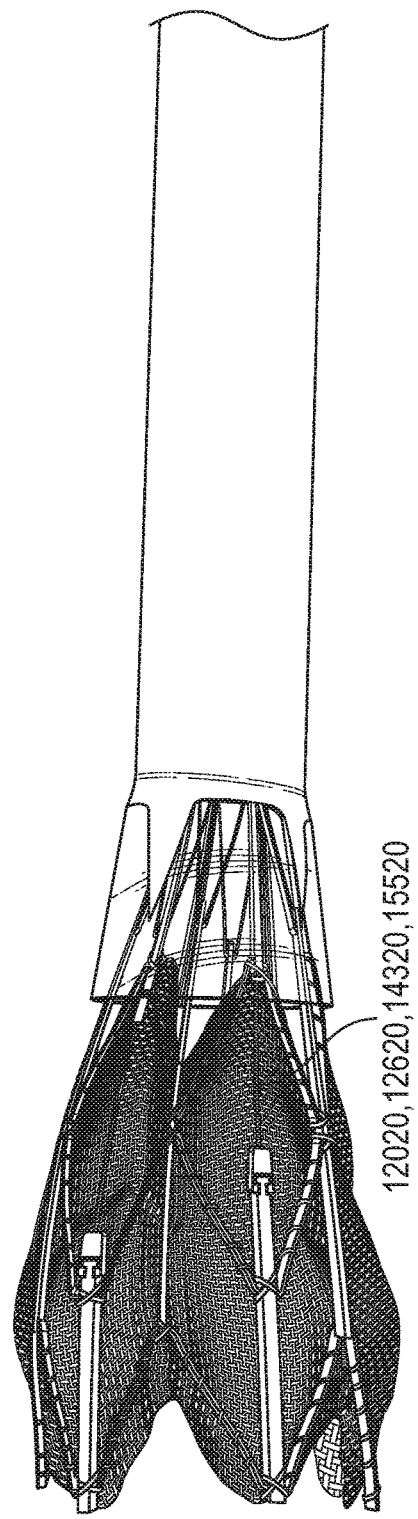

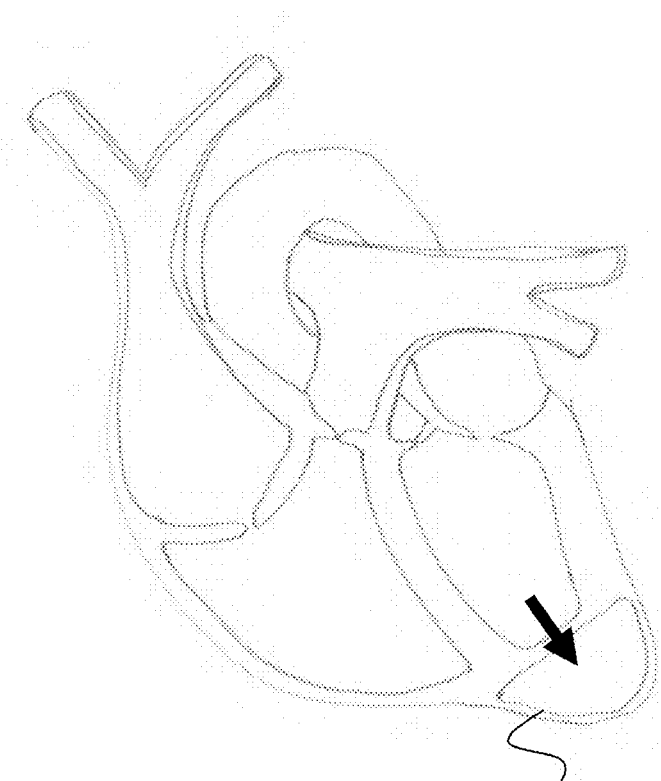
FIG. 241  24100
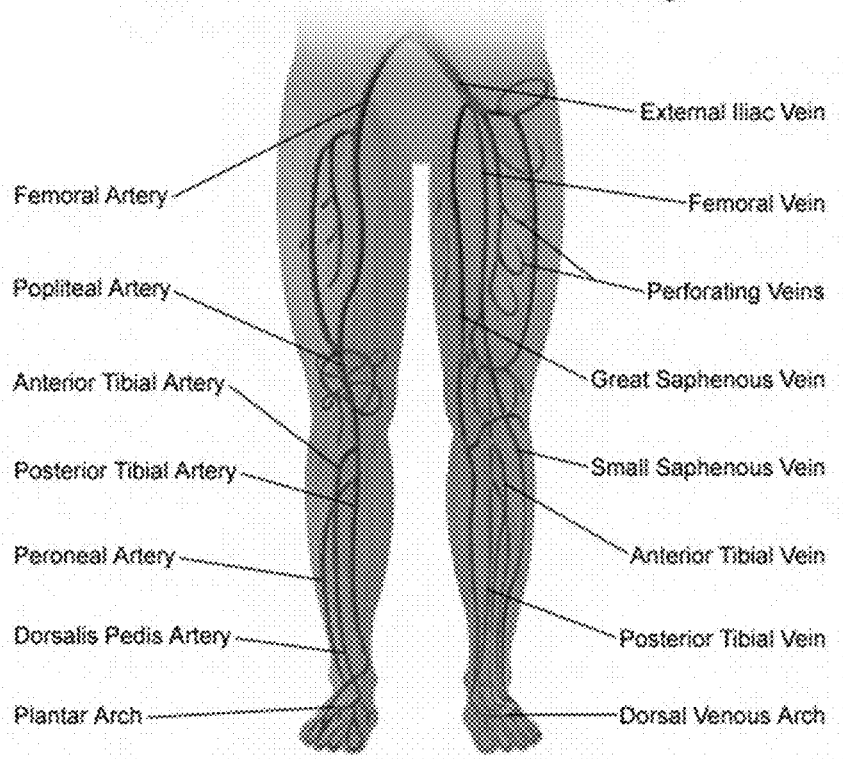
FIG. 242

ACTIVELY CONTROLLABLE STENT, STENT GRAFT, HEART VALVE AND METHOD OF CONTROLLING SAME

CROSS-REFERENCE TO RELATED APPLICATIONS

This application claims the benefit of U.S. Provisional Patent Application No. 61/824,264, filed May 16, 2013, and is a continuation-in-part of U.S. patent application Ser. No. 13/772,203, filed Feb. 20, 2013, and Ser. No. 13/656,717, filed Oct. 21, 2012, now U.S. Pat. No. 9,566,178. U.S. patent application Ser. No. 13/772,203 claims the benefit of U.S. Provisional Patent Application Nos. 61/739,711, filed Dec. 19, 2012, 61/717,037, filed Oct. 22, 2012, 61/682,558, filed Aug. 13, 2012, and 61/601,961, filed Feb. 22, 2012. U.S. patent application Ser. No. 13/656,717 claims the benefit of U.S. Provisional Patent Application Nos. 61/682,558, filed Aug. 13, 2012, 61/601,961, filed Feb. 22, 2012, 61/591,753, filed Jan. 27, 2012, 61/585,937, filed Jan. 12, 2012, and 61/550,004, filed Oct. 21, 2011. The prior applications are incorporated by reference herein in their entireties.

STATEMENT REGARDING FEDERALLY SPONSORED RESEARCH OR DEVELOPMENT

Not Applicable

FIELD OF THE INVENTION

The present invention lies in the field of stents, stent grafts, heart valves (including aortic, pulmonary, mitral and tricuspid), and methods and systems for controlling and implanting stents, stent grafts and heart valves.

BACKGROUND OF THE INVENTION

Medical and surgical implants are placed often in anatomic spaces where it is desirable for the implant to conform to the unique anatomy of the targeted anatomic space and secure a seal therein, preferably without disturbing or distorting the unique anatomy of that targeted anatomic space.

While the lumens of most hollow anatomic spaces are ideally circular, in fact, the cross-sectional configurations of most anatomic spaces are, at best, ovoid, and may be highly irregular. Such lumenal irregularity may be due to anatomic variations and/or to pathologic conditions that may change the shape and topography of the lumen and its associated anatomic wall. Examples of anatomic spaces where such implants may be deployed include, but are not limited to, blood vessels, the heart, other vascular structures, and vascular defects (such as thoracic and abdominal aortic aneurysms).

For a patient to be a candidate for existing endograft methods and technologies, to permit an adequate seal, a proximal neck of, ideally, at least 12 mm of normal aorta must exist downstream of the left subclavian artery for thoracic aortic aneurysms or between the origin of the most inferior renal artery and the origin of the aneurysm in the case of abdominal aneurysms. Similarly, ideally, at least 12 mm of normal vessel must exist distal to the distal extent of the aneurysm for an adequate seal to be achieved. The treatment of Aortic Stenosis through Transcather Aortic Valve Replacement (TAVR) is becoming more common. The limitations of current TAVR techniques do not allow for repositioning of the implant once it has been deployed in place. Further, the final expanded diameter of the current devices is fixed making pre-sizing a critical and difficult step.

Migration of existing endografts has also been a significant clinical problem, potentially causing leakage and profusion of aneurysms and/or compromising necessary vascular supplies to arteries such as the coronary, carotid, subclavian, renal, or internal iliac vessels. This problem only has been addressed partially by some existing endograft designs, in which barbs or hooks have been incorporated to help retain the endograft at its intended site. However, most existing endograft designs are solely dependent on radial force applied by varying length of stent material to secure a seal against the recipient vessel walls.

Because of the limitations imposed by existing vascular endograft devices and endovascular techniques, a significant number of abdominal and thoracic aneurysms repaired in the U.S. are still managed though open vascular surgery, instead of the lower morbidity of the endovascular approach.

Pre-sizing is required currently in all prior art endografts. Such pre-sizing based on CAT-scan measurements is a significant problem. This leads, many times, to mis-sized grafts. In such situations, more graft segments are required to be placed, can require emergency open surgery, and can lead to an unstable seal and/or migration. Currently there exists no endograft that can be fully repositioned after deployment.

Thus, a need exists to overcome the problems with the prior art systems, designs, and processes as discussed above.

SUMMARY OF THE INVENTION

The invention provides surgical implant devices and methods for their manufacture and use that overcome the hereinafore-mentioned disadvantages of the heretofore-known devices and methods of this general type and that provide such features with improvements that increase the ability of such an implant to be precisely positioned and sealed, with better in situ accommodation to the local anatomy of the targeted anatomic site. The invention provides an adjustment tool that can remotely actuate an adjustment member(s) that causes a configuration change of a portion(s) of an implant, which configuration change includes but is not limited to diameter, perimeter, shape, and/or geometry or a combination of these, to create a seal and provide retention of an implant to a specific area of a target vessel or structure even when the cross-sectional configuration of the anatomic space is non-circular, ovoid, or irregular.

The invention provides an actively controllable stent, stent graft, stent graft assembly, heart valve, and heart valve assembly, and methods and systems for controlling and implanting such devices that overcome the hereinafore-mentioned disadvantages of the heretofore-known devices and methods of this general type and that provide such features with control both in opening and closing and in any combination thereof even during a surgical procedure or after completion of a surgical procedure.

One exemplary aspect of the present invention is directed towards novel designs for endovascular implant grafts, and methods for their use for the treatment of aneurysms (e.g., aortic) and other structural vascular defects. An endograft system for placement in an anatomic structure or blood vessel is disclosed in which an endograft implant comprises, for example, a non-elastic tubular implant body with at least an accommodating proximal end. Accommodating, as used herein, is the ability to vary a configuration in one or more ways, which can include elasticity, expansion, contraction, and changes in geometry. Both or either of the proximal and distal ends in an implant according to the present invention further comprise one or more circumferential expandable sealable collars and one or more expandable sealing devices, capable of being expanded upon deployment to achieve the desired seal between the collar and the vessel's inner wall. Exemplary embodiments of such devices can be found in co-pending U.S. patent application Ser. No. 11/888,009, filed Jul. 31, 2007, and Ser. No. 12/822,291, filed Jun. 24, 2010, which applications have been incorporated herein in their entireties. Further embodiments of endovascular implants and delivery systems and methods according to the present invention may be provided with retractable retention tines or other retention devices allowing an implant to be repositioned before final deployment. In other embodiments, the implant can be repositioned after final deployment. An endograft system according to the present invention further comprises a delivery catheter with an operable tubular sheath capable of housing a folded or compressed endograft implant prior to deployment and capable of retracting or otherwise opening in at least its proximal end to allow implant deployment. The sheath is sized and configured to allow its placement via a peripheral arteriotomy site, and is of appropriate length to allow its advancement into, for example, the aortic valve annulus, ascending aorta, aortic arch, and thoracic or abdominal aorta, as required for a specific application. Sheath movement is provided in a novel manner by manual actuation and/or automatic actuation.

While some post-implantation remodeling of the aortic neck proximal to an endovascular graft (endograft) has been reported, existing endograft technology does not allow for the management of this condition without placement of an additional endograft sleeve to cover the remodeled segment. Exemplary prostheses of the present invention as described herein allow for better accommodation by the implant of the local anatomy, using an actively controlled expansion device for the sealing interface between the prosthesis collar and the recipient vessel's inner wall. Furthermore, exemplary prostheses of the present invention as disclosed herein are provided with a controllably releasable disconnect mechanism that allows remote removal of an adjustment tool and locking of the retained sealable mechanism after satisfactory positioning and sealing of the endograft. In some exemplary embodiments according to the present invention, the controllably releasable disconnect mechanism may be provided in a manner that allows post-implantation re-docking of an adjustment member to permit post-implantation repositioning and/or resealing of a prostheses subsequent to its initial deployment.

Certain aspects of the present invention are directed towards novel designs for sealable endovascular implant grafts and endovascular implants, and methods for their use for the treatment of aortic aneurysms and other structural vascular defects and/or for heart valve replacements. Various embodiments as contemplated within the present invention may include any combination of exemplary elements as disclosed herein or in the co-pending patent applications referenced above.

In an exemplary embodiment according to the present invention, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath that may be openable or removable at the internal end and a main implant delivery catheter lumen containing within a compressed or folded endovascular implant. Further, an endovascular implant comprises a non-elastic tubular implant body with an accommodating proximal end terminating in a proximal sealable circumferential collar that may be expanded by the operator to achieve a fluid-tight seal between the proximal sealable circumferential collar and the internal walls of the blood vessel proximal to the vascular defect. Moreover, an endovascular implant may further comprise a non-elastic tubular implant body with an accommodating distal end terminating in a distal sealable circumferential collar controlled by a distal variable sealing device, which may be expanded by the operator to achieve a fluid-tight seal between the distal sealable circumferential collar and the internal walls of the blood vessel distal to the vascular defect.

In a further exemplary embodiment according to the present invention, an implant interface is provided for a sealable attachment of an implant to a wall within the lumen of a blood vessel or other anatomic conduit.

In a yet further exemplary embodiment according to the present invention, an implant gasket interface is provided for a sealable attachment of an implant to a wall within the lumen of a blood vessel or other anatomic conduit, wherein the sealable attachment provides for auto-adjustment of the seal while maintaining wall attachment to accommodate post-implantation wall remodeling.

Still other exemplary embodiments of endografts and endograft delivery systems according to the present invention serve as universal endograft cuffs, being first placed to offer their advantageous anatomic accommodation capabilities, and then serving as a recipient vessel for other endografts, including conventional endografts.

Furthermore, exemplary embodiments of endografts and endograft delivery systems according to the present invention may be provided with a mechanism to permit transfer of torque or other energy from a remote operator to an adjustment member comprising a sealable, adjustable circumferential assembly controlled by an adjustment tool, which may be detachable therefrom and may further cause the assembly to lock upon detachment of the tool. In some exemplary embodiments of the present invention, the variable sealing device may be provided with a re-docking element that may be recaptured by subsequent operator interaction, allowing redocking and repositioning and/or resealing of the endograft at a time after its initial deployment.

Moreover, the various exemplary embodiments of the present invention as disclosed herein may constitute complete endograft systems, or they may be used as components of a universal endograft system as disclosed in co-pending patent applications that may allow the benefits of the present invention to be combined with the ability to receive other endografts.

Additionally, the present invention encompasses sealable devices that may be used in other medical devices such as adjustable vascular cannulas or other medical or surgical devices or implants, such as heart valves.

With the foregoing and other objects in view, there is provided, in accordance with the invention, a method for implanting a stent includes contracting a self-expanding/forcibly-expanding stent of a shape-memory material set to a given shape to a reduced implantation size with a delivery system having drive wires. The stent has a selectively adjustable assembly with adjustable elements operatively connected to the drive wires such that, when the adjustable elements are adjusted by the drive wires, a configuration change in at least a portion of the self-expanding stent occurs. The contracted stent is inserted into a native annulus in which the stent is to be implanted. The drive wires are rotated with the delivery system to forcibly expand the stent into the native annulus. While rotating the drive wires, a torque applied to the drive wires is determined with the delivery system. Rotation of the drive wires is stopped based upon a value of the determined torque.

With the objects of the invention in view, there is also provided a method for implanting a stent includes contracting a stent to a reduced implantation size with a delivery system having drive wires. The stent has a selectively adjustable assembly with adjustable elements operatively connected to the drive wires such that, when the adjustable elements are adjusted by the drive wires, a configuration change in at least a portion of the stent occurs. The contracted stent is inserted into a native annulus in which the stent is to be implanted. The drive wires are rotated with the delivery system to forcibly expand the stent into the native annulus. While rotating the drive wires, a torque applied to the drive wires is determined with the delivery system. Rotation of the drive wires is stopped based upon a value of the determined torque.

With the objects of the invention in view, there is also provided a method for implanting a stent includes contracting a stent to a reduced implantation size with a delivery system having drive wires. The stent has a selectively adjustable assembly with adjustable elements operatively connected to the drive wires such that, when the adjustable elements are adjusted by the drive wires, a configuration change in at least a portion of the stent occurs. The contracted stent is inserted into a native annulus in which the stent is to be implanted. The drive wires are move with the delivery system to forcibly expand the stent into the native annulus. While moving the drive wires, a torque applied to the drive wires is determined with the delivery system. Movement of the drive wires is stopped based upon a value of the determined torque.

In accordance with another mode of the invention, a user is provided with a dynamic value of the torque and permitting the user to change the expansion and contraction of the stent.

In accordance with a further mode of the invention, the stent is disconnected from the delivery system to implant the stent in the native annulus.

In accordance with an added mode of the invention, the delivery system has at least one drive wire motor connected to the drive wires for rotating the drive wires and the stopping step is carried out by measuring a current required to drive the at least one drive wire motor and stopping the at least one drive wire motor and thereby the rotation of the drive wires based upon a value of the current.

In accordance with an additional mode of the invention, an outward radial force imposed by the expanding stent lattice on the native annulus is calculated with the value of the current and the at least one drive wire motor and thereby the rotation of the drive wires is stopped based upon a value of the calculated outward radial force.

In accordance with a concomitant mode of the invention, the delivery system has at least one drive wire motor connected to the drive wires for rotating the drive wires and the stopping step is carried out by determining an outward radial force imposed by the expanding stent lattice based upon a current required to drive the at least one drive wire motor and stopping the at least one drive wire motor and thereby the rotation of the drive wires based upon a value of the a value of the calculated outward radial force.

Although the invention is illustrated and described herein as embodied in an actively controllable stent, stent graft, stent graft assembly, heart valve, and heart valve assembly, and methods and systems for controlling and implanting such devices, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which:

FIG. 8 is a fragmentary, perspective view of the stent deployment system of FIG. 6;

FIG. 9 is a fragmentary, perspective view of the stent deployment system of FIG. 1 from above the distal end with the system in an expanded state and with the assembly-fixed needles in an extended state;

FIG. 10 is a fragmentary, longitudinal cross-sectional view of the stent deployment system of FIG. 9 showing the rear half in a partially expanded state of the stent lattice;

FIG. 11 is a fragmentary, longitudinal cross-sectional view of the stent deployment system of FIG. 10 showing the front half in a further expanded state;

FIG. 21 is a fragmentary, side elevational view from an outer side of an alternative exemplary embodiment of a jack assembly according to the invention in a stent-contracted state with a drive sub-assembly in a connected state and with a needle sub-assembly in a retracted state;

FIG. 22 is a fragmentary, cross-sectional view of the jack assembly of FIG. 21;

FIG. 23 is a fragmentary, cross-sectional view of the jack assembly of FIG. 21 in a partially stent-expanded state;

FIG. 30 is a fragmentary, cross-sectional view of another alternative exemplary embodiment of a jack assembly according to the invention in a stent-contracted state with a drive sub-assembly in a connected state and with a needle sub-assembly in a retracted state;

FIG. 31 is a fragmentary, cross-sectional view of the jack assembly of FIG. 30 in a partially stent-expanded state;

FIG. 32 is a fragmentary, cross-sectional view of the jack assembly of FIG. 31 with the needle sub-assembly in an actuated state with extension of the needle;

FIG. 33 is a fragmentary, cross-sectional view of the jack assembly of FIG. 32 with the drive sub-assembly in a disconnected state and the needle sub-assembly in a disconnected state;

FIG. 61 is a side perspective view of the stent system portion of FIG. 58 in a partially expanded state;

FIG. 62 is a top plan view of the stent system portion of FIG. 61;

FIG. 63 is a side elevational view of the stent system portion of FIG. 61;

FIG. 66 is a fragmentary, perspective view of a delivery system according to the invention for the aortic valve assembly of FIG. 64 with the aortic valve assembly in the process of being implanted and in the right iliac artery;

FIG. 67 is a fragmentary, perspective view of the delivery system and aortic valve assembly of FIG. 66 with the aortic valve assembly in the process of being implanted and in the abdominal aorta;

FIG. 68 is a fragmentary, perspective view of the delivery system and aortic valve assembly of FIG. 66 with the aortic valve assembly in the process of being implanted and being adjacent the aortic valve implantation site;

FIG. 69 is a fragmentary, perspective view of the delivery system and aortic valve assembly of FIG. 66 with the aortic valve assembly implanted in the heart;

FIG. 105 is a fragmentary, front elevational and partially cross-sectional view of a self-contained, self-powered, actively controllable stent graft delivery and integral control system according to the invention with the prosthesis in an expanded state with the graft material in cross-section showing a rear half thereof;

FIG. 106 is a perspective view of the control portion of the system of FIG. 105 as a wireless sub-system;

FIG. 107 is a fragmentary, front elevational view of another exemplary embodiment of a self-contained, self-powered, actively controllable stent graft delivery and separate tethered control system according to the invention with different controls and with the prosthesis in an expanded state;

Figure 120:
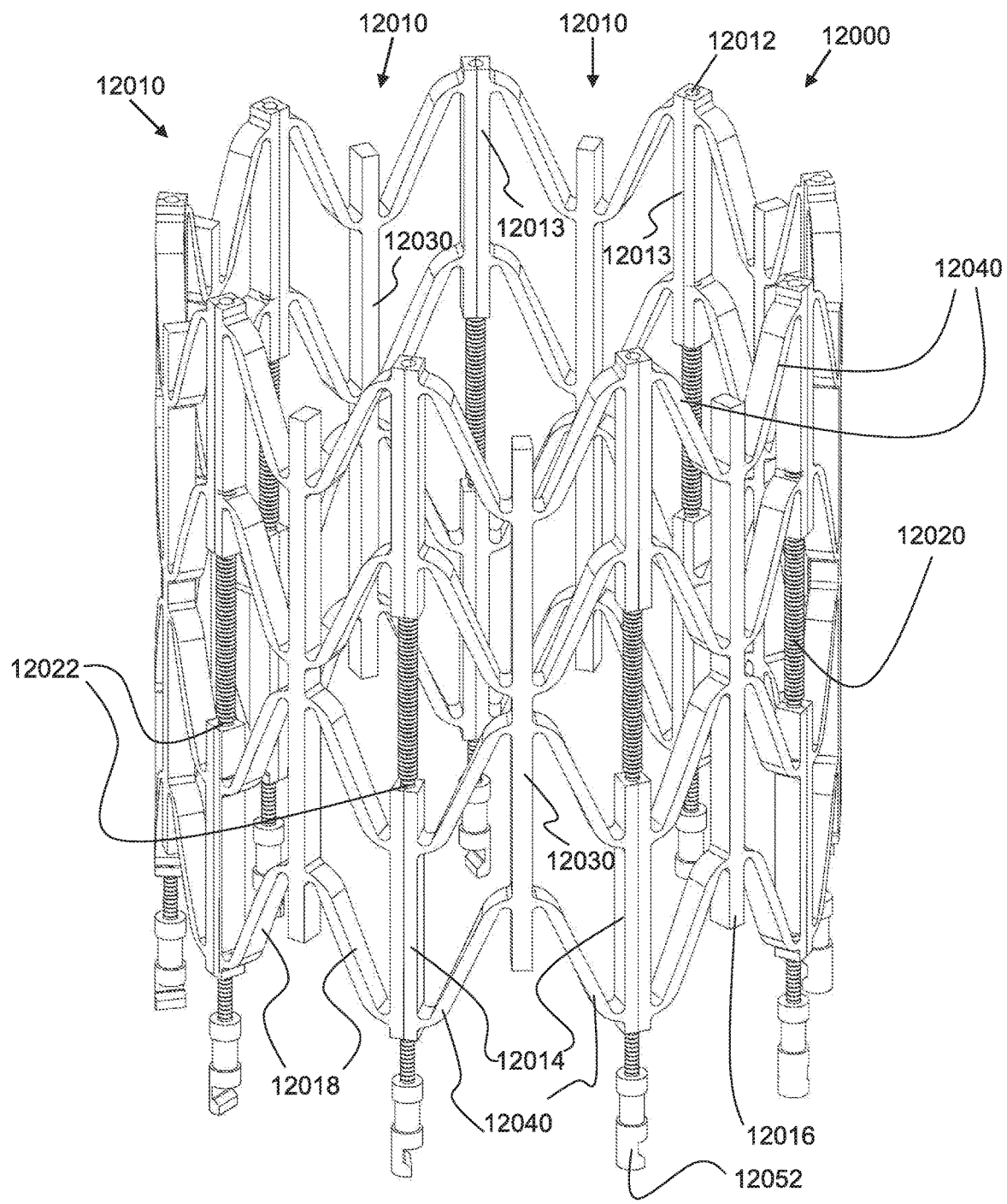
Figure 121:
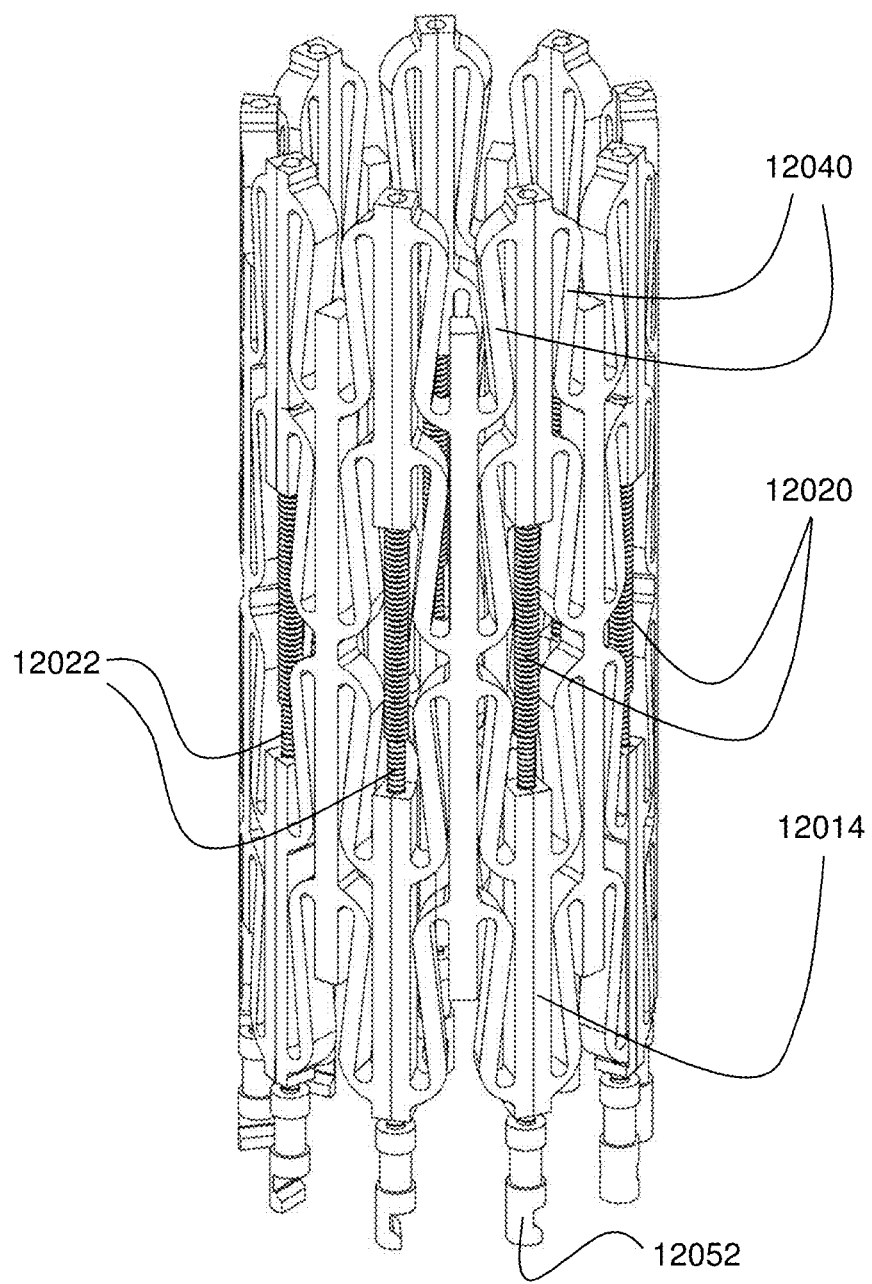
Figure 122:
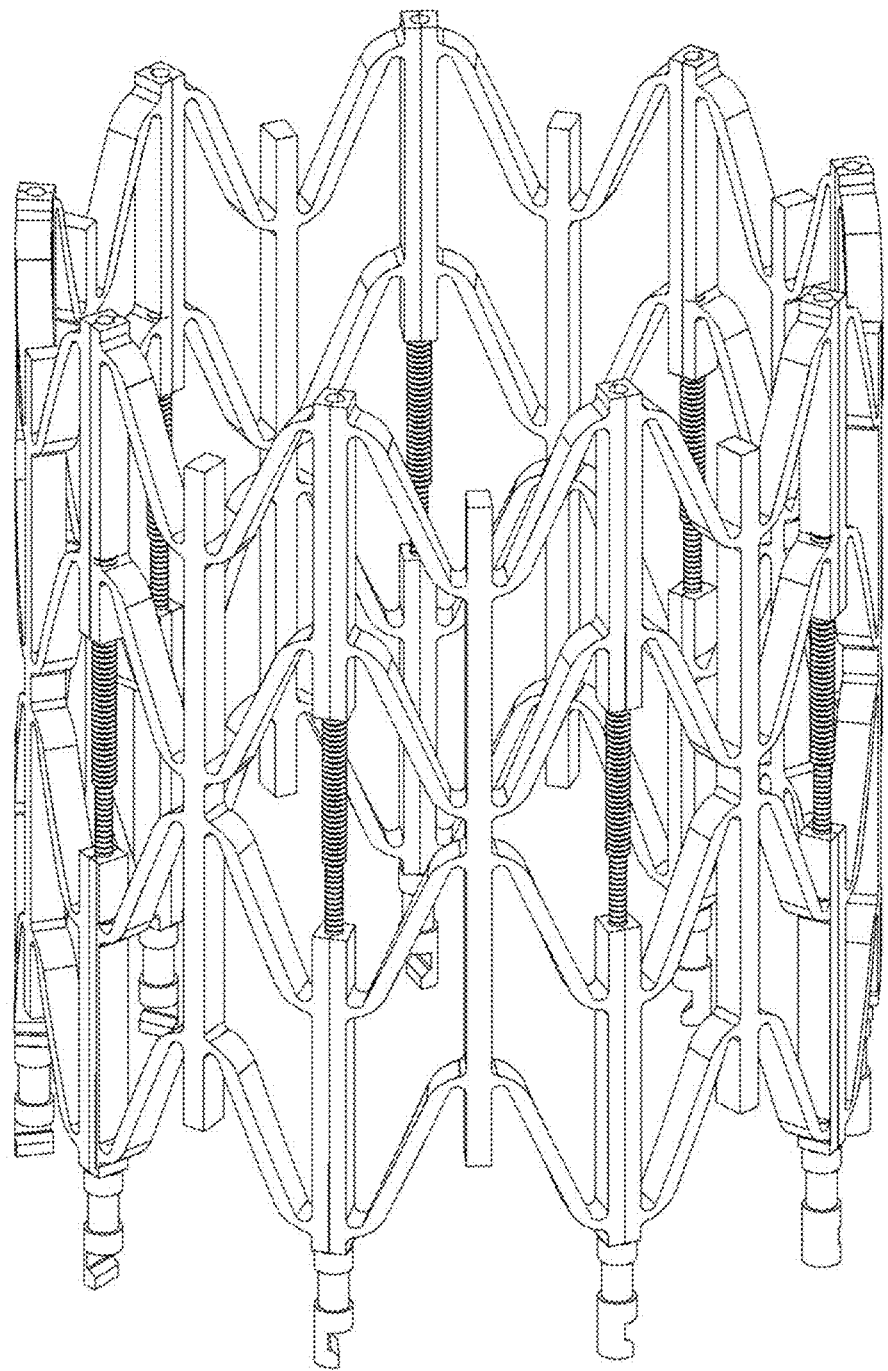
Figure 123:
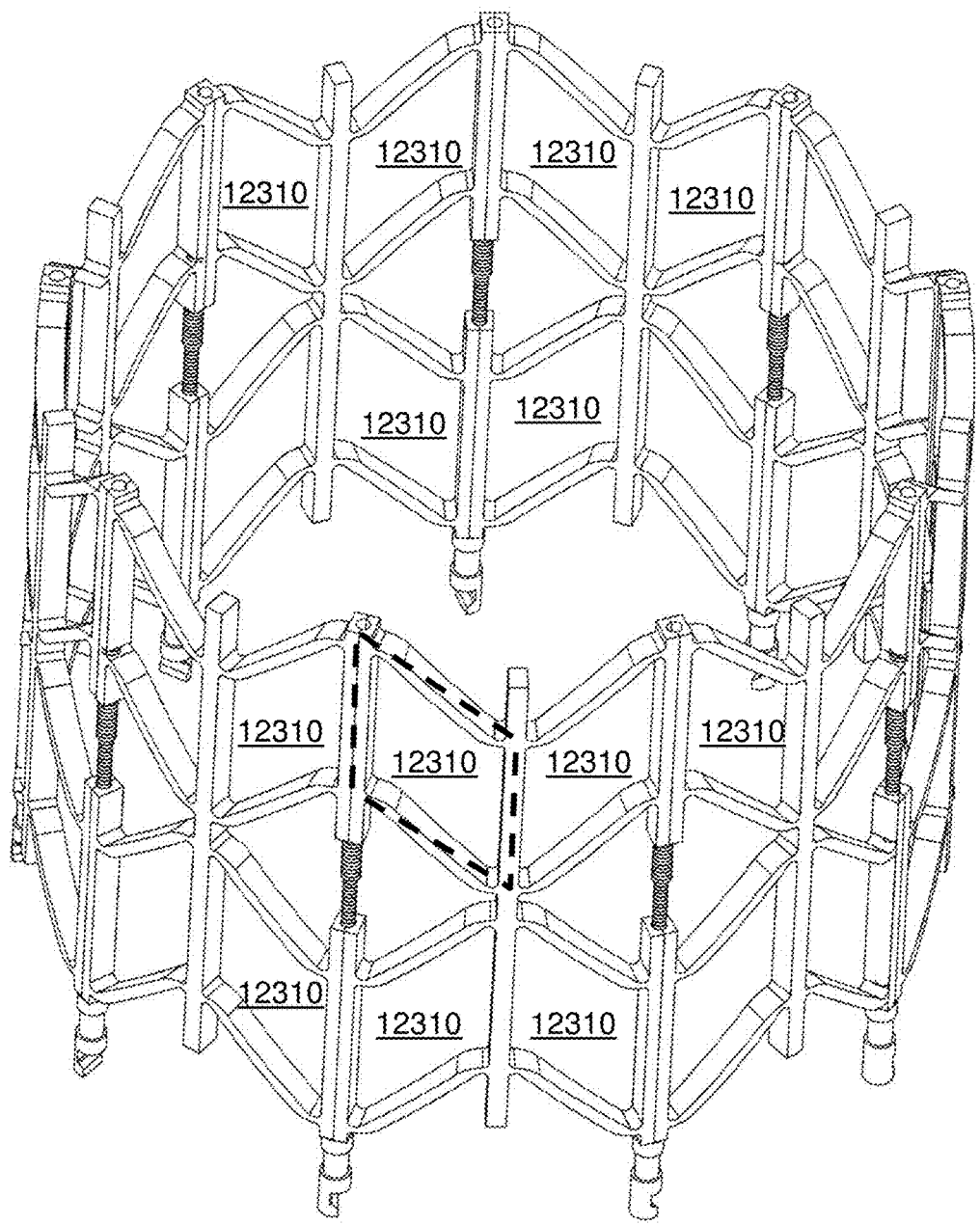
Figure 124:
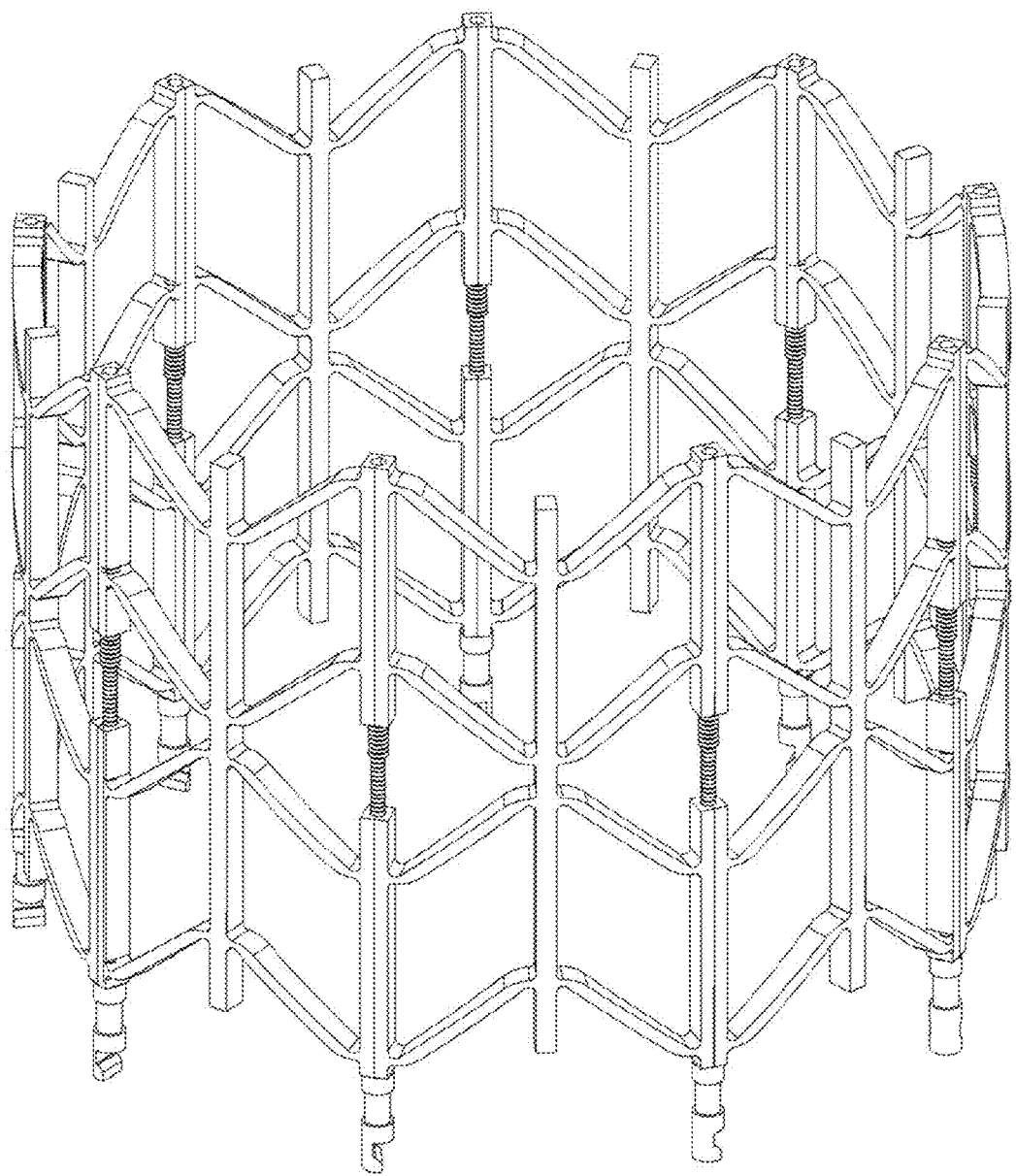
Figure 125:
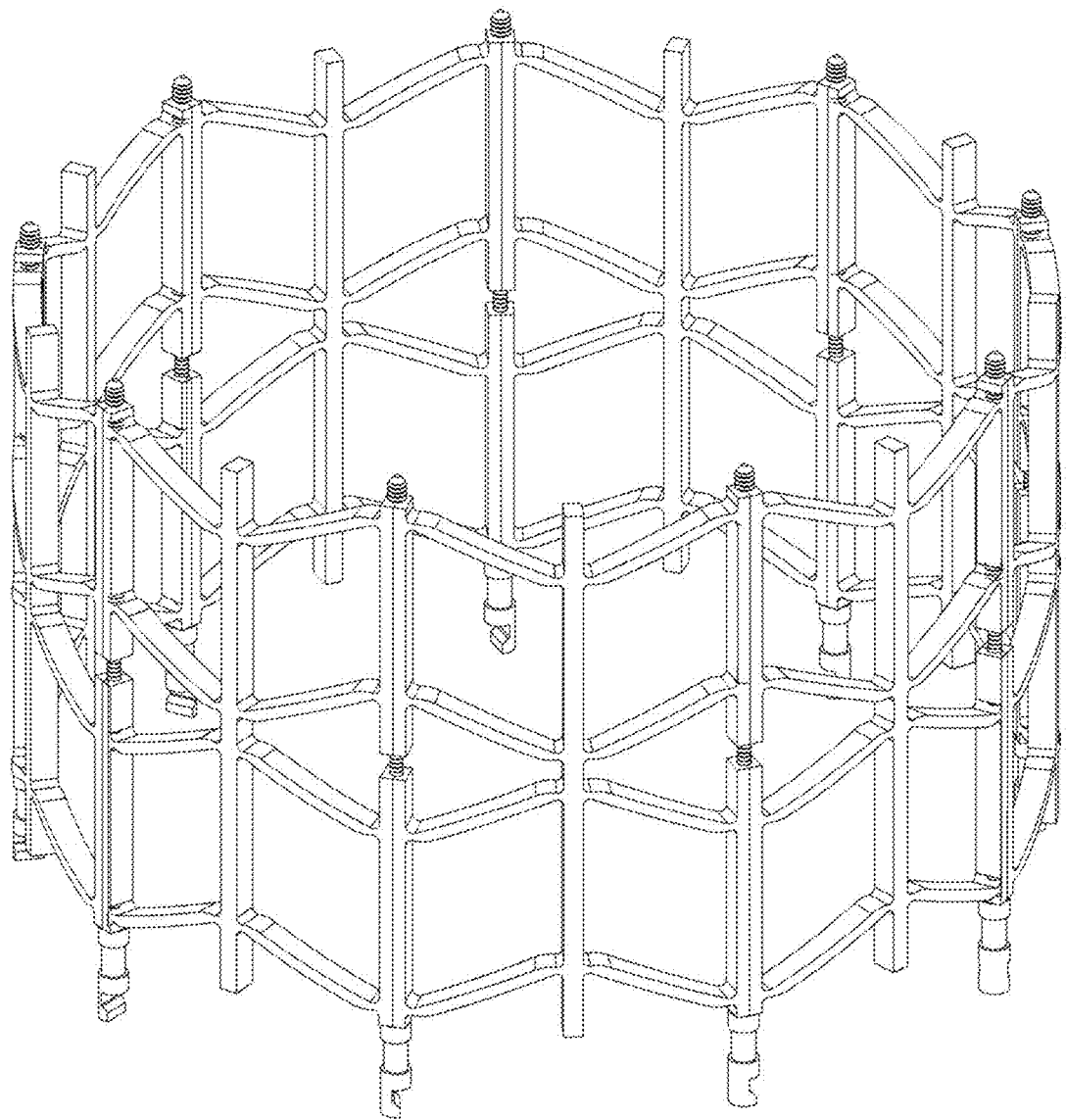
Figure 126:
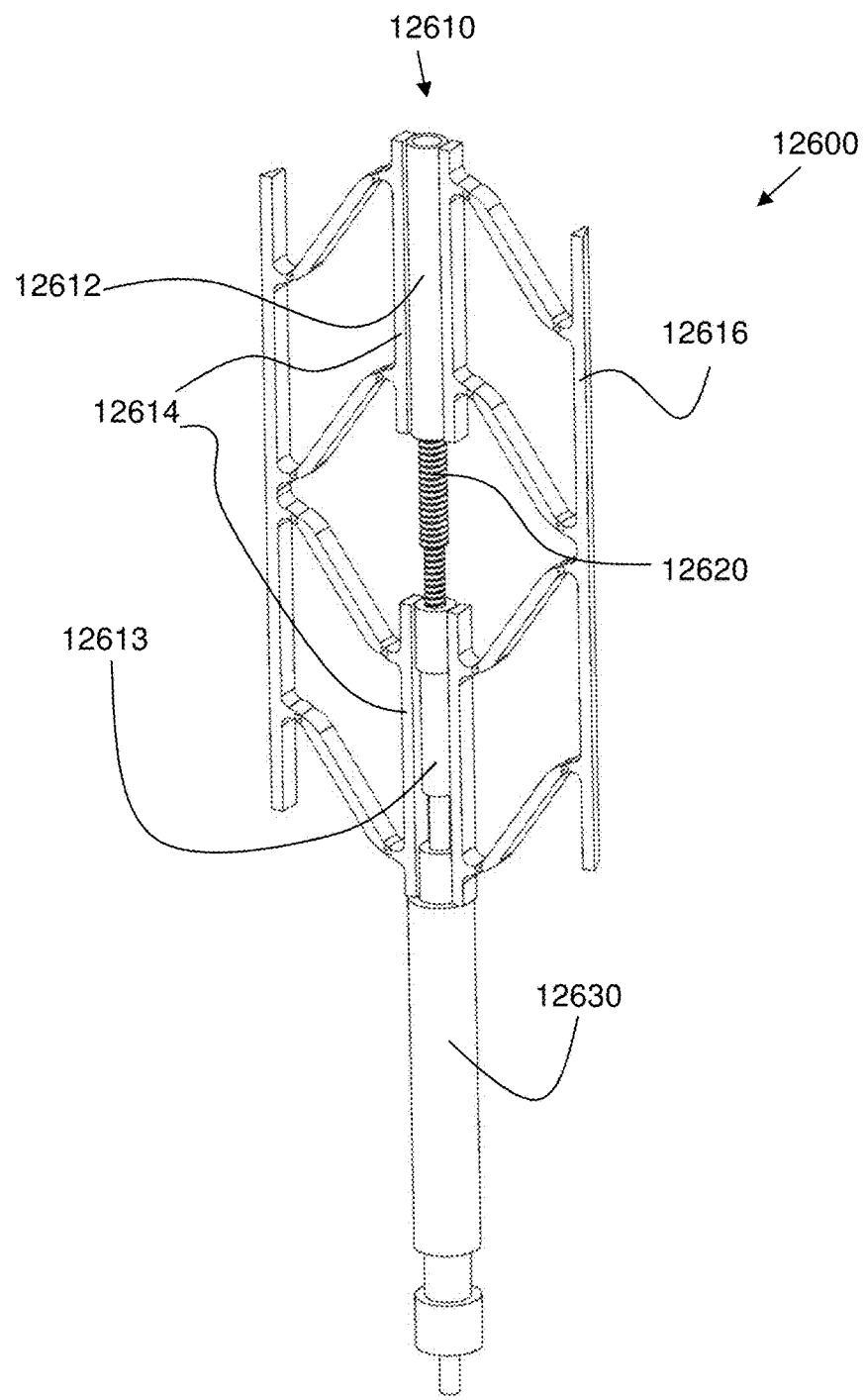
Figure 127:
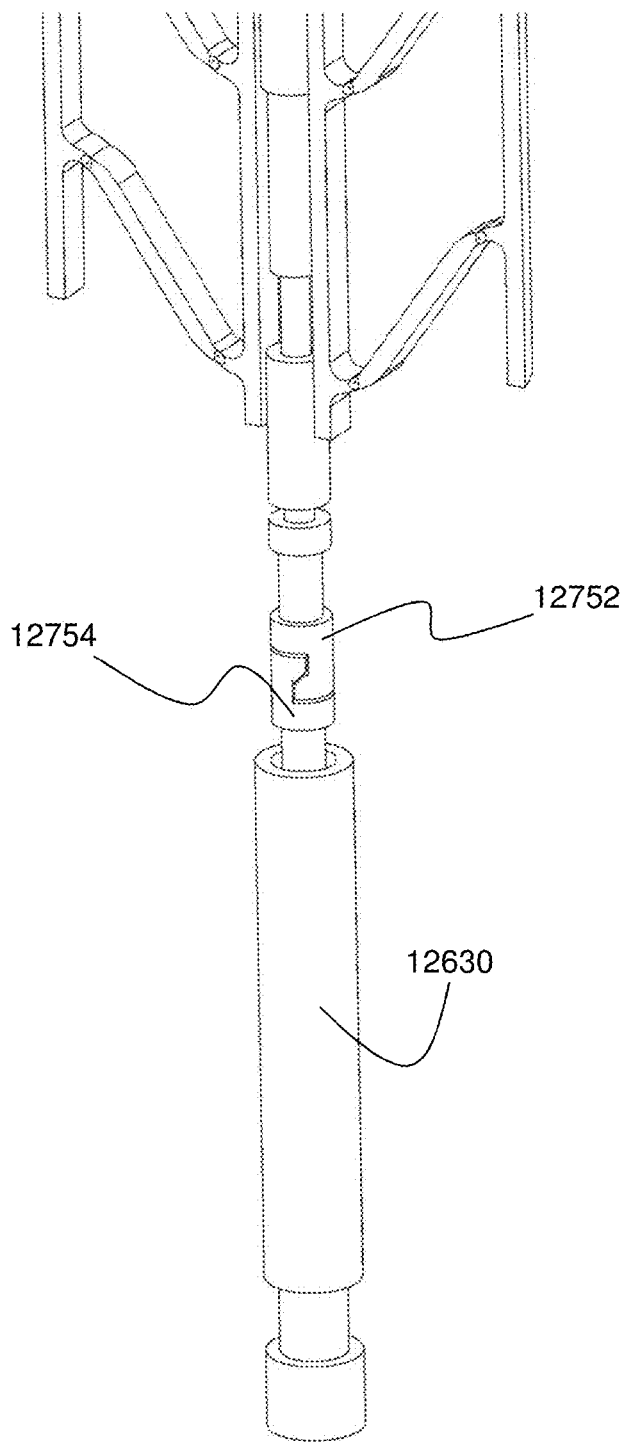
Figure 128:
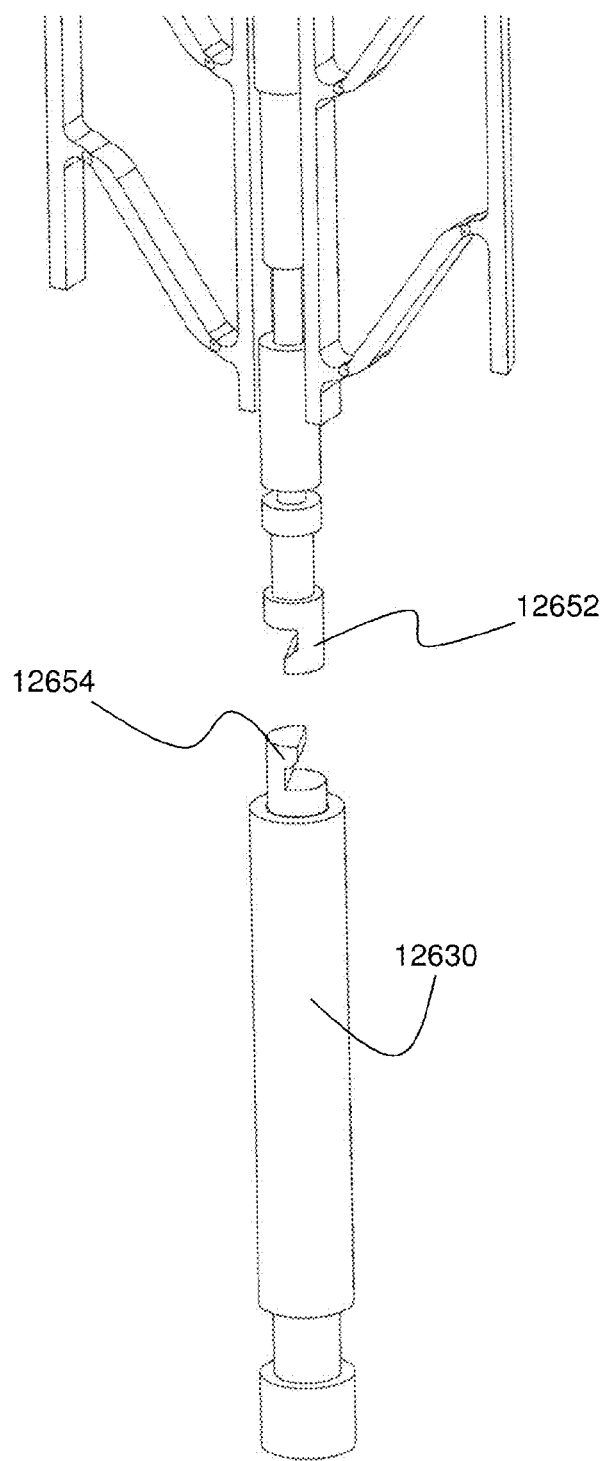
Figure 129:
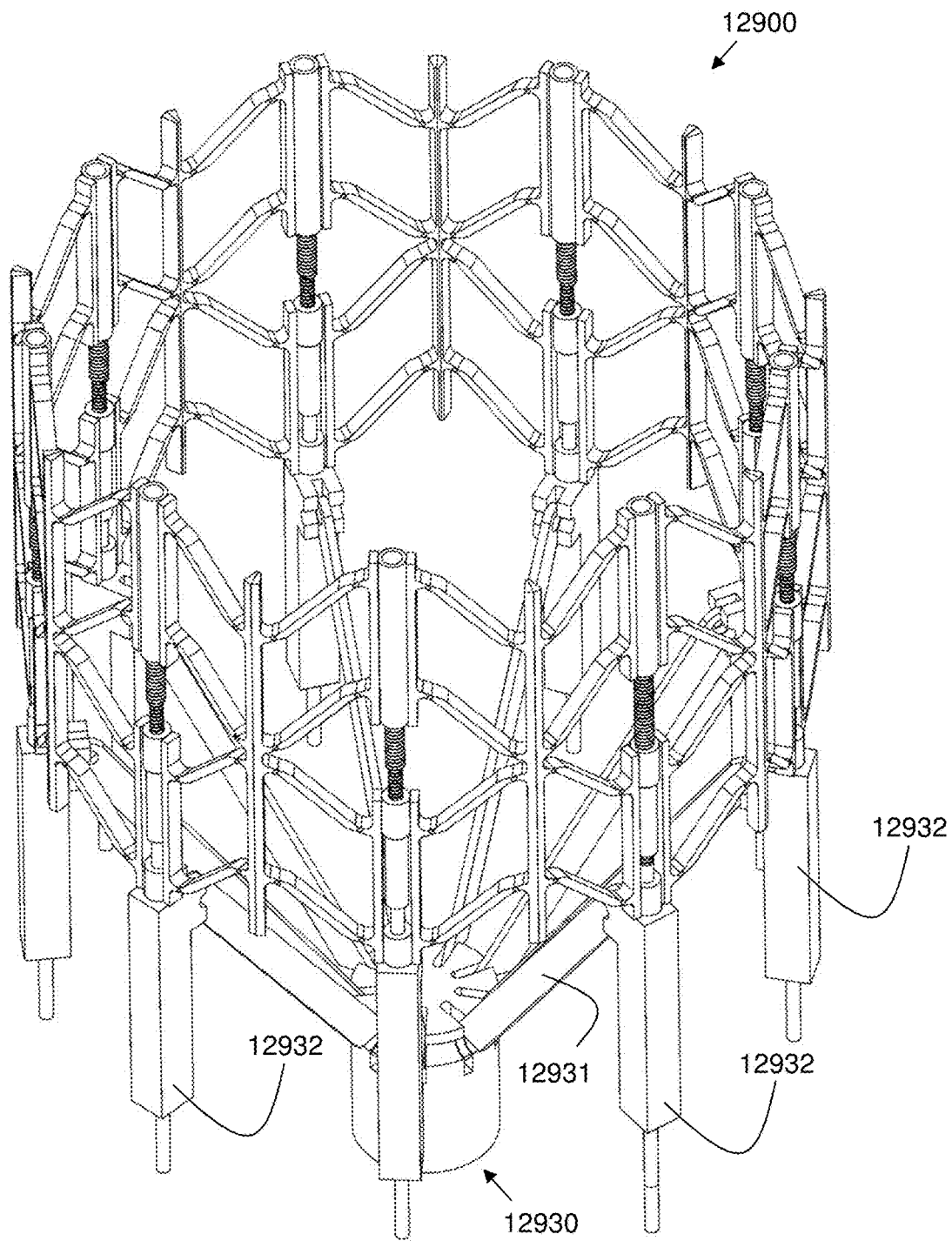
Figure 130:
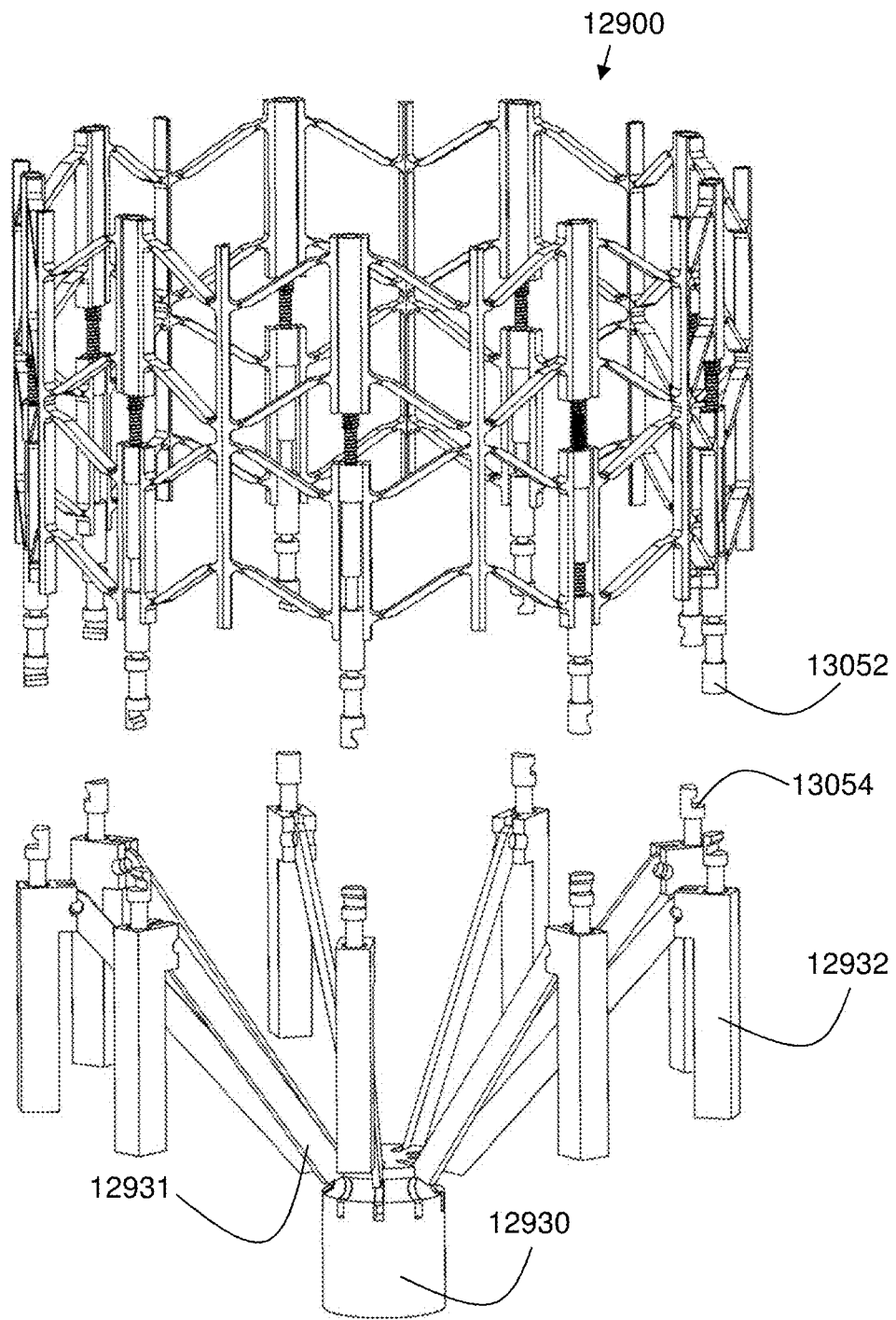
Figure 131:
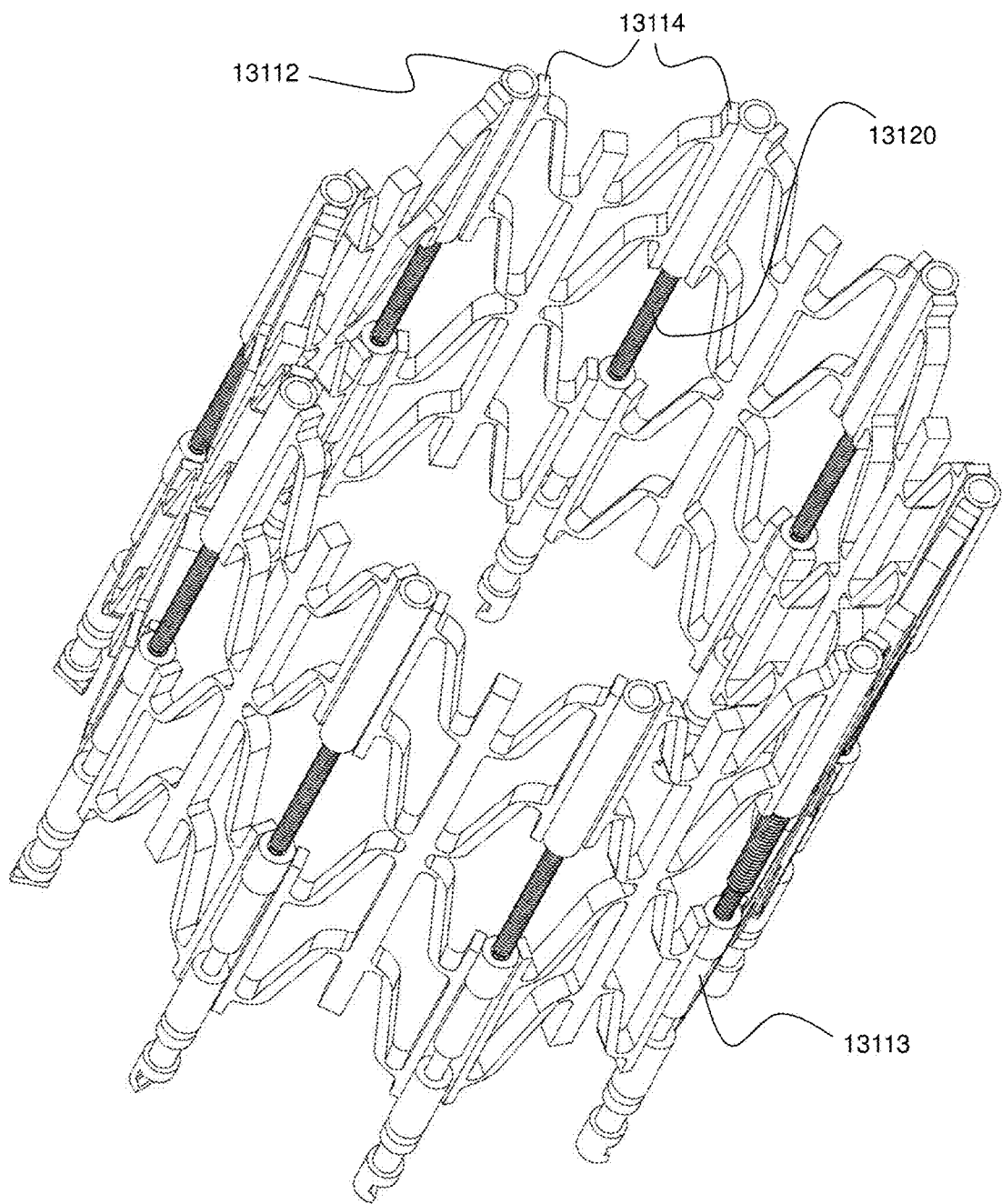
Figure 132:
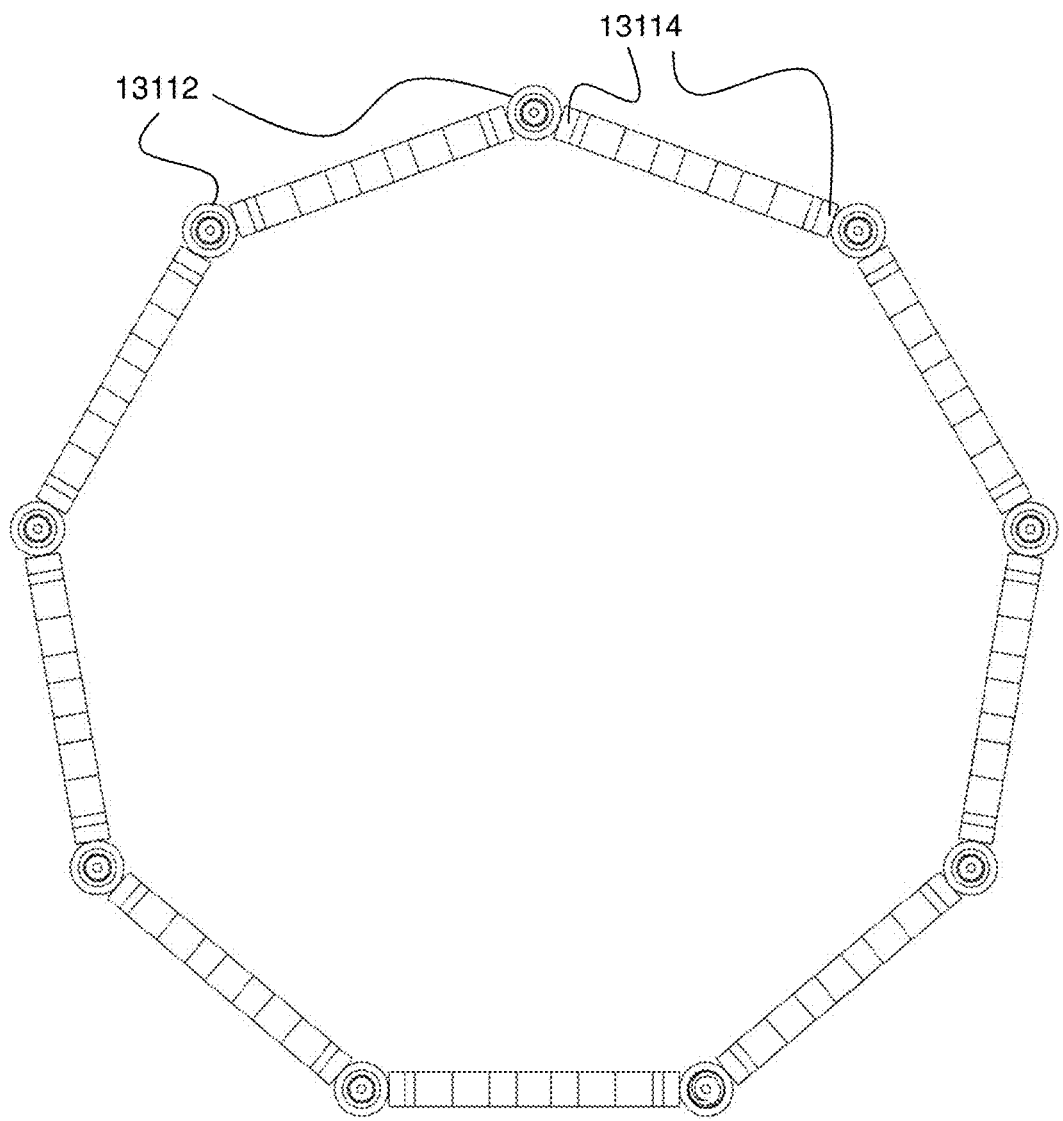
Figure 133:
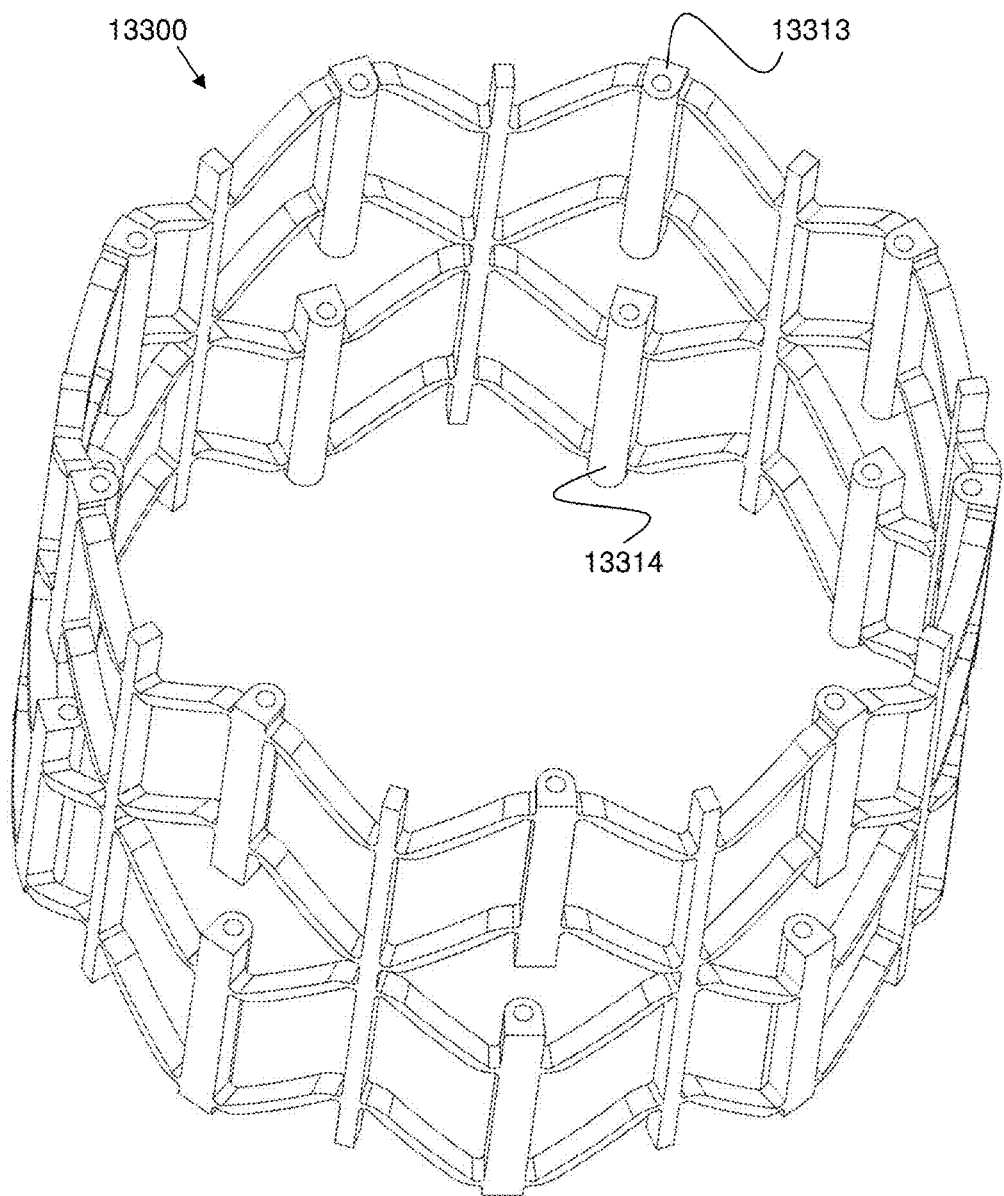
Figure 134:
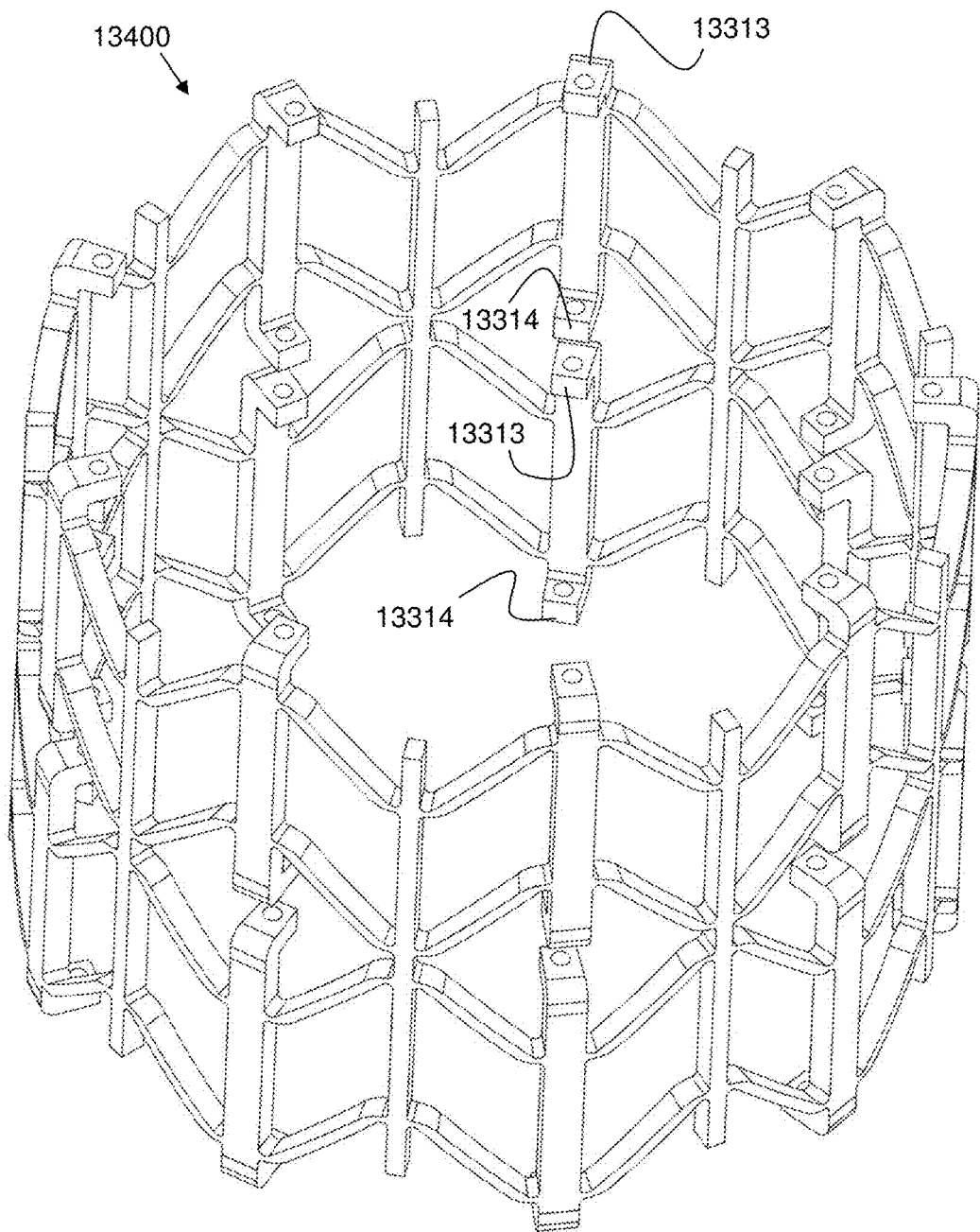
Figure 135:
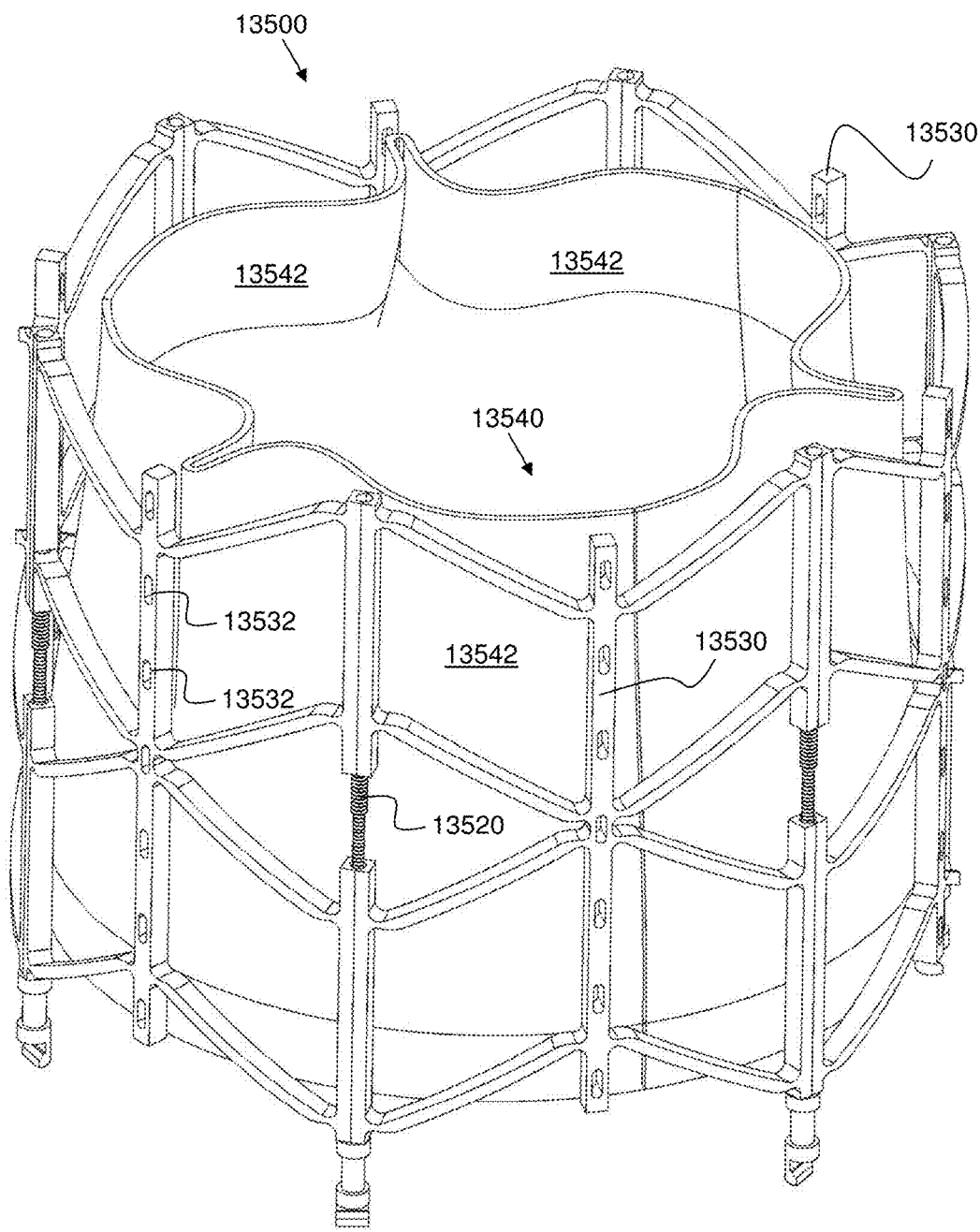
Figure 136:
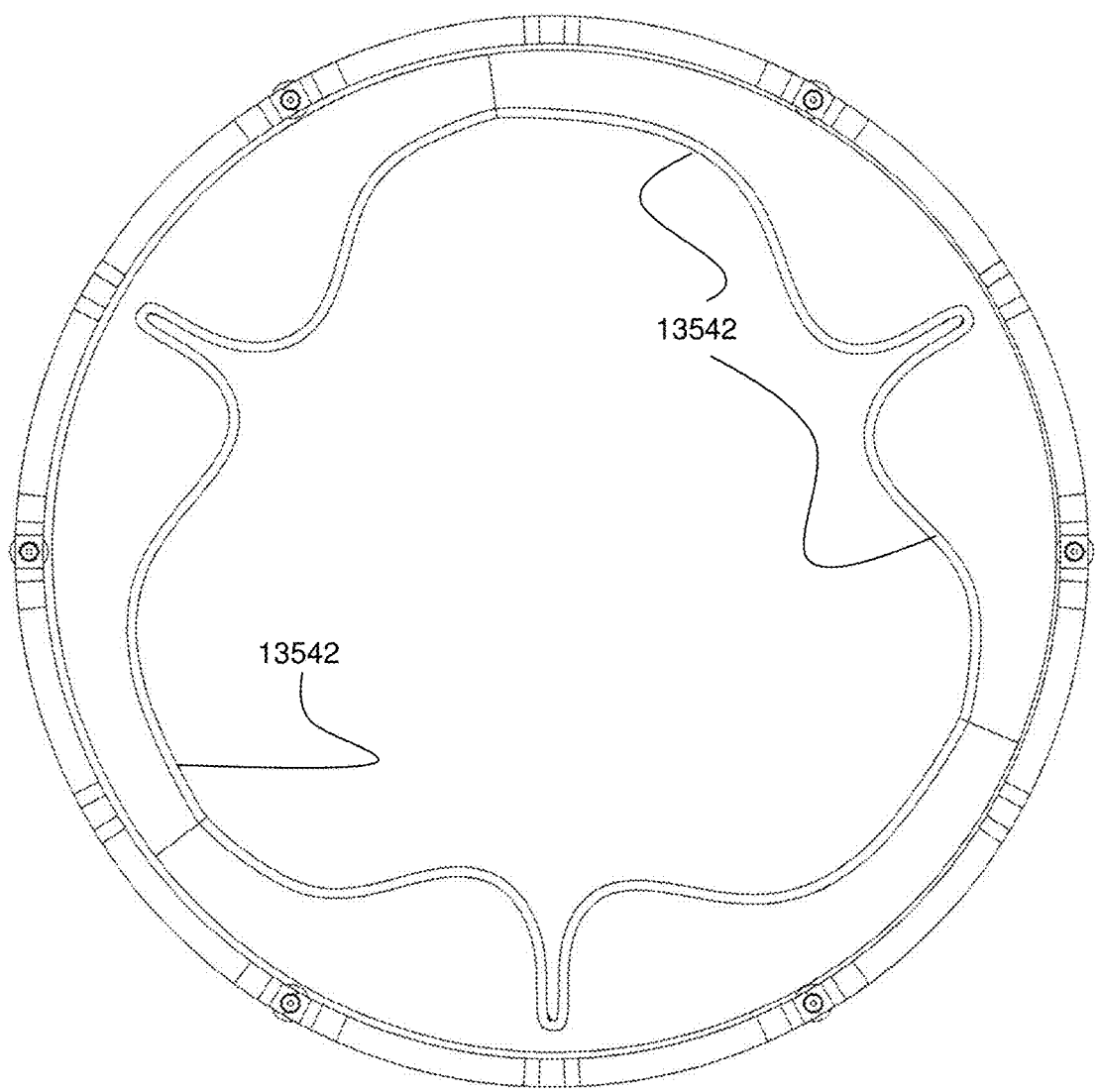
Figure 137:
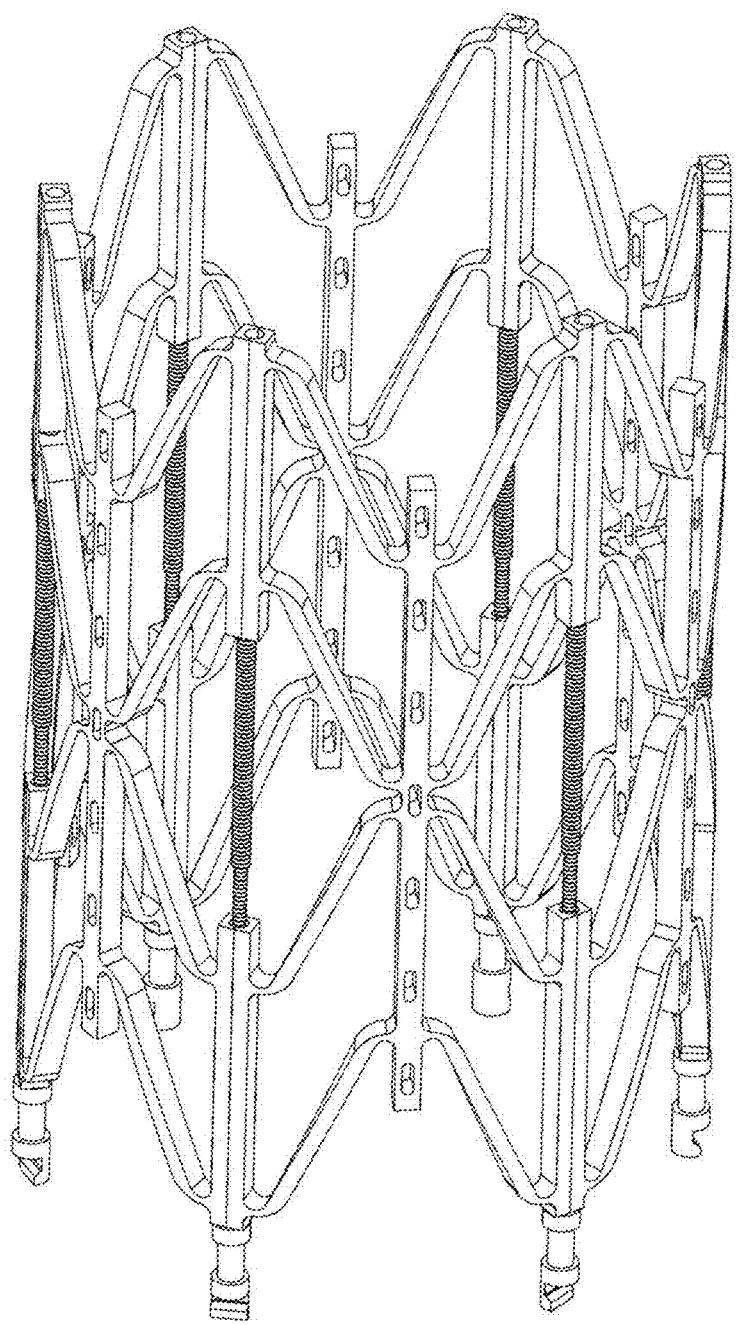
Figure 138:
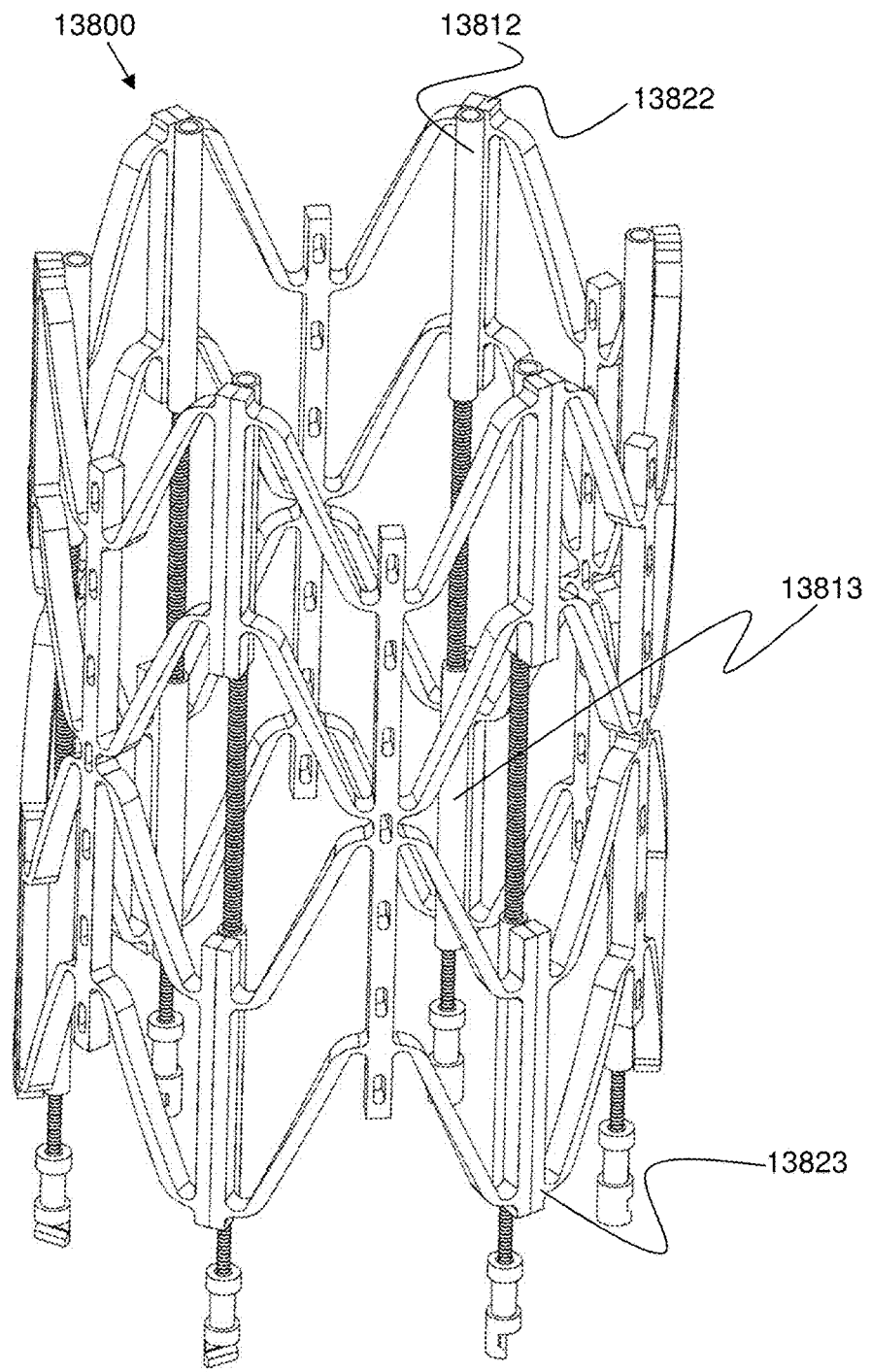
Figure 139:
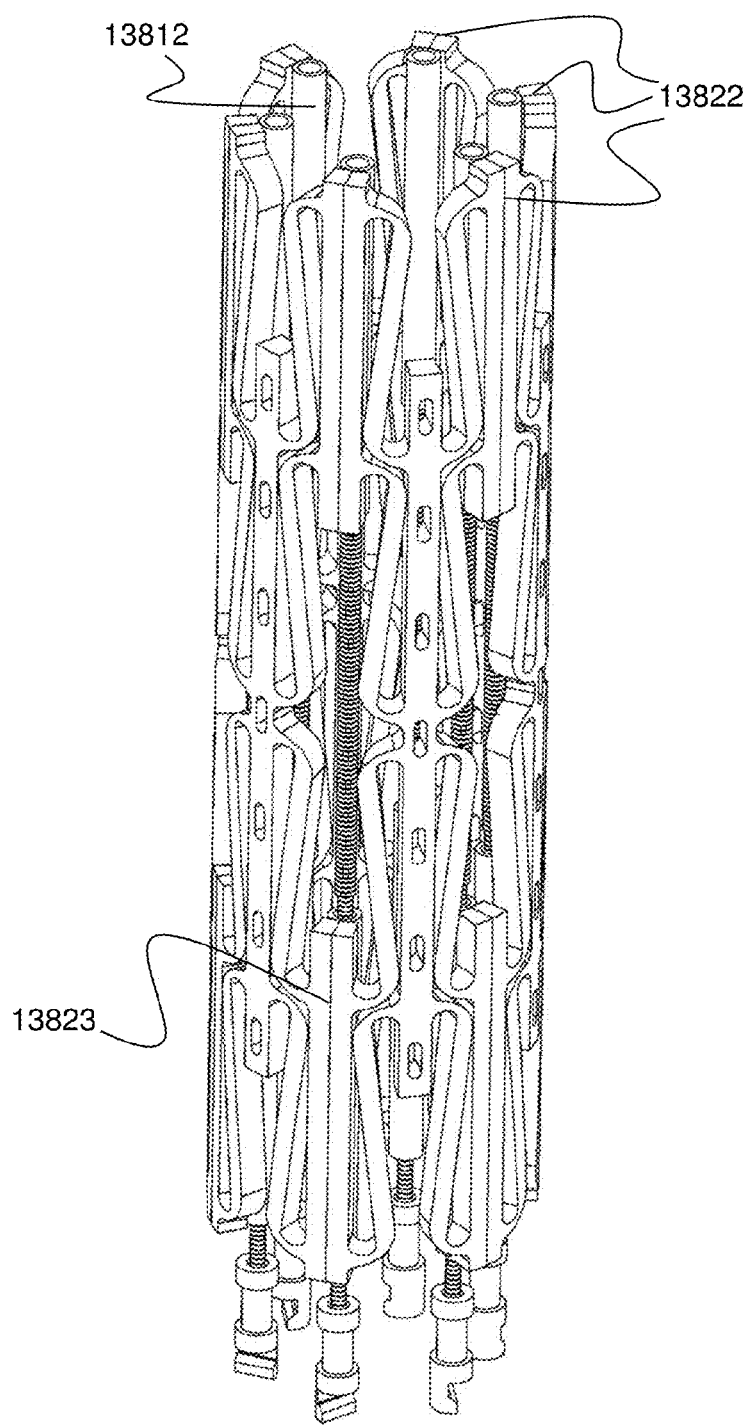
Figure 140:
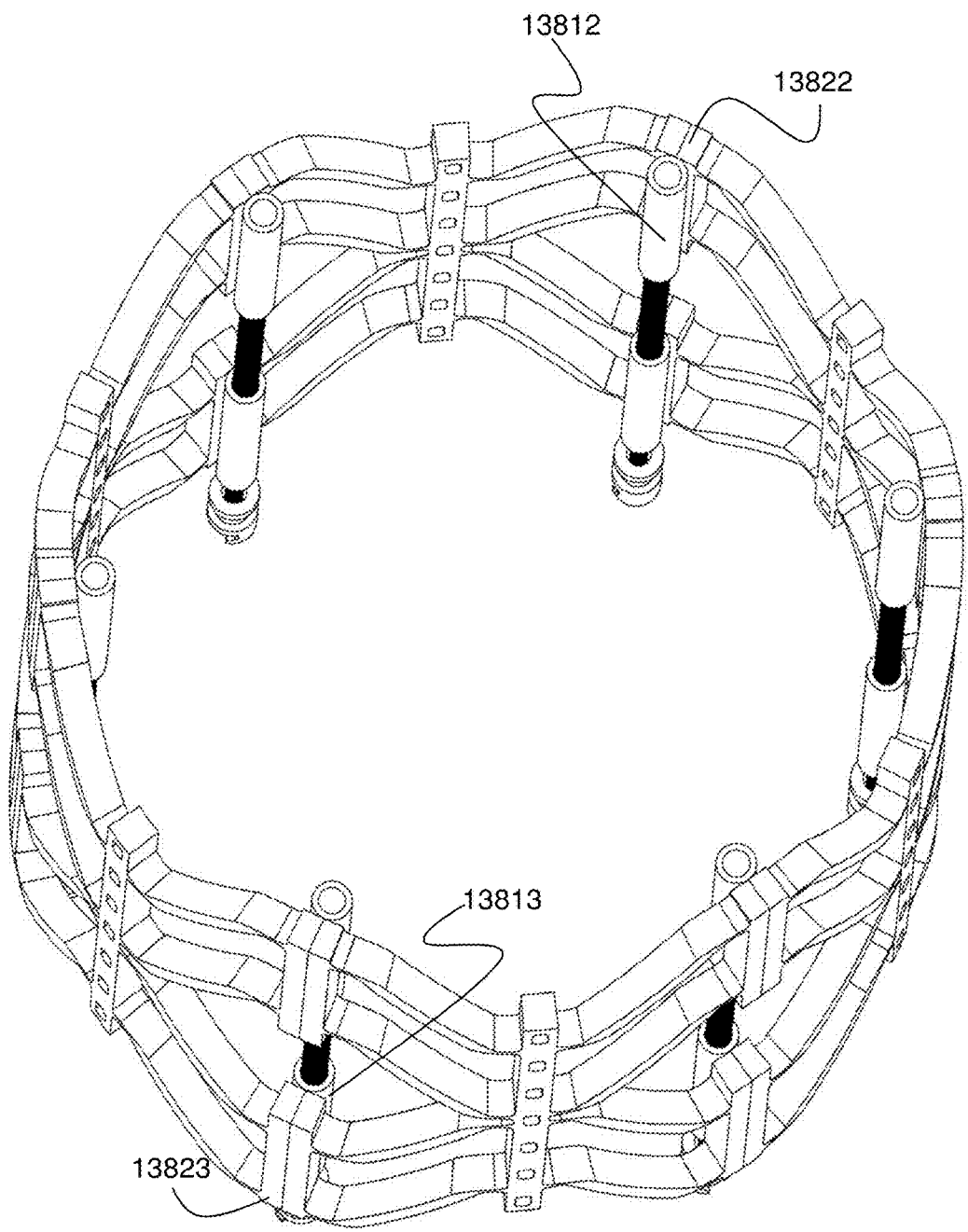
Figure 141:
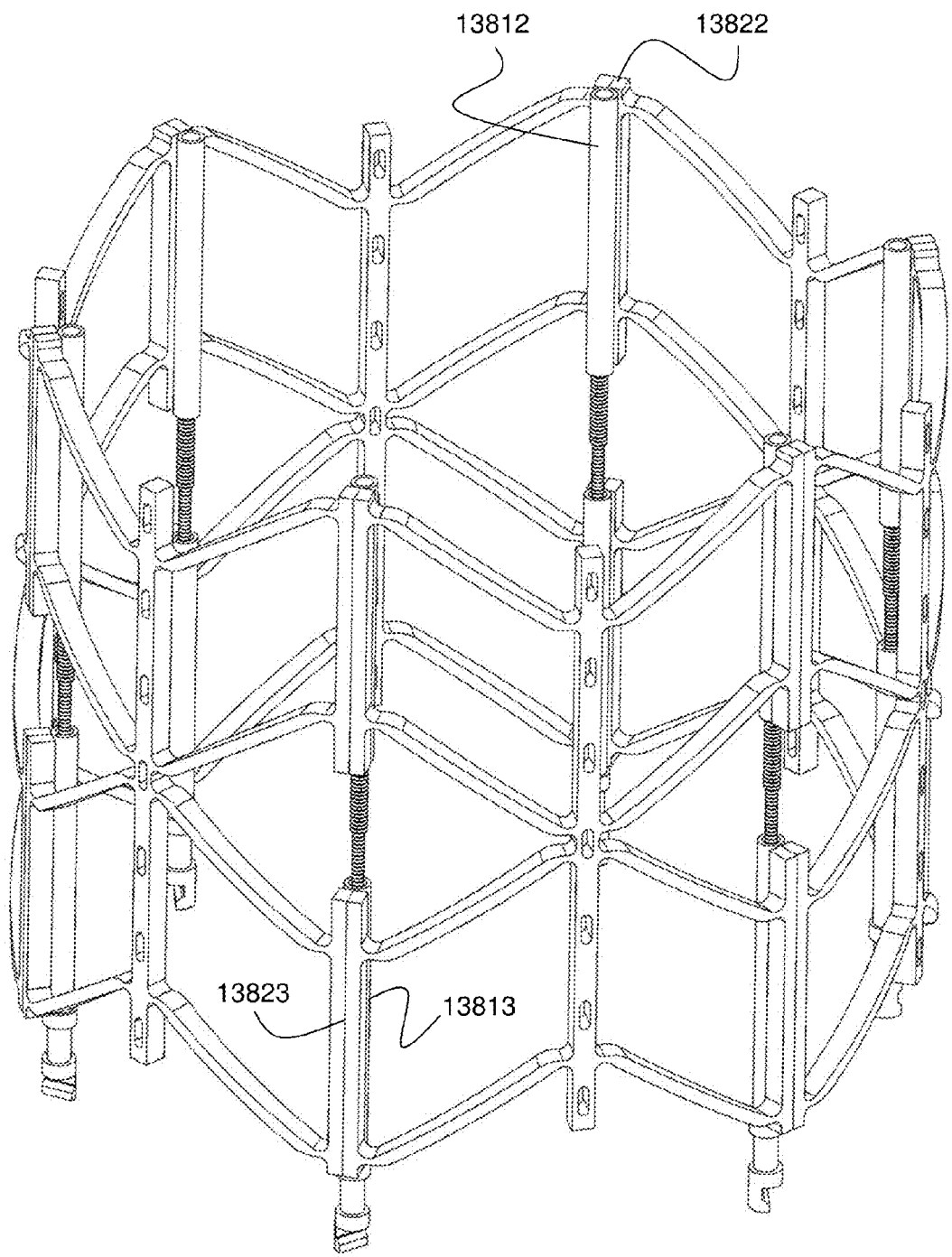
Figure 142:
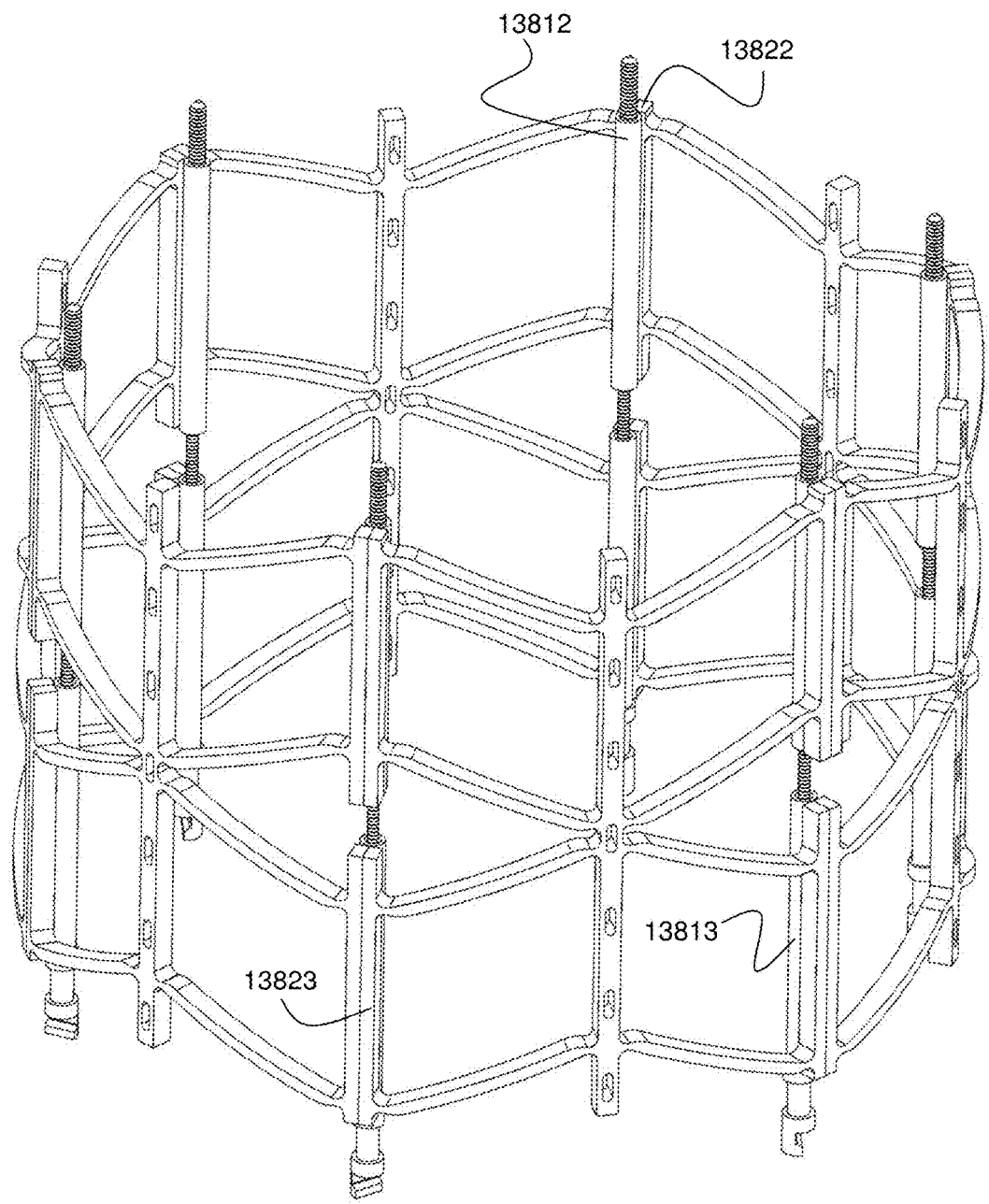
Figure 143:
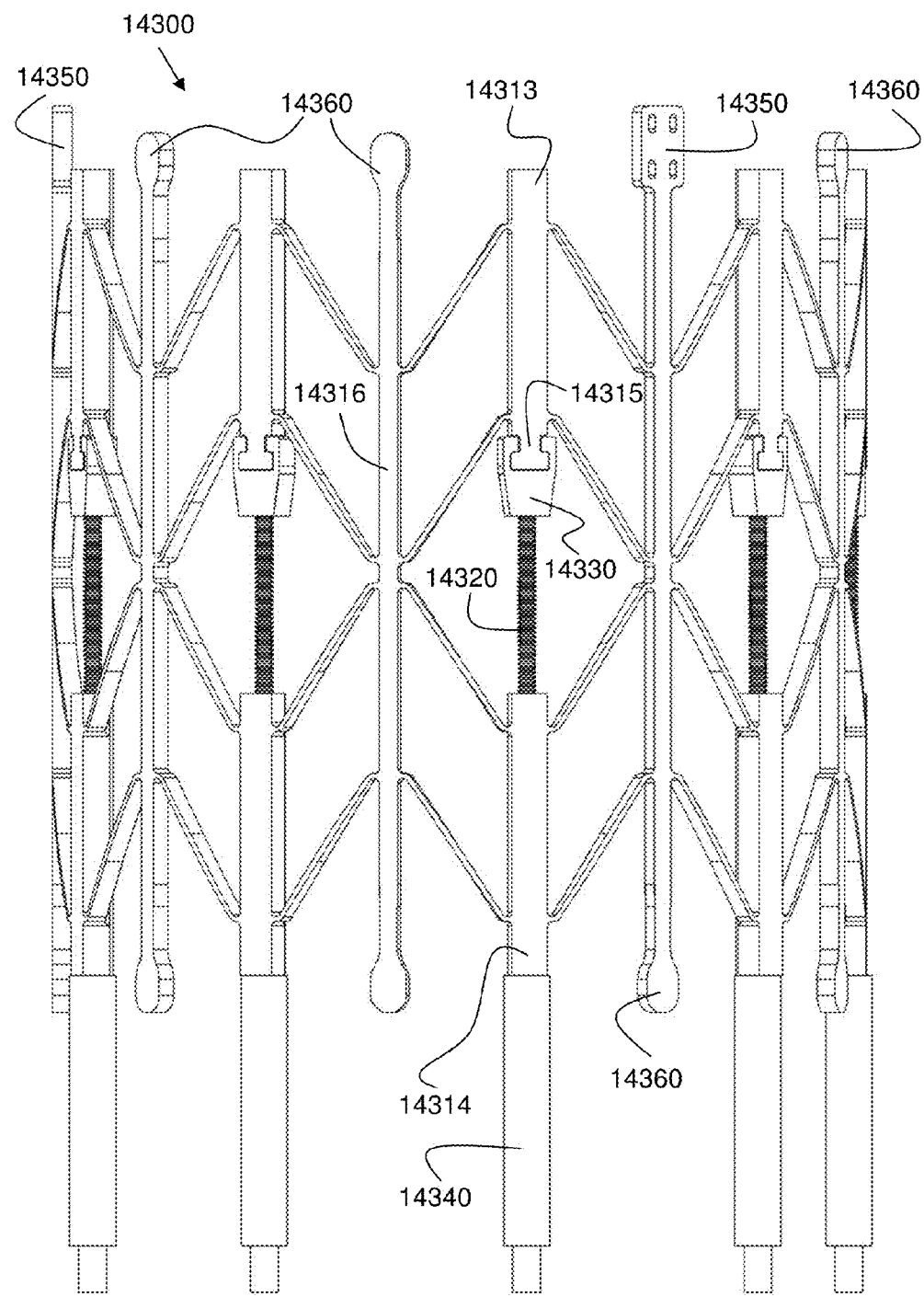
Figure 144:
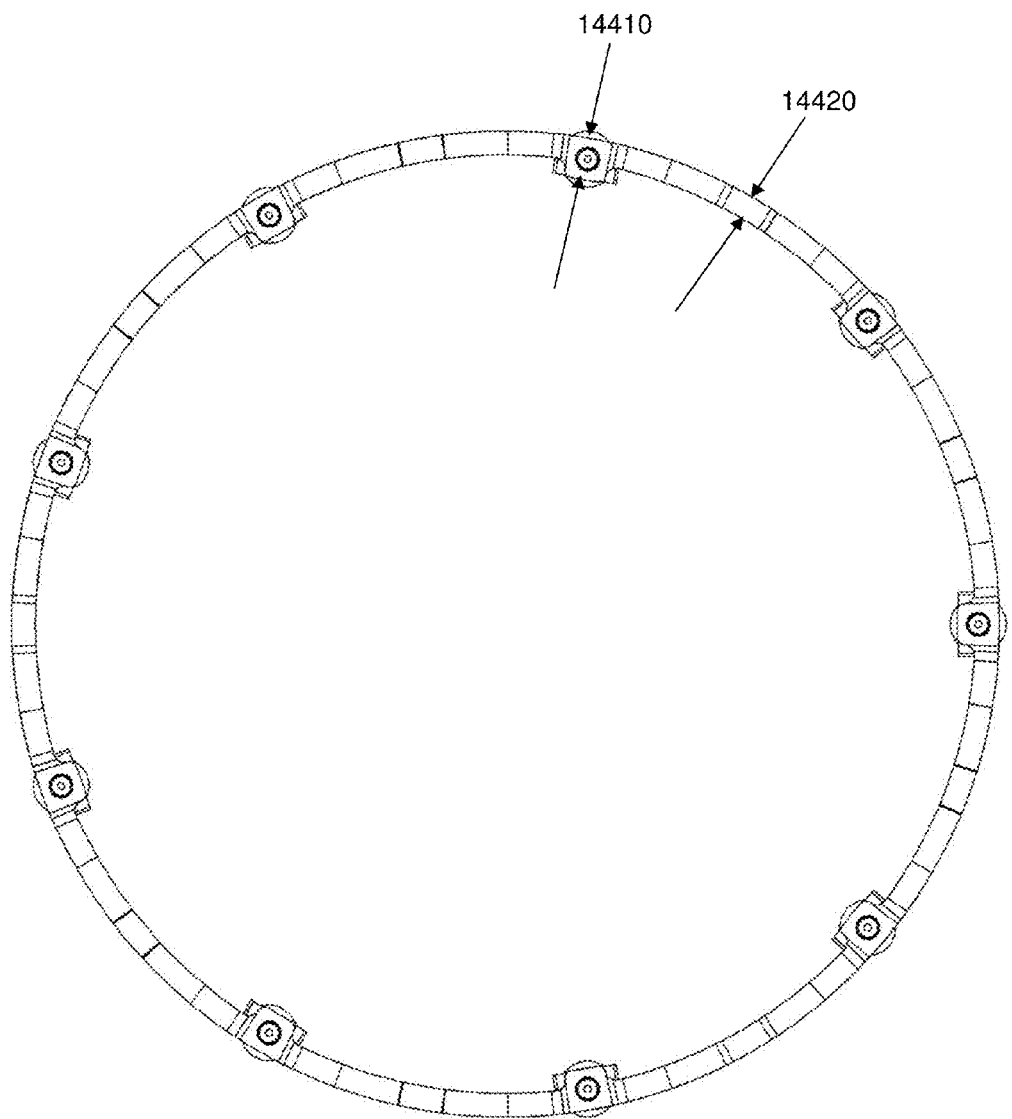
Figure 145:
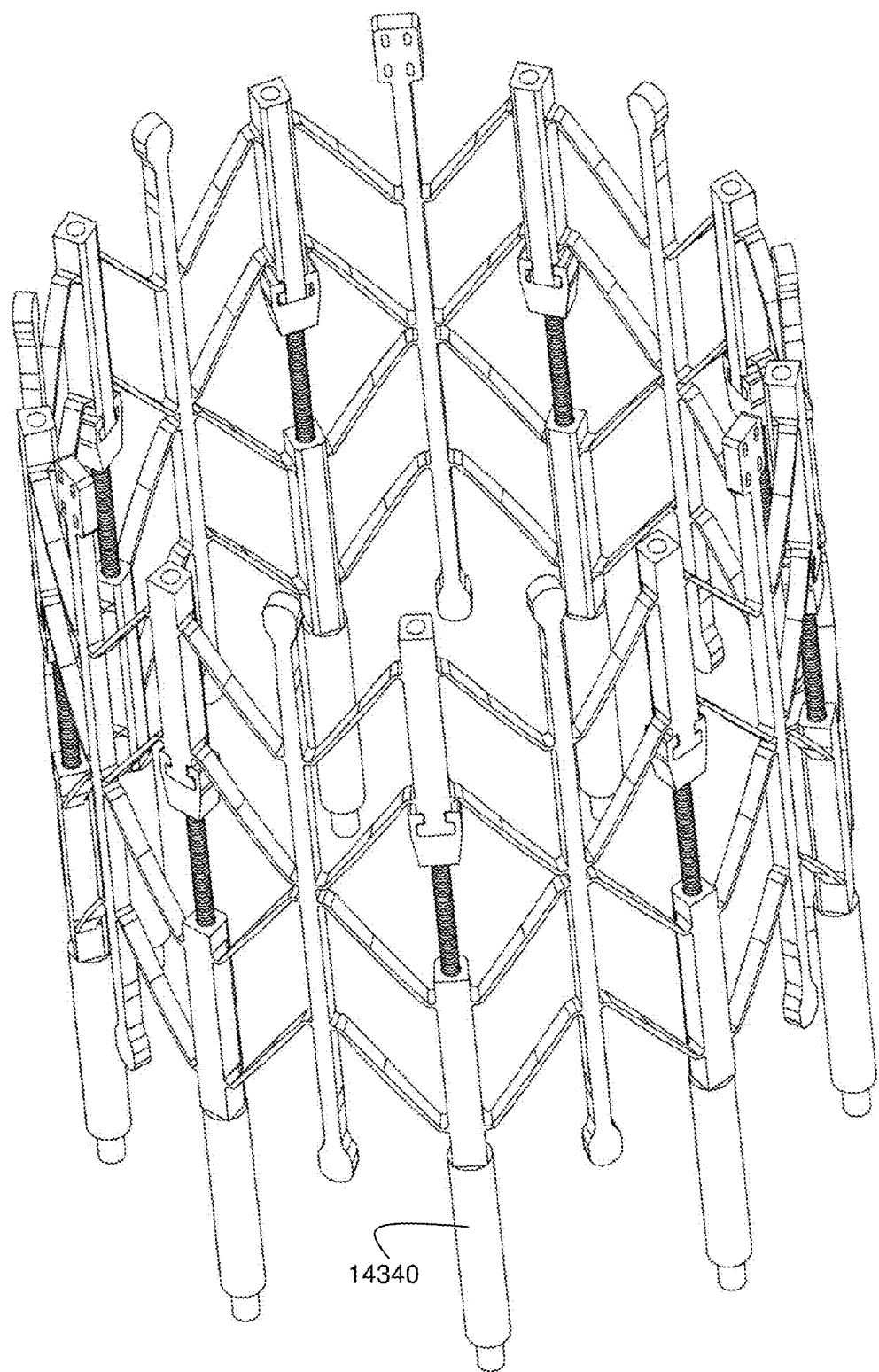
Figure 146:
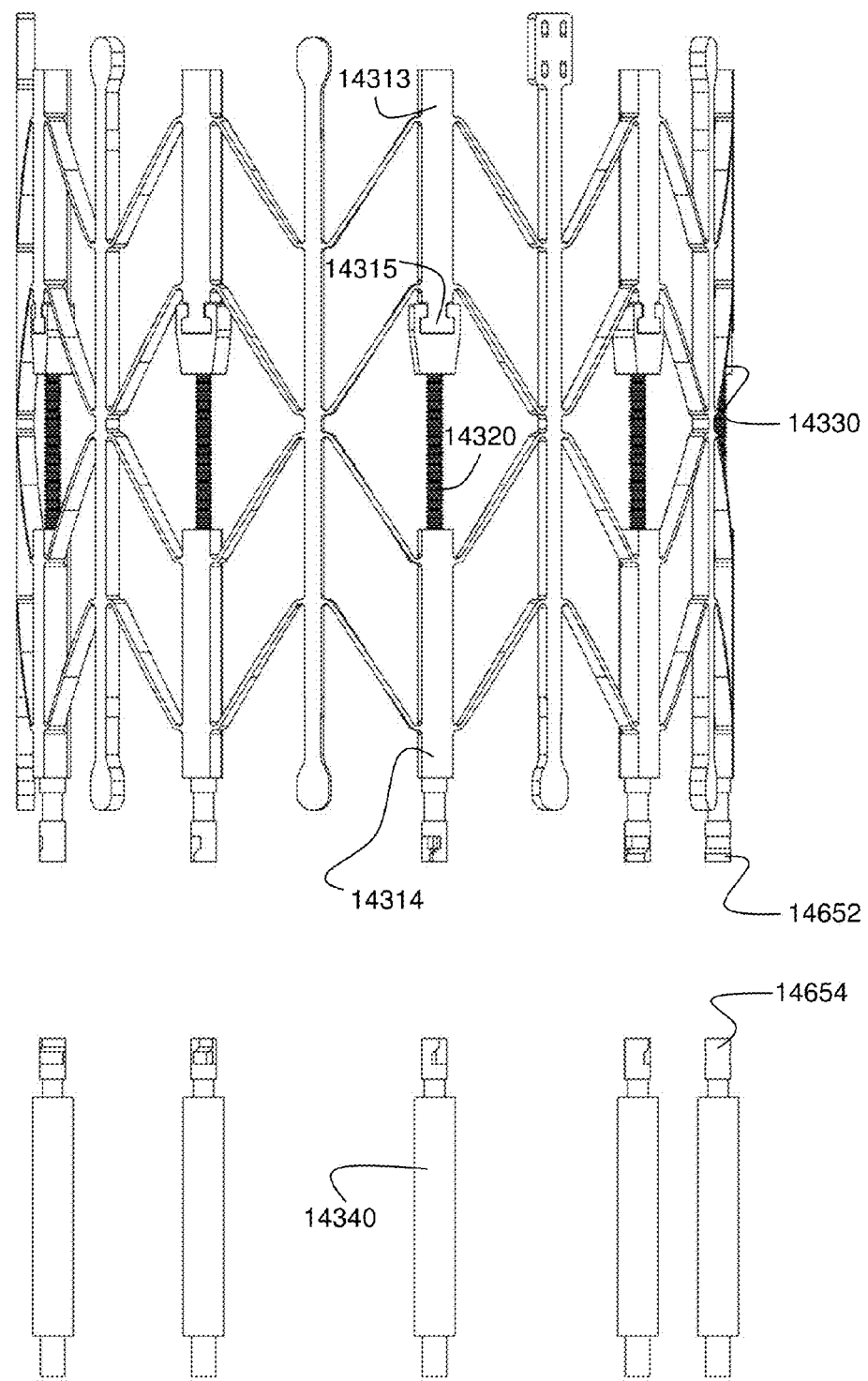
Figure 147:
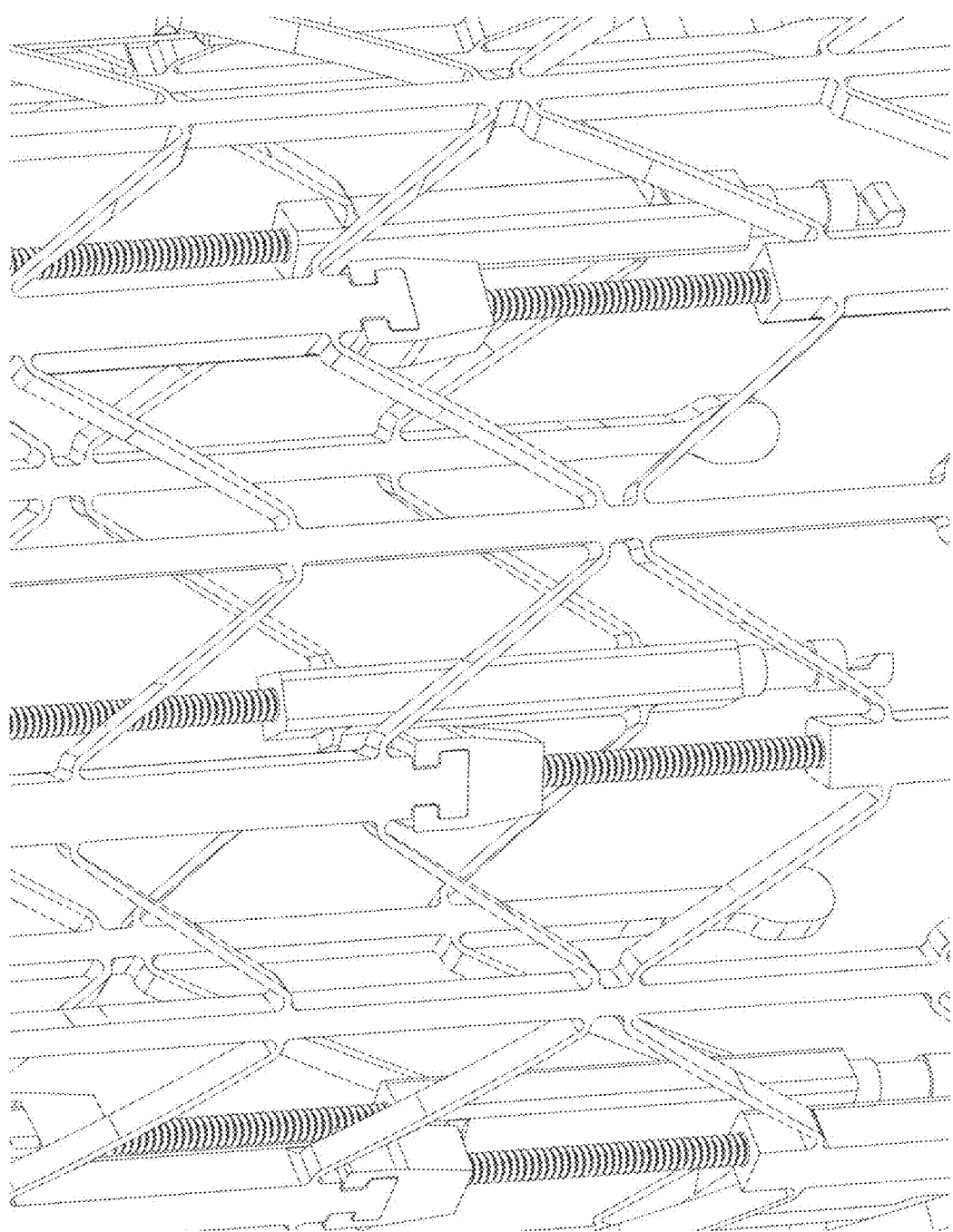
Figure 148:
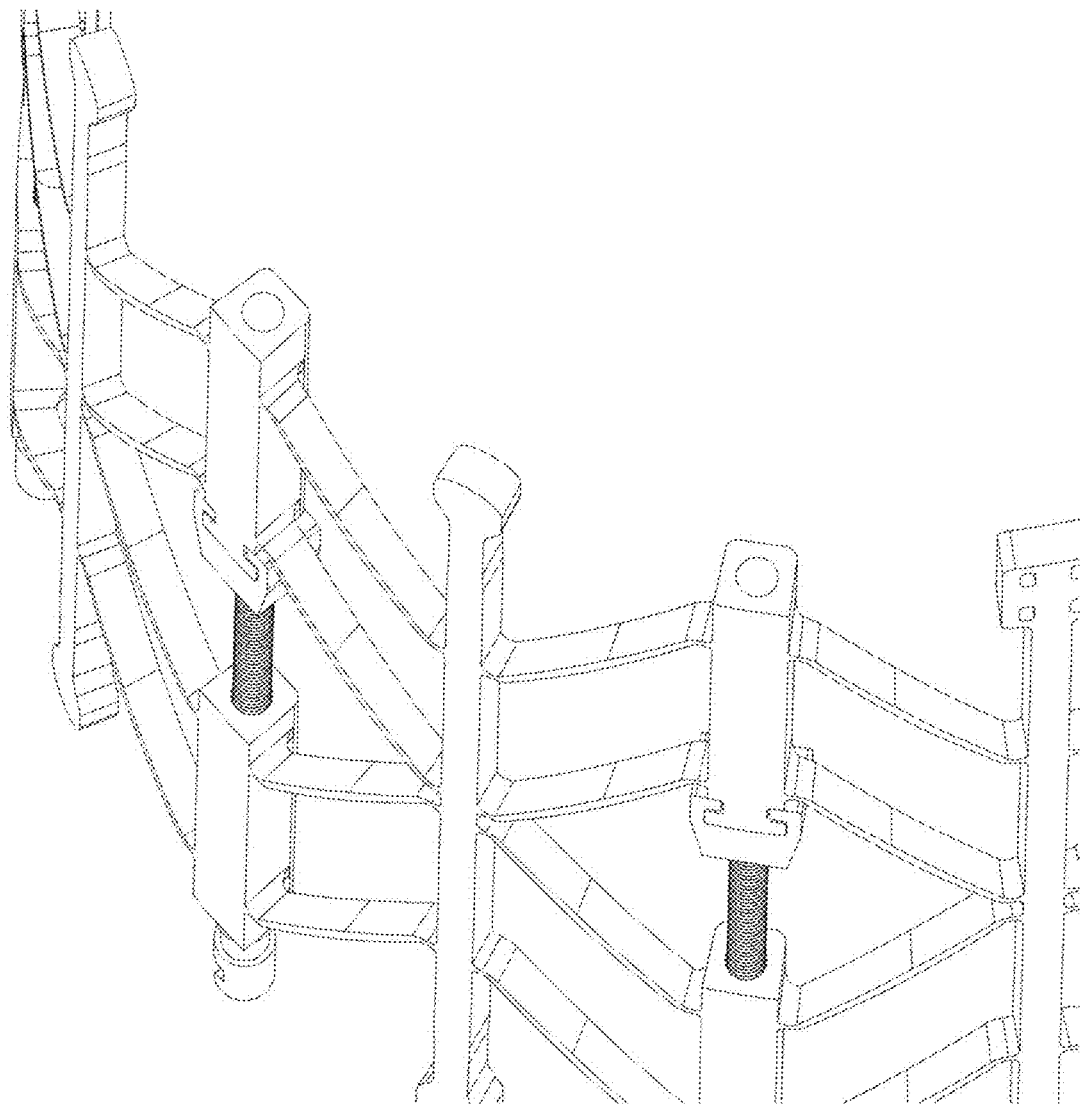
Figure 149:
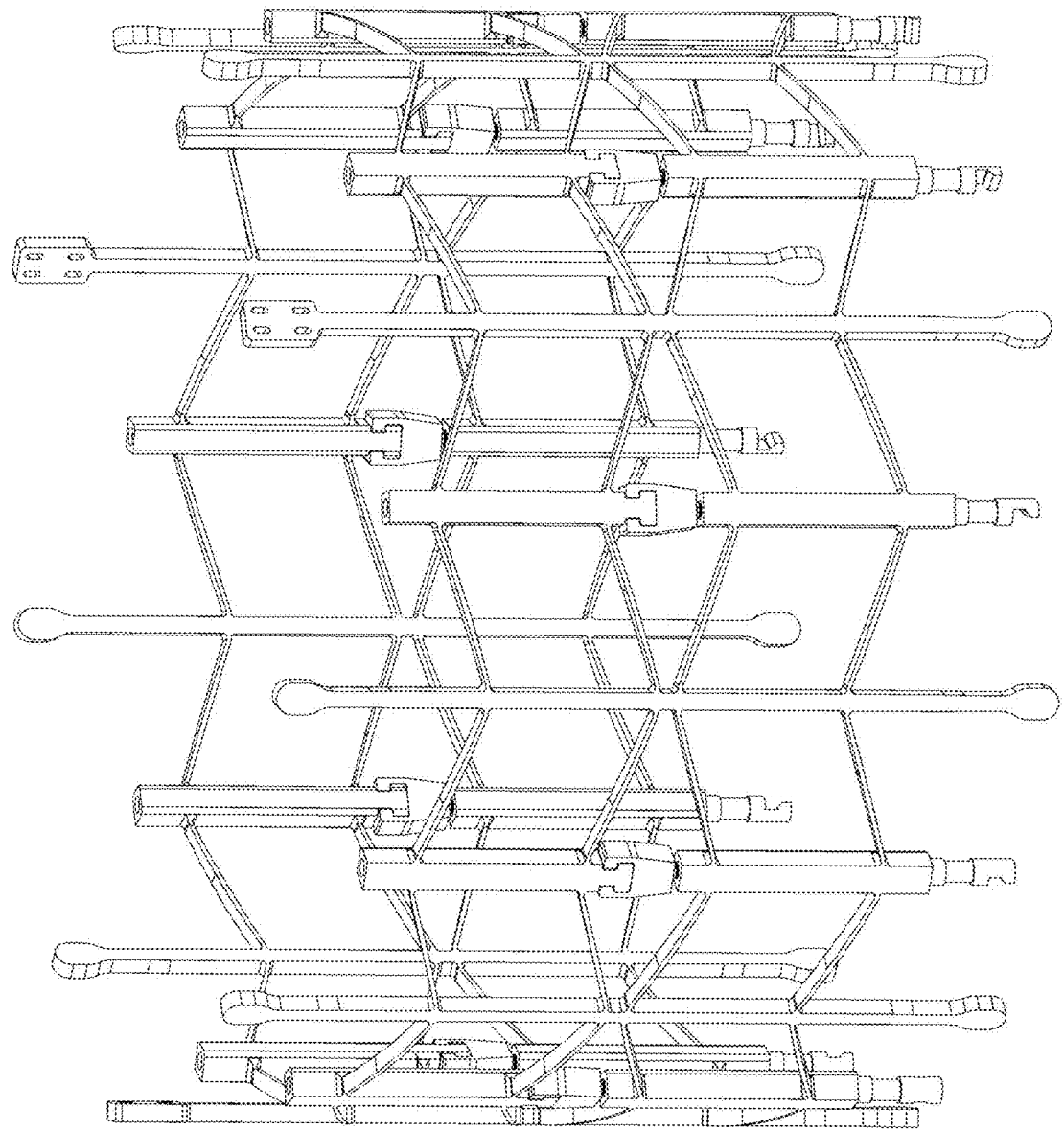
Figure 150:
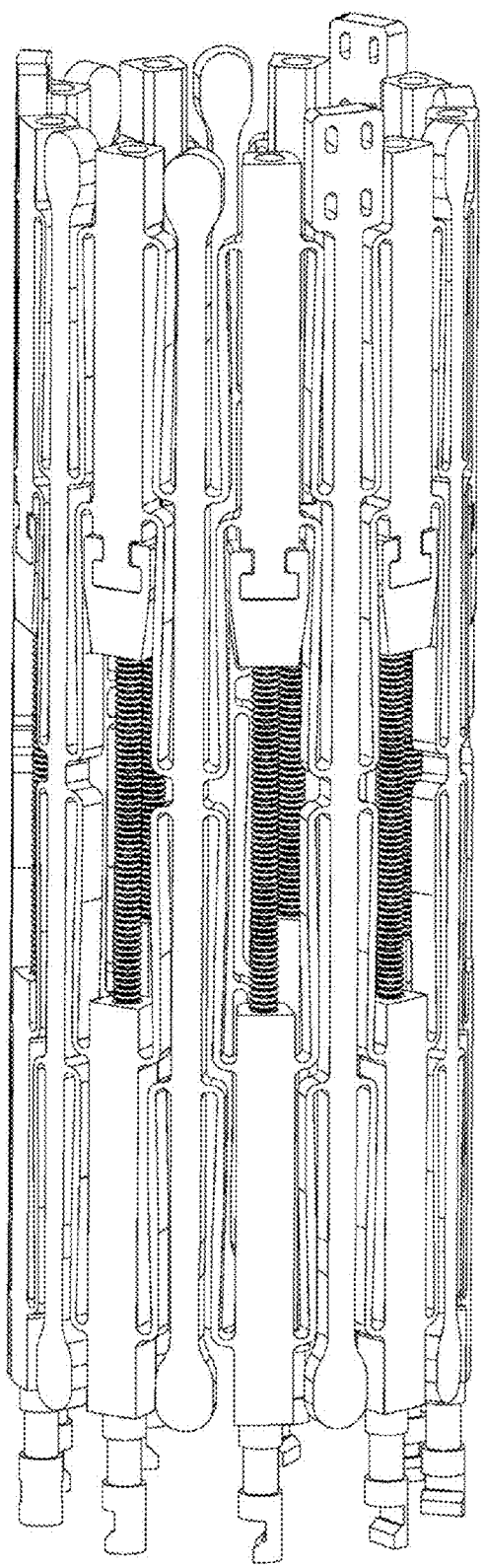
Figure 151:
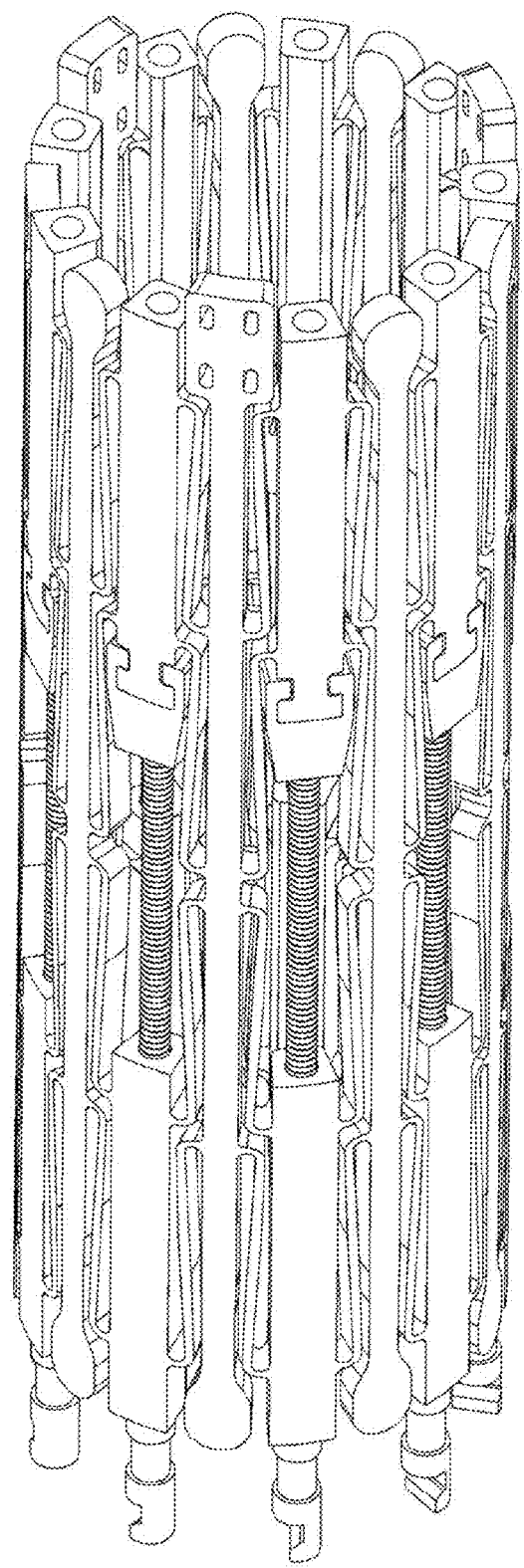
Figure 152:
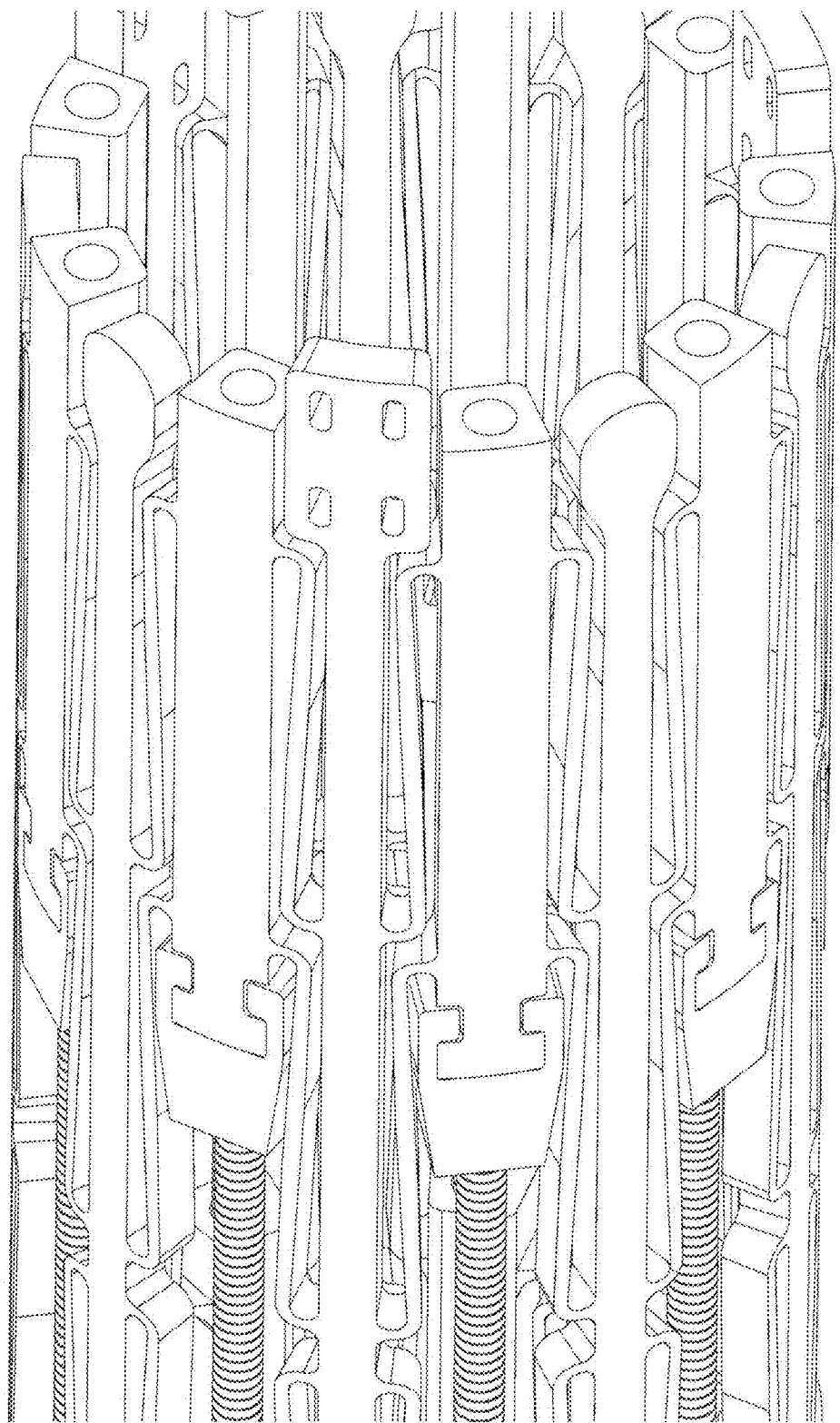
Figure 153:
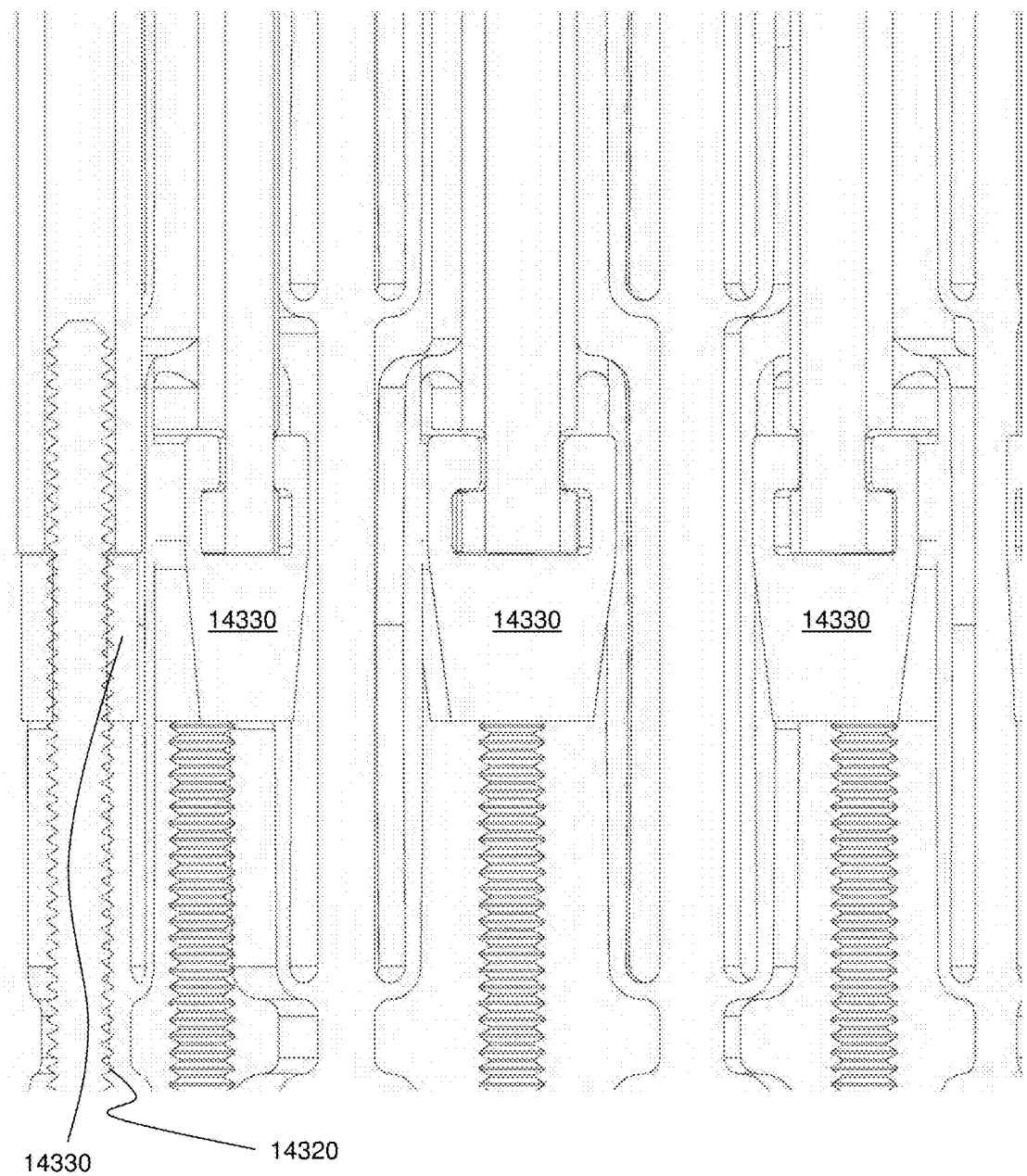
Figure 154:
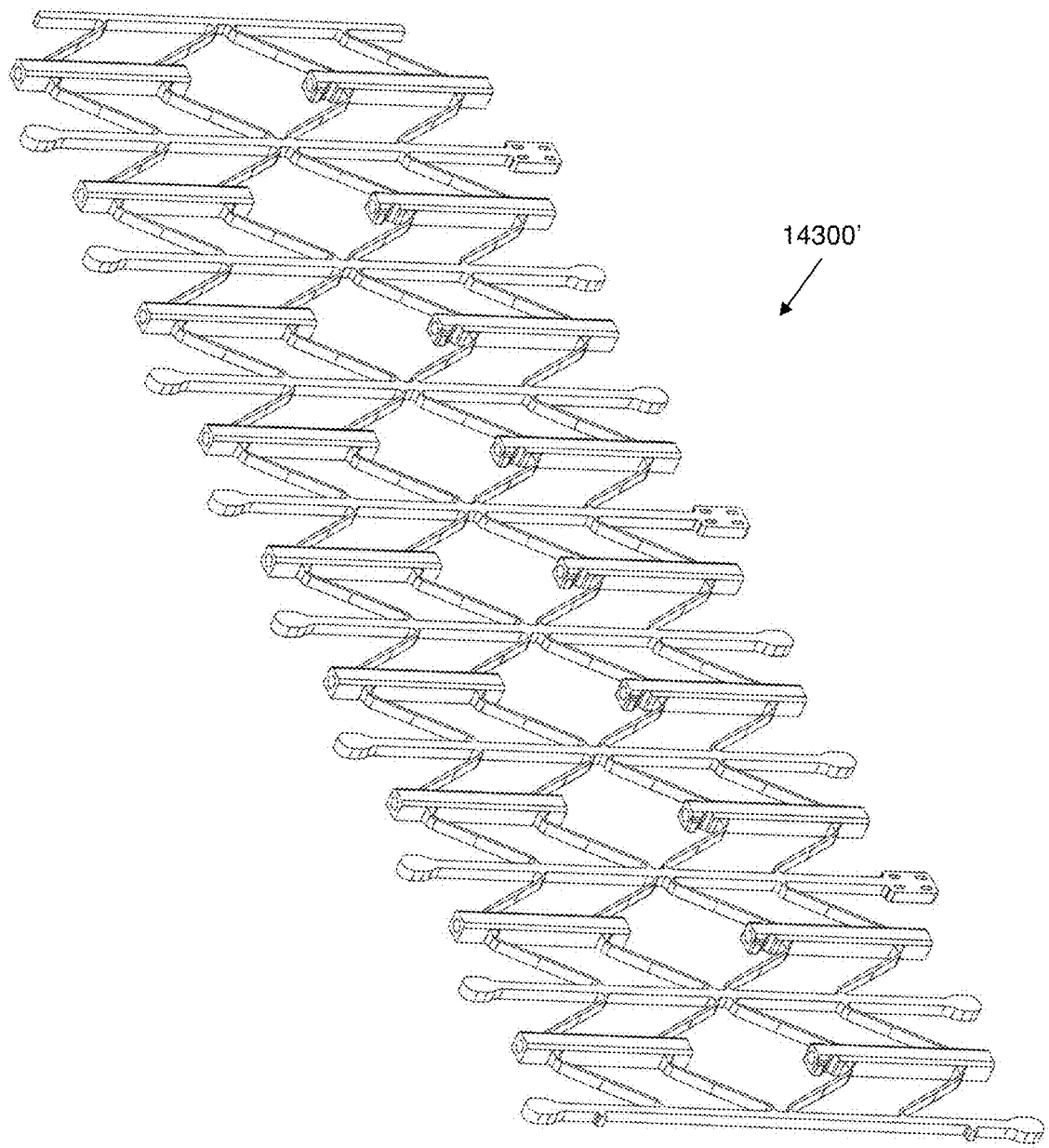
Figure 155:
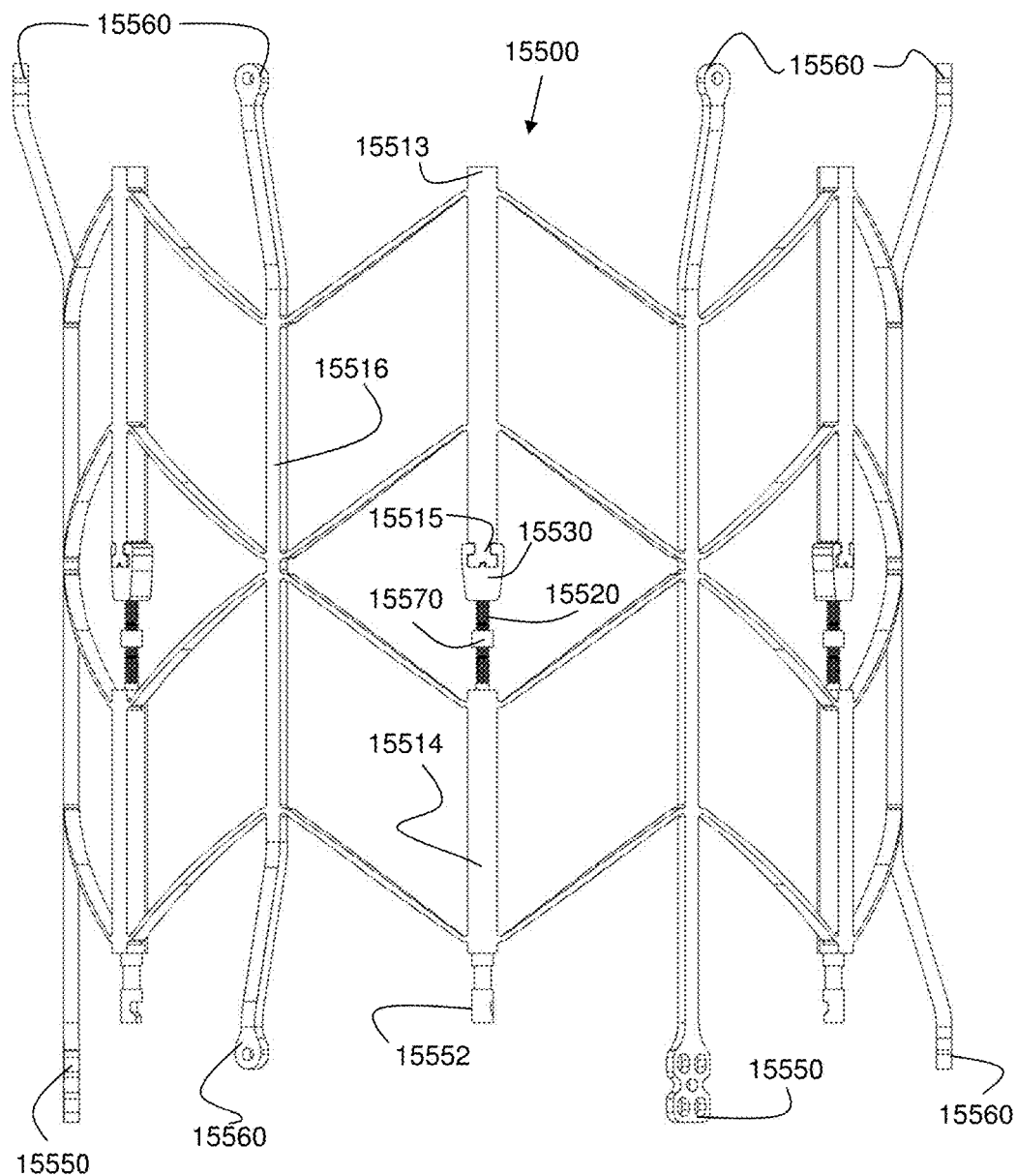
Figure 156:
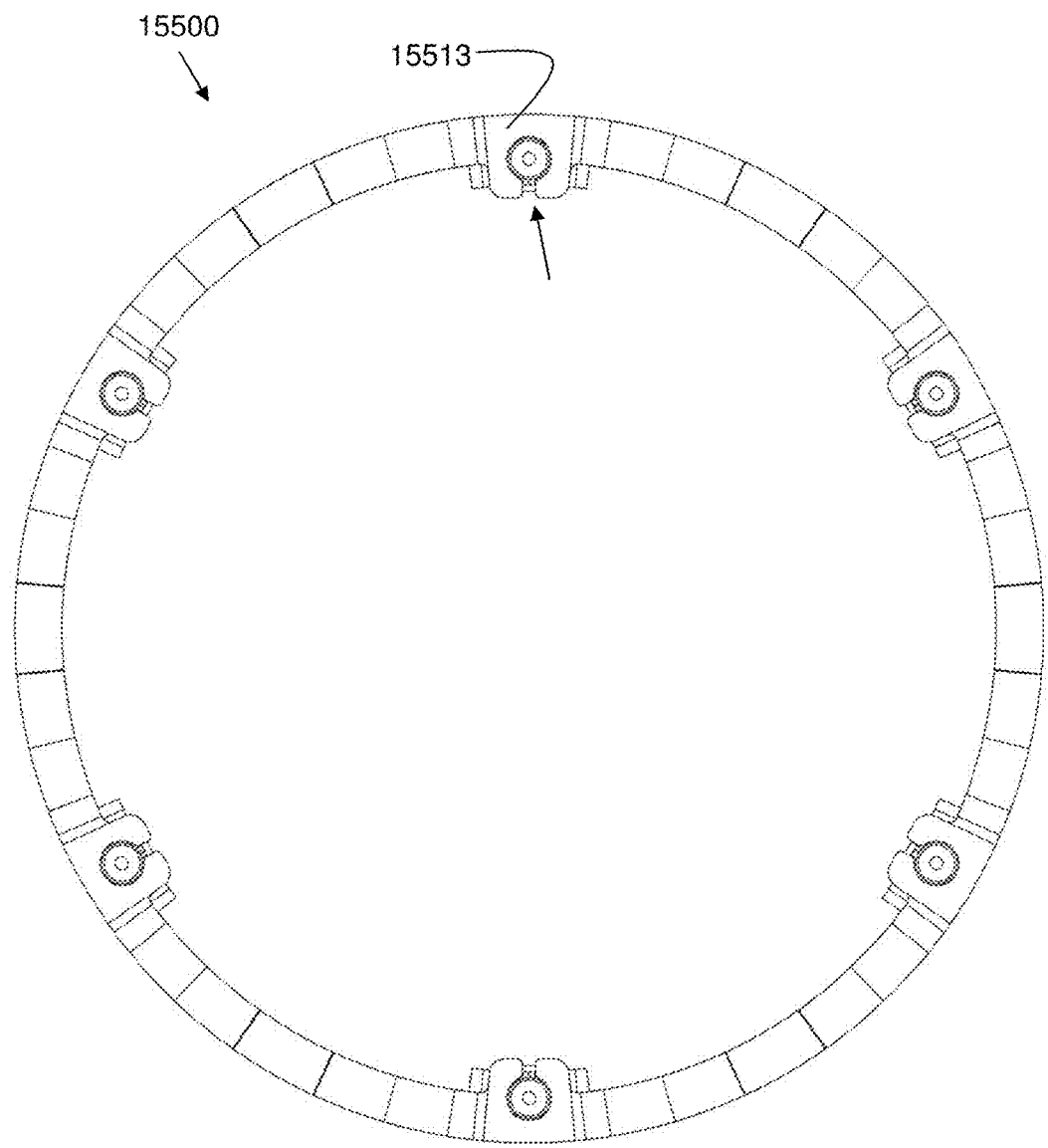
Figure 157:
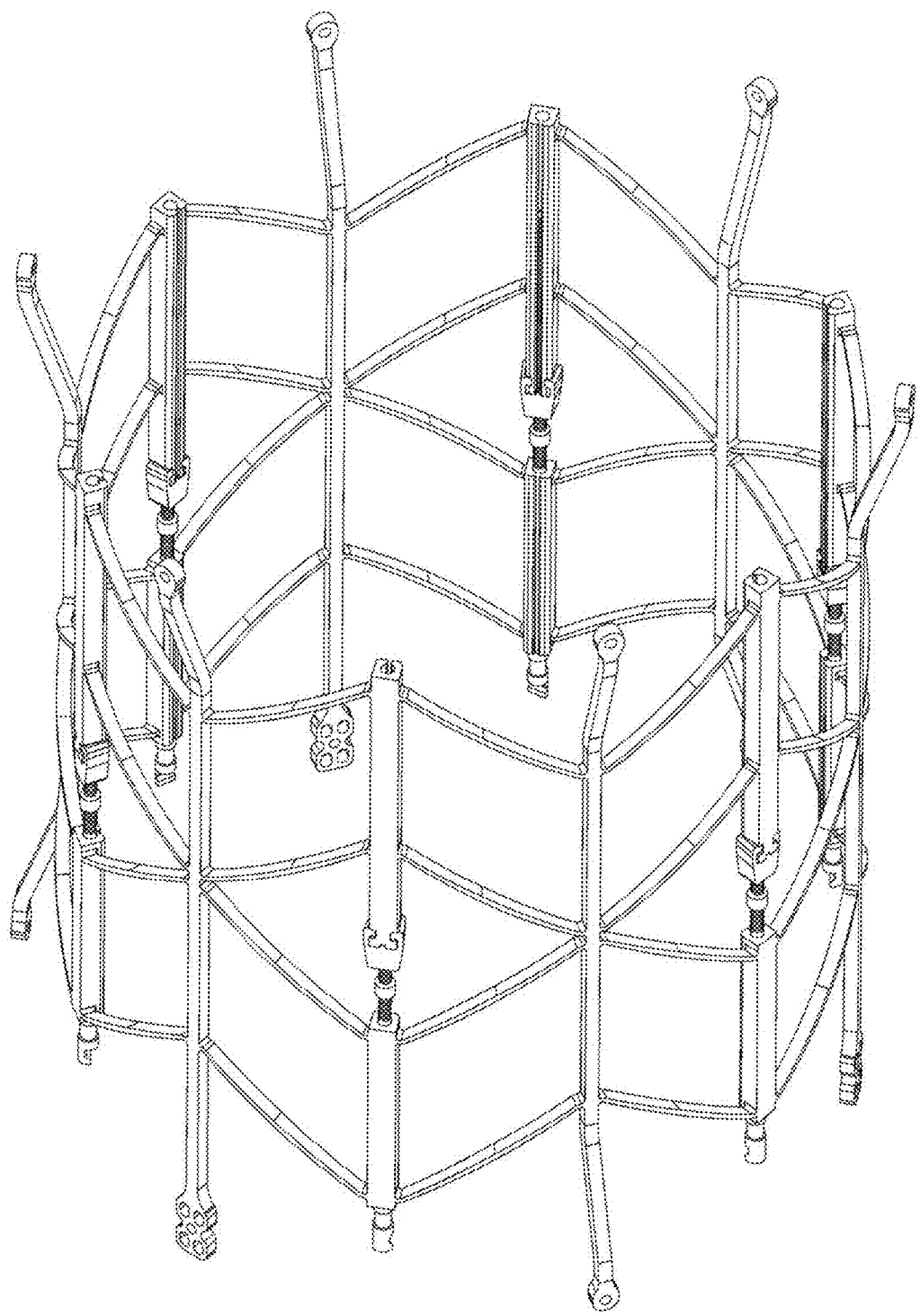
Figure 158:
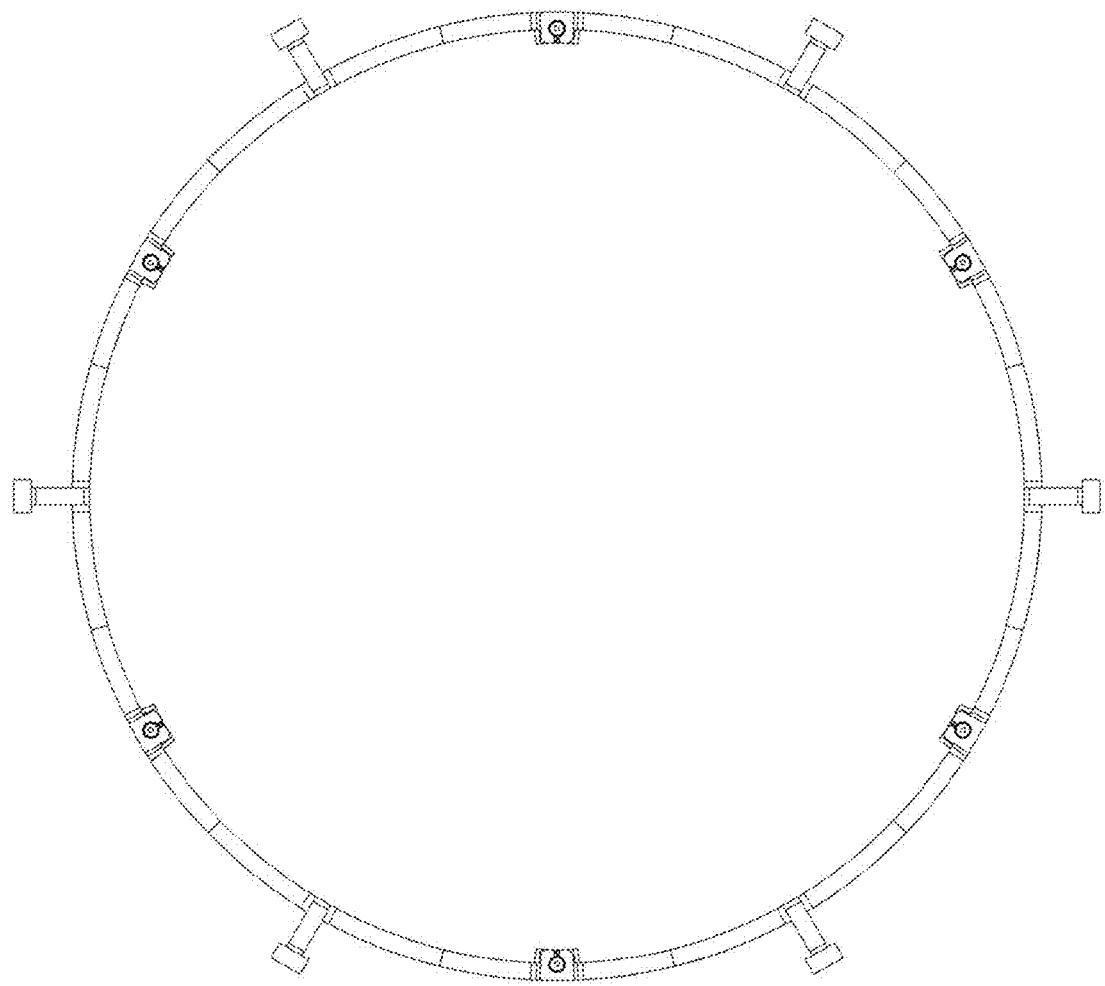
Figure 159:
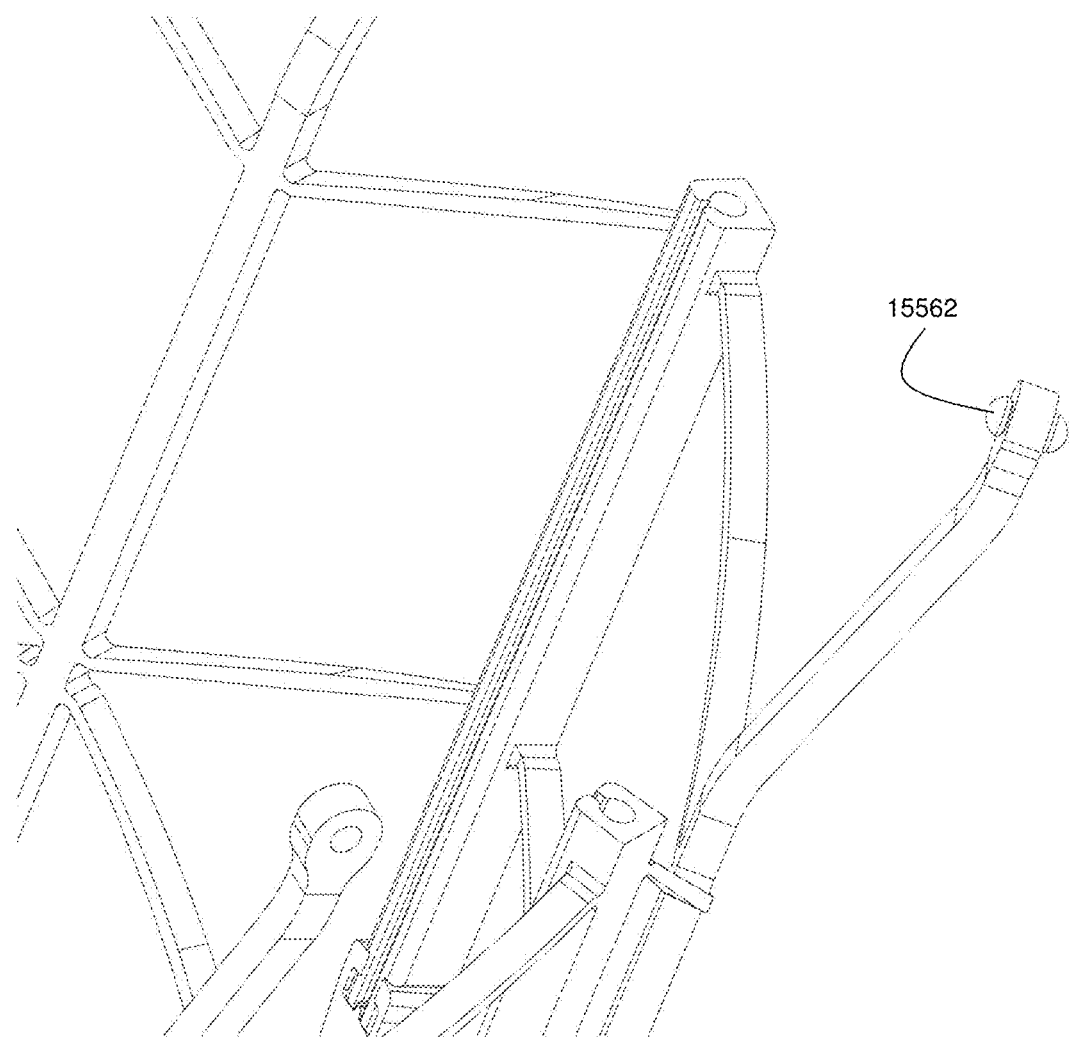
Figure 160:
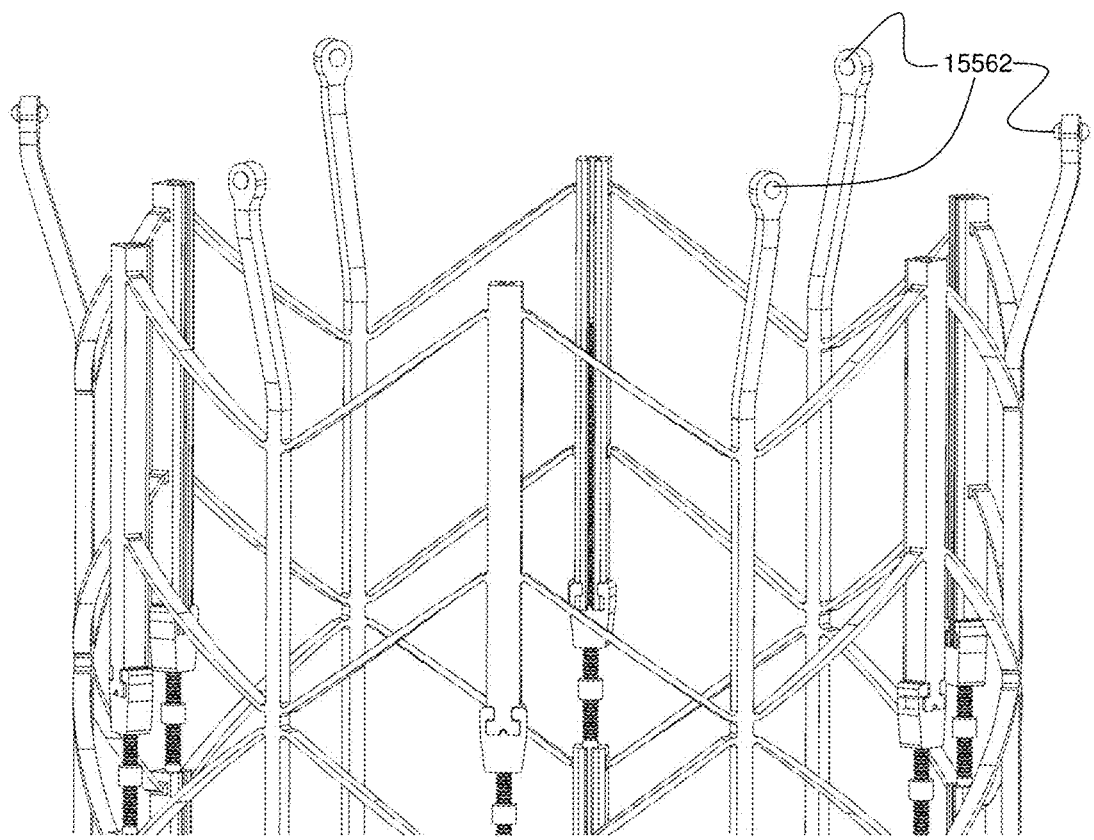
Figure 164:
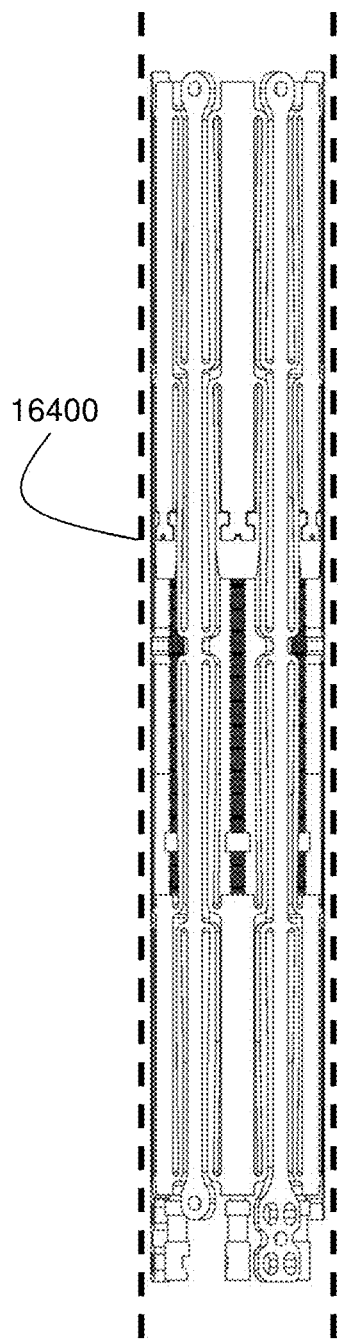
Figure 165:
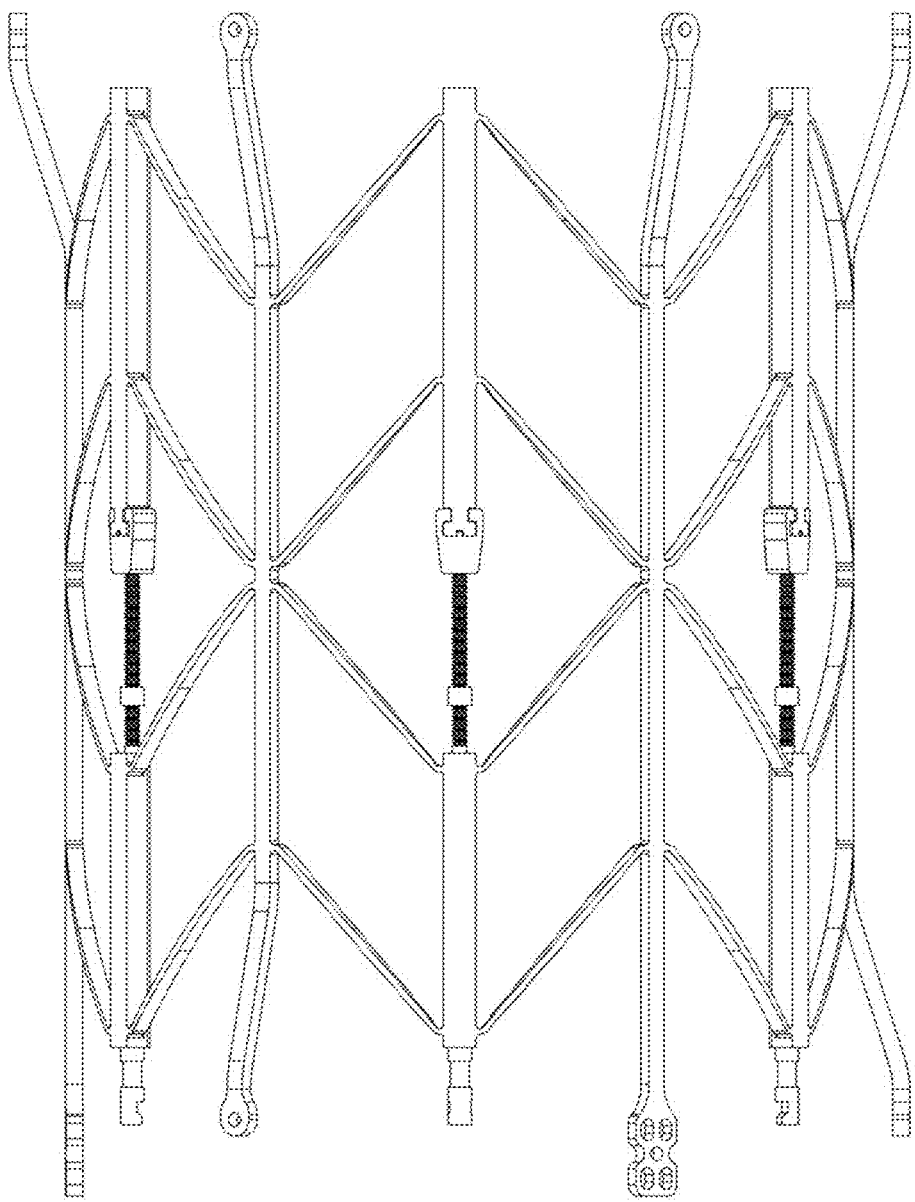
Figure 166:
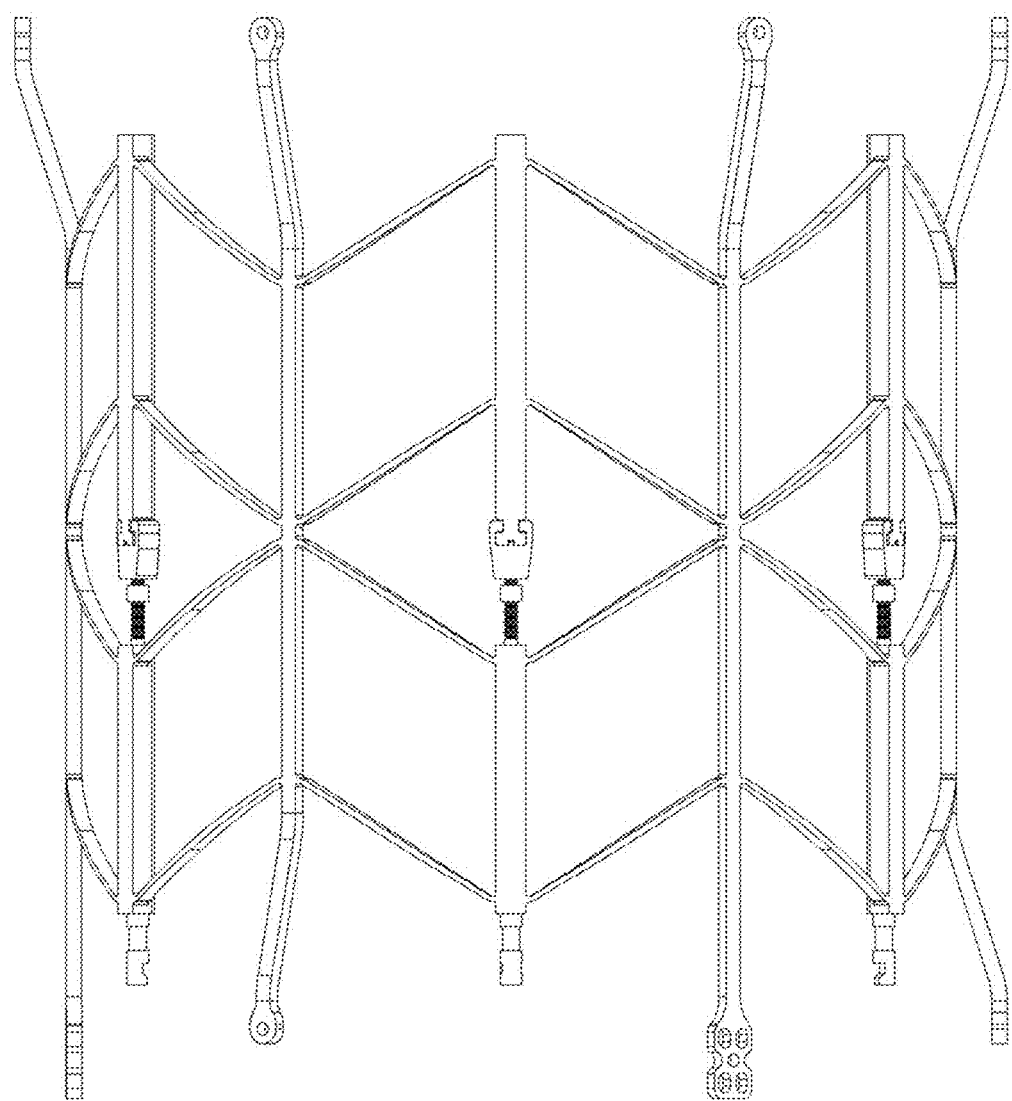
Figure 167:
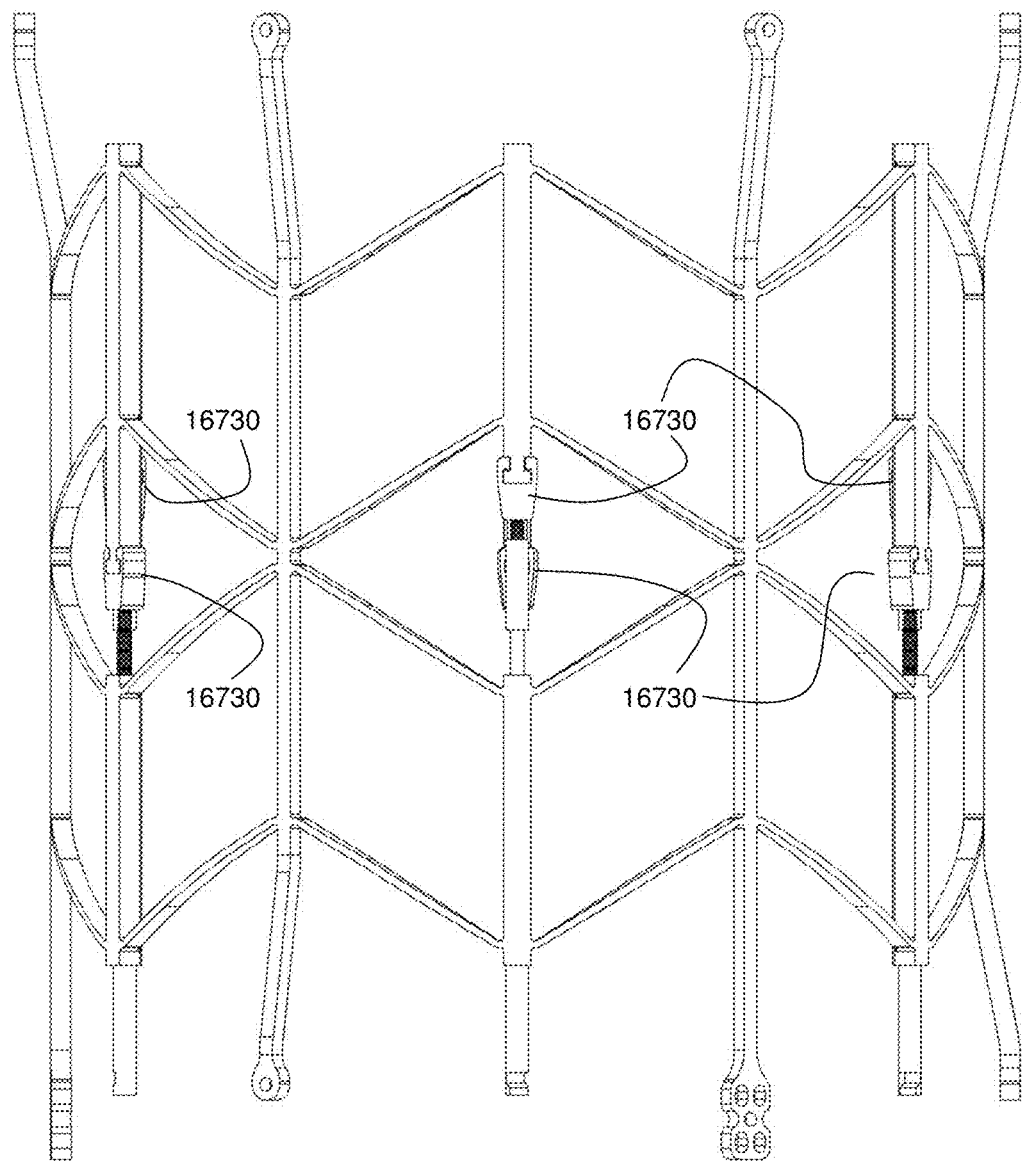
Figure 168:
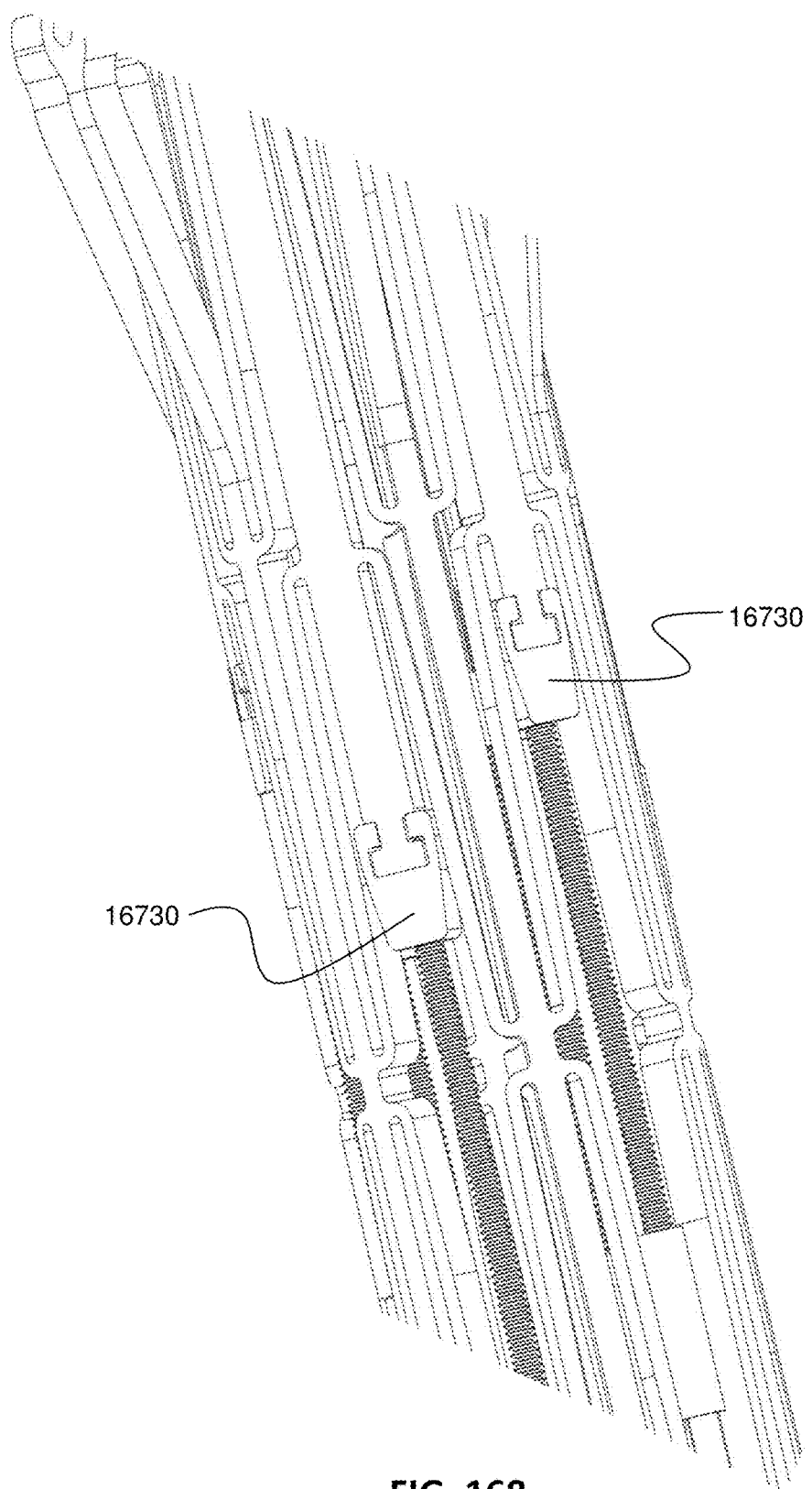
Figure 169:
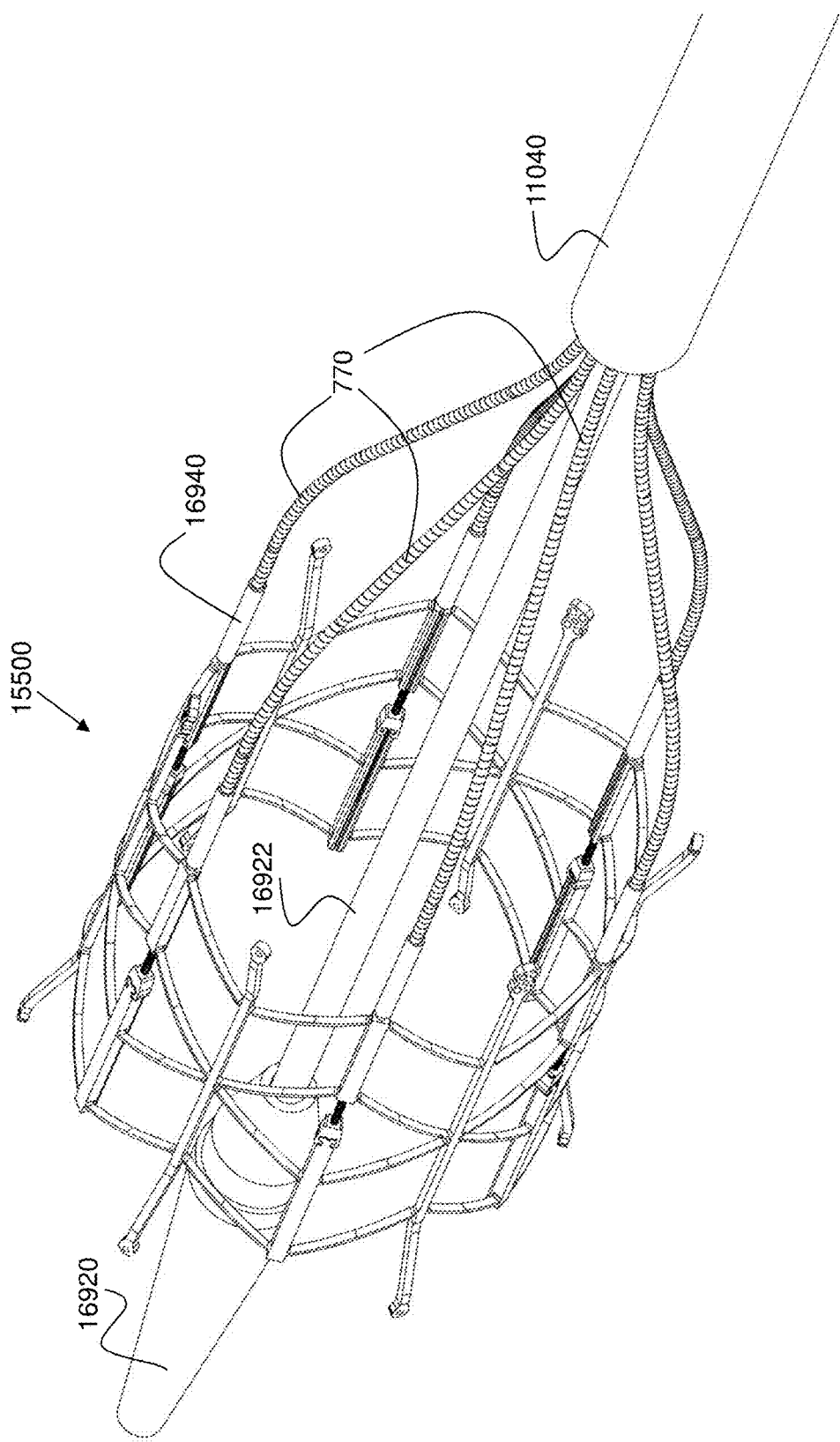
Figure 170:
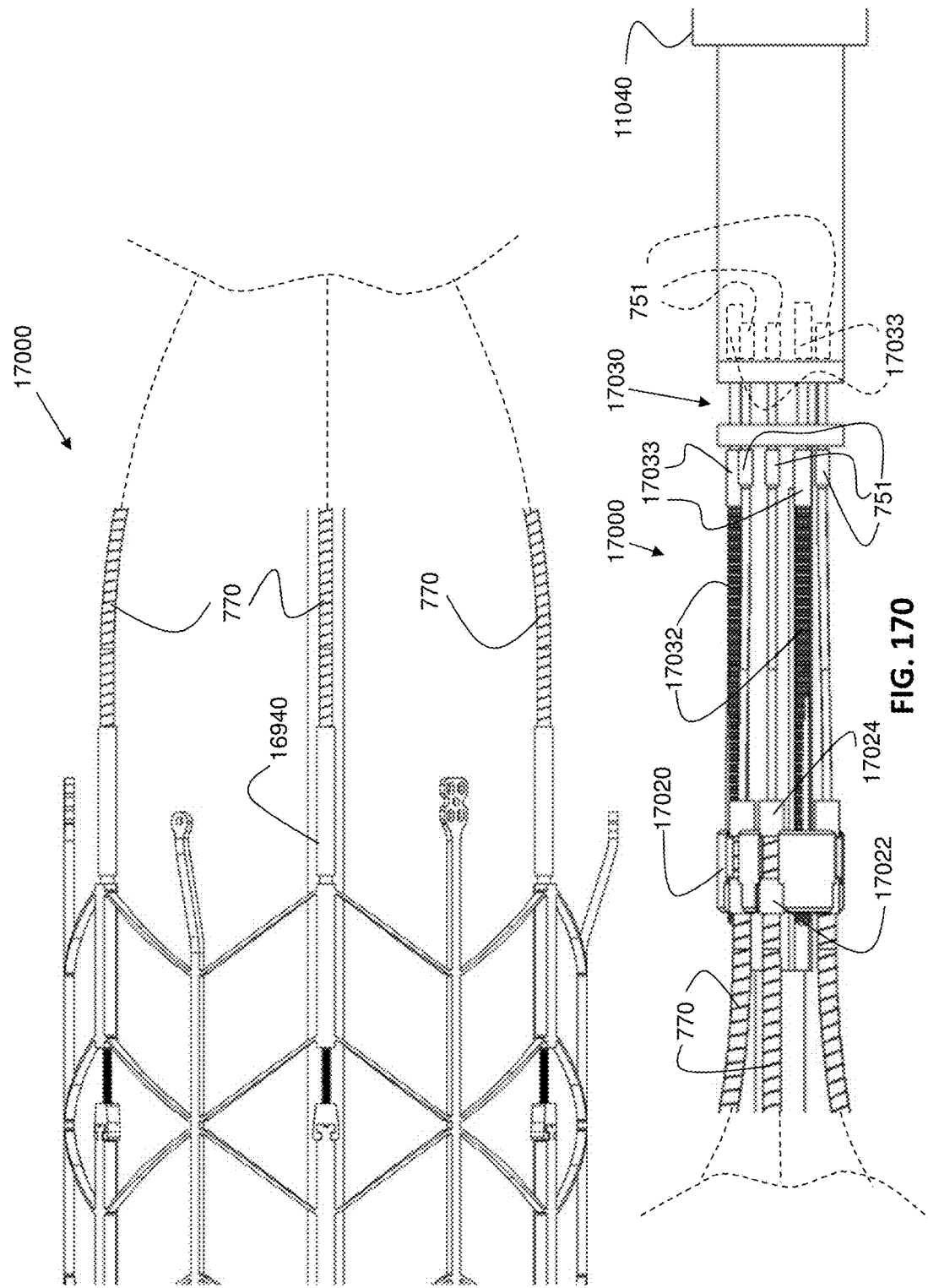
Figure 171:
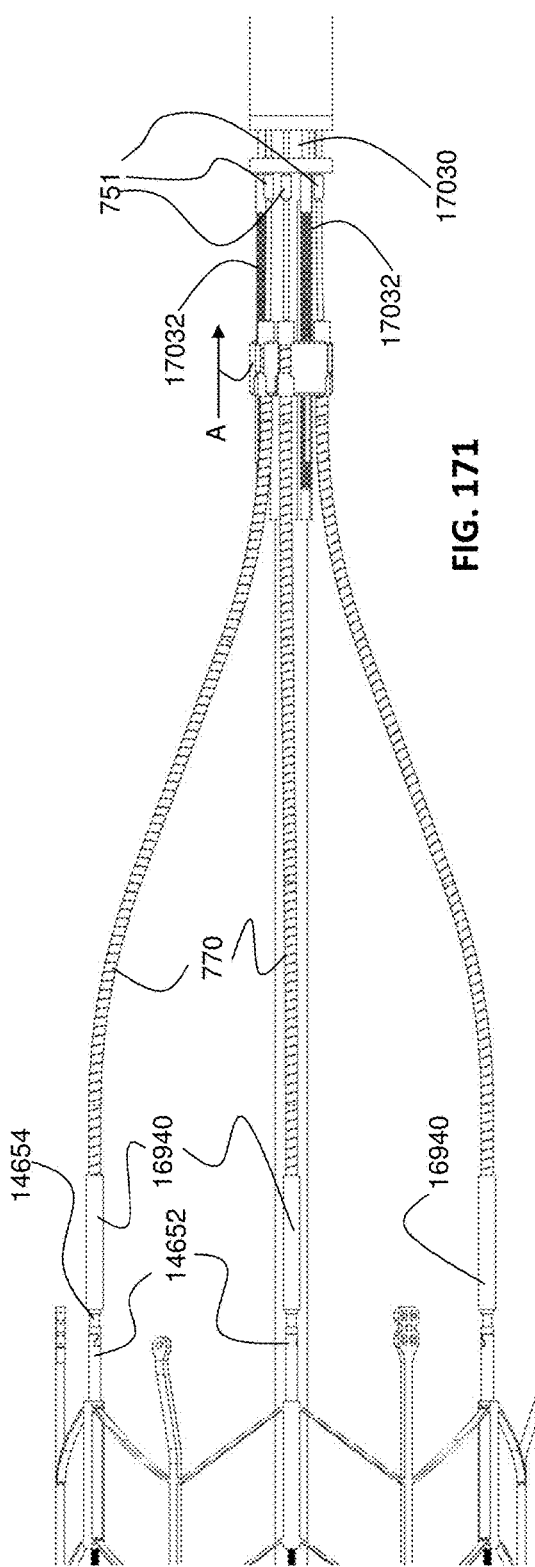
Figure 172:
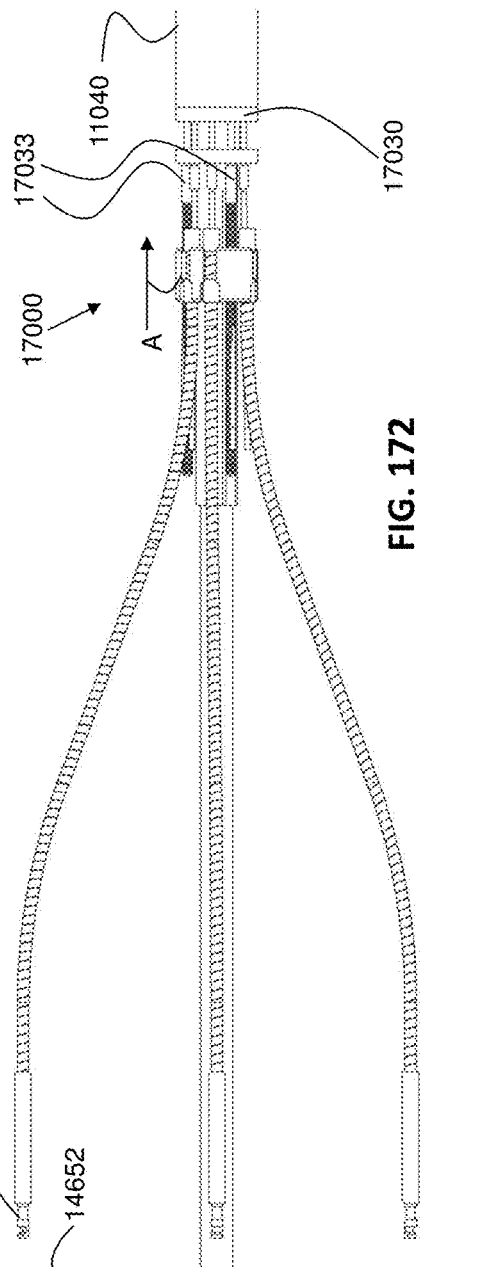
Figure 173:
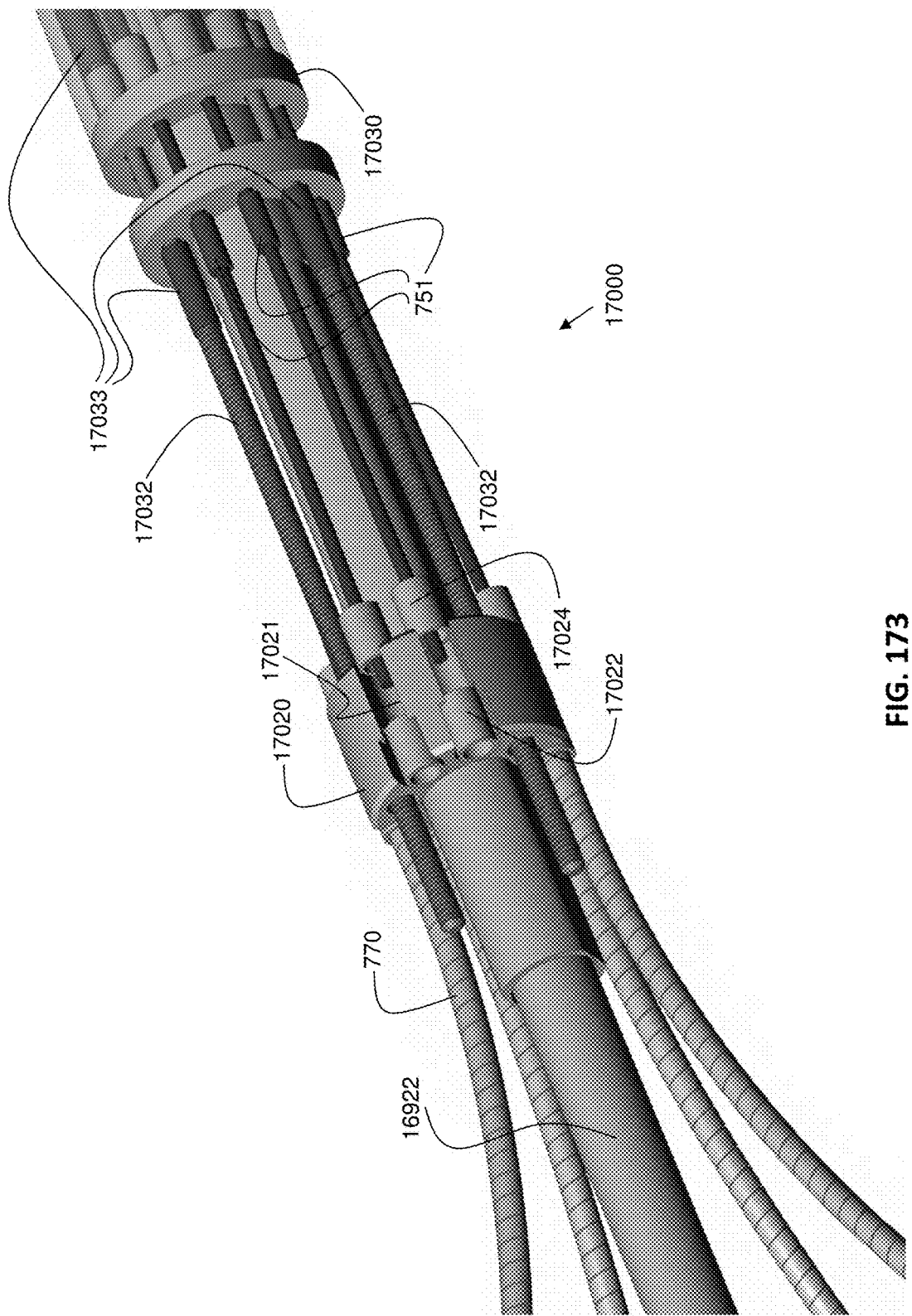
Figure 174:
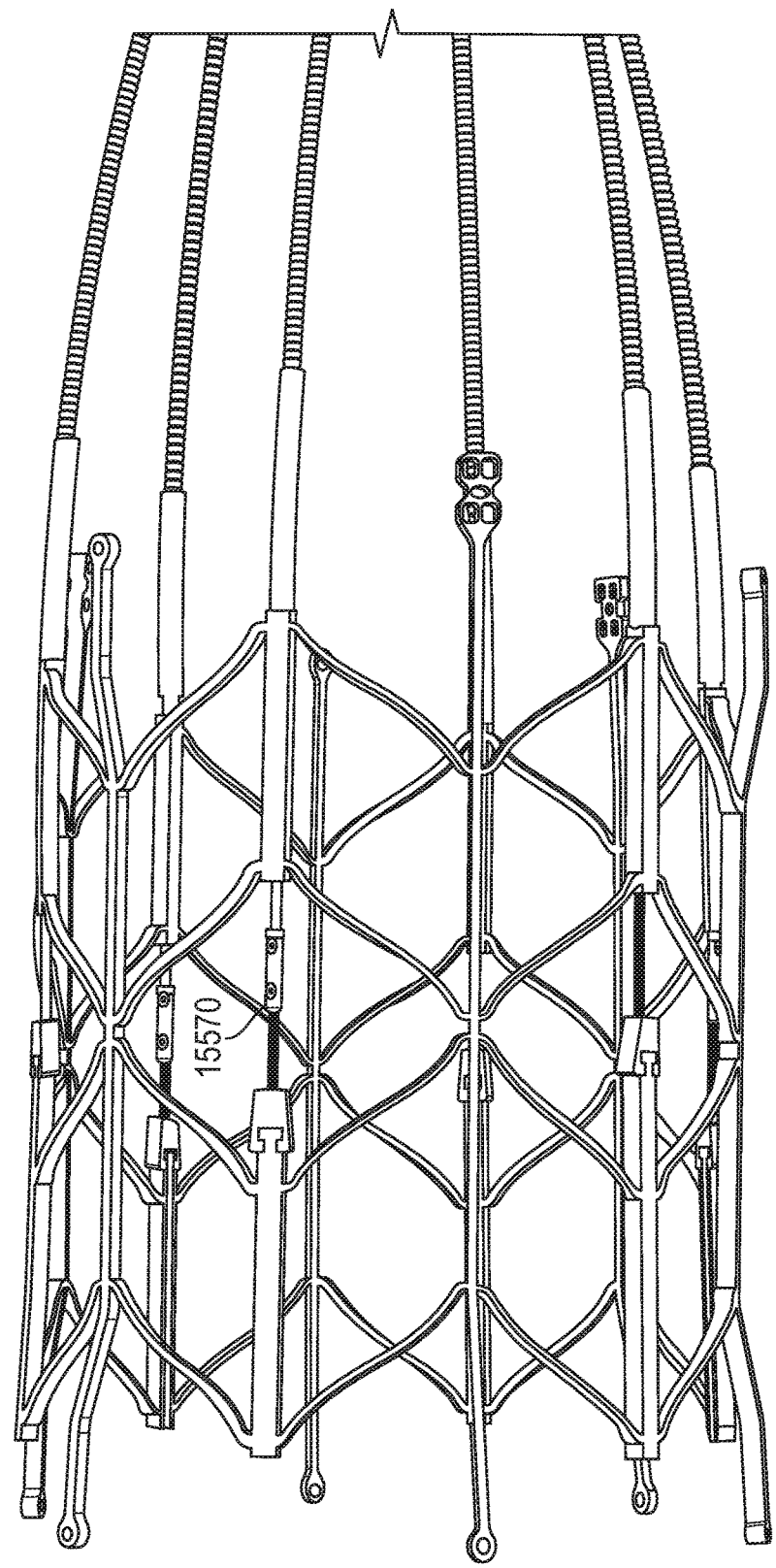
Figure 175:
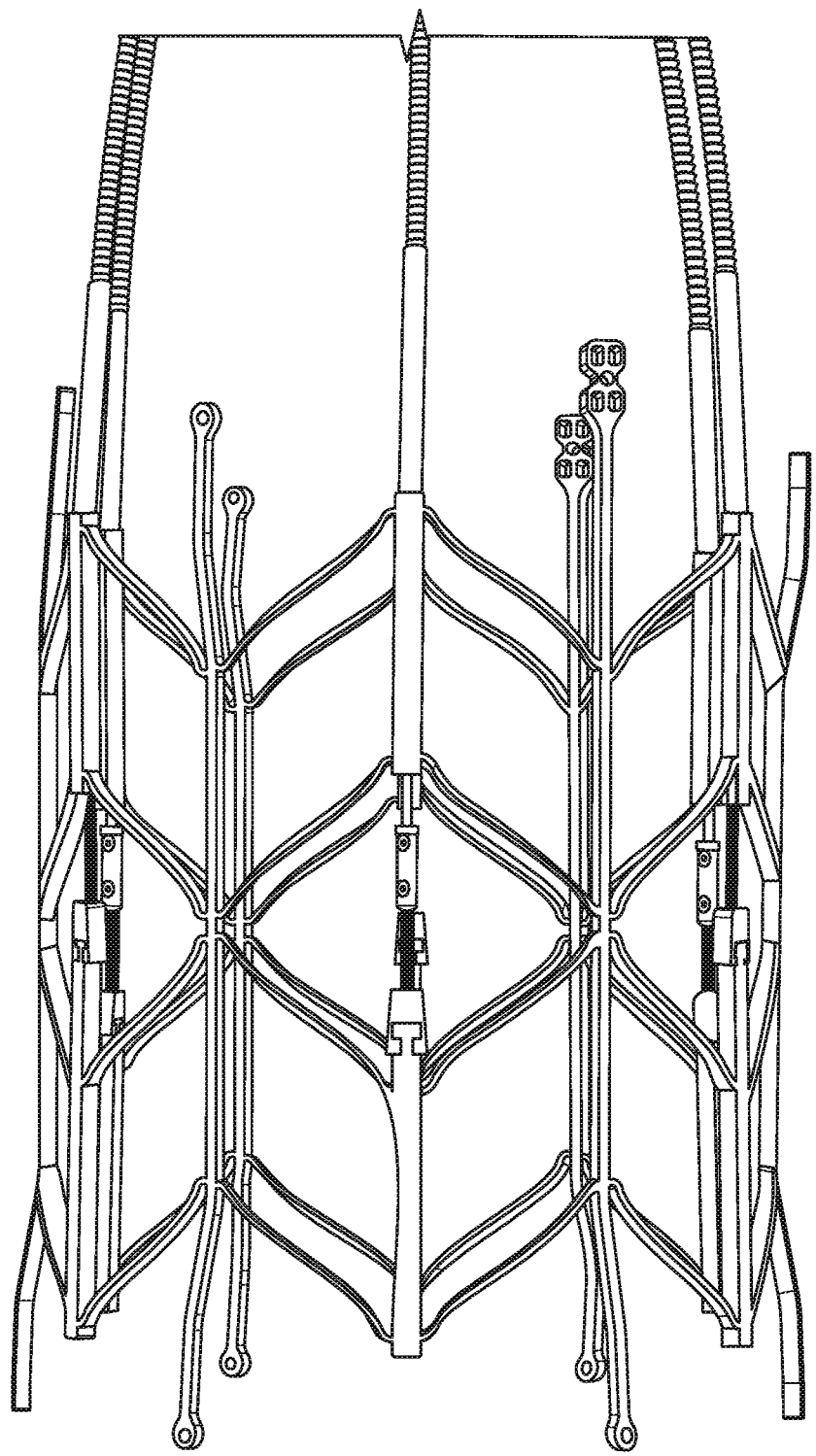
Figure 176:
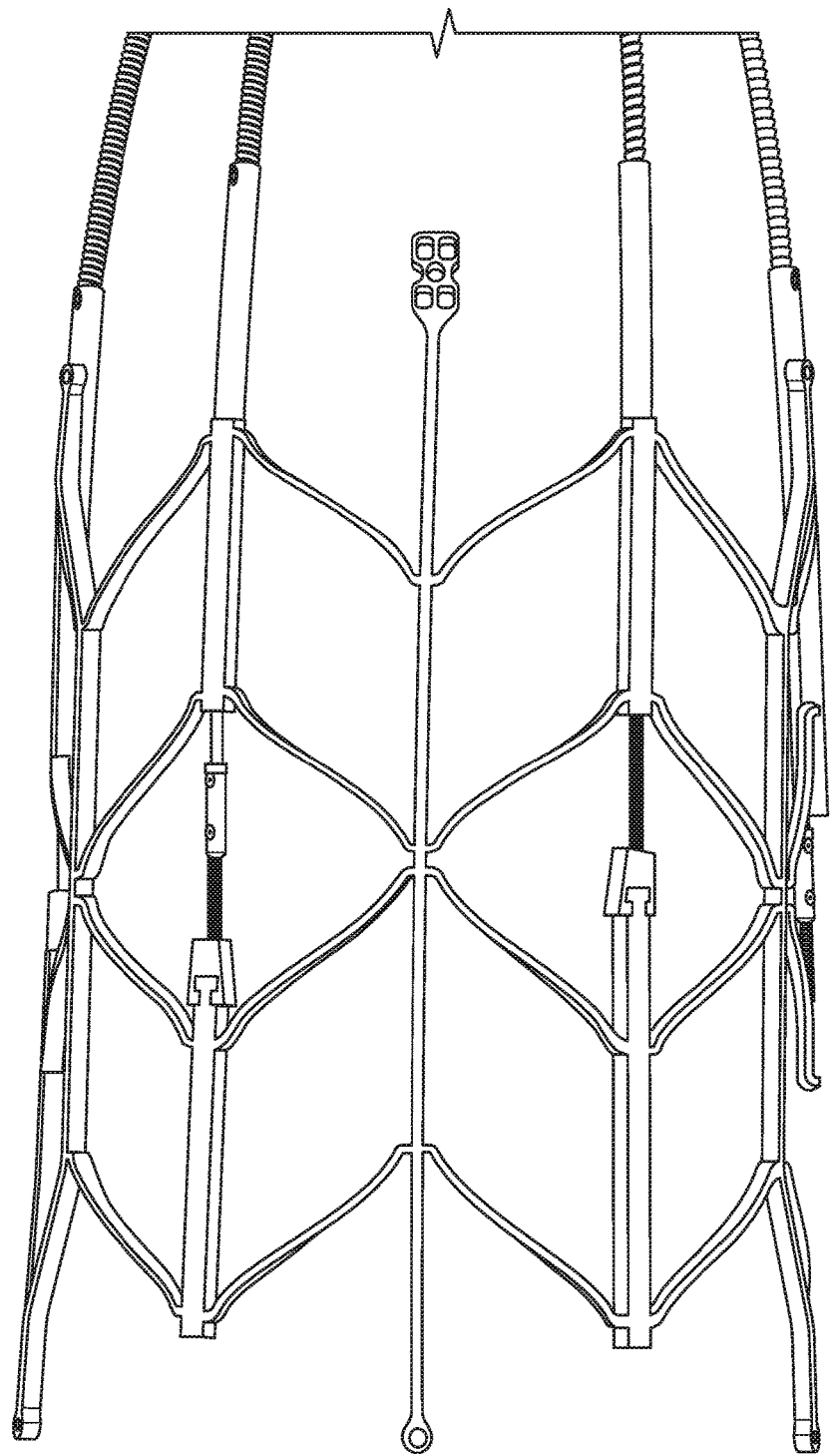
Figure 177:
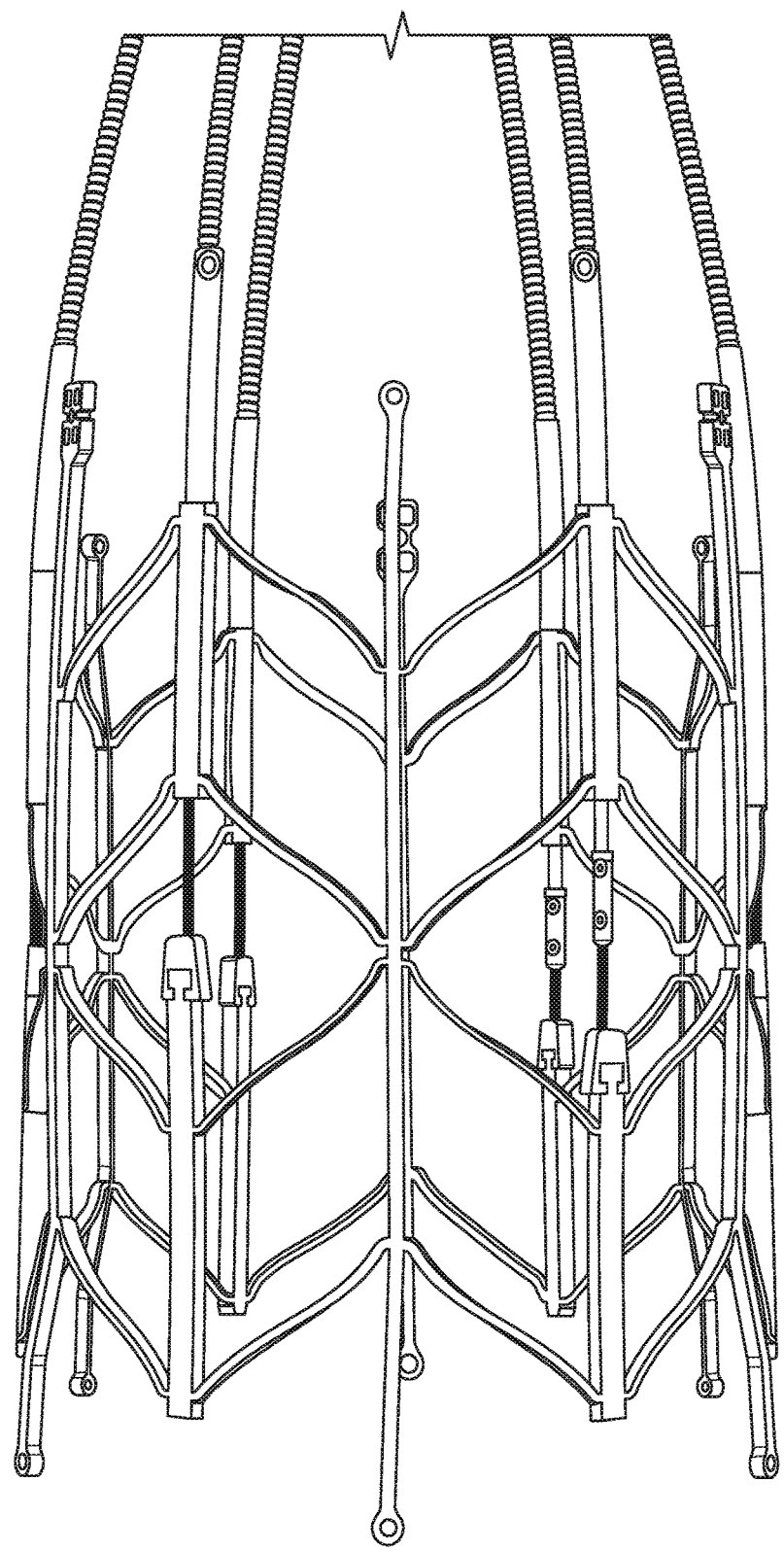
Figure 178:
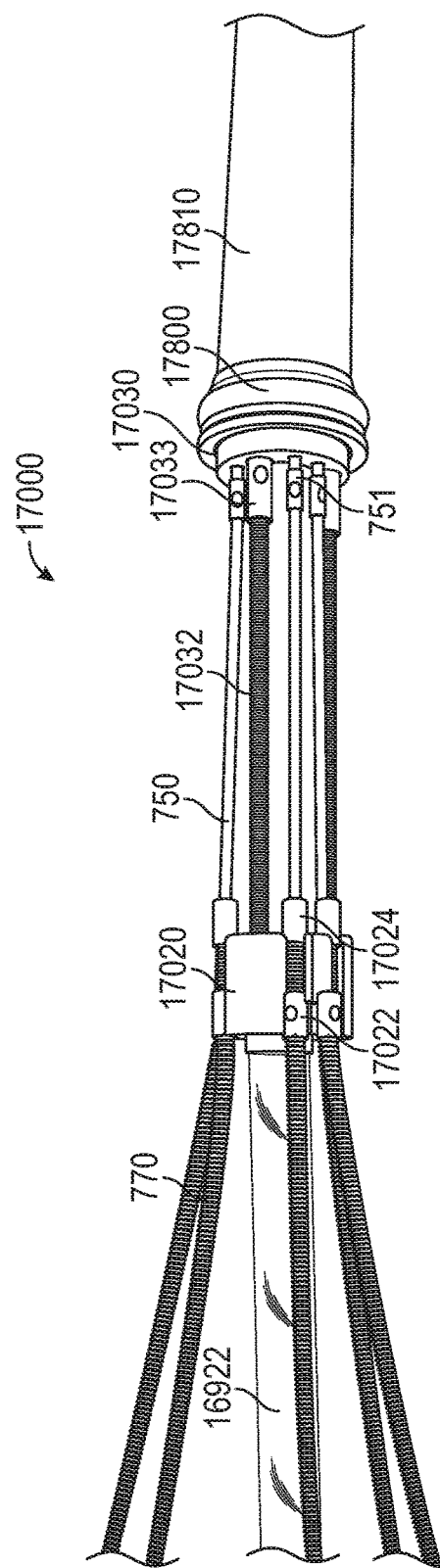
Figure 179:
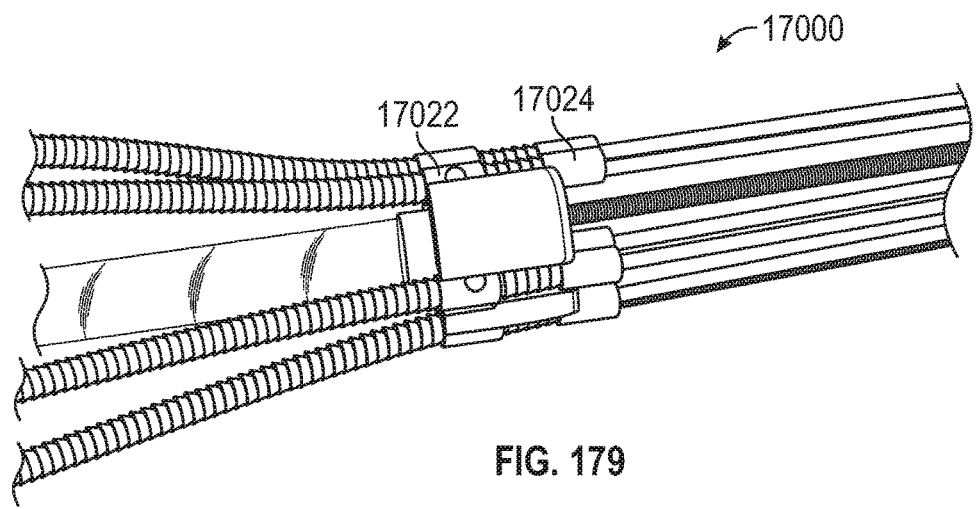
Figure 180:
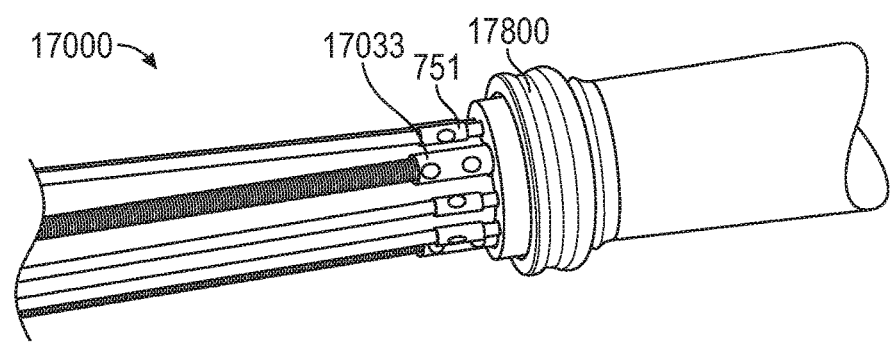
Figure 181:
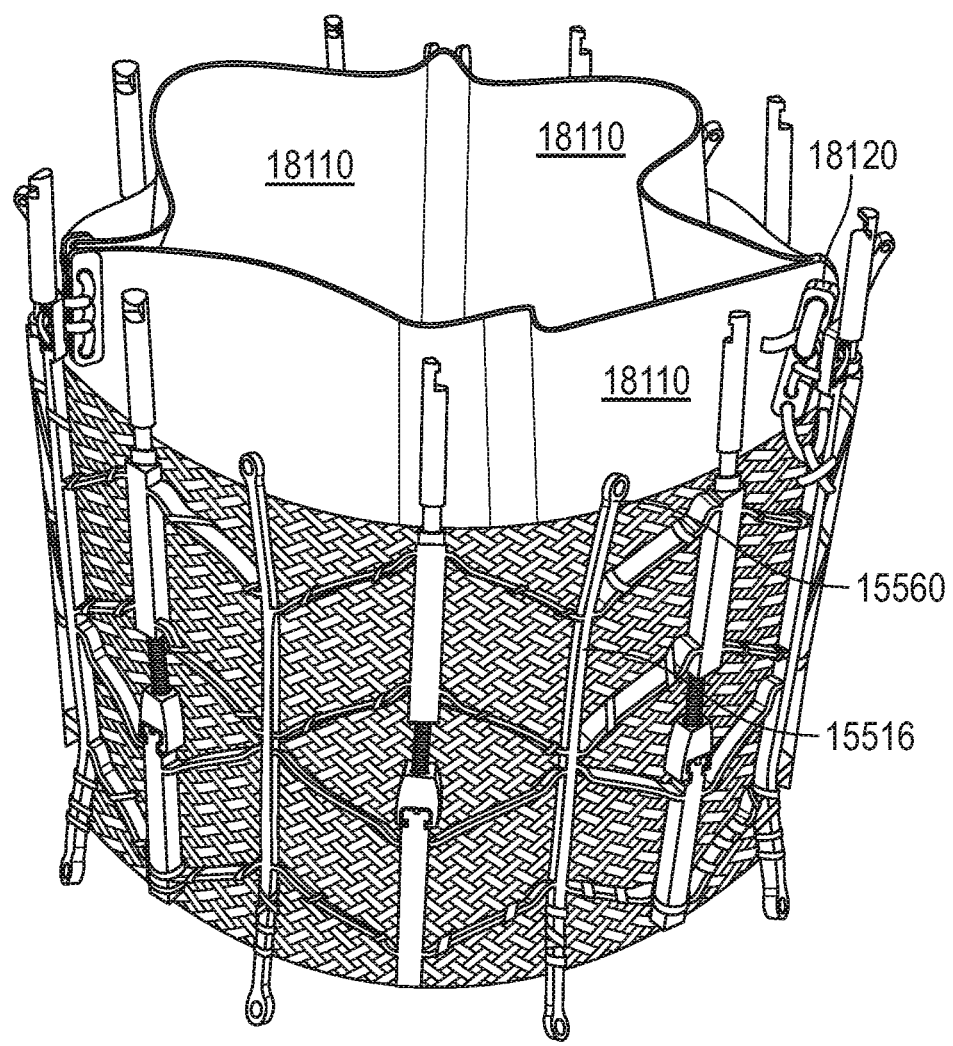
Figure 182:
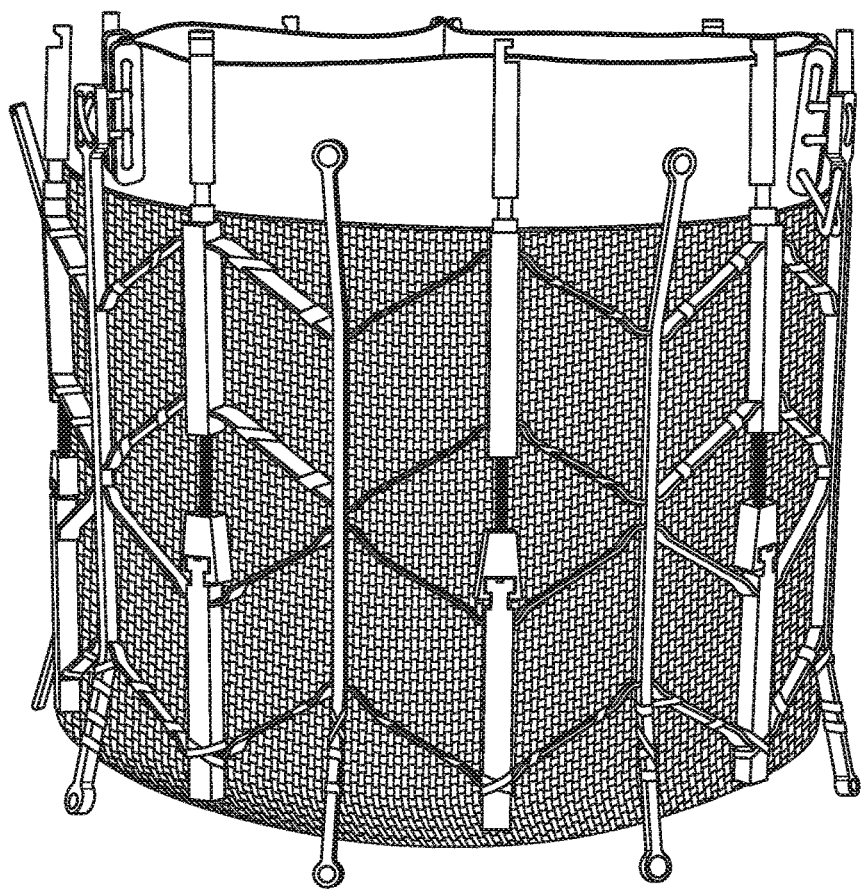
Figure 183:
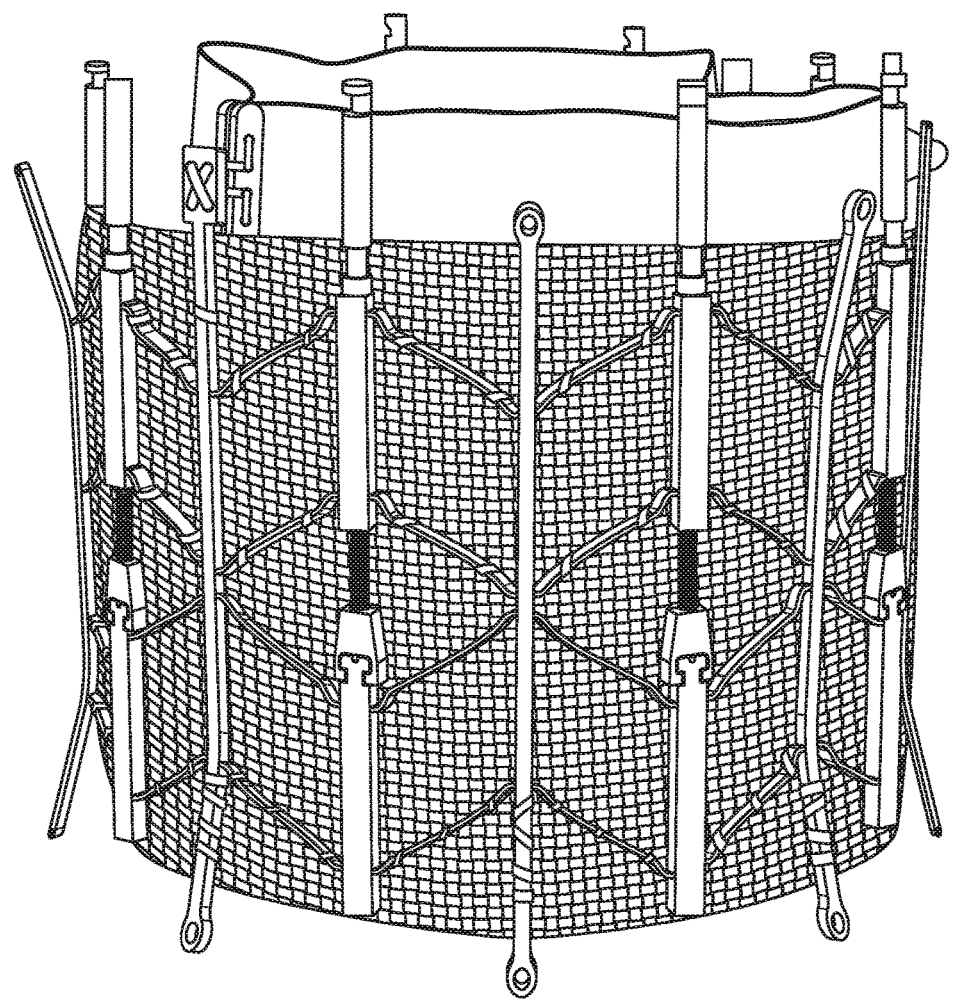
Figure 184:
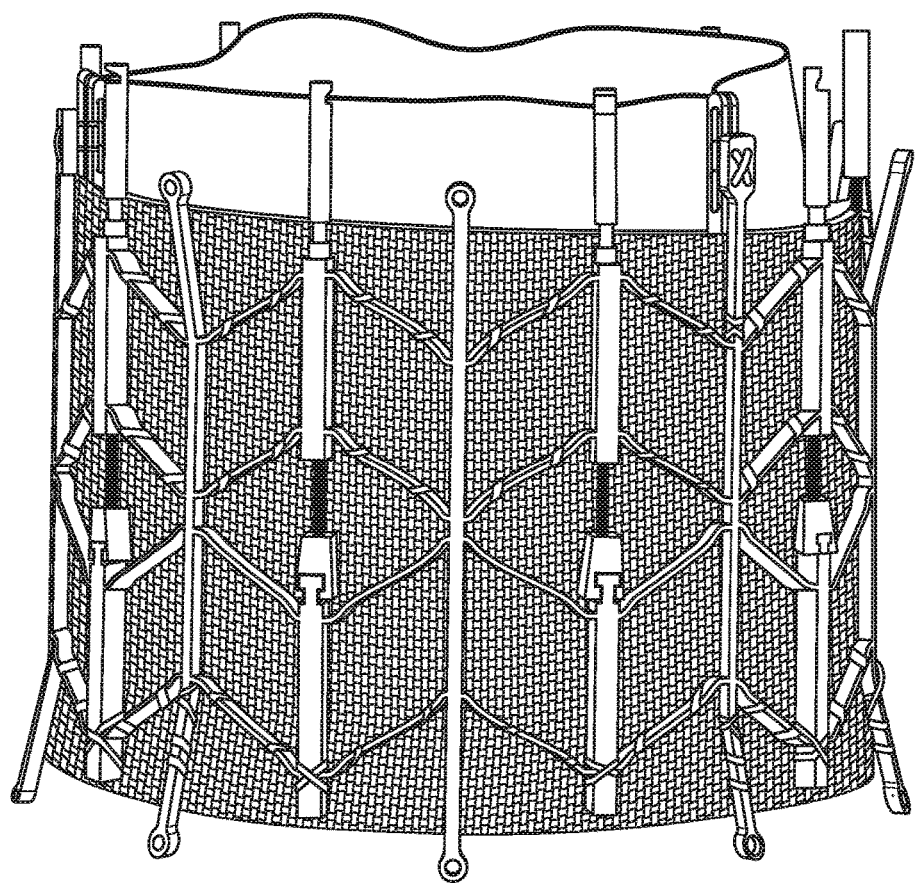
Figure 185:
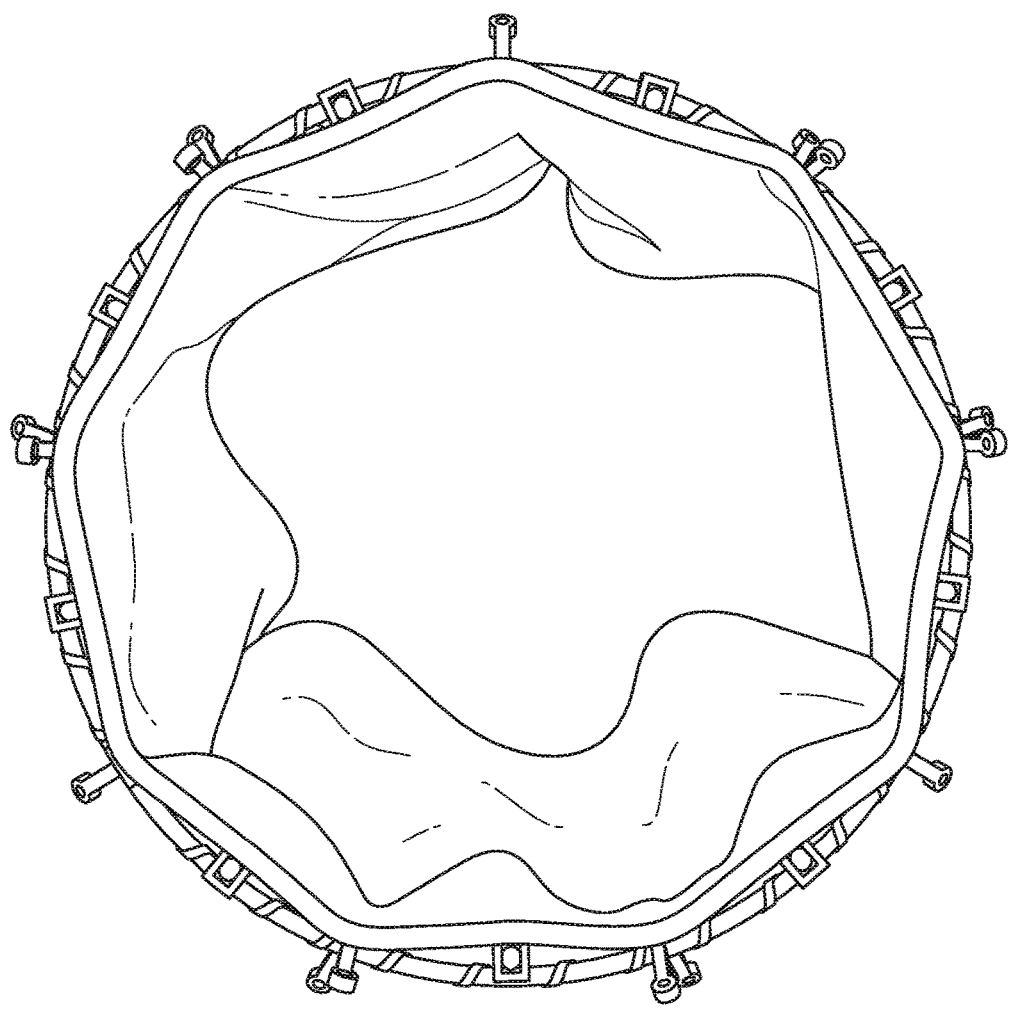
Figure 186:
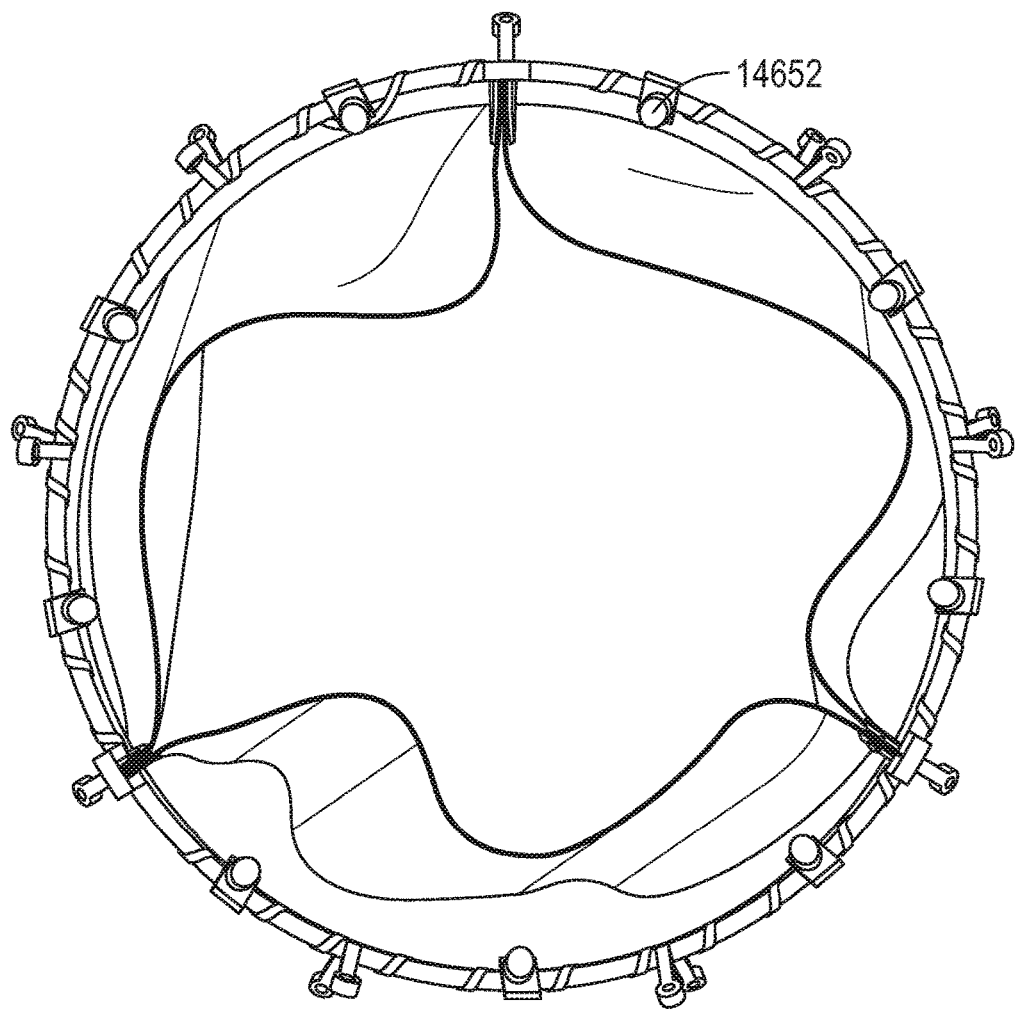
Figure 187:
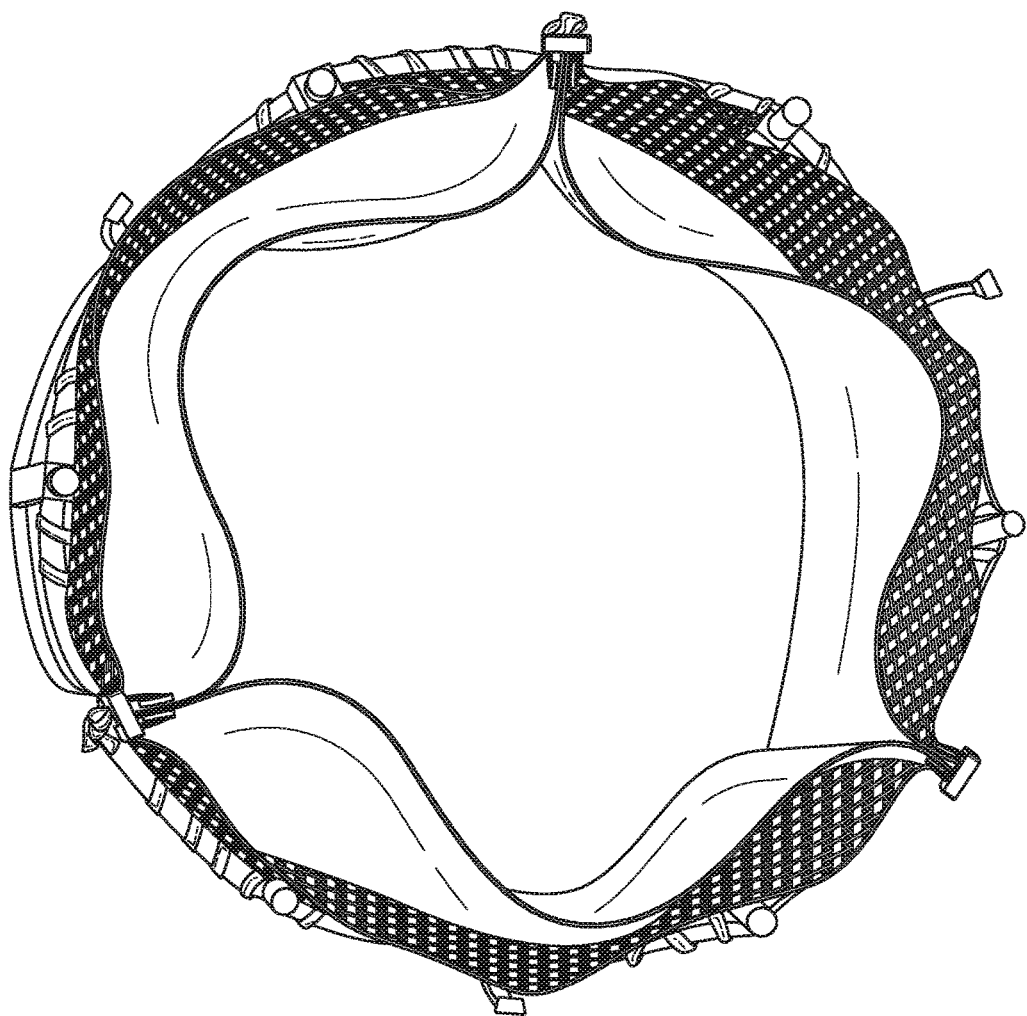
Figure 188:
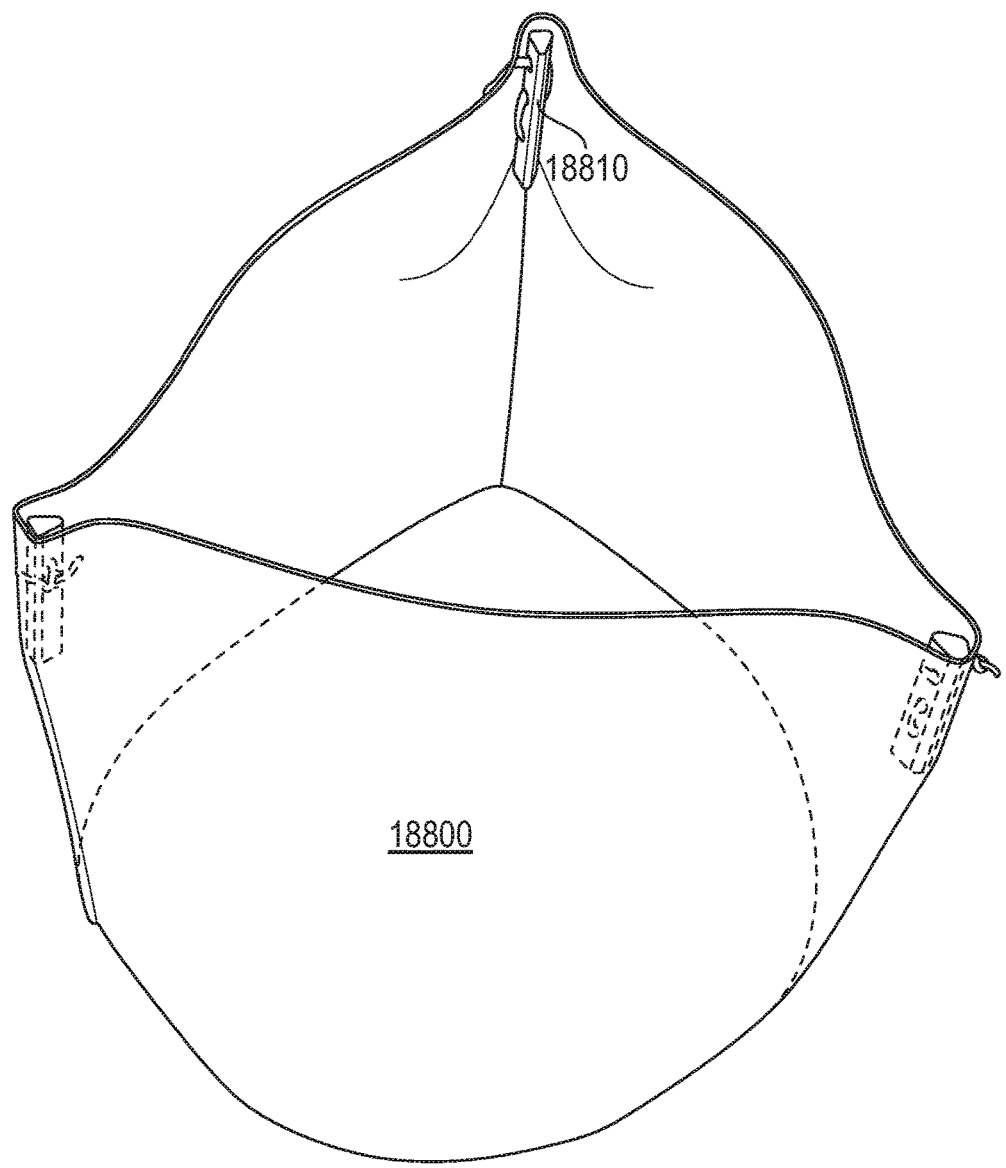
Figure 189:
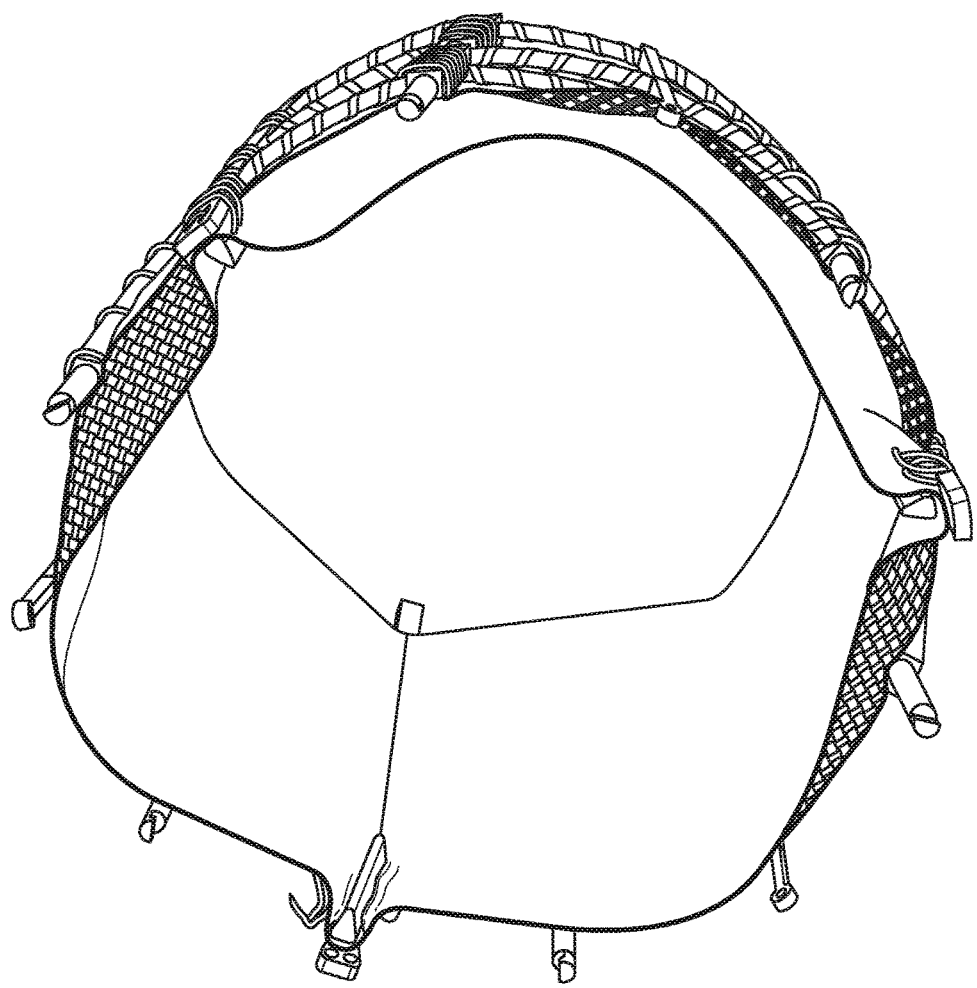
Figure 190:
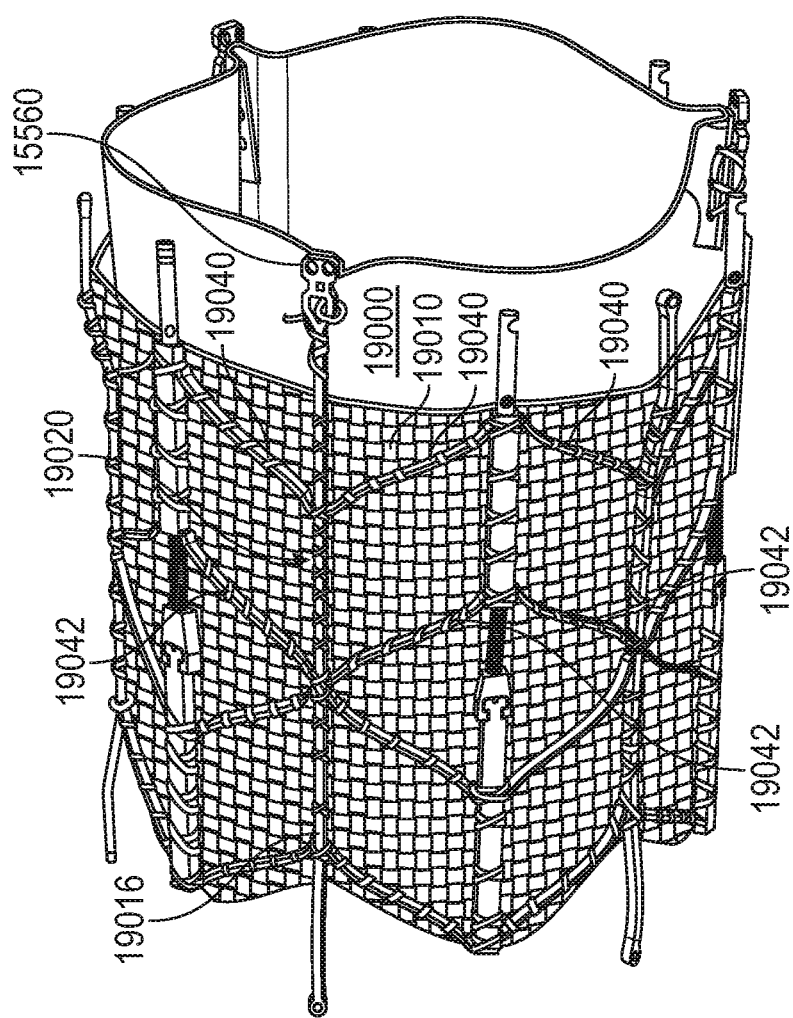
Figure 191:
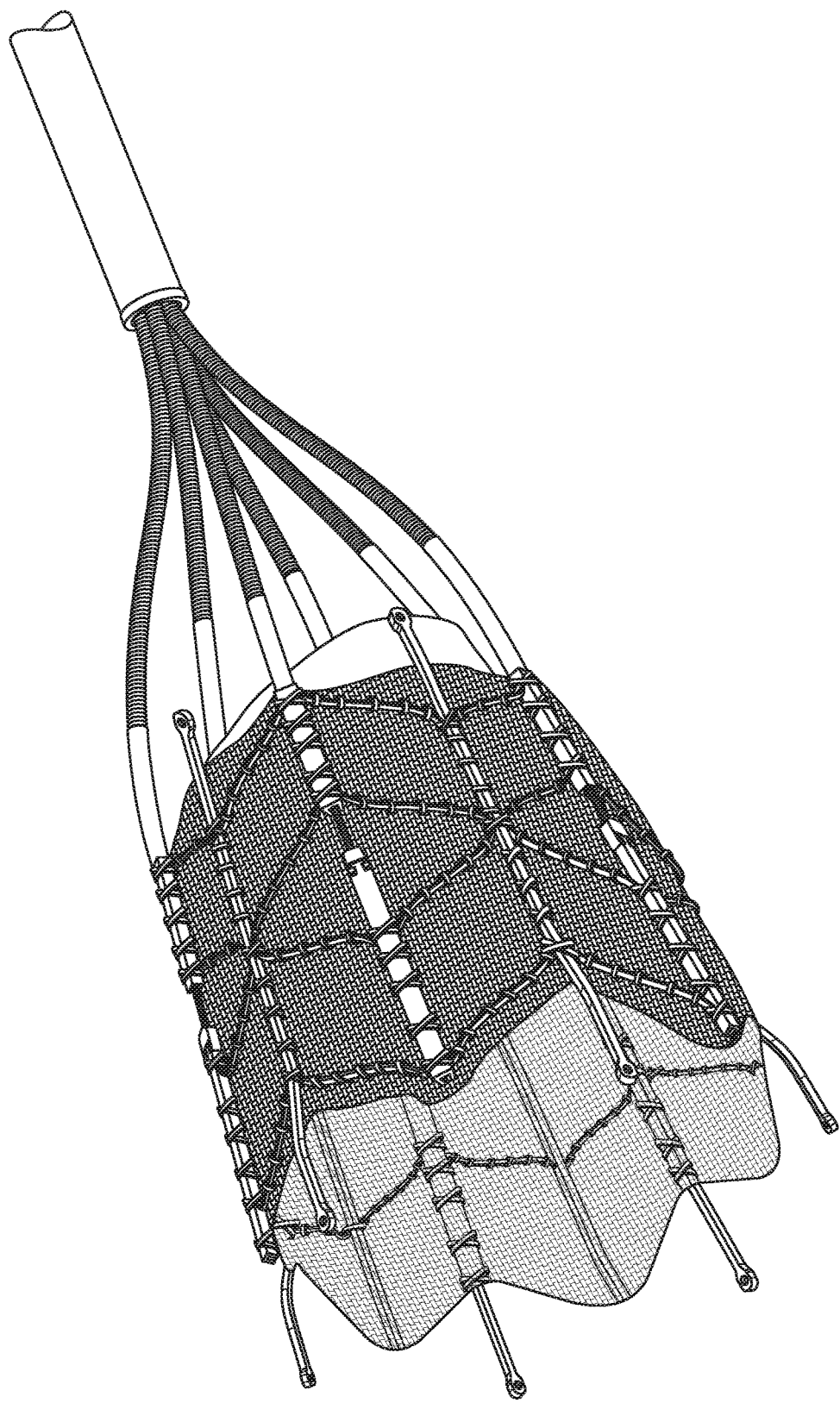
Figure 192:
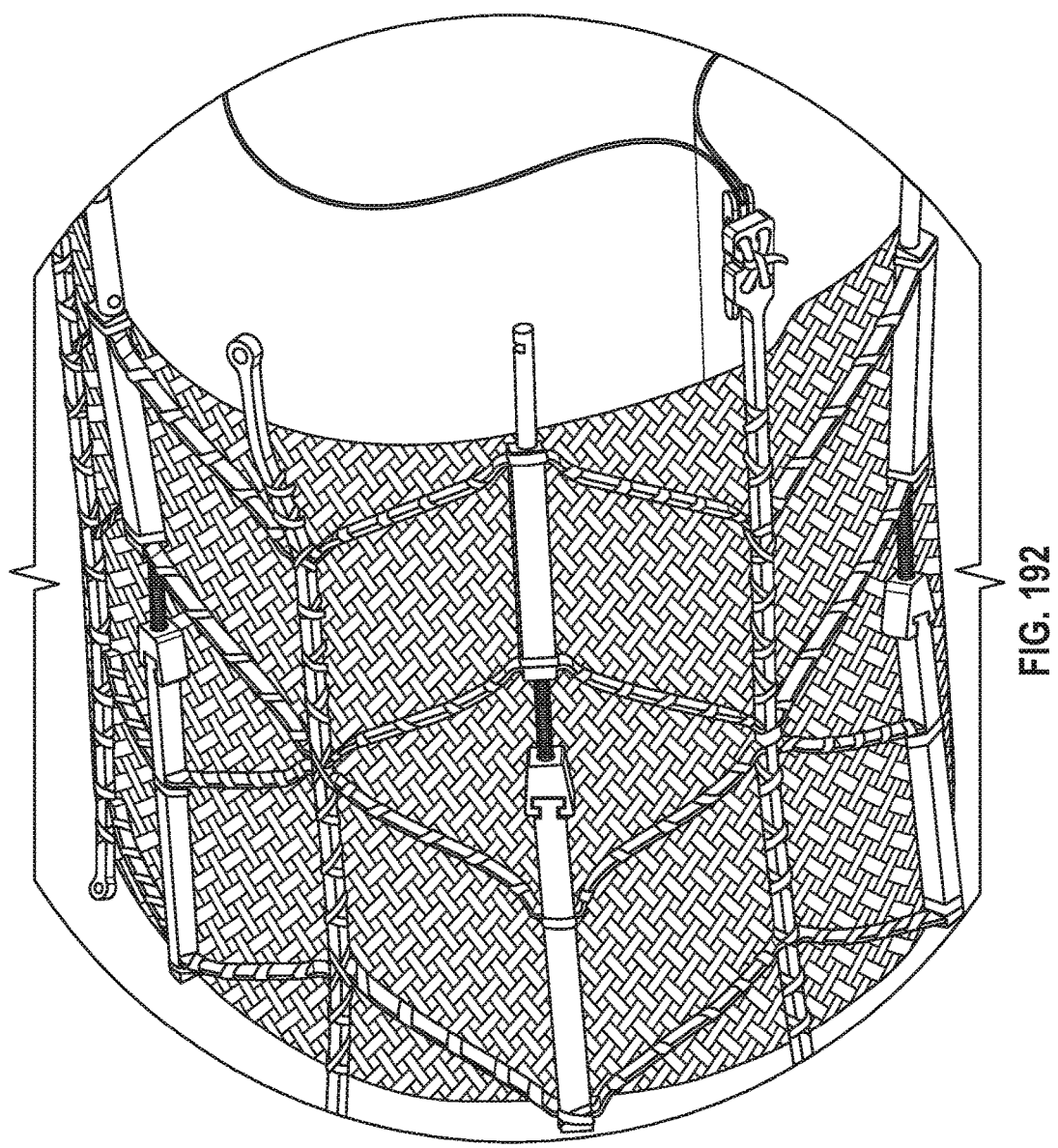
Figure 193:
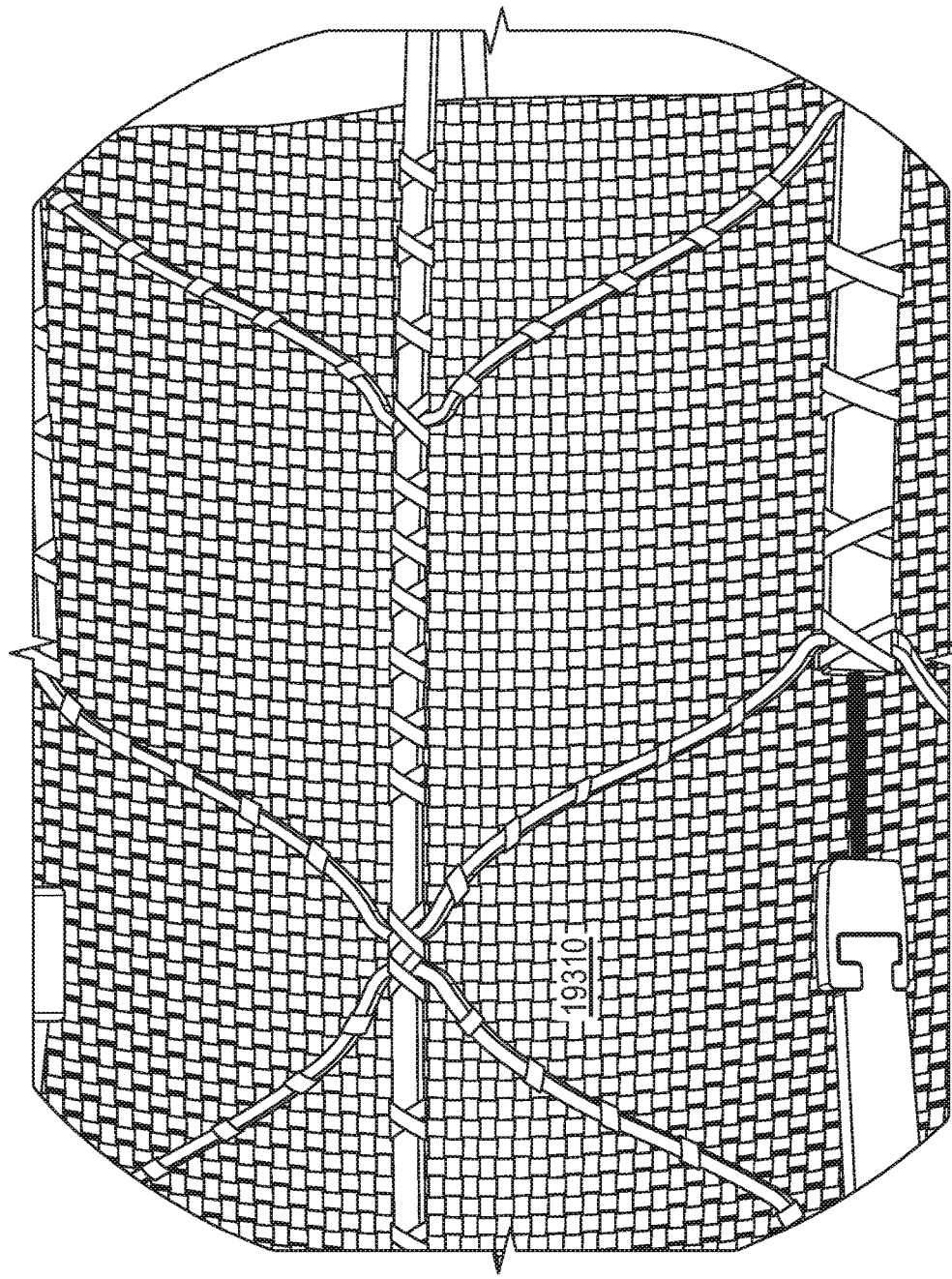
Figure 194:
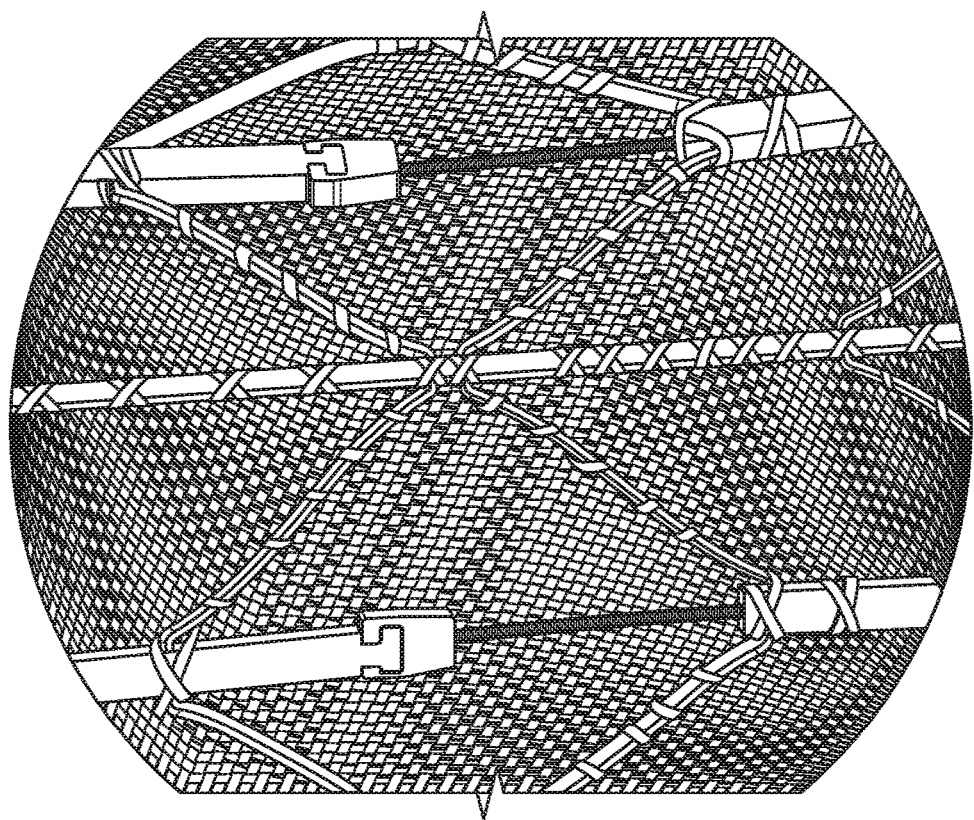
Figure 195:
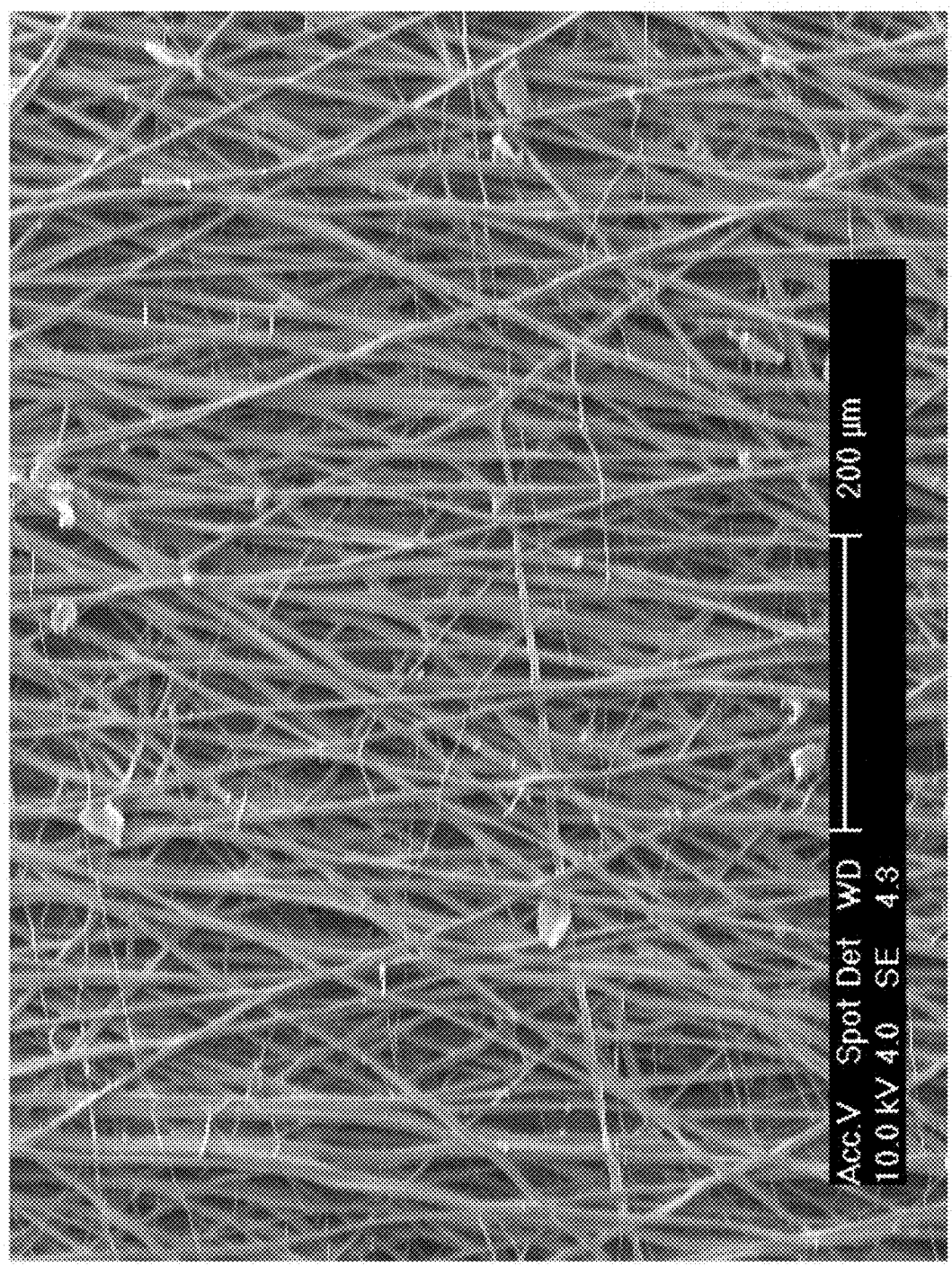
Figure 196:
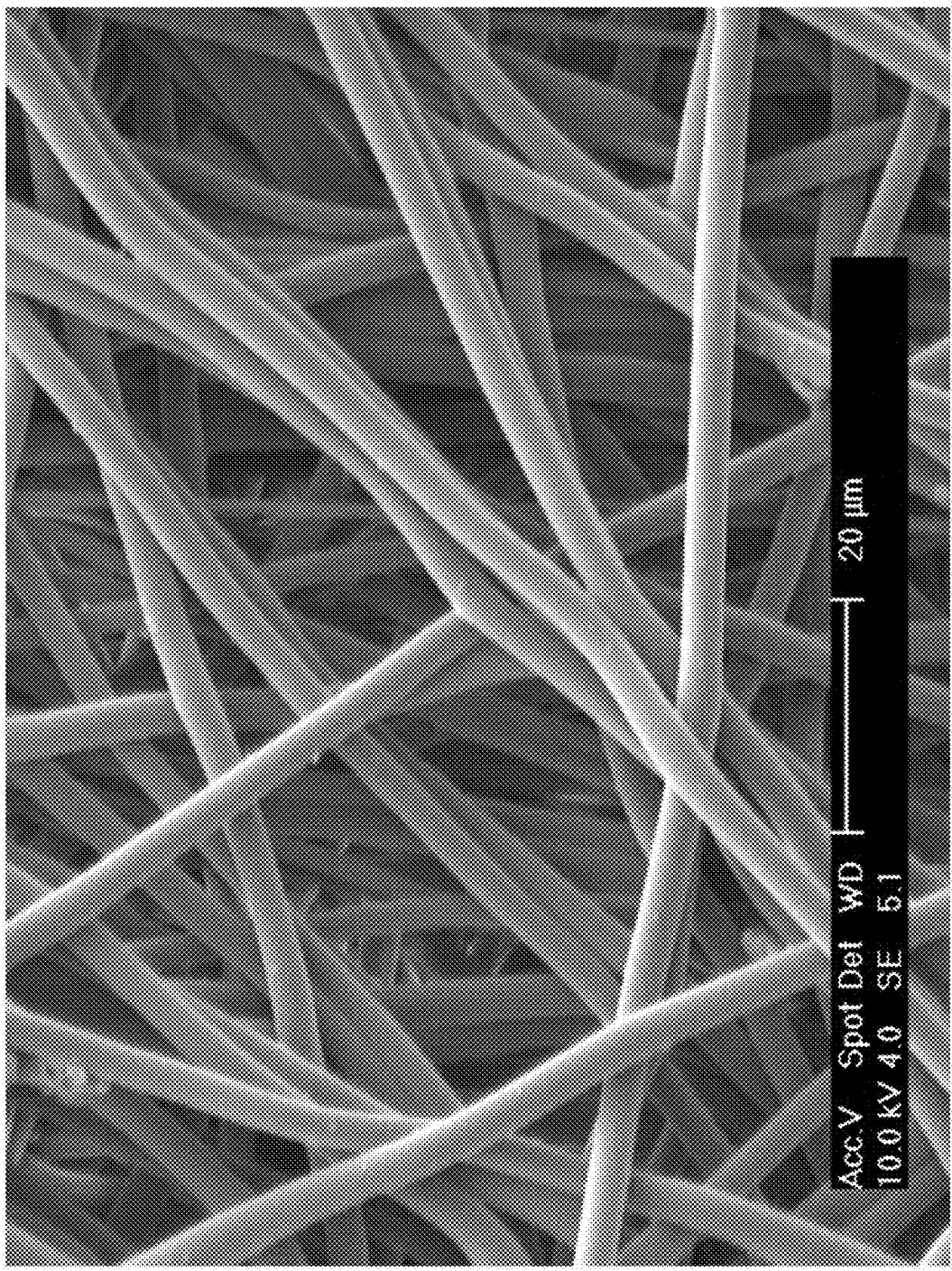
Figure 197:
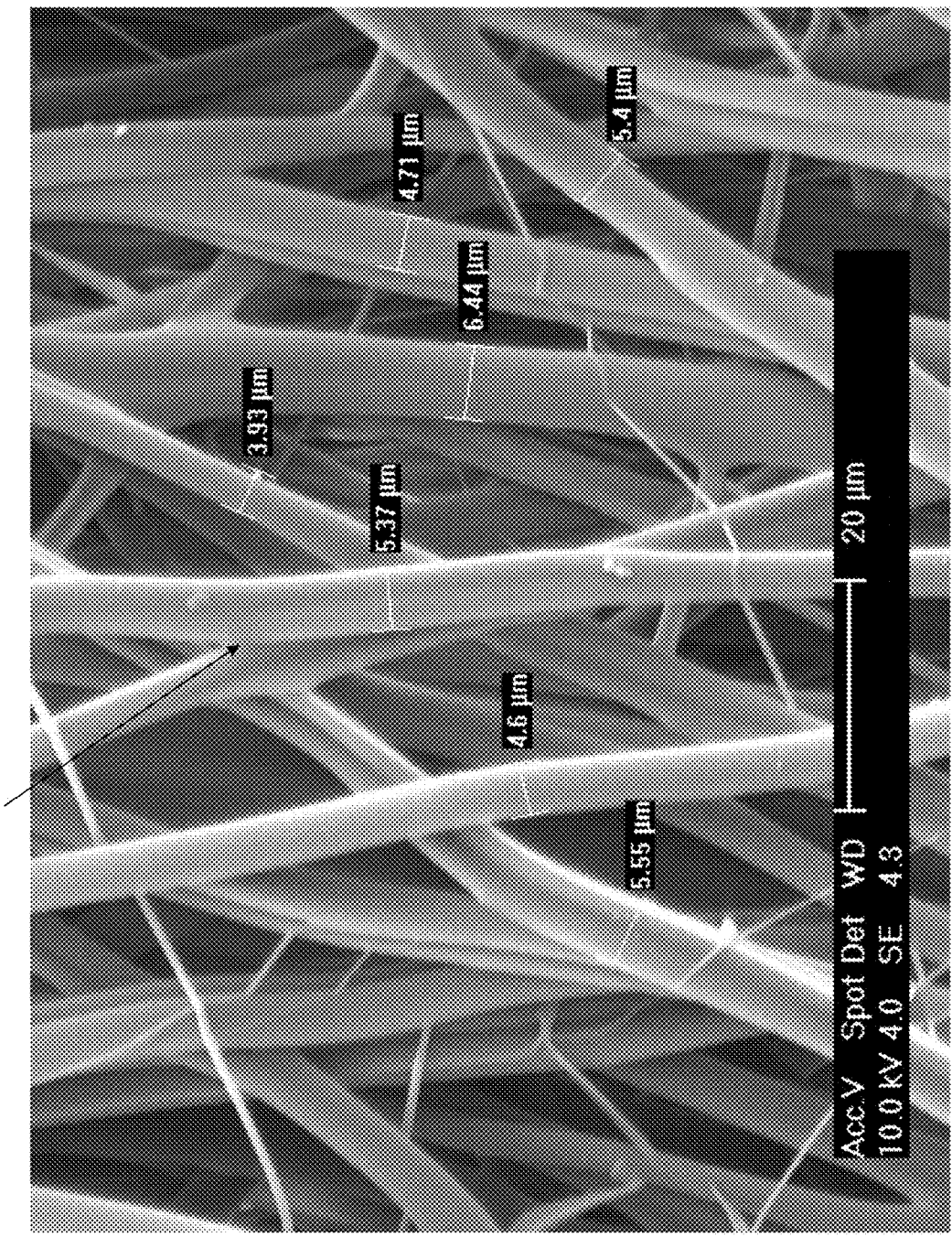
Figure 198:
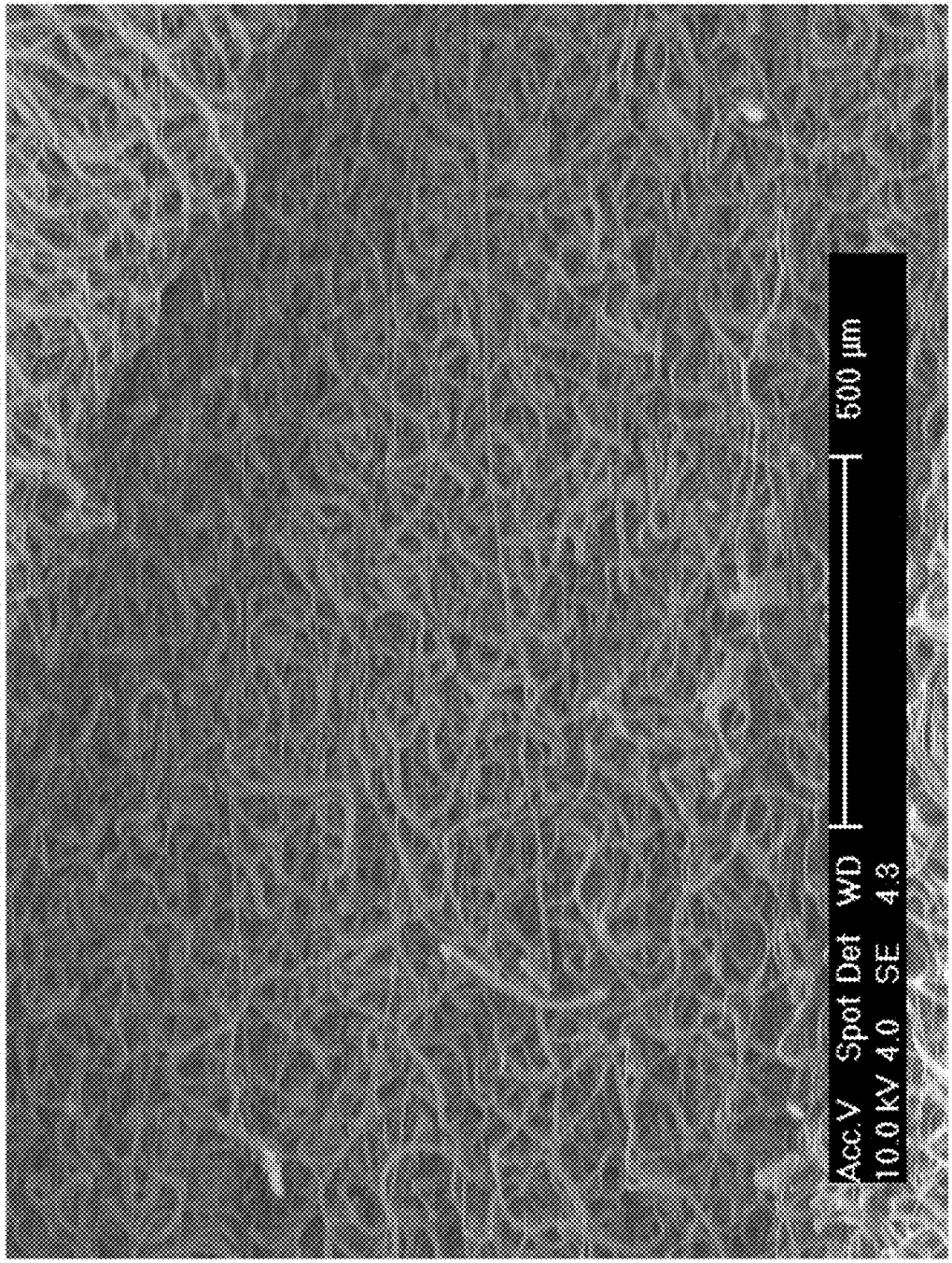
Figure 199:
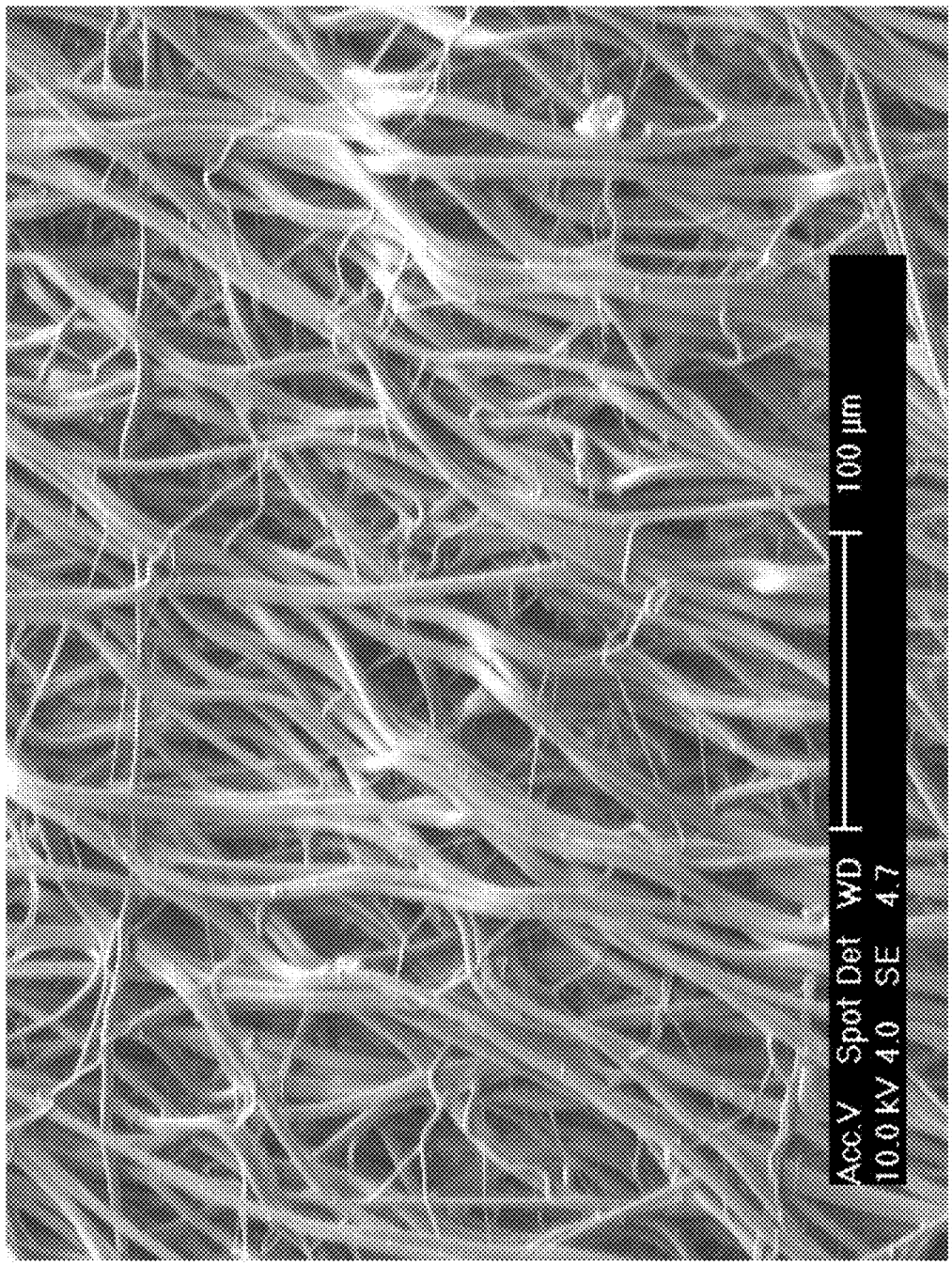
Figure 200:
Figure 201:
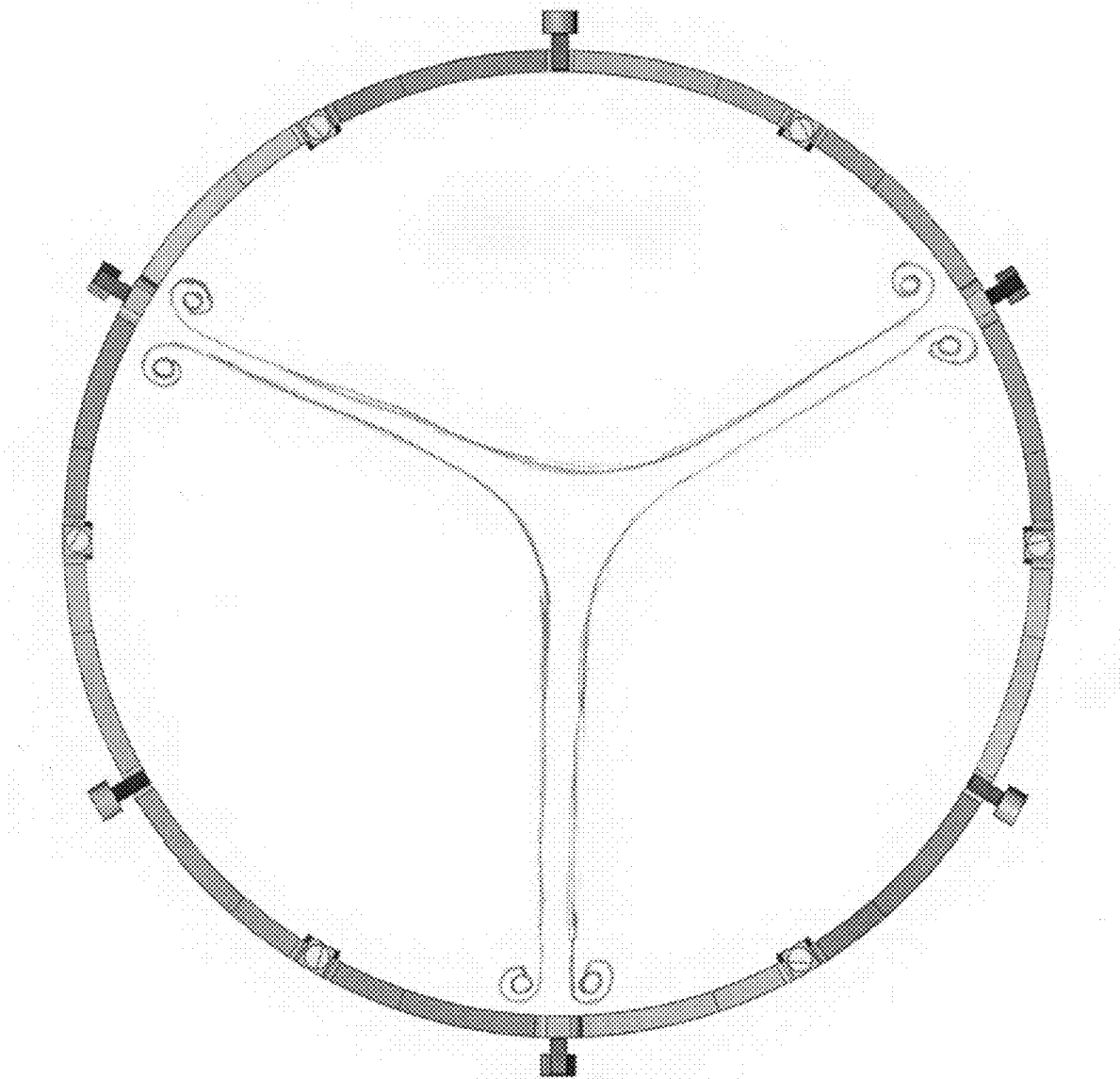
Figure 202:
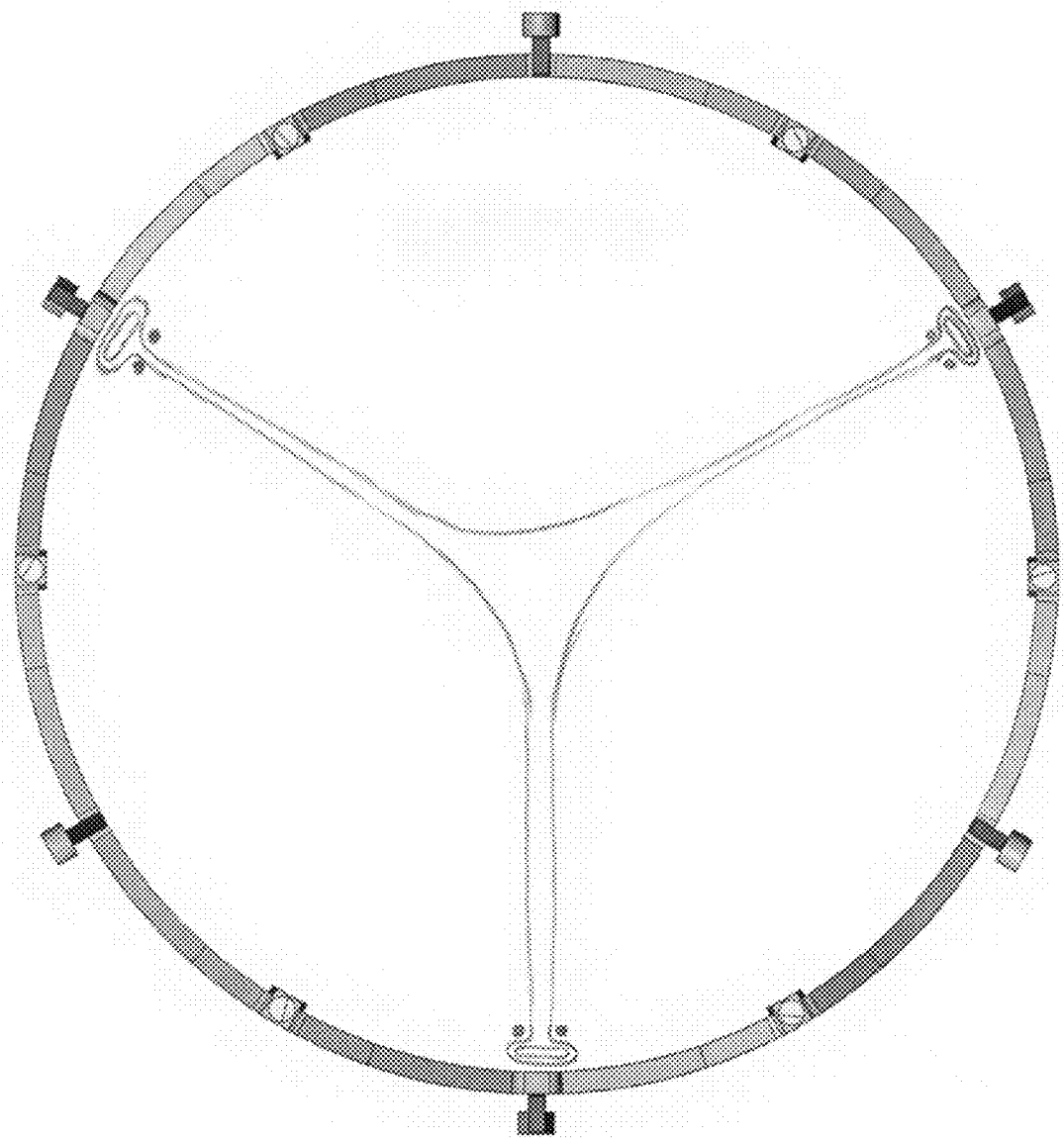
Figure 203:
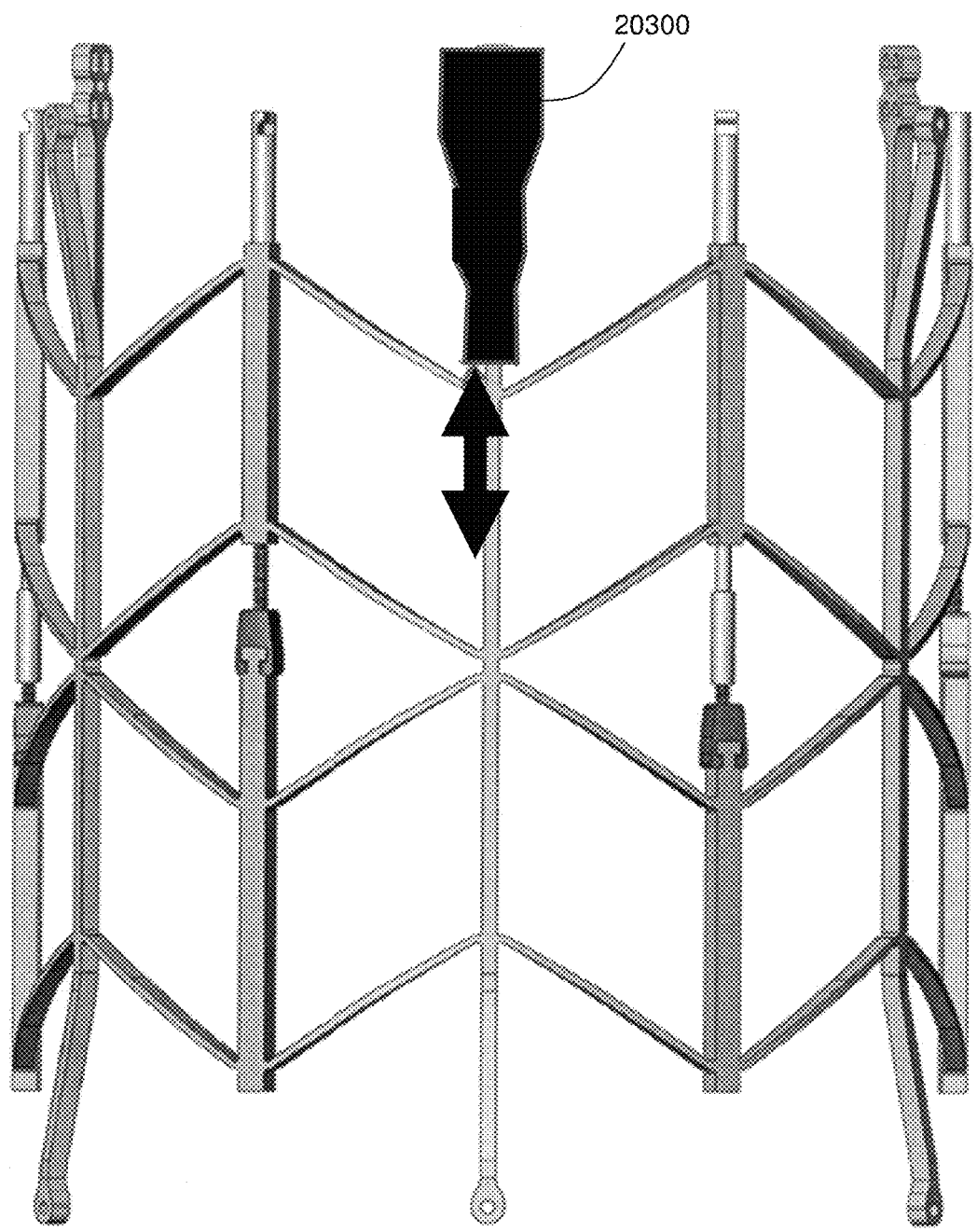

FIG. 120 is a perspective view of an exemplary embodiment of a self-expanding/forcibly-expanding lattice of an implantable stent assembly having nine lattice segments in a native, self-expanded position with jack screw assemblies disposed between adjacent pairs of repeating portions of the lattice, with jack screws through a wall of the lattice, and with each jack screw backed out in a thread-non-engaged state to allow crimp of lattice for loading into a stent delivery system;

FIG. 121 is a perspective view of the lattice of FIG. 120 in a contracted/crimped state for loading into the stent delivery system with each jack screw in a thread-non-engaged state;

FIG. 122 is a perspective view of the lattice of FIG. 121 after being allowed to return to the native position of the lattice in a deployment site with each jack screw in a thread-engaged state for further outward expansion or inward contraction of the lattice;

FIG. 123 is a perspective view of the lattice of FIG. 122 partially expanded from the state shown in FIG. 122 with each jack screw in a thread-engaged state for further outward expansion or inward contraction of the lattice;

FIG. 124 is a tilted perspective view of the lattice of FIG. 123 partially expanded from the state shown in FIG. 123 with each jack screw in a thread-engaged state for further outward expansion or inward contraction of the lattice;

FIG. 125 is a perspective view of the lattice of FIG. 124 further expanded near a maximum expansion of the lattice with each jack screw in a thread-engaged state;

FIG. 126 is a fragmentary, enlarged perspective and longitudinal cross-sectional view of a portion of two adjacent halves of repeating portions of an alternative exemplary embodiment of a self-expanding/forcibly-expanding lattice of an implantable stent assembly with a separate jack screw assembly connecting the two adjacent halves and with a lattice-disconnect tube of a stent delivery system in an engaged state covering a pair of drive screw coupler parts therein and with the jack screw in a thread-engaged state for further outward expansion or inward contraction of the lattice;

FIG. 127 is a fragmentary, further enlarged portion of the two adjacent halves of the repeating portions and intermediate jack screw assembly of FIG. 125 with the disconnect tube in a disengaged state with respect to the pair of drive screw coupler parts;

FIG. 128 is a fragmentary enlarged portion of the two adjacent halves of the repeating portions and intermediate jack screw assembly of FIG. 125 with the disconnect tube in a disengaged state and with the pair of drive screw coupler parts disconnected from one another;

FIG. 129 is a perspective view of another exemplary embodiment of a self-expanding/forcibly-expanding lattice of an implantable stent assembly having nine separate lattice segments with an exemplary embodiment of a proximal disconnect block of a stent delivery system as an alternative to the disconnect tube of FIGS. 126 to 128 with the proximal disconnect block in an engaged state covering a pair of drive screw coupler parts therein and with each jack screw in a thread-engaged state for further outward expansion or inward contraction of the lattice;

FIG. 130 is a perspective view of the lattice of FIG. 129 with the proximal disconnect blocks of the delivery system disconnected from the lattice with the proximal disconnect block in a disengaged state with respect to the pair of drive screw coupler parts and illustrating how all of the pairs of drive screw coupler parts can be coupled for simultaneous release;

FIG. 131 is a perspective view of another exemplary embodiment of a self-expanding/forcibly-expanding lattice of an implantable stent assembly having nine separate lattice segments connected to intermediate tubes for jack screws with each jack screw in a thread-engaged state for further outward expansion or inward contraction of the lattice;

FIG. 132 is a top plan view of the lattice of FIG. 131;

FIG. 133 is a perspective view of another exemplary embodiment of a self-expanding/forcibly-expanding lattice of an implantable stent assembly having nine lattice segments with locally thicker sections of lattice to accommodate and connect to non-illustrated jack screw assemblies;

FIG. 134 is a perspective view of another exemplary embodiment of a self-expanding/forcibly-expanding lattice of an implantable stent assembly having nine lattice segments with bent-over tabs for connecting to non-illustrated jack screw assemblies;

FIG. 135 is a perspective view of another exemplary embodiment of a self-expanding/forcibly-expanding lattice of an implantable valve assembly having six lattice segments in an expanded position with jack screw assemblies disposed between adjacent pairs of repeating portions of the lattice and having three valve leaflets and jack screws through a wall of the lattice in a thread-non-engaged state of the jack screw;

FIG. 136 is a plan view of the valve assembly of FIG. 135;

FIG. 137 is a perspective view of the valve assembly of FIG. 135 in a partially compressed state of the lattice without the valve leaflets and with each jack screw in a thread-non-engaged state;

FIG. 138 is a perspective view of another exemplary embodiment of a self-expanding/forcibly-expanding lattice of an implantable valve assembly having six lattice segments in a native, self-expanded position with jack screw assemblies attached at an interior surface between adjacent pairs of segments of the lattice without the valve leaflets and with each of the jack screws in a thread-engaged state for further outward expansion or inward contraction of the lattice;

FIG. 139 is a perspective view of the lattice of FIG. 138 in a contracted/crimped state for loading into the stent delivery system with each jack screw in a thread-non-engaged state;

FIG. 140 is a tilted perspective view of the lattice of FIG. 138;

FIG. 141 is a perspective view of the lattice of FIG. 138 partially expanded from the state shown in FIG. 138 with each jack screw in an engaged state for further outward expansion or inward contraction of the lattice;

FIG. 142 is a perspective view of the lattice of FIG. 138 further expanded near a maximum expansion of the lattice with each jack screw in an engaged state for further outward expansion or inward contraction of the lattice;

FIG. 143 is a side elevational view of another exemplary embodiment of a self-expanding/forcibly-expanding lattice of an implantable stent assembly having nine lattice segments in a native, self-expanded position with jack screw assemblies integral with the stent assembly and with each of the jack screws in a thread-engaged state for outward expansion and inward contraction of the lattice and with a portion of the stent assembly delivery system having connector control tubes with one connector control tube shown in transparent form;

FIG. 144 is a top plan view of the lattice of FIG. 143;

FIG. 145 is a perspective view of the lattice of FIG. 143 from above;

FIG. 146 is a side elevational view of the lattice of FIG. 143 with the connector control tubes of the delivery system in a non-engaged state and the respective connector portions of the jack screw assemblies and the delivery system shown in a disconnected state after implantation;

FIG. 147 is an enlarged, fragmentary, perspective view of a portion of the lattice of FIG. 143 from outside a side thereof;

FIG. 148 is an enlarged, fragmentary, perspective view of a portion of the lattice of FIG. 143 from above a top thereof;

FIG. 149 is a perspective view of the lattice of FIG. 143 from above a side thereof with the lattice expanded by the jack screw assemblies almost to a fullest expanded extent;

FIG. 150 is a perspective view of the lattice of FIG. 143 from a side thereof with the lattice contracted by the jack screw assemblies almost to a fullest contracted extent;

FIG. 151 is a perspective view of the lattice of FIG. 150 from a side thereof tilted with respect to FIG. 150;

FIG. 152 is a fragmentary, enlarged, perspective view of an upper portion of the lattice of FIG. 151;

FIG. 153 is a fragmentary, enlarged, perspective and vertical cross-sectional view of an intermediate portion of the lattice of FIG. 150;

FIG. 154 is a perspective view of the lattice of FIG. 143 before manufacture of the stent assembly and illustrating one exemplary embodiment for manufacturing the lattice of the stent assembly;

FIG. 155 is a side elevational view of another exemplary embodiment of a self-expanding/forcibly-expanding lattice of an implantable stent assembly having six lattice segments in a partially expanded state with each of the jack screws in a thread-engaged state for further outward expansion and in a slacked state for inward contraction of the lattice, with jack screw assemblies integral with the stent assembly through key-hole slots in the lattice, and with an alternative exemplary embodiment of outer lattice fixation paddles bent outwards to shape the lattice into a longitudinal hourglass;

FIG. 156 is a top plan view of the implantable stent assembly of FIG. 155 showing the key-hole slots in the lattice for the jack screw assemblies;

FIG. 157 is a perspective view of the lattice of FIG. 156 from above a side of the top thereof;

FIG. 158 is a top plan view of the lattice of FIG. 156;

FIG. 159 is an enlarged, fragmentary, perspective view of a portion of a top of the lattice of FIG. 156;

FIG. 160 is a perspective view of an upper portion of the lattice of FIG. 156 from the outside of a side thereof;

FIG. 161 is a side elevational view of the lattice of FIG. 156 in a self-expanded, natural state with each of the jack screws in a thread-engaged state for outward expansion and in a slacked state for inward contraction of the lattice;

FIG. 162 is a side elevational view of the lattice of FIG. 161 in a self-expanded, natural state with each of the jack screws in a thread-engaged state for inward contraction and in a slacked state for outward expansion of the lattice;

FIG. 163 is a side elevational view of the lattice of FIG. 162 in a forcibly contracted state with each of the jack screws in a thread-engaged state for further inward contraction or outward expansion of the lattice;

FIG. 164 is a side elevational view of the lattice of FIG. 163 in a forcibly contracted state by a delivery sheath;

FIG. 165 is a side elevational view of the lattice of FIG. 161 in a forcibly expanded state with each of the jack screws in a thread-engaged state for further outward expansion or inward contraction of the lattice;

FIG. 166 is a side elevational view of the lattice of FIG. 165 in a further forcibly expanded state with each of the jack screws in a thread-engaged state for further outward expansion or inward contraction of the lattice;

FIG. 167 is a side elevational view of another exemplary embodiment of a self-expanding/forcibly-expanding lattice of an implantable stent assembly having six lattice segments in a forcibly expanded position with jack screw assemblies having intermediate jack screw nuts longitudinally staggered about the circumference of the lattice;

FIG. 168 is a fragmentary, perspective view of the lattice of FIG. 167 in a forcibly contracted position showing the staggered positions of the jack screw nuts;

FIG. 169 is a fragmentary, perspective view of a distal end of an exemplary embodiment delivery system containing the lattice of FIGS. 156 to 166 in a forcibly expanded and implantation-ready state;

FIG. 170 is a fragmentary, side elevational view of the delivery system and lattice of FIG. 169 with the connector control sub-assembly in a lattice-connected state;

FIG. 171 is a fragmentary, side elevational view of the delivery system and lattice of FIG. 169 with the connector control sub-assembly in a lattice-disconnected state with each of the disconnect tubes respectively retracted proximally from each of the jack-screw-connector pairs but before the jack-screw-connector pairs disconnect from one another;

FIG. 172 is a fragmentary, side elevational view of the delivery system and lattice of FIG. 169 with the connector control sub-assembly in a lattice-disconnected state with each of the jack-screw-connector pairs disconnected from one another and with the jack-screw-connector portion of the delivery system separated from the lattice;

FIG. 173 is a fragmentary, enlarged perspective view of the connector-control portion of the delivery system and lattice of FIGS. 169 to 172 with two control coils for two connector tubes removed to show distal and proximal sleeves residing in respective counter-bores of a tube-control puck and with a distal portion of the respective two jack-screw-control wires removed;

FIG. 174 is a photograph of a fragmentary, perspective view from a side of an exemplary embodiment of a delivery system and lattice of FIGS. 167 to 168 in a forcibly expanded state of the lattice;

FIG. 175 is a photograph of a fragmentary, perspective view from a side of the delivery system and lattice of FIG. 174 rotated with respect to FIG. 174;

FIG. 176 is a photograph of a fragmentary, perspective view from a side of the delivery system and lattice of FIG. 174;

FIG. 177 is a photograph of a fragmentary, perspective view from a side of the delivery system and lattice of FIG. 174 rotated with respect to FIG. 174;

FIG. 178 is a photograph of a fragmentary, perspective view from a side of a lattice control portion of the delivery system of FIG. 174;

FIG. 179 is a photograph of a fragmentary, enlarged, perspective view from a side of a distal portion of the lattice control portion of the delivery system of FIG. 178;

FIG. 180 is a photograph of a fragmentary, perspective view from a side of a proximal portion of the lattice control portion of the delivery system of FIG. 178;

FIG. 181 is a photograph of a perspective view from a side of an exemplary embodiment of a self-expanding/forcibly-expanding implantable heart valve assembly having nine lattice segments in an expanded state and with valve leaflets in an open state;

FIG. 182 is a photograph of a side view of the heart valve assembly of FIG. 181;

FIG. 183 is a photograph of a side view of the heart valve assembly of FIG. 181 rotated with respect to the view shown in FIG. 182;

FIG. 184 is a photograph of a side view of the heart valve assembly of FIG. 183;

FIG. 185 is a photograph of an upstream plan view of the heart valve assembly of FIG. 181;

FIG. 186 is a photograph of a downstream plan view of the heart valve assembly of FIG. 181;

FIG. 187 is a photograph of a downstream plan view of an exemplary embodiment of a self-expanding/forcibly-expanding implantable heart valve assembly having six lattice segments in an expanded state and with valve leaflets in an open state;

FIG. 188 is a photograph of a valve leaflet assembly of the heart valve assembly of FIG. 187;

FIG. 189 is a photograph of a downstream perspective view of the heart valve assembly of FIG. 187;

FIG. 190 is a photograph of a side perspective view of the heart valve assembly of FIG. 187;

FIG. 191 is a photograph of a downstream perspective view of the heart valve assembly of FIG. 187 forcibly expanded in an exemplary embodiment of a delivery system;

FIG. 192 is a photograph of a perspective view of the heart valve assembly of FIG. 187;

FIG. 193 is a photograph of an enlarged, perspective view from a side of an exemplary embodiment of a self-expanding/forcibly-expanding implantable heart valve assembly;

FIG. 194 is a photograph of an enlarged perspective view from a side of the heart valve assembly of FIG. 193 rotated with respect to the view of FIG. 193;

FIG. 195 is a photograph of an enlarged portion of an exemplary embodiment of a graft portion of a heart valve assembly in an unstretched state;

FIG. 196 is a photograph of a further enlarged first portion of the graft of FIG. 195;

FIG. 197 is a photograph of a further enlarged second portion of the graft of FIG. 195;

FIG. 198 is a photograph of the graft portion of the heart valve assembly of FIG. 195 in stretched with a 100% extension;

FIG. 199 is a photograph of the graft portion of the heart valve assembly of FIG. 198 after the stretch is removed;

FIG. 200 is a cross-sectional view of an exemplary embodiment of an adjustable valve leaflet sub-assembly of a heart valve assembly;

FIG. 201 is a cross-sectional view of another exemplary embodiment of an adjustable valve leaflet sub-assembly of a heart valve assembly;

FIG. 202 is a cross-sectional view of another exemplary embodiment of an adjustable valve leaflet sub-assembly of a heart valve assembly;

FIG. 203 is a side elevational view of an exemplary embodiment of an adjustment shim that, when moved longitudinally, takes up more or lets out more of the valve leaflet edge to shorten or lengthen the overlap portions of the valve leaflets.

Figure 204:
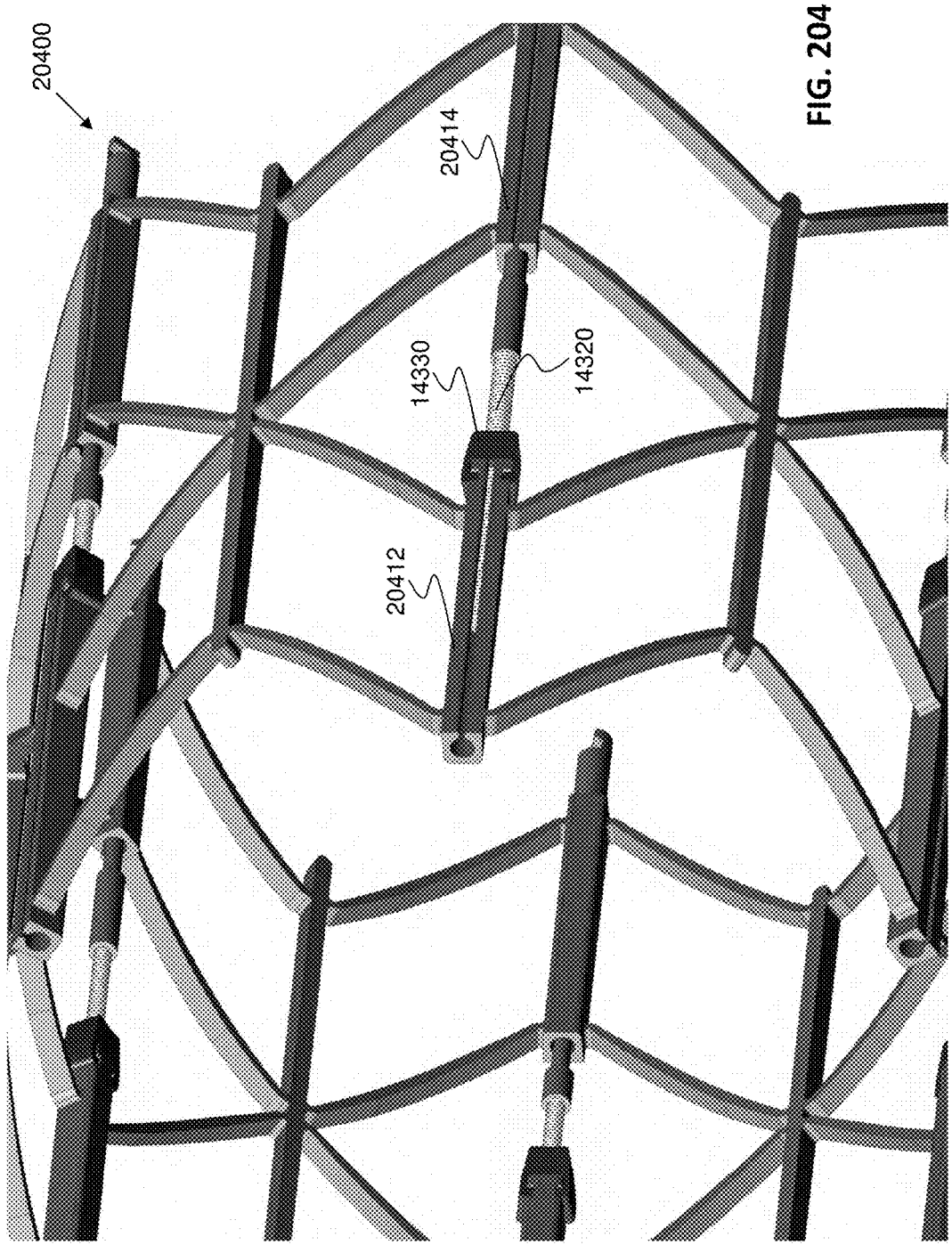
Figure 205:
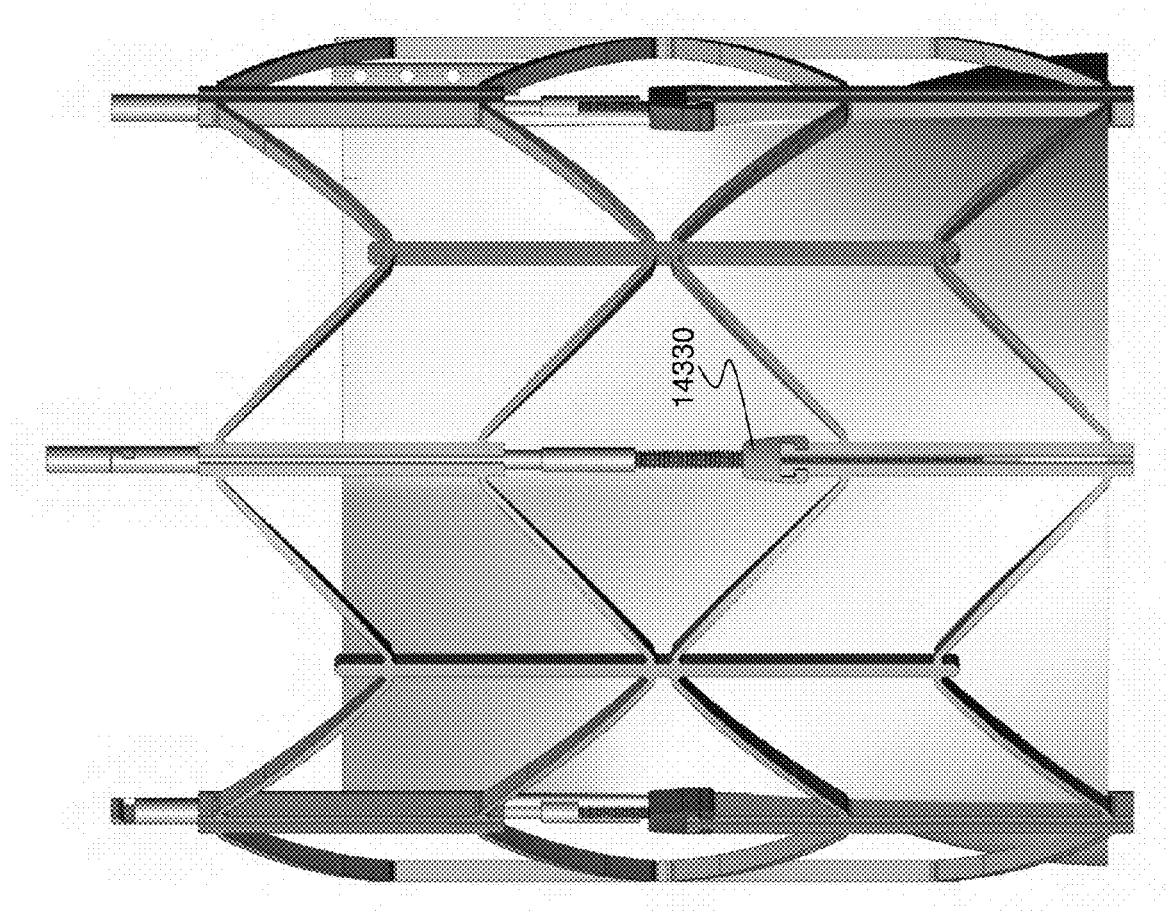
Figure 206:
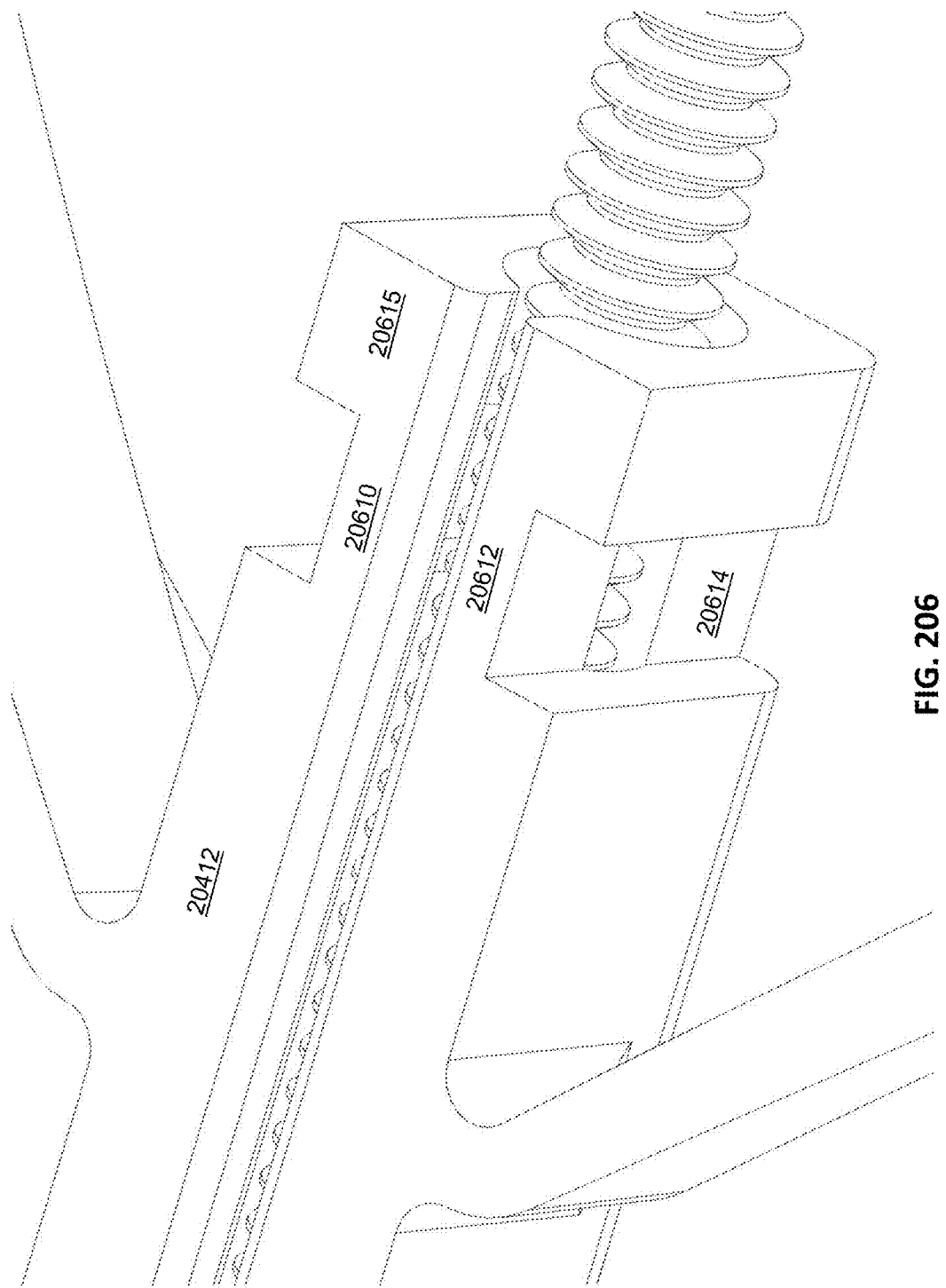
Figure 207:
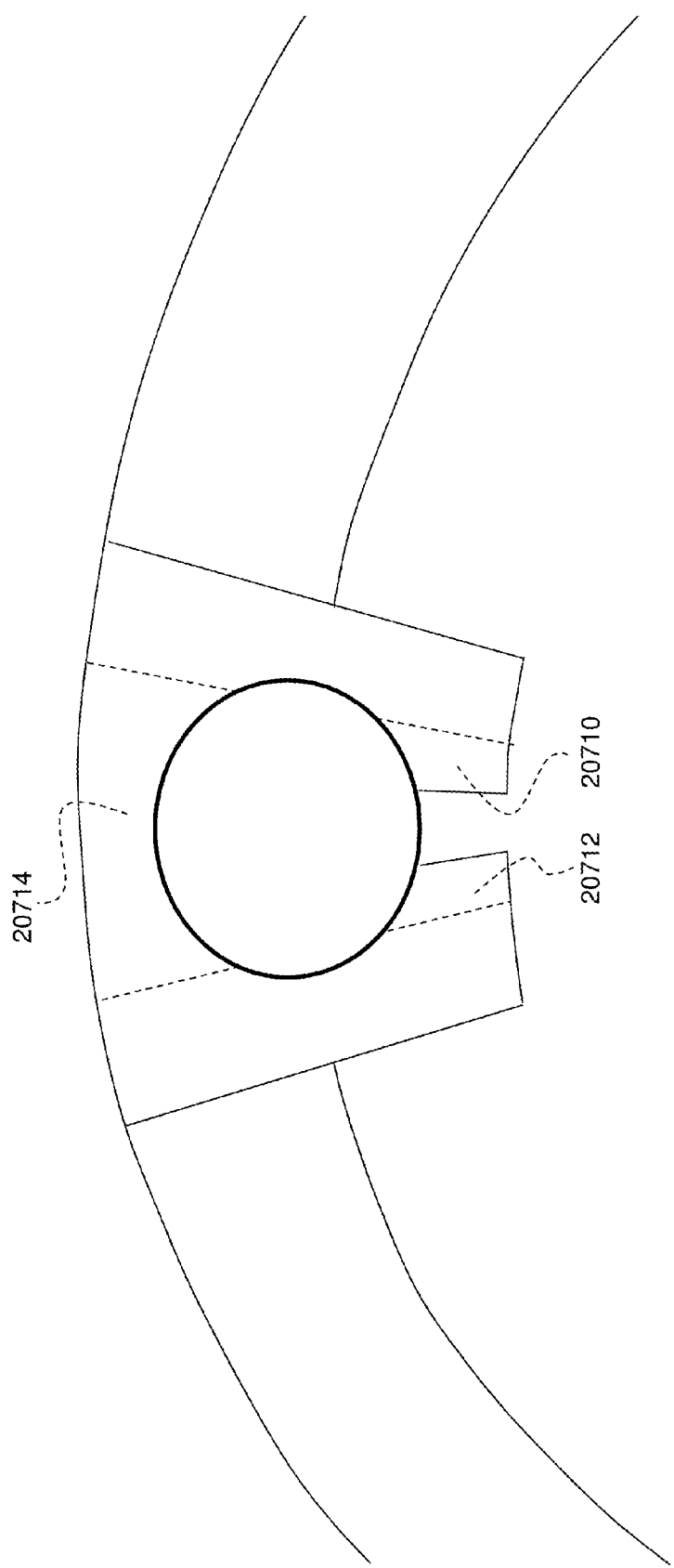
Figure 208:
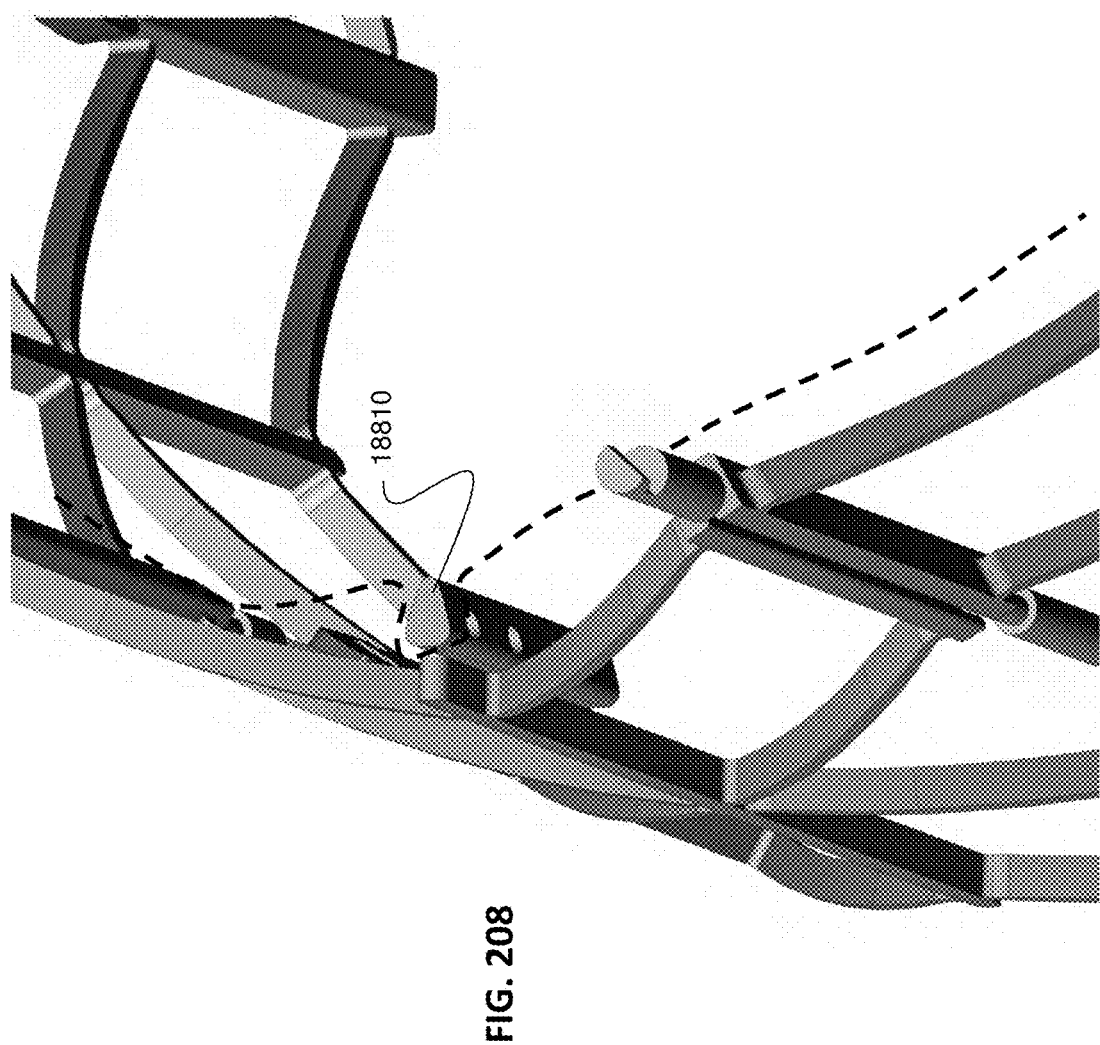
Figure 209:
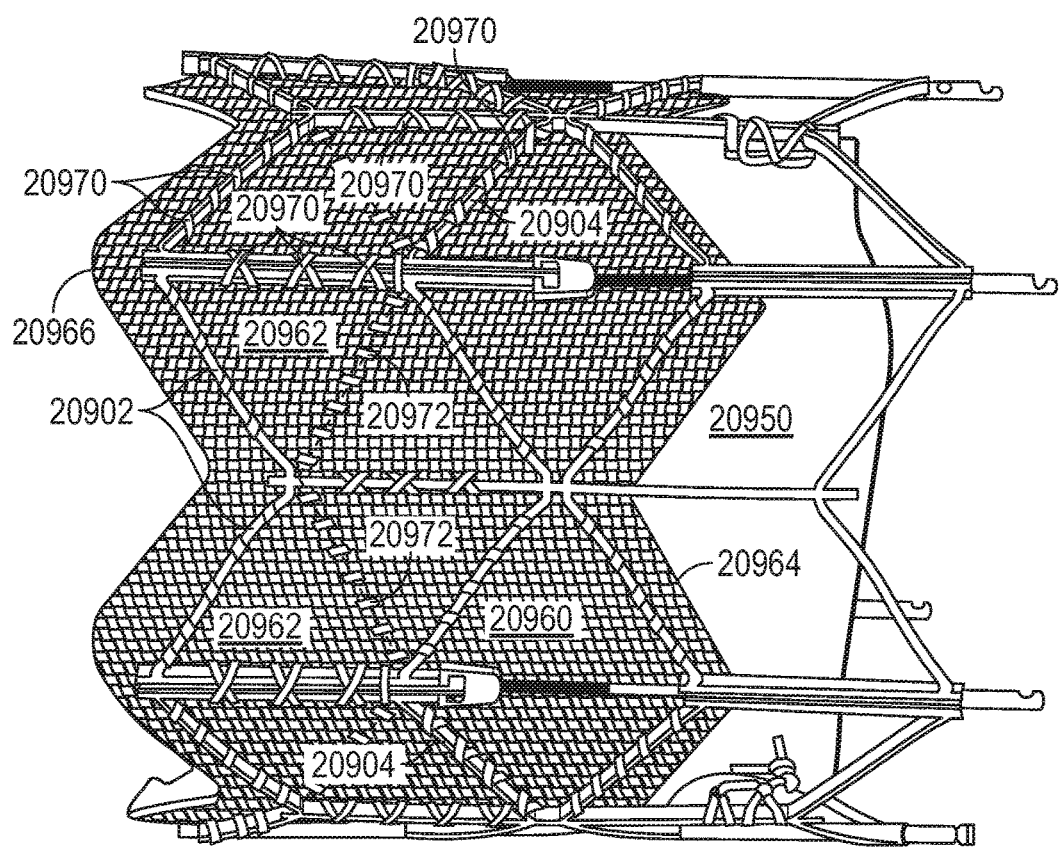
Figure 210:
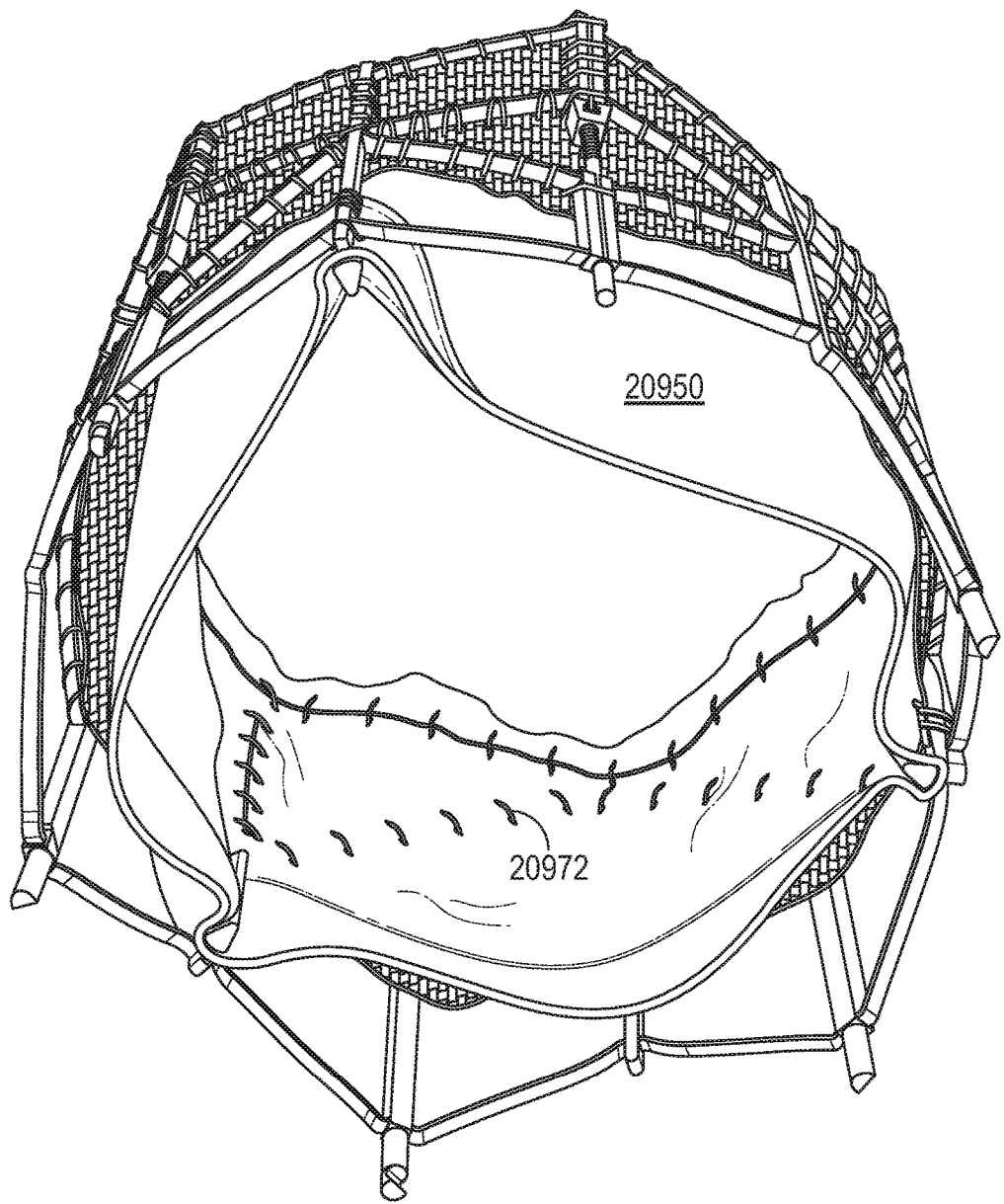
Figure 211:
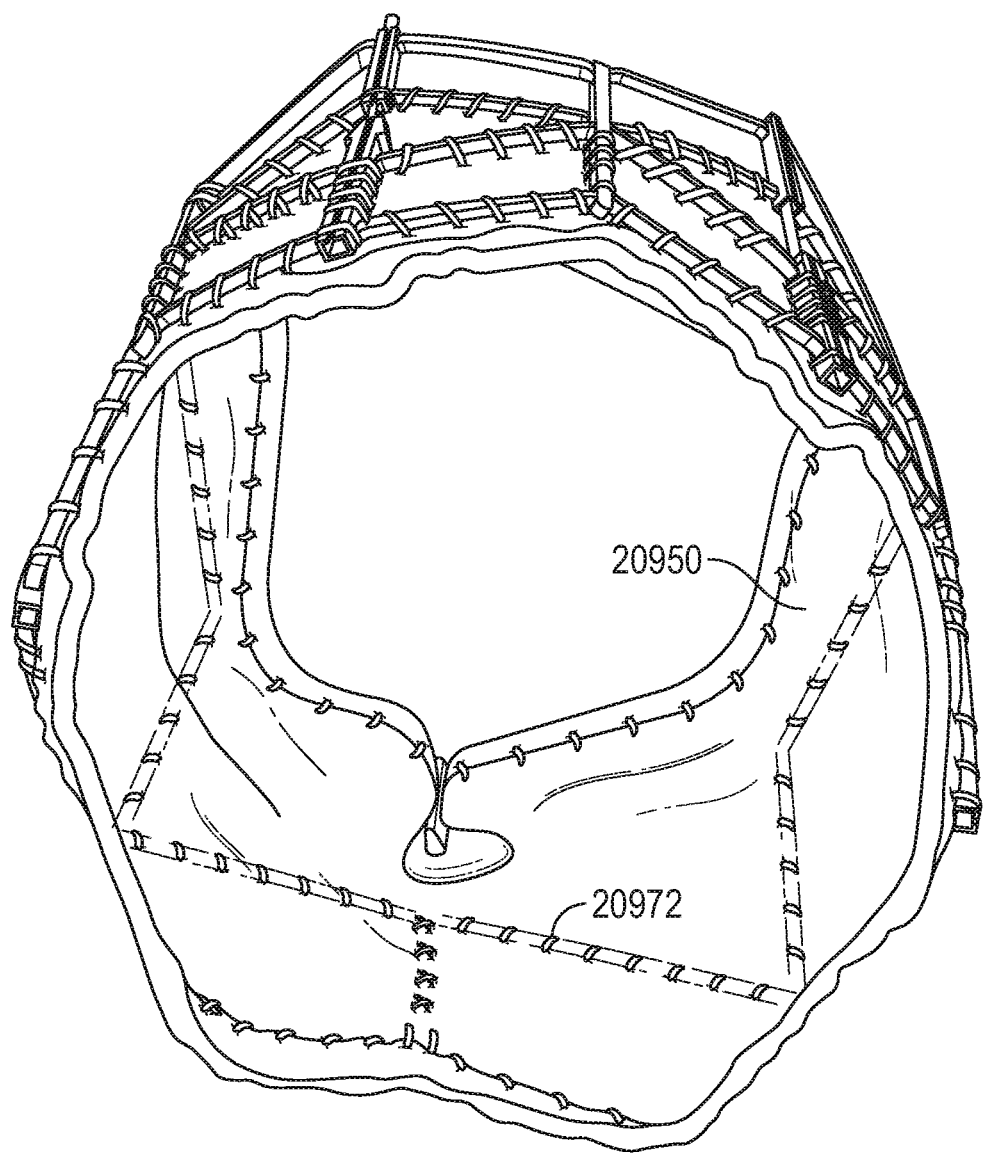
Figure 216:
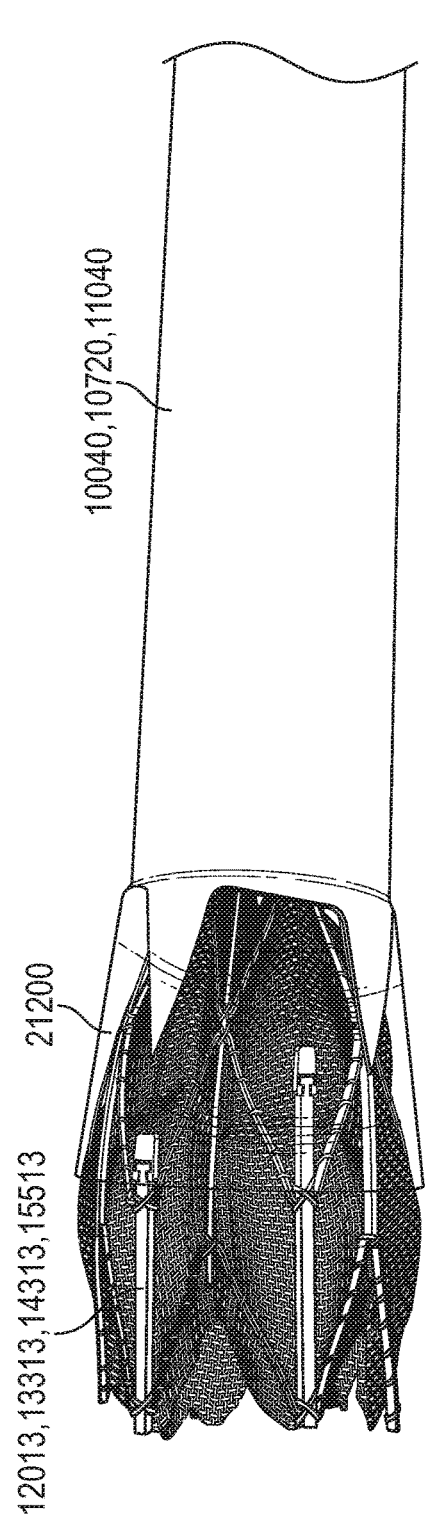
Figure 217:
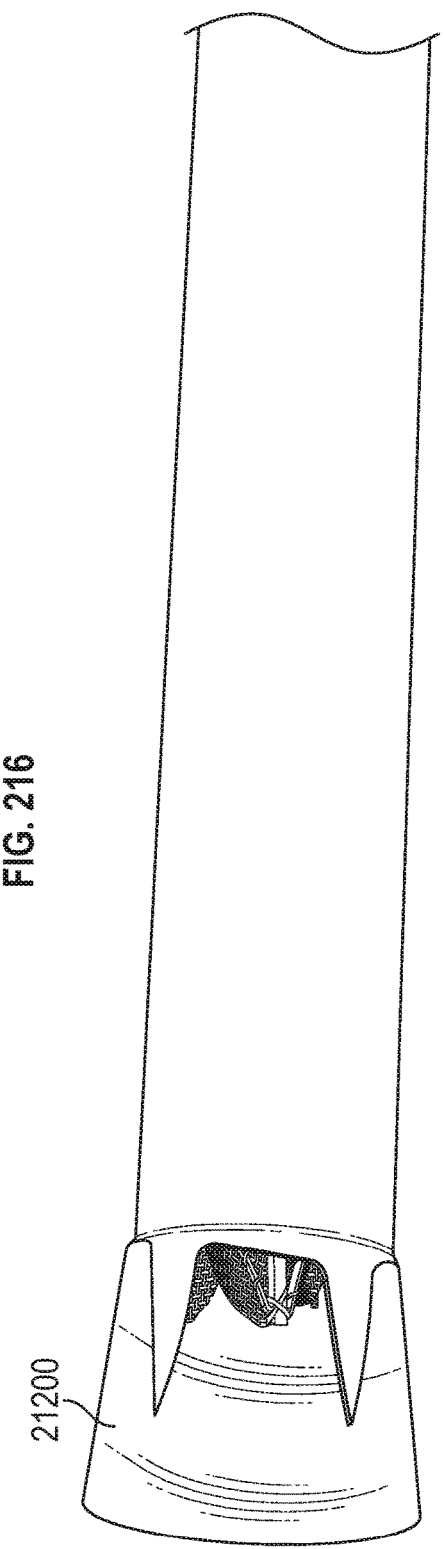
Figure 218:
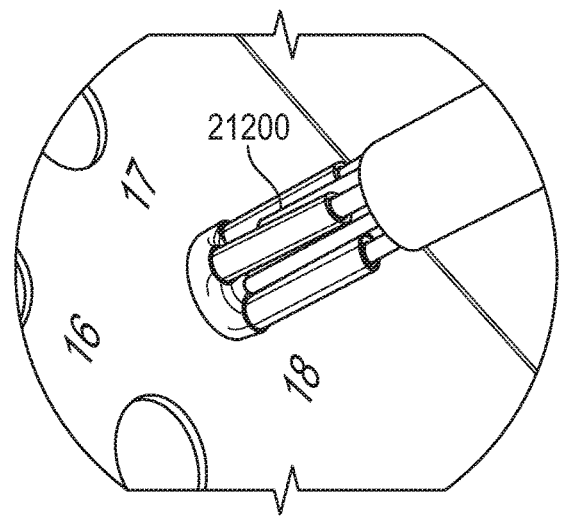
Figure 219:
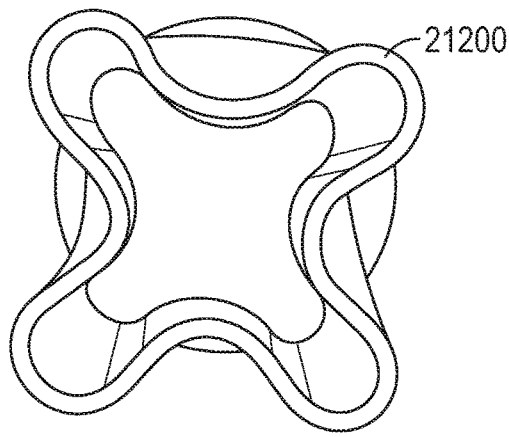
Figure 220:
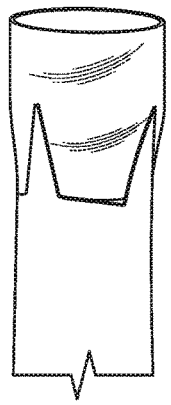
Figure 221:
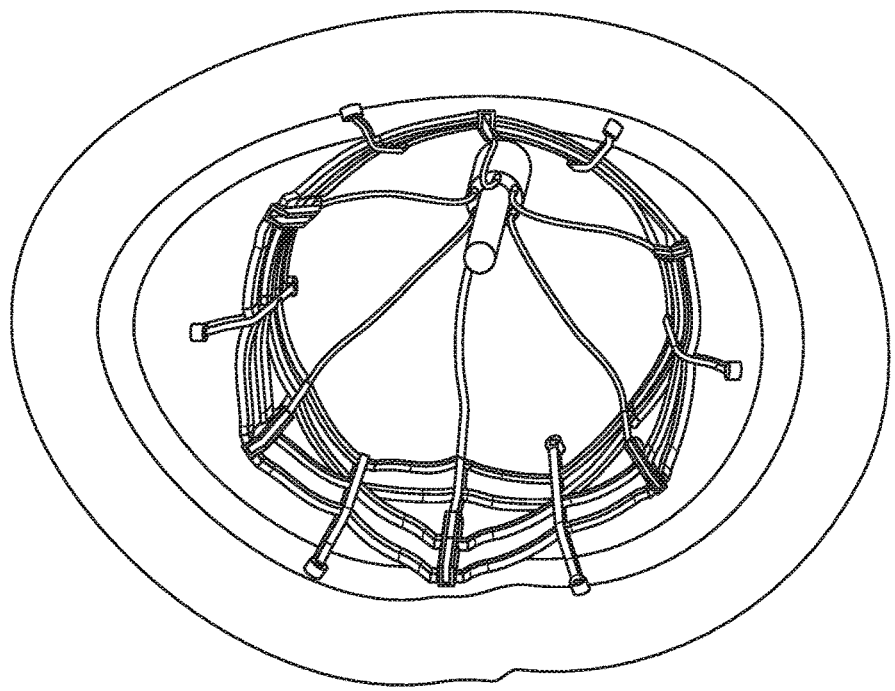
Figure 222:
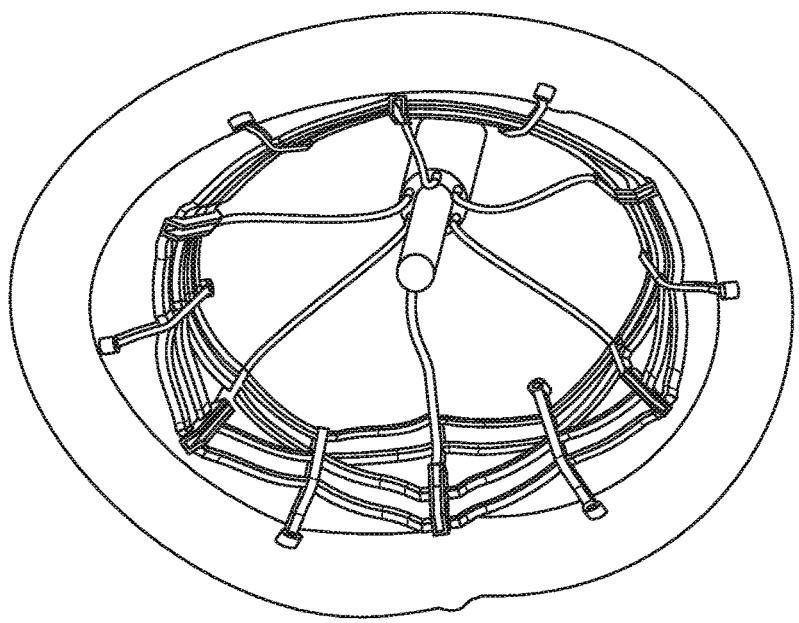
Figure 223:
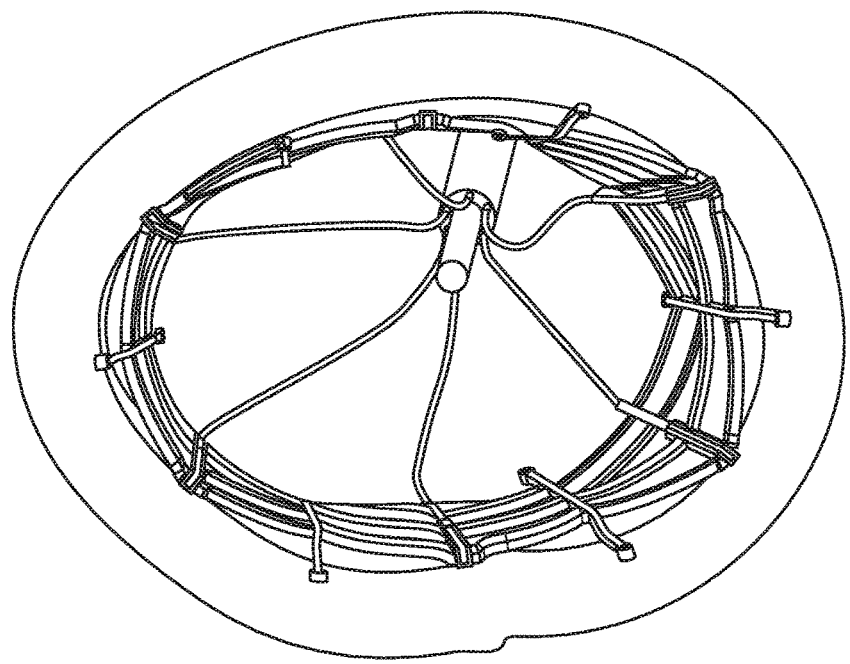
Figure 224:
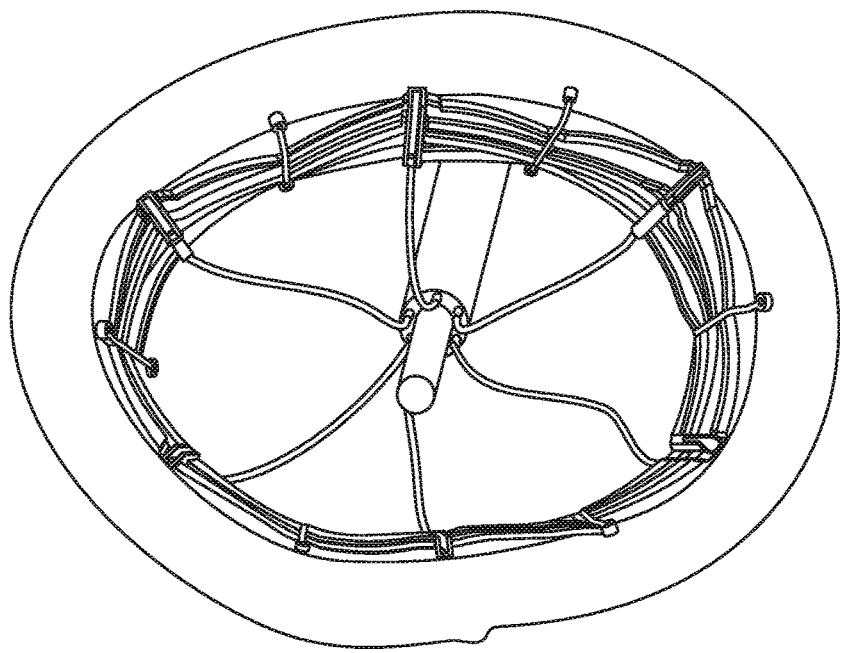
Figure 225:
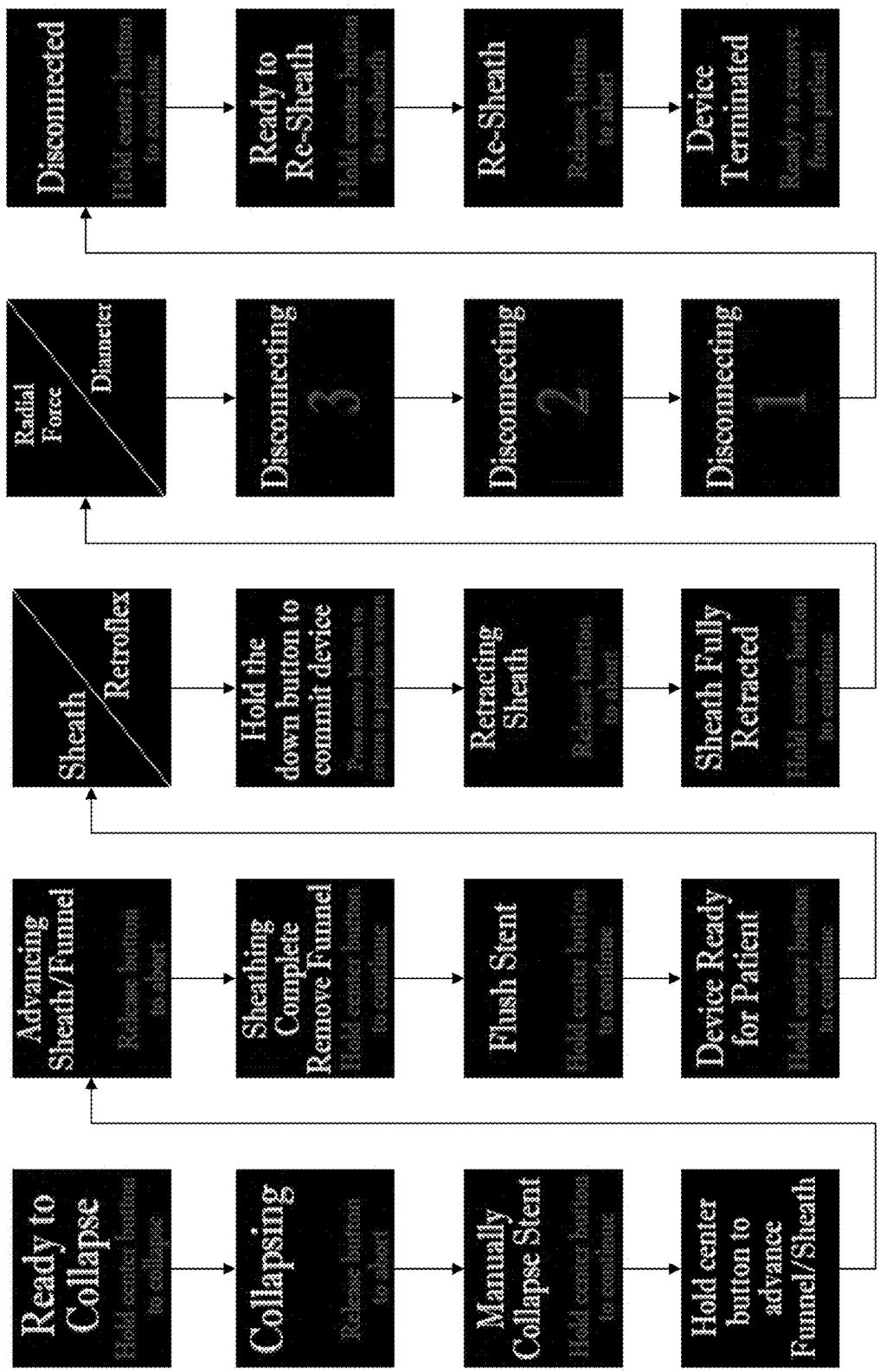
Figure 226:
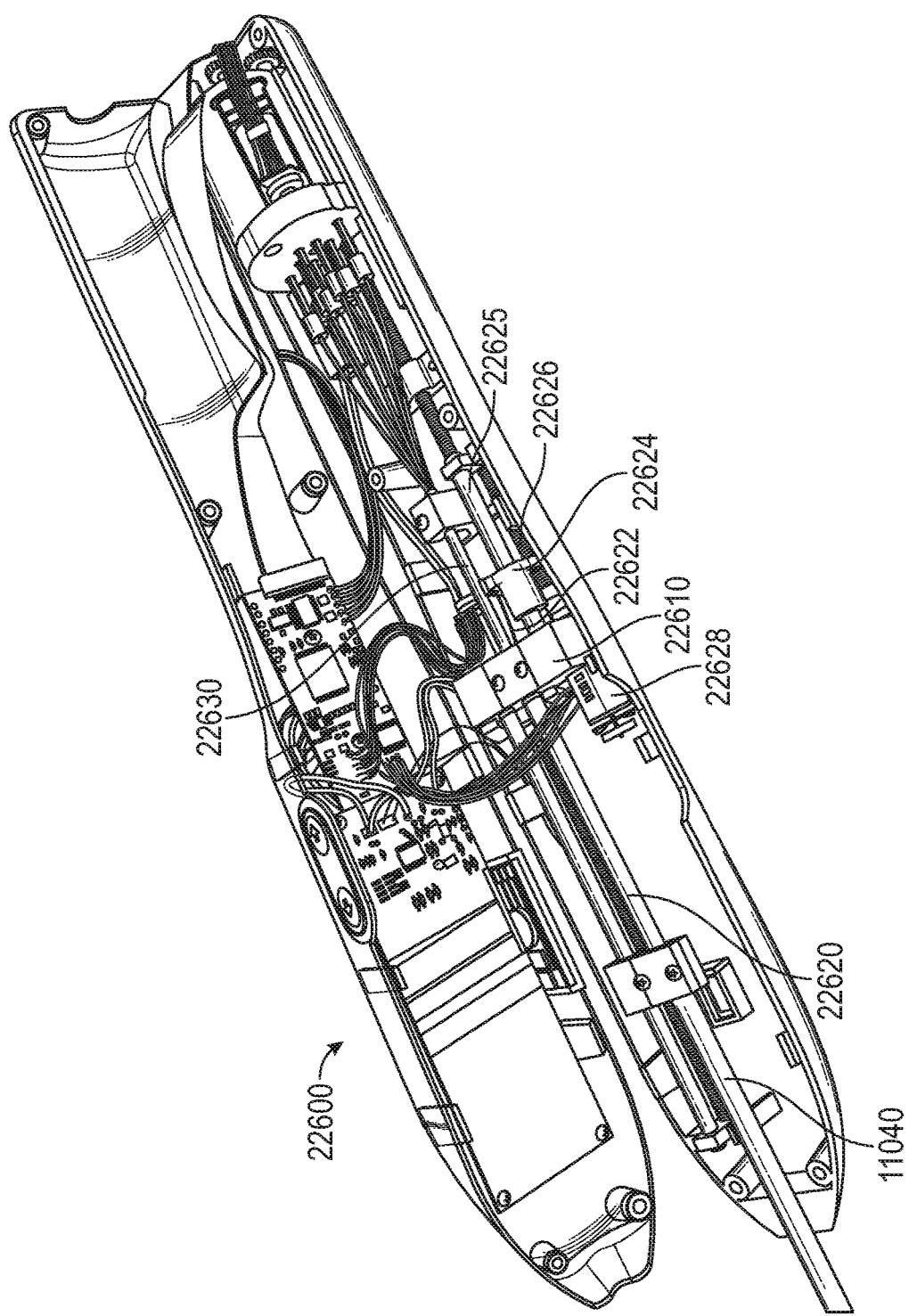
Figure 227:
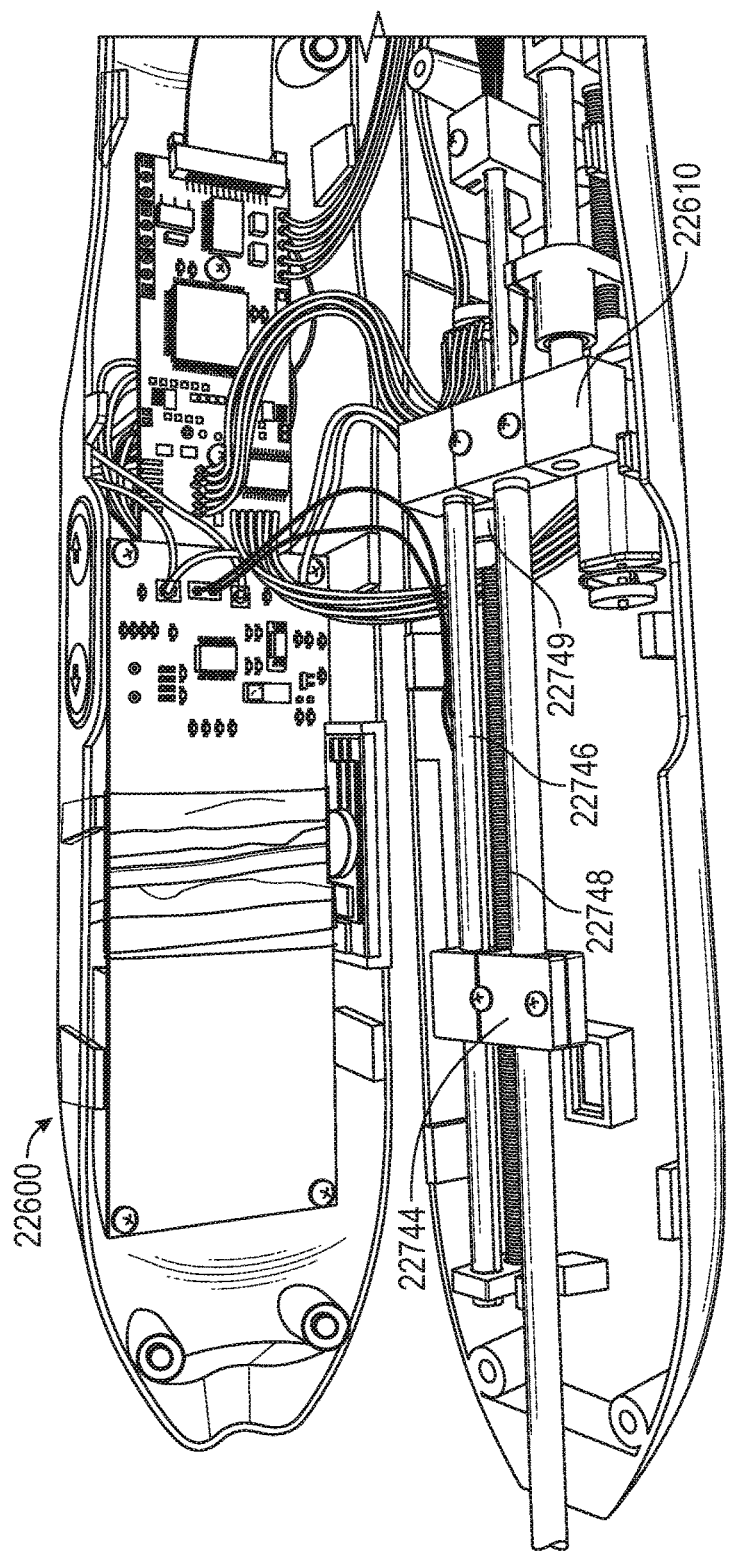
Figure 228:
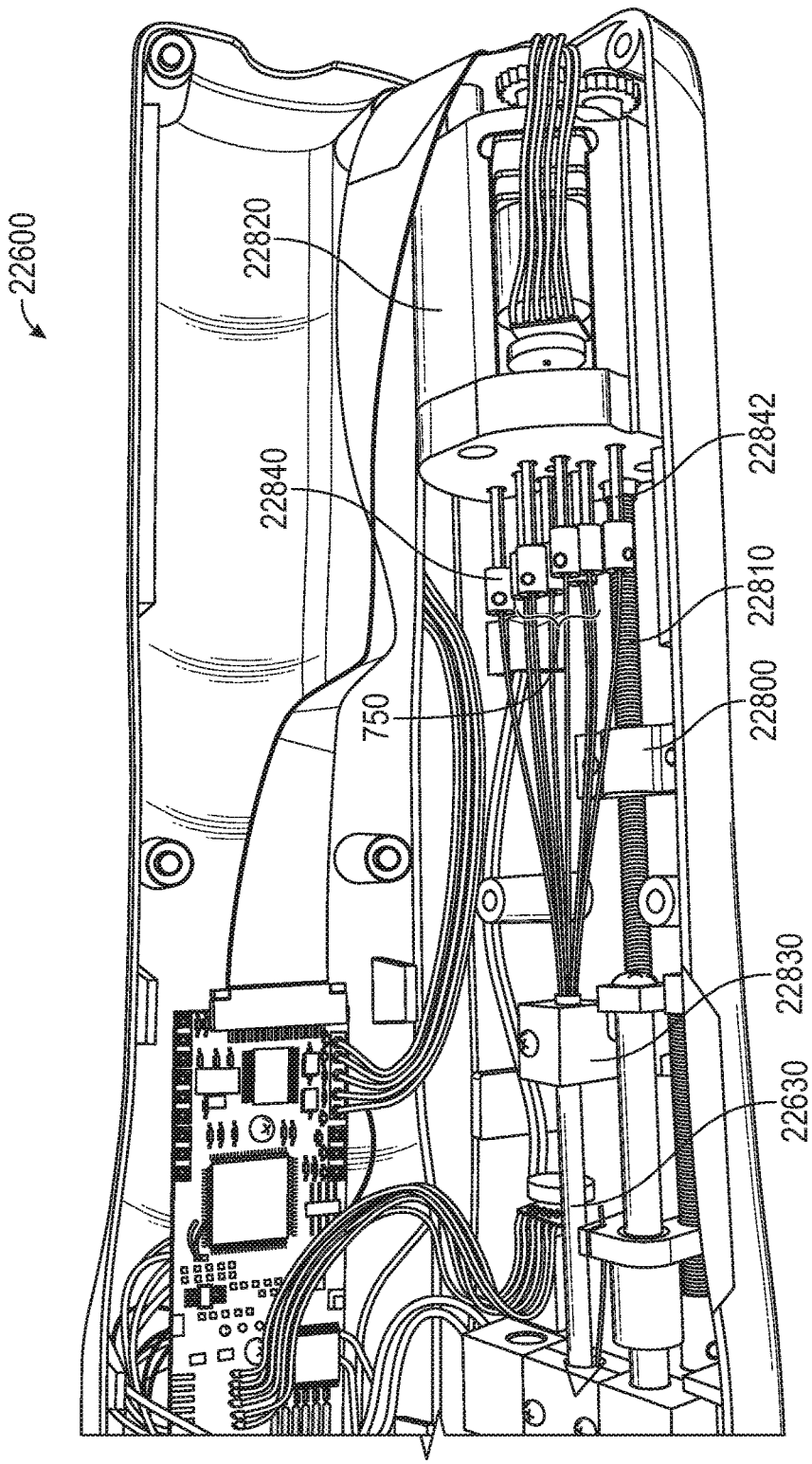
Figure 229:
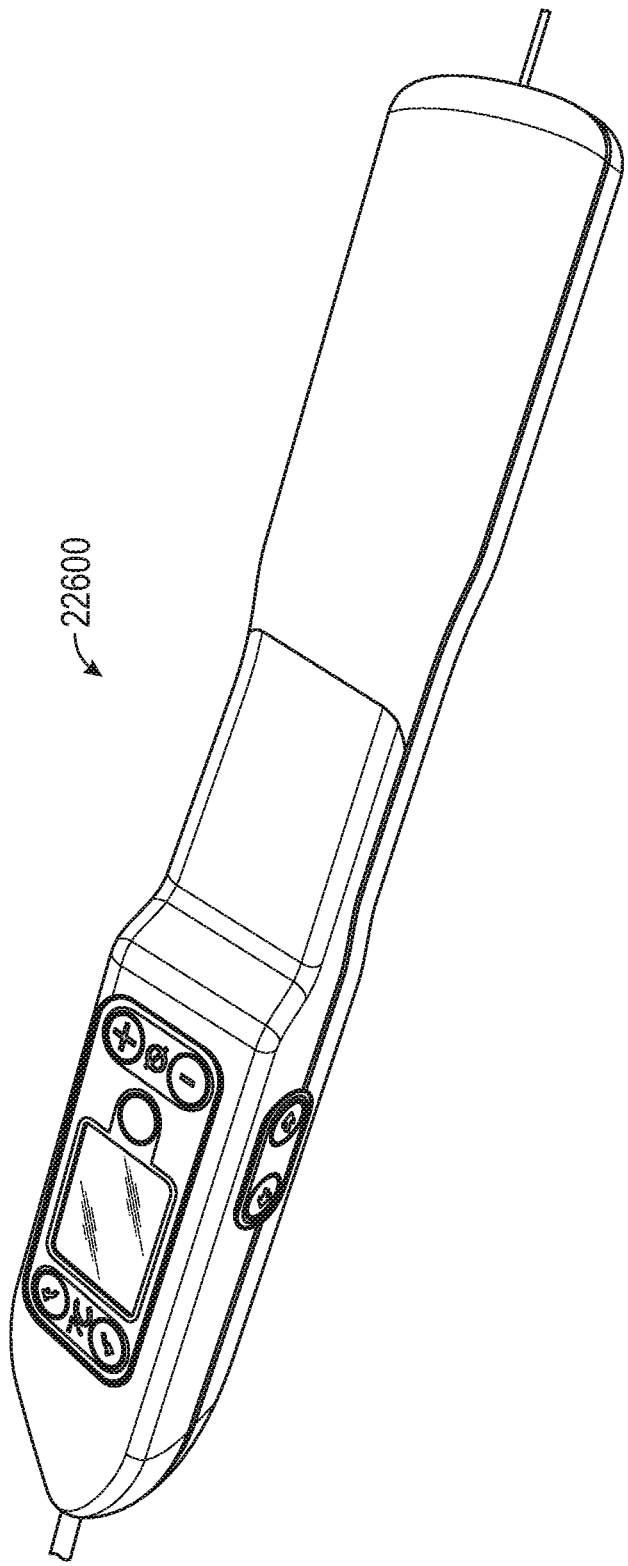
Figure 230:
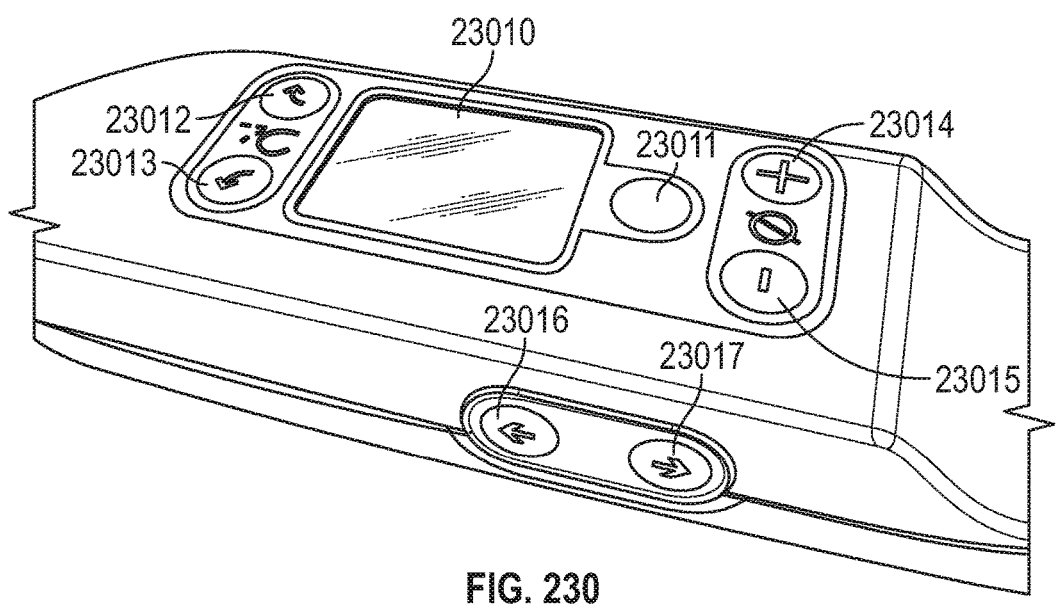
Figure 231:
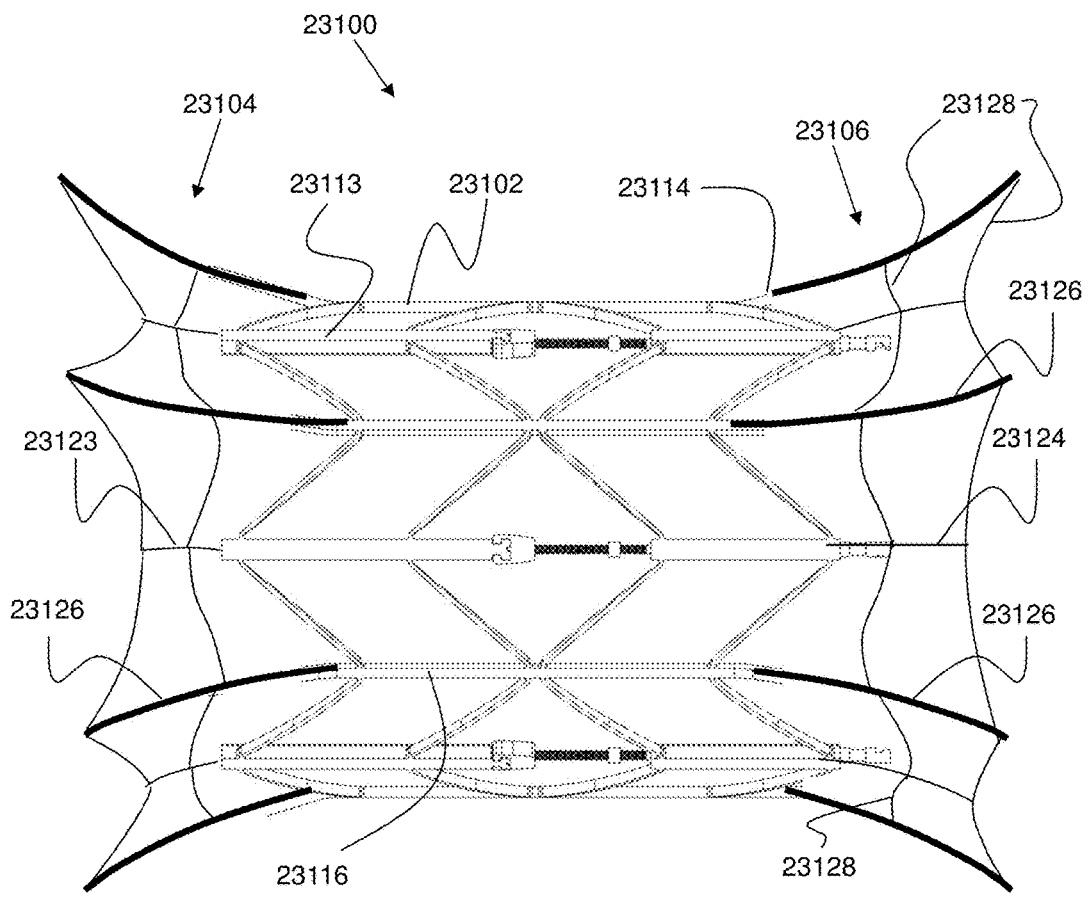
Figure 232:
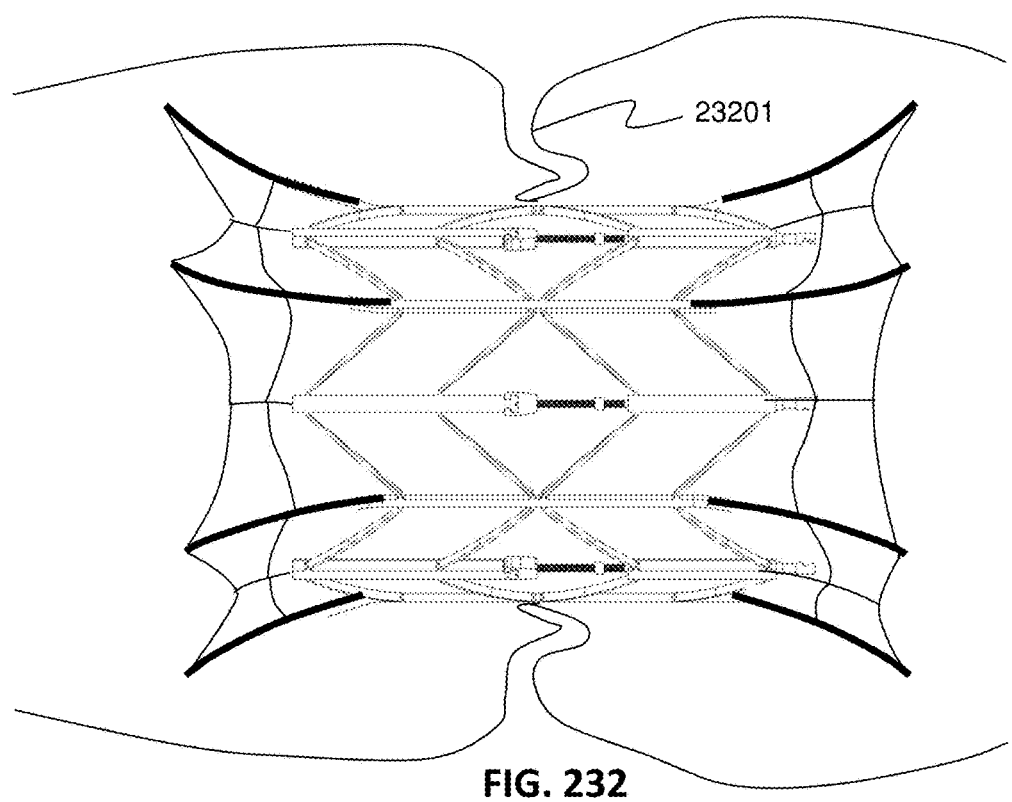
Figure 233:
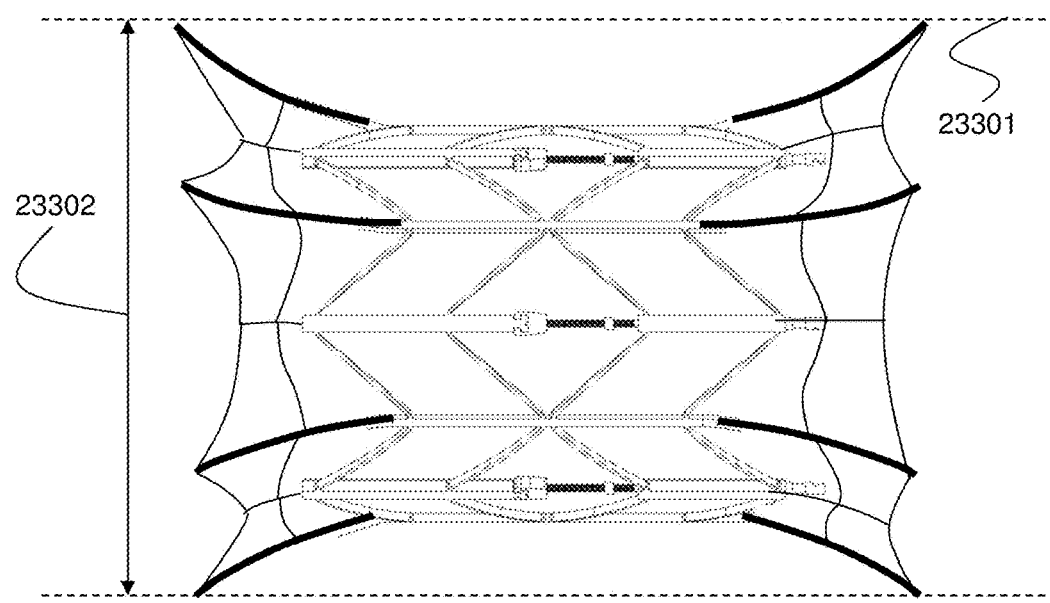
Figure 234:
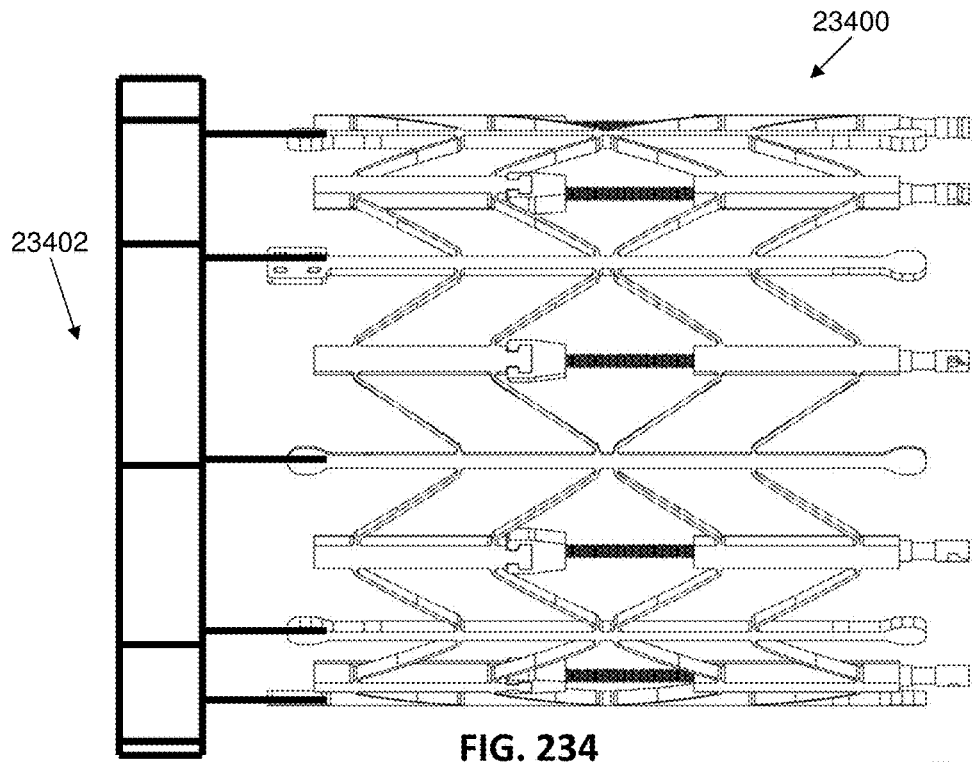
Figure 235:
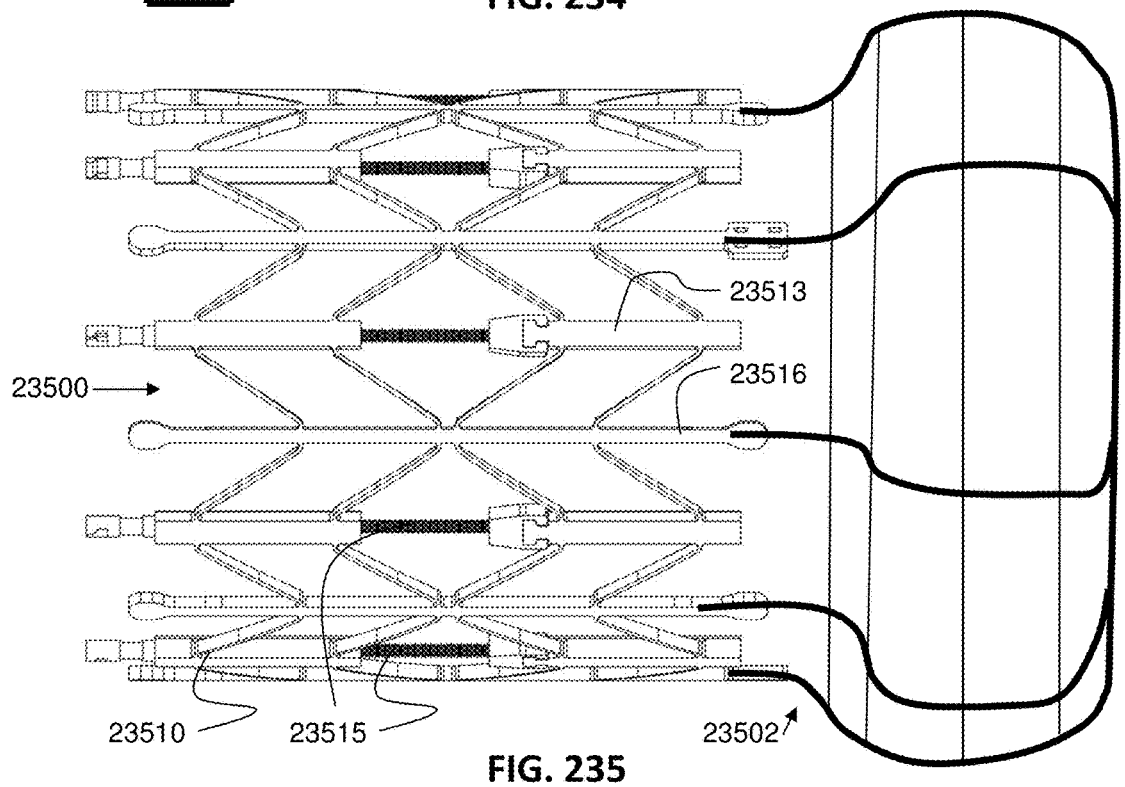
Figures 236, 237:
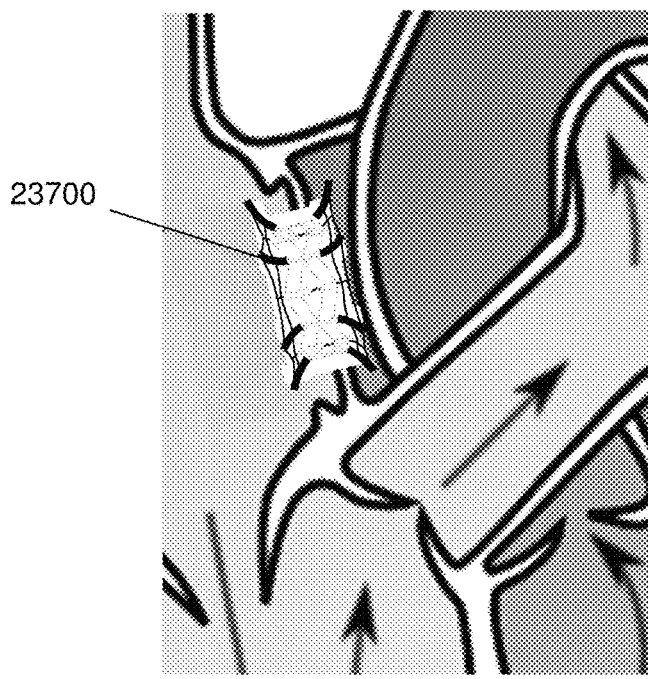
Figures 238, 239:
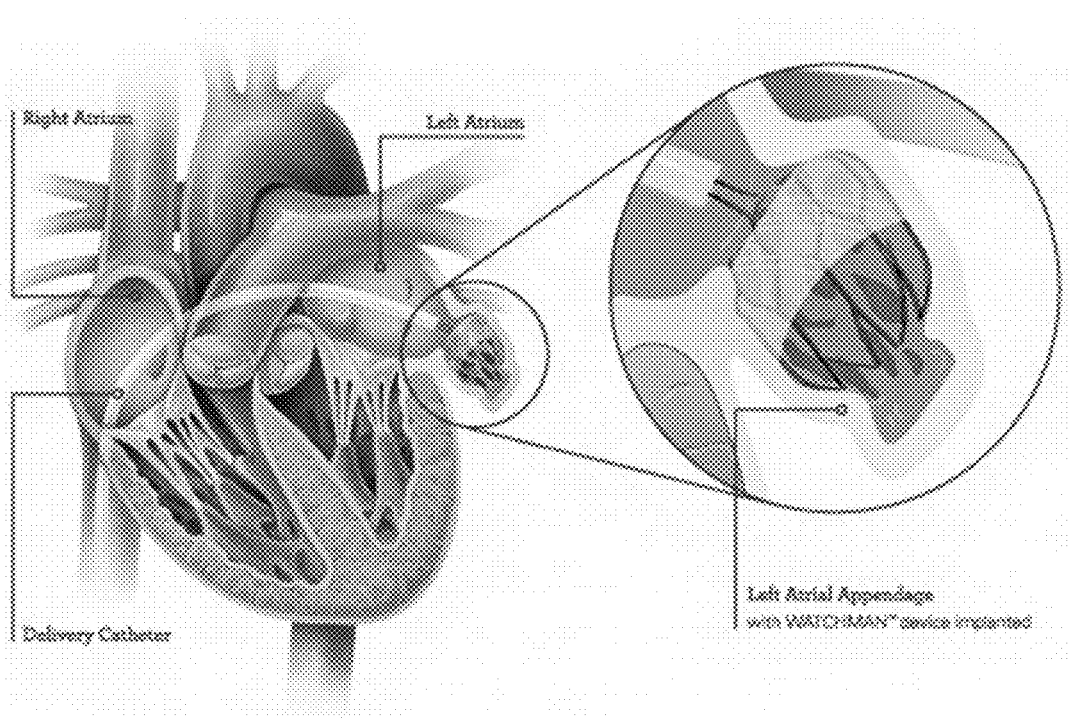
Figure 240:
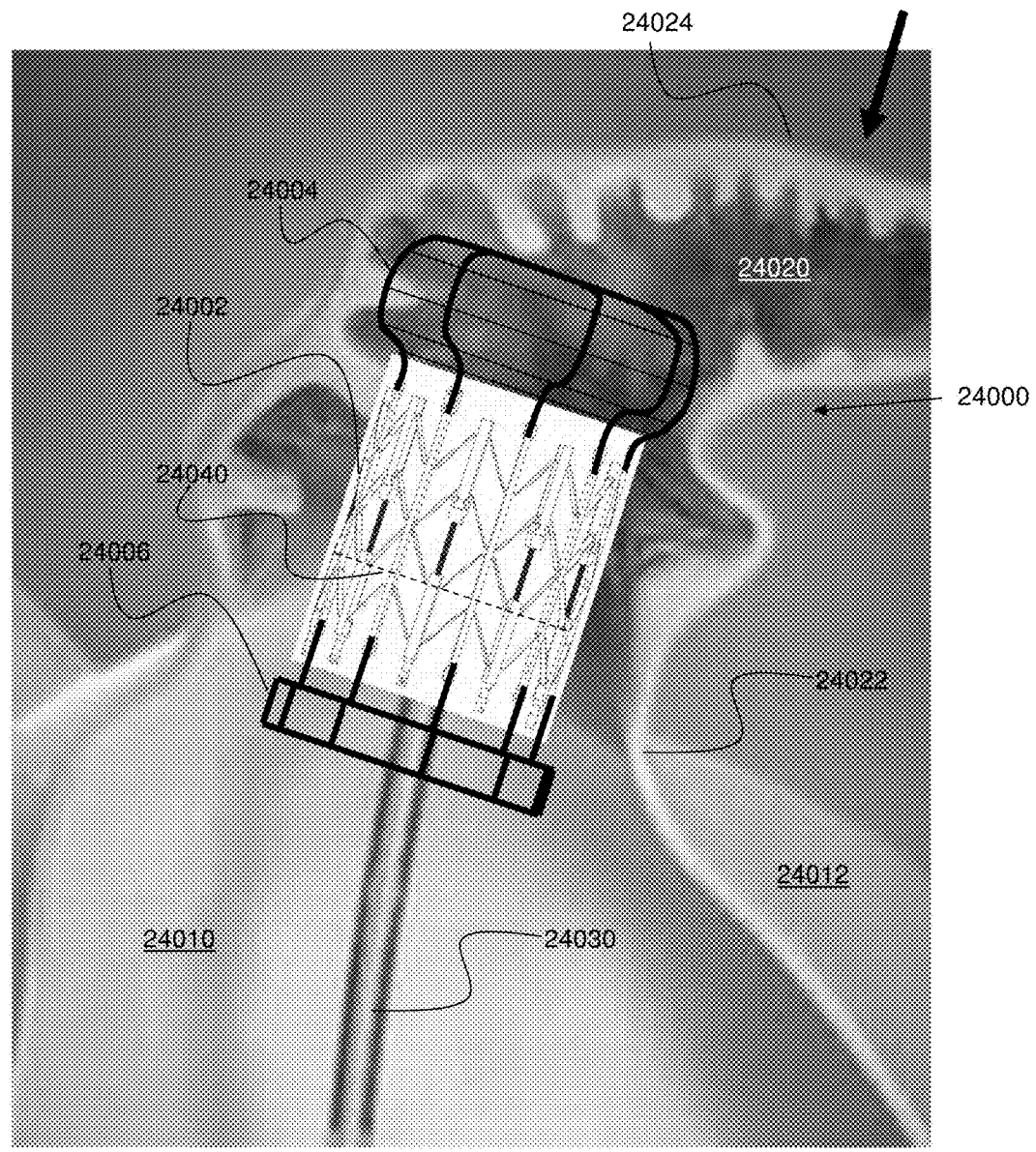
Figure 243:
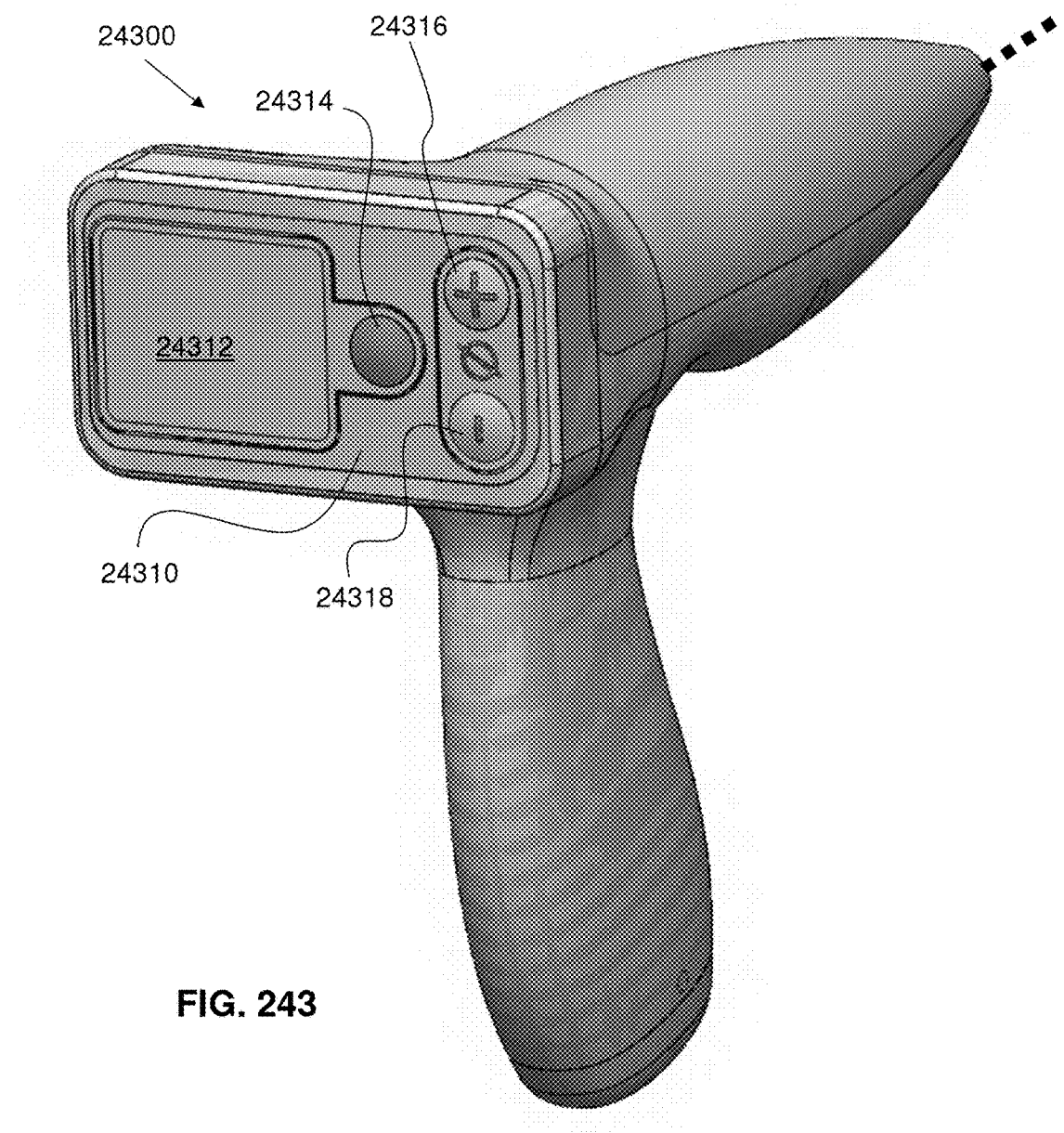
Figure 244:
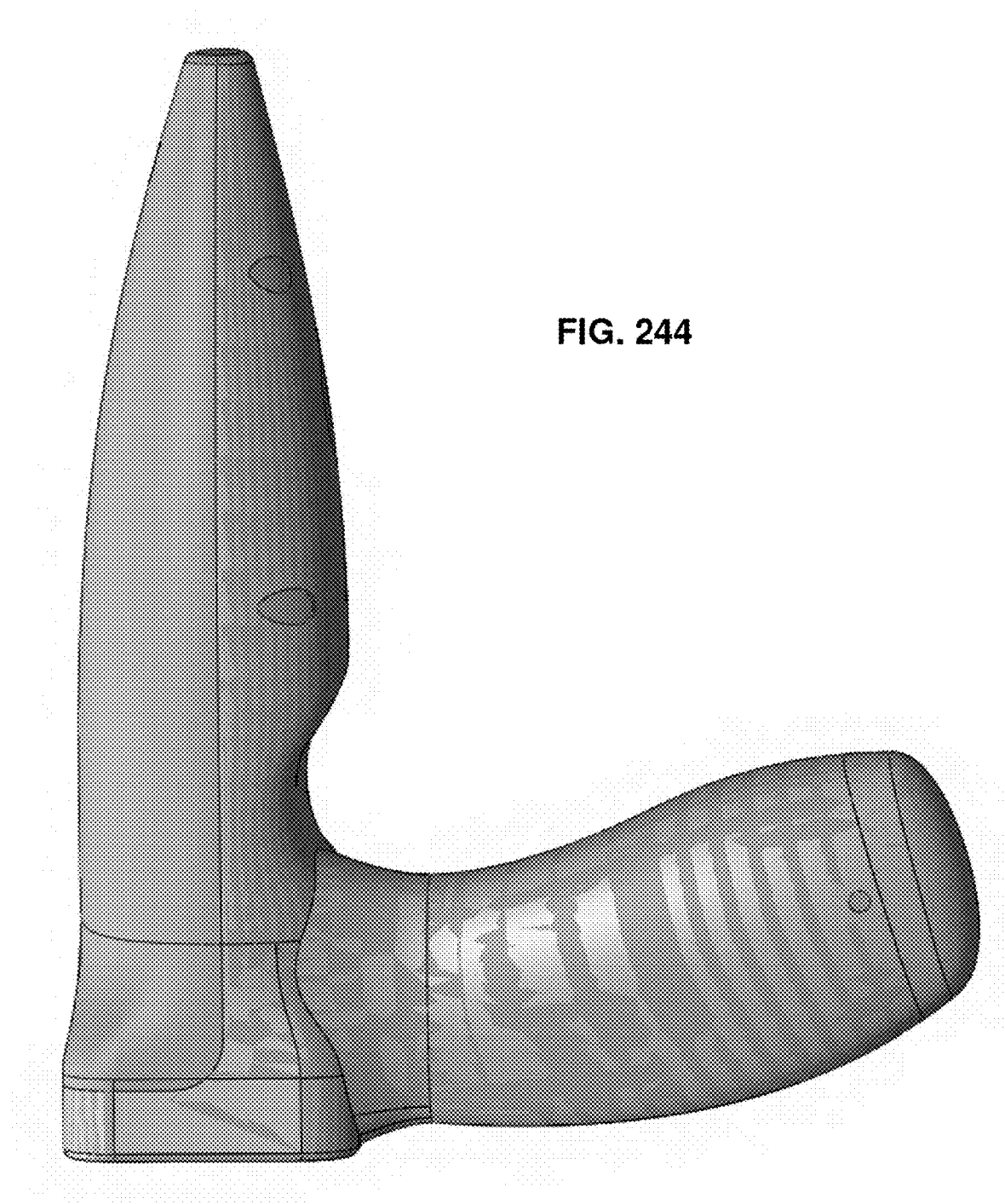
Figure 245:
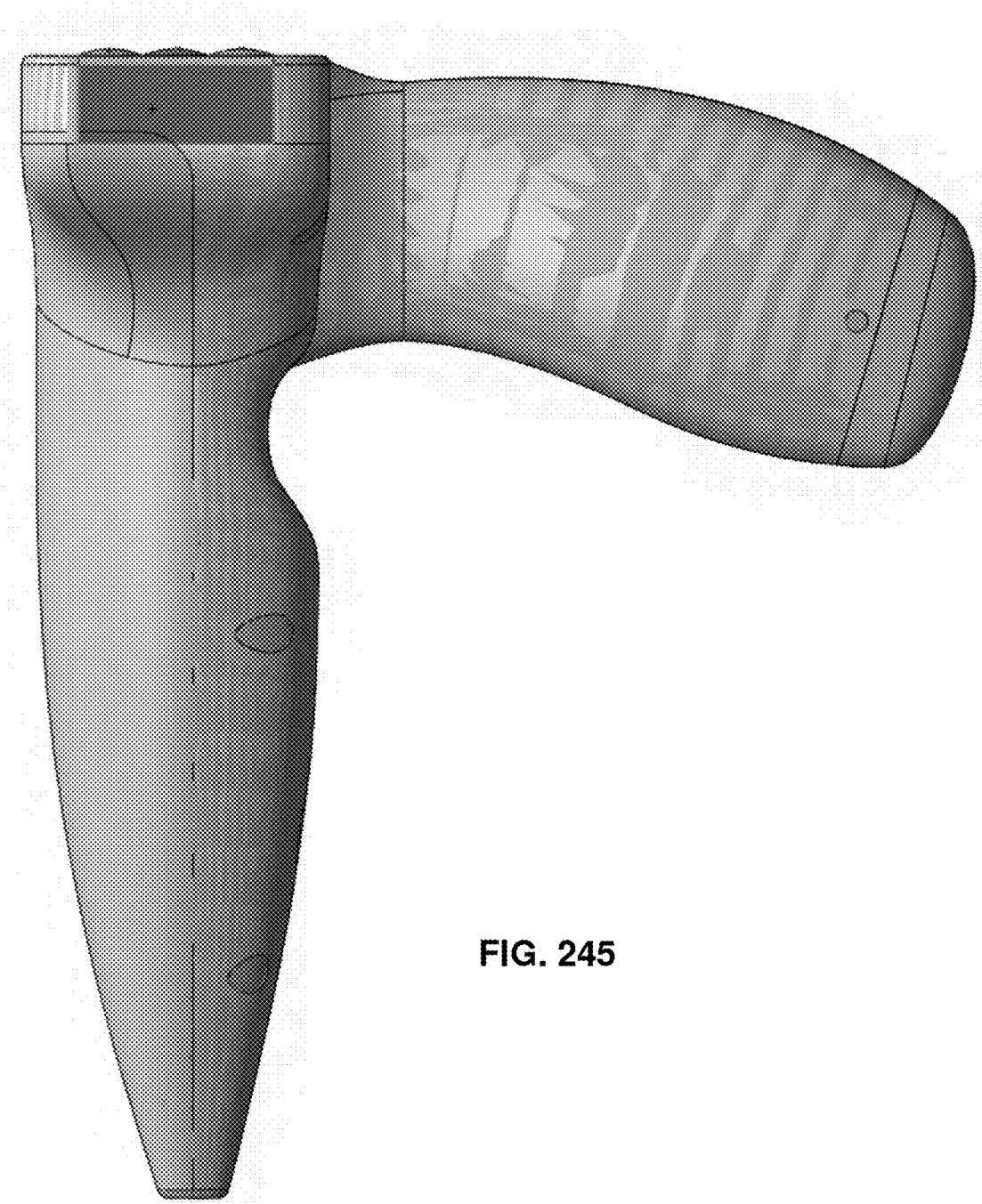
Figure 246:
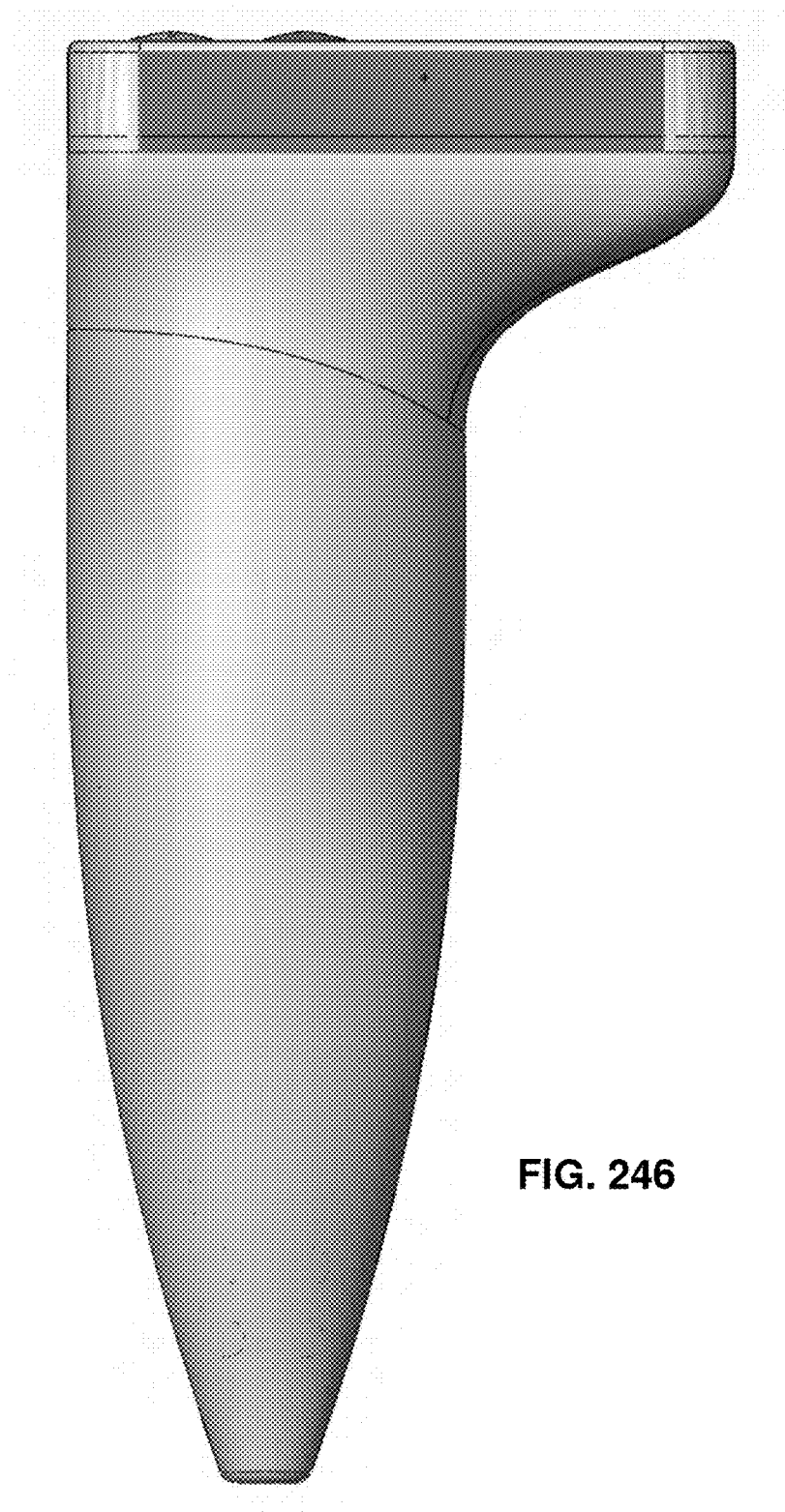
Figure 247:
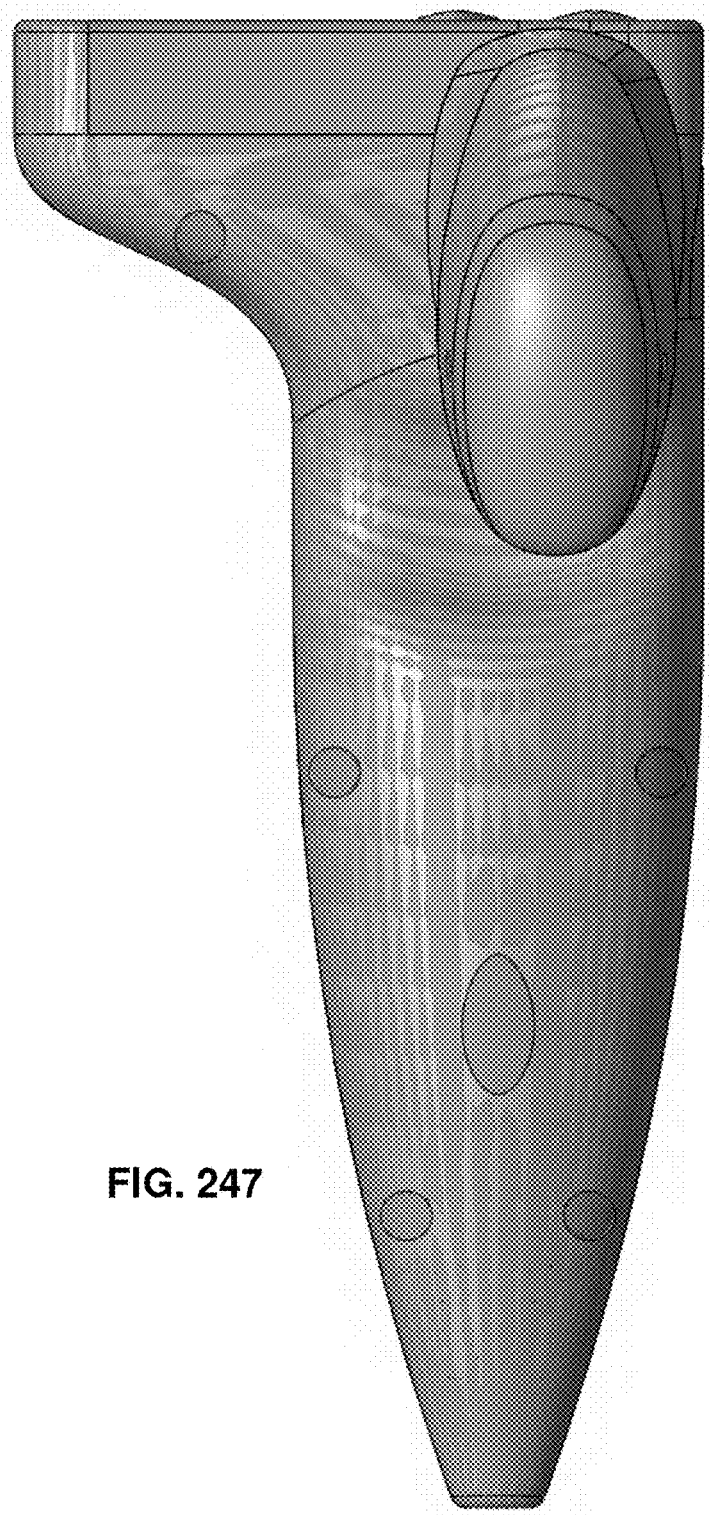
Figure 248:
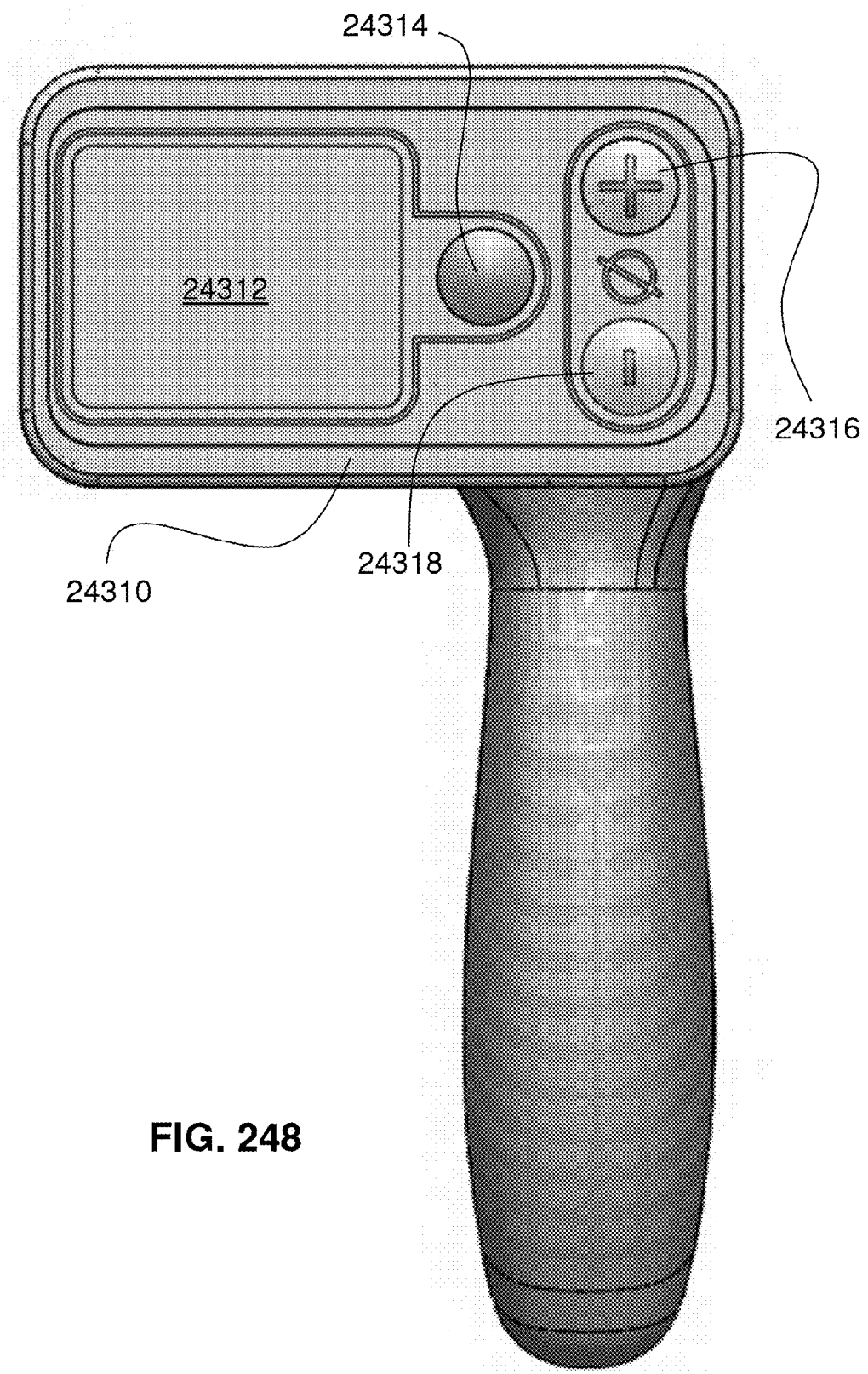
Figure 249:
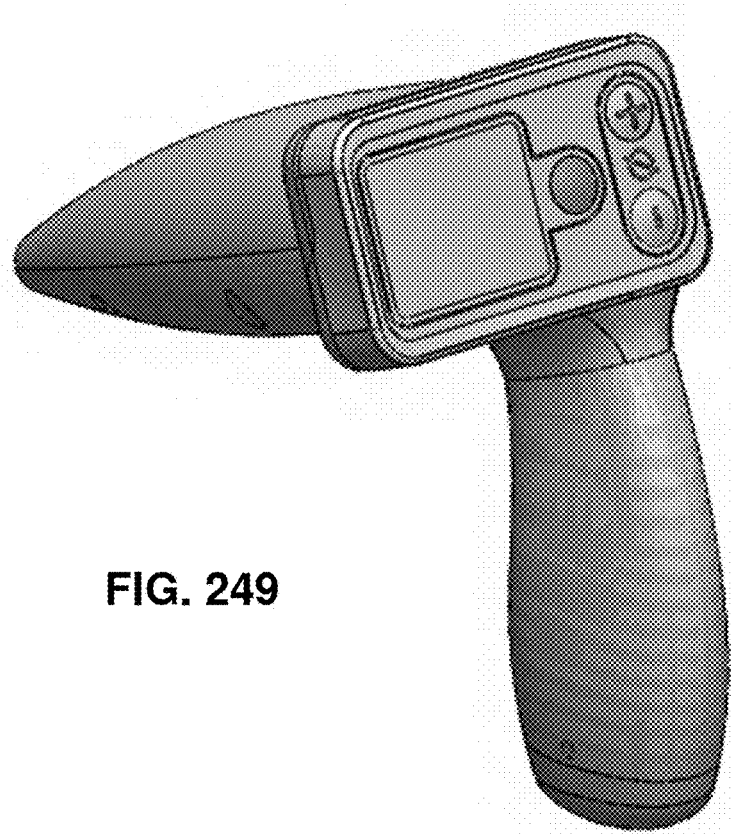
Figure 250:
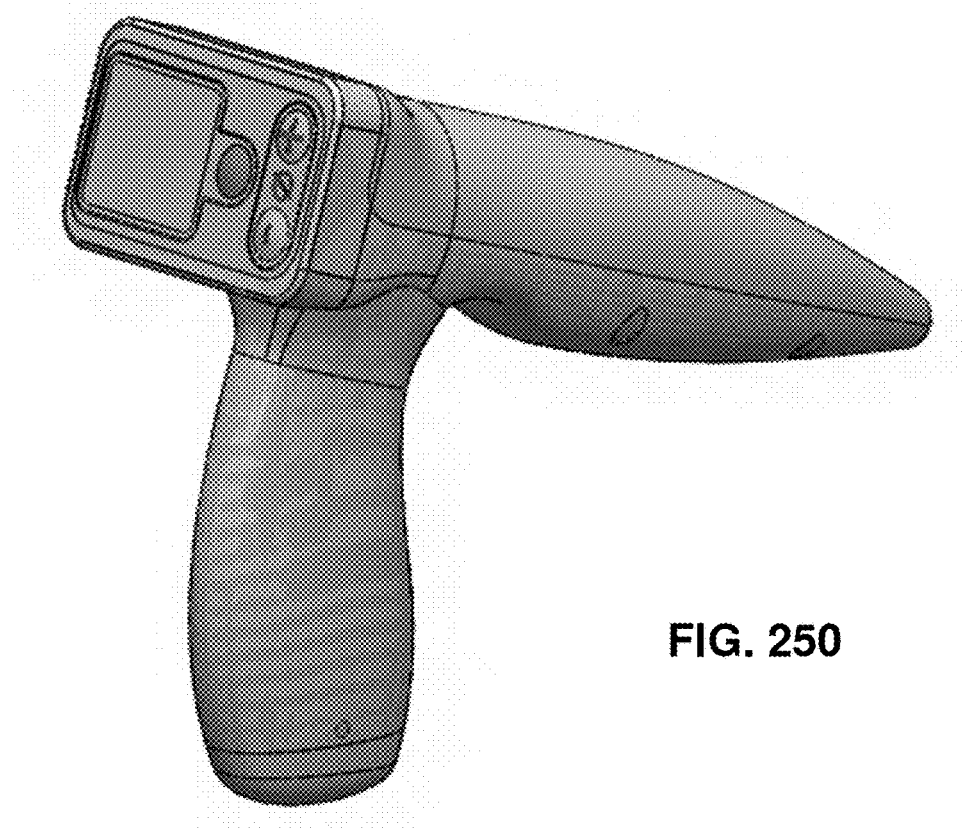
Figure 251:
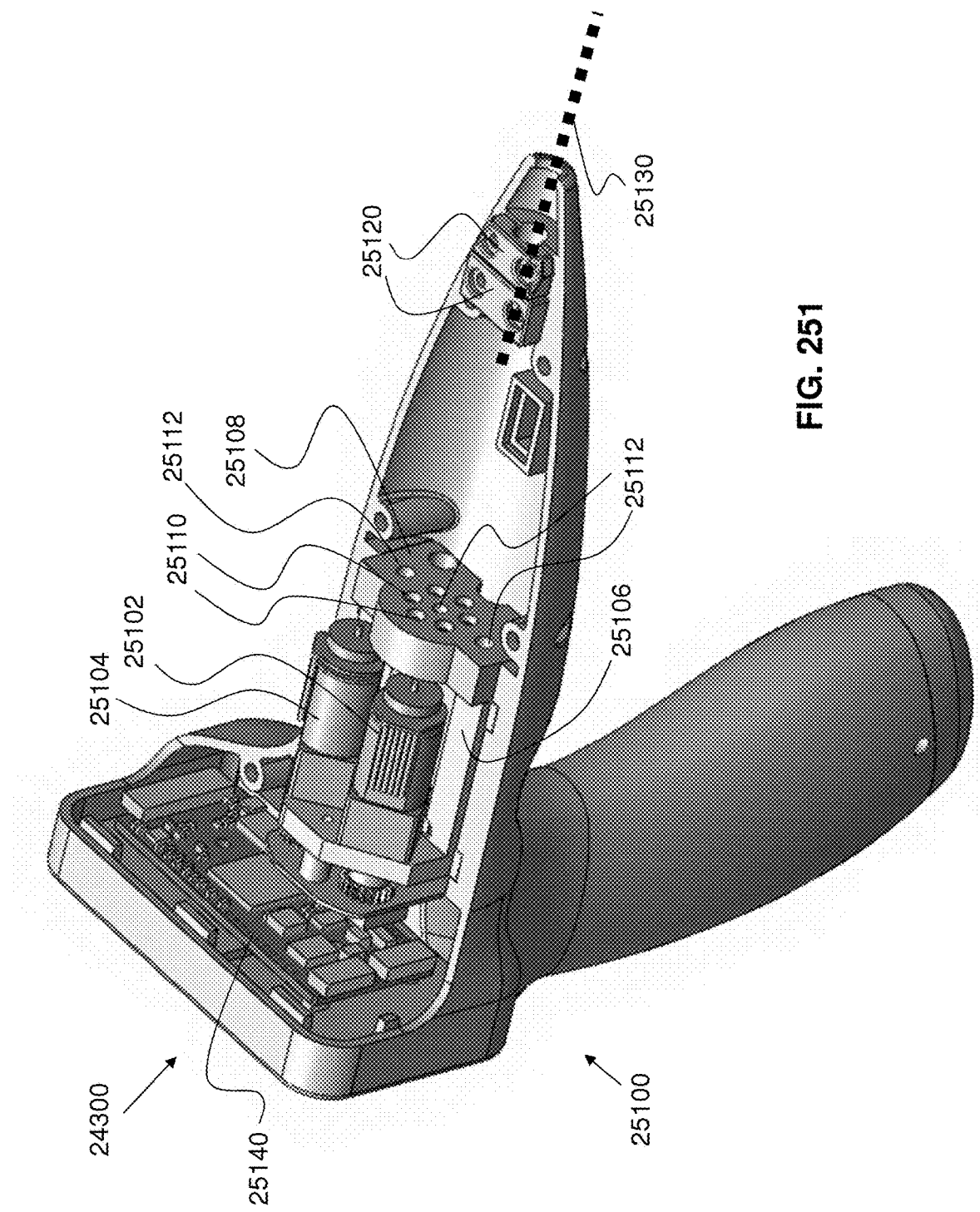
Figure 252:
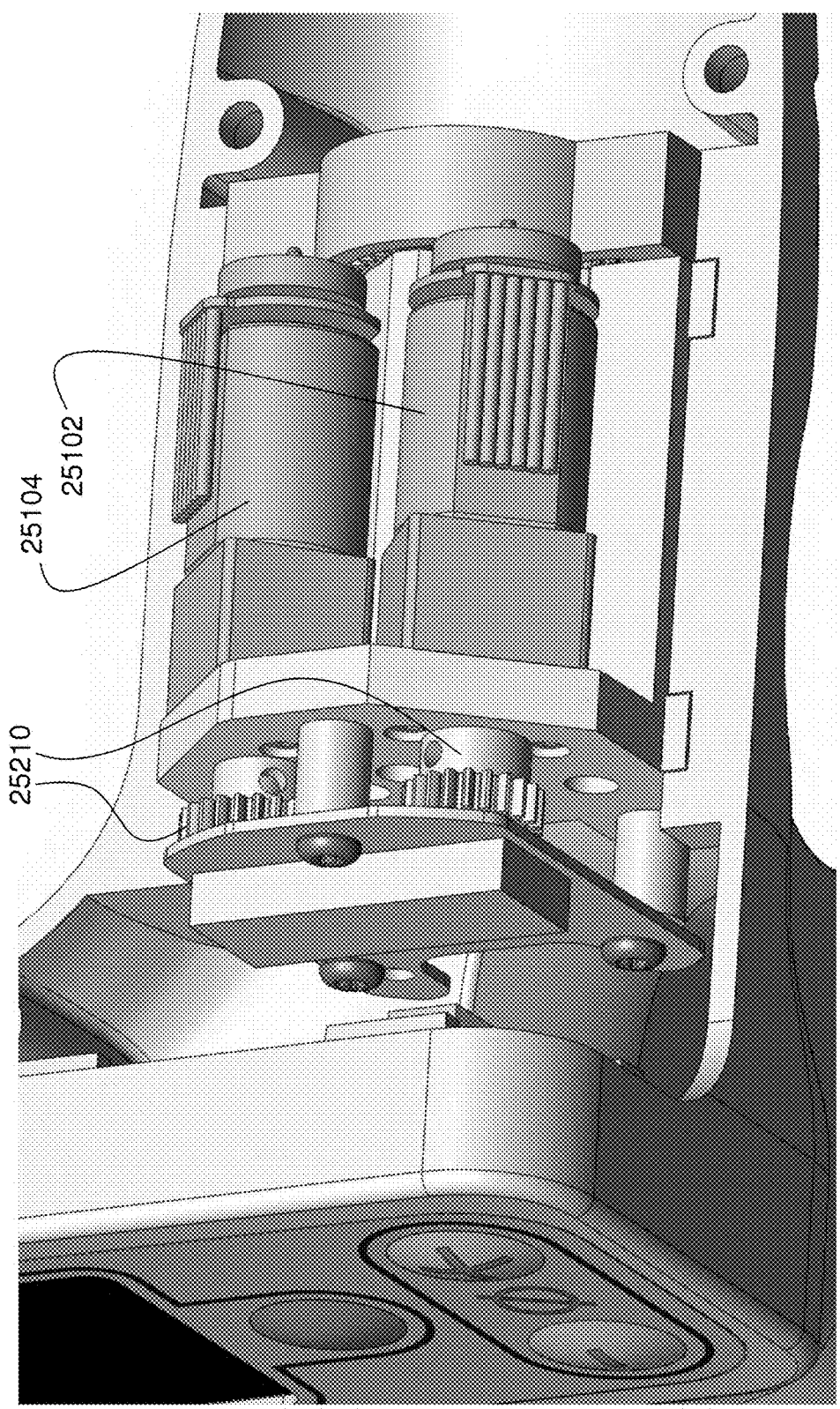
Figure 253:
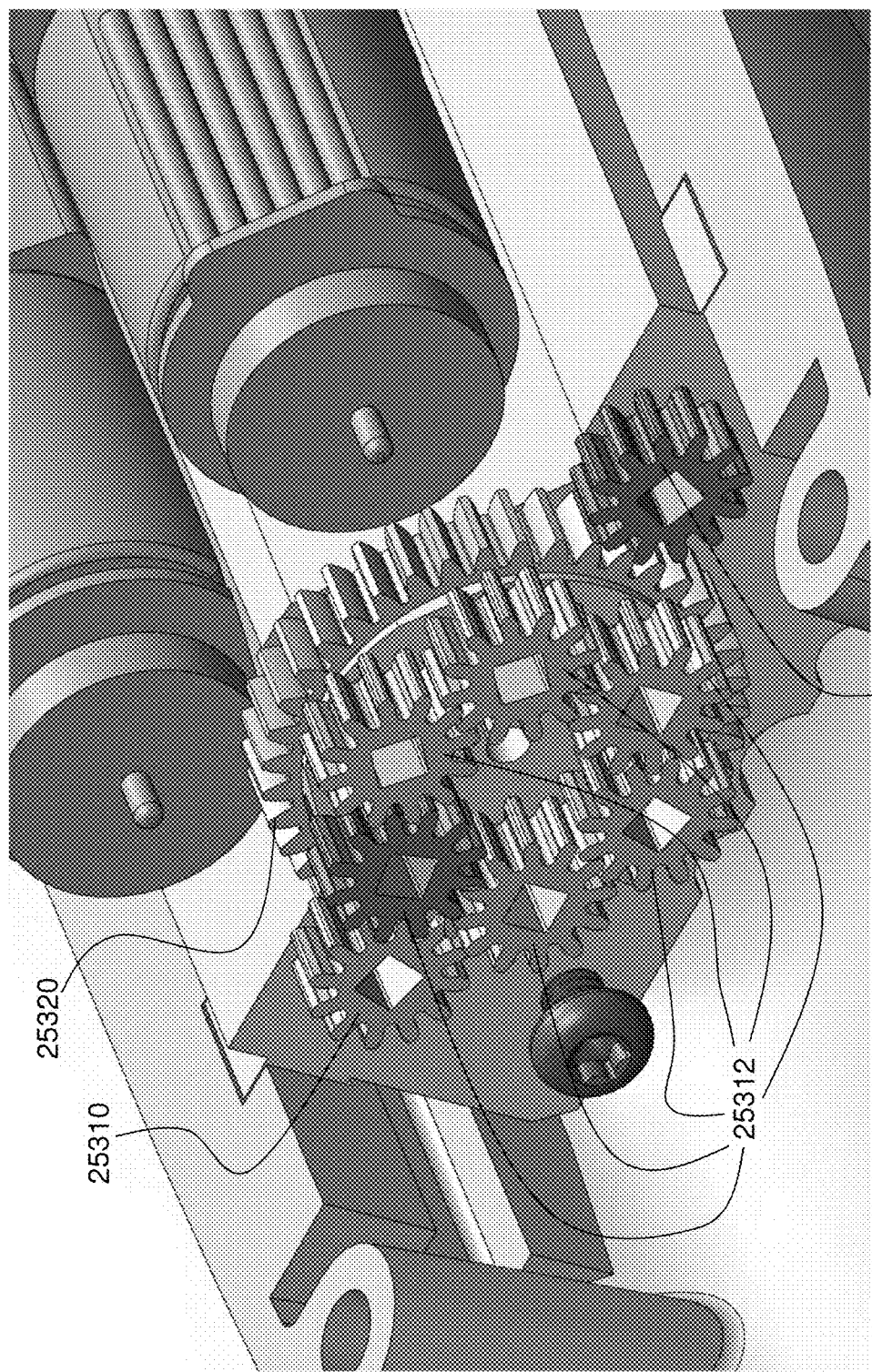
Figure 254:
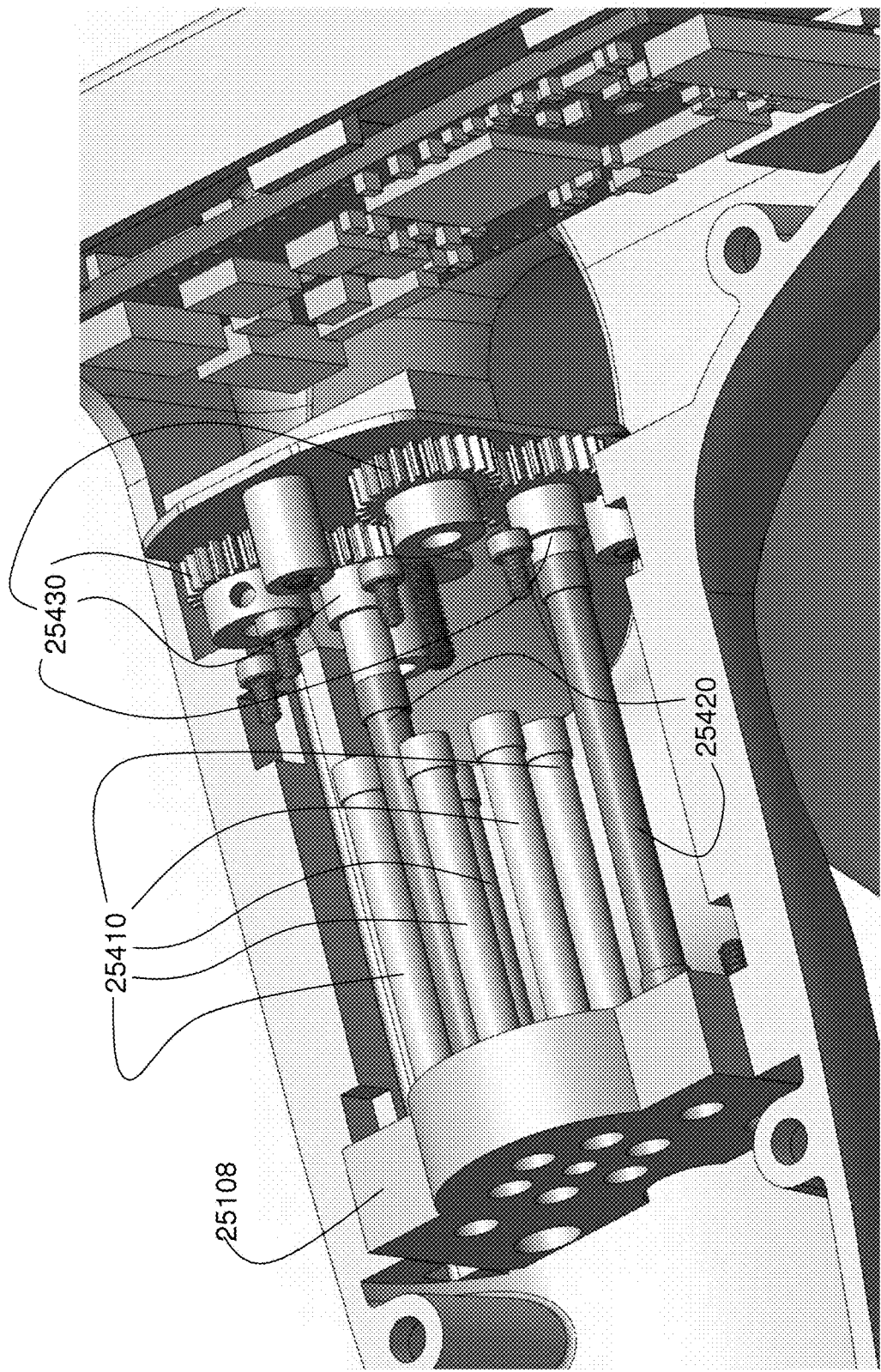
Figure 255:
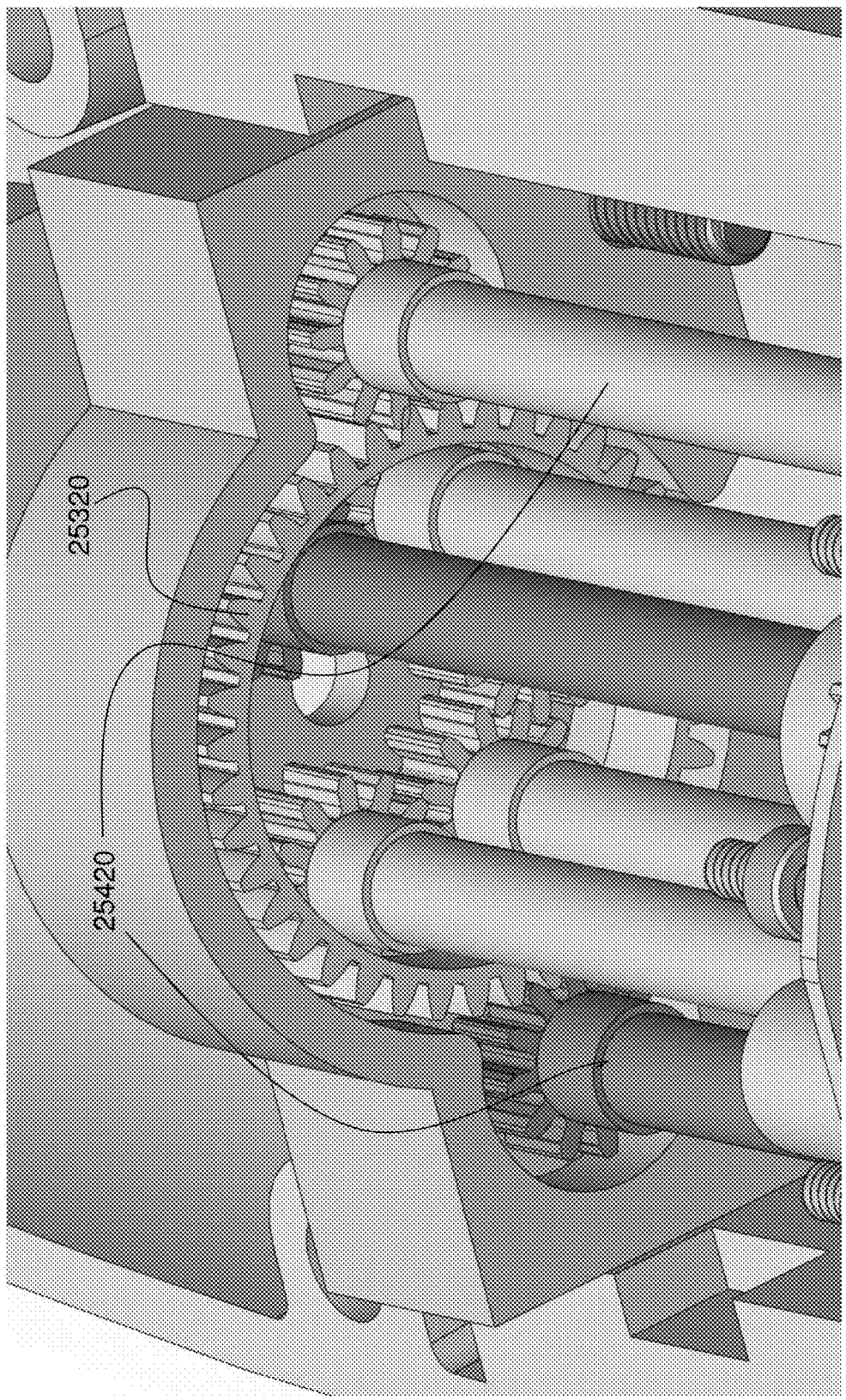
Figure 256:
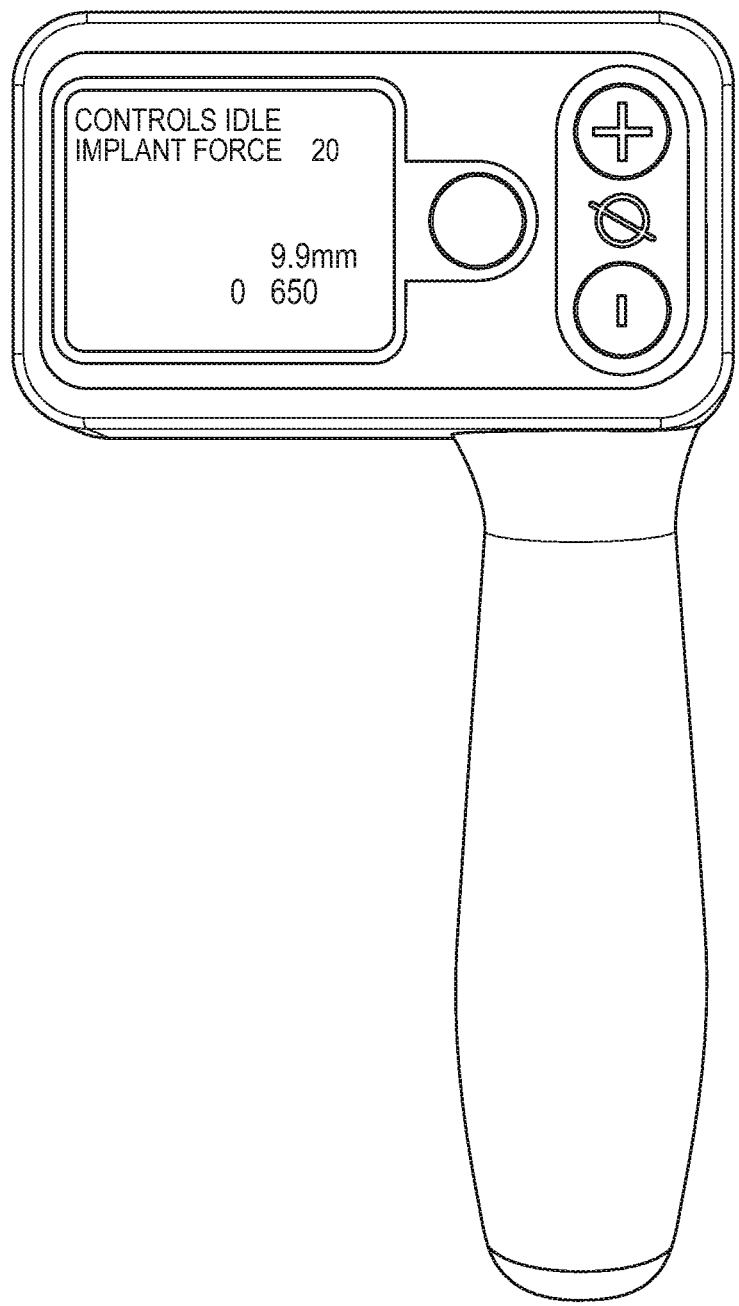
Figure 257:
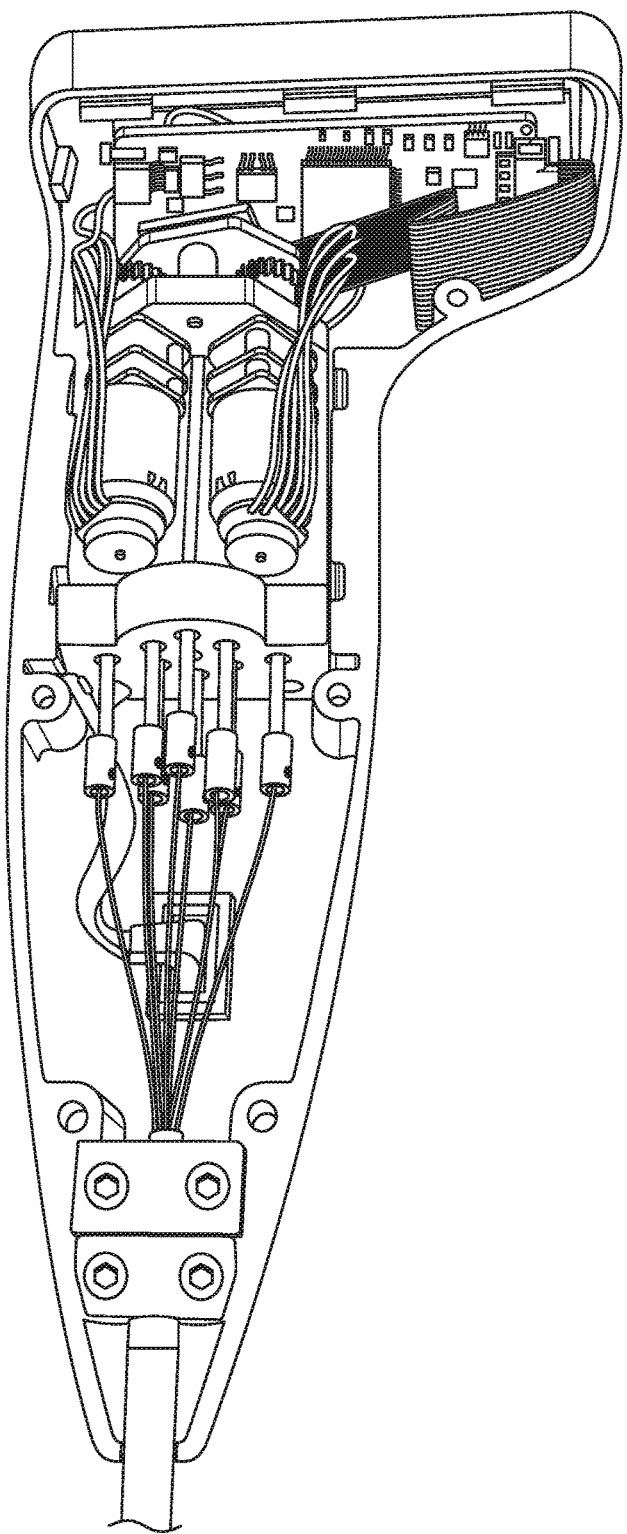
Figure 258:
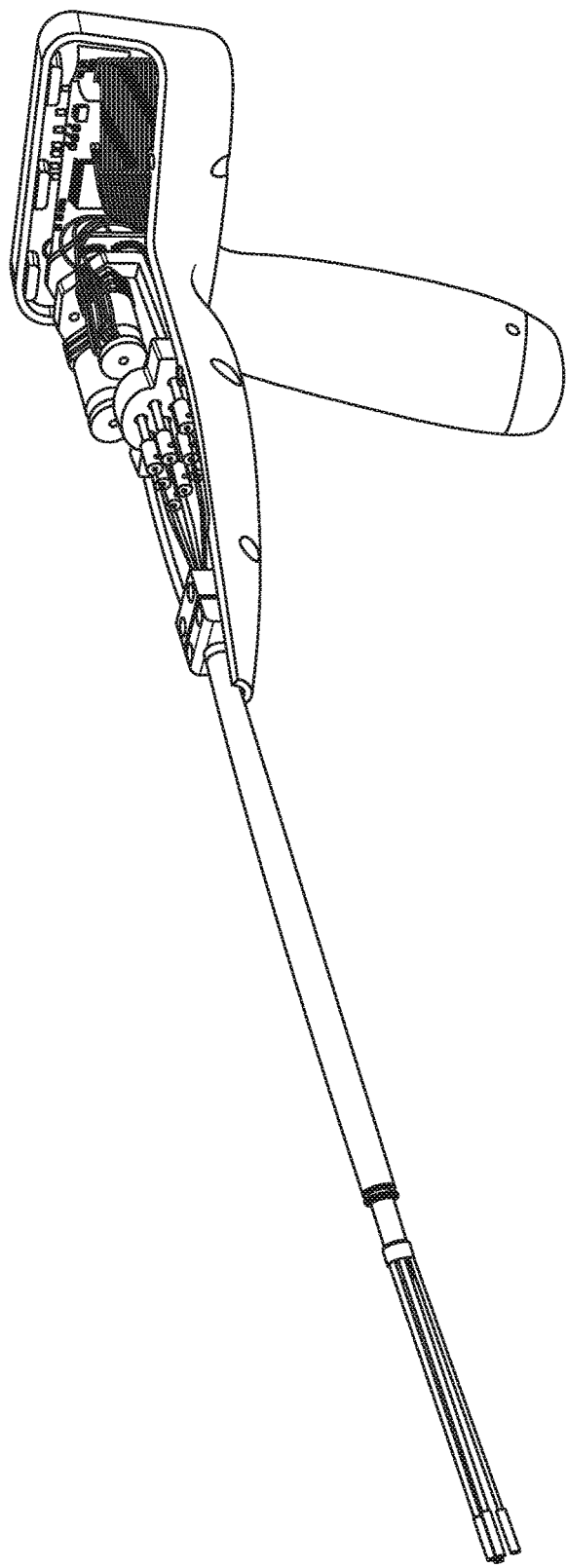
Figure 259:
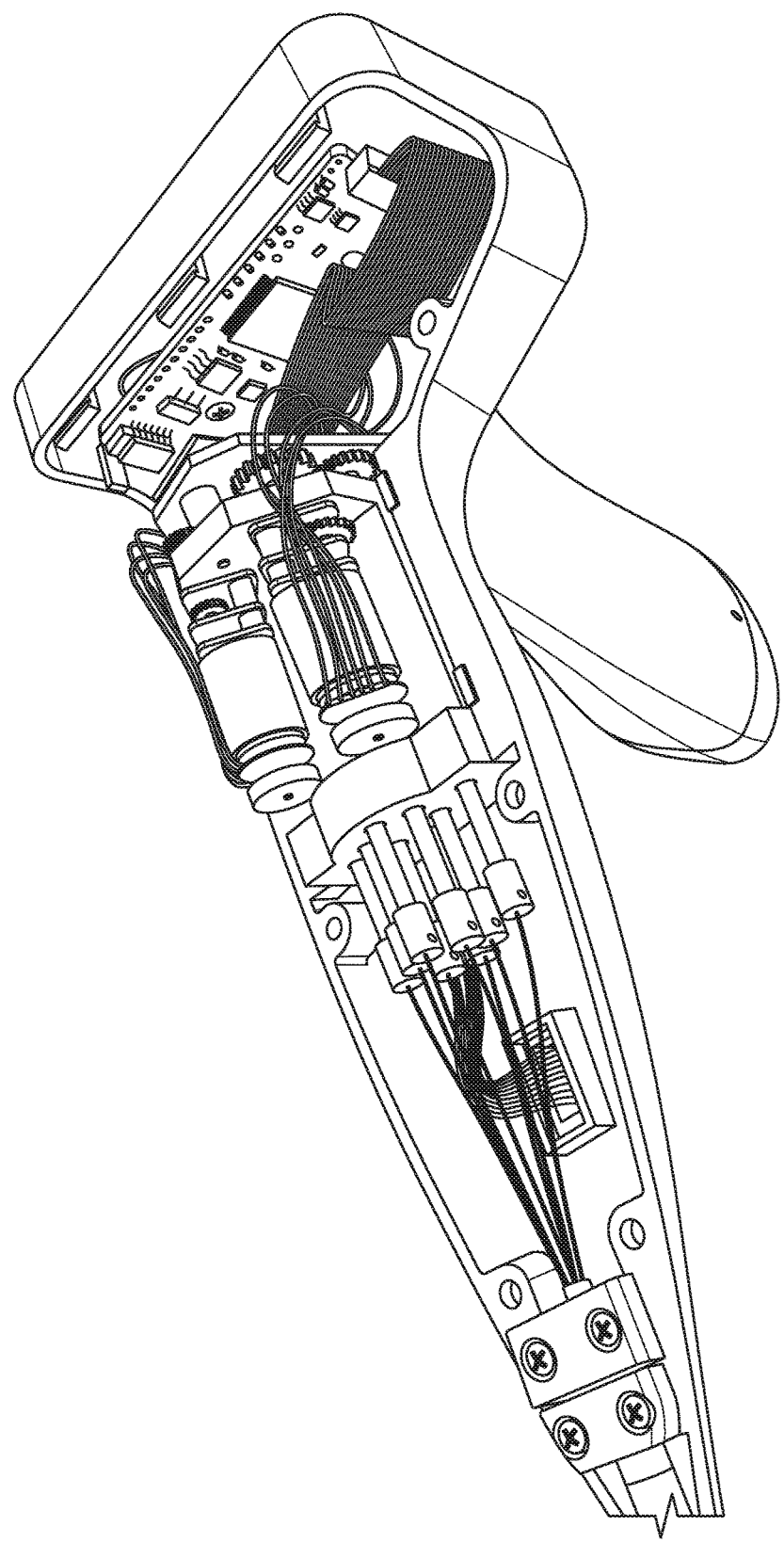
Figure 260:
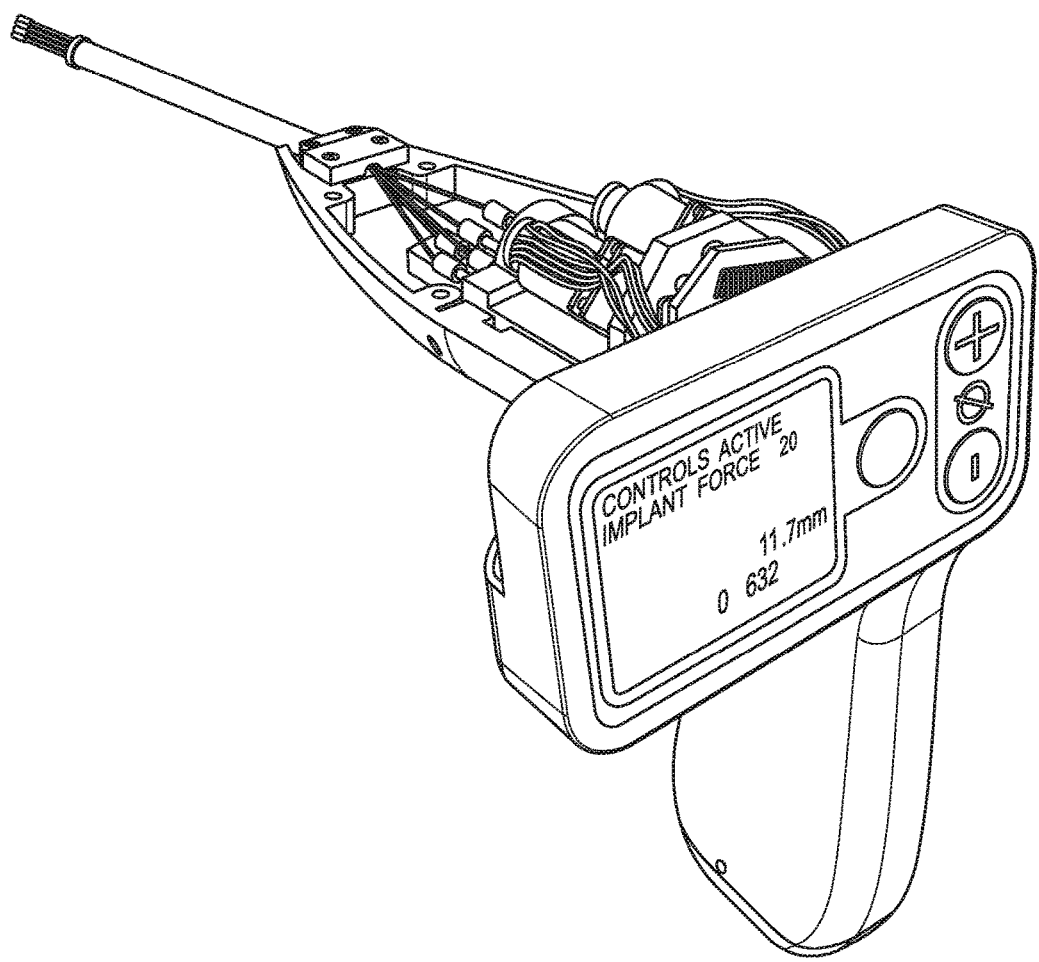
Figure 261:
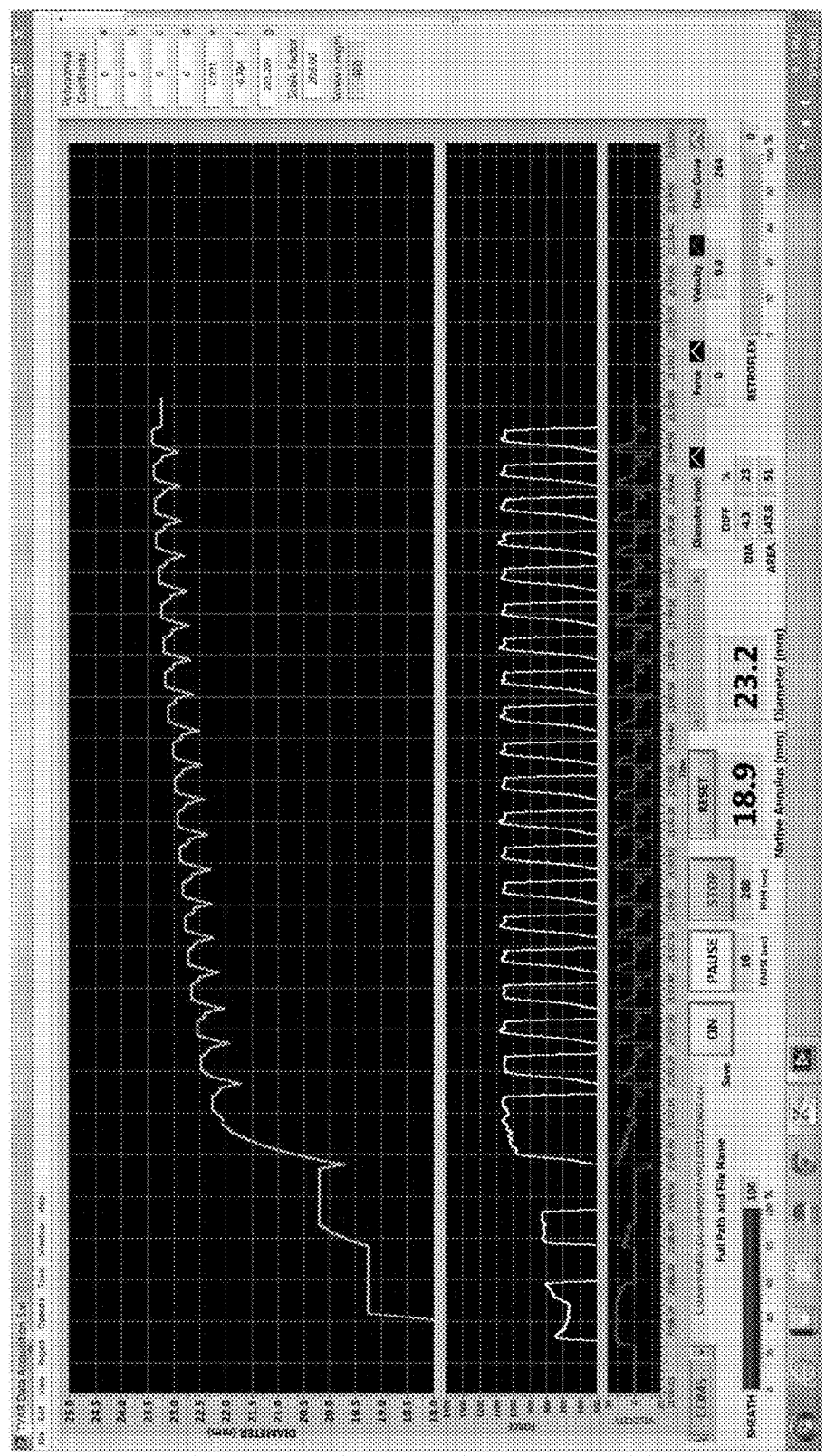
Figure 262:
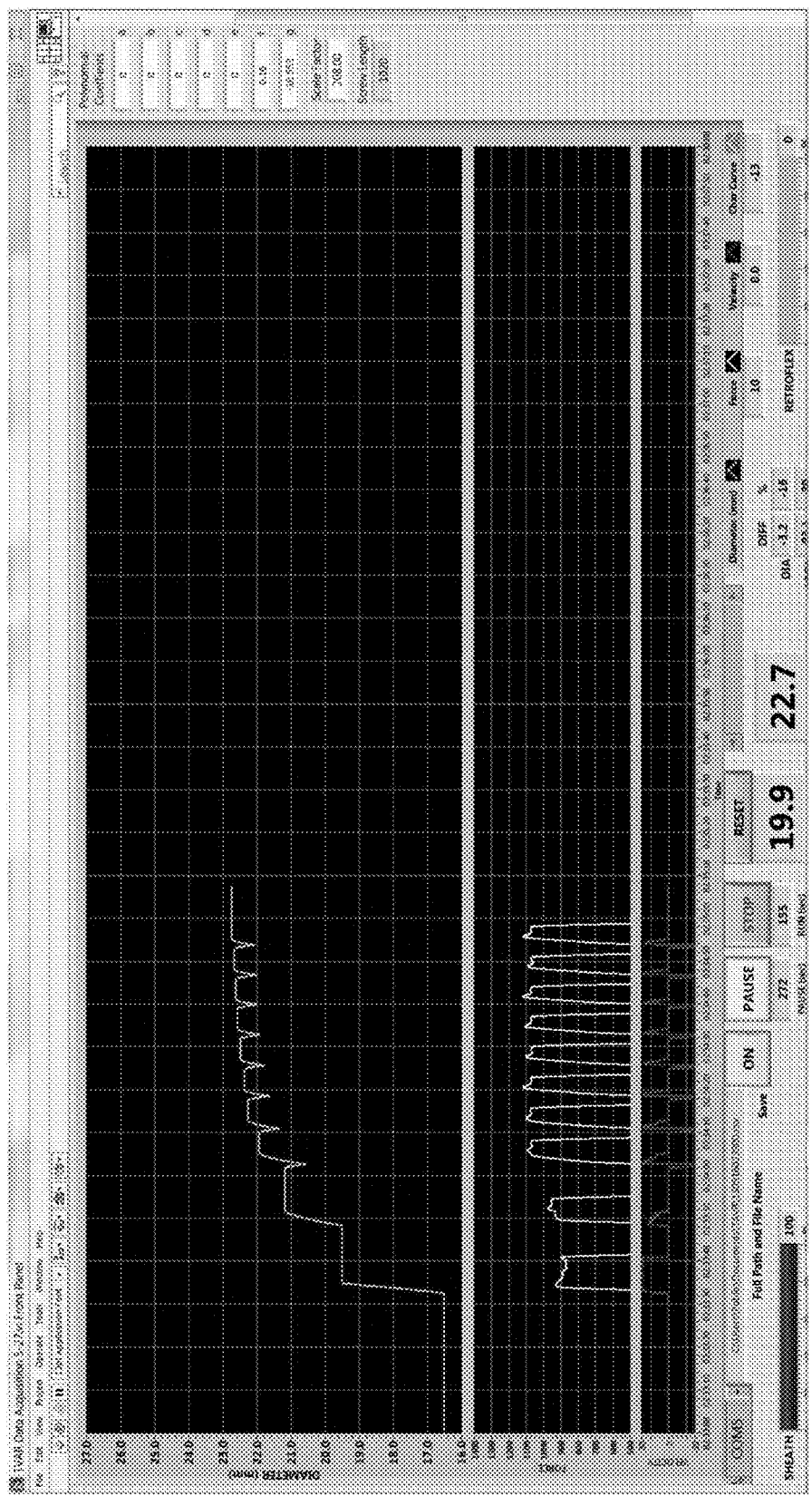
Figure 263:
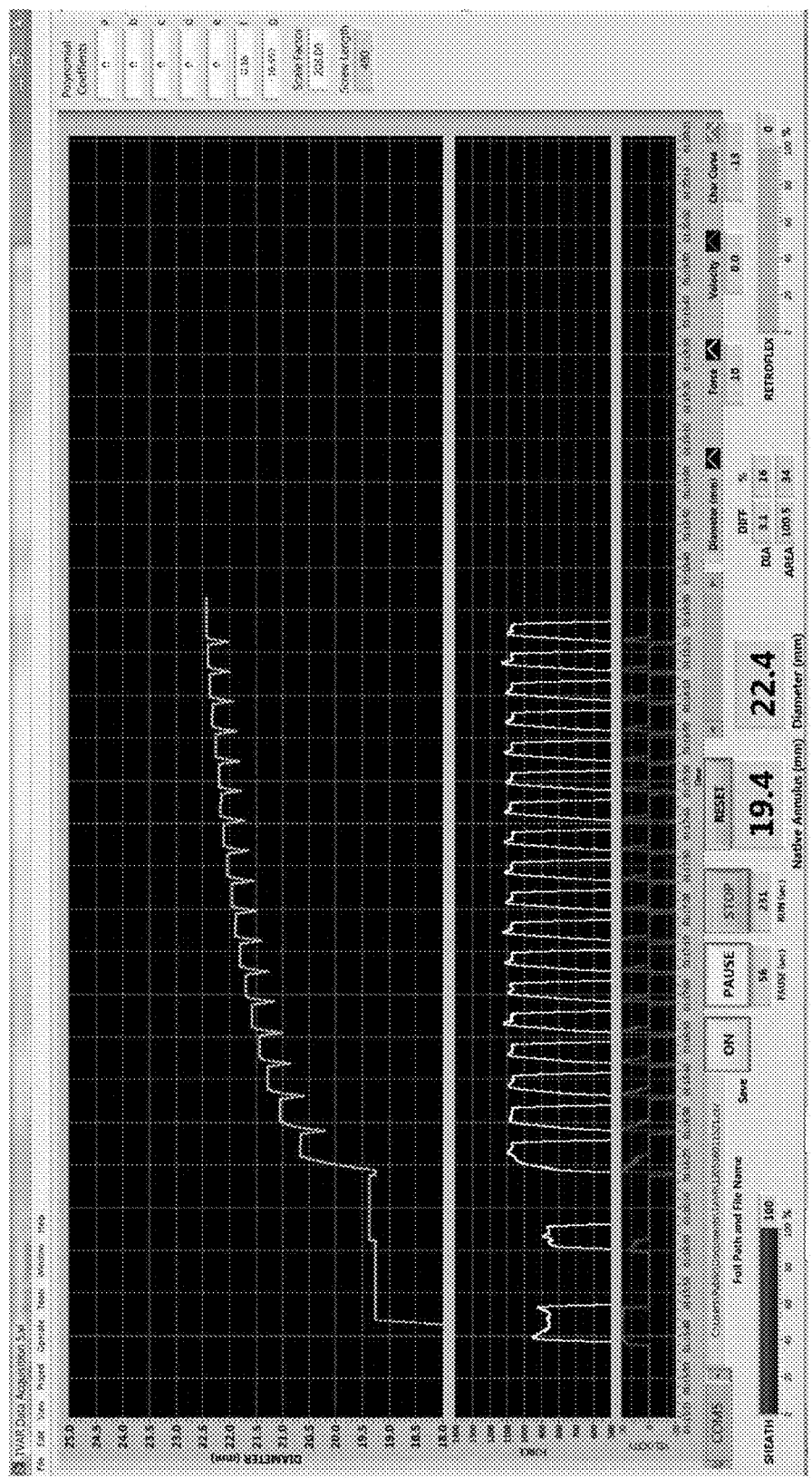
Figure 264:
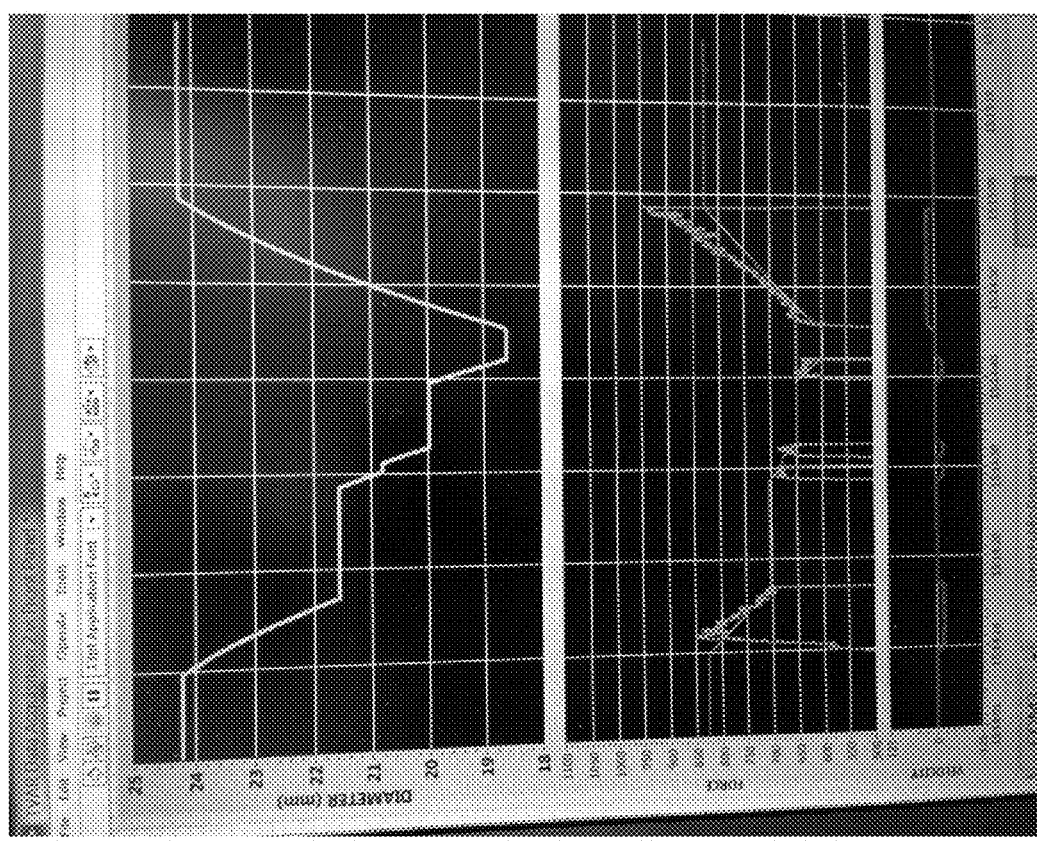
Figure 266:
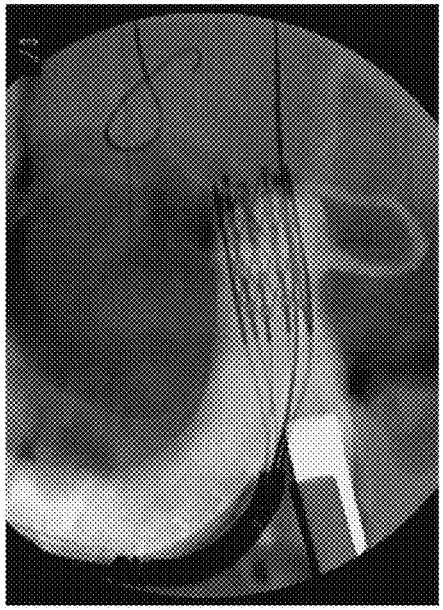
Figure 268:
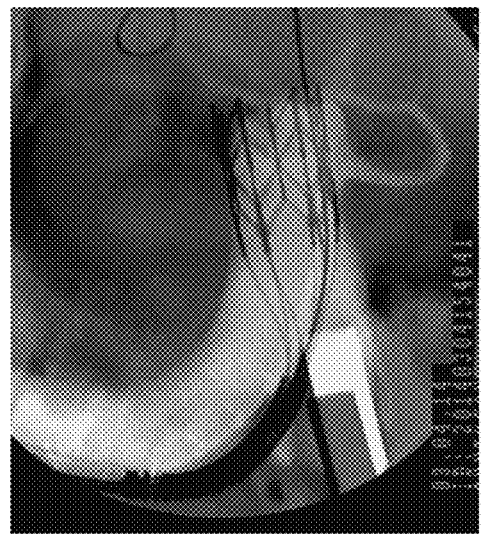
Figure 265:
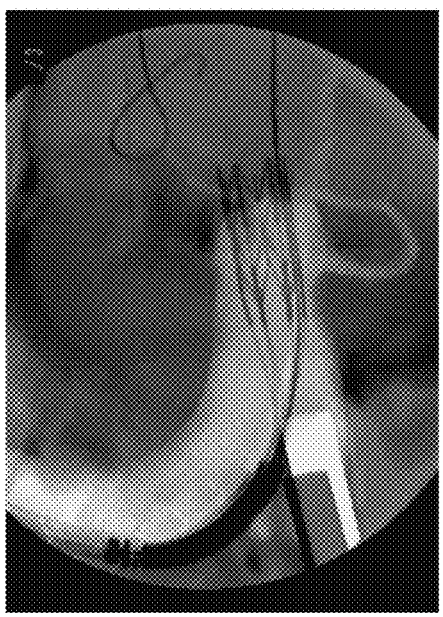
Figure 267:
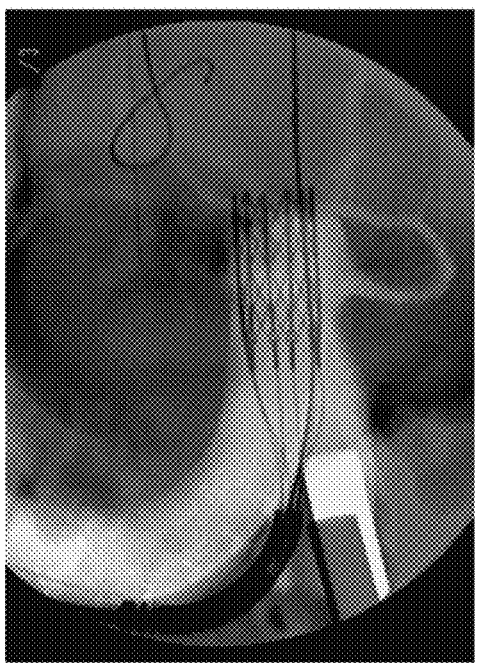
Figure 269:
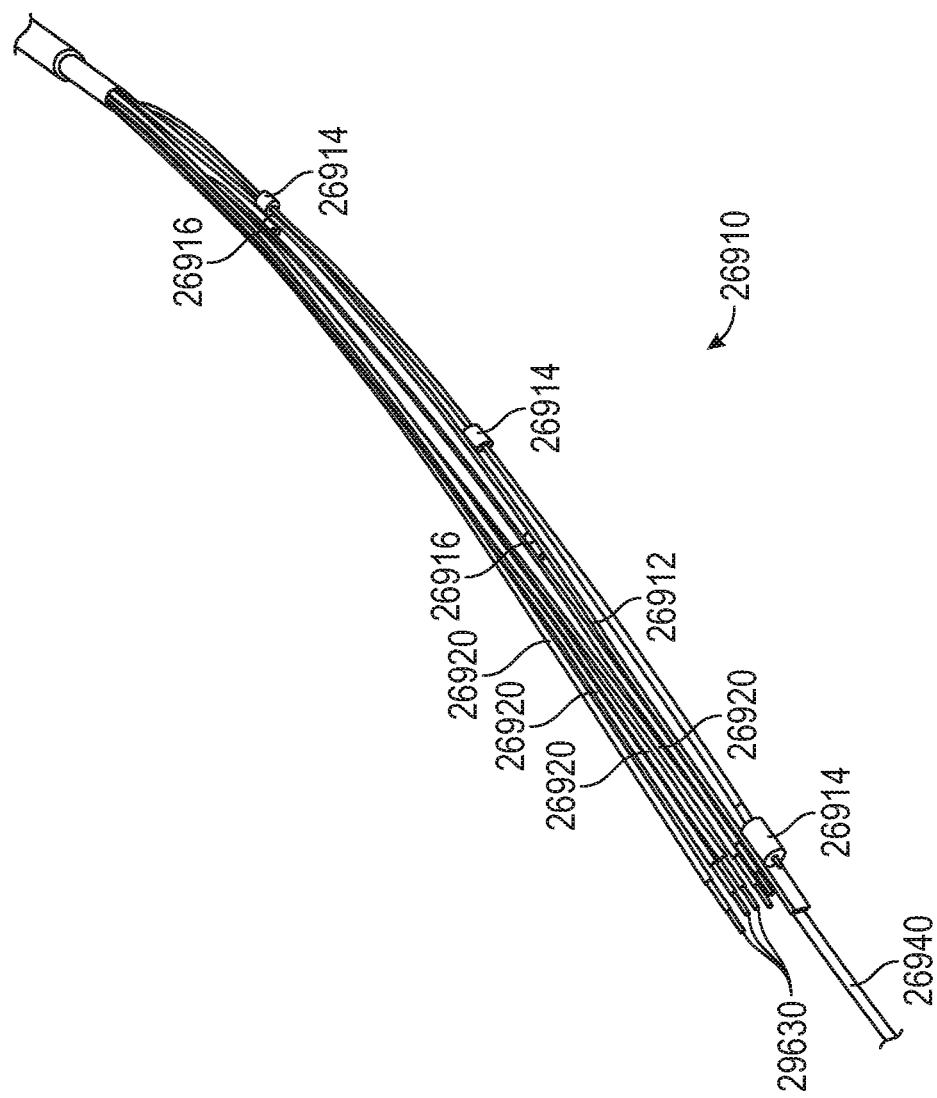
Figure 270:
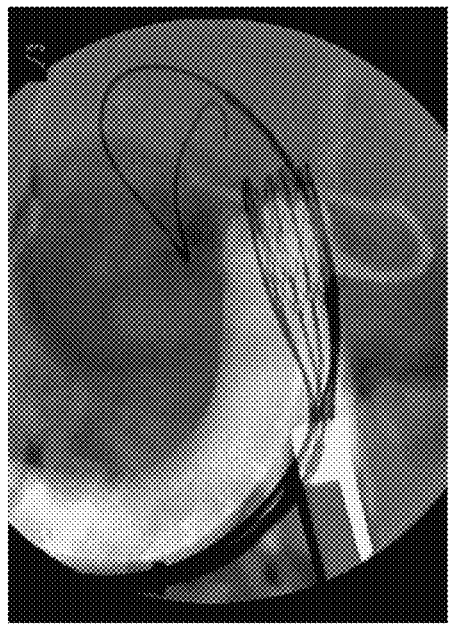
Figure 272:
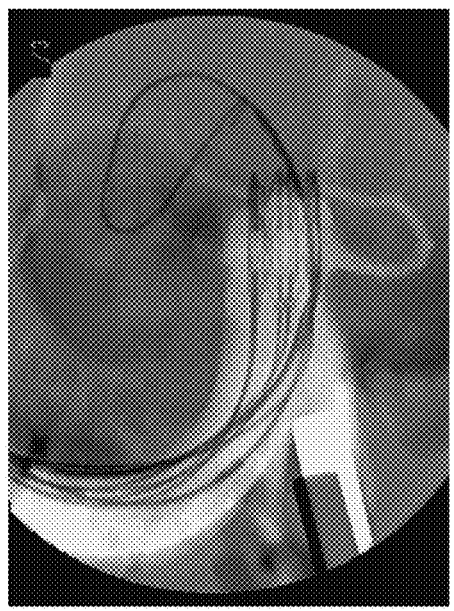
Figure 271:
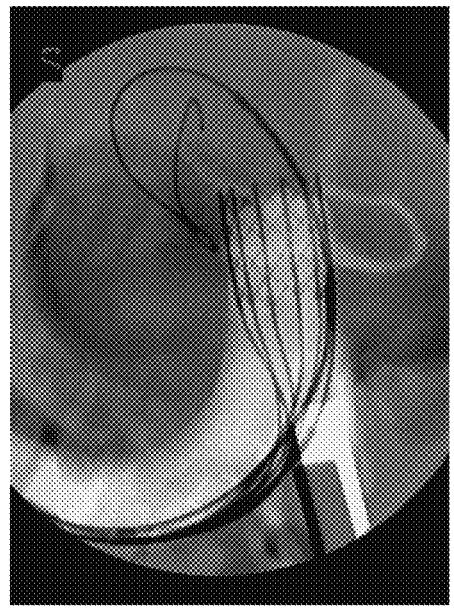

FIG. 204 is a fragmentary, perspective view of an exemplary embodiment of a self-expanding/forcibly-expanding implantable stent assembly having six lattice segments in an expanded state and with an alternative embodiment of a jack screw assembly having an outer-facing jack screw keyhole;

FIG. 205 is a side elevational view of the implantable stent assembly of FIG. 204 with a valve sub-assembly;

FIG. 206 is a fragmentary, enlarged portion of the outer-facing jack screw keyhole of the stent assembly of FIG. 204;

FIG. 207 is a fragmentary, enlarged, top plan and partially hidden view of an inner-facing jack screw keyhole;

FIG. 208 is a fragmentary, enlarged, perspective view of the stent assembly of FIG. 204 with an exemplary embodiment of a valve leaflet commisure connector;

FIG. 209 is a side perspective view of an exemplary embodiment of a self-expanding/forcibly-expanding implantable valve assembly having six lattice segments in an expanded state and with an alternative embodiment of securing the valve sub-assembly to the lattice and graft;

FIG. 210 is a perspective view of a downstream side of the self-expanding/forcibly-expanding implantable valve assembly of FIG. 209;

FIG. 211 is a perspective view of an upstream side of the self-expanding/forcibly-expanding implantable valve assembly of FIG. 209;

FIG. 212 is a photograph of an exemplary embodiment of a self-expanding/forcibly-expanding implantable valve assembly connected to a distal end of an exemplary embodiment of a delivery system with the valve assembly and the delivery approximately in an implantation state;

FIG. 213 is a photograph of the valve assembly and delivery system of FIG. 212 with the valve assembly in an intermediate re-sheathing state where the lattice-disconnector tubes partially re-sheathed;

FIG. 214 is a photograph of the valve assembly and delivery system of FIG. 212 with the valve assembly in an intermediate re-sheathing state where the lattice-disconnector tubes are re-sheathed and a proximal portion of the valve assembly is re-sheathed;

FIG. 215 is a photograph of the valve assembly and delivery system of FIG. 212 with the valve assembly in an intermediate re-sheathing state where the valve assembly is half re-sheathed;

FIG. 216 is a photograph of the valve assembly and delivery system of FIG. 212 with the valve assembly in an intermediate re-sheathing state where the valve assembly is approximately three-quarters re-sheathed;

FIG. 217 is a photograph of the valve assembly and delivery system of FIG. 212 with the valve assembly re-sheathed into the delivery catheter;

FIG. 218 is a photograph of a manufacturing process for creating a distal end of an exemplary embodiment of a delivery catheter sized to fit within an 18-French hole;

FIG. 219 is a photograph of an end plan view of the distal end of the delivery catheter of FIG. 218 without the remainder of the delivery system;

FIG. 220 is a photograph of a side perspective view of the distal end of the delivery catheter of FIG. 218 after the valve assembly has been extended and/or re-sheathed;

FIG. 221 is a photograph of an exemplary embodiment of a self-expanding/forcibly-expanding implantable stent assembly having six lattice segments in an intermediate expanded state without a valve sub-assembly and inside an irregular-shaped implantation site;

FIG. 222 is a photograph of the stent assembly of FIG. 221 in an further intermediate expanded state;

FIG. 223 is a photograph of the stent assembly of FIG. 221 in an further intermediate expanded state;

FIG. 224 is a photograph of the stent assembly of FIG. 221 in an implanted state within the irregular-shaped implantation site;

FIG. 225 is a process flow diagram of an exemplary embodiment of a method for controlling implantation of a self-expanding and forcibly-expanding device according to the described embodiments FIG. 226 is a fragmentary, exploded, perspective view of an exemplary embodiment of a distal control handle for implanting a self-expanding and forcibly-expanding device;

FIG. 227 is a fragmentary, exploded, perspective view of a distal portion of the distal control handle of FIG. 226 from a side thereof;

FIG. 228 is a fragmentary, exploded, perspective view of a proximal portion of the distal control handle of FIG. 226 from a side thereof;

FIG. 229 is a perspective view of an alternative embodiment of the distal control handle of FIG. 226 from above a side thereof;

FIG. 230 is a fragmentary, perspective view of a proximal portion of the distal control handle of FIG. 229 from above a side thereof;

FIG. 231 is a side elevational view of an exemplary embodiment of a self-expanding and forcibly-expanding implant;

FIG. 232 is a fragmentary, side elevational view of the self-expanding and forcibly-expanding implant of FIG. 231 inside a valve orifice;

FIG. 233 is a fragmentary, side elevational view of the self-expanding and forcibly-expanding implant of FIG. 231 inside a cylindrical vessel;

FIG. 234 is a side elevational view of an exemplary embodiment of a self-expanding and forcibly-expanding implant with a barbell-shaped extension on a distal end thereof;

FIG. 235 is a side elevational view of an exemplary embodiment of a self-expanding and forcibly-expanding implant with a bulb-shaped extension on a distal end thereof;

FIG. 236 is a fragmentary, diagrammatic cross-sectional view of a heart having an atrial septal defect;

FIG. 237 is a fragmentary, diagrammatic cross-sectional view of the heart of FIG. 236 having an exemplary embodiment of a self-expanding and forcibly-expanding implant implanted within the atrial septal defect;

FIG. 238 is a fragmentary, diagrammatic cross-sectional view of a heart in which a WATCHMAN® device is implanted within the left atrial appendage;

FIG. 239 is a fragmentary, diagrammatic, enlarged cross-sectional view of the heart of FIG. 238 with a view of the left atrial appendage;

FIG. 240 is a fragmentary, diagrammatic cross-sectional view of a left atrium and a left atrial appendage of a heart with a self-expanding and forcibly-expanding implant partially expanded in the appendage;

FIG. 241 is a fragmentary, diagrammatic cross-sectional view of a heart having a left ventricular aneurysm;

FIG. 242 is a fragmentary illustration of the arterial and venous circulation of the human legs;

FIG. 243 is a perspective view of an alternative embodiment of a distal control handle according to the invention from above a right rear thereof and with the distal prosthesis delivery system removed;

FIG. 244 is a right side elevational view of the distal control handle of FIG. 243;

FIG. 245 is a left side elevational view of the distal control handle of FIG. 243;

FIG. 246 is a top plan view of the distal control handle of FIG. 243;

FIG. 247 is a bottom plan view of the distal control handle of FIG. 243;

FIG. 248 is a rear elevational view of the distal control handle of FIG. 243;

FIG. 249 is a perspective view of the distal control handle of FIG. 243 from above the right rear corner;

FIG. 250 is a perspective view of the distal control handle of FIG. 243 from above the left rear;

FIG. 251 is a perspective view of the distal control handle of FIG. 243 from above the right upper front side with a top half of a casing removed and with the distal prosthesis delivery system removed;

FIG. 252 is a perspective view of a motor and transmission assembly of the distal control handle of FIG. 251 from above;

FIG. 253 is a perspective view of the front of the motor assembly of the distal control handle of FIG. 251 with a distal transmission cover removed;

FIG. 254 is a perspective view of the front of the motor assembly of the distal control handle of FIG. 251 with a proximal transmission cover and motors removed;

FIG. 255 is a perspective view of the rear of the motor assembly of the distal control handle of FIG. 251 with the proximal transmission cover and motors removed;

FIG. 256 is a photograph of the rear of the distal control handle of FIG. 243;

FIG. 257 is a photograph of the distal control handle of FIG. 243 from above with the top half of the casing removed;

FIG. 258 is a photograph of a delivery system with the distal control handle of FIG. 243 from in front of a left side thereof with the top half of the casing removed;

FIG. 259 is a photograph of the delivery system of FIG. 258 from above the left side thereof;

FIG. 260 is a photograph of the delivery system of FIG. 258 from behind a left side thereof;

FIG. 261 is a multi-variable display of an exemplary embodiment of a method for determining a characteristic curve of an implant for detecting a native annulus size according to the invention;

FIG. 262 is a multi-variable display of the method for determining the characteristic curve of FIG. 261 with an different implant;

FIG. 263 is a multi-variable display of the method for determining the characteristic curve of FIG. 261 with an different implant;

FIG. 264 is a multi-variable display of a method for detecting a native annulus size according to the invention;

FIG. 265 is a fluoroscopic image of an exemplary embodiment of a delivery system with a self-expanding and forcibly-expanding aortic valve implant in a partially expanded state;

FIG. 266 is a fluoroscopic image of the delivery system and valve implant of FIG. 265 rotated counter-clockwise;

FIG. 267 is a fluoroscopic image of the delivery system and valve implant of FIG. 265 rotated clockwise;

FIG. 268 is a fluoroscopic image of the delivery system and valve implant of FIG. 265 expanded to an implantation position;

FIG. 269 is a fragmentary perspective view of an exemplary embodiment an angular correction device of a distal end of a stent delivery system;

FIG. 270 is a fluoroscopic image of an exemplary embodiment of an angular correction device at a distal end of a delivery system with a self-expanding and forcibly-expanding aortic valve implant in a partially expanded state;

FIG. 271 is a fluoroscopic image of the angular correction device, the delivery system, and the valve implant of FIG. 270 expanded to an implantation position; and FIG. 272 is a fluoroscopic image of the angular correction device, the delivery system, and the valve implant of FIG. 270 with the angular correction device actuated to rotate the implant clockwise.

DETAILED DESCRIPTION OF THE INVENTION

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

The terms "program," "programmed", "programming," "software," "software application," and the like as used herein, are defined as a sequence of instructions designed for execution on a computer system. A "program," "software," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the present invention. Referring now to the figures of the drawings in detail and first, particularly to FIGS. 1 to 19, there is shown a first exemplary embodiment of an actively controllable stent deployment system 100 according to the invention. Even though this exemplary embodiment is illustrated as a stent deployment system without the presence of a stent graft, this embodiment is not to be considered as limited thereto. Any stent graft embodiment according the invention as disclosed herein can be used in this embodiment. The stent graft is not shown in these figures for clarity. Further, as used herein, the terms "stent" and "stent graft" are used herein interchangeably. Therefore, any embodiment where a stent is described without referring to a graft should be considered as referring to a graft additionally or in the alternative, and any embodiment where both a stent and a graft are described and shown should be considered as also referring to an embodiment where the graft is not included.

In contrast to prior art self-expanding stents, the actively controllable stent deployment system 100 includes a stent lattice 110 formed by interconnected lattice struts 112, 114. In this exemplary embodiment, pairs of inner and outer struts 114, 112 are respectively connected to adjacent pairs of inner and outer struts 114, 112. More particularly, each pair of inner and outer struts 114, 112 are connected pivotally at a center point of each strut 114, 112. The ends of each inner strut 114 of a pair is connected pivotally to ends of adjacent outer struts 112 and the ends of each outer strut 112 of a pair is connected pivotally to ends of adjacent inner struts 114. In such a configuration where a number of strut pairs 114, 112 are connected to form a circle, as shown in each of FIGS. 1 to 19, a force that tends to expand the lattice 110 radially outward will pivot the struts 114, 112 at each pivot point and equally and smoothly expand the entire lattice 110 from a closed state (see, e.g., FIG. 3) to any number of open states (see FIGS. 4 to 13). Similarly, when the stent lattice 110 is at an open state, a force that tends to contract the stent lattice 110 radially inward will pivot the struts 114, 112 at each pivot point and equally and smoothly contract the entire stent lattice 110 towards the closed state. This exemplary configuration, therefore, defines a repeating set of one intermediate and two outer pivot points about the circumference of the stent lattice 110. The single intermediate pivot point 210 is, in the exemplary embodiment shown in FIGS. 1 to 19, located at the center point of each strut 112, 114. On either side of the single intermediate pivot point 210 is a vertically opposing pair of outer pivot points 220.

Figure 7:
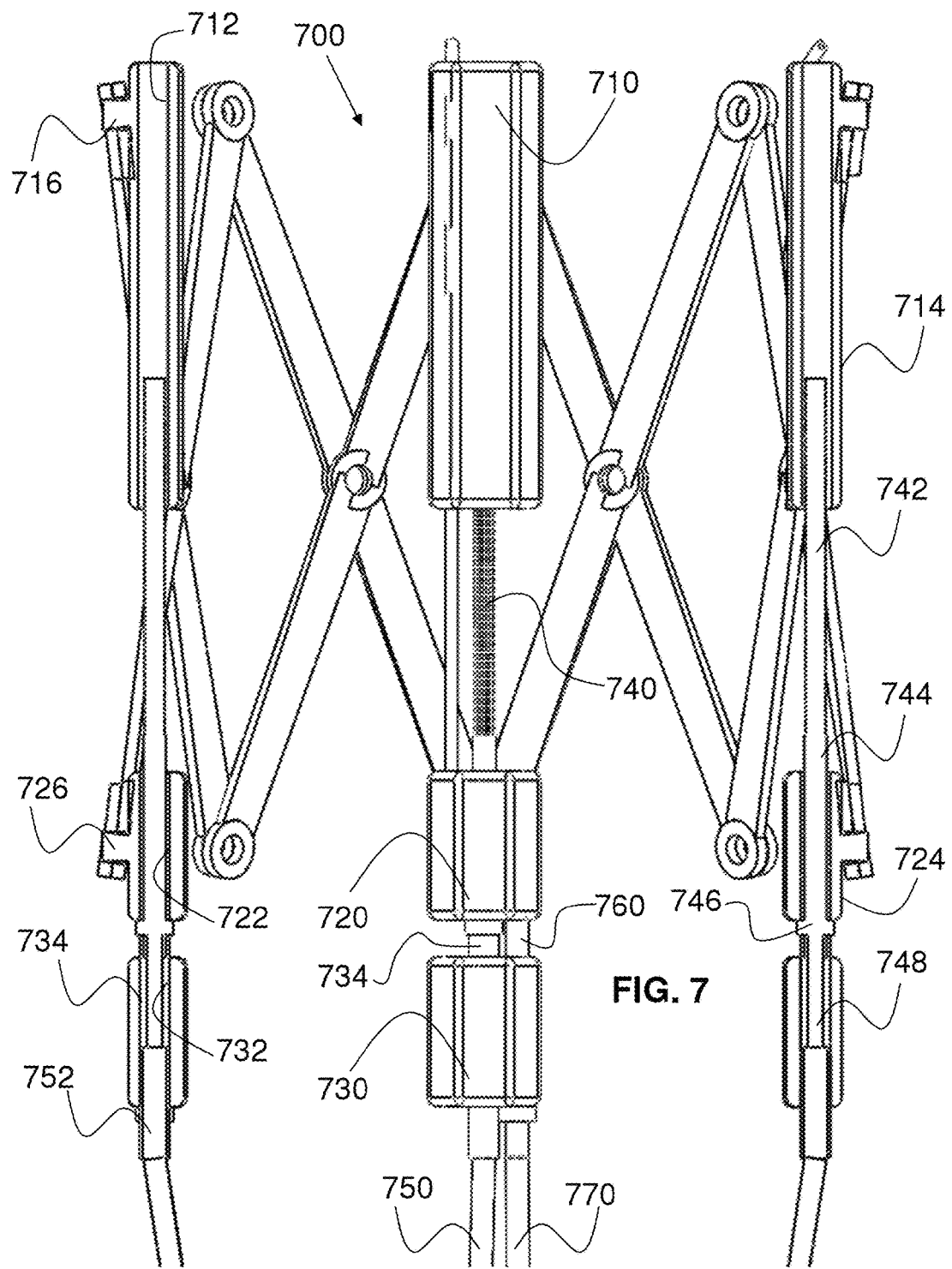
FIG. 7 is a fragmentary, longitudinally cross-sectional view of a rear half of the stent deployment system of FIG. 6.

To provide such expansion and contraction forces, the actively controllable stent deployment system 100 includes at least one jack assembly 700 that is present in each of FIGS. 1 to 19 but is described, first, with regard to FIG. 7. Each jack assembly 700 has a distal drive block 710, a proximal drive block 720, and a disconnector drive block 730. A drive screw 740 connects the distal drive block 710 to the proximal drive block 720. The drive screw 740 has a distal threaded drive portion 742 having corresponding threads to a threaded drive bore 712 of the distal drive block 710. The drive screw 740 has an intermediate unthreaded portion 744 that rotates freely within a smooth drive bore 722 of the proximal drive block 720. In the embodiment shown, the inner diameter of the smooth drive bore 722 is slightly larger than the outer diameter of the unthreaded portion 744 so that the unthreaded portion 744 can freely rotate within the smooth drive bore 722 substantially without friction. As used here, and in any of the other exemplary embodiments, substantially without friction means that the drive screw 740 can be turned when intended by a drive screw motor (as explained below) but does not turn when the lattice is disconnected from the drive motor. This characteristic is a result of having the lead angle of the thread on the drive screw 740 be very small, for example, between approximately 1 and approximately 10 degrees, in particular, between approximately 3 and approximately 7 degrees, further, between approximately 4 and approximately 5 degrees. This low angle makes turning the drive screw 740 to impart motion as described herein very easy but back-driving the screw almost impossible without damaging the drive screw 740. Based upon this attribute, the stent lattice (and other stent lattices described herein) become self-locking. The drive screw 740 also has an intermediate collar 746 just proximal of the proximal drive block 720. The outer diameter of the intermediate collar 746 is greater than the inner diameter of the smooth drive bore 722. Lastly, the drive screw 740 has a proximal key portion 748 extending from the intermediate collar 746 in a proximal direction. The jack assembly 700 is configured to retain the drive screw 740 within the distal drive block 710 and the proximal drive block 720 in every orientation of the stent lattice 110, from the closed state, shown in FIG. 3, to a fully open state, shown in FIG. 11, where the distal drive block 710 and the proximal drive block 720 touch one another.

Each jack assembly 700 is attached fixedly to the stent lattice 110 at a circumferential location thereon corresponding to the vertically opposing pair of outer pivot points 220. In one exemplary embodiment of the jack assembly 700 shown in FIGS. 1 to 19, the outer surface 714 of the distal drive block 710 and the outer surface 724 of the proximal drive block 720 each have a protruding boss 716, 726 having an outer shape that is able to fixedly connect to a respective one of the outer pivot points 220 of the stent lattice 110 but also rotationally freely connect thereto so that each of the inner and outer struts 114, 112 connected to the boss 716, 726 pivots about the boss 716, 726, respectively. In this exemplary embodiment, each boss 716, 726 is a smooth cylinder and each outer pivot point 220 is a cylindrical bore having a diameter corresponding to the outer smooth surface of the cylinder but large enough to pivot thereon without substantial friction. The materials of the boss 716, 726 and the outer pivot points 220 of the inner and outer struts 114, 112 can be selected to have substantially frictionless pivoting.

Accordingly, as the drive screw 740 rotates between the open and closed states, the unthreaded portion 744 of the drive screw 740 remains longitudinally stable within the proximal drive block 720. In contrast, the distal threaded drive portion 742 progressively enters the threaded drive bore 712 from the proximal end to the distal end thereof as the stent lattice 110 expands outwardly. As shown in the progressions of FIG. 2 to FIG. 4 and FIGS. 5 to 7 to 8 to 9, as the drive screw 740 rotates within the proximal drive block 720, the distal drive block 710 moves closer and closer to the proximal drive block 720, thereby causing a radial expansion of the stent lattice 110.

To implant the stent lattice 110 in a tubular anatomic structure (such as a vessel or a valve seat), the stent lattice 110 needs to be disconnected from the delivery system. Delivery of the stent lattice 110 to the anatomic structure will be described in further detail below. When the stent lattice 110 enters the implantation site, it will be most likely be in the closed state shown in FIG. 3, although for various reasons, the stent lattice 110 can be expanded partially, if desired, before reaching the implantation site. For purposes of explaining the disconnect, the extent of expansion is not relevant. When at the implantation site, the stent lattice 110 will be expanded by rotating the drive screw 740 in a corresponding expansion direction (the direction of threads of the drive screw 740 and the drive bore 712 will determine if the drive screw 740 needs to be rotated clockwise or counter-clockwise). The stent lattice 110 is expanded to a desired expansion diameter, for example as shown in the progression of FIGS. 4 to 9 or FIGS. 10 to 11, so that it accommodates to the natural geometry of the implantation site, even if the geometry is non-circular or irregular. When the implantation diameter is reached, e.g., in FIGS. 9 and 11, the jack assemblies 700 need to be disconnected from the remainder of the stent deployment system 100.

To accomplish disconnect of the jack assemblies 700, the disconnector drive block 730 is provided with two lumens. A first lumen, the drive lumen 732, accommodates a drive wire 750 that is able to rotationally engage the proximal key portion 748. Use of the word wire for the drive wire 750 does not mean that this structure is a solid cord. The drive wire 750 can also be a hollow tube, a coil, or any other structure that can perform the functions described herein. In the exemplary embodiment shown, which is most clearly illustrated in FIG. 19, the proximal key portion 748 has a square cross-sectional shape. A drive wire bushing 734 rotationally freely but longitudinally fixedly resides in the drive lumen 732. The drive wire bushing 734 is connected to the drive wire 750 either as an integral part thereof or through a connection sleeve 752. Regardless of the connection design, any rotation of the drive wire 750 in either direction will cause a corresponding rotation of the drive wire bushing 734. A key hole 738 at the distal end of the disconnector drive block 730 and having an internal shape corresponding to a cross-section of the proximal key portion 748 allows a rotationally fixed but longitudinally free connection to occur with the proximal key portion 748. In the exemplary embodiment shown in FIG. 19, the key hole 738 also has a square cross-sectional shape.

Figure 14:
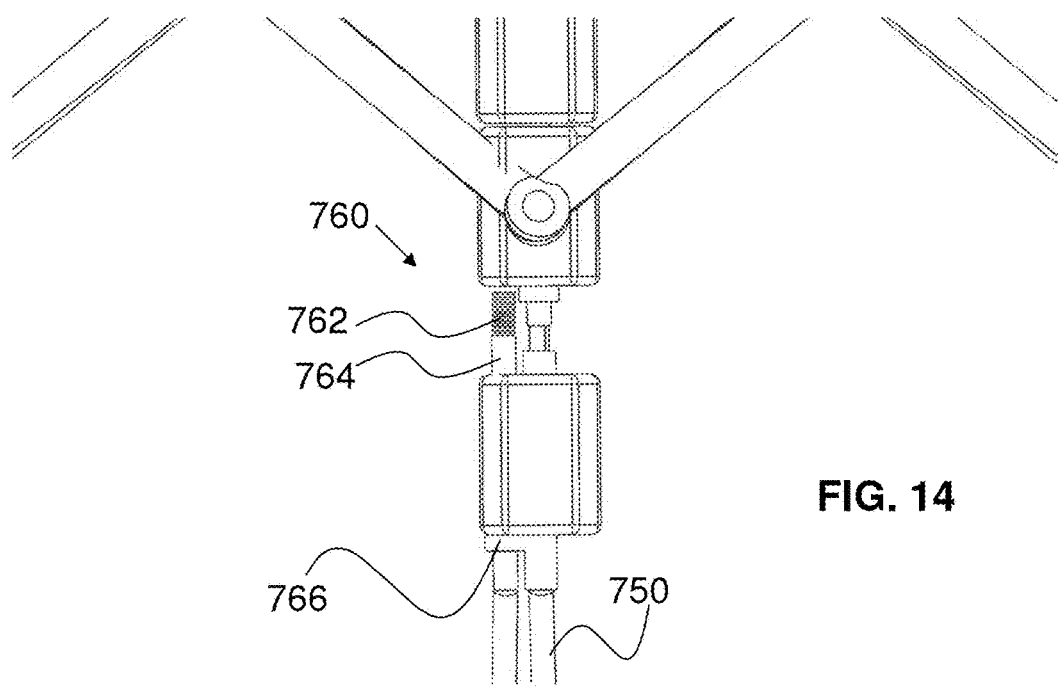
FIG. 14 is a fragmentary, longitudinally cross-sectional view of an enlarged portion of the stent deployment system of FIG. 12 in the partially disengaged state.
Figure 15:
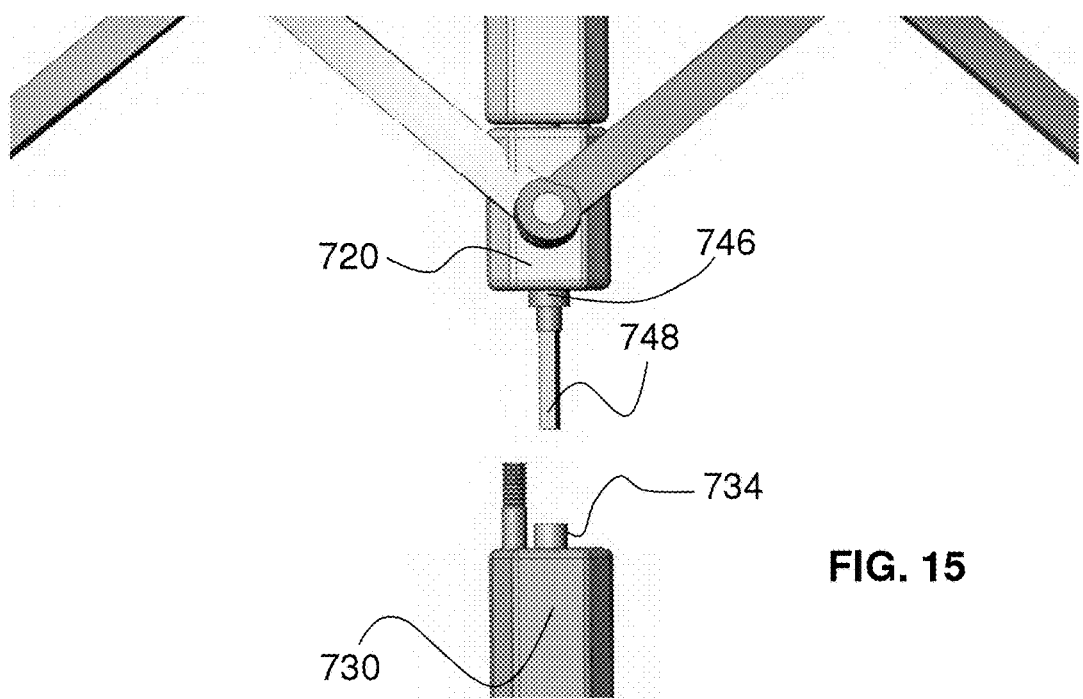
FIG. 15 is a fragmentary, longitudinally cross-sectional view of an enlarged portion of the stent deployment system of FIG. 13 in a disengaged state.
Figure 16:
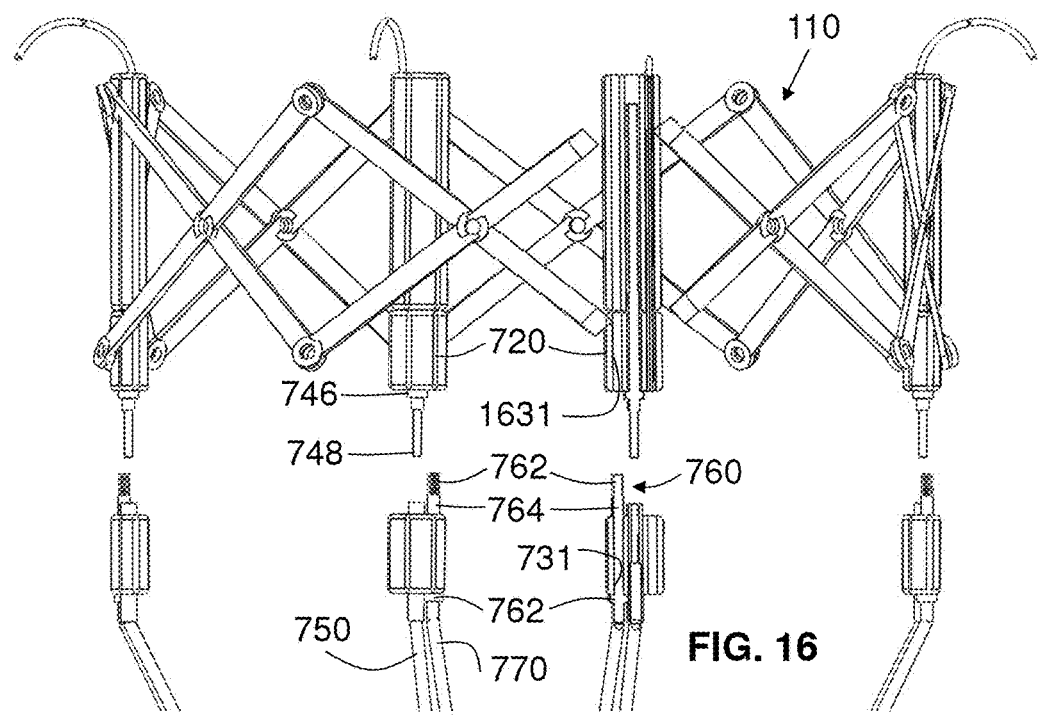
FIG. 16 is a fragmentary, partially cross-sectional, side elevational view of the stent deployment system of FIG. 9 rotated about a longitudinal axis, with the deployment control assembly in the disengaged state, and showing a cross-section of a portion of the deployment control assembly.

The disconnector drive block 730 also has a second lumen, a disconnect lumen 731, which is best shown in FIGS. 14 and 16. Residing in the disconnect lumen 731 in a rotationally free but longitudinally fixed manner is a retainer screw 760. The retainer screw 760 has a distal threaded portion 762, an intermediate shaft 764, and a proximal connector 766. The distal threaded portion 762 has an exterior thread corresponding to an internal thread of a connect lumen 1631, which is located in the proximal drive block 720 and is coaxial with the disconnect lumen 731. The intermediate shaft 764 has a smooth exterior surface and a cross-sectional shape that is slightly smaller than the cross-sectional shape of the disconnect lumen 731 so that it can be rotated freely within the disconnect lumen 731 substantially without friction (as above, this turns with the controlling motor but remains fixed when disconnected, i.e., it is self-locking). The proximal connector 766 has a flange with an outer diameter greater than the inner diameter of the disconnect lumen 731. The proximal connector 766 is connected at a proximal end thereof to a disconnect wire 770, which connection can either be an integral part thereof or through a secondary connection, such as a weld or connection sleeve. Use of the word wire for the disconnect wire 770 does not mean that this structure is a solid cord. The disconnect wire 770 can also be a hollow tube, a coil, or any other structure that can perform the functions described herein.

With such a configuration of the proximal drive block 720 and the disconnector drive block 730 of a jack assembly 700, rotation in a securing direction will longitudinally secure the proximal drive block 720 to the disconnector drive block 730 so that the stent lattice 110 remains connected to the drive wire 750 and the disconnect wire 770. In the connected state, the stent lattice 110 may be extended outward and retracted inward as many times as needed until implantation alignment occurs according to the surgeon's desire. Likewise, rotation in a disconnecting direction will longitudinally release the proximal drive block 720 from the disconnector drive block 730 so that the stent lattice 110 disconnects entirely from the drive wire 750 and the disconnect wire 770.

Figure 12:
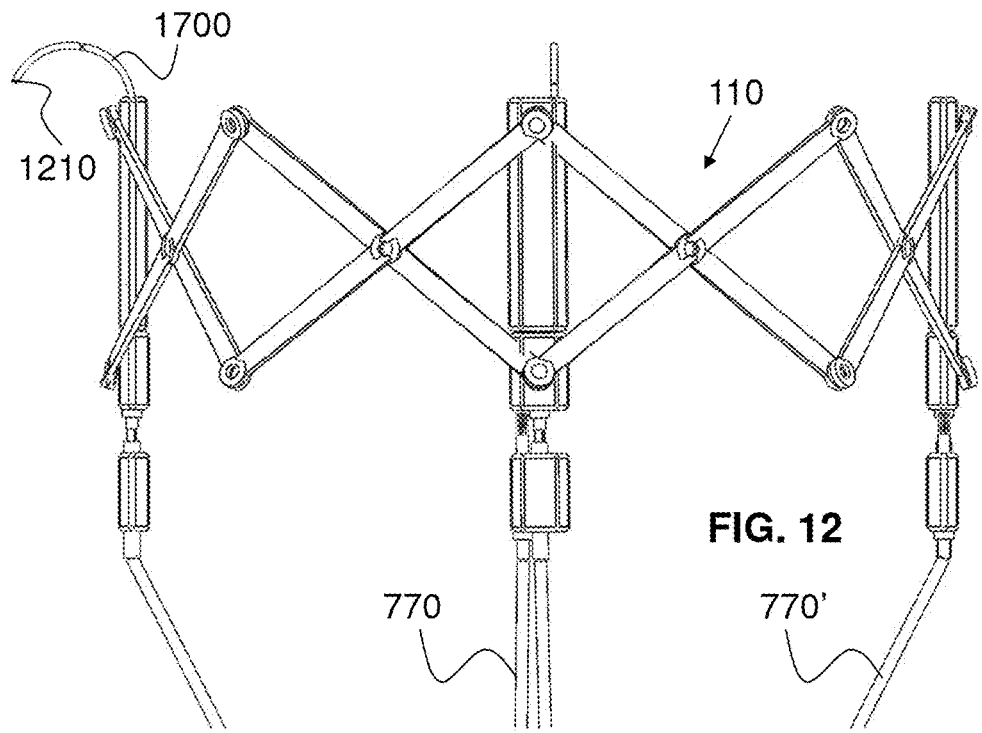
FIG. 12 is a fragmentary, longitudinal cross-sectional view of the stent deployment system of FIG. 11 with a deployment control assembly in a partially disengaged state.
Figure 13:
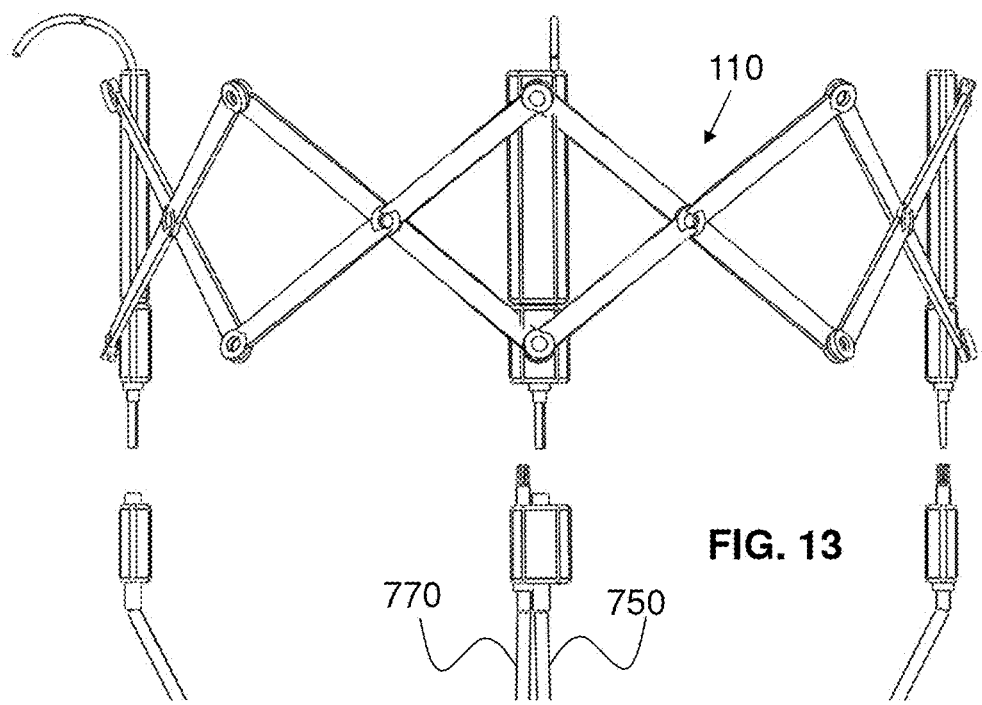
FIG. 13 is a fragmentary, longitudinally cross-sectional view of the stent deployment system of FIG. 12 with the deployment control assembly in a disengaged state.

This process is illustrated with regard to FIGS. 10 to 19. In the exemplary illustration of FIG. 10, the stent lattice 110 is not fully expanded. Because the distal threaded portion 762 of the retainer screw 760 is threaded within the connect lumen 1631 of the proximal drive block 720, the disconnector drive block 730 remains longitudinally fixed to the proximal drive block 720—ideally, a configuration that exists from the time that the stent deployment system 100 first enters the patient and at least up until implantation of the stent lattice 110 occurs. Expansion of the stent lattice 110 is finished in the configuration of FIG. 11 and, for purposes of this example, it is assumed that the stent lattice 110 is correctly implanted at the implantation site. Therefore, disconnection of the delivery system can occur. It is noted that this implantation position just happens to be at a circumferential extreme of the stent lattice 110 because the distal drive block 710 and the proximal drive block 720 are touching. In actual use, however, it is envisioned that such touching does not occur when expanded for implantation and, in such a state, there is a separation distance between the distal drive block 710 and the proximal drive block 720 to give the stent lattice 110 room to expand further into the implantation site if needed. Disconnection of the stent lattice 110 begins by rotating the disconnect wire 770 in a direction that unscrews the threaded portion 762 of the retainer screw 760 from the connect lumen 1631. As the stent lattice 110 is implanted with expansive force at the implantation site, the disconnector drive block 730 moves proximally as unthreading occurs. Complete unthreading of the retainer screw 760 is shown in FIGS. 12 and 14. In a configuration with more than one jack assembly 700 (the configuration of FIGS. 1 to 19 has 4, for example), each disconnect wire 770, 770' will rotate synchronously to have each disconnector drive block 730 disconnect from its respective proximal drive block 720 substantially simultaneously, as shown in FIG. 12. Such synchronous movement will be described in greater detail below. With the stent lattice 110 implanted, as shown in FIGS. 13, 15, 18, and 19, the delivery system for the stent lattice 110 can be withdrawn proximally away from the implantation site and be retracted out from the patient.

It is noted that the exemplary embodiment of FIGS. 1 to 19 shows the actively controllable stent deployment system 100 as having four jack assemblies 700 equally spaced around the circumference of the lattice 110. This configuration is merely exemplary and any number of jack assemblies 700 can be used to expand and contract the lattice 110, including a minimum of one jack assembly 700 in total and a maximum of one jack assembly 700 for each intersection between each inner and outer strut pair 112, 114. Herein, three and four jack assemblies 700 are depicted and used to show particularly well performing configurations. By using an even number, counter-rotating screws can be used to null the torque.

Figure 20:
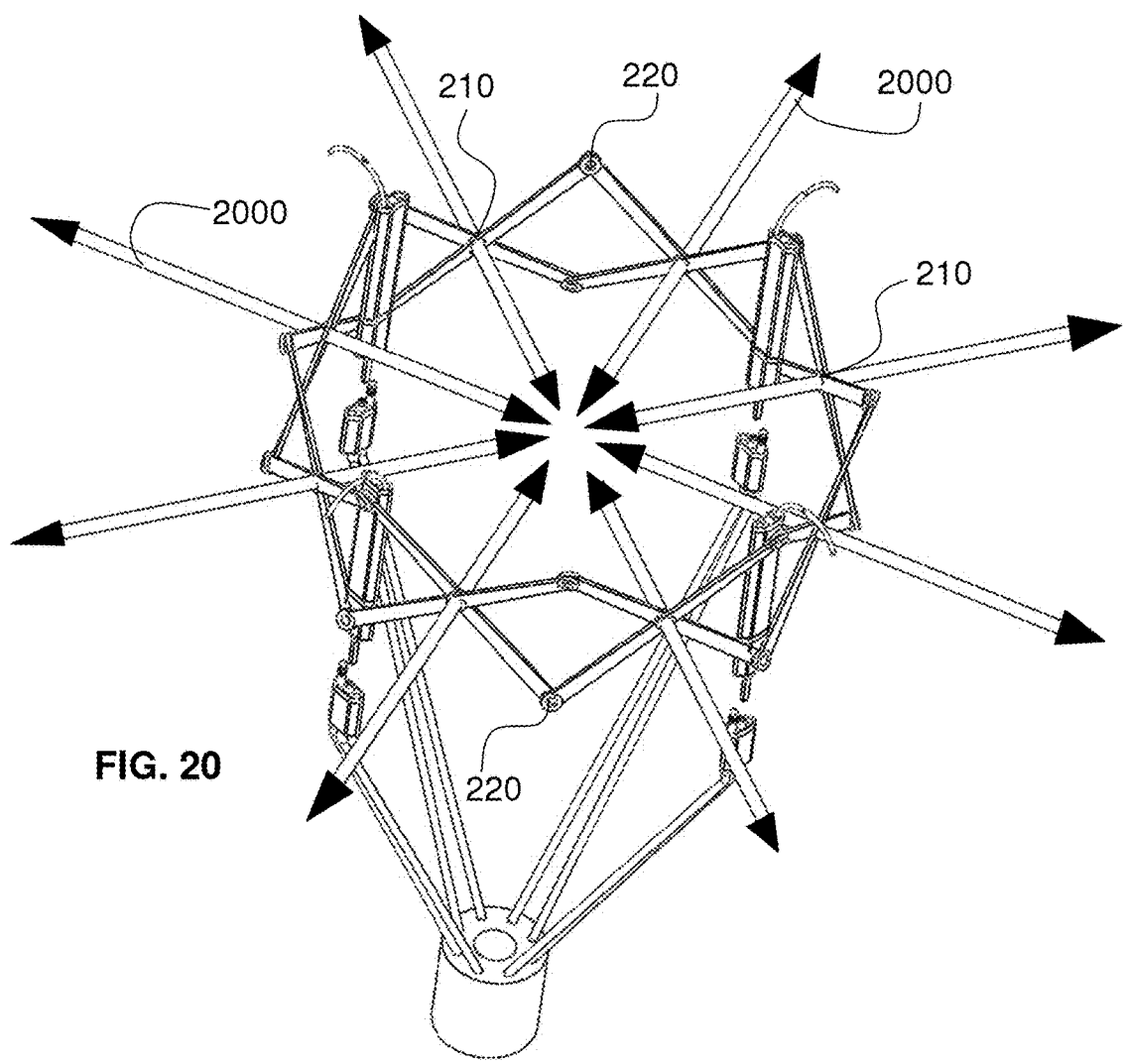
FIG. 20 is a fragmentary, perspective view of the stent deployment system of FIG. 18 with a diagrammatic illustration of paths of travel of strut crossing points as the stent is moved between its expanded and contracted states.

FIG. 20 is provided to further explain how the stent lattice 110 moves when it is expanded and contracted. As set forth above, the actively controllable stent deployment system 100 is based upon the construction of the stent lattice 110 and the attachment of the proximal and distal drive blocks 720, 710 of at least one jack assembly 700 to at least one set of the vertically opposing upper and lower pivot points 220 of the stent lattice 110. With the exemplary connections 716, 726 and pivot points 210, 220 shown in FIGS. 1 to 19, a longitudinal vertical movement of one of the proximal or distal drive blocks 720, 710 with respect to the other will expand or contract the stent lattice 110 as described herein. FIG. 20 illustrates with solid cylinders 2000 a radial path of travel that each intermediate pivot point 210 will traverse as the stent lattice 110 is moved between its expanded state (e.g., FIG. 9) and its contracted state (e.g., FIG. 2). Because the travel path is linear, the stent lattice 110 expands and contracts smoothly and equally throughout its circumference.

It is noted that the struts 112, 114 shown in FIGS. 1 to 19 appear to not be linear in certain figures. Examples of such non-linearity are the struts in FIGS. 10 and 11. Therein, each strut 112, 114 appears to be torqued about the center pivot point such that one end is rotated counter-clockwise and the other is rotated clockwise. This non-linearity can create the hourglass figure that will help fix the graft into an implantation annulus and to create a satisfactory seal at the top edge of the implant. The non-linear illustrations are merely limitations of the computer design software used to create the various figures of the drawings. Such non-linear depictions should not be construed as requiring the various exemplary embodiments to have the rotation be a part of the inventive struts or strut configuration. Whether or not the various struts 112, 114 will bend, and in what way they will bend, is dependent upon the characteristics of the material that is used to form the struts 112, 114 and upon how the pivot joints of the lattice 110 are created or formed. The exemplary materials forming the struts 112, 114 and the pivots and methods for creating the pivots are described in further detail below. For example, they can be stamped, machined, coined or similar from the family of stainless steels and cobalt chromes.

Figure 17:
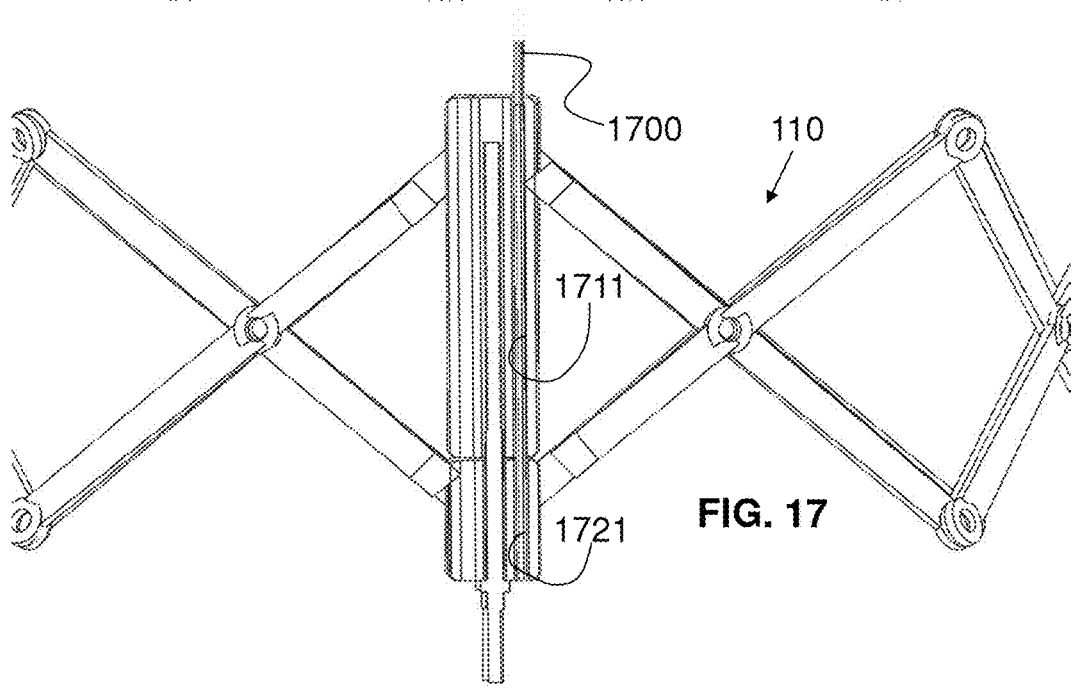
FIG. 17 is a fragmentary, longitudinally cross-sectional view of the stent deployment system of FIG. 16 showing a cross-section of a drive portion of a stent assembly with a fixed needle.
Figure 18:
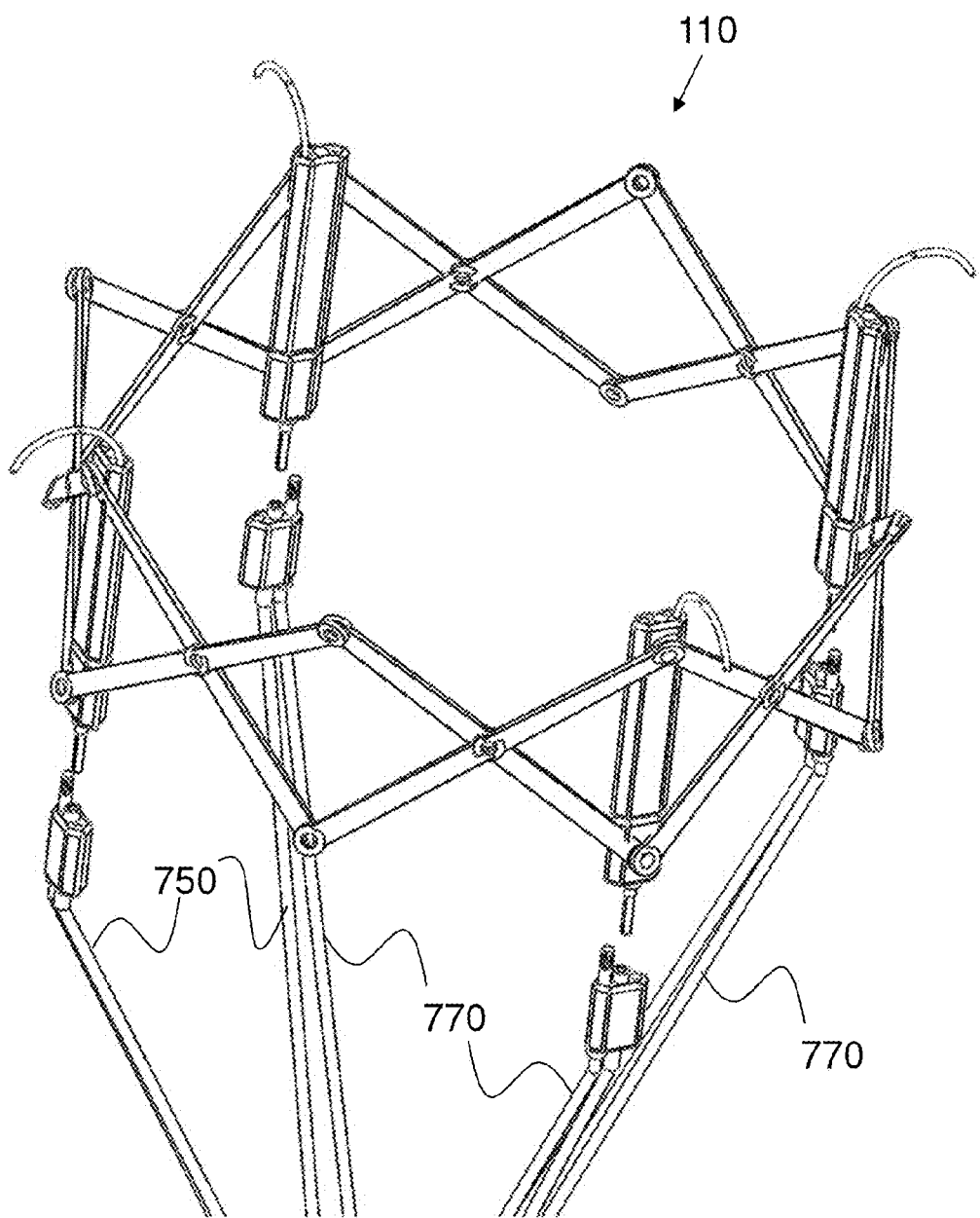
FIG. 18 is a fragmentary, perspective view of the stent deployment system of FIG. 16.
Figure 19:
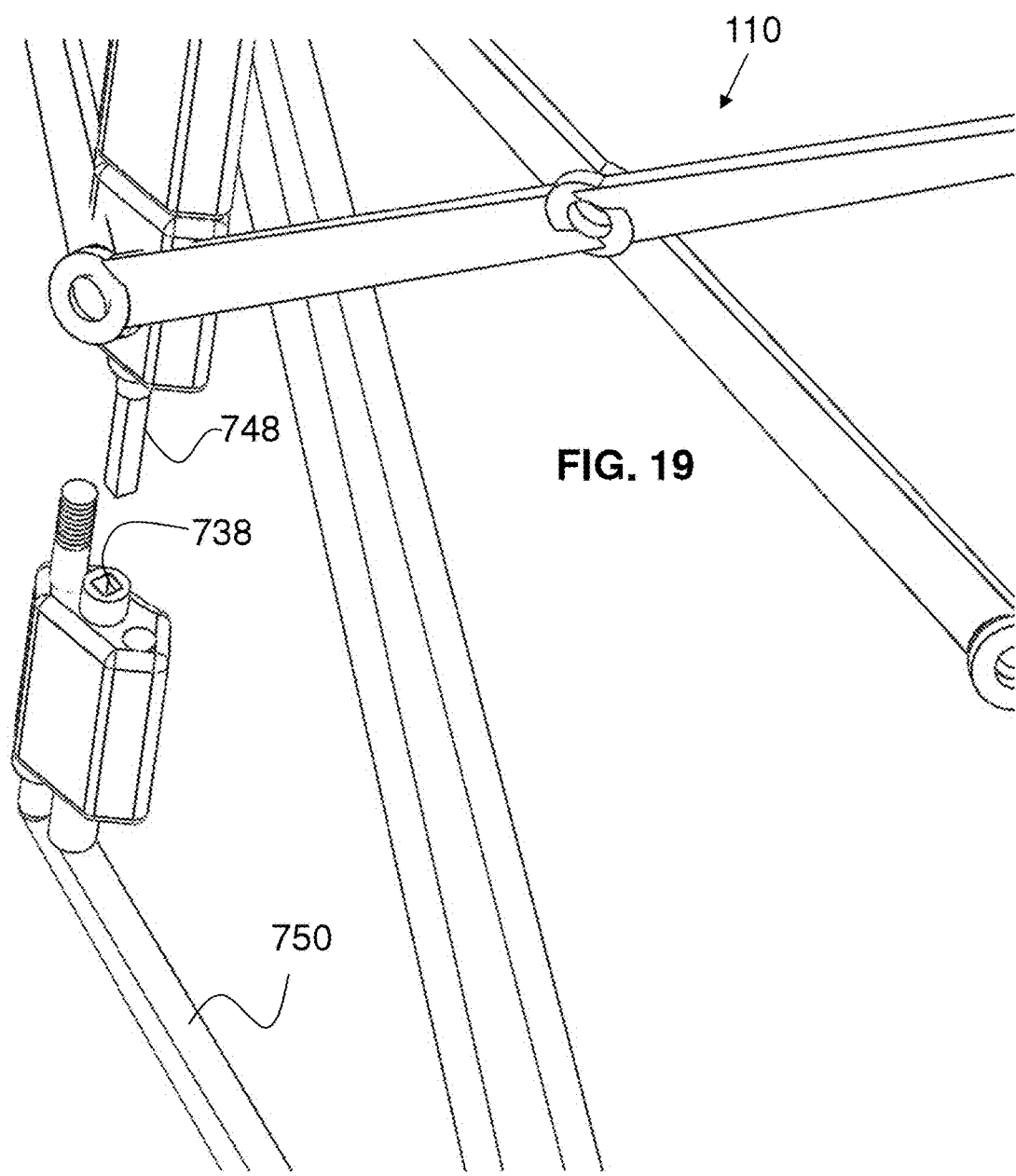
FIG. 19 is a fragmentary, perspective view of an enlarged portion of the stent deployment system of FIG. 18.

With the invention, force is applied actively for the controlled expansion of the stent lattice 110. It may be desirable to supplement the outwardly radial implantation force imposed on the wall at which the stent lattice 110 is implanted. Prior art stent grafts have included barbs and other similar devices for supplementing the outward forces at the implantation site. Such devices provide a mechanical structure(s) that impinge(s) on and/or protrude(s) into the wall of the implantation site and, thereby, prevent migration of the implanted device. The systems and methods of the invention include novel ways for supplementing the actively applied outward expansion force. One exemplary embodiment includes actively controllable needles, which is described, first, with reference to FIG. 17. In this exemplary embodiment, the distal drive block 710 and the proximal drive block 720 contain a third lumen, a distal needle lumen 1711 and a proximal needle lumen 1721. Contained within both of the distal and proximal needle lumens 1711, 1721 is a needle 1700. In an exemplary embodiment, the needle 1700 is made of a shape memory material, such as Nitinol, for example. The needle 1700 is preset into a shape that is, for example, shown in the upper left of FIG. 12 (or it can form a majority or an entirety of a closed circle). A portion that remains in the distal and proximal needle lumens 1711, 1721 after implantation of the stent lattice 110 can be preset into a straight shape that is shown in FIG. 17. A tissue-engaging distal portion of the needle 1700, however, is formed at least with a curve that, when extended out of the distal drive block 710, protrudes radially outward from the center longitudinal axis of the stent lattice 110. In such a configuration, as the needle 1700 extends outward, it drives away from the outer circumferential surface 714 (see FIG. 5) of the distal drive block 710 (i.e., towards the viewer out from the plane shown in FIG. 5). The needle 1700 also has a longitudinal extent that places the distal tip 1210 within the distal needle lumen 1711 when the stent lattice 110 is in the closed state, e.g., shown in FIG. 2.

Figure 5:
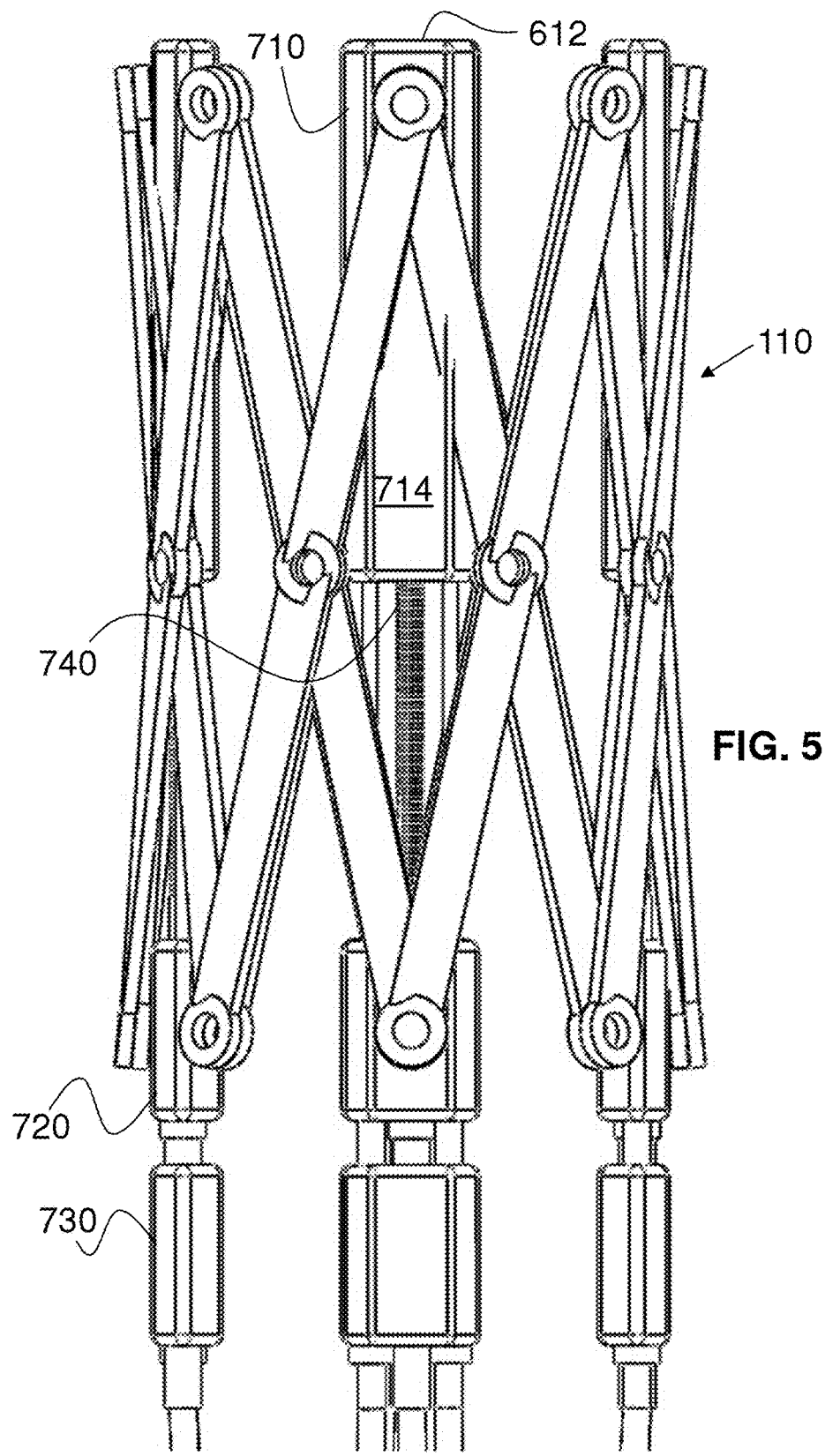
FIG. 5 is a fragmentary, side elevational view of the stent deployment system of FIG. 2 in a partially deployed state.

Deployment of the needles 1700 in each jack assembly 700 (or the number of needles can be any number less than the number of jack assemblies 700) is illustrated, for example, starting with FIG. 5. In this example, the needles 1700 in each of the four jack assemblies 700 has a length that is shorter than the longitudinal end-to-end distance of the proximal and distal drive blocks 720, 710 because the needles 1700 have not yet protruded from the distal upper surface 612 of each distal drive block 710 even though the stent lattice 110 is partially expanded. When the stent lattice 110 has expanded slightly further, however, as shown in FIG. 7, the needles 1700 begin protruding from the distal upper surface 612. As the needles 1700 are pre-bent as set forth above, the needles 1700 immediately begin bending into the natural pre-set curved shape. See also FIGS. 7 and 8. FIG. 10 illustrates two needles 1700 even further extended out from the distal needle lumen 1711 (only two are shown because this is a cross-section showing only the rear half of the stent lattice 110). FIG. 11 illustrates two needles 1700 in a fully extended position (as the distal and proximal drive blocks 710, 720 touch one another in the most-expanded state of the stent lattice 110). FIGS. 9, 13, 16, 17, 18, and 21 also show the needles 1700 in an extended or fully extended state.

Figure 1:
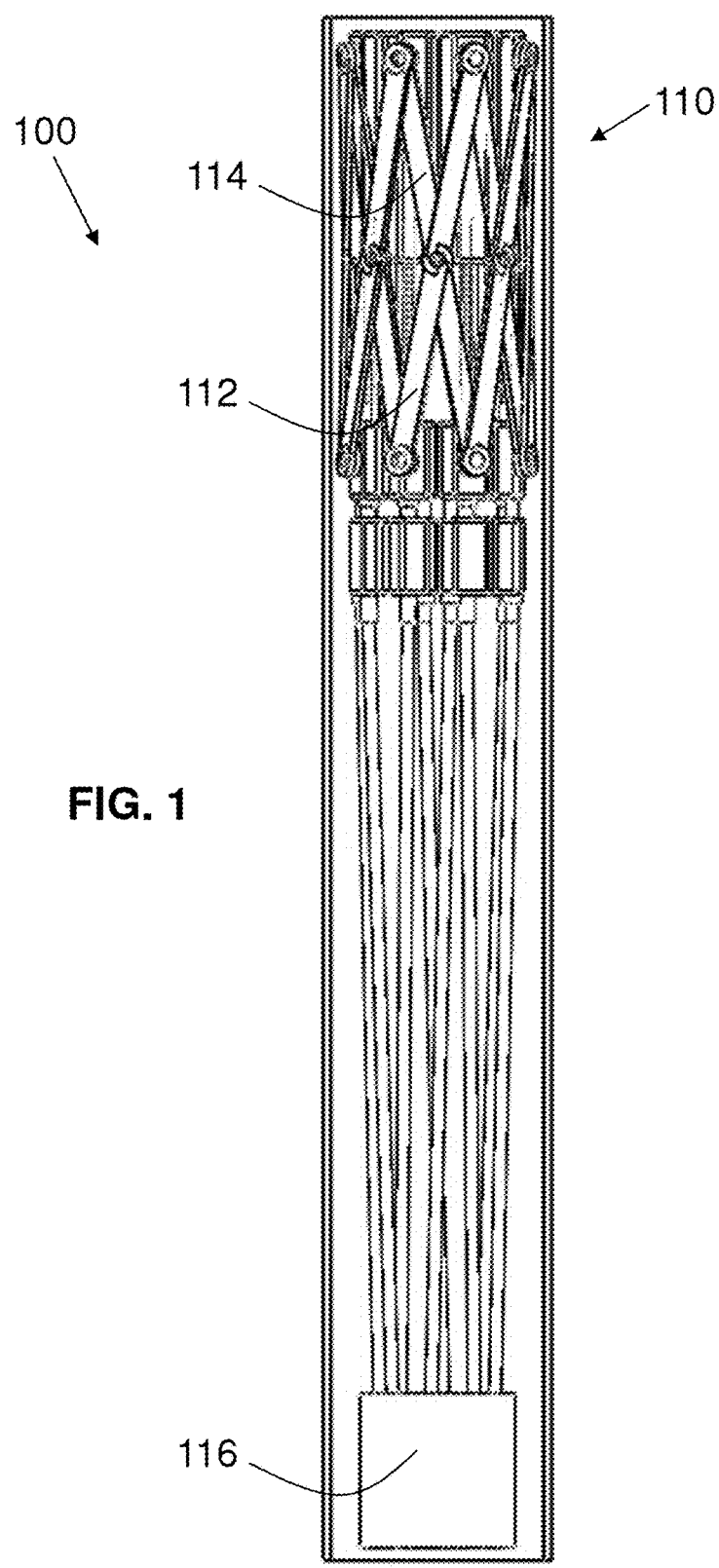
FIG. 1 is a fragmentary, partially longitudinally cross-sectional, side elevational view of an exemplary embodiment of an actively controllable stent/stent graft deployment system of the present invention in a non-deployed state with a front half of the outer catheter removed.
Figure 2:
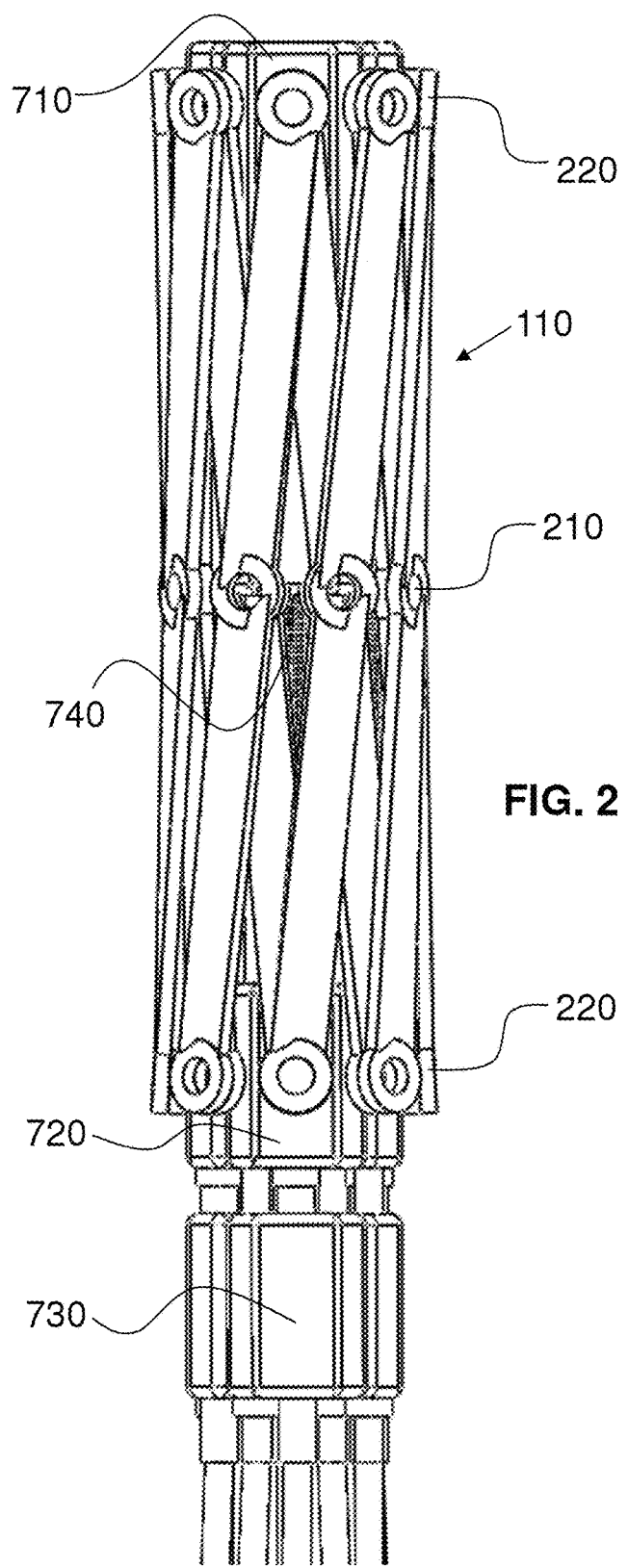
FIG. 2 is a fragmentary, side elevational view of an enlarged distal portion of the stent deployment system of FIG. 1.
Figure 3:
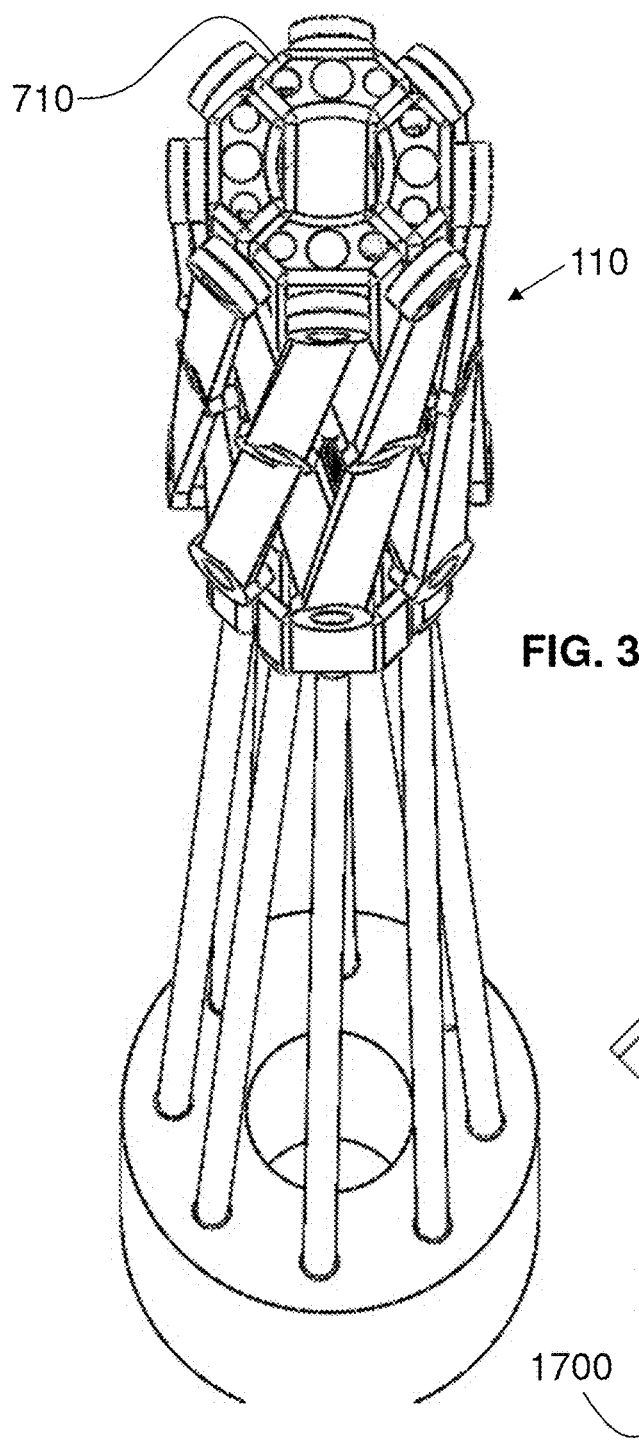
FIG. 3 is a fragmentary, perspective view of the stent deployment system of FIG. 1 from above the distal end.
Figure 6:
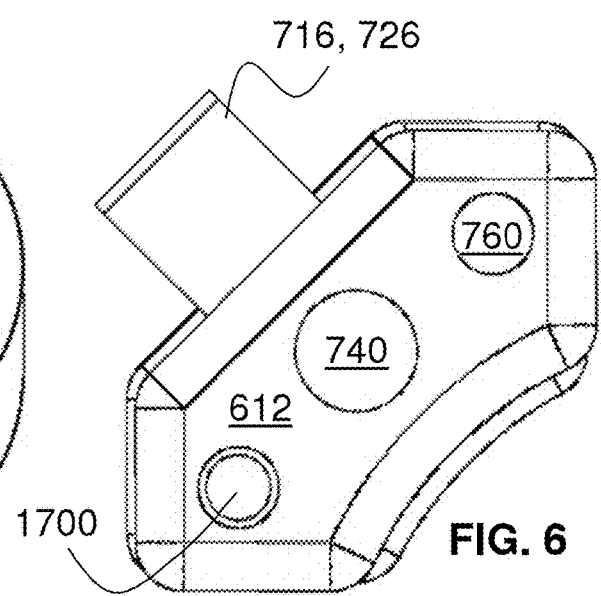
FIG. 6 is a is a top plan view of a drive portion of the stent deployment system of FIG. 2.
Figure 4:
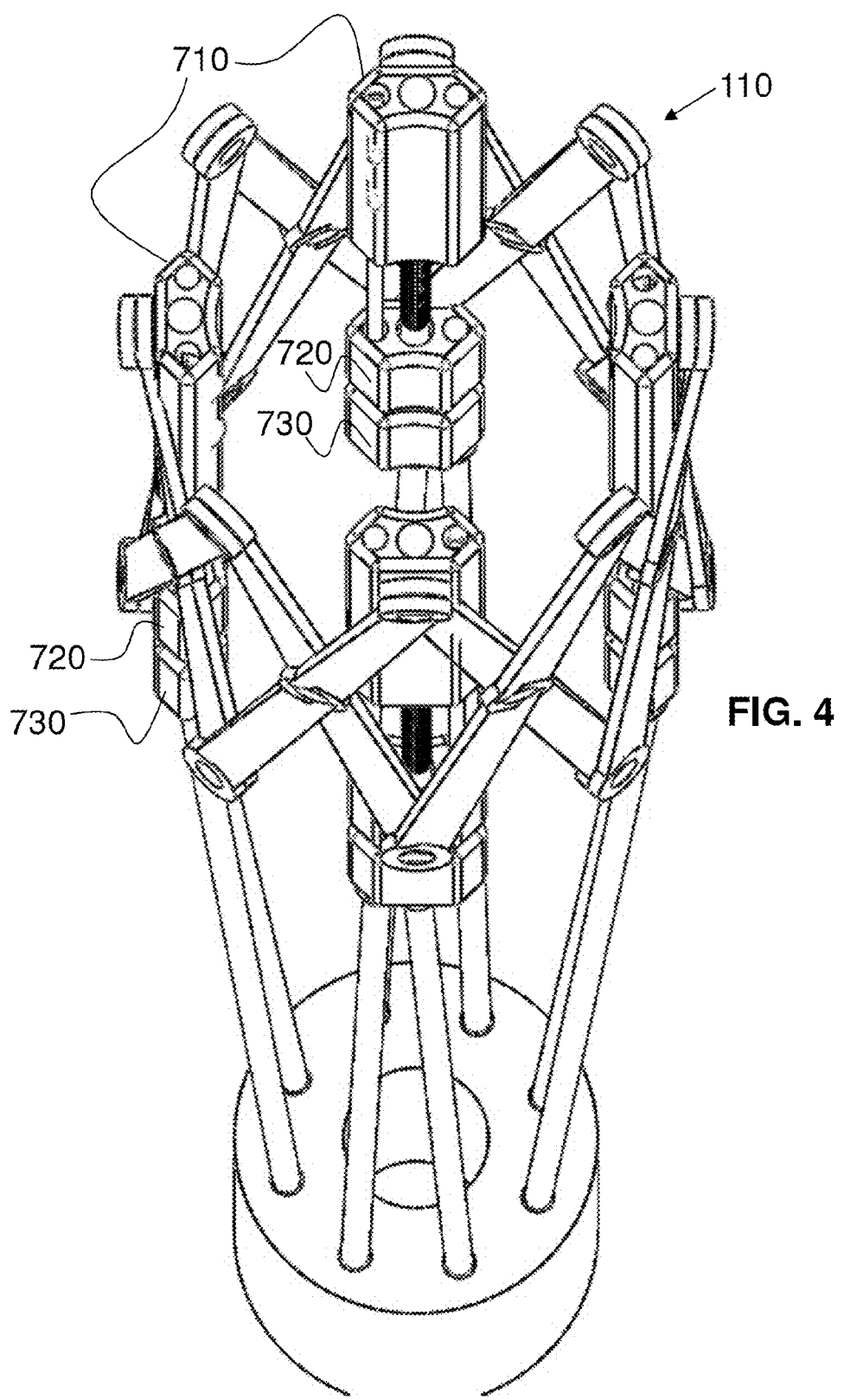
FIG. 4 is a fragmentary, perspective view of the stent deployment system of FIG. 1 from above the distal end with the system in a partially deployed state.

How the needles 1700 each extend from the distal drive block 710 can be explained in a first exemplary embodiment with reference to FIG. 17. A proximal portion of the needle 1700 is connected fixedly inside the proximal needle lumen 1721. This can be done by any measure, for example, by laser welding. In contrast, the intermediate and distal portions of the needle 1700 is allowed to entirely freely slide within the distal needle lumen 1711. With the length set as described above, when the distal and proximal drive blocks 710, 720 are separated completely, as shown in FIG. 3, the needle 1700 resides in both distal and proximal needle lumens 1711, 1721. As one of the distal and proximal drive blocks 710, 720 begins to move towards the other (as set forth above, the exemplary embodiment described with regard to these figures has the distal drive block 710 move towards the proximal drive block 720), the proximal portion of the needle 1700 remains in the proximal needle lumen 1721 but the distal portion of the needle 1700 begins to exit the distal upper surface 612, which occurs because the intermediate and distal portions of the needle 1700 are disposed slidably in the distal needle lumen 1711. This embodiment where the proximal portion of the needle 1700 is fixed in the proximal needle lumen 1721 is referred to herein as dependent control of the needles 1700. In other words, extension of the needles 1700 out from the distal needle lumen 1711 occurs dependent upon the relative motion of the distal and proximal drive blocks 710, 720.

Figure 24:
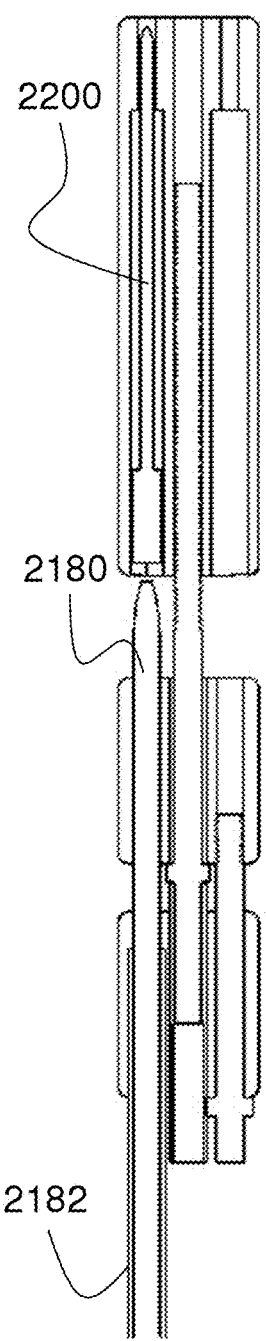
FIG. 24 is a fragmentary, cross-sectional view of the jack assembly of FIG. 23 with a needle pusher in a partially actuated state before extension of the needle.
Figure 25:
FIG. 25 is a fragmentary, cross-sectional view of the jack assembly of FIG. 24 with the needle pusher in another partially actuated state with the needle pusher in another partially actuated state with an extension of the needle.

Alternatively, the supplemental retention of the stent lattice 110 at the implantation site can occur with independent control of the needles. FIGS. 21 to 29 illustrate such an exemplary embodiment of a system and method according to the invention. Where similar parts exist in this embodiment to the dependently controlled needles 1700, like reference numerals are used. The jack assembly 2100 is comprised of a distal drive block 710, a proximal drive block 720, a disconnector drive block 730, a drive screw 740, a drive wire 750 (shown diagrammatically with a dashed line), a retainer screw 760, and a disconnect wire 770. Different from the jack assembly 700 of FIGS. 1 to 19, the jack assembly 2100 also includes a needle 2200 and a needle pusher 2210 and both the proximal drive block 720 and the disconnector drive block 730 each define a co-axial third lumen therein to accommodate the needle pusher 2210. More specifically, the distal drive block 710 includes a first pusher lumen 2211, the proximal drive block 720 includes a second pusher lumen 2221 and the disconnector drive block 730 includes a third pusher lumen 2231. As described above, the retainer screw 760 keeps the proximal drive block 720 and the disconnector drive block 730 longitudinally grounded to one another up until and after implantation of the stent lattice 110 and separation of the delivery system occurs. Rotation of the drive screw 740 causes the distal drive block 710 to move towards the proximal drive block 720, thereby expanding the stent lattice 110 to the desired implantation diameter. This movement is shown in the transition between FIG. 22 and FIG. 23. Now that the stent lattice 110 is determined to be properly implanted within the implantation site, it is time to deploy the needles 2200. Deployment starts by advancing the needle pusher 2180 as shown in FIG. 24. The needle pusher 2810 can, itself, be the control wire for advancing and retracting the needle 2200. Alternatively, and/or additionally, a needle control wire 2182 can be attached to or shroud the needle pusher 2180 to provide adequate support for the needle pusher 2180 to function. Continued distal movement of the needle pusher 2180 causes the needle 2200 to extend out from the distal upper surface 612 and, due to the preset curvature of the memory-shaped needle 2200, the needle tip curves outward and into the tissue of the implantation site. This curvature is not illustrated in FIG. 25 because the curvature projects out of the plane of FIG. 25.

Figure 26:
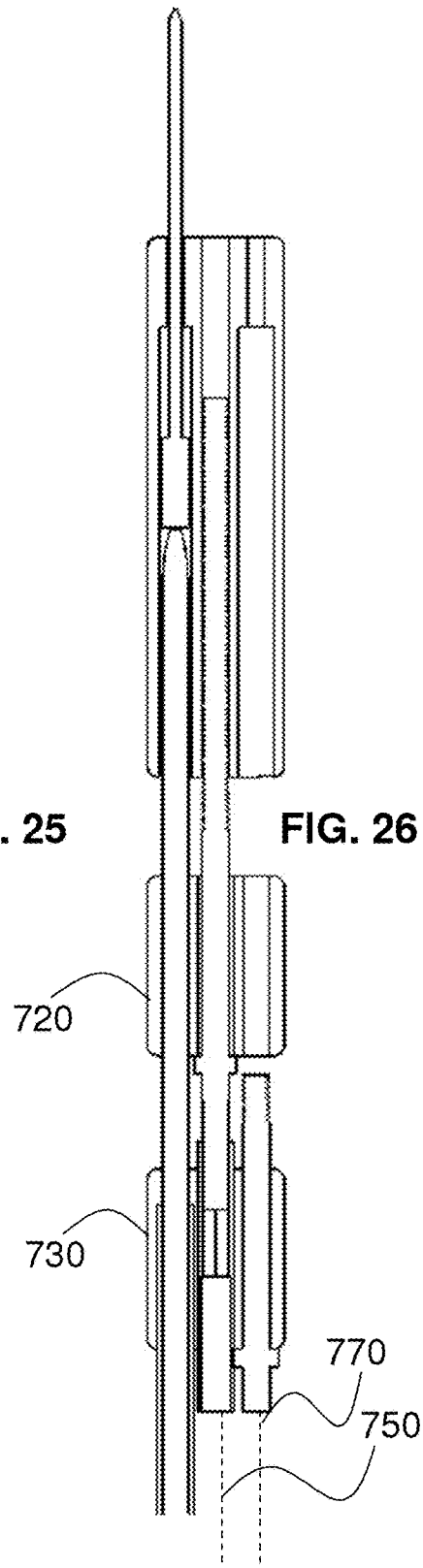
FIG. 26 is a fragmentary, cross-sectional view of the jack assembly of FIG. 25 with the drive sub-assembly in a partially disconnected state without retraction of the needle pusher.
Figure 27:
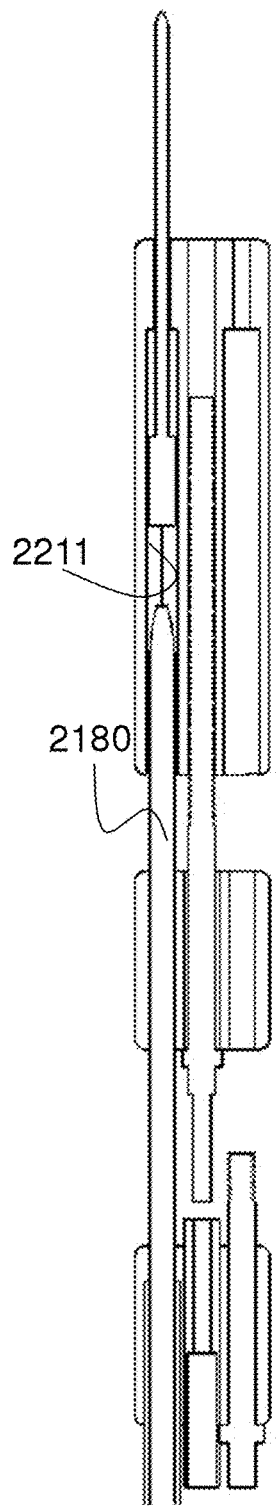
FIG. 27 is a fragmentary, cross-sectional view of the jack assembly of FIG. 26 with the drive sub-assembly in a further partially disconnected state with partial retraction of the needle pusher.
Figure 28:
FIG. 28 is a fragmentary, cross-sectional view of the jack assembly of FIG. 27 with the drive sub-assembly in a still a further partially disconnected state with further retraction of the needle pusher.
Figure 29:
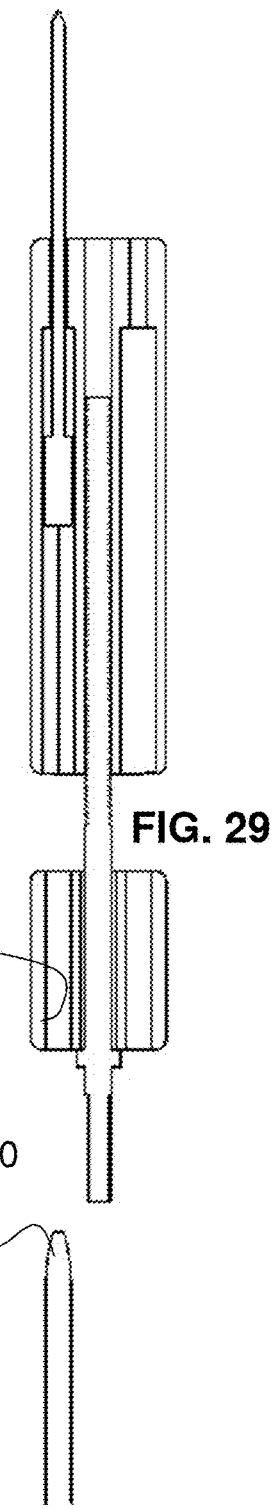
FIG. 29 is a fragmentary, cross-sectional view of the jack assembly of FIG. 23 with the drive sub-assembly and the needle pusher in a disconnected state.

Now that the stent lattice 110 is implanted and the needles 2200 are extended, disconnection of the stent lattice 110 occurs. First, as shown in FIG. 26, the retainer screw 760 is rotated to disconnect the proximal drive block 720 from the disconnector drive block 730 and a proximally directed force is imparted onto one or both of the drive wire 750 and the disconnect wire 770. This force moves the disconnector drive block 730 distally to remove the proximal key portion 748 of the drive screw 740 out from the keyhole 738, as shown in the progression from FIGS. 26 to 27. Simultaneously, distal movement of the disconnector drive block 730 starts the withdrawal of the needle pusher 2180 from the first pusher lumen 2211 (if not retracted earlier). Continued distal movement of the disconnector drive block 730 entirely removes the needle pusher 2180 from the first pusher lumen 2211, as shown in FIG. 28. Finally, withdrawal of the stent lattice delivery system entirely from the implantation site removes the needle pusher 2180 out from the second pusher lumen 2221 leaving only the implanted stent lattice 110, the jack assembly(ies) 2100, and the needle(s) 2200 at the implantation site.

FIGS. 30 to 37 illustrate another exemplary embodiment of an independent needle deployment system and method according to the invention. Where similar parts exist in this embodiment to the embodiments described above, like reference numerals are used. The jack assembly 3000 is comprised of a distal drive block 3010, a proximal drive block 3020, a disconnector drive block 3030, a drive screw 3040, a drive wire 750, a retainer screw 760, and a disconnect wire 770. The jack assembly 3000 also includes a needle 3070 and a needle movement sub-assembly 3090. The needle movement sub-assembly 3090 is comprises of a needle support 3092, a needle base 3094, a needle disconnect nut 3096, and a needle disconnect wire 3098.

The distal drive block 3010 defines three longitudinal lumens. The first is a support rod lumen 3012 and is defined to slidably retain a support rod 3080 therein. As rotational torque is imparted when any screw associated with the jack assembly 3000 rotates, the support rod 3080 is employed to minimize and/or prevent such torque from rotating the distal and proximal drive blocks 3010, 3020 and disconnector drive block 3030 with respect to one another and, thereby, impose undesirable forces on the stent lattice 110. The longitudinal length of the support rod 3080 is selected to not protrude out from the distal upper surface 3011 of the distal drive block 3010 in any expansion or retracted state of the stent lattice 110. The second vertically longitudinal lumen is the drive screw lumen 3014. As in previous embodiments, the drive screw lumen 3014 is configured with internal threads corresponding to external threads of the drive screw 740 and the longitudinal vertical length of the drive screw lumen 3014 is selected to have the drive screw 740 not protrude out from the distal upper surface 3011 of the distal drive block 3010 in any expansion or retracted state of the stent lattice 110. Finally, the distal drive block 3010 defines a needle assembly lumen that is comprises of a relatively wider proximal needle lumen 3016 and a relatively narrower distal needle lumen 3018, both of which will be described in greater detail below.

In comparison to other proximal drive blocks described above, the proximal drive block 3020 of jack assembly 3000 defines two vertically longitudinal lumens. The first lumen is a drive screw lumen 3024. In this exemplary embodiment, the drive screw 740 is longitudinally fixedly connected to the proximal drive block 3020 but is rotationally freely connected thereto. To effect this connection, a distal drive screw coupler part 3052 is fixedly secured to the proximal end of the drive screw 740 within a central bore that is part of the drive screw lumen 3024 of the proximal drive block 3020. The distal drive screw coupler part 3052 is shaped to be able to spin along its vertical longitudinal axis (coaxial with the vertical longitudinal axis of the drive screw 740) freely within the central bore of the drive screw lumen 3024. A distal portion of the drive screw lumen 3024 is necked down to have a diameter just large enough to allow a portion of the drive screw 740 (e.g., non-threaded) to spin therewithin substantially without friction. Through a circular port 3100 in a side of the proximal drive block 3020, the distal drive screw coupler part 3052 can be, for example, spot-welded to the proximal non-threaded end of the drive screw 740. With such a connection, the drive screw 740 is longitudinally fixedly grounded to the proximal drive block 3020 within the central bore of the drive screw lumen 3024. This means that rotation of the drive screw 740 causes the distal drive block 3010 to move towards the proximal drive block 3020 and, thereby, cause an expansion of the stent lattice 110 connected to the jack assembly 3000, for example, at bosses 3600 shown in FIG. 36. Fasteners 3610 in the form of washers, rivet heads, or welds, for example, can hold the stent lattice 110 to the bosses 3600. Further expansion of the drive screw coupler 3052, 3054 is made below with regard to the disconnector drive block 3030.

The second lumen within the proximal drive block 3020 of jack assembly 3000 is a retainer screw lumen 3022. A distal portion of the retainer screw lumen 3022 is shaped to fixedly hold a proximal end of the support rod 3080 therein; in other words, the support rod 3080 is fastened at the distal portion of the retainer screw lumen 3022 and moves only with movement of the proximal drive block 3020. Fastening can occur by any measures, for example, by corresponding threads, welding, press fitting, or with adhesives. A proximal portion of the retainer screw lumen 3022 has interior threads corresponding to exterior threads of the retainer screw 760. Accordingly, disconnection of the disconnector drive block 3030 from the proximal drive block 3020 is carried out by rotation of the retainer screw 760 fixedly connected to disconnector wire 770. Connection between the retainer screw 760 and the disconnector wire 770 can be accomplished by any measures, including for example, a hollow coupler sheath fixedly connected to both the distal end of the disconnector coupler wire 770 and the proximal end of the retainer screw 760 as shown in FIG. 30. As described above, the retainer screw 760 keeps the proximal drive block 3020 and the disconnector drive block 3030 longitudinally grounded to one another until after implantation of the stent lattice 110 and separation of the delivery system occurs.

This exemplary embodiment also has an alternative to the device and method for uncoupling the drive screw 740 from the remainder of the jack assembly 3000, in particular, the two-part drive screw coupler 3052, 3054. The distal drive screw coupler part 3052 as, at its proximal end, a mechanical coupler that is, in this exemplary embodiment, a semicircular boss extending in the proximal direction away from the drive screw 740. The proximal drive screw coupler part 3054, has a corresponding semicircular boss extending in the distal direction towards the drive screw 740. These can be seen, in particular, in the enlarged view of FIG. 37. Therefore, when the two semicircular bosses are allowed to interconnect, any rotation of the proximal drive screw coupler part 3054 will cause a corresponding rotation of the distal drive screw coupler part 3052. The disconnector drive block 3030 has a screw coupler bore 3031 shaped to retain the distal drive screw coupler part 3052 therein. As in the proximal drive block 3020, the screw coupler bore 3031 is shaped to surround the proximal drive screw coupler part 3054 and allow the proximal drive screw coupler part 3054 to rotate freely therewithin substantially without friction. A proximal portion of the screw coupler bore 3031 is necked down to a smaller diameter to prevent removal of the proximal drive screw coupler part 3054 after it is fixedly connected to the drive wire 750 either directly or through, for example, a hollow coupler as shown in FIGS. 30 to 37.

Implantation of the stent lattice 110 with the jack assembly 3000 is described with regard to FIGS. 30 through 35. First, rotation of the drive screw 740 causes the distal drive block 3010 to move towards the proximal drive block 3020, thereby expanding the stent lattice 110 to the desired implantation diameter. This movement is shown in the transition between FIG. 30 and FIG. 31. Now that the stent lattice 110 is properly within the implantation site, deployment of the needles 3070 can occur. Deployment starts by advancing the needle sub-assembly 3090 as shown in the transition between FIGS. 31 and 32. Continued distal movement of the needle subassembly 3090 causes the needle 3070 to extend out from the distal upper surface 3011 and, due to the preset curvature of the memory-shaped needle 3070, the tip of the needle 3070 curves outward and into the tissue of the implantation site. This curvature is not illustrated in FIGS. 32 and 33 because the curvature projects out of the plane of these figures.

In comparison to previous proximal drive blocks above, the disconnector drive block 3030 does not have a lumen associated with the needle 3070. Only distal drive block 3010 has a lumen therein to accommodate the needle 3070. More specifically, the distal drive block 3010 includes a distal needle lumen 3018 and a proximal needle lumen 3016. The distal needle lumen 3018 is shaped to accommodate the needle 3070 only. In contrast to other needle lumens, however, the proximal needle lumen 3016 is non-circular in cross-section and, in the exemplary embodiment, is ovular in cross-section. This shape occurs because the memory-shaped needle 3070 is supported on its side along its proximal extent by a needle support 3092, which is fastened side-to-side, for example, by welding. The needle support 3092 has a relatively higher columnar strength than the needle 3070 and, therefore, when fixedly connected to the side of the needle 3070, the needle support 3092 significantly increases the connection strength to the needle 3070 at its side than if the needle 3070 was controlled only from the very proximal end thereof. A high-strength, exterior threaded needle base 3094 is fixedly attached to the proximal end of the needle support 3092. This configuration also keeps the needle clocked properly so that its bend direction is away from the center of the lattice and most directly attaches to the vessel wall.

Figure 36:
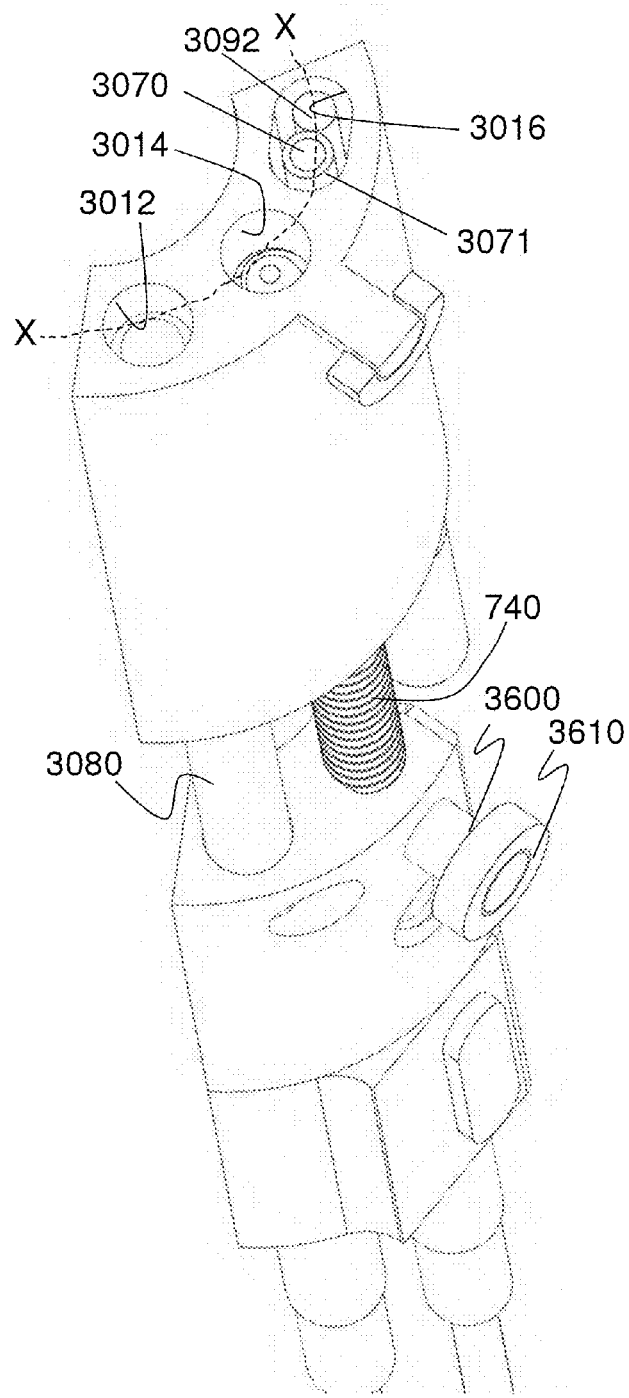
FIG. 36 is a fragmentary, partially cross-sectional, perspective view from above the jack assembly of FIG. 30 showing the interior of the distal drive block.

Control of the needle 3070 is, as above, carried out by a needle disconnect wire 3098 (depicted with dashed lines). Attached to the distal end of the disconnect wire 3098 is a needle disconnect nut 3096 defining a distal bore with interior threads corresponding to the exterior threads of the needle base 3094. In this configuration, therefore, rotation of the needle disconnect wire 3098 causes the needle disconnect nut 3096 to either secure to the needle base 3094 or remove from the needle base 3094 so that disconnection of the delivery system from the stent lattice 110 can occur. The top side of the distal drive block 3010 is cross-sectioned in FIG. 36 at the boss 3600 to show the shapes of the various lumens therein. As described above, the support rod lumen 3012 is a smooth, circular-cross-sectional bore to allow the support rod 3080 to slide longitudinally vertically therein. Similarly, the distal-portion of the drive screw lumen 3014 is also a smooth, circular-cross-sectional bore to allow the drive screw 740 to move longitudinally vertically therein as it is rotated and the threads engage the proximal threaded portion of the drive screw lumen 3014. The proximal needle lumen 3016, in contrast, is non circular (e.g., ovular) to accommodate the cylindrical-shaped needle 3070 and the side-by-side-connected, cylindrical-shaped, needle support 3092. As shown in the view of FIG. 36, at least the contacting portion of the needle 3070 to the needle support 3092 is shrouded with a connector sleeve 3071, which has material properties that allow it to be fixedly connected to the needle 3070 and, at the same time, to the needle support 3092.

Figure 34:
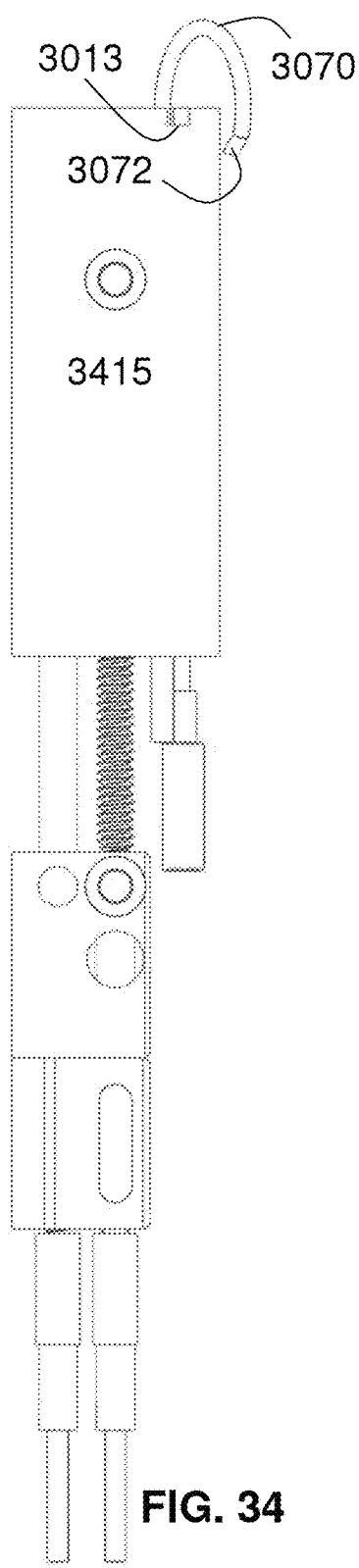
FIG. 34 is a fragmentary, perspective view of the jack assembly of FIG. 33 with the extended needle rotated slightly to the right of the figure.
Figure 35:
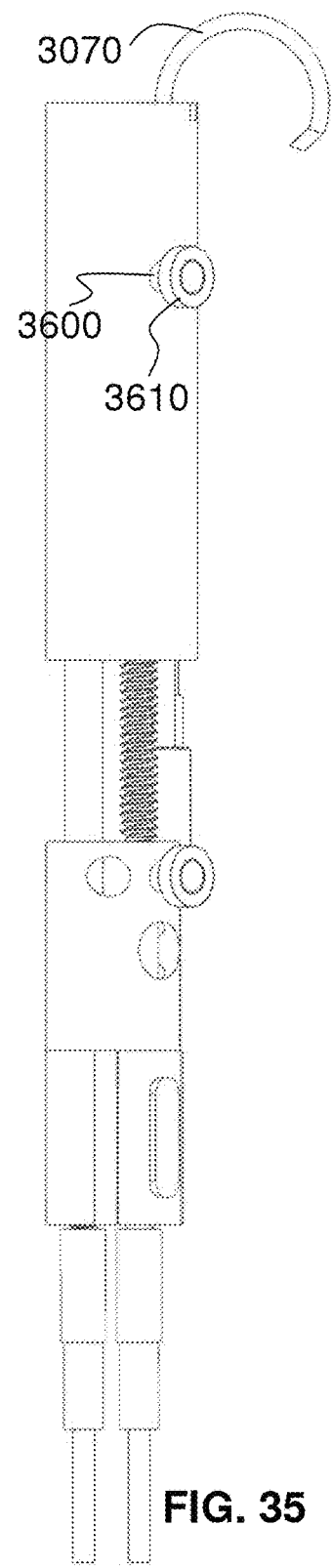
FIG. 35 is a fragmentary, perspective view of the jack assembly of FIG. 34 rotated to the right by approximately 45 degrees.

Extension of the needle 3070 out from the distal upper surface 3011 by the distal movement of the disconnect wire 3098 is illustrated by the transition from FIG. 31 to FIG. 32. Only a small portion of the needle 3070 extends from the distal upper surface 3011 because the views of FIGS. 30 to 33 are vertical cross-sections along a curved intermediate plane shown, diagrammatically, with dashed line X-X in FIG. 36. As the needle 3070 extends in front of this sectional plane, it is cut off in these figures. FIGS. 34 and 35, however clearly show the extended needle 3070 curving out and away from the outer side surface 3415, however, merely for clarity purposes, the needle 3070 is rotated on its longitudinal axis slightly to the right so that it can be seen in FIG. 34 and seen better in FIG. 35. It is note that another exemplary embodiment of the needle 3070 includes a hooked or bent needle tip 3072. Correspondingly, the distal drive block 3010 includes a needle tip groove 3013 to catch the bent needle tip 3072 and utilize it in a way to keep tension on the needle 3070 and the needle disconnect wire 3098. The bend in the needle tip 3072 also allows the needle 3070 to penetrate earlier and deeper than without such a bend. Another advantage for having this bend is that it requires more load to straighten out the tip bend than the overall memory shape of the needle and, thereby, it keeps the needle located distally in the jack assembly 3000. If sufficient space exists in the distal drive block, a plurality of needles (e.g., a forked tongue) could be used.

Figure 37:
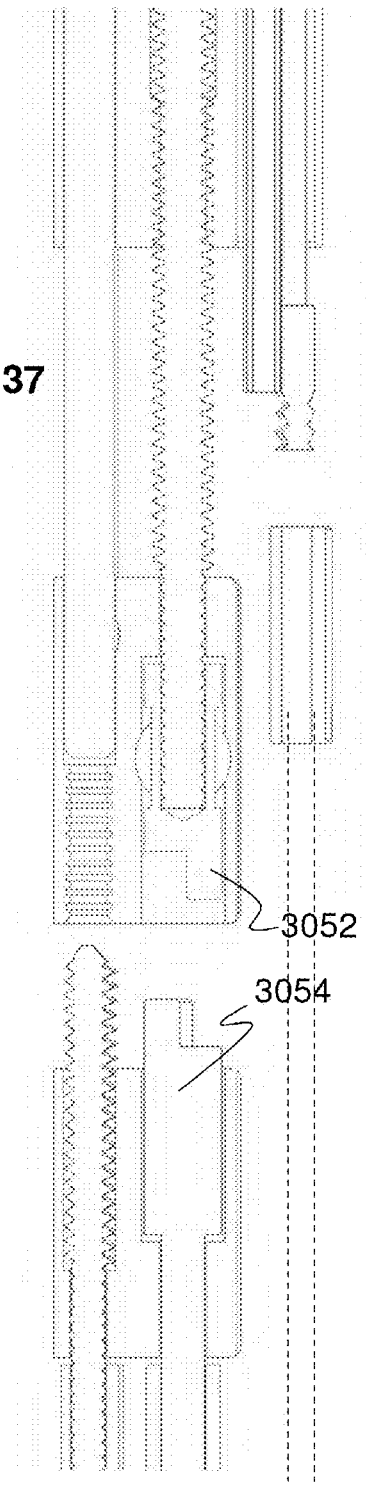
FIG. 37 is a fragmentary, enlarged, cross-sectional view of the jack assembly of FIG. 33.
Figure 38:
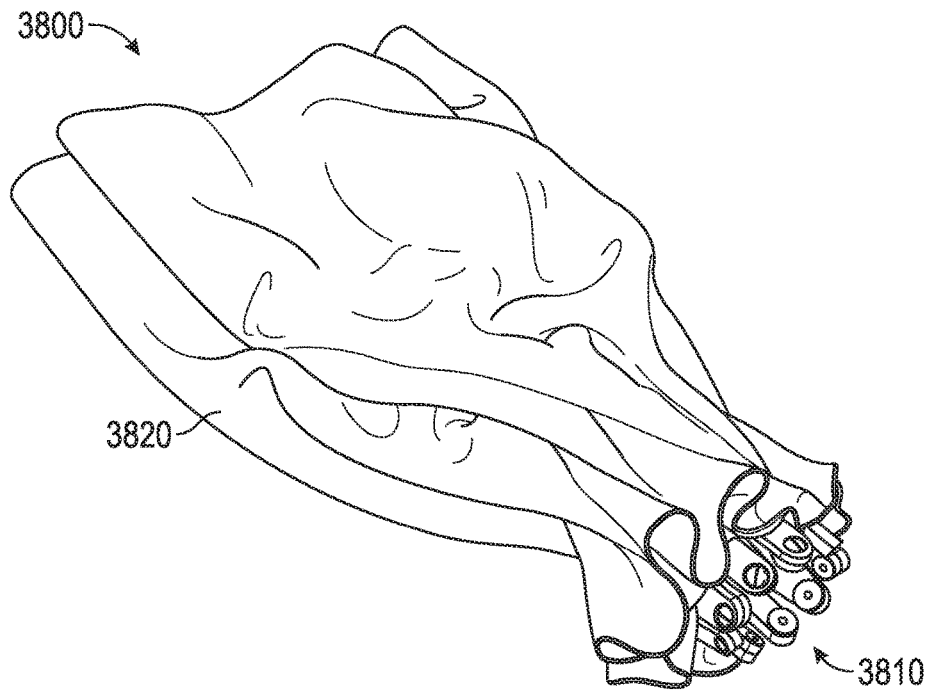
FIG. 38 is a photograph of a perspective view from above the upstream end of another exemplary embodiment of an actively controllable stent graft according to the invention in a substantially contracted state.

Removal of the delivery system is described with regard to FIGS. 32, 33, and 37 after the stent lattice 110 is implanted and the needle 3070 of each jack assembly 3000 is extended. The retainer screw 760 keeps the proximal drive block 3020 and the disconnector drive block 3030 longitudinally grounded to one another up until implantation of the stent lattice 110 and extension of the needles 3070 (if needles 3070 are included). Separation of the delivery system begins by rotation of the disconnector wire 770 to unscrew the retainer screw 760 from the retainer screw lumen 3022, which occurs as shown in the transition from FIG. 32 to FIG. 33. Because the two parts of the drive screw coupler 3052, 3054 are not longitudinally fastened to one another, the drive screw coupler 3052, 3054 does not hinder disconnection of the disconnector drive block 3030 in any way. Before, at the same time, or after removal of the retainer screw 760 from the retainer screw lumen 3022, the needle disconnect wire 3098 is rotated to, thereby, correspondingly rotate the needle disconnect nut 3096. After a number of rotations, a needle disconnect nut 3096 is entirely unscrewed from the threads of the needle base 3094, which is shown in FIG. 33, for example. The delivery system, including the disconnector drive block 3030, its control wires (drive wire 750 and disconnect wire 770), and the needle disconnect wire 3098 and disconnect nut 3096, can now be removed from the implantation site.

Figure 39:
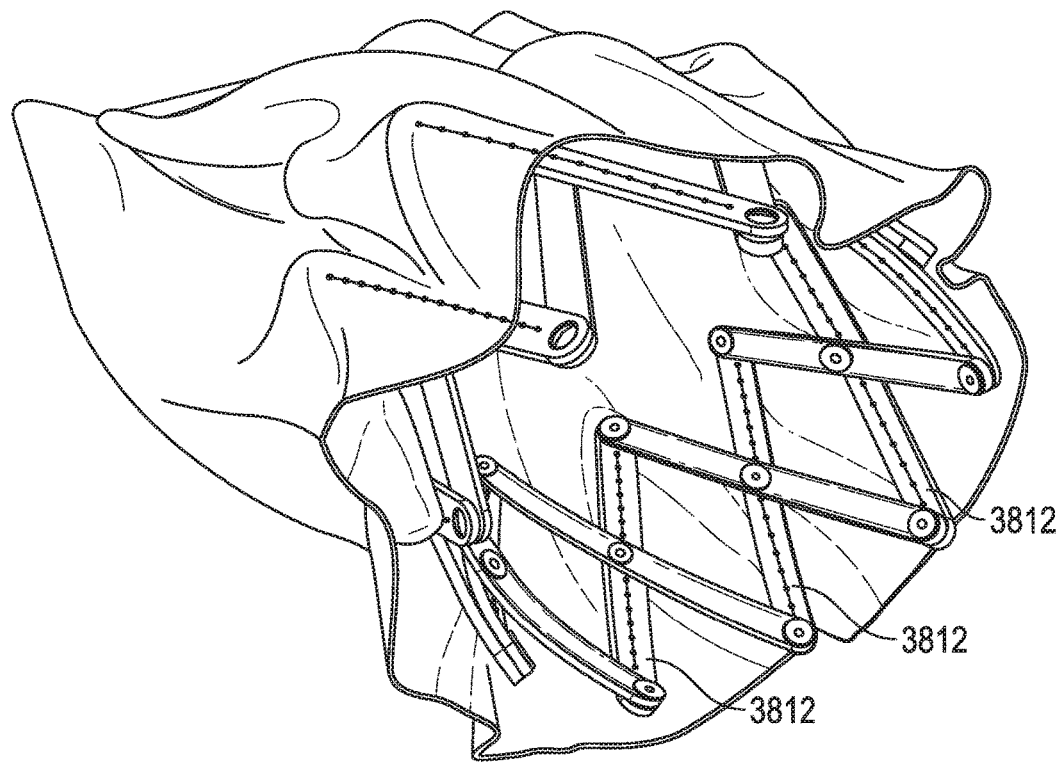
FIG. 39 is a photograph of a perspective view of the stent graft of FIG. 38 in a partially expanded state.
Figure 40:
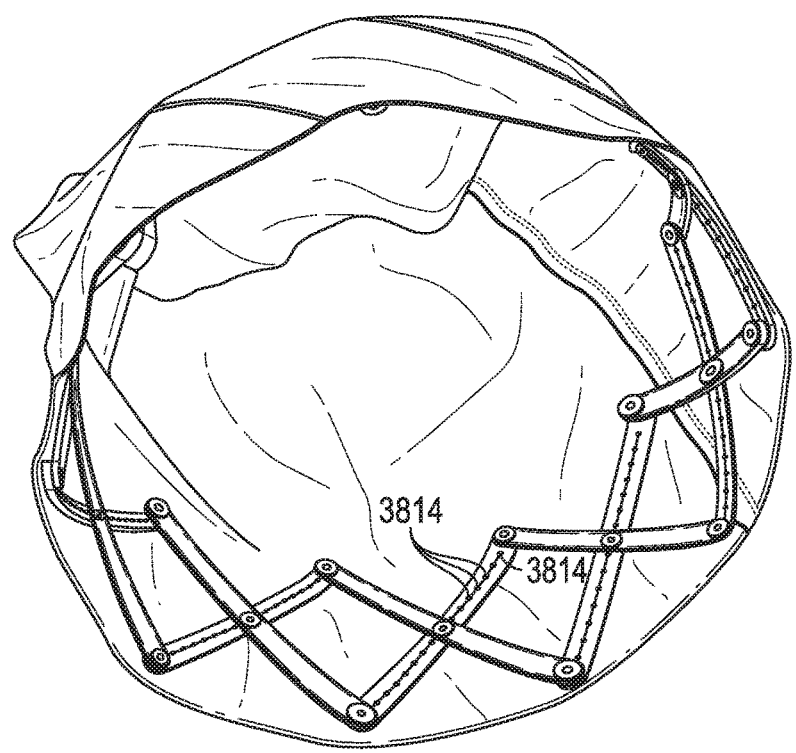
FIG. 40 is a photograph of a perspective view of the stent graft of FIG. 38 in an expanded state.
Figure 41:
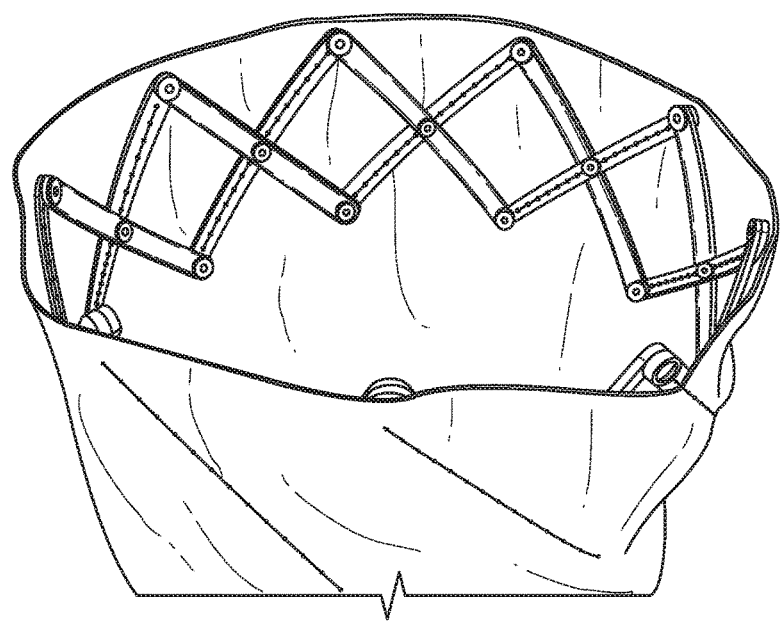
FIG. 41 is a photograph of a side perspective view of the stent graft of FIG. 38 in an expanded state.
Figure 42:
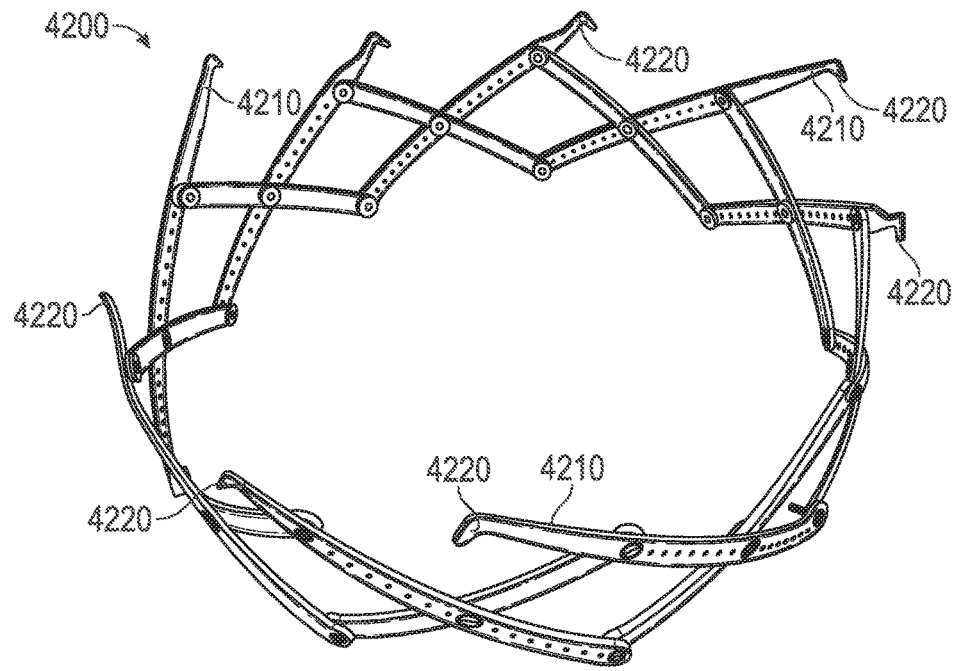
FIG. 42 is a photograph of a perspective view of another exemplary embodiment of an actively controllable stent for a stent graft according to the invention in a substantially expanded state with integral upstream anchors.
Figure 43:
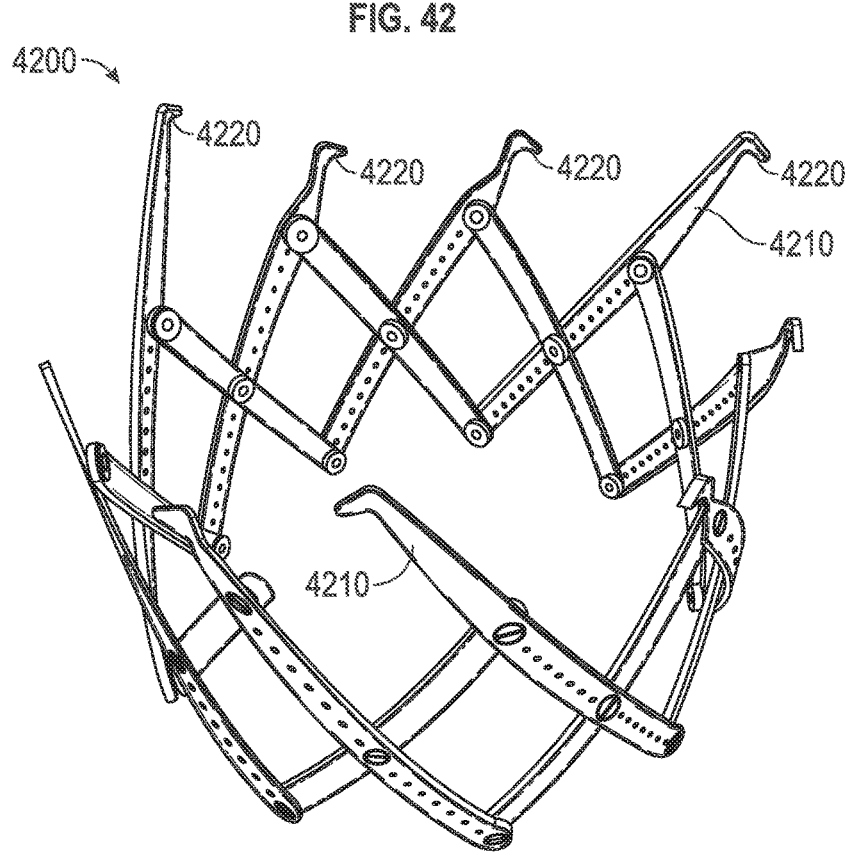
FIG. 43 is a photograph of a perspective view of the stent of FIG. 42 in a partially expanded state.
Figure 44:
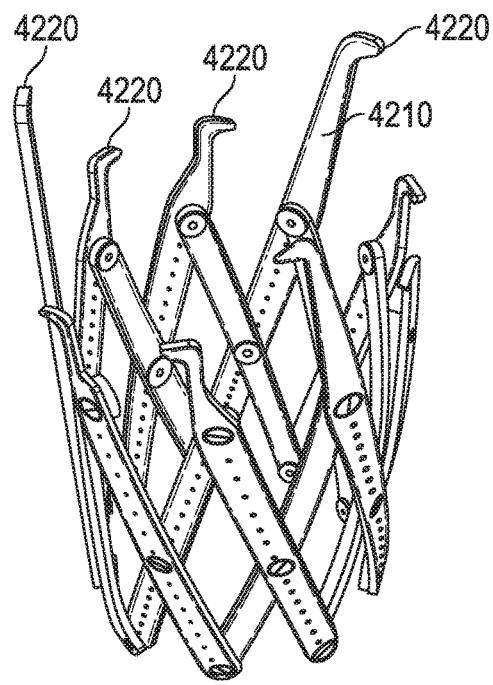
FIG. 44 is a photograph of a perspective view of the stent of FIG. 42 in another partially expanded state.
Figure 45:
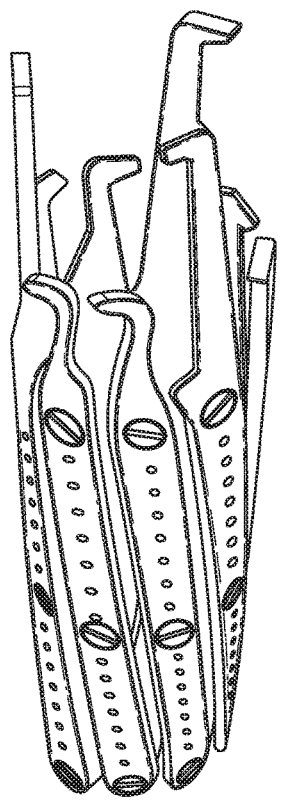
FIG. 45 is a photograph of a perspective view of the stent of FIG. 42 in a substantially contracted state.
Figure 46:
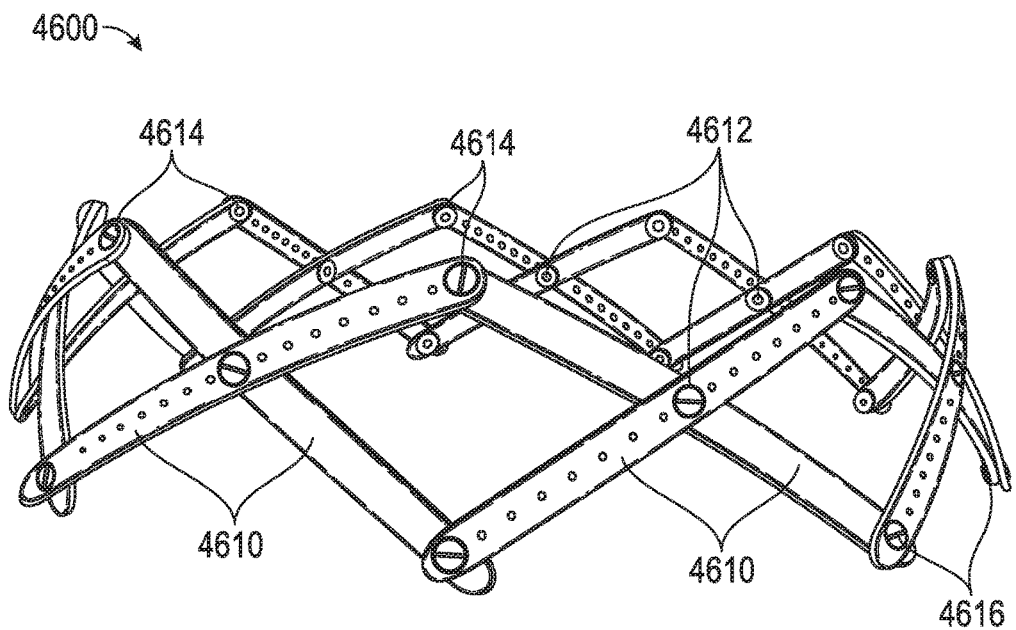
FIG. 46 is a photograph of a side perspective view of another exemplary embodiment of an actively controllable stent for a stent graft according to the invention in a substantially expanded state with a tapered outer exterior.
Figure 47:
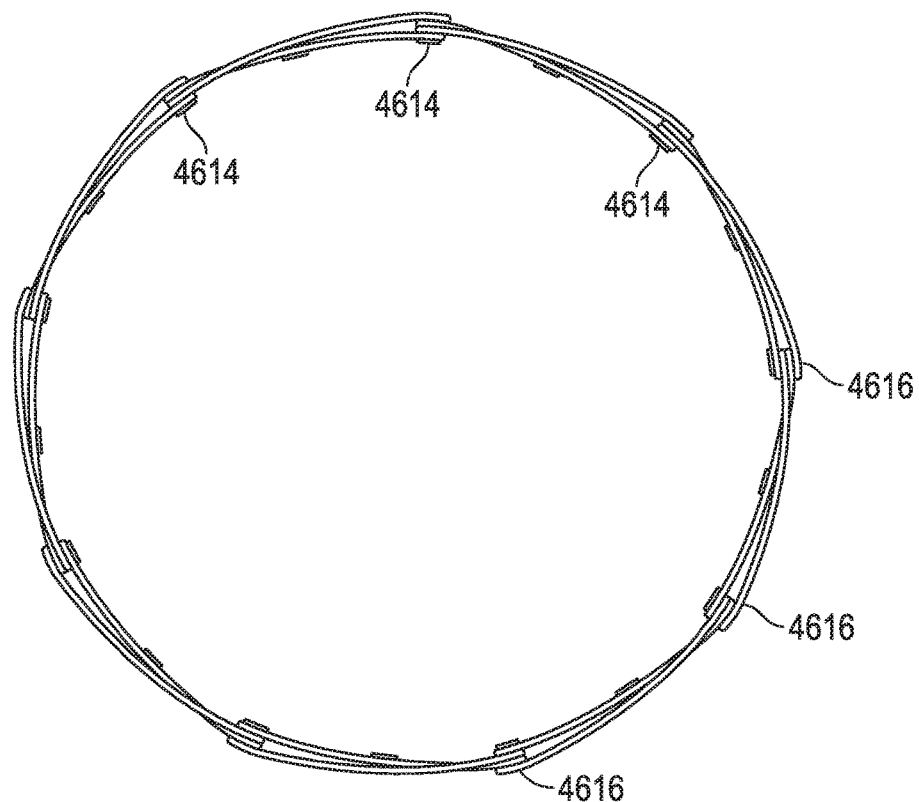
FIG. 47 is a photograph of a top perspective view of the stent of FIG. 46.

Other exemplary embodiments of the stent lattice according to the invention is shown with regard to FIGS. 38 to 50. In a first exemplary embodiment, the stent lattice is a proximal stent 3810 of a stent graft 3800. The proximal stent 3810 is connected to and covered on its exterior circumferential surface with a graft 3820. With the proximal stent 3810 in a partially expanded state in FIG. 39 and other expanded states in FIGS. 40 and 41, it can be seen that the outer struts 3812 have at least one throughbore 3814, in particular, a line of throughbores from one end to the other, extending through the outer strut 3812 in a radial direction. These throughbores allow the graft 3820 to be sewn to the outer struts 3812.

As described above, it can be beneficial for stents to have barbs, hooks, or other measures that catch and do not release tissue when they contact the tissue at or near an implantation site. FIGS. 42 to 45 illustrate one exemplary embodiment of the invention. When constructing the stent lattice 4200, attachment of the three pivot points makes each outer strut 4230 curve about its center pivot point, as can be seen in the lower right corner of FIG. 44, for example. Past the outer two pivot points of each outer strut 4230, however, there is no curve imparted. The invention takes advantage of this and provides extensions 4210 and barbs 4220 on one or more ends of the outer struts 4230 because the lack of curvature at the ends of the outer strut 4230 means that the outer portion will extend outward from the circumferential outer surface of the stent lattice 4200. In the expanded configuration of the stent lattice 4200 shown in FIG. 42, it can be seen that the extensions 4210 and barbs 4220 each project radially outward from the outer circumferential surface of the stent lattice 4200 and the points of the barbs 4220 also point radially outward, even if at a shallow angle.

Figure 48:
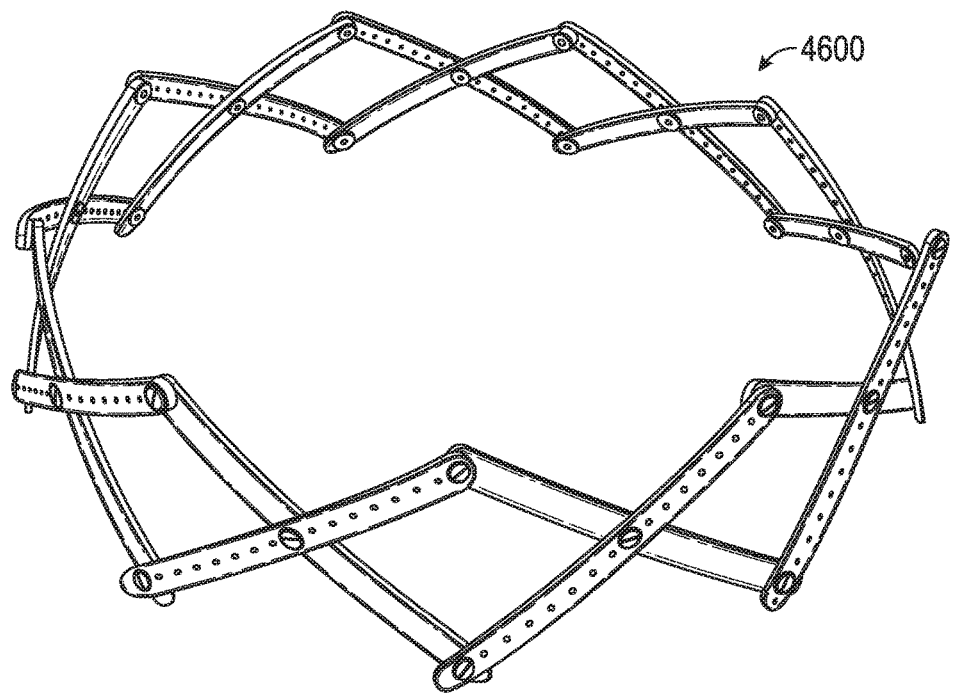
FIG. 48 is a photograph of a perspective view of the stent of FIG. 46 from above a side.
Figure 49:
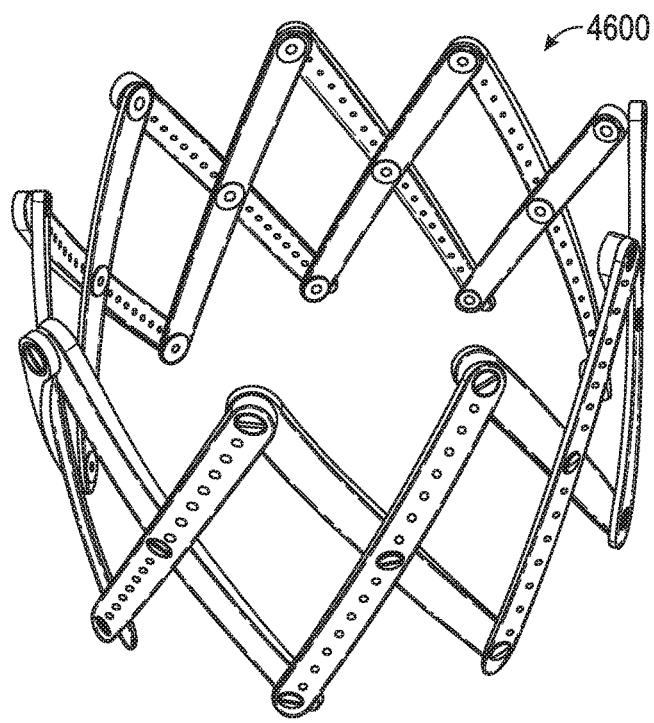
FIG. 49 is a photograph of a perspective view of the stent of FIG. 46 from above a side with the stent in a partially expanded state.
Figure 50:
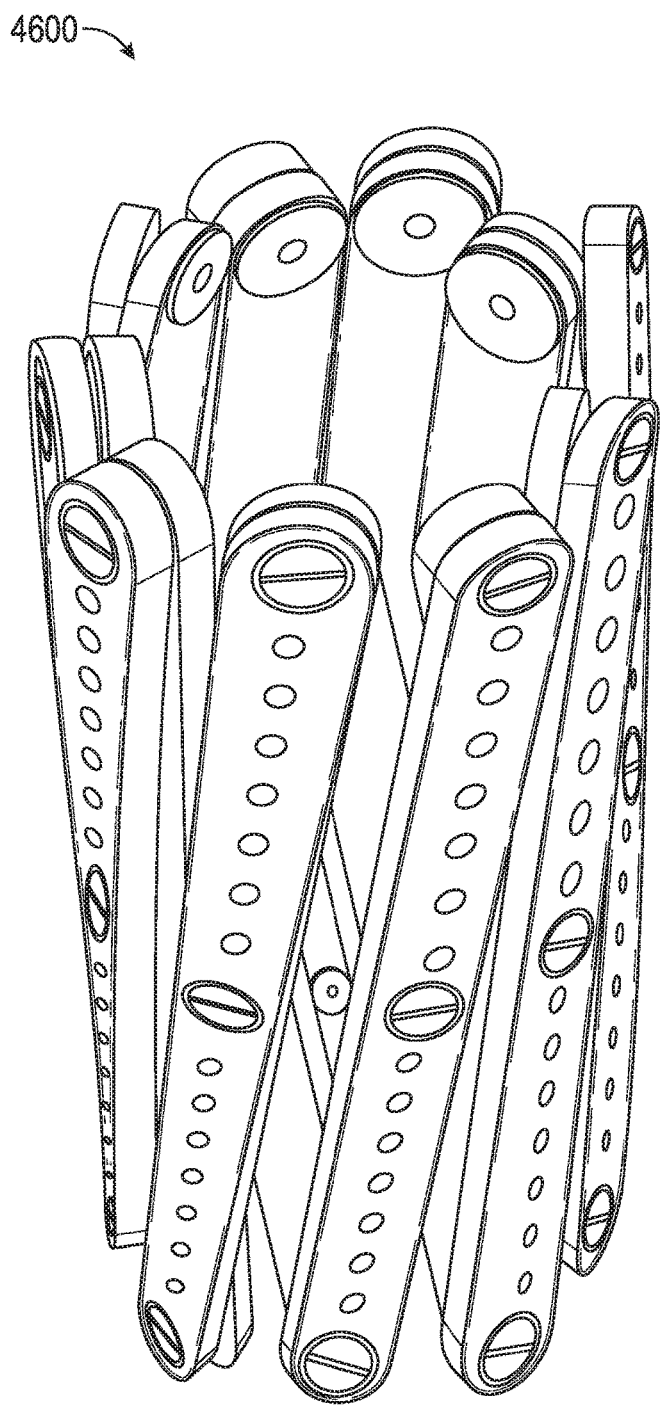
FIG. 50 is a photograph of a perspective view of the stent of FIG. 46 from above a side with the stent in a substantially contracted state.

It is noted that each of the exemplary embodiments of the stent lattices illustrated above has the intermediate pivot point at the center point of each strut. Having the intermediate pivot point in the center is only exemplary and can be moved away from the center of each strut. For example, as shown in FIGS. 46 to 50, the stent lattice 4600 can have the intermediate center pivot 4612 of the struts 4610 be closer to one end 4614 than the other end 4616. When the center pivot 4612 is off-center, the side closer to the one end 4614 tilts inwards so that the outer circumferential surface of the stent lattice 4600 takes the shape of a cone. FIGS. 48, 49, and 50 illustrate the conical stent lattice 4600 expanded, partially expanded, and almost completely retracted, respectively.

Figure 51:
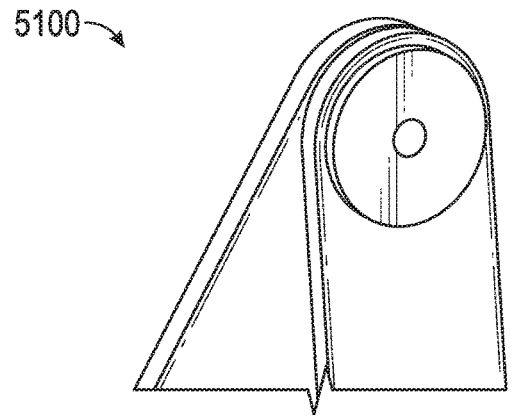
FIG. 51 is a photograph of an exemplary embodiment of a low-profile joint assembly for actively controllable stents/stent grafts according to the invention.
Figure 52:
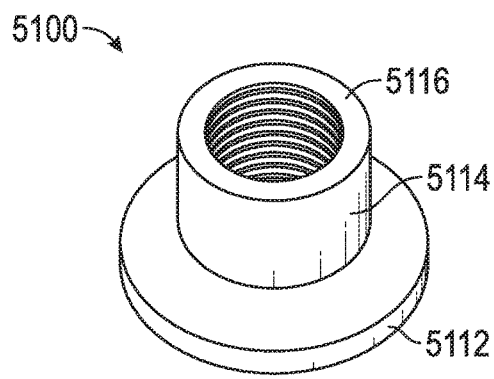
FIG. 52 is a photograph of struts of the joint assembly of FIG. 51 separated from one another.
Figure 53:
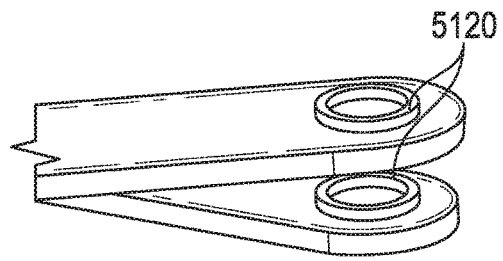
FIG. 53 is a photograph of a rivet of the joint assembly of FIG. 51.
Figure 54:
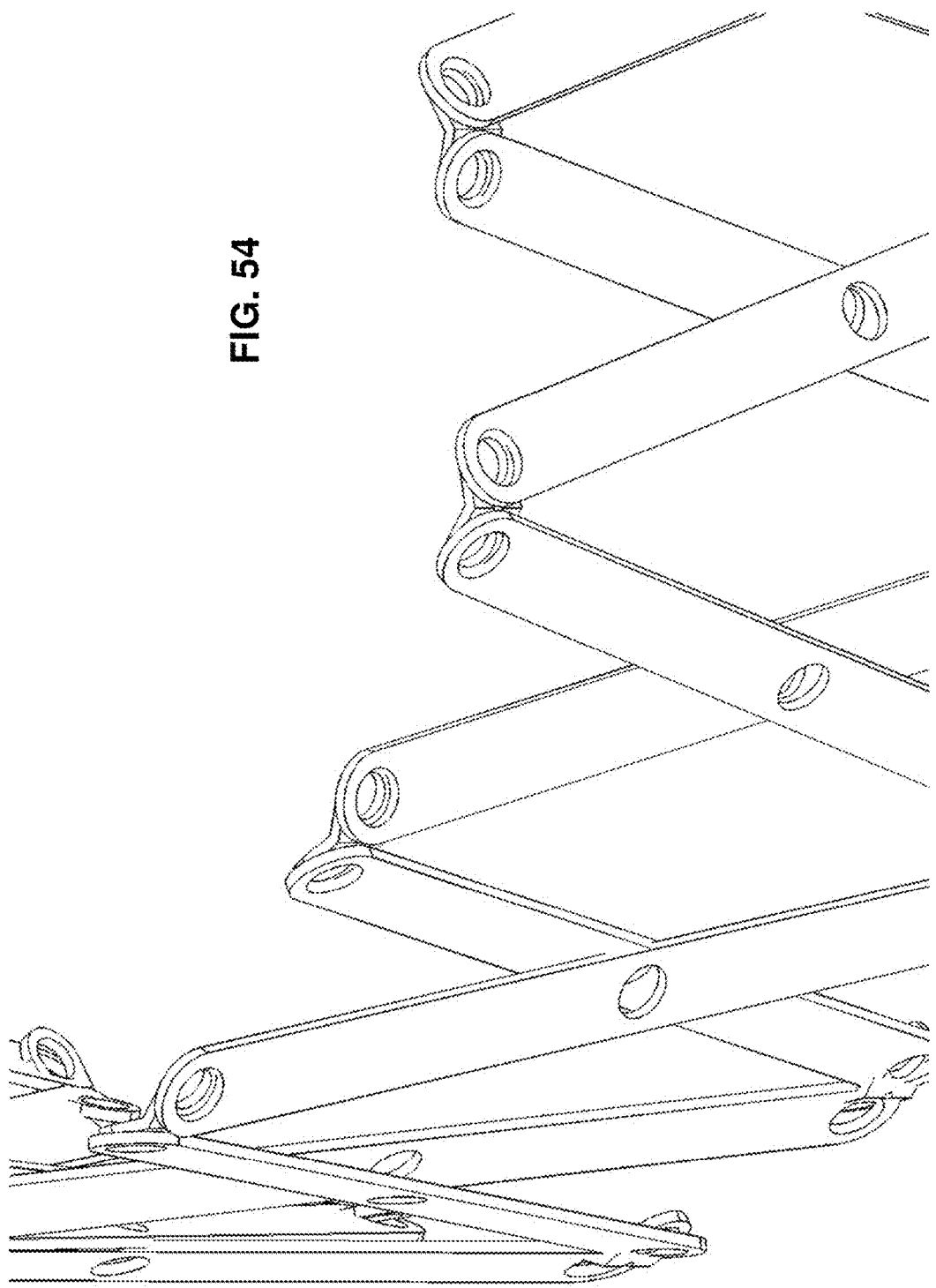
FIG. 54 is a fragmentary, side perspective view of another exemplary embodiment of an actively controllable stent system for a stent graft according to the invention in a substantially expanded state with a tapered outer exterior.
Figure 55:
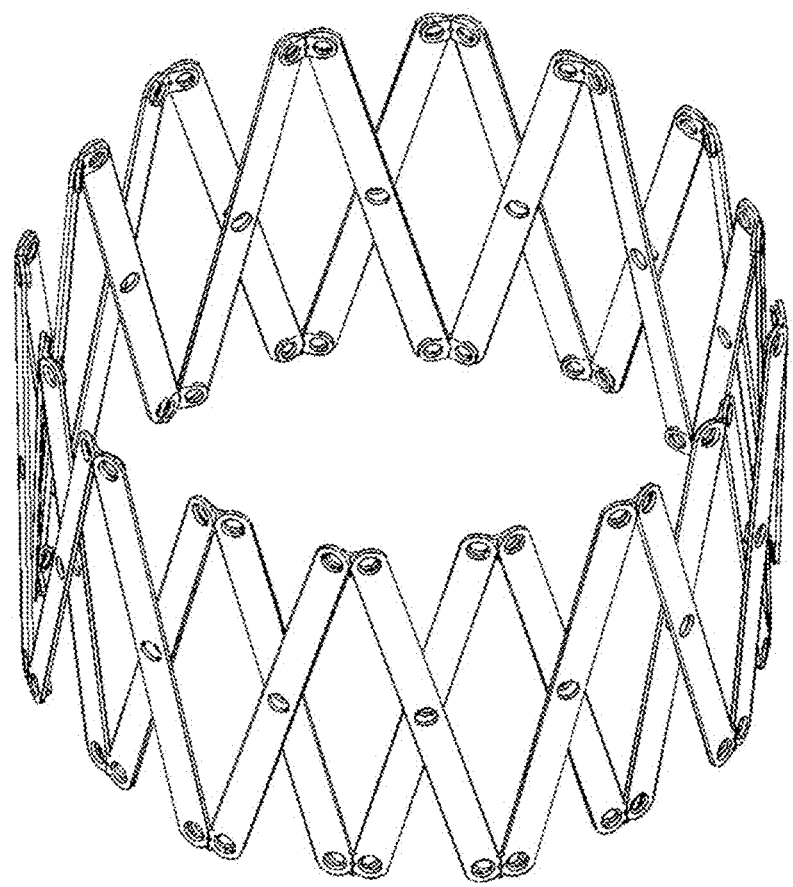
FIG. 55 is a side perspective view of the stent system of FIG. 54.
Figure 56:
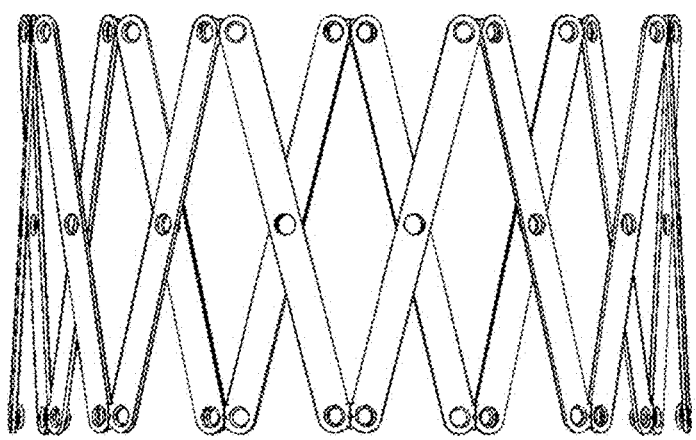
FIG. 56 is a side elevational view of the stent system of FIG. 54.

The exemplary stent lattice embodiments in FIGS. 38 to 50 show the pivot points connected by screws. Any number of possible pivoting connections can be used at one or more or all of the pivot points. One exemplary embodiment of a strut-connection assembly 5100 can be seen in FIGS. 51 to 53. Because the stent lattice of the invention is intended to be small and fit in very small anatomic sites (e.g., heart valve, aorta, and other blood vessels), it is desirable to have the lattice struts be as thin as possible (i.e., have a low profile). The profile of the screws shown in FIGS. 38 to 50 can be reduced even further by the inventive strut-connection system 5100 as shown in FIGS. 51 to 53. FIG. 51 illustrates one such low-profile connection, which is formed using a rivet 5110 and forming the rivet bores in the each of the strut ends with one of a protrusion 5120 and an opposing indention (the latter not illustrated in FIG. 52). The rivet 5110 is formed with a low-profile rivet head 5112, an intermediate cylindrical boss 5114, and a slightly outwardly expanded distal end 5116 (see FIG. 53). By placing two of the ends of the struts next to one another as shown in FIG. 52, with one of the protrusions 5120 placed inside the indention of the opposing strut, the two strut ends form a pivot that is able to slide about the central pivot axis. The rivet 5110 is merely used to lock to strut ends against one another by having the expanded distal end 5116 enter through one of the non-illustrated indention sides of the strut and exit through the protrusion-side of the opposing strut. It is the features on the struts that form the pivot and not the features of the rivet 5110.

Figure 57:
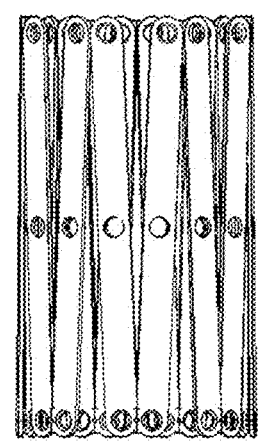
FIG. 57 is a side elevational view of the stent system of FIG. 54 in a substantially contracted state.
Figure 58:
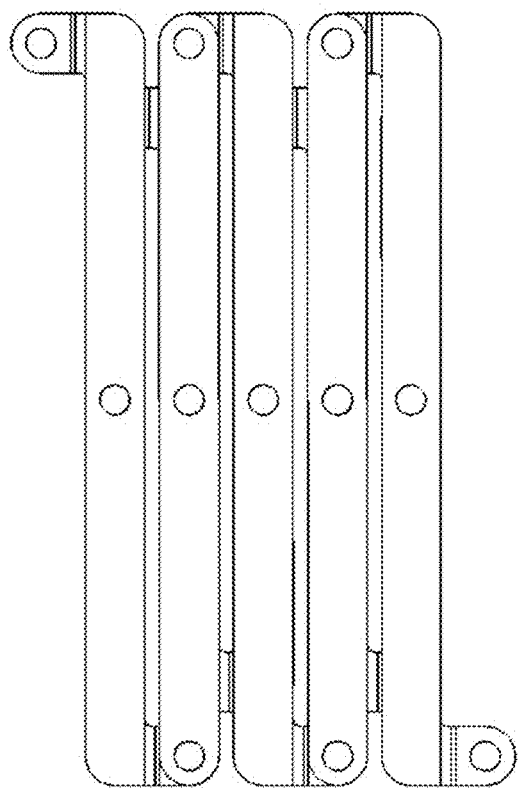
FIG. 58 is a side elevational view of another exemplary embodiment of a portion of an actively controllable stent system for a stent graft according to the invention in a substantially contracted state.
Figure 59:
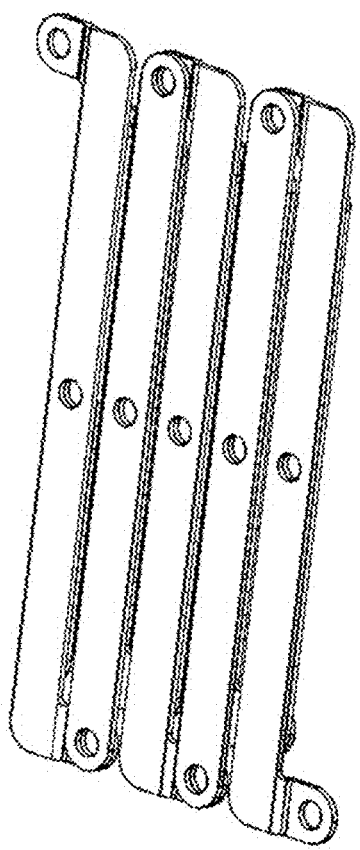
FIG. 59 is a perspective view of the stent system portion of FIG. 58.
Figure 60:
FIG. 60 is a top plan view of the stent system portion of FIG. 58.

FIGS. 54 to 63 illustrate various alternative configurations of the struts in stent lattices according to exemplary embodiments of the invention. Each of the different lattice configurations provides different characteristics. One issue that occurs with lattices having alternating struts is that expansion and contraction of the adjacent struts can adversely rub against the graft securing measures (e.g., stitchings). With that consideration, the invention provides two separate cylindrical sub-lattices in the embodiment of FIGS. 54 to 57. Each of the crossing points of the interior and exterior sub-lattices is connected via fasteners (e.g., rivets, screws, and the like). The outer ends of the struts, however, are not directly connected and, instead, are connected by intermediate hinge plates having two throughbores through which a fastener connects respectively to each of the adjacent strut ends. The intermediate hinge plates translate longitudinally towards each other upon expansion of the stent lattice and never have any portion of stent lattice pass in front or behind them. These hinge plates, therefore, could serve as connection points to the graft or could connect to a band or a rod, the band serving to join the two hinge plates together and, thereby, further spread the expansion forces on the graft. In an exemplary embodiment where the graft material has a transition zone where expansible material transitions to non-expansible material (and back again if desired), such bands or rods could extend further past the longitudinal end of the lattice and provide an attachment or securing point for a non-expansible portion of the graft material. In this configuration, as shown in FIG. 57, for example, if graft material is attached to the outer sub-lattice, then, there is no interruption and the graft is not damaged with the struts acting as scissors. FIGS. 58 to 63 illustrate another exemplary embodiment of the strut lattices according to the invention in which the inner sub-lattice is shorter in the longitudinally vertical direction than the outer sub-lattice.

The exemplary actively controllable stent lattices of the invention can be used in devices and methods in which prior art self-expanding stents have been used. In addition to the example of a proximal stent shown in the exemplary stent graft of FIGS. 38 to 41, the technology described herein and shown in the instant stent delivery systems and methods for delivering such devices can be use in any stent graft or implant, such as those used in abdominal or thoracic aneurysm repair. Additionally, the exemplary stent lattices of the invention can be used in replacement heart valves, for example.

Referring now to the figures of the drawings in detail and first, particularly to FIGS. 64 to 70, there is shown a first exemplary embodiment of an actively controllable aortic valve assembly and methods and systems for controlling and implanting such devices. Even though the exemplary embodiment is shown for an aortic valve, the invention is not limited thereto. The invention is equally applicable to pulmonary, mitral and tricuspid valves.

Figure 64:
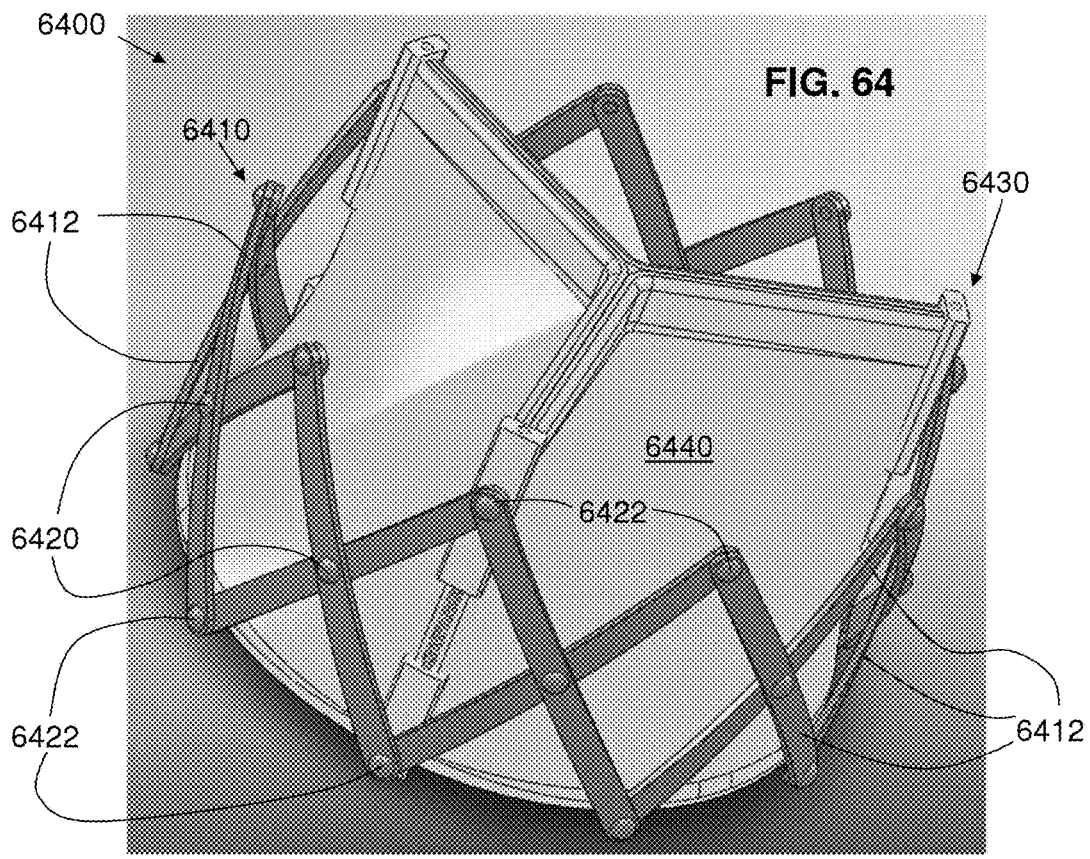
FIG. 64 is a perspective view of a downstream side of an exemplary embodiment of a replacement valve assembly according to the invention in an expanded state.
Figure 65:
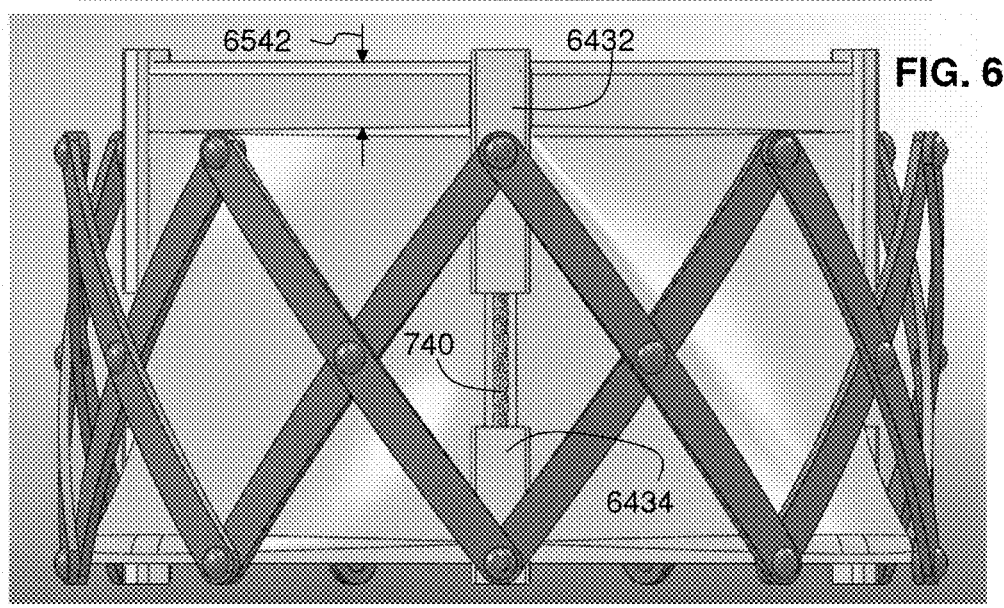
FIG. 65 is a side elevational view of the valve assembly of FIG. 64.

The inventive technology used, for example, with regard to aortic valve repair includes a replacement aortic valve assembly 6400 according to the invention. One exemplary aortic valve assembly 6400 is depicted in FIGS. 64 and 65. FIG. 64 illustrates an adjustable lattice assembly 6410 similar to that shown in FIG. 103. In particular, the lattice assembly 6410 includes a number of struts 6412 crossing one another in pairs and pivotally connected to one another in an alternating manner at crossing points 6420 and end points 6422 of the struts 6412. Like the embodiment in FIG. 103, the lattice assembly 6410 is controlled, in this exemplary embodiment, by a set of three jack assemblies 6430 each having a proximal drive block 6432, a distal drive block 6434, and a drive screw 740 connecting the proximal and distal drive blocks 6432, 6434 together. In this exemplary embodiment, the drive screw 740 performs as above, it is longitudinally fixed but rotationally freely connected to the distal and proximal drive blocks 6432, 6434 such that, when rotated in one direction, the distal and proximal drive blocks 6432, 6434 move away from one another and, when rotated in the other direction, the distal and proximal drive blocks 6432, 6434 move towards one another. In such a configuration, the former movement radially contracts the lattice assembly 6410 and the latter movement expands the lattice assembly 6410. The lattice assembly 6410 shown in FIGS. 64 and 65 is in its expanded state, ready for implantation such that it accommodates to the natural geometry of the implantation site. Connected at least to the three jack assemblies 6430 at an interior side of one or both of the distal and proximal drive blocks 6432, 6434 is an exemplary embodiment of a three-leaf valve assembly 6440 (e.g., an aortic valve assembly). The valve assembly 6440 can be made of any desired material and, in an exemplary configuration, is made of bovine pericardial tissue or latex.

An exemplary embodiment of a delivery system and method shown in FIGS. 66 to 70 and disclosed herein can be used to percutaneously deploy the inventive aortic valve assembly 6440 in what is currently referred to as Transcatheter Aortic-Valve Implantation, known in the art under the acronym TAVI. As set forth above, this system and method can equally be used to deploy replacement pulmonary, mitral and tricuspid valves as well. The configuration of the delivery system and the valve assembly 6440 as an aortic valve assembly provide significant advantages over the prior art. As is known, current TAVI procedures have a risk of leak between an implanted device and the aortic valve annulus, referred to as paravalvular leak. Other disadvantages of prior art TAVI procedures include both migration (partial movement) and embolism (complete release). The reason for such movement is because, before use and entry into the patient, the prior art replacement aortic valves are required to be crushed manually by the surgeon onto an interior balloon that will be used to expand that valve again when ready for implantation. Because the native annulus of the implantation site is not circular, and due to the fact that the balloon forces the implanted pre-crushed valve to take a final shape of the circular balloon, prior art implants do not conform to the native annulus. Not only are such prior art systems hard to use, they provide no possibility of repositioning the implanted valve once the balloon has expanded.

Figure 70:
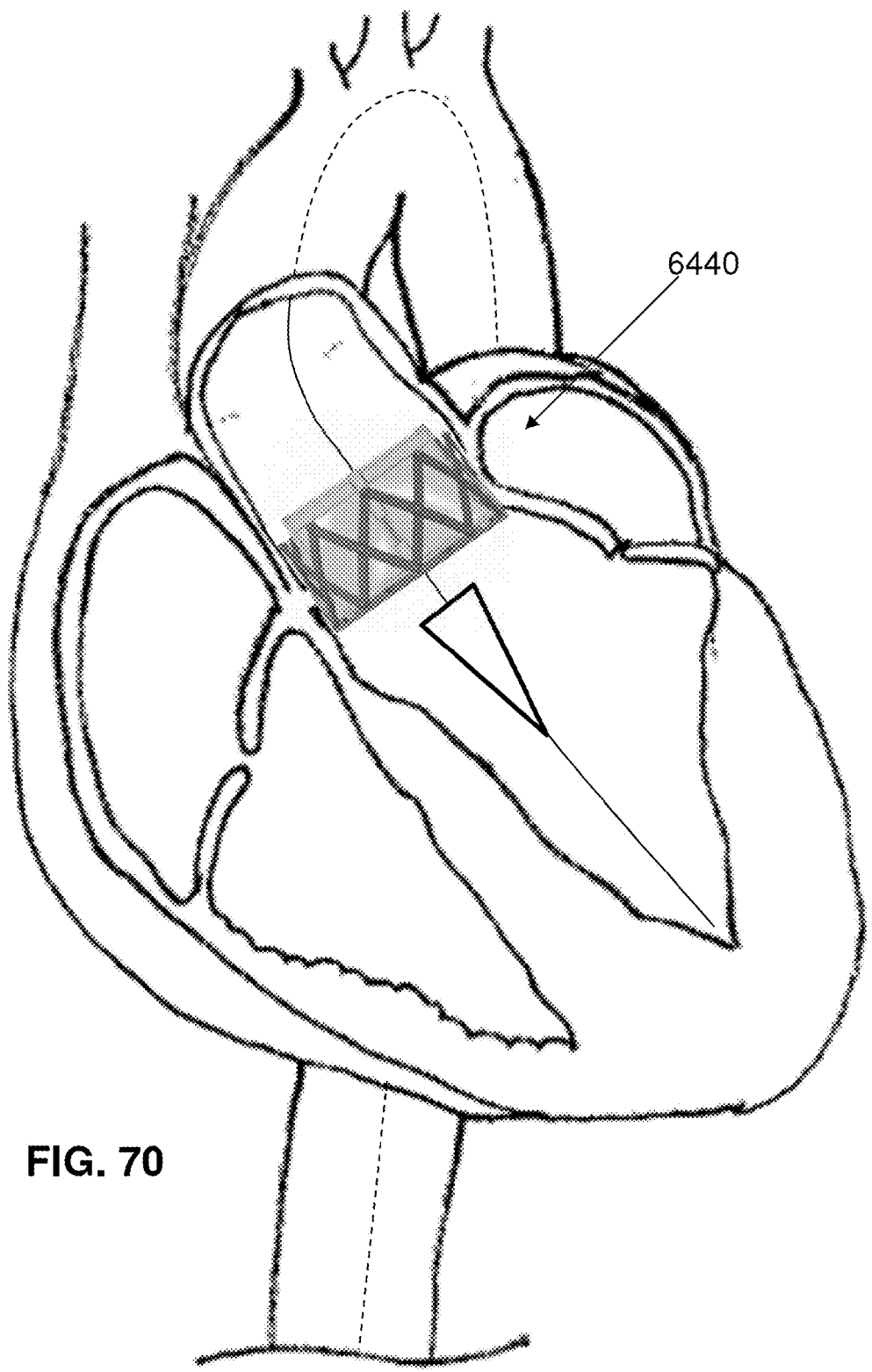
FIG. 70 is a fragmentary, enlarged, perspective view of the delivery system and the aortic valve assembly of FIG. 69 implanted at an aortic valve implantation site.
Figure 71:
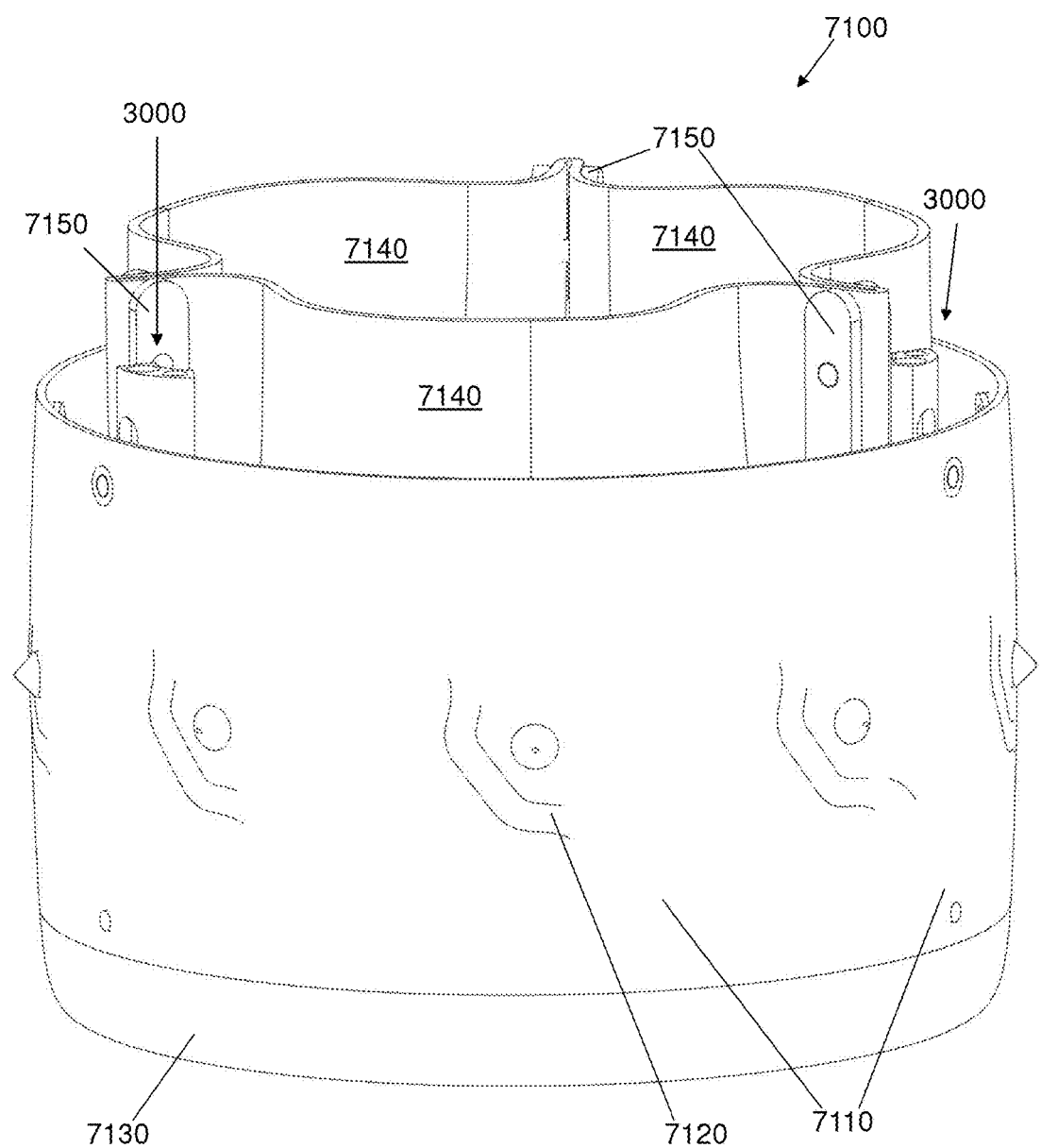
FIG. 71 is a perspective view of a side of another exemplary embodiment of a replacement aortic valve assembly according to the invention in an expanded state.
Figure 72:
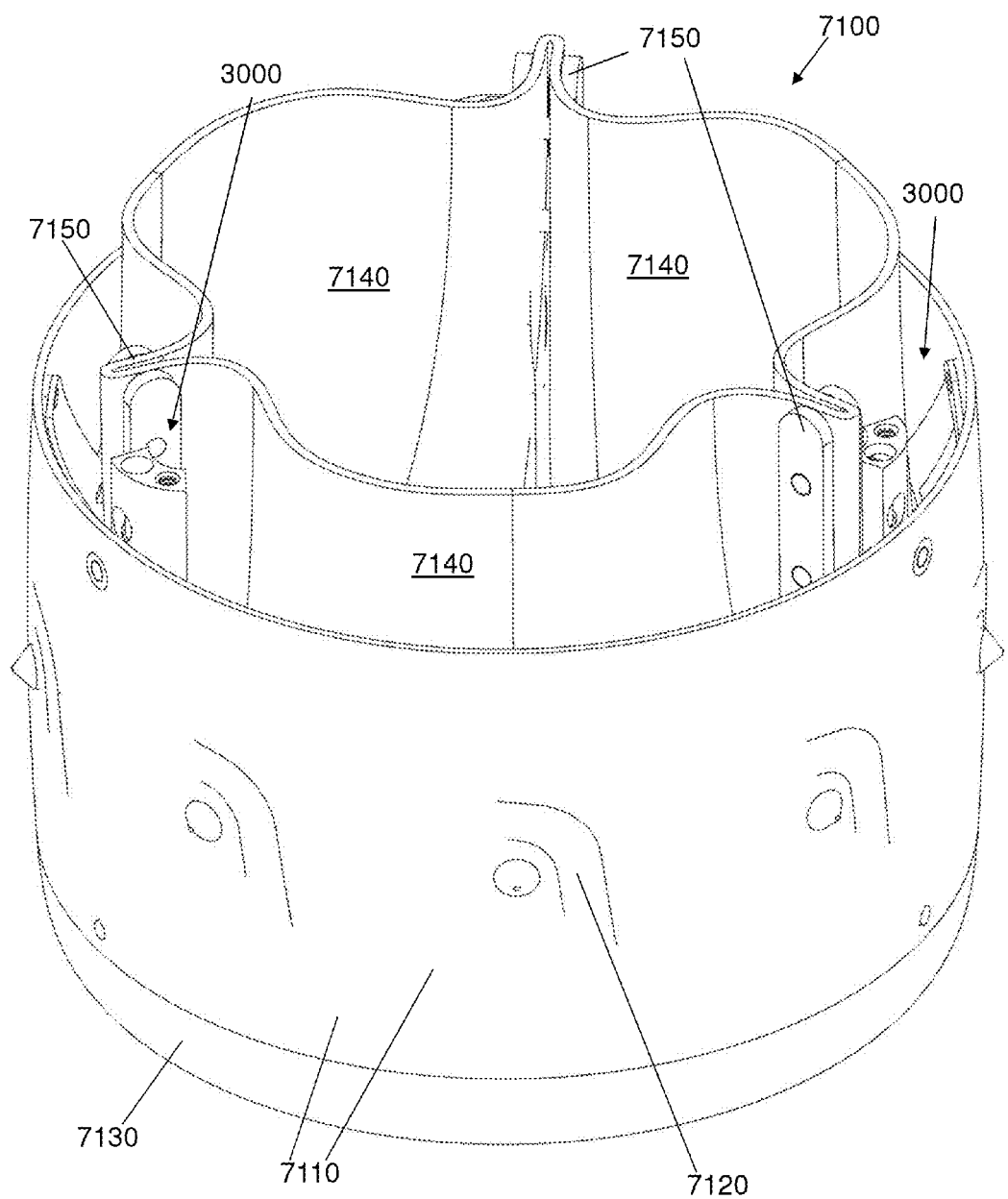
FIG. 72 is a perspective view of the replacement aortic valve assembly of FIG. 71 from above a downstream side thereof.

The progression of FIGS. 66 to 70 illustrates an exemplary implantation of the inventive aortic valve assembly 6440. Various features of the delivery system are not illustrated in these figures for reasons of clarity. Specifically, these figures show only the guidewire 6610 and the nose cone 6620 of the delivery system. FIG. 66 shows the guidewire 6610 already positioned and the aortic valve assembly 6440 in a collapsed state resting in the delivery system just distal of the nose cone 6620. In this illustration, the aortic valve assembly 6440 and nose cone 6620 are disposed in the right iliac artery. FIG. 67 depicts the aortic valve assembly 6440 and nose cone 6620 in an advanced position on the guidewire 6610 within the abdominal aorta adjacent the renal arteries. FIG. 68 shows the aortic valve assembly 6440 just adjacent the aortic valve implantation site. Finally, FIGS. 69 and 70 show the aortic valve assembly 6440 implanted in the heart before the nose cone 6620 and/or the guidewire 6610 are retracted.

The inventive delivery system and aortic valve assembly 6440 eliminate each of the disadvantageous features of the prior art. First, there is no need for the surgeon to manually crush the implanted prosthesis. Before the aortic valve assembly 6440 is inserted into the patient, the delivery system simply reduces the circumference of the lattice 6410 automatically and evenly to whatever diameter is desired by the surgeon, the delivery system requires, or is reduced in diameter by the manufacturer and loaded into the delivery system for later implantation. The stent and valve assemblies described herein can be reduced to a loading diameter of between 4 mm and 8 mm, and, in particular, 6 mm, to fit inside a 16-20 French sheath, in particular, an 18 French or smaller delivery sheath. When the aortic valve assembly 6440 reaches the implantation site, the surgeon causes the delivery system to evenly and automatically expand the aortic valve assembly 6440. As this expansion is slow and even into the implant position, it is gentle on calcification at the implant site. Likewise, the even expansion allows the lattice structure to assume the native, non-circular perimeter of the implant site not only due to the way the delivery system expands the lattice assembly 6410, but also because the hinged connections of each of the struts 6412 allows the lattice assembly 6410 to bend and flex naturally after implantation dependent upon the corresponding non-uniform tissue wall adjacent to each pivoting strut 6412 (assumption of the natural shape of the implantation wall also occurs with the alternative non-hinged embodiments disclosed herein). Due to these facts, a better seating of the implant occurs, which leads axiomatically to a better paravalvular seal. The inventive delivery system sizes the prosthesis precisely, instead of the gross adjustment and installation present in the prior art. Another significant disadvantage of the prior art is that a balloon is used within the central opening of the valve to expand the valve, thus completely occluding the aorta and causing tremendous backpressure on the heart, which can be hazardous to the patient. The valves described herein, in contrast, remain open during deployment to, thereby, allow continuous blood flow during initial deployment and subsequent repositioning during the procedure and also start the process of acting as a valve even when the implant is not fully seated at the implantation site.

Significantly, prior art TAVI systems require a laborious sizing process that requires the replacement valve to be sized directly to the particular patient's annulus, which sizing is not absolutely correct. With the delivery system and aortic valve assemblies described herein, however, the need to size the valve assembly beforehand no longer exists—all that is needed is to select an implant having somewhere within an intermediate position of the implant's expansion range the approximate diameter of the annulus at the implantation site. Additionally, with regard to both stent graft and valve systems described herein, because the stent assemblies are adjustable, they can be adjusted even after being implanted within a vessel for a long period of time. For example, when conducting a TAVI process in children having congenital defects, there is a need to remove and implant a new valve after a few years because of the patient's growth. The assemblies described herein, in contrast to the prior art, can be re-docked well after implantation and further expanded, either at regular intervals or periodically, to adjust for the patient's growth.

The aortic valve assembly 6440 is configured to have a valve leaf overlap 6542 (see FIG. 65) that is more than sufficient when the aortic valve assembly 6440 is at its greatest diameter and, when the aortic valve assembly 6440 is smaller than the greatest diameter, the valve leaf overlap 6542 merely increases accordingly. An exemplary range for this overlap can be between approximately 1 mm and approximately 3 mm.

A further significant advantage not provided by prior art TAVI systems is that the inventive delivery system and valve assembly can be expanded, contracted, and re-positioned as many times operatively as desired, but also the inventive delivery system and valve assembly can be re-docked post-operatively and re-positioned as desired. Likewise, the learning curve for using the inventive delivery system and valve assembly is drastically reduced for the surgeon because an automatic control handle (described in further detail below) performs each operation of extending, retracting, adjusting, tilting, expanding, and/or contracting at a mere touch of a button (see, e.g., FIGS. 105 to 107).

Another exemplary use of the inventive lattice assembly and delivery system is for a latticework-actuated basket filter, which can be either added to the devices, systems, and methods disclosed herein or which can stand-alone. Such an embolic umbrella can perform better than, for example, the EMBOL-X® Glide Protection System produced by Edward Lifesciences. Such a filter would be attached to the docking jacks so that it expands in place automatically as the device is expanded but would be removed with the delivery system without any additional efforts on the part of the surgeon.

Figure 75:
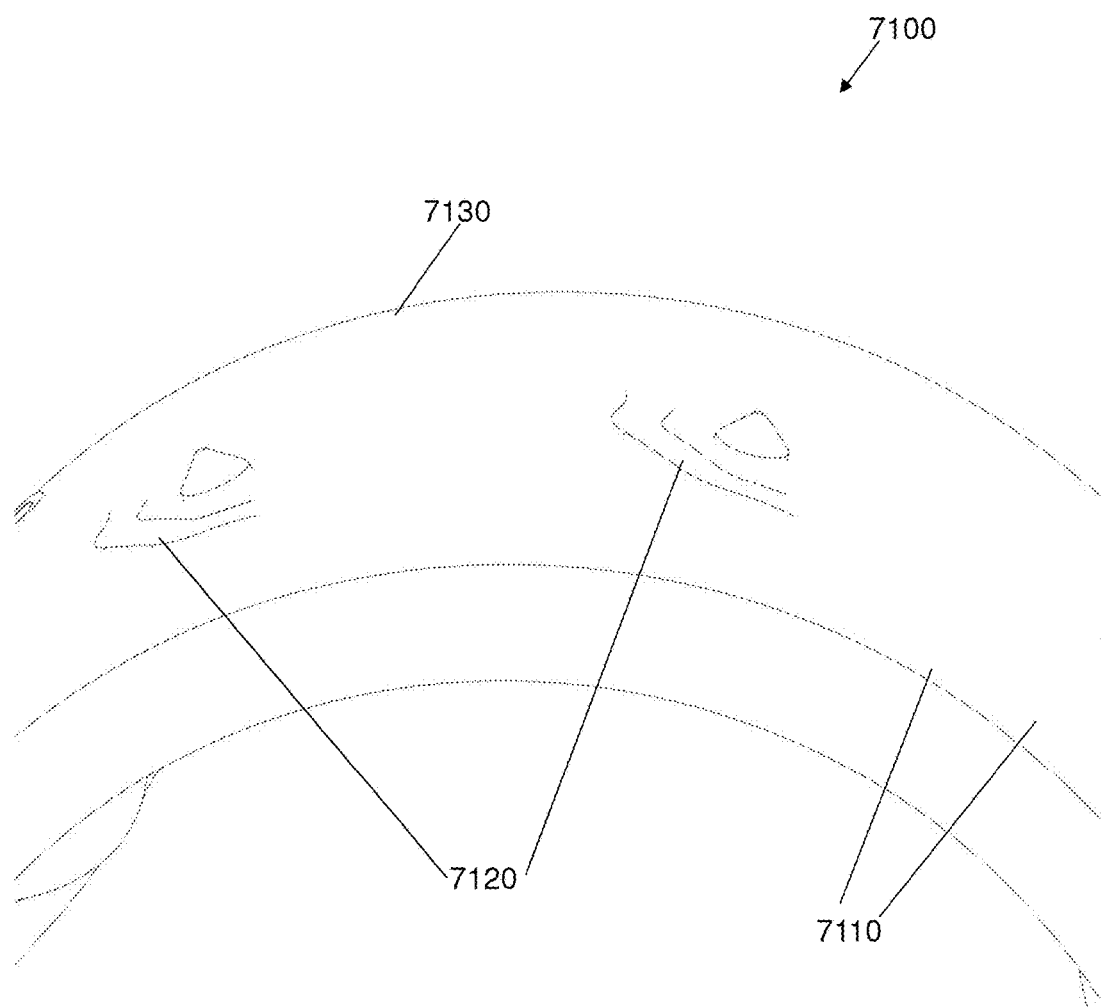
FIG. 75 is a perspective view of an enlarged portion of the replacement aortic valve assembly of FIG. 74.
Figure 76:
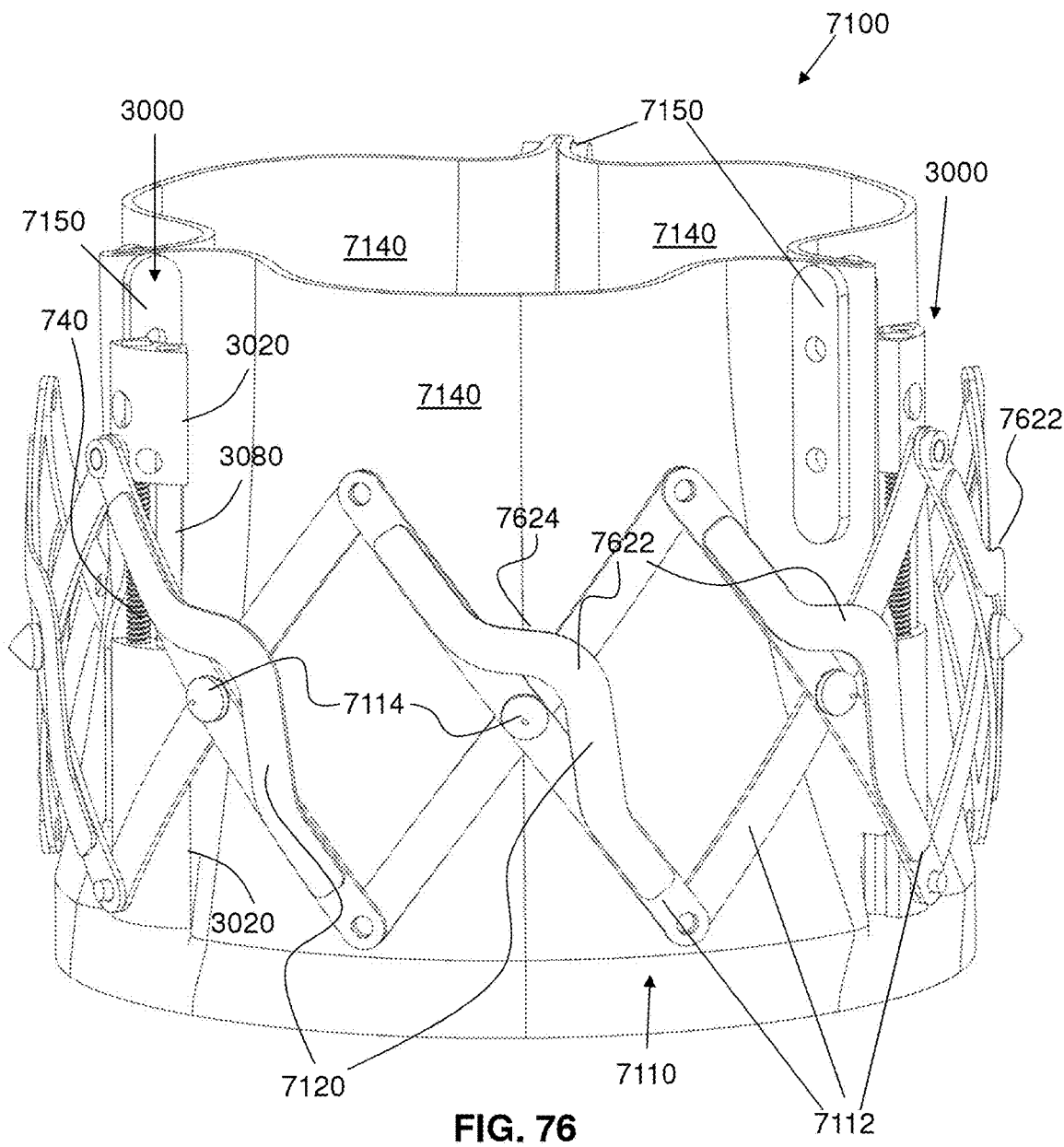
FIG. 76 is a perspective view of the replacement aortic valve assembly of FIG. 71 from a side thereof with the graft material removed.
Figure 77:
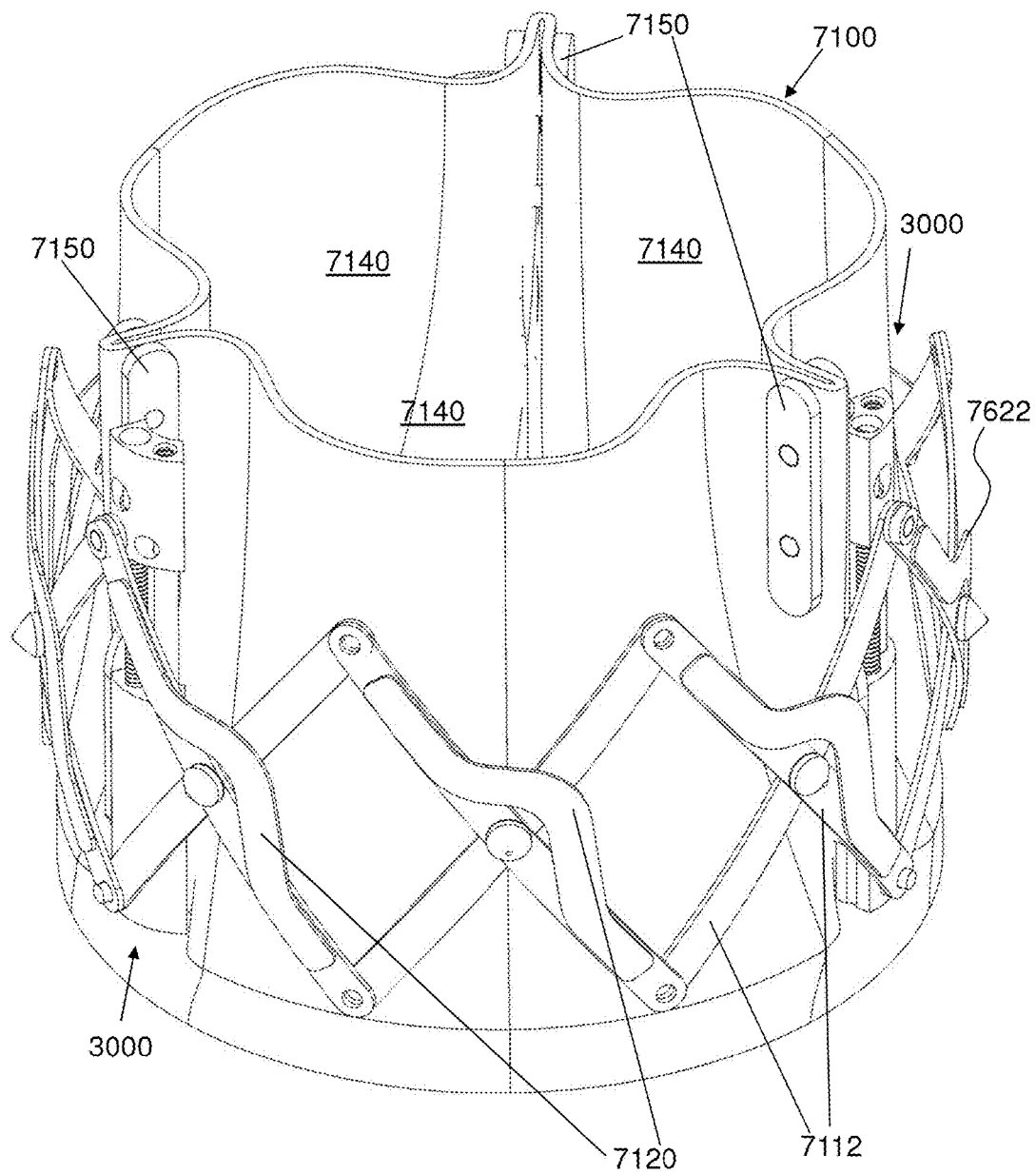
FIG. 77 is a perspective view of the replacement aortic valve assembly of FIG. 76 from above a downstream side thereof.

Another exemplary embodiment of a replacement heart valve assembly 7100 according to the invention is shown in FIGS. 71 to 83. Even though the exemplary embodiment is shown for an aortic valve, the invention is not limited thereto. This embodiment is equally applicable to pulmonary, mitral and tricuspid valves with appropriate changes to the valve leaflets, for example. The replacement heart valve assembly 7100 shown in various views in FIGS. 71 to 75 is comprised of a stent lattice 7110, graft enclosures 7120, jack assemblies 3000, graft material 7130, valve leaflets 7140, and commisure plates 7150. Operation and construction of the replacement heart valve assembly 7100 is explained with reference to FIGS. 76 to 83 with various views therein having the graft material 7130 and/or the valve leaflets 7140 removed. In FIGS. 75 and 76, the replacement heart valve assembly 7100 is in an expanded state (when used herein, "expanded state" does not mean that the state shown is the greatest expanded state of the prosthesis; it means that the prosthesis is expanded sufficiently enough to be sized for an implantation in some anatomic site) such that it accommodates to the natural geometry of the implantation site. With the graft material removed (see, e.g., FIG. 76), the structure around the three valve leaflets 7140 is easily viewed. The proximal and distal drive blocks 3020, 3010 have internal configurations and the support rod 3080, the drive screw 740, and the distal drive screw coupler part 3052 disposed therein.

The stent lattice 7110 is similar to previous embodiments described herein except for the center pivot points of each strut 7112 of the stent lattice 7110 and the graft enclosures 7120. In the exemplary embodiment shown, the center pivot points are not merely pivoting connections of two struts 7112 of the stent lattice 7110. In addition, the outer-most circumferential surface of the pivoting connection comprises a tissue anchor 7114, for example, in the form of a pointed cone in this exemplary embodiment. Other external tissue anchoring shapes are equally possible, including spikes, hooks, posts, and columns, to name a few. The exterior point of the tissue anchor 7114 supplements the outward external force imposed by the actively expanded stent lattice 7110 by providing structures that insert into the adjacent tissue, thereby further inhibiting migration and embolism.

The graft enclosures 7120 also supplement the outward external force imposed by the actively expanded stent lattice 7110 as explained below. A first characteristic of the graft enclosures 7120, however, is to secure the graft material 7130 to the replacement heart valve assembly 7100. The graft material 7130 needs to be very secure with respect to the stent lattice 7110. If the graft material 7130 was attached, for example, directly to the outer struts 7112 of the stent lattice 7110, the scissoring action that the adjacent struts 7112 perform as the stent lattice 7110 is expanded and contracted could adversely affect the security of the graft material 7130 thereto—this is especially true if the graft material 730 was sewn to the outer struts 7112 and the thread passed therethrough to the inside surface of the outer strut 7112, against which the outer surface of the inner strut 7112 scissors in use. Accordingly, the graft enclosures 7120 are provided at a plurality of the outer struts 7112 of the stent lattice 7110 as shown in FIGS. 71 to 87. Each graft enclosure 7120 is fixedly attached at one end of its ends to a corresponding end of an outer strut 7112. Then, the opposing, free end of the graft enclosure 7120 is woven through the inner side of the graft material 7130 and then back from the outer side of the graft material 7130 to the inner side thereof as shown in FIGS. 71 to 75, for example. The opposing, free end of the graft enclosure 7120 is fixedly attached to the other end of the outer strut 7112. This weaving reliably secures the outer circumferential side of the graft material 7130 to the stent lattice 7110.

As mentioned above, graft enclosures 7120 simultaneously supplement the outward external force imposed by the actively expanded stent lattice 7110 with edges and protrusions that secure the replacement heart valve assembly 7100 at the implantation site. More specifically, the graft enclosures 7120 are not linear as are the exemplary embodiment of the outer struts 7112 of the stent lattice 7110. Instead, they are formed with a central offset 7622, which can take any form and, in these exemplary embodiments, are wave-shaped. This central offset 7622 first allows the graft enclosure 7120 to not interfere with the tissue anchor 7114. The central offset 7622 also raises the central portion of the graft enclosure 7120 away from the stent lattice 7110, as can be seen, for example, to the right of FIGS. 76 and 77 and, in particular, in the views of FIGS. 82 and 83. The radially outward protrusion of the central offset 7622 inserts and/or digs into adjacent implantation site tissue to, thereby, inhibit any migration or embolism of the replacement heart valve assembly 7100. By shaping the central offset 7622 appropriately, a shelf 7624 is formed and provides a linear edge that traverses a line perpendicular to the flow of blood within the replacement heart valve assembly 7100. In the exemplary embodiment of the central offset 7622 shown in FIGS. 76, 77, and 79 to 81, the shelf 7624 is facing downstream and, therefore, substantially inhibits migration of the replacement heart valve assembly 7100 in the downstream direction when exposed to systolic pressure. Alternatively, the central offset 7622 can be shaped with the shelf 7624 is facing upstream and, therefore, substantially inhibits migration of the replacement heart valve assembly 7100 in the upstream direction when exposed to diastolic pressure. The graft material needs to be able to stay intimately attached to the lattice throughout a desired range of terminal implantable diameters. To accomplish this, the graft material is made from a structure of material that moves in a fashion like that of the lattice. That is to say, as its diameter increases, its length decreases. This kind of movement can be accomplished with a braid of yarns or through the fabrication of graft material where its smallest scale fibers are oriented similarly to a braid, allowing them to go through a scissoring action similar to the lattice. One exemplary embodiment of the material is a high end-count braid made with polyester yarns (e.g., 288 ends using 40-120 denier yarn). This braid can, then, be coated with polyurethane, silicone, or similar materials to create stability and reduce permeability by joining all the yarns together. These coatings can be doped or filled with radiopaque material to improve visibility under fluoroscopy. The amount of coating (polyurethane, for example) can be varied to be increased where high-wear or trimming occurs. If the braid is trimmed by laser-cutting, for example, the cutting process seals the cut edge to prevent fraying and allows for reduction or elimination of the need for a coating, such as polyurethane. Likewise, a spun-fiber tube can be made with similar polymers forming strands from approximately 2-10 microns in diameter. These inventive graft fabrication methods provide for a material that will be about 0.005" to 0.0015" (0.127 mm to 0.381 mm) thick and have all the physical properties necessary. See, for example, FIGS. 195-199. A thin material is desirable to reduce the compacted diameter for easier introduction into the patient. This material is also important in a stent graft prosthesis where the lattice is required to seal over a large range of possible terminal diameters. The adjustable material is able to make the transition from the final terminal diameter of the upstream cuff to the main body of the graft.

Figure 73:
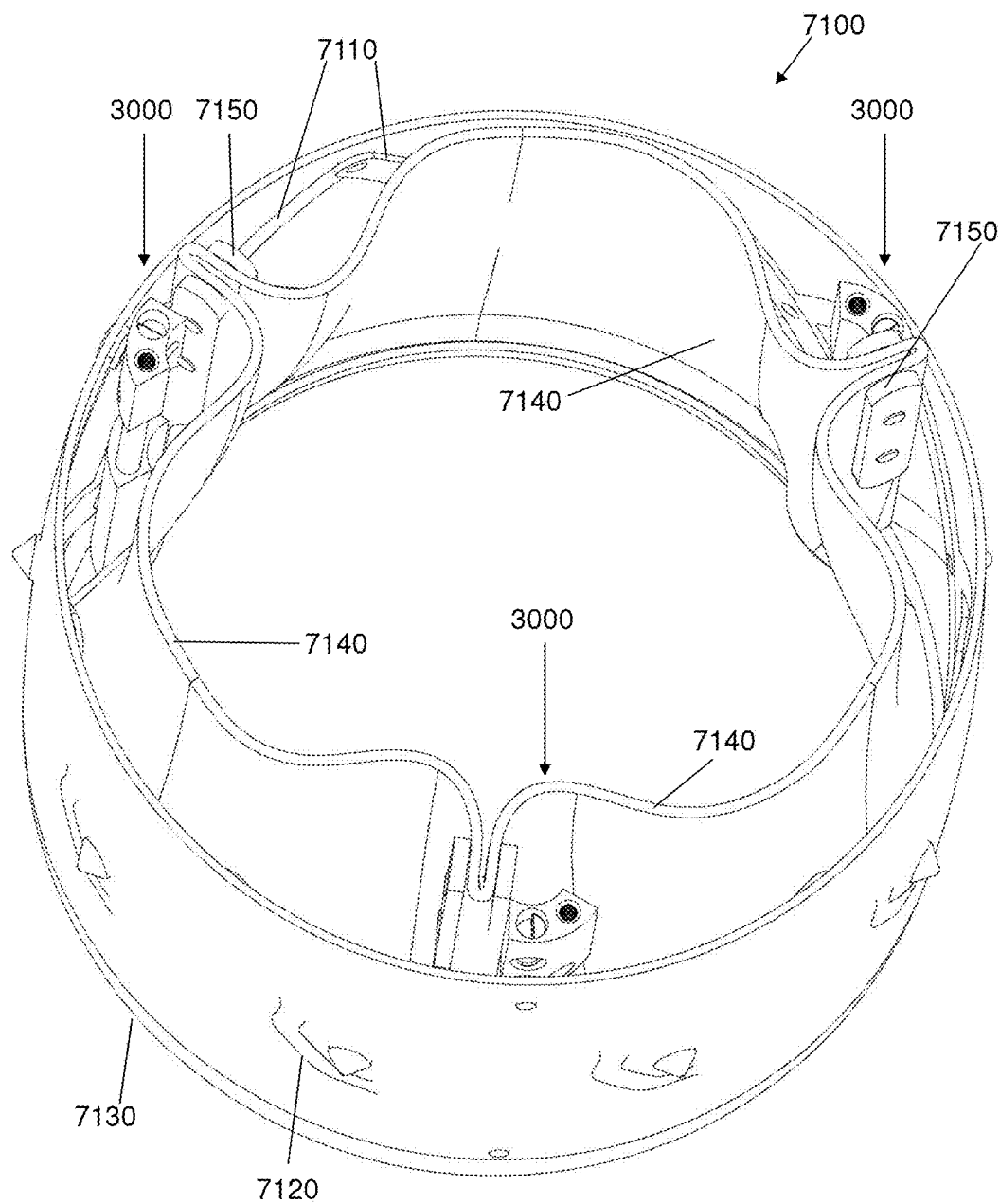
FIG. 73 is a perspective view of the replacement aortic valve assembly of FIG. 71 from above a downstream end thereof.
Figure 74:
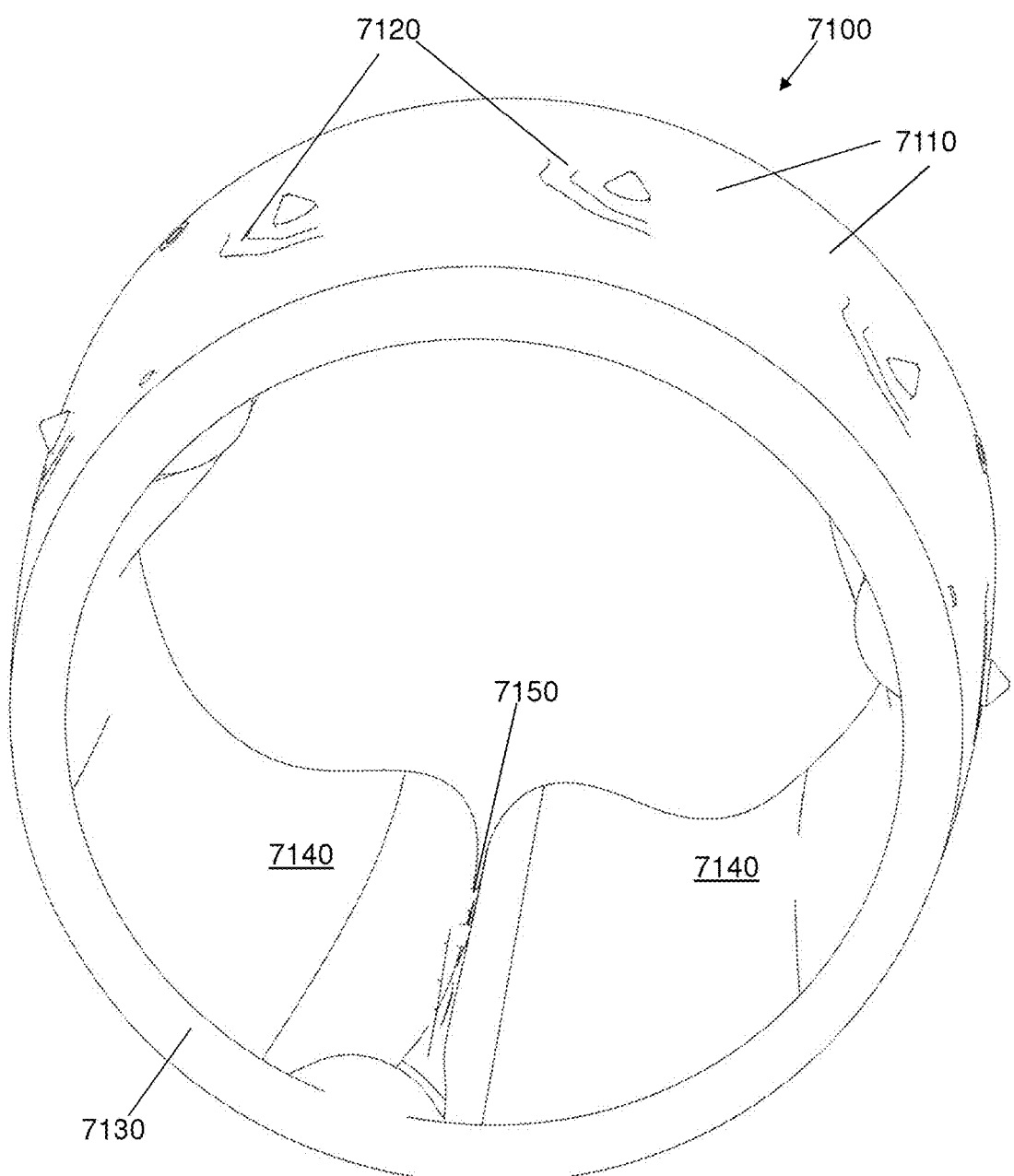
FIG. 74 is a perspective view of the replacement aortic valve assembly of FIG. 71 from below an upstream end thereof.
Figure 82:
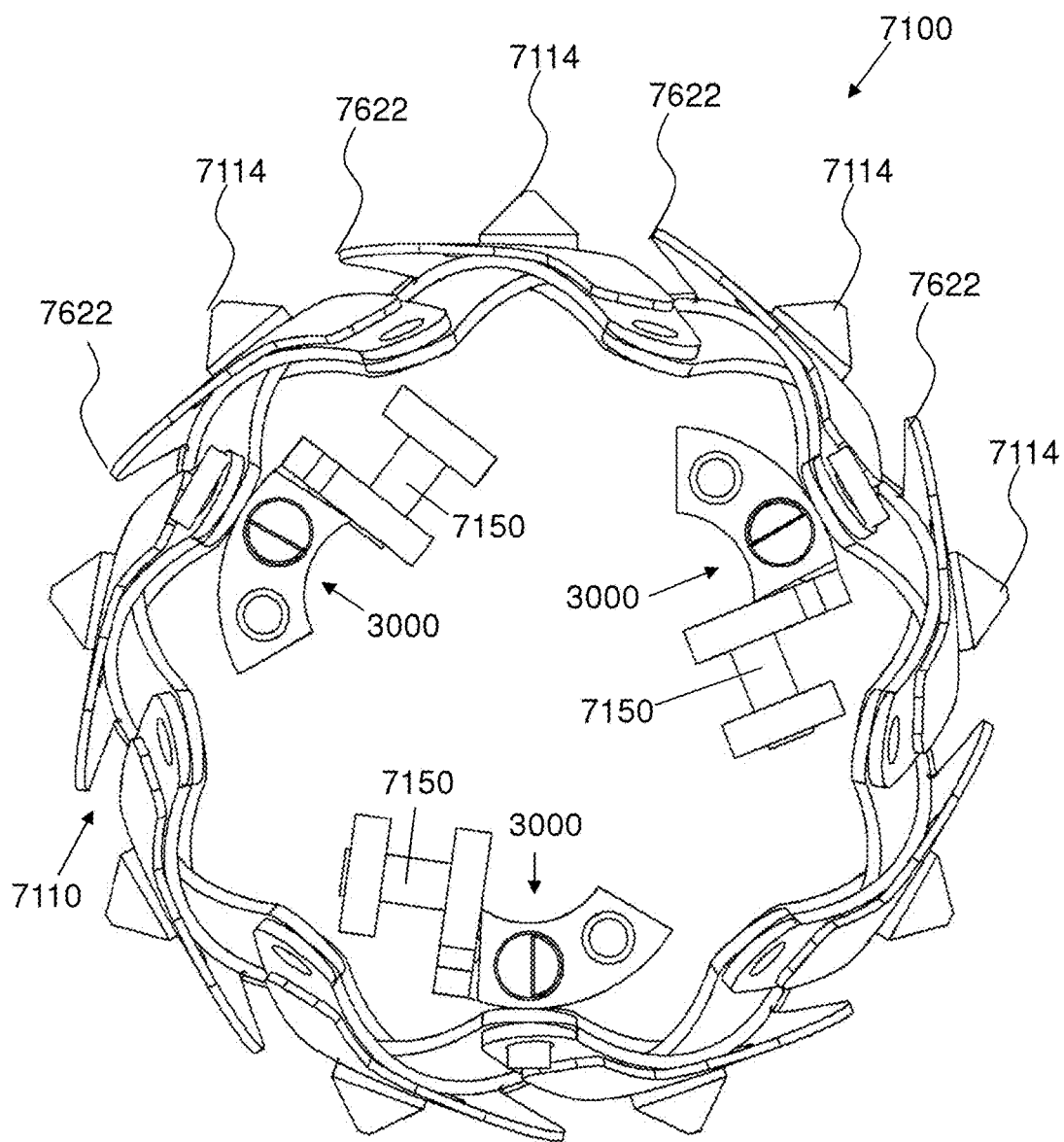
FIG. 82 is a downstream plan view of the replacement aortic valve assembly of FIG. 79 in an intermediate expanded state.
Figure 83:
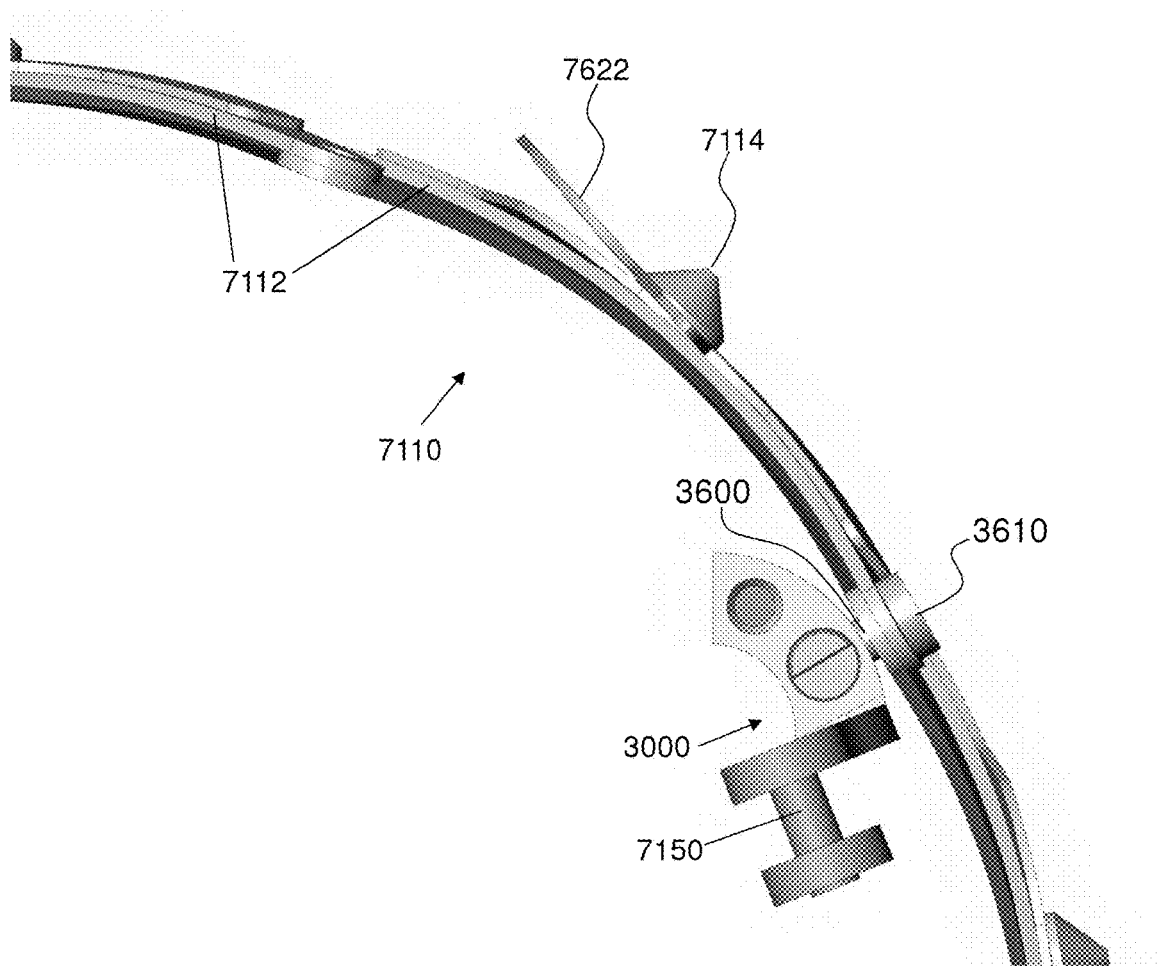
FIG. 83 is an enlarged downstream plan view of a portion of the replacement aortic valve assembly of FIG. 79 in an expanded state.

As best shown in FIG. 73, the valve leaflets 7140 are connected by commisure plates 7150 to the jack assemblies 3000. Fixed connection of the commisure plates 7150 to the jack assemblies 3000 is best shown in FIGS. 82 and 83. Each valve leaflet 7140 is connected between two adjacent commisure plates 7150. Each commisure plate 7150 is comprises of two vertically disposed flat plates having rounded edges connected, for example, by pins projecting orthogonally to the flat plates. Pinching of the flat plates against the two adjacent valve leaflets 7140 securely retains the valve leaflets 7140 therein while, at the same time, does not form sharp edges that would tend to tear the captured valve leaflets 7140 therein during prolonged use. This configuration, however, is merely exemplary. This could be replaced with a simpler rod design around which the leaflets are wrapped and stitched into place.

Even though each valve leaflet 7140 can be a structure separate from the other valve leaflets 7140, FIGS. 71 to 78 illustrate the three leaflets 7140 as one piece of leaf-forming material pinched, respectively, between each of the three sets of commisure plates 7150 (the material can, alternatively, pinch around the commisure plate or plates). The upstream end of the valve leaflets 7140 must be secured for the replacement heart valve assembly 7100 to function.

Figure 78:
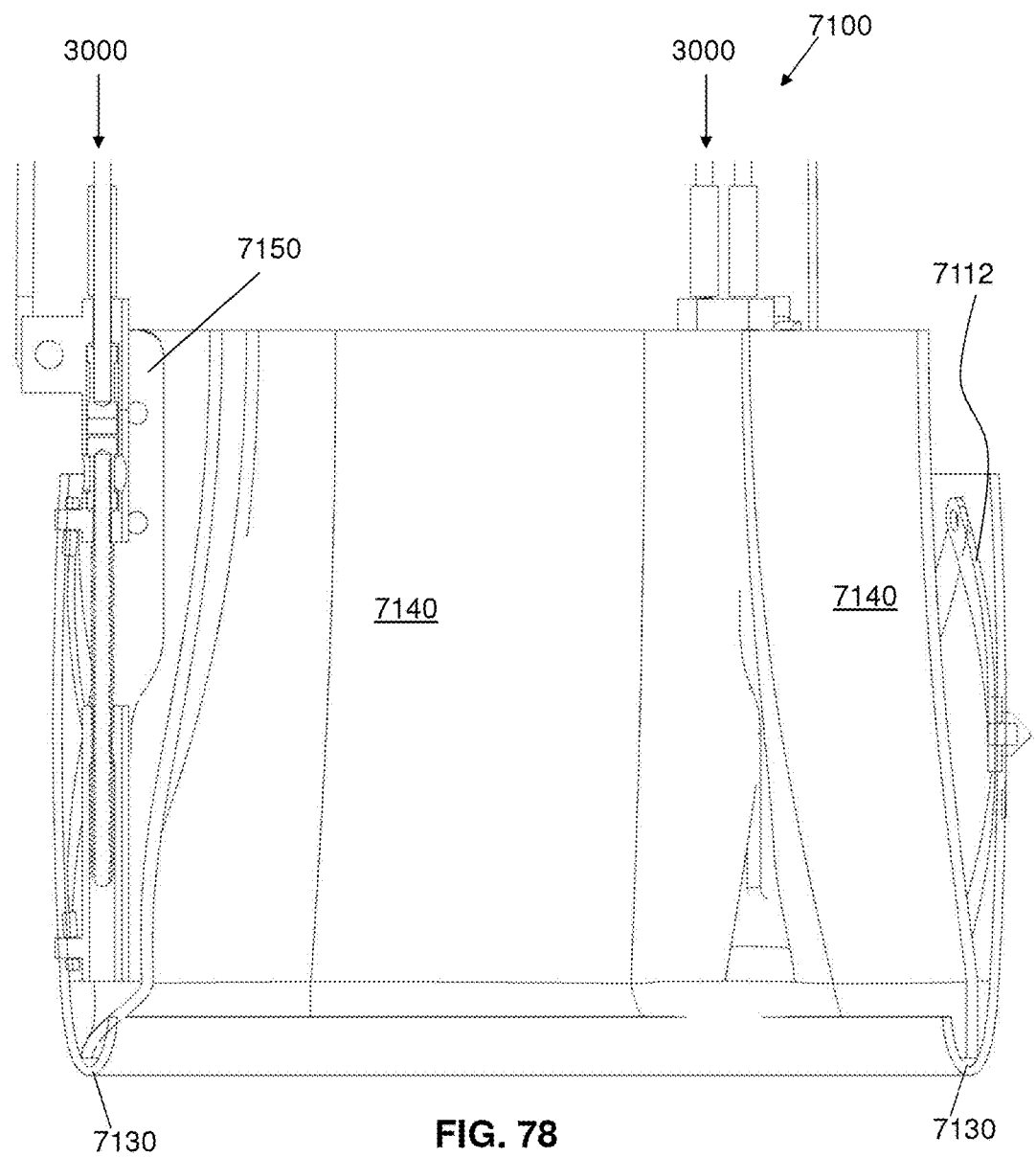
FIG. 78 is a side elevation, vertical cross-sectional view of the replacement aortic valve assembly of FIG. 76.

Therefore, in an exemplary embodiment, the upstream end of the graft material 7130 is wrapped around and fixedly connected to the replacement heart valve assembly 7100 at the upstream side of the valve leaflets 7140, as shown in FIG. 78. In such a configuration, the upstream edge of the valve leaflets 7140 is secured to the graft material 7130 entirely around the circumference of the stent lattice 7110. Stitches can pass through the two layers of graft and the upstream edge of the leaflet material to form a hemmed edge.

Figure 79:
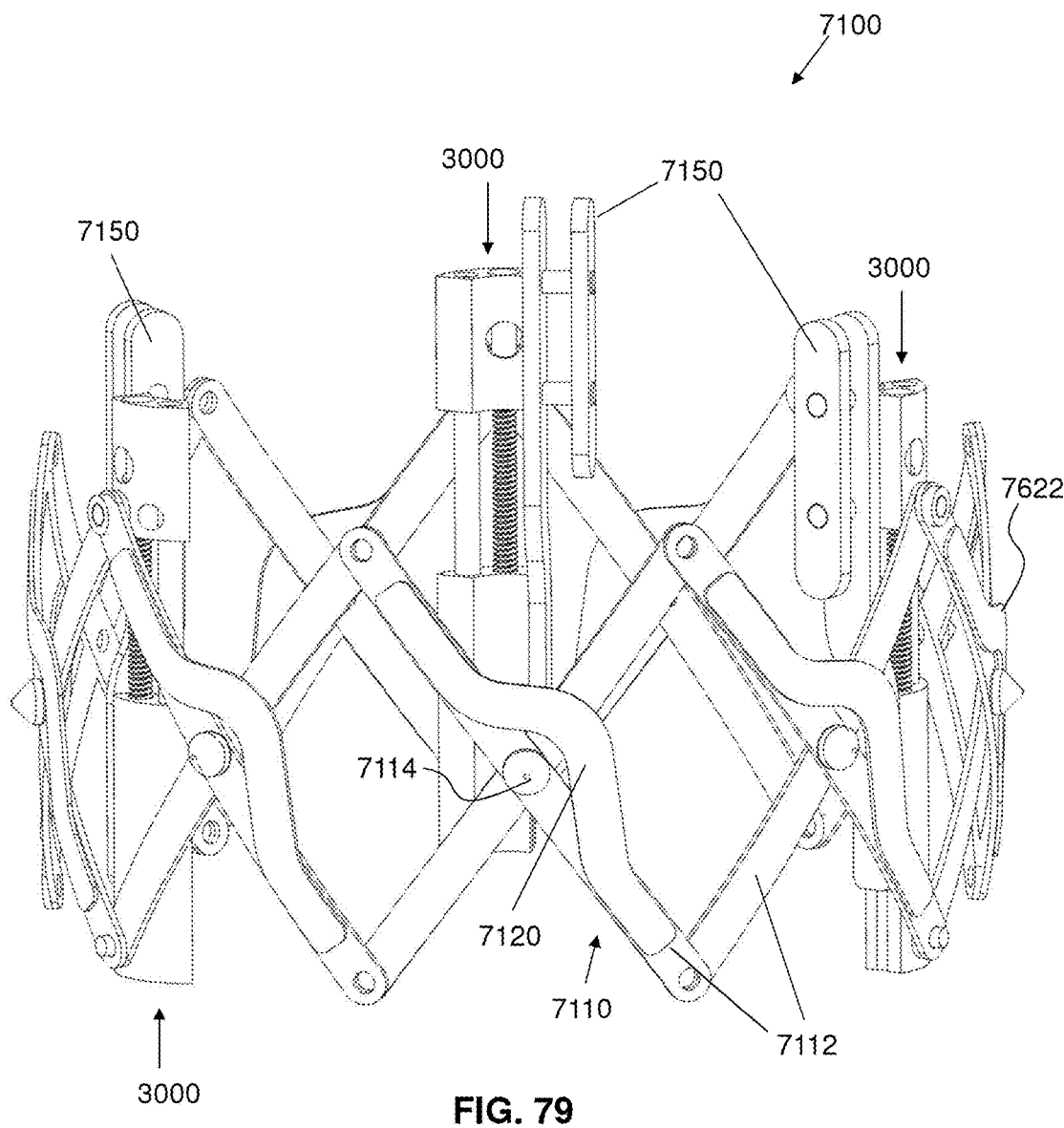
FIG. 79 is a perspective view of the replacement aortic valve assembly of FIG. 76 from a side thereof with the valve material removed, with the stent lattice in an expanded state.
Figure 80:
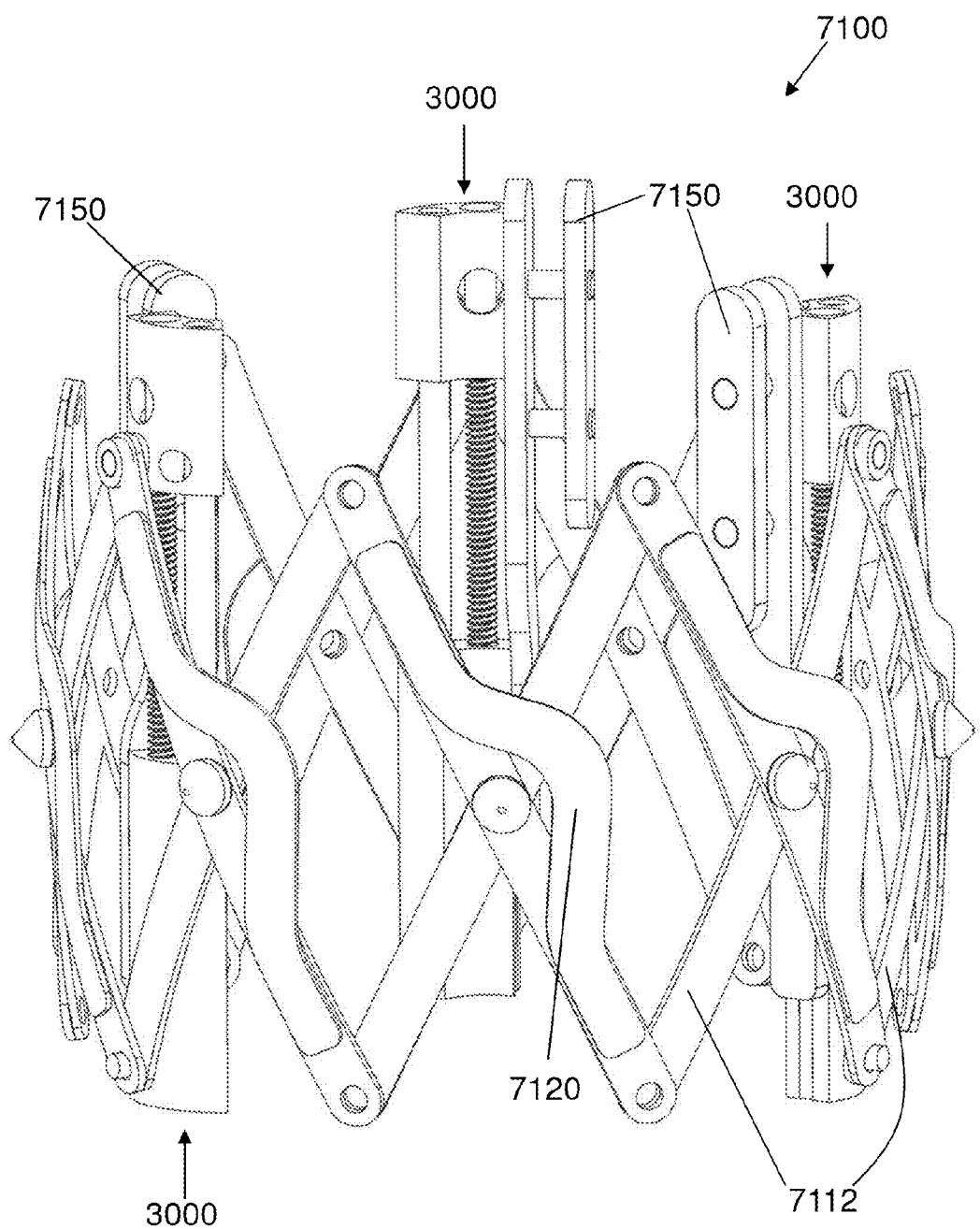
FIG. 80 is a perspective view of the replacement aortic valve assembly of FIG. 79 with the stent lattice in an intermediate expanded state.
Figure 81:
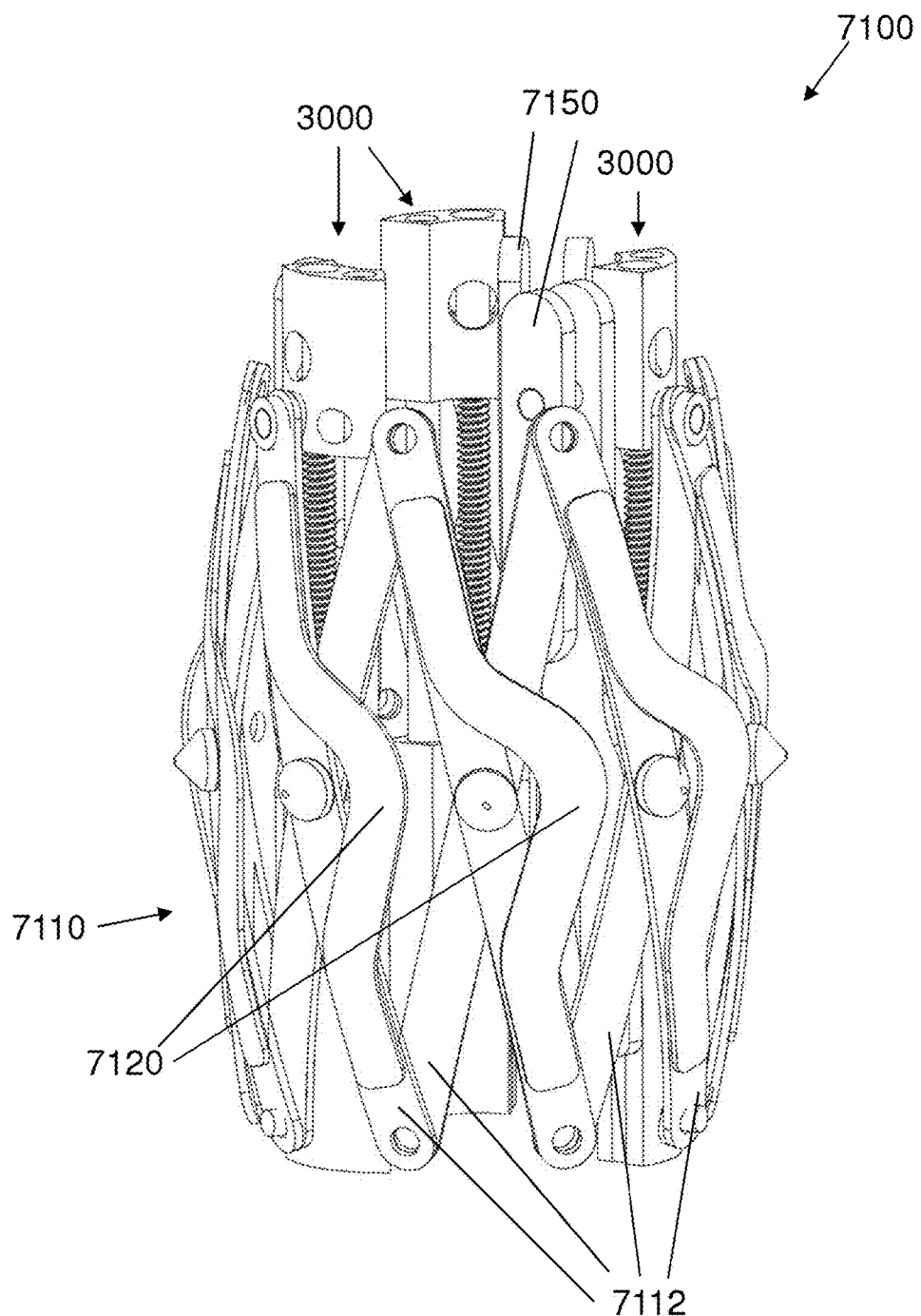
FIG. 81 is a perspective view of the replacement aortic valve assembly of FIG. 79 with the stent lattice in an almost contracted state.

FIGS. 79 to 81 show the stent lattice 7110 in various expanded and contracted states with both the graft material 7130 and the valve leaflets 7140 removed. FIG. 79 illustrates the stent lattice 7110 and jack assemblies 3000 in an expanded state where the tissue anchor 7114 and the central offset 7622 protrude radially out from the outer circumferential surface of the stent lattice 7110 such that the stent lattice 7110 accommodates to the natural geometry of the implantation site. FIG. 80 illustrates the stent lattice 7110 and the jack assemblies 3000 in an intermediate expanded state and FIG. 81 illustrates the stent lattice 7110 and the jack assemblies 3000 in a substantially contracted state.

Figure 84:
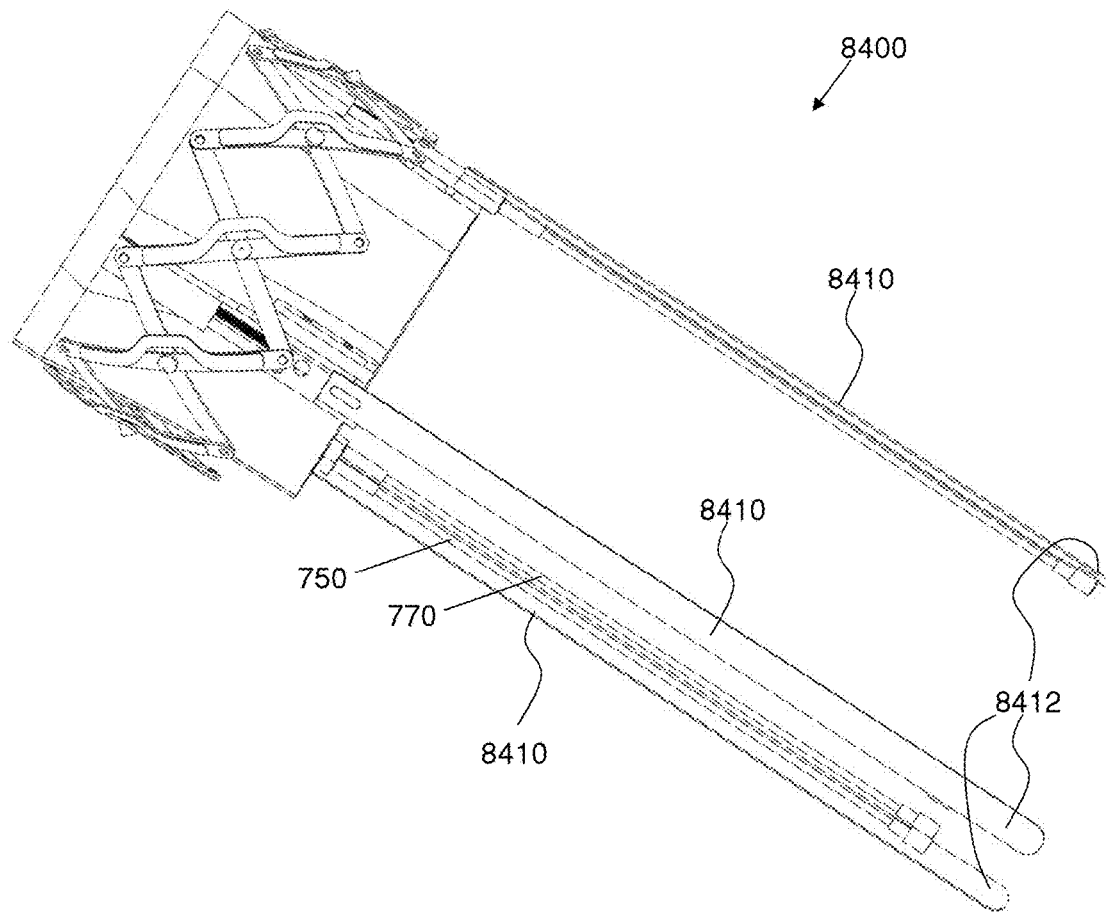
FIG. 84 is a side elevational view of the replacement aortic valve assembly of FIG. 79 in an expanded state, with graft material removed, and with distal portions of an exemplary embodiment of a valve delivery system.
Figure 85:
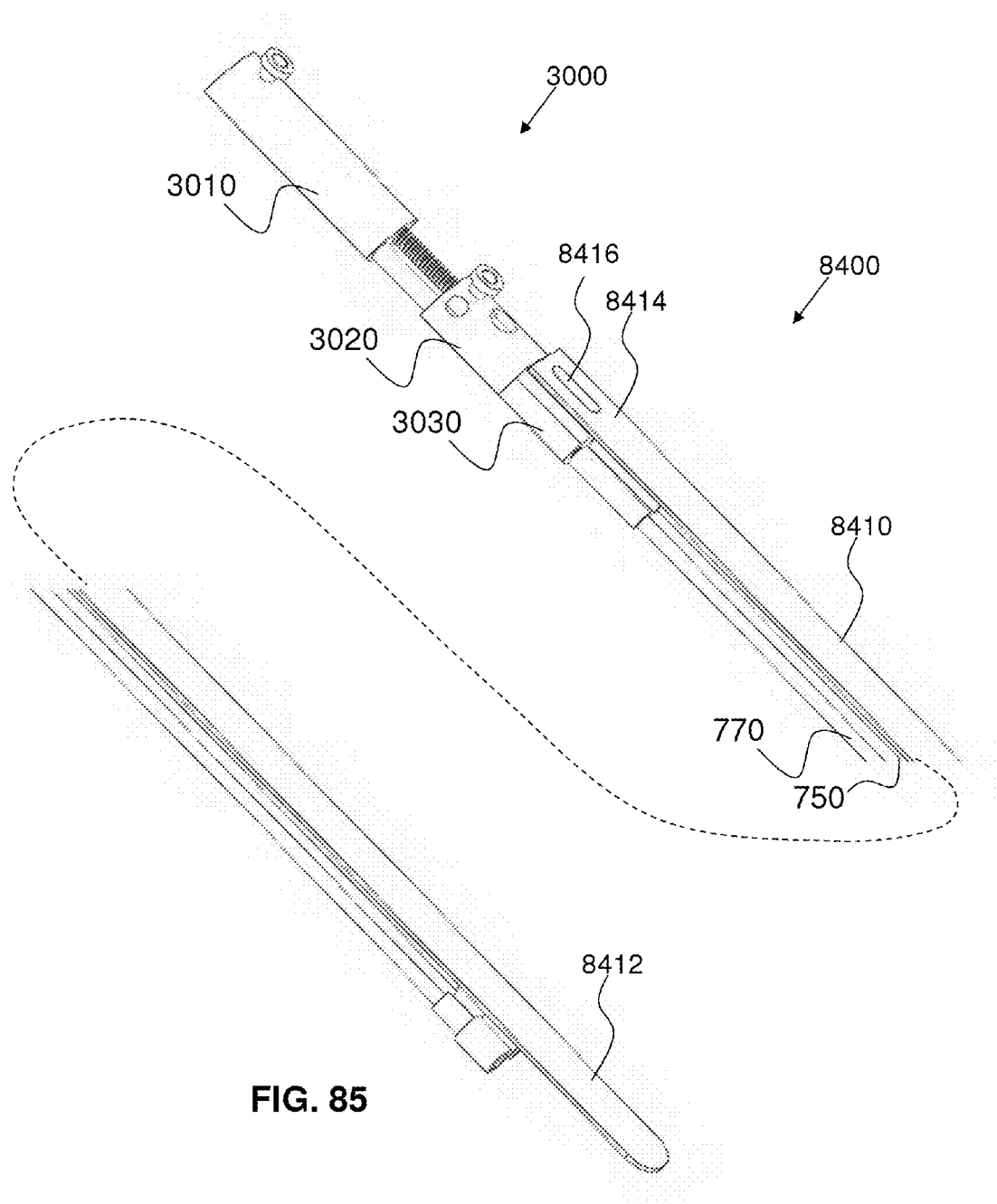
FIG. 85 is a perspective view of an exemplary embodiment of a jack assembly of the replacement aortic valve assembly of FIG. 84 from a side thereof with the valve delivery system sectioned.

FIGS. 84 and 85 show an exemplary embodiment of a support system 8400 of the delivery system and method according to the invention for both supporting the jack assemblies 3000 and protecting the various control wires 750, 770, 2182, 3098 of the jack assemblies 3000. In these figures, the support bands 8410 are shown as linear. This orientation is merely due to the limitations of the computer drafting software used to create the figures. These support bands 8410 would only be linear as shown when unconnected to the remainder of the delivery system for the replacement heart valve assembly 7100. When connected to the distal end of the delivery system, as diagrammatically shown, for example, in FIGS. 1, 3, 4, and 9 with a wire-guide block 116, all control wires 750, 770, 2182, 3098 will be directed inwardly and held thereby. Similarly, the proximal ends 8412 of the support bands 8410 will be secured to the wire-guide block 116 and, therefore, will bend radially inward. In the exemplary embodiment of the support bands 8410 shown in FIGS. 84 and 85, the distal ends 8414 thereof are fixedly secured to the disconnector drive block 3030 by an exemplary hinge assembly 8416. In this exemplary embodiment, therefore, the support bands 8410 are of a material and thickness that allows the delivery system to function. For example, while traveling towards the implantation site, the replacement heart valve assembly 7100 will traverse through a curved architecture. Accordingly, the support bands 8410 will have to bend correspondingly to the curved architecture while, at the same time, providing enough support for the control wires 750, 770, 2182, 3098 to function in any orientation or curvature of the delivery system.

Figure 86:
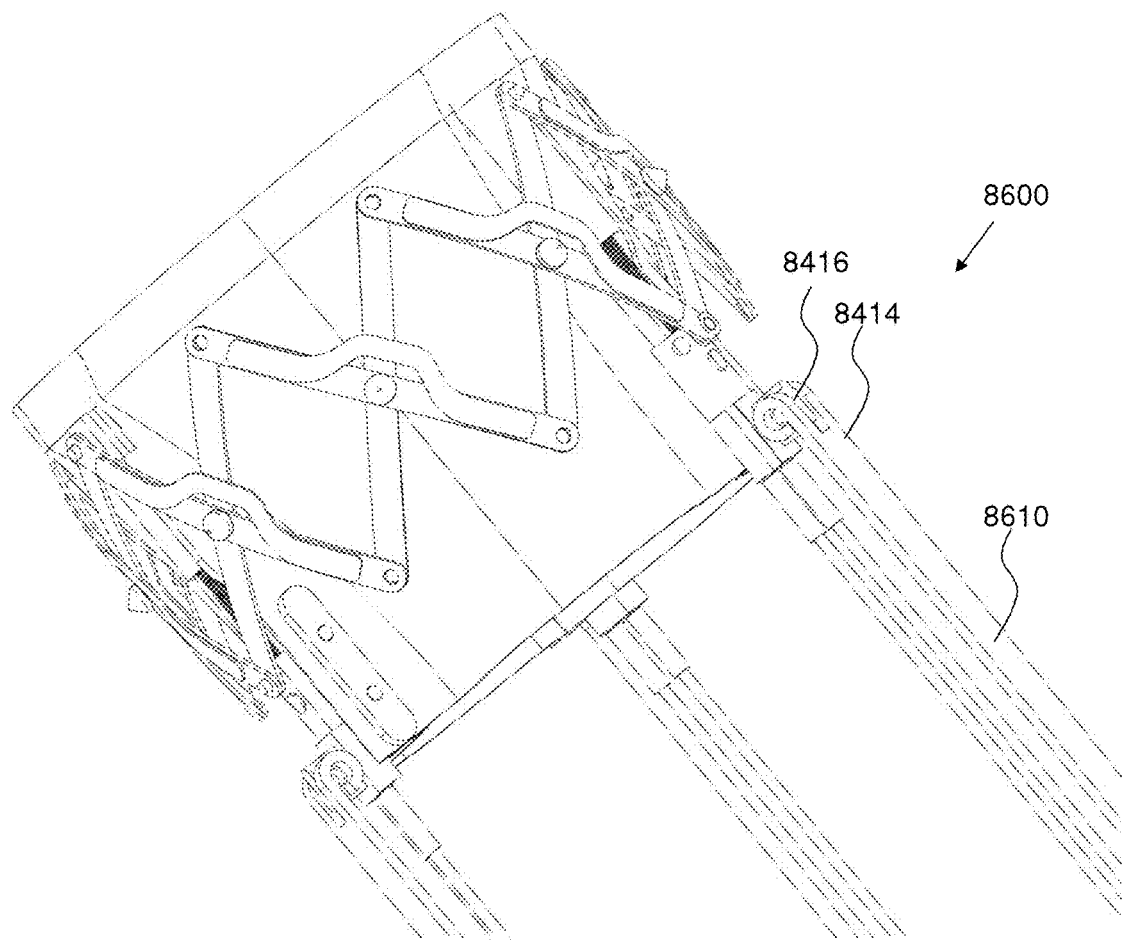
FIG. 86 is a perspective view of the replacement aortic valve assembly of FIG. 79 in an expanded state, with graft material removed, and with distal portions of another exemplary embodiment of a valve delivery system.
Figure 87:
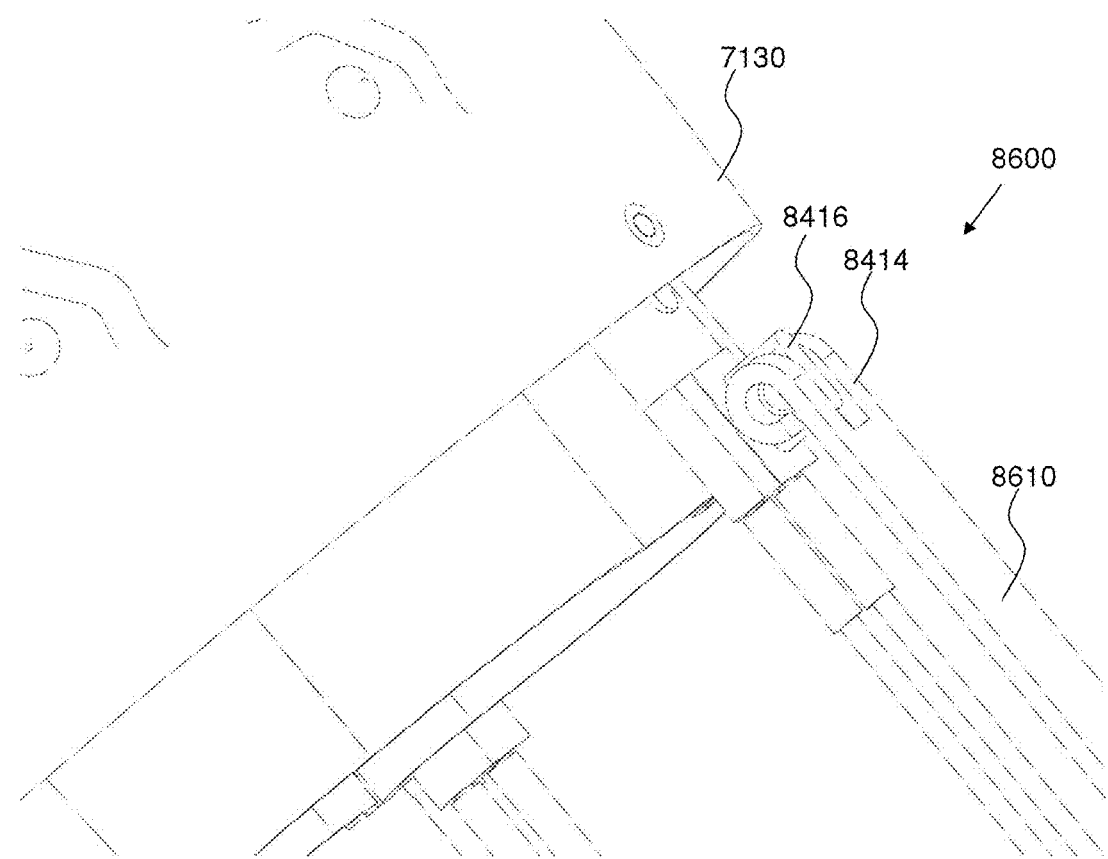
FIG. 87 is a fragmentary, enlarged perspective view of the replacement aortic valve assembly of FIG. 86 with graft material shown.

An alternative exemplary connection assembly of the support bands 8610 according to the invention is shown in FIGS. 86 and 87. The distal end 8614 of each support band 8610 is connected to the disconnector drive block 3030 by a hinge assembly 8416. The hinge assembly 8416, for example, can be formed by a cylindrical fork at the distal end 8614 of the support band 8610, an axle (not illustrated), and a radially extending boss of the disconnector drive block 3030 defining an axle bore for the axle to connect the cylindrical fork to the boss. In such a configuration, the support bands 8610 can have different material or physical properties than the support bands 8410 because bending movements are adjusted for with the hinge assembly 8416 instead of with the bending of the support bands 8410 themselves. The proximal end of the support bands 8610 are not shown in either FIG. 86 or 87. Nonetheless, the proximal ends can be the same as the distal end of the support bands 8610 or can be like the distal end 8614 of the support bands 8410. By pre-biasing the support bands to the outside, they can help reduce or eliminate the force required to deflect the control wires.

Figure 88:
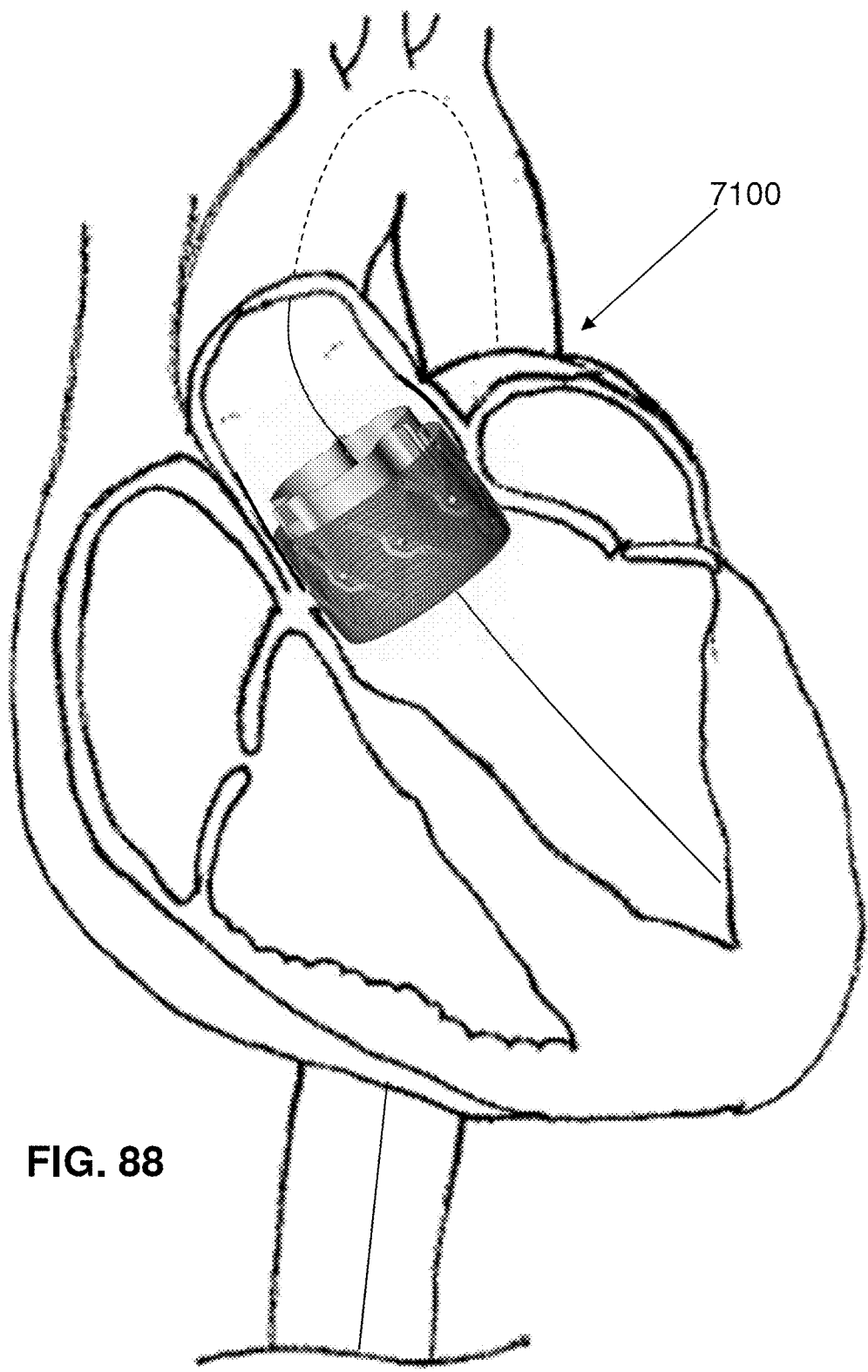
FIG. 88 is a fragmentary, enlarged, perspective view of the delivery system and the aortic valve assembly of FIG. 71 implanted at an aortic valve implantation site.
Figure 89:
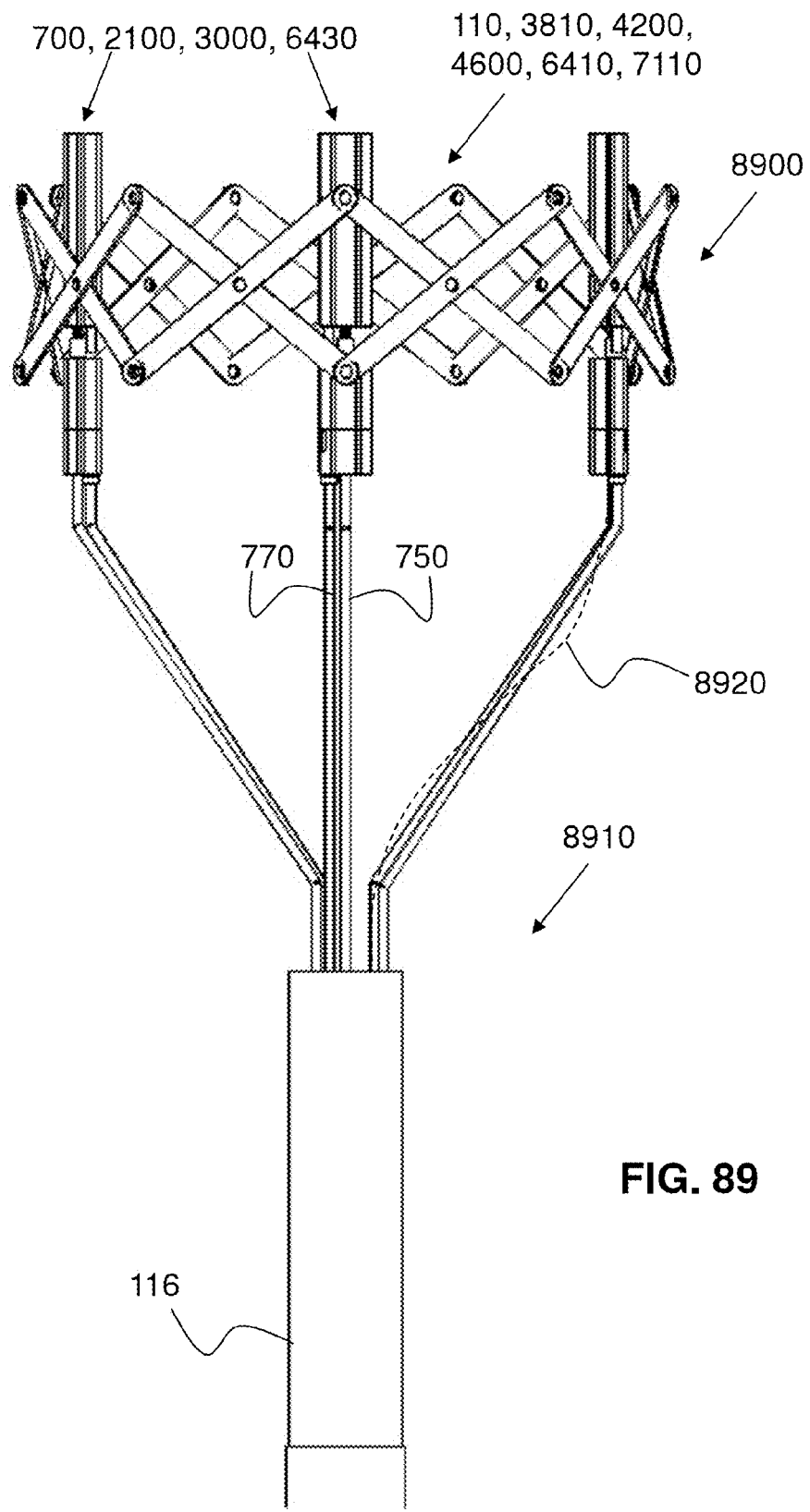
FIG. 89 is a fragmentary, side elevational view of another exemplary embodiment of an actively controllable and tiltable stent graft system according to the invention in a partially expanded state and a non-tilted state.

An embodiment of the replacement heart valve assembly 7100 as an aortic valve is shown implanted within the diseased valve leaflets of a patient's heart in FIG. 88. As can be seen in this figure, the natural valve takes up some room at the midline of the replacement heart valve assembly 7100. Therefore, the stent lattice of the replacement heart valve assembly 7100 can be made to have a waistline, i.e., a narrower midline, to an hourglass shape instead of the barrel shape. In such a configuration, the replacement heart valve assembly 7100 is naturally positioned and held in place.

A further exemplary embodiment of the inventive actively controllable stent lattice and the delivery system and method for delivering the stent lattice are shown in FIGS. 89 to 93. In this embodiment, the prosthesis 8900 includes a stent lattice 110, 3810, 4200, 4600, 6410, 7110 and three jack assemblies 700, 2100, 3000, 6430. These figures also illustrate a distal portion of an exemplary embodiment of a delivery system 8910 for the inventive prosthesis 8900. Shown with each jack assembly 700, 2100, 3000, 6430 are the drive and disconnect wires 750, 700, which are illustrated as extending proximally from the respective jack assembly 700, 2100, 3000, 6430 into a wire guide block 116. Due to the limitations of the program generating the drawing figures, these wires 750, 770 have angular bends when traversing from the respective jack assembly 700, 2100, 3000, 6430 towards the wire guide block 116. These wires, however, do not have such angled bends in the invention. Instead, these wires 750, 770 form a gradual and flattened S-shape that is illustrated diagrammatically in FIG. 89 with a dashed line 8920. Operation of the prosthesis 8900 is as described above in all respects except for a tilting feature regarding the wires 750, 770. Specifically, rotation of the drive wire 750 in respective directions will contract and expand the stent lattice 110, 3810, 4200, 4600, 6410, 7110. Then, when the stent lattice 110, 3810, 4200, 4600, 6410, 7110 is implanted correctly in the desired anatomy, the disconnect wire 770 will be rotated to uncouple the proximal disconnector drive block and, thereby, allow removal of the delivery system 8910. This embodiment provides the delivery system 8910 with a prosthesis-tilting function. More specifically, in the non-illustrated handle portion of the delivery system 8910, each pair of drive and disconnect wires 750, 770 are able to be longitudinally fixed to one another and, when all of the pairs are fixed respectively, each pair can be moved distally and/or proximally.

Figure 90:
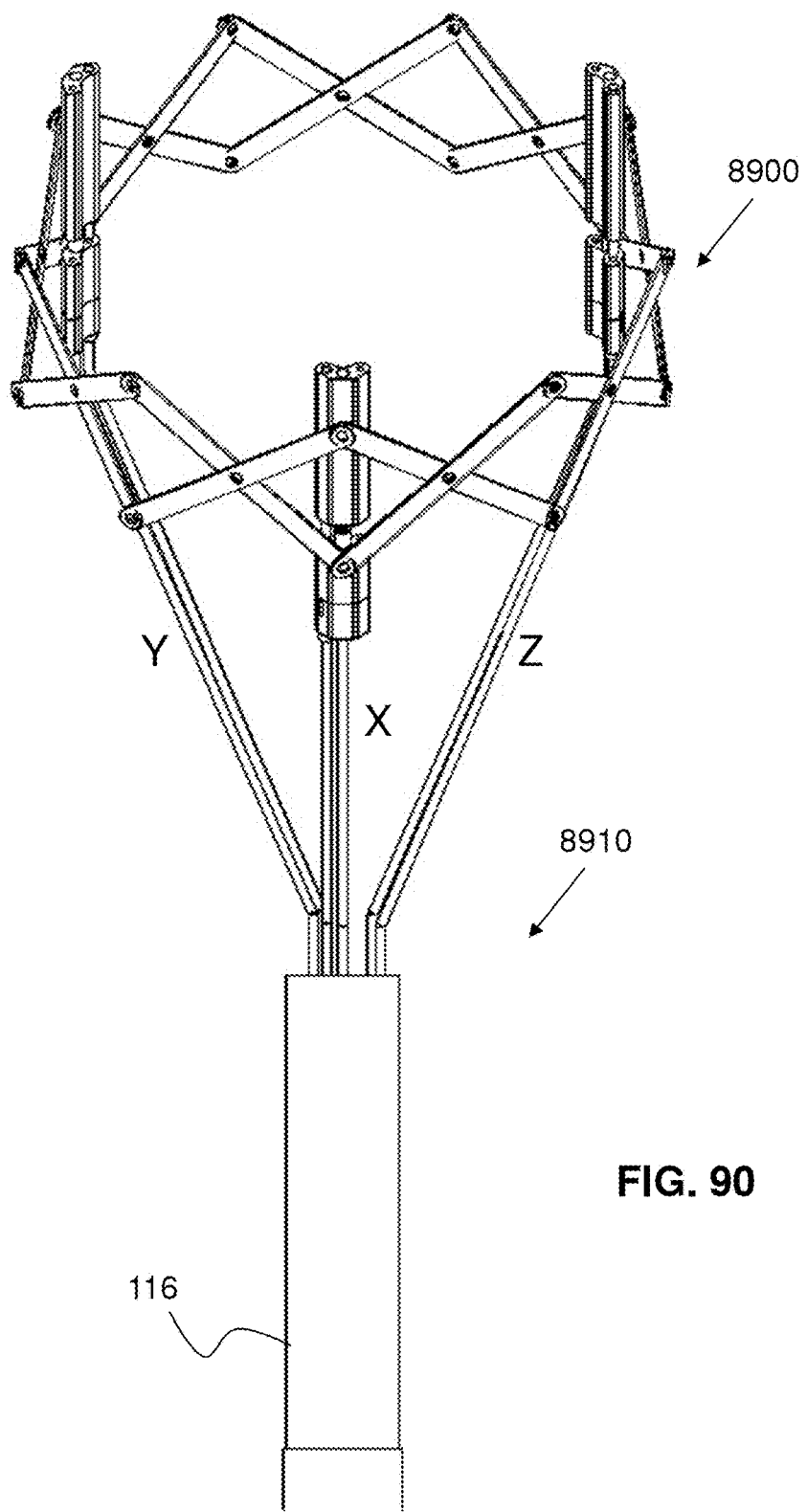
FIG. 90 is a fragmentary, side elevational view of the system of FIG. 89 in a partially tilted state from a front thereof.
Figure 91:
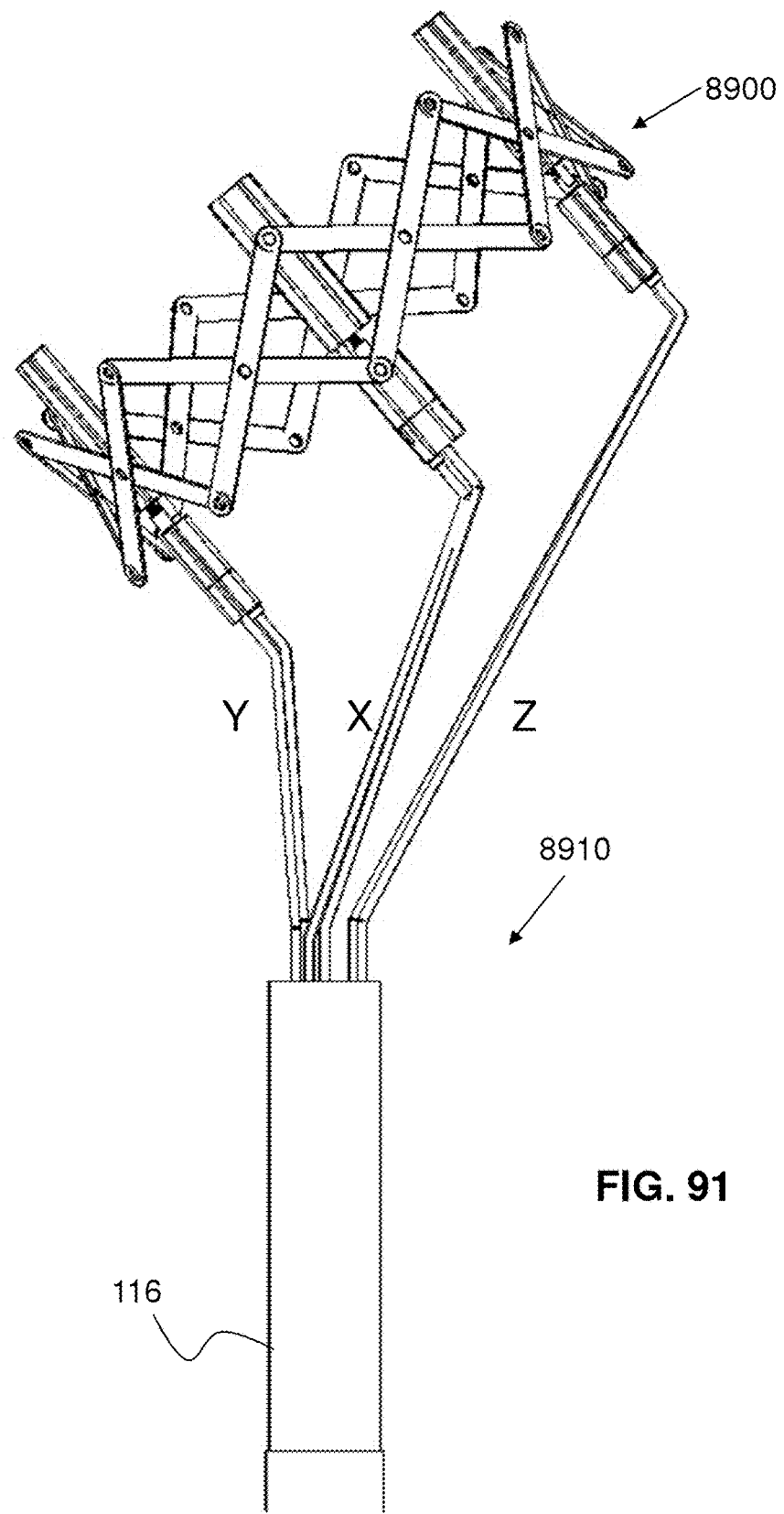
FIG. 91 is a fragmentary, side elevational view of the system of FIG. 90 in another partially tilted state.
Figure 92:
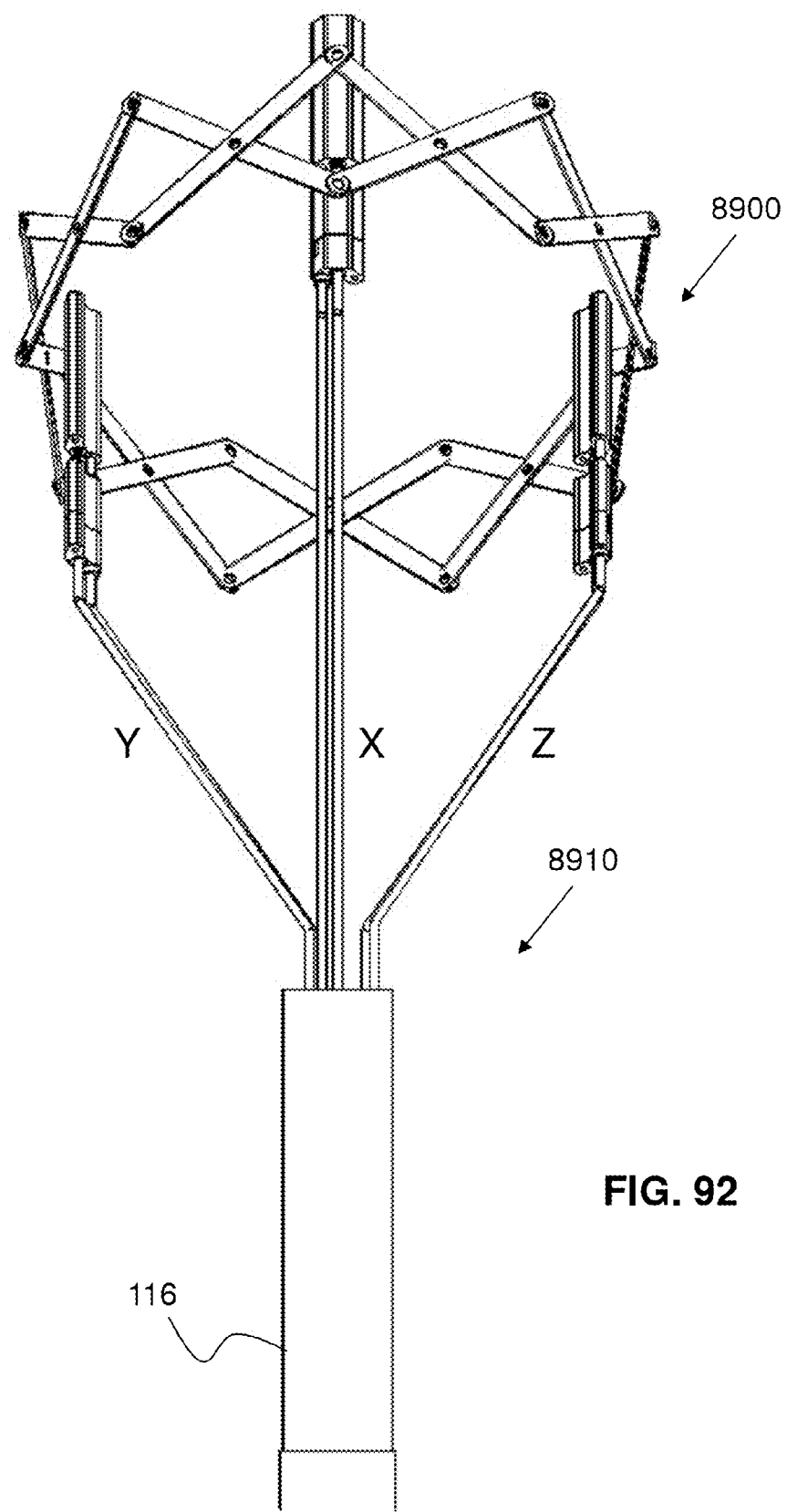
FIG. 92 is a fragmentary, side elevational view of the system of FIG. 90 in yet another partially tilted state.
Figure 93:
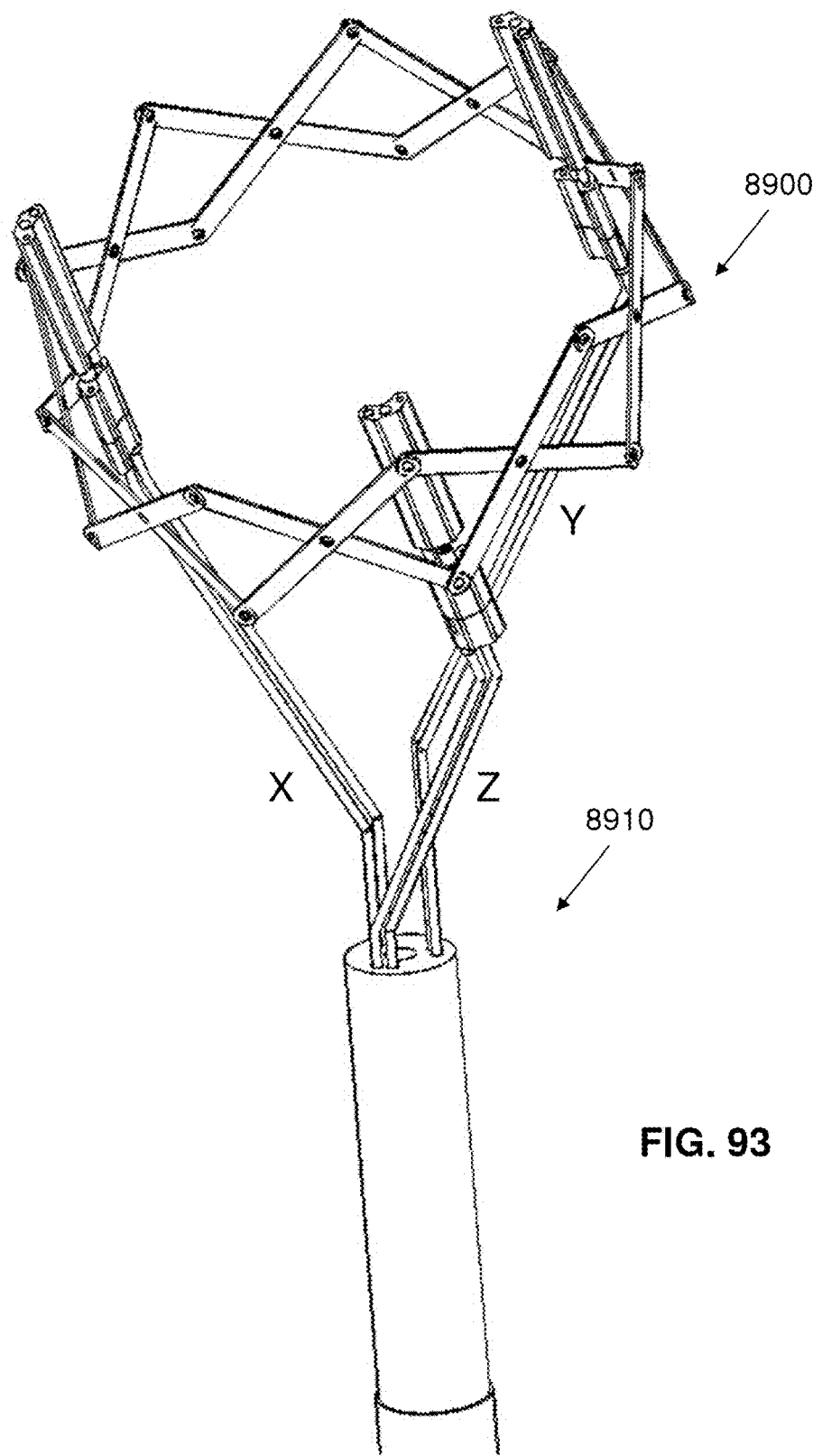
FIG. 93 is a fragmentary, perspective view of the system of FIG. 90 in yet another partially tilted state.

In such a configuration, therefore, if the wires 750, 770 labeled with the letter X are moved proximally together and the other two pairs of wires Y and Z are moved distally, then the entire prosthesis 8900 will tilt into the configuration shown in FIG. 90. Alternatively, if the wires X are kept in position, the wires Y are moved proximally and the wires Z are moved distally, then the entire prosthesis 8900 will tilt into the configuration shown in FIG. 91. Likewise, if the wires X are moved distally and the wires Y and Z are moved proximally, then the entire prosthesis 8900 will tilt into the configuration shown in FIG. 92. Finally, if the wires X are extended distally, the wires Y are extended further distally, and the wires Z are moved proximally, then the entire prosthesis 8900 will tilt into the configuration shown in FIG. 93.

Still a further exemplary embodiment of the inventive actively controllable stent lattice and the delivery system and method for delivering the stent lattice are shown in FIGS. 94 to 102. In this embodiment, the prosthesis 9400 is a stent graft having a proximal, actively controlled stent lattice 110, 3810, 4200, 4600, 6410, 7110 and only two opposing jack assemblies 700, 2100, 3000, 6430. Instead of two additional jack assemblies 700, 2100, 3000, 6430, this embodiment contains two opposing pivoting disconnector drive blocks 9430. These disconnector drive blocks 9430, as shown for example in the view of FIG. 96 rotated circumferentially ninety degrees, have bosses 9432 extending radially outward and forming the central pivot joint for the two crossing struts 9410. The two disconnector drive blocks 9430 act as pivots to allow the prosthesis 9400 to tilt in the manner of a swashplate when the two opposing sets of control wires 750, 770 are moved in opposing distal and proximal directions.

Figure 94:
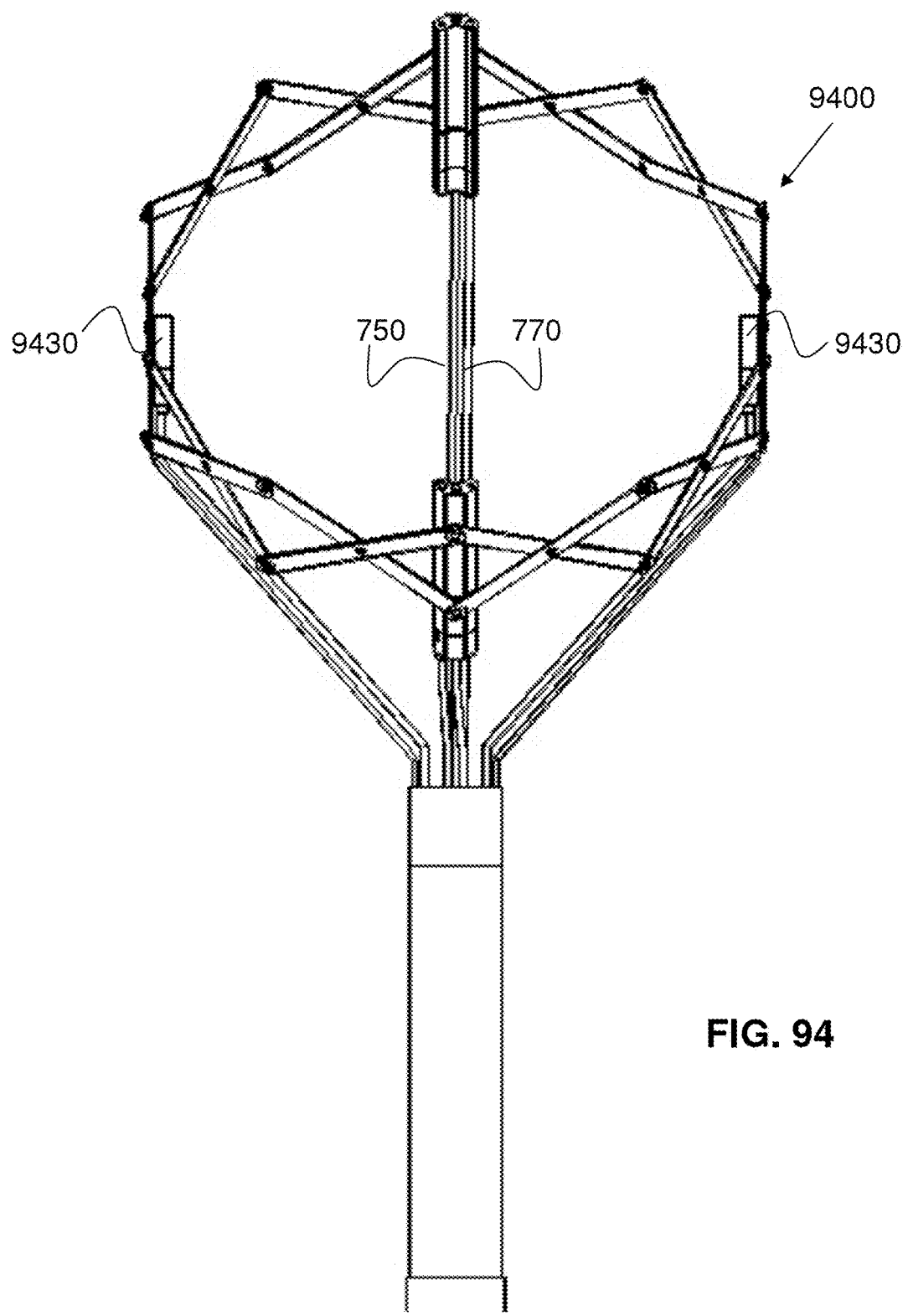
FIG. 94 is a fragmentary, partially cross-sectional, side elevational view of another exemplary embodiment of an actively controllable and tiltable stent graft system according to the invention in an expanded state and a partially front-side tilted state
Figure 95:
FIG. 95 is a fragmentary, perspective view of the system of FIG. 94 in a non-tilted state.
Figure 96:
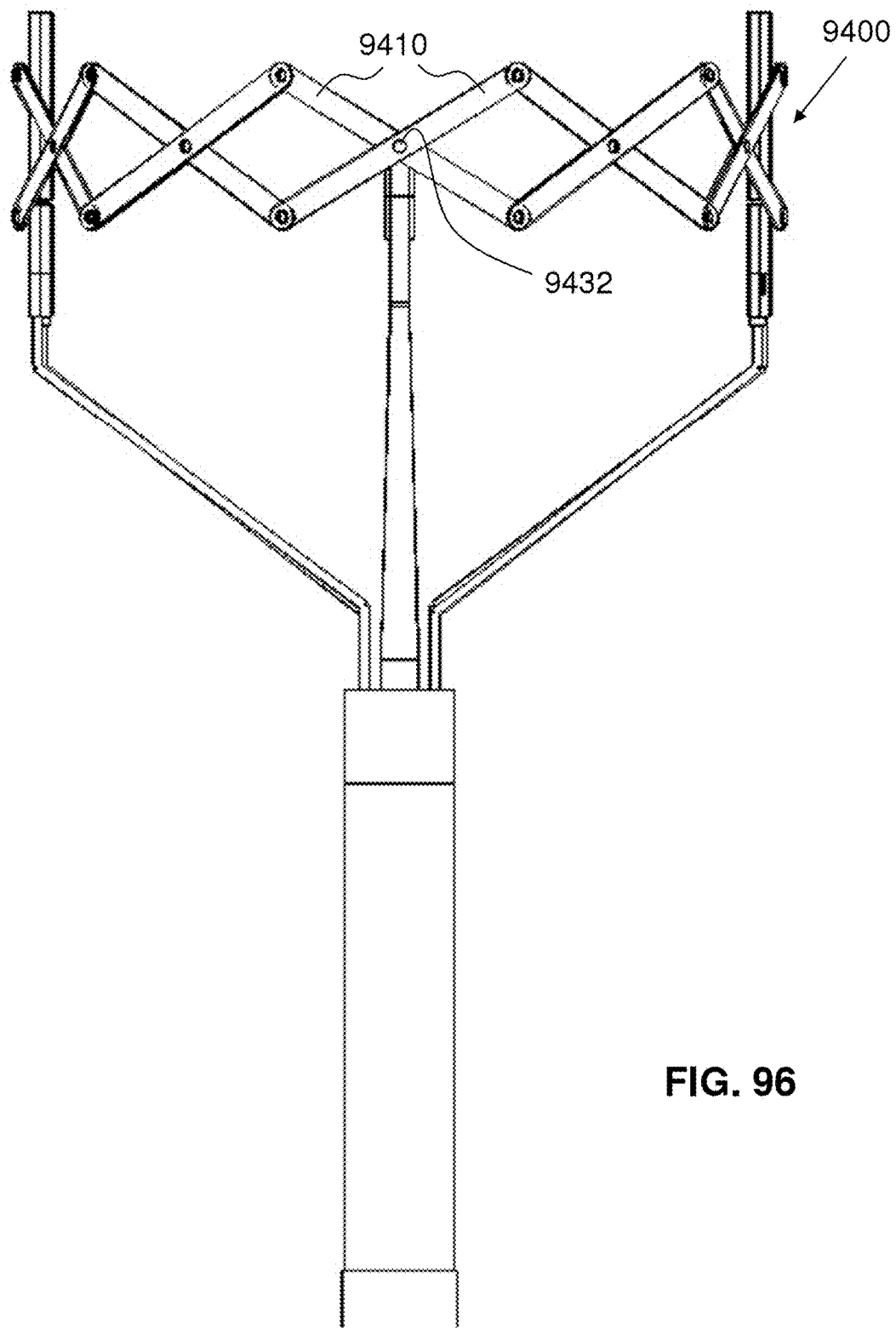
FIG. 96 is a fragmentary, side elevational view of the system of FIG. 94 in a non-tilted state.
Figure 97:
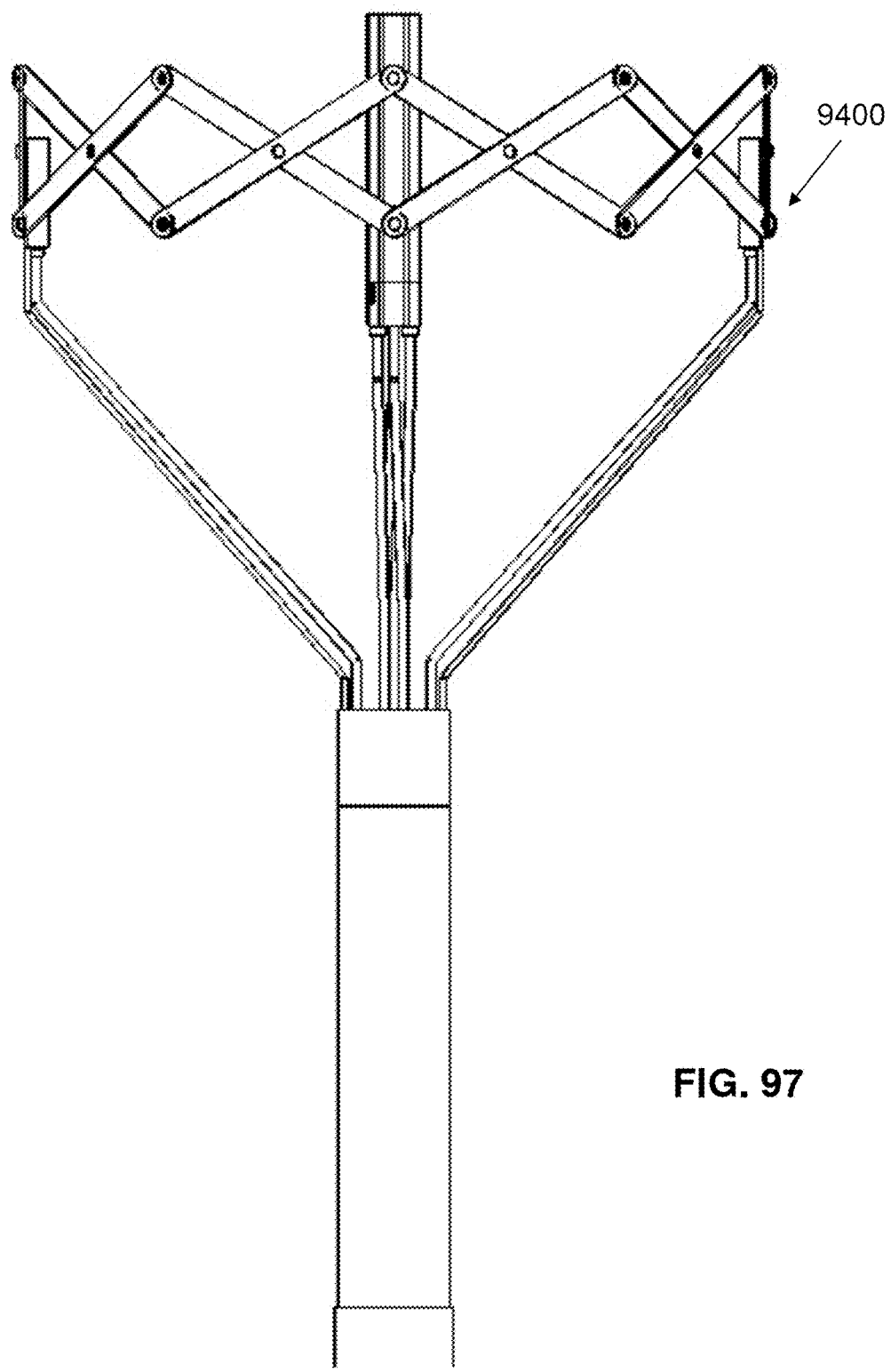
FIG. 97 is a fragmentary, side elevational view of the system of FIG. 96 rotated approximately 90 degrees with respect to the view of FIG. 96.
Figure 98:
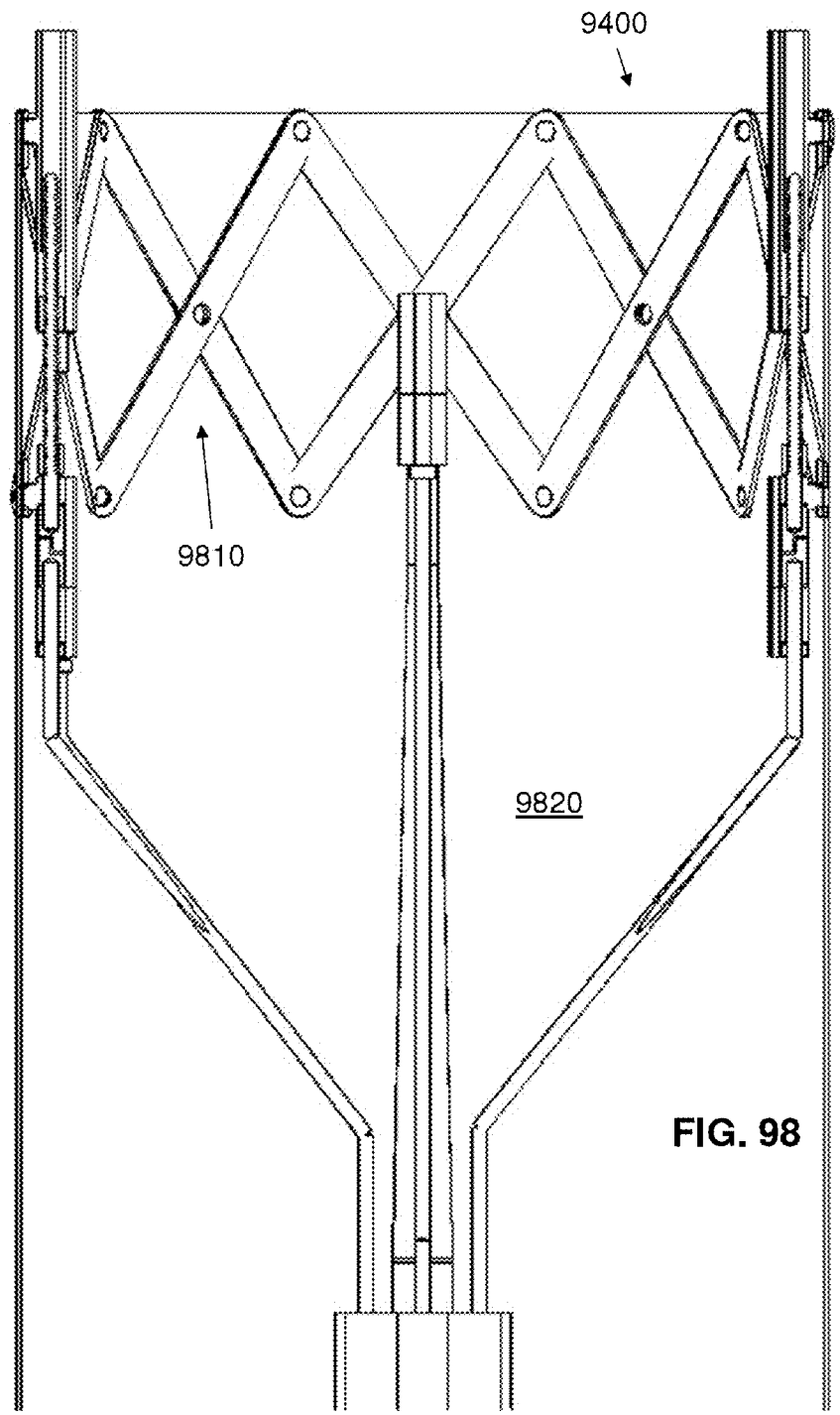
FIG. 98 is a fragmentary, longitudinally cross-sectional, side elevational view of the system of FIG. 94 showing the rear half of the system and a tubular graft material in a non-tilted state and partially expanded state.
Figure 99:
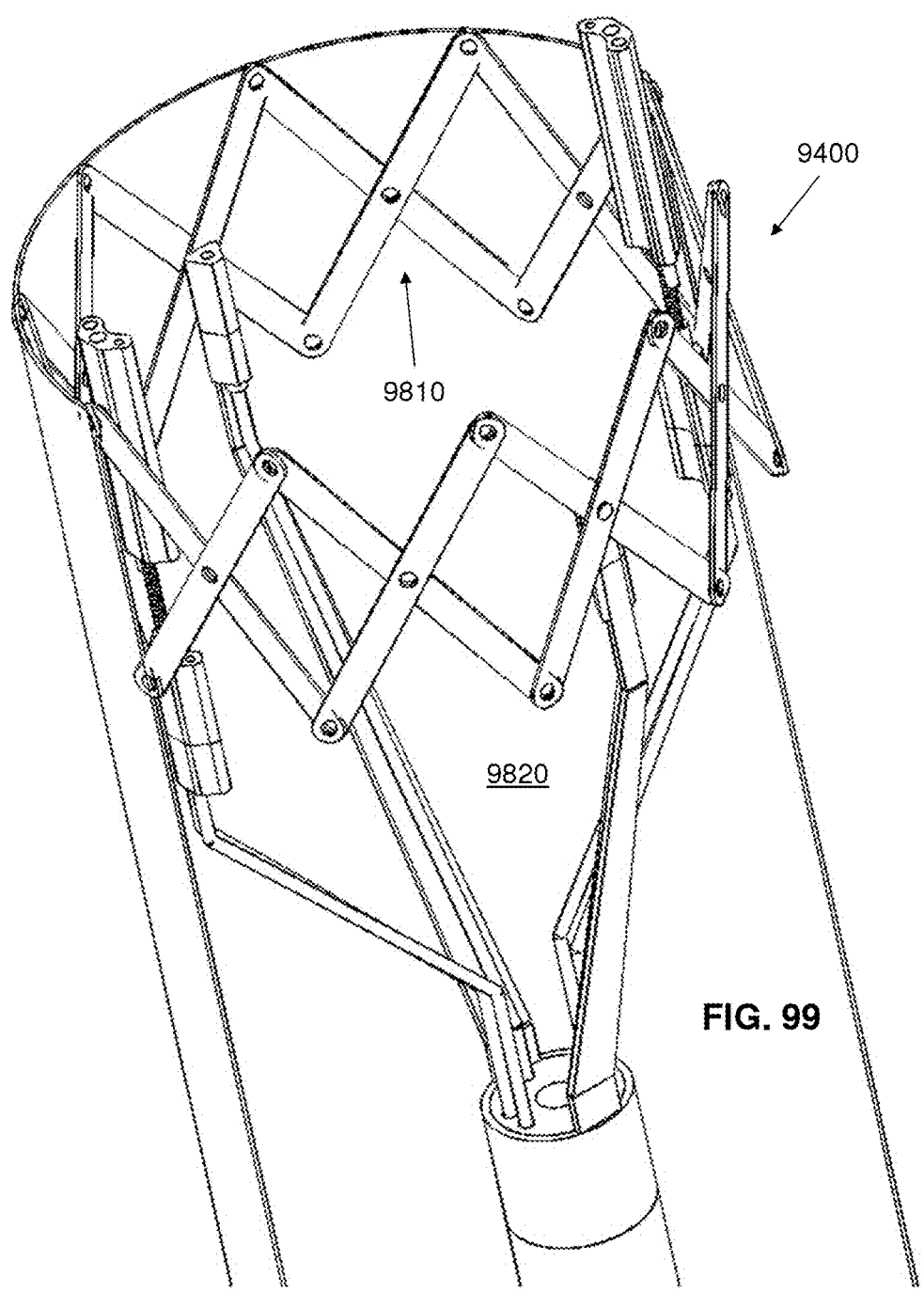
FIG. 99 is fragmentary, partially cross-sectional, perspective view of the system of FIG. 94 showing the rear half of the tubular graft material and in a non-tilted state and a partially expanded state.

FIG. 94 shows the near set of control wires 750, 770 moved proximally and the far set moved distally. In FIG. 95, the swashplate of the prosthesis 9400 is untilted, as is the prosthesis 9400 in FIGS. 96 and 97, the latter of which is merely rotated ninety degrees as compared to the former. FIGS. 98 and 99 depict the prosthesis 9400 as part of a stent graft having the stent lattice 9810 inside a proximal end of a tubular shaped graft 9820.

Figure 100:
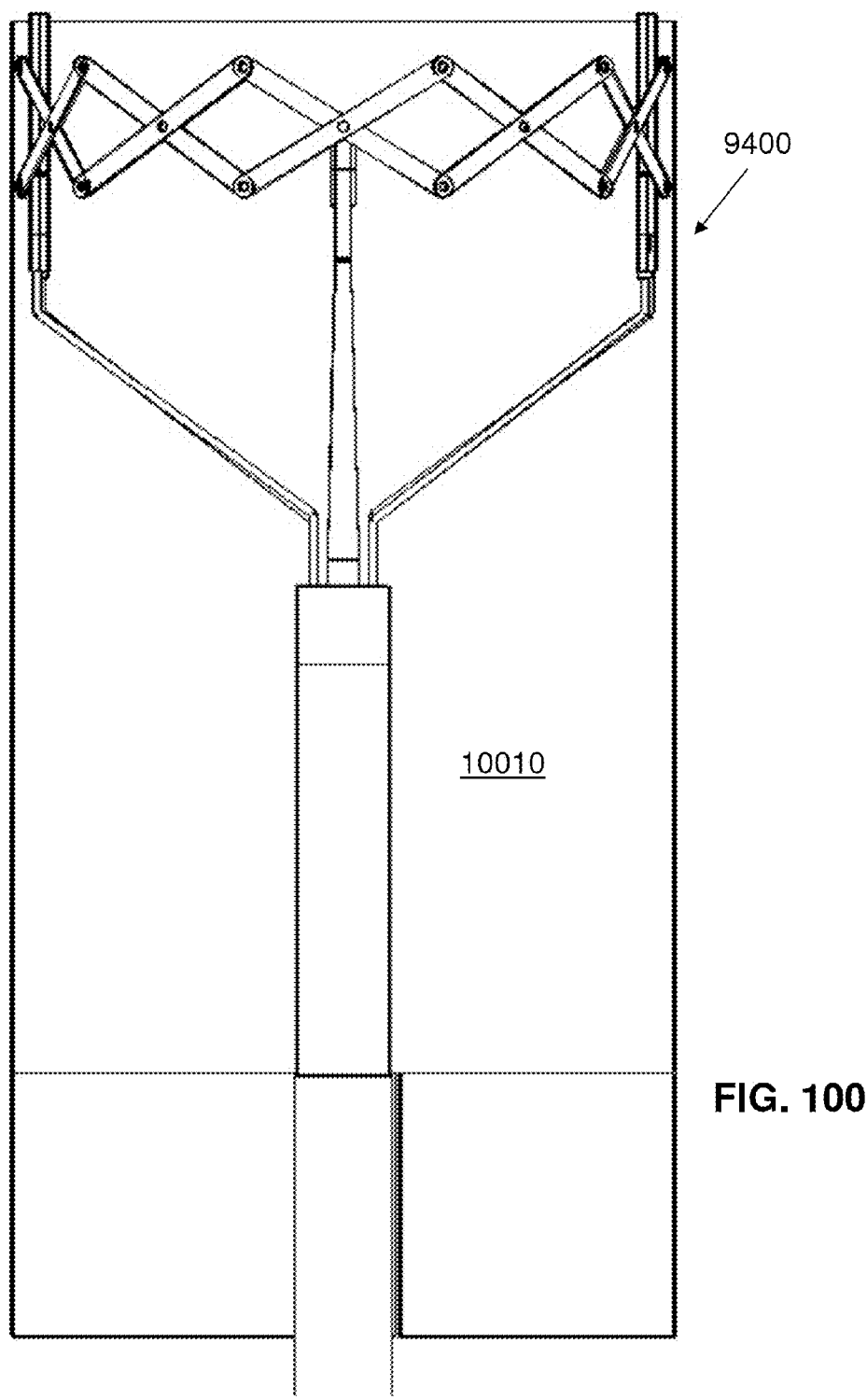
FIG. 100 is a fragmentary, partially cross-sectional, side elevational view of the system of FIG. 94 showing the rear half of graft material for a bifurcated vessel and in a non-tilted state.
Figure 101:
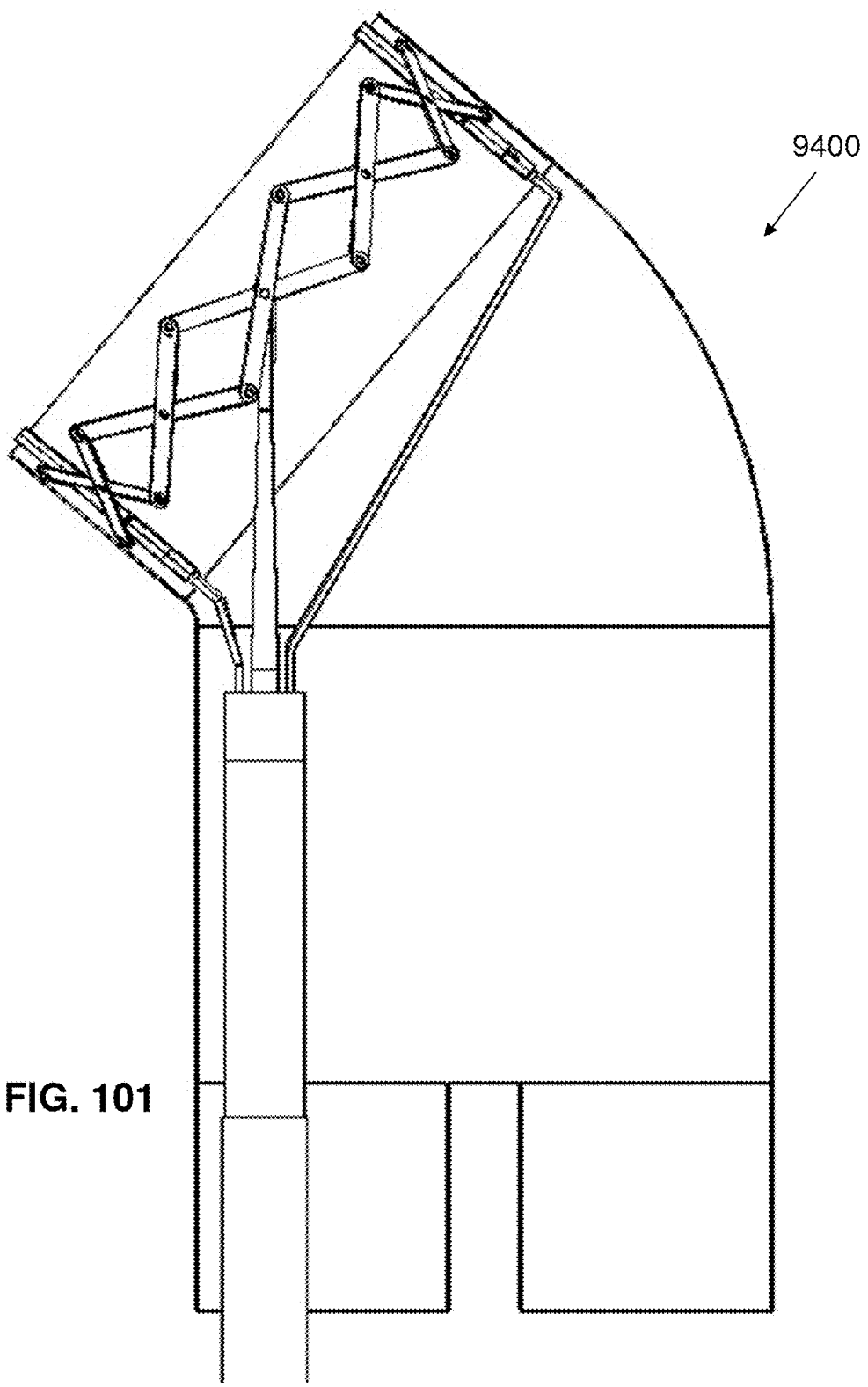
FIG. 101 is a fragmentary, partially cross-sectional, side elevational view of the system of FIG. 100 in an expanded state and a partially tilted state.
Figure 102:
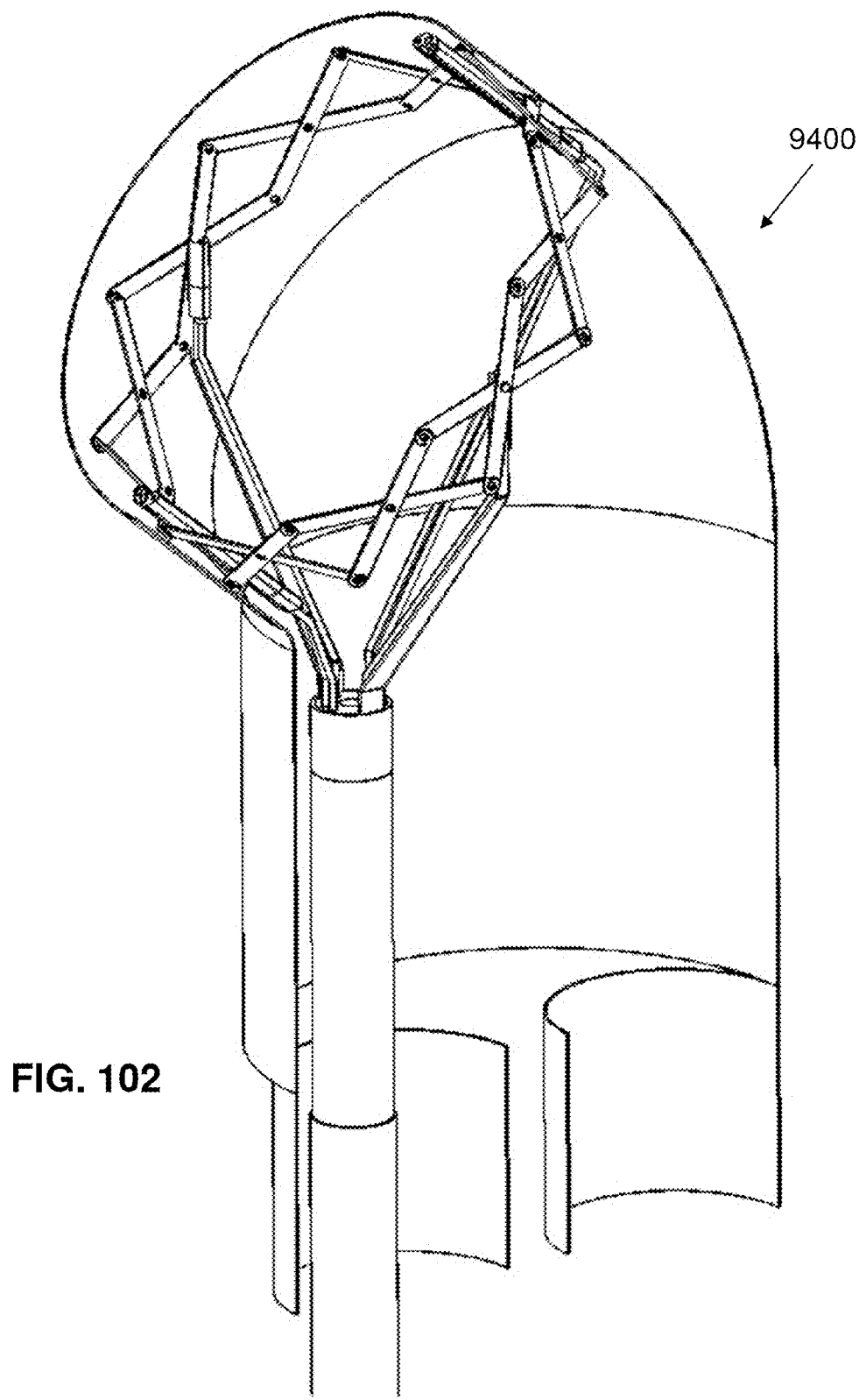
FIG. 102 is a fragmentary, partially cross-sectional, side elevational view of the system of FIG. 101 rotated approximately 45 degrees with respect to the view of FIG. 101.

The prosthesis 9400 in FIGS. 100 to 102 is also a stent graft but, in this exemplary embodiment, the graft 10010 is bifurcated, for example, to be implanted in an abdominal aorta. FIGS. 101 and 102 show how the proximal end of the prosthesis 9400 can be tilted with the swashplate assembly of the invention, for example, in order to traverse a tortuous vessel in which the prosthesis 9400 is to be implanted, such as a proximal neck of abdominal aortic aneurysm.

Figure 103:
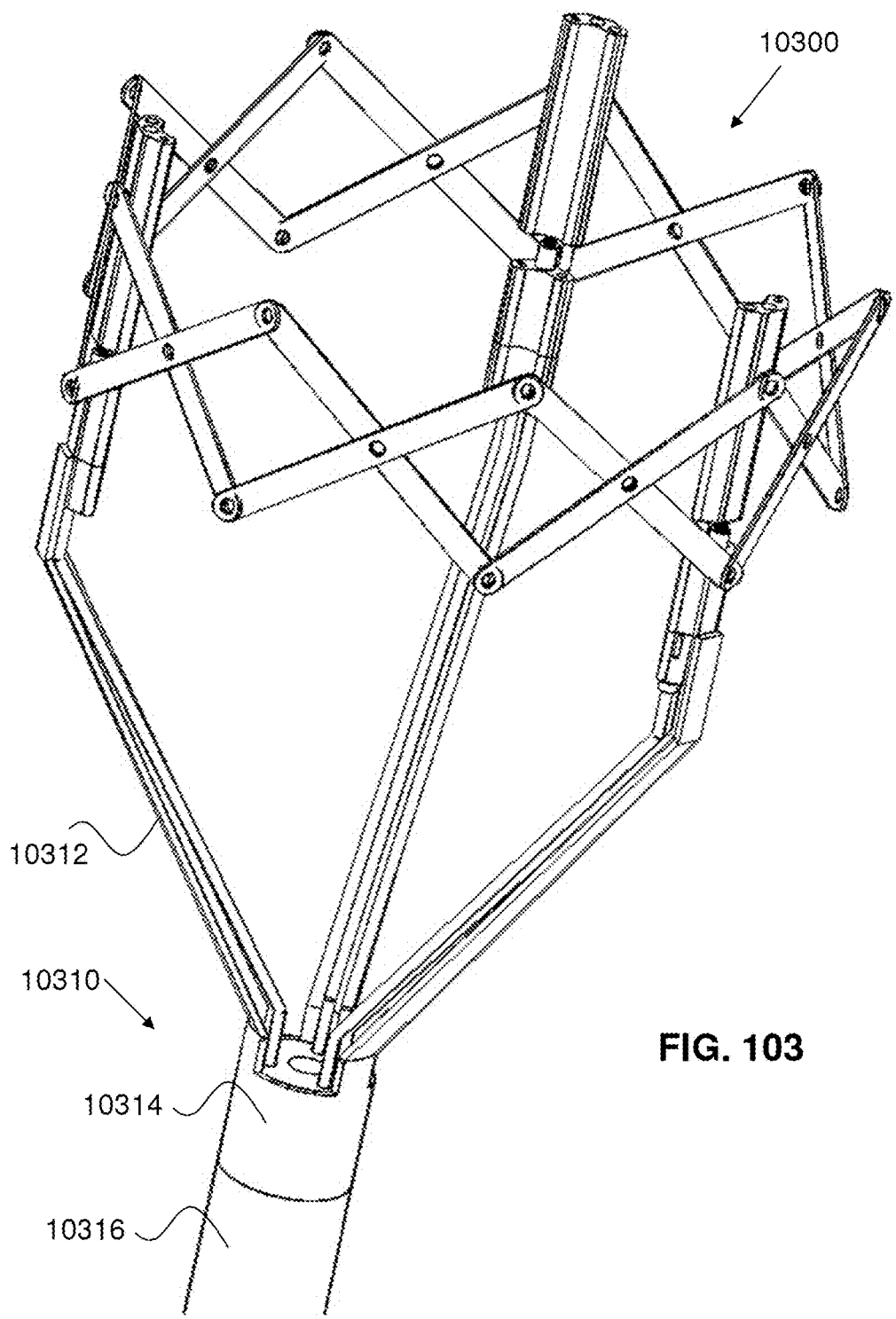
FIG. 103 is a fragmentary, side perspective view of another exemplary embodiment of an actively controllable stent graft system according to the invention in an expanded state.
Figure 104:
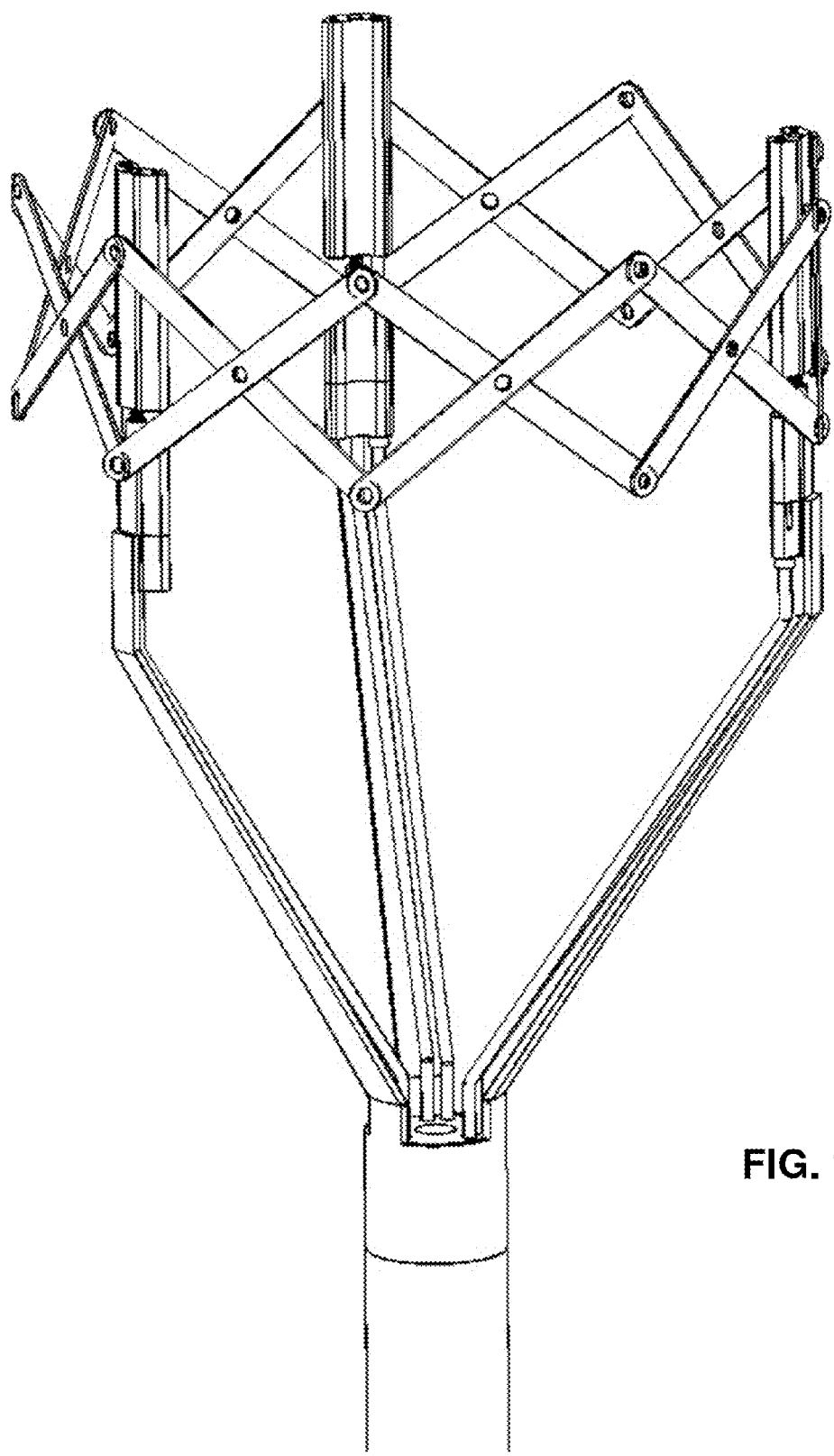
FIG. 104 is a fragmentary, side elevational view of the system of FIG. 103.

The exemplary embodiment of the prosthesis 10300 shown in FIGS. 103 and 104 does not include the swashplate assembly. Instead, the delivery system includes a distal support structure 10310 that ties all of the support bands 10312 to a cylindrical support base 10314 connected at the distal end of the delivery catheter 10316.

An exemplary embodiment of the entire delivery system 10500 for the prosthesis 10300 is depicted in FIGS. 105 to 107. In FIG. 105, the delivery system is entirely self-contained and self-powered and includes the actively controllable stent lattice with an integral control system 10510. The prosthesis 10300 is in an expanded state and the graft material is in cross-section to show a rear half. An alternative to the integral control system 10510 is a wireless control device 10600 that wirelessly communicates 10610 control commands to the system. Another alternative to the integral control system 10510 shown in FIG. 107 separates the control device 10700 with a cord 10710 for communicating control commands to the system. In this exemplary embodiment, the controls comprise four rocker switches 10712, 10714, 10716, 10718 arranged in a square, each of the switches having a forward position, a neutral central position, and a rearward position.

Figure 108:
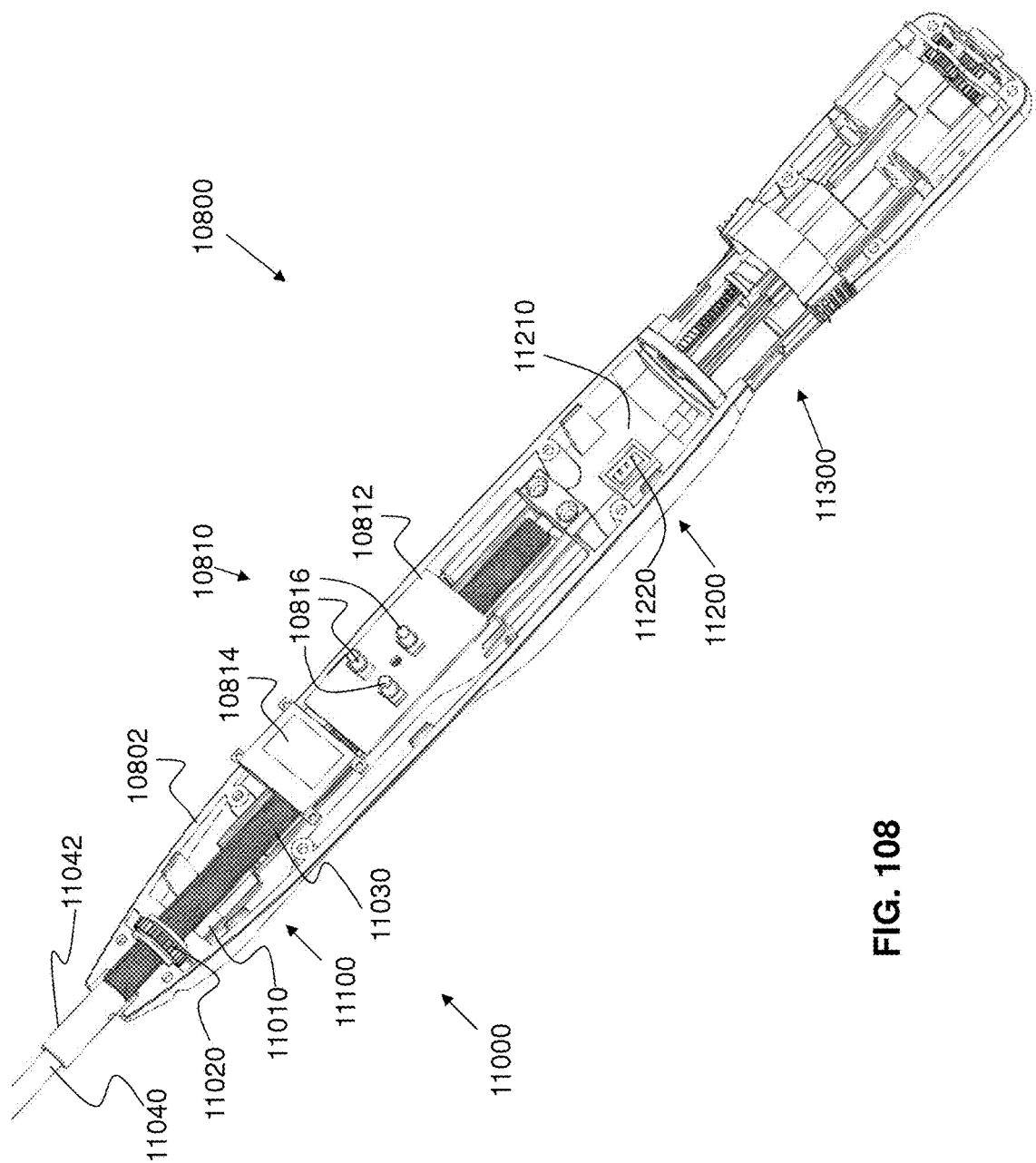
FIG. 108 is a fragmentary, perspective view of a control handle of an exemplary embodiment of a self-contained, self-powered, actively controllable prosthesis delivery device according to the invention from above a left side thereof with the upper handle half and power pack removed.
Figure 109:
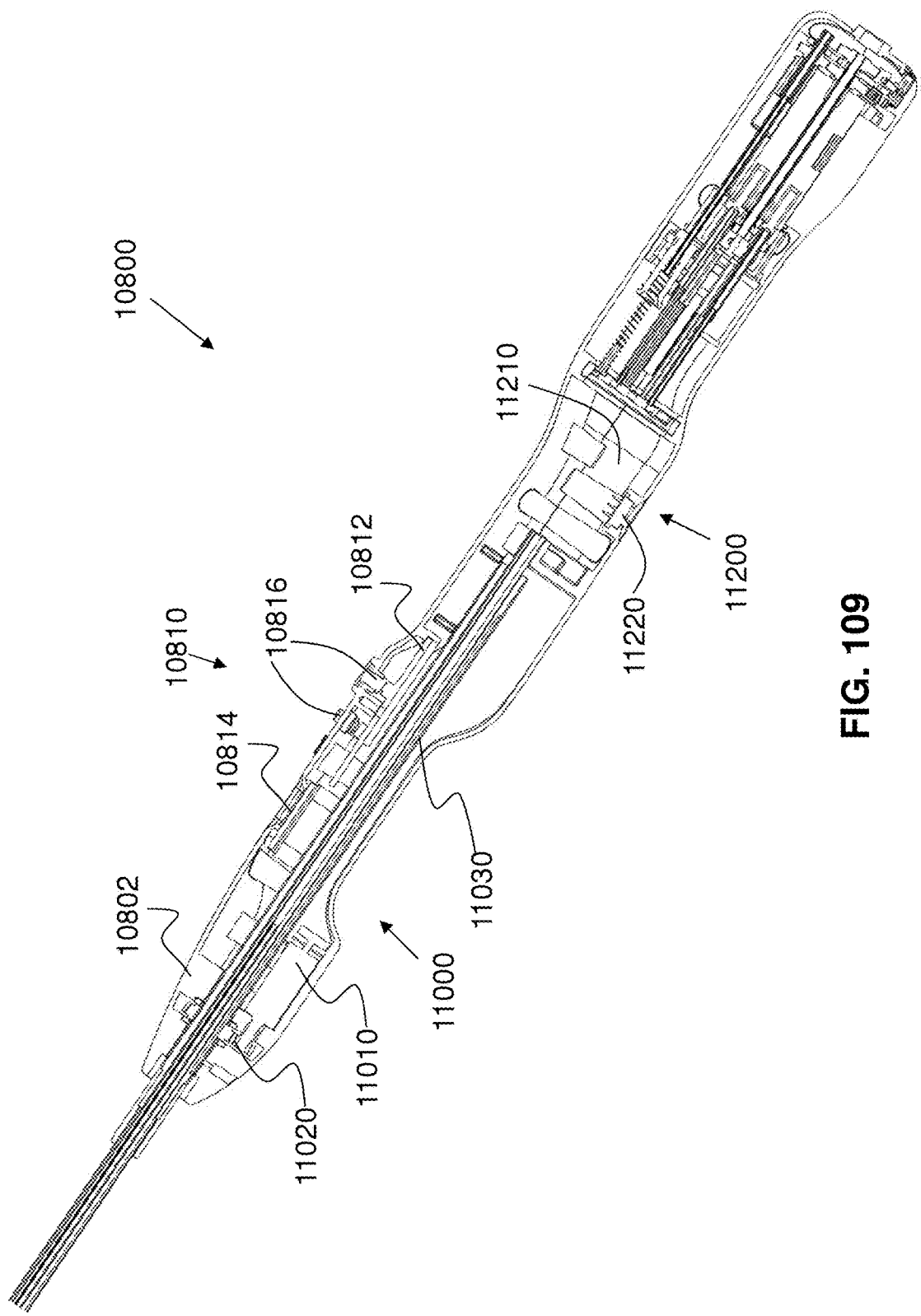
FIG. 109 is a fragmentary, vertically cross-sectional view of the handle of FIG. 108 with the power pack removed.
Figure 110:
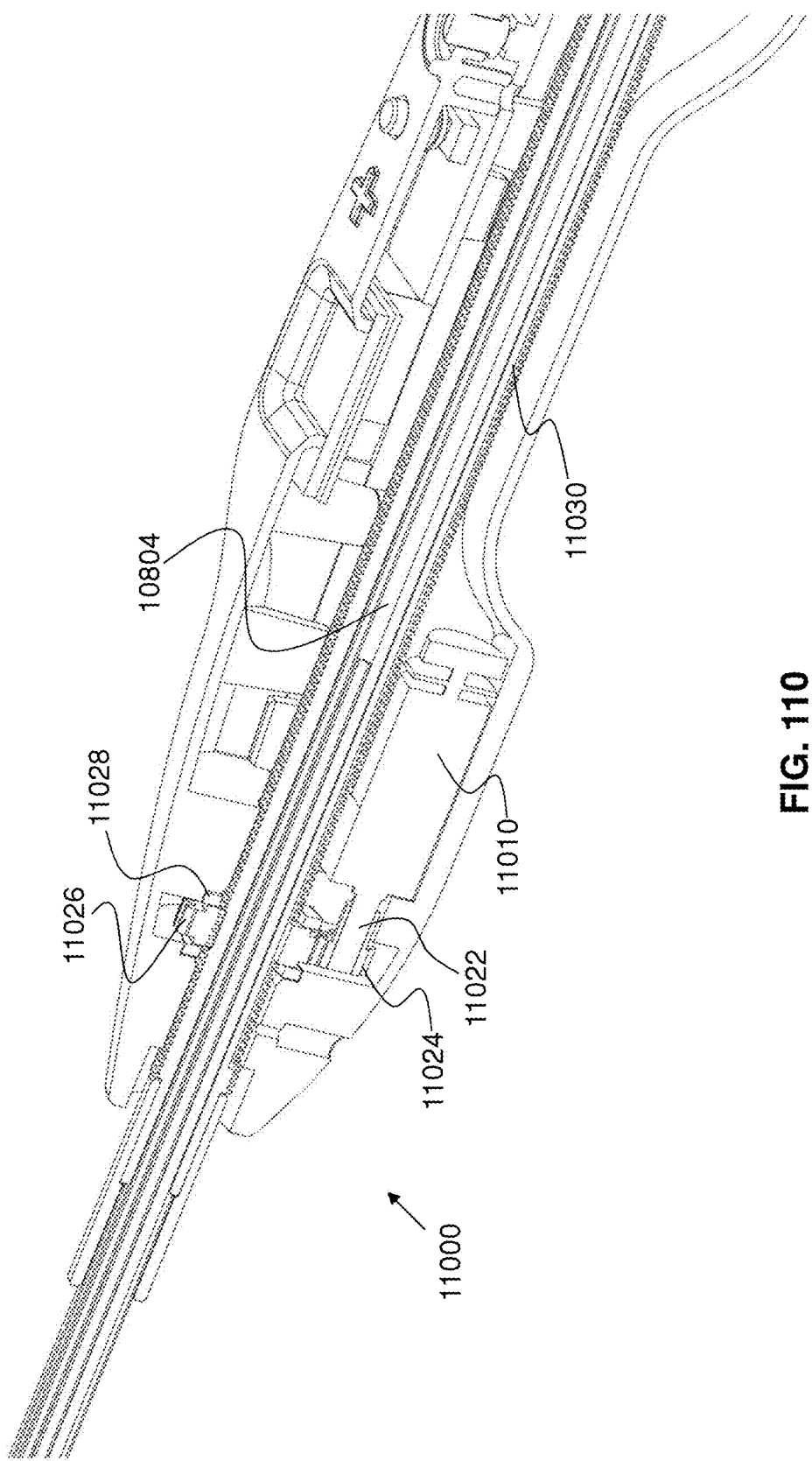
FIG. 110 is a fragmentary, enlarged, vertically cross-sectional and perspective view of a sheath-movement portion of the handle of FIG. 108 from above a left side thereof.

Yet another exemplary embodiment of a control handle 10800 for operating a prosthesis having the actively controllable stent lattice according to the invention is depicted in FIGS. 108 to 118. The views of FIGS. 108 and 109 show various sub-assemblies contained within the control handle 10800. A user-interface sub-assembly 10810 includes a circuit board 10812 having circuitry programmed to carry out operation of the systems and methods according to the invention. Electronics of the user-interface sub-assembly 10810 comprise a display 10814 and various user input devices 10816, such as buttons, switches, levers, toggles, and the like. A sheath-movement sub-assembly 11000 includes a sheath-movement motor 11010, a sheath movement transmission 11020, a sheath movement driveshaft 11030, and a translatable delivery sheath 11040. A strain relief 11042 is provided to support the delivery sheath 11040 at the handle shell 10802. A power sub-assembly 11200 is sized to fit within the handle 10800 in a power cell compartment 11210 containing therein power contacts 11220 that are electrically connected to at least the circuit board 10812 for supplying power to all electronics on the control handle 10800 including all of the motors. A needle-movement sub-assembly 11300 controls deployment of the needles and keeps tension on the needles continuously even when the delivery sheath 11040 is bent through tortuous anatomy and different bends are being imposed on each of the needles. The needles are three in number in this exemplary embodiment. Finally, a jack engine 11600 controls all movements with regard to the jack assemblies.

The user-interface sub-assembly 10810 allows the surgeon to obtain real-time data on all aspects of the delivery system 10800. For example, the display 10814 is programmed to show the user, among other information, deployment status of the stent lattices, the current diameter of the stent lattices, any swashplate articulation angle of the stent lattice to better approximate an actual curved landing site, all data from various sensors in the system, and to give audio feedback associated with any of the information. One informational feedback to user can be an indicator on the display 10814 that the delivery sheath 11040 is retracted sufficiently far to completely unsheath the prosthesis. Other information can be a force feedback indicator showing how much force is being imparted on the lattice from the vessel wall, e.g., through a torque meter, a graphical change in resistance to the stepper motor, a mechanical slip clutch, direct load/pressure sensors on lattice. With such information, the prosthesis can have Optimal Lattice Expansion (OLE), achieve its best seal, have a decrease in migration and embolization, and have an amount of outward force limited (i.e., a force ceiling) to stop expansion before tissue damage occurs. A suitably sized visual indicator can even show in a 1:1 ratio the actual diameter position of the stent lattice. Other possible sensors for taking measurements inside and/or outside the prosthesis (e.g., above and below touchdown points of lattice) can be added into the inventive powered delivery system or handle. These devices include, for example, a video camera, a flow wire to detect flow showing blood passing around prosthesis/double lumen catheter and showing pressure gradients, a Doppler device, an intrinsic pressure sensor/transducer, an impedance of touchdown zone, fractional flow reserve, and an intracardiac/intravascular ultrasound. For an example of the latter sensor, an ultrasound device could be incorporated into the nose cone of the delivery system and can be extended or retracted to provide assistance in positioning the implant. Additionally and/or alternatively, by measuring pressure above and below the implant, pressure sensors or lumens to pressure sensors located within the handle can provide a pressure gradient useable to calculate orifice area when coupled with cardiac output.

Having all of the user interface actuators 10816 within reach of a single finger of the user provides unique and significant advantages by allowing the surgeon to have one-hand operation of the entire system throughout the entire implantation procedure. In all mechanical prior art systems when torque is applied, the second hand is needed. Pushing of single button or toggling a multi-part switch eliminates any need for the user's second hand. Using different kinds of buttons/switches allows the user to be provided with advanced controls, such as the ability to have coarse and fine adjustments for any sub-procedure. For example, expansion of the lattice can, initially, be coarse by automatically directly expanded out to a given, pre-defined diameter. Then, further expansion can be with fine control, such as a millimeter at a time. The varying of diameter can be both in the open and close directions. If the prosthesis needs to be angled, before, during, and/or after varying the expansion diameter, the user can individually manipulate each jack screw or control wires to gimbal the upstream end of implant so that it complies with vessel orientation; both during diameter/articulation changes, the physician can inject contrast to confirm leak-tightness. Even though the exemplary embodiment of the needle deployment shown is manual, this deployment can be made automatic so that, once the prosthesis is implanted, and only after the user indicates implantation is final, an automatic deployment of the engaging anchors can be made. With regard to undocking the delivery system, this release can be with a single touch, for example, of a push button. Also, with an integrated contrast injection assembly, a single touch can cause injection of contrast media at the implantation site.

Figure 111:
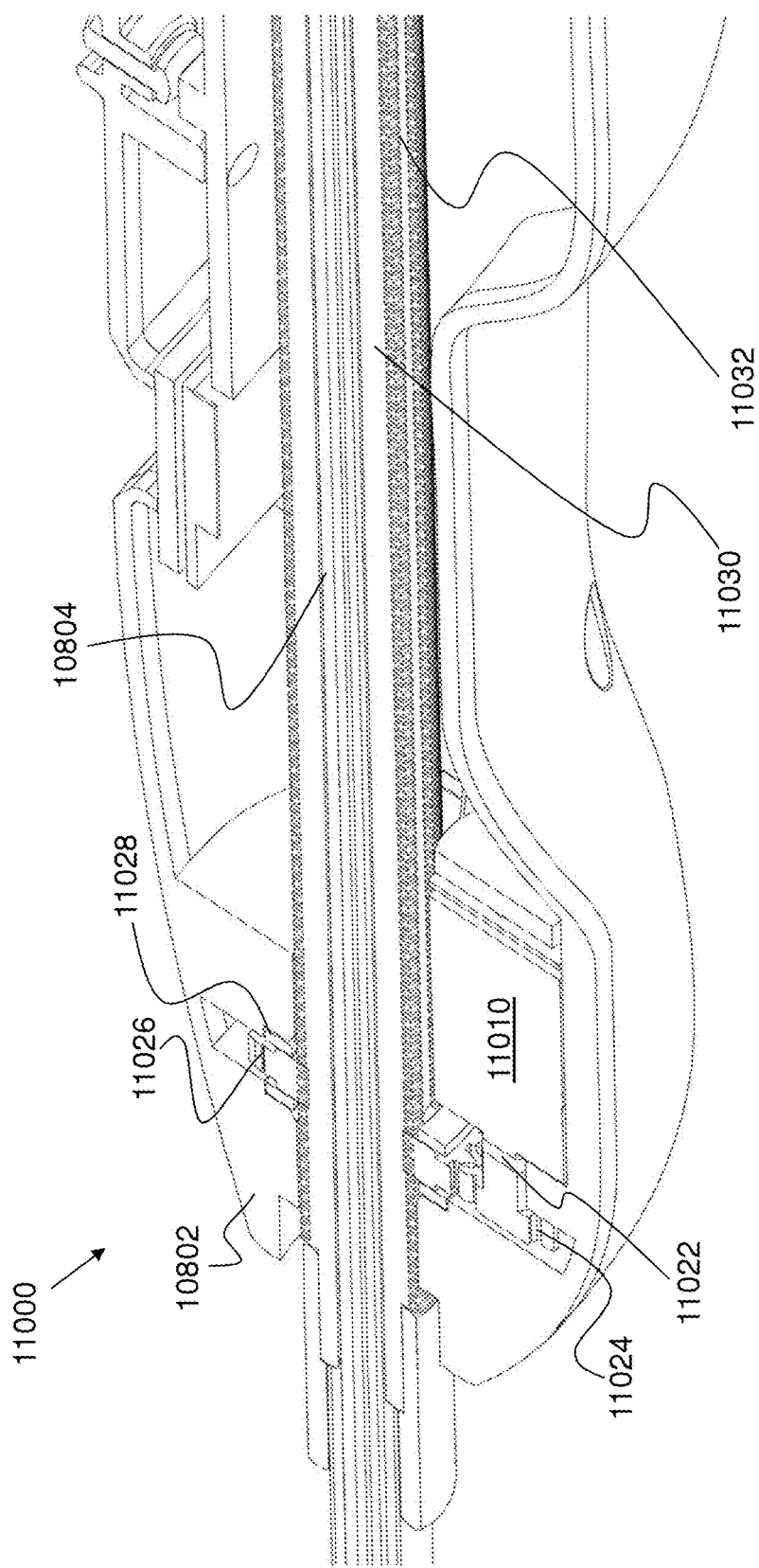
FIG. 111 is a fragmentary, further enlarged, vertically cross-sectional view of the sheath-movement portion of FIG. 110 from below a left side thereof.
Figure 112:
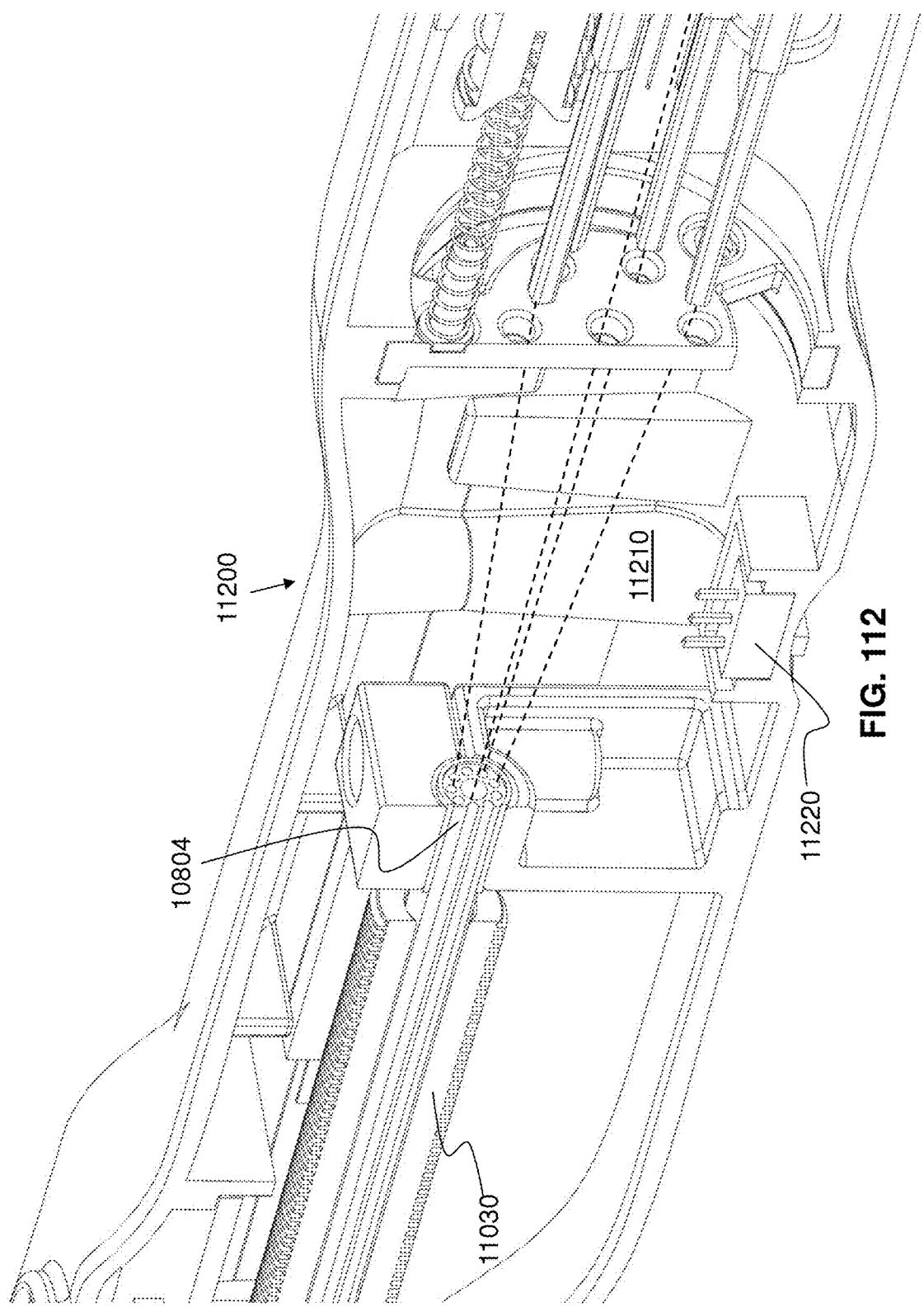
FIG. 112 is a fragmentary, enlarged, vertically cross-sectional view of a power portion of the handle of FIG. 108 viewed from a proximal side thereof.

The sheath-movement sub-assembly 11000 also can be controlled by a single button or switch on the circuit board 10812. If the user interface is a two-position toggle, distal depression can correspond with sheath extension and proximal depression can correspond with sheath retraction. Such a switch is operable to actuate the sheath movement motor 11010 in the two rotation directions. Rotation of the motor axle 11022, therefore, causes the transmission 11024, 11026 to correspondingly rotate, thereby forcing the threaded sheath movement driveshaft 11030 to either extend distally or retract proximally. The exemplary embodiment of the transmission includes a first gear 11024 directly connected to the motor axle 11022. The first gear 11024 is meshed with the outside teeth of a larger, hollow, driveshaft gear. The interior bore of the driveshaft gear 11026 has threads corresponding to the exterior threads of the sheath movement driveshaft 11030. As such, when the driveshaft gear 11026 rotates, the sheath movement driveshaft 11030 translates. The driveshaft gear 11026 is surrounded by a bushing 11028 to allow rotation within the housing shell 10802. In order to prevent rotation of the sheath movement driveshaft 11030, as shown in FIG. 111, the sheath movement driveshaft 11030 has a longitudinal keyway 11032 that has a cross-sectional shape corresponding to a key that is grounded to the handle shell 10802. The sheath movement driveshaft 11030 also is hollow to accommodate a multi-lumen rod 10804 (shown best in FIG. 112) housing, within each respective lumen, any of the control wires 750, 770, 2182, 3098 and the guidewire 6610, these lumens corresponding to those within the wire guide block 116 at the distal end of the delivery sheath 10040.

The size and shape of the power sub-assembly 11200 is limited in shape only by the power cell compartment 11210 and the various wires and rods that traverse from the needle-movement sub-assembly 11300 and the jack engine 11600 therethrough until they enter the lumens of the multi-lumen rod 10804. Some of these wires and rods are illustrated with dashed lines in FIG. 112. Power distribution to the circuit board 10812 and/or to the motors is carried out through power contacts 11220. Such power distribution lines are not illustrated for reasons of clarity. This method or similar such as a rack and pinion or drag wheels can be used to drive the sheath extension and retraction.

Figure 113:
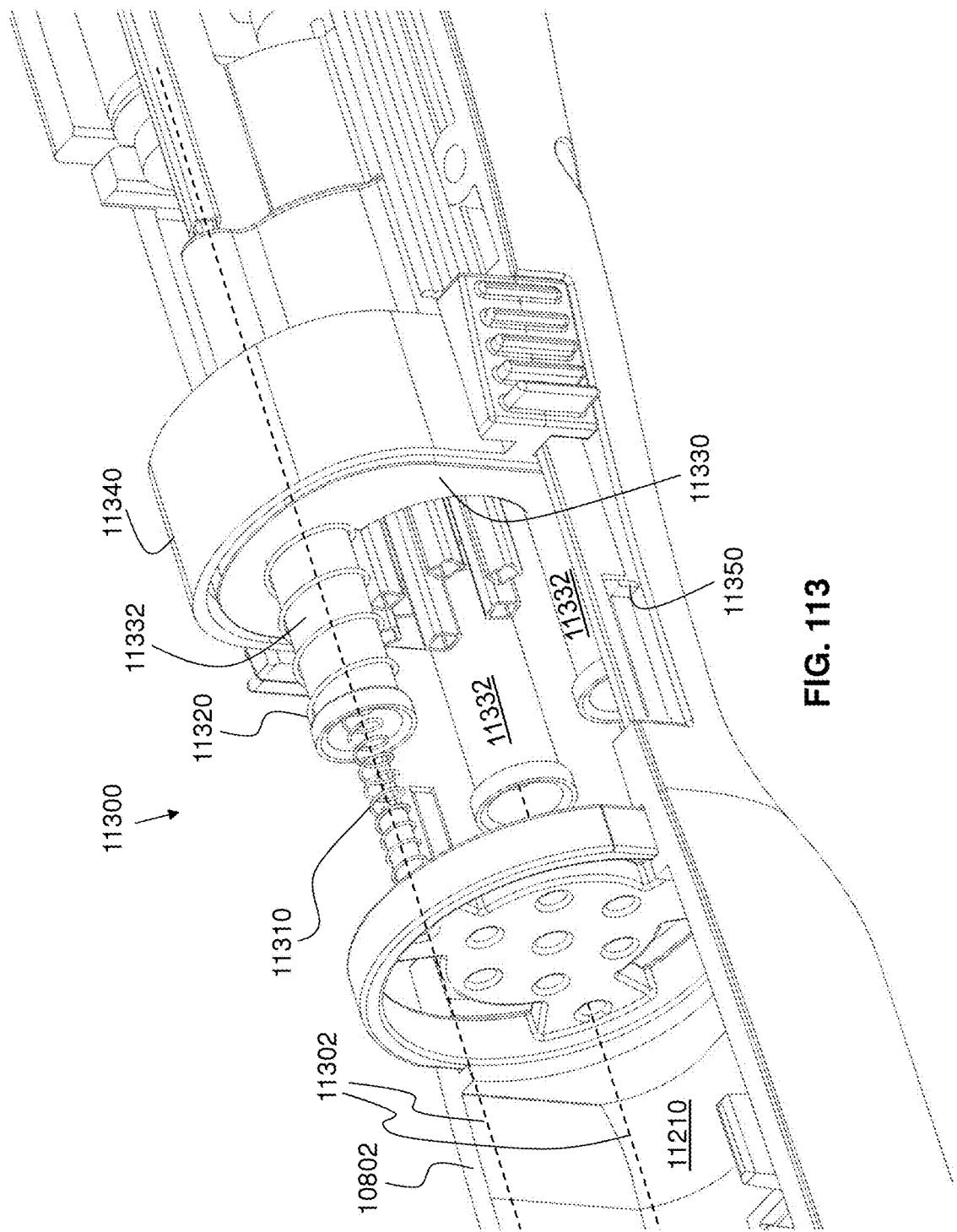
FIG. 113 is a fragmentary, perspective view of a needle control portion of the handle of FIG. 108 from above a distal side with the upper handle half and power pack removed and with the needle control in a lattice-contracted and needle-stowed position.
Figure 114:
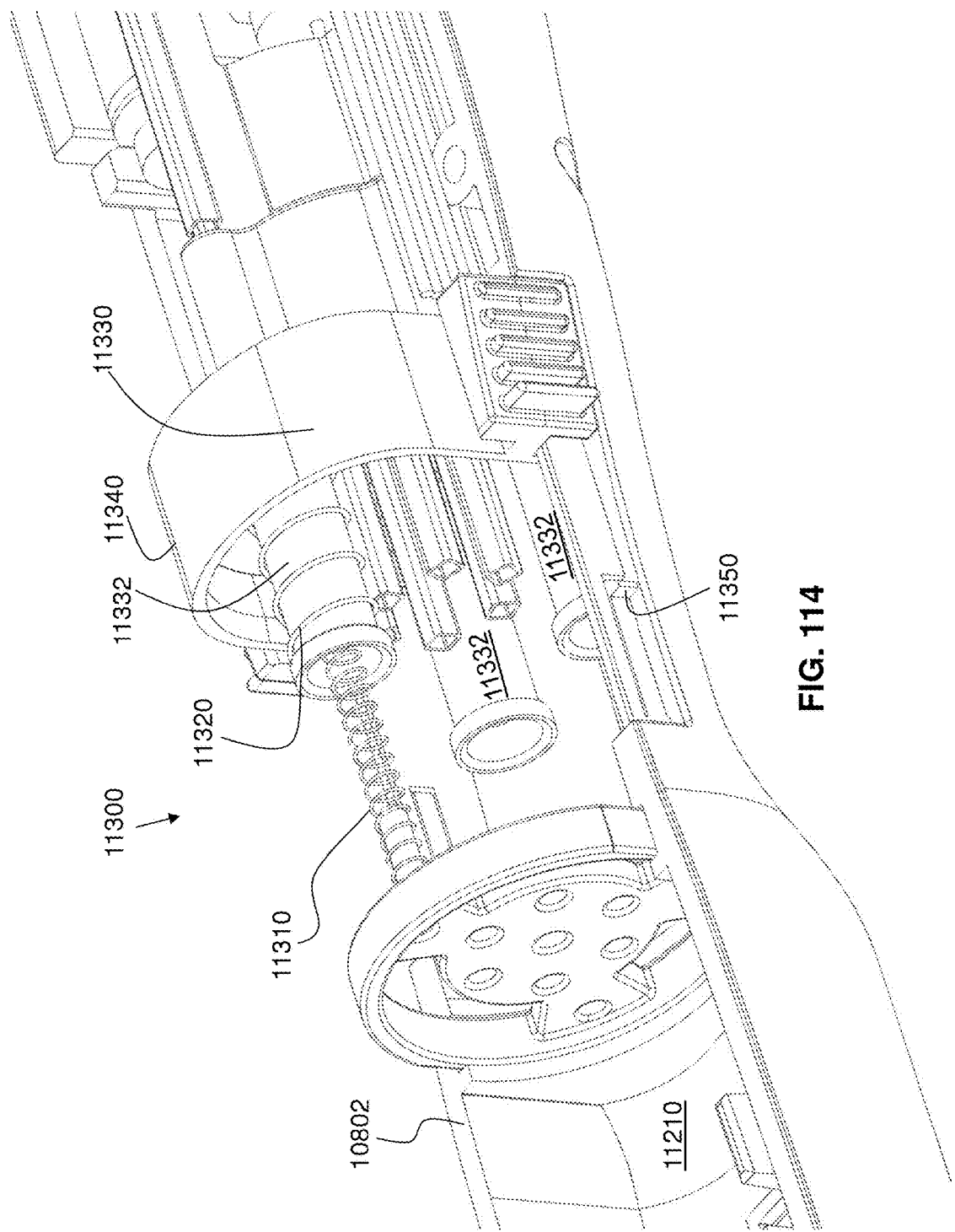
FIG. 114 is a fragmentary, perspective view of the needle control portion of the handle of FIG. 113 with the needle control in a lattice-expanded and needle-stowed position.
Figure 115:
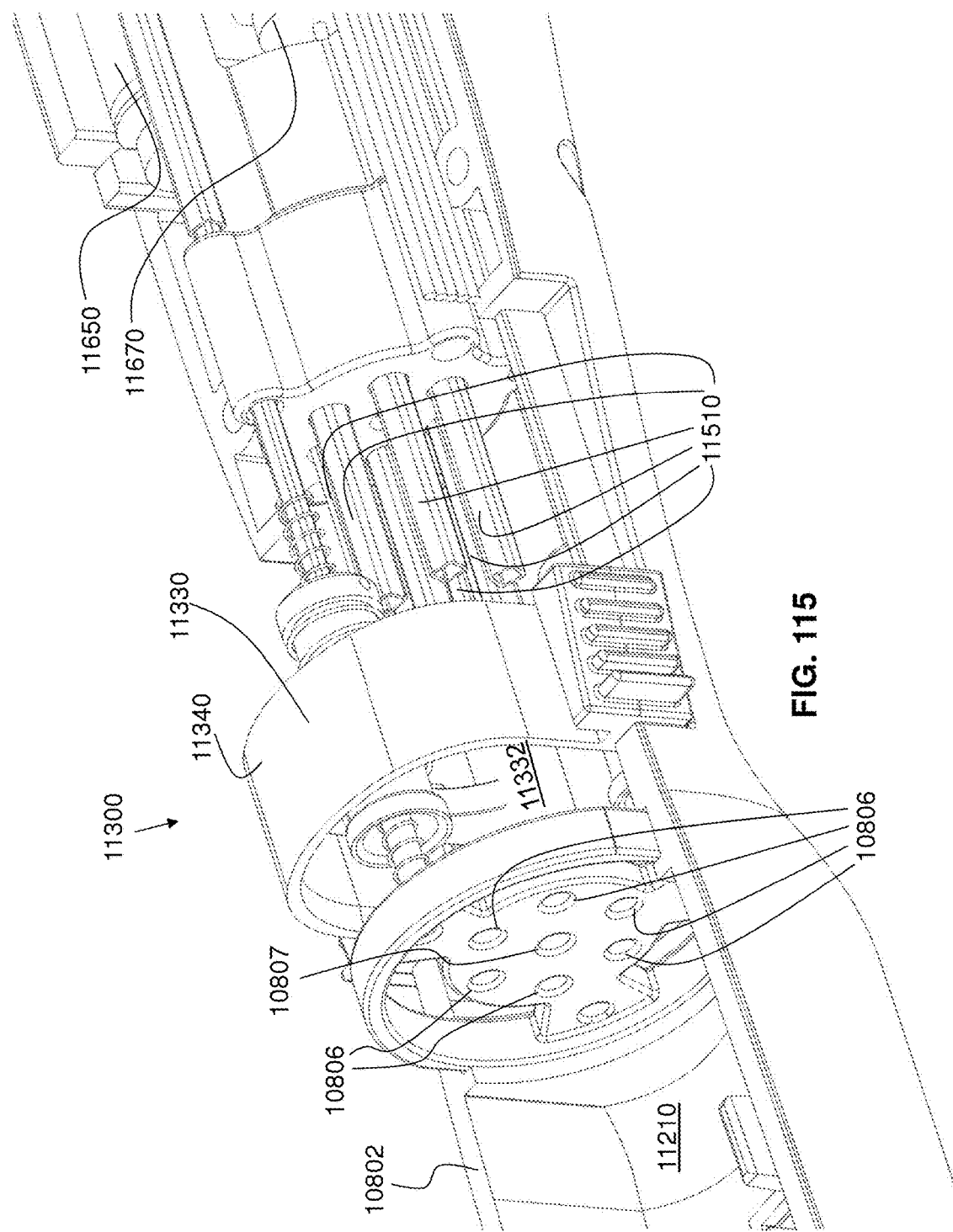
FIG. 115 is a fragmentary, perspective view of the needle control portion of the handle of FIG. 114 with the needle control in a needle-extended position.
Figure 116:
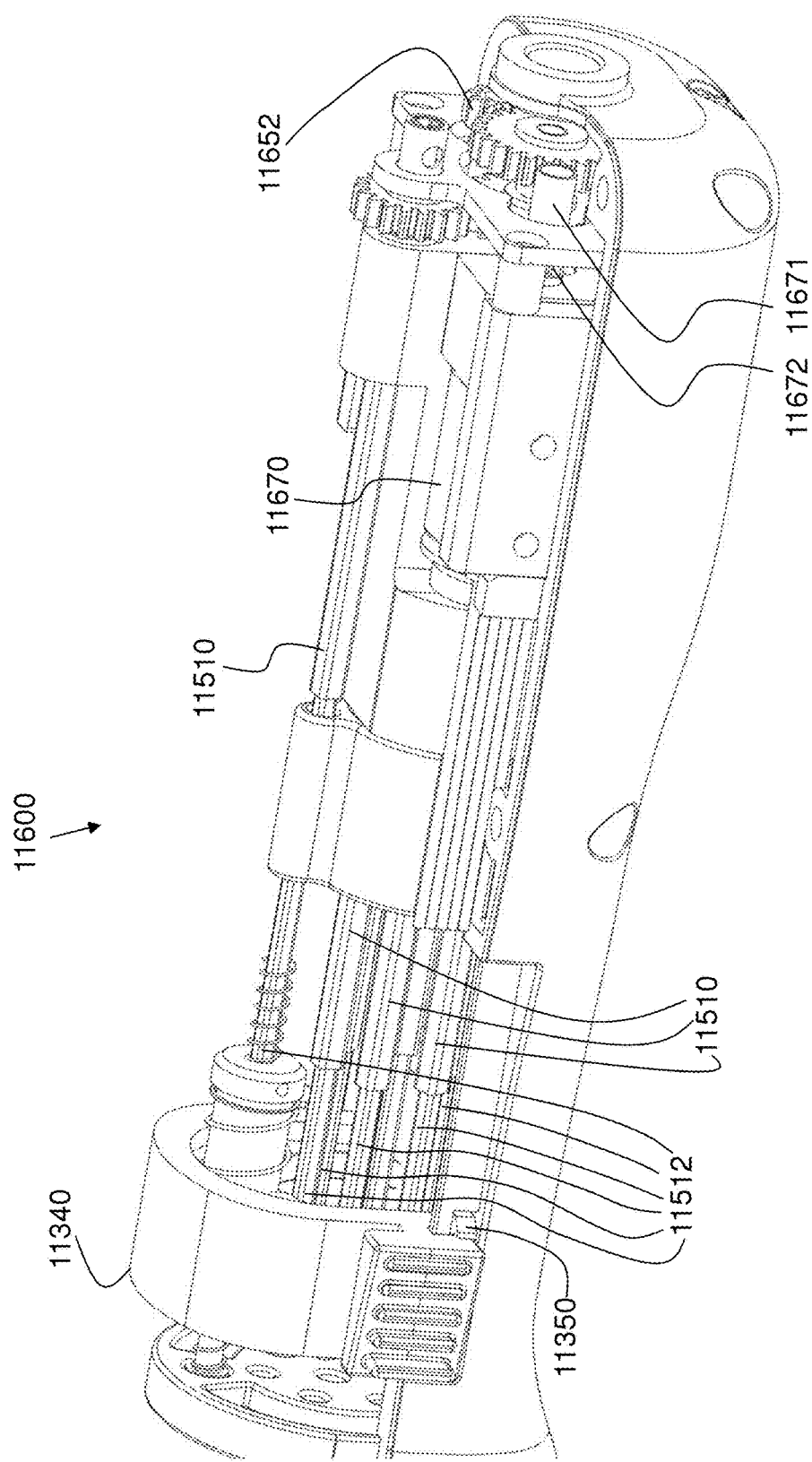
FIG. 116 is a fragmentary, perspective view of an engine portion of the handle of FIG. 108 from above a left side thereof with the upper handle half removed.

The needle-movement sub-assembly 11300 is described with reference to FIGS. 113 to 115, and best with regard to FIG. 113. Each of the needle rods 11302 that connect to the needles in the prosthesis to the needle-movement sub-assembly 11300 is associated with a tension spring 11310, an overstroke spring 11320, and a control tube 11332. The three control tubes 11332 are longitudinally held with respect to a control slider 11330 by the overstroke spring 11320. As long as the force on the needles is not greater than the force of the overstroke spring 11320, movement of the needle rod 11302 will follow the control slider 11330. A needle deployment yoke 11340 slides with respect to the shell 10802 of the control handle 10800. When the needle deployment yoke 11340 contacts the control slider 11330 as it moves distally, the needle deployment yoke 11340 carries the control slider 11330 and the needle rods 11302 distally to, thereby, deploy the needles. The transition from FIGS. 113 to 114 shows how the tension spring 11310 keeps tension on the needles by biasing the control slider 11330 proximally. Deployment of the needles is shown by the transition from FIGS. 114 to 115. As mentioned above, the needles 3070 each a have bent needle tip 3072. In a configuration where the needles 3070 are connected directly all the way back to the needle-movement sub-assembly 11300, there is a high likelihood that bending of the delivery catheter 11040 will impart various different forces on the needle rods 11302. These forces will tend to pull or push the needle rods 11302 and, thereby possibly extend the needles 3070 when not desired. Accordingly, each tension spring 11310 is longitudinally connected to the needle rod 11302 to compensate for these movements and keep the bent needle tip 3072 within the needle tip groove of the 3013 distal drive block 3010.

Because deployment of the needles is intended (ideally) to be a one-time occurrence, a yoke capture 11350 is provided at the end of the yoke stroke. Capture of the yoke 11340 can be seen in FIG. 116. Of course, this capture can be released by the user if such release is desired. Finally, if too much force is imparted on the needles when being deployed, the force of the overstroke spring 11320 is overcome and the control tube 11332 is allowed to move with respect to the control slider 11330. The compression of the overstroke spring 11320 cannot be shown in FIG. 115 because of the limitation of the software that created FIG. 115.

The jack engine 11600 is configured to control all rotation of parts within the various jack assemblies 700, 2100, 3000, 6430. The exemplary embodiment of the control handle 10800 shown in FIGS. 108 to 118 utilizes three jack assemblies similar to jack assemblies 3000 and 6430. In other words, the needles are separate from the proximal drive blocks of both assemblies and only two rotational control wires 750, 770 are needed. Therefore, for the three jack assemblies, six total control wires are required—three for the drive wires 750 and three for the disconnect wires 770. These control wires 750, 770 are guided respectively through six throughbores 10806 (surrounding the central guidewire throughbore 10807 in FIG. 115) and proximally end and are longitudinally fixed to a distal part 11512 of each of six telescoping wire control columns 11510, shown in FIGS. 115 and 116. All control wires, even the needle rods 11302, terminate at and are fixed longitudinally to a distal part 11512 of a respective telescoping wire control column 11510. Each part of these telescoping wire control columns 11510, 11512 are rigid so that rotation of the proximal part thereof causes a corresponding rotation of the distal part 11512 and, thereby, rotation of the corresponding control wire 750 or 770. The reason why all control wires, even the needle rods 11302, terminate at and are fixed longitudinally to a distal part 11512 of a respective telescoping wire control column 11510 is because tortious curving of the wires/rods from their proximal ends to the distal ends longitudinally fixed at the stent assembly to be implanted will cause the wires to move longitudinally. If there is no play, the wires/rods will impart a longitudinal force on any parts to which they are grounded, for example, to the threaded connection at the stent assembly at the distal end. This longitudinal force is undesirable and is to be avoided to prevent, for example, the drive screws from breaking loose of their threads. To avoid this potential problem, the proximal end of each wire/rod is longitudinally fixed to the distal part 11512 of a respective telescoping wire control column 11510. The distal part 11512 is keyed to the wire control column 11510, for example, by having an outer square rod shape slidably movable inside a corresponding interior square rod-shaped lumen of the proximal part of the wire control column 11510. In this configuration, therefore, any longitudinal force on any wire/rod will be taken up by the respective distal part 11512 moving longitudinally proximal or distal depending on the force being exerted on the respective wire/rod.

Torque limiting is required to prevent breaking the lattice or stripping the threads of the drive screw. This can be accomplished in software by current limiting or through a clutch mechanism disposed between the drive motors and the sun gears. An integral contrast injection system can be incorporated into the handle of the delivery system through another lumen. With a powered handle, therefore, a powered injection as part of handle is made possible.

Figure 117:
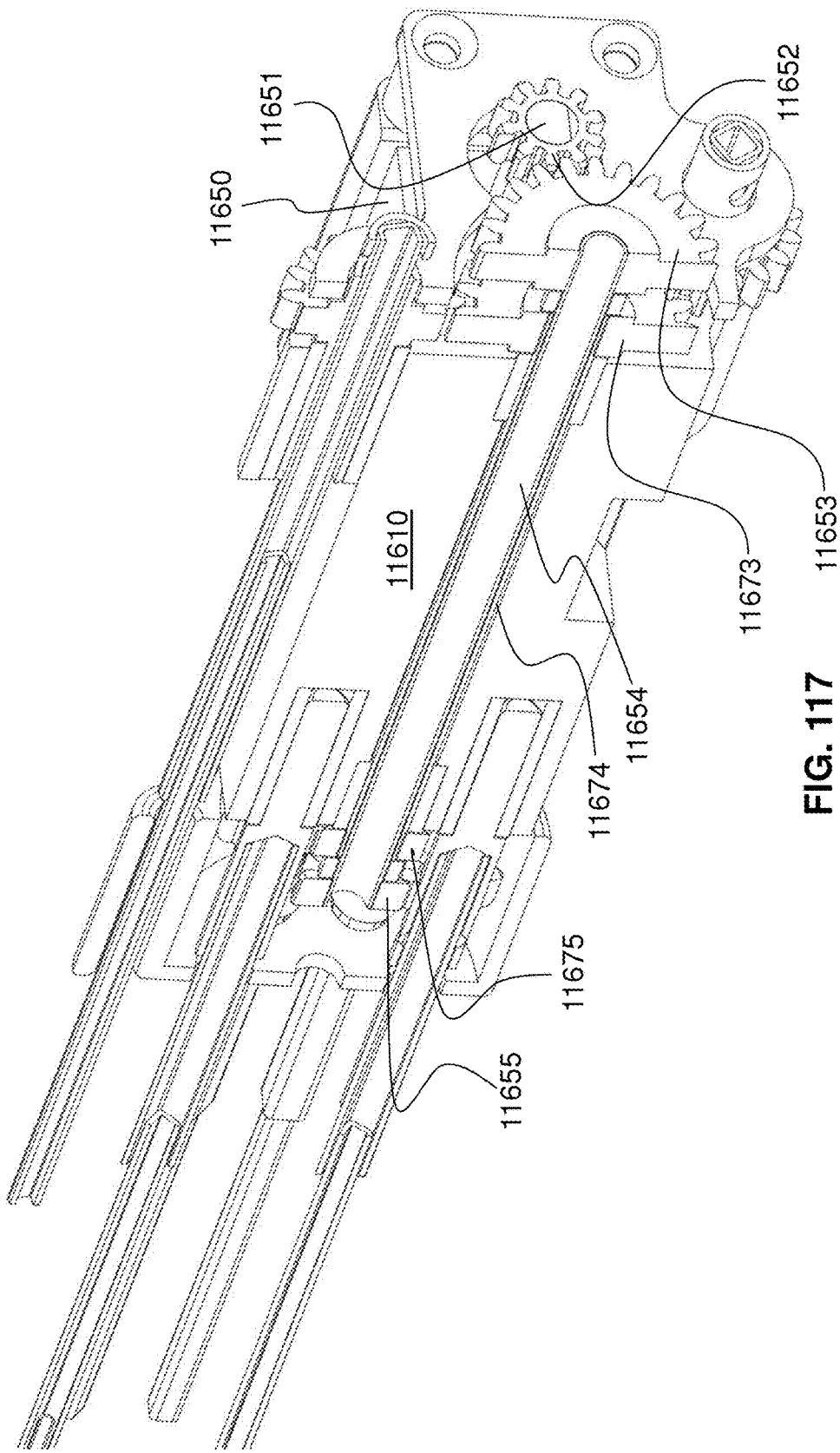
FIG. 117 is a fragmentary, enlarged, vertically cross-sectional view of the engine portion of FIG. 116 viewed from a proximal side thereof.
Figure 118:
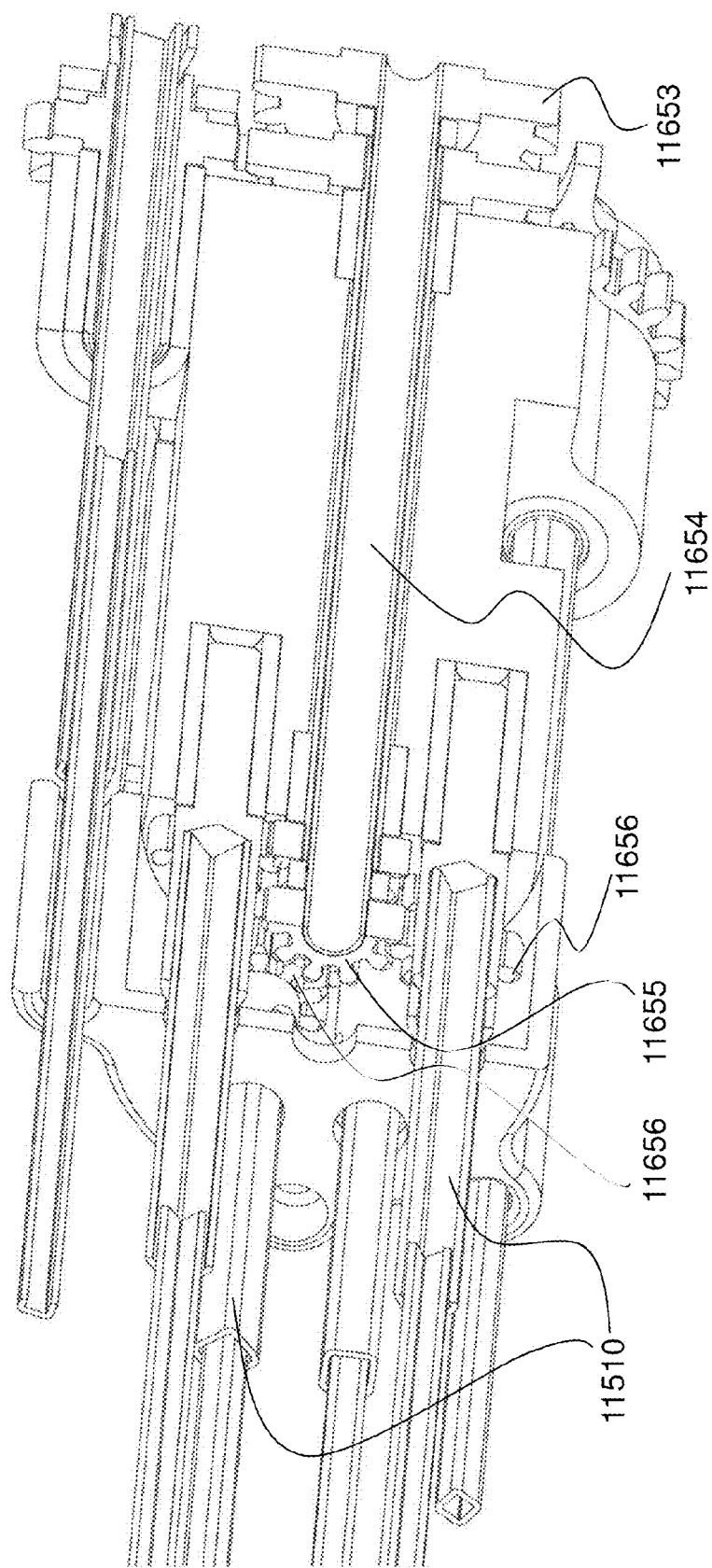
FIG. 118 is a fragmentary, enlarged, vertically cross-sectional view of the engine portion of the handle portion of FIG. 117 viewed from a distal side thereof.

Because all of the drive wires 750 need to rotate simultaneously, and due to the fact that all of the disconnect wires also need to rotate simultaneously, the jack engine 11600 includes a separate control motor 11650, 11670 (see FIG. 115) and separate transmission for each set of wires 750, 770. The view of FIG. 117 illustrates the transmission for the drive-screw control motor 11650. At the output shaft 11651 of the drive-screw control motor 11650 is a first drive gear 11652 interconnected with a larger second drive gear 11653. The second drive gear 11653 is part of a coaxial planetary gear assembly and has a central bore therein for passing therethrough the guidewire 6610. A hollow rod 11654 is fixedly connected in the central bore and extends through a transmission housing 11610 to a distal side thereof, at which is a third drive gear 11655, as shown in FIG. 118. The third drive gear 11655 is interconnected with three final drive gears 11656, each of the final drive gears 11656 being fixedly connected to a respective proximal part of one of the three telescoping wire control columns 11510 associated with each drive wire 750. Accordingly, when the drive-screw control motor 11650 rotates, the three final drive gears 11656 rotate the control columns 11510 that rotate the drive screws of the jack assemblies 3000, 6430.

The disconnect control motor 11670 operates in a similar manner. More specifically and with regard to FIG. 116, the output shaft 11671 of the disconnect control motor 11670 is a first disconnect gear 11672 interconnected with a larger second disconnect gear 11673. The second disconnect gear 11673 is part of a coaxial planetary gear assembly and has a central bore therein for passing therethrough the guidewire 6610. A hollow rod 11674 is fixedly connected in the central bore about the hollow rod 11654 and extends through the transmission housing 11610 to the distal side thereof, at which is a third disconnect gear 11675 (also disposed about the hollow rod 11654), as shown in FIG. 118. The third disconnect gear 11675 is interconnected with three final disconnect gears (not illustrated), each of the final disconnect gears being fixedly connected to a respective proximal part of one of the three telescoping wire control columns 11510 associated with each disconnect wire 770. Accordingly, when the disconnect control motor 11670 rotates, the three final disconnect gears rotate the control columns 11710 that rotate the retainer screws of the jack assemblies 3000, 6430. The activation of the disconnect drive also unscrews the needle connections when included. One exemplary embodiment for having the needles disconnect before the entire implant is set free from the docking jacks provides a lower number of threads on the needle disconnects.

Not illustrated herein is the presence of a manual release for all actuations of the delivery system. Such manual releases allow for either override of any or all of the electronic actuations or aborting the implantation procedure at any time during the surgery. Manual release sub-assemblies are present for retraction and extension of the delivery sheath, expansion and contraction of all stent lattices, and undocking of all disconnect drive blocks. One exemplary embodiment for each of the manual releases is a lever and ratcheting assembly that permits rotation in only one direction. Manual releases are utilized, for example, when something is detected as being wrong, if there is a failure of the electronics or software, or if the battery dies, and the user desires to remove the delivery system from the patient without implanting the stent lattice or other embodiments of the stent assemblies. With regard to the delivery sheath, for example, manual release means that it is desired to either retract or extend the delivery sheath. In the extension direction, the delivery sheath is extended as much as possible so that resheathing can possibly be accomplished, at which time the distal nose cone is retracted into the delivery sheath. In such a situation, the mechanism will progressively extend the delivery sheath distally until the user determines that the force required to further extend the delivery sheath is too large or the delivery sheath has extended as far as designed. In each case of the various manual release mechanisms described, the mechanisms will have torque and/or force limiting devices that prevent the user from inputting to much force that would break the system. In the retraction direction, the delivery sheath is retracted as much as possible so that implantation of the implant can still be accomplished. In such a situation, the mechanism will progressively retract the delivery sheath distally until the user determines that the force required to further extend the delivery sheath is too large or the delivery sheath has retracted as far as needed for implantation to occur. With regard to the stent lattice embodiments, manual release means that it is desired to contract the stent lattice as much as possible. Accordingly, the ratchet will progressively rotate all drive screws in the direction that causes contraction of the stent lattice. It is equally possible to have this manual release be bi-directional so that forcible expansion of the stent lattice can occur. Likewise, a separate manual release can be uni-directional to only rotate in a direction to expand the stent lattice. With regard to undocking of the disconnect drive blocks, the manual release would only be used in a situation where implantation was acceptable and desired but, for some reason, one or more of the control tubes preventing disconnect was not allowing the disconnect to occur. In such a situation, a ratchet could progressively retract the coils/wires connected to the control tubes. As this movement is only longitudinal and is in the nature of a few millimeters, the ratchet could be replaced by a lever or pull knob. Finally, with regard to retraction of the nose cone (and its control lumen) manual release means that it is desired to move the nose cone as much as possible proximally so that resheathing can possibly be accomplished. In such a situation, the ratchet will progressively retract the nose cone control lumen proximally until the user determines that the force required to further retract the nose cone is too large or the nose cone has retracted as far as desired.

Based upon the above, therefore, the delivery system control handle 10800 is entirely self-contained and self-powered and is able to actively control any prosthesis having the stent lattice and jack assemblies of the invention. An alternative embodiment to the combined drive of multiple control wires with a single motor as described above is a configuration providing a single drive motor for each of the control wires. With such a configuration, for example with respect to the jack screw drives, each motor is monitored for the amount of turns and synchronized with the other motors so that substantially simultaneous rotation of the jack screws occurs. The same monitoring is possible for the multiple control wires for disconnecting the implant. A beneficial result of independent driving of control wires is that it becomes possible to monitor the torque requirements and position of each drive wire. If a particular drive wire experiences a variation, the software can have built in allowances (based on testing potential faults, such as one drive screw being jammed or rubbing on the implantation site) to either allow the implantation to continue or to notify the user that some aspect is in fault. In such a case, the user can attempt a contraction/re-expansion to clear the fault, or, if needed or desired, a repositioning or recapture of the prosthesis.

Figure 119:
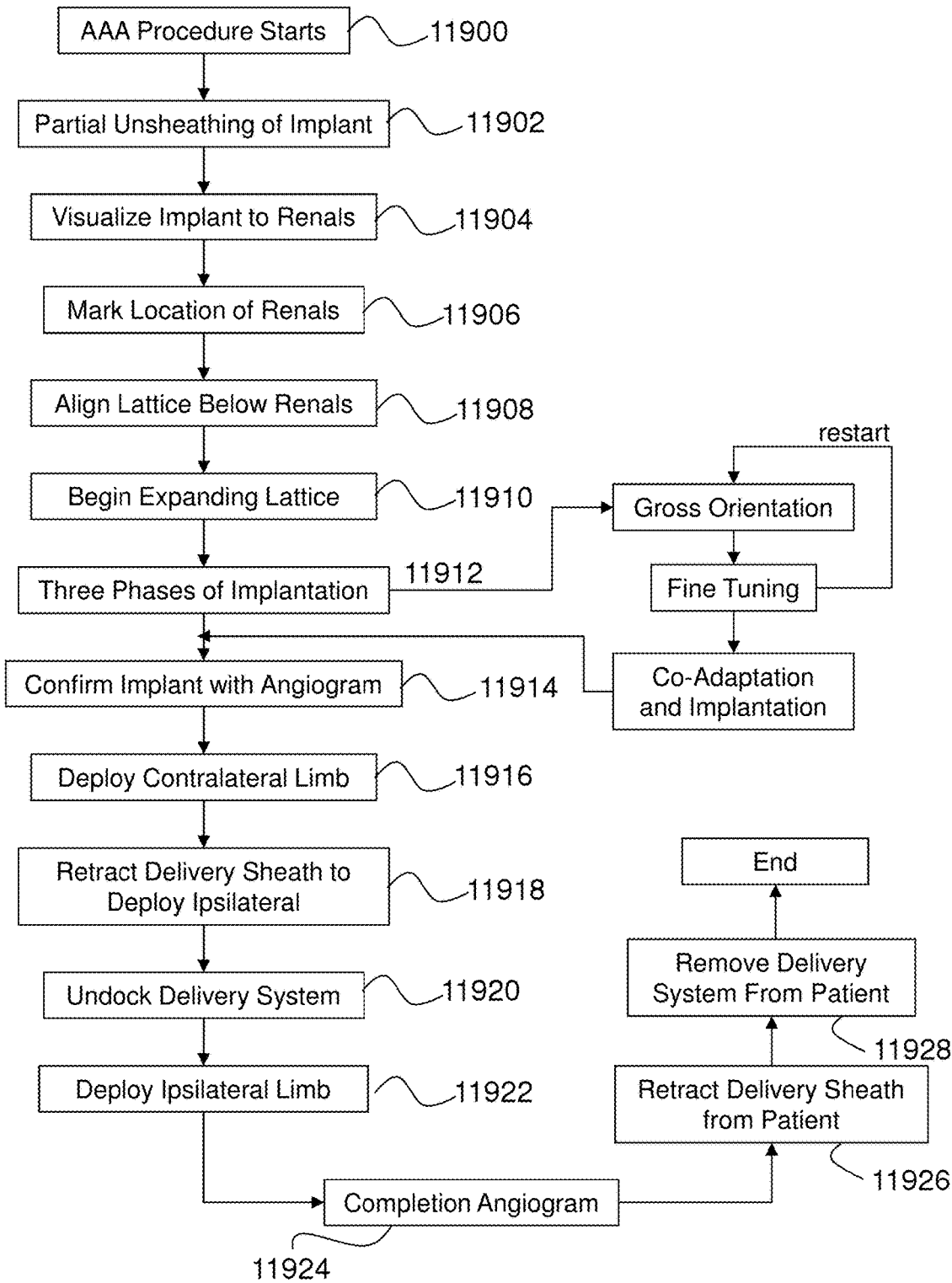
FIG. 119 is a flow diagram of an exemplary embodiment of a procedure for implanting an abdominal aorta prosthesis according to the invention.

An exemplary embodiment of a process for delivering an abdominal aortic stent graft of the invention as shown in FIG. 107 with the stent lattice as a proximal stent is described with regard to the flow chart of FIG. 119. The procedure is started in Step 11900 where the lattice has been translated through the femoral artery to the implantation site just downstream of the renal arteries. Actuation of the upper left button rearward in Step 11902 causes the delivery sheath 10720 to unsheathe from the AAA implant 10730 sufficient to expose the actuatable end (e.g., stent lattice) of the implant 10730 (which can be shown, for example, by the progression from FIG. 217 to FIG. 212—a direction opposite the re-sheathing progression which is shown in the progression from FIGS. 212 to 217). In Step 11904, visualization, such as through fluoroscopy, provides the user with feedback to show where the distal end 10732 of the prosthesis 10730 is situated. In this position, the stent lattice is in a contracted state (the expanded state is shown in the view of FIG. 107). Radiopaque markers on the prosthesis 10730 are visible to show the proximal most points of the prosthesis 10730. In Step 11906, another surgery staff, typically, has marked the location of the renal arteries on the screen (on which the surgeon sees the markers) with a pen or marker. In Step 11908, the surgeon translates the lattice of the prosthesis 10730 with the radiopaque markers to a location targeted below the renal arteries. The physician begins to expand the lattice in Step 11910 by pressing the upper right button forward (i.e., forward=open and rearward=close). Depending upon the desire of the surgeon or as set in the programming of the control device 10700, the lattice can open incrementally (which is desirable due to blood flow issues) or can be expanded fluidly outward. Implantation occurs in Step 11912 and has three phases. In the first phase of implantation, the physician performs a gross orientation of the proximal end of the prosthesis 10730 until touchdown in the abdominal aorta. In the second phase, the physician fine-tunes the implantation using intermittent expansion prior to coaptation in all three dimensions and, in the third phase, the proximal end of the implant 10730 is either satisfactorily coapted or, if the physician is not satisfied with the coaptation, then the physician reduces the diameter of the stent lattice and starts, again, with phase two. It is noted that the control device 10700 can be programmed to, at the first touch of the upper right button, to go to a particular diameter opening. For example, if the implantation site is predetermined to be approximately 20 mm, then the control device 10700 can be programmed to expand directly to 15 mm and, for each touch of the upper right button thereafter, expansion will only occur by 1 mm increments no matter how long the upper right button is pushed forward. During Step 11912, the physician is able to view all of the various feedback devices on the control handle, such as the real time diameter of the prosthesis, the angulation thereof, a comparison to a predetermined aortic diameter of the touchdown point, an intravascular ultrasound assessing proximity to wall, and when wall touch occurs. With the digital display 10711 of the invention, the physician can even see an actual representation of the expanding lattice demonstrating all of the characteristics above. During the various implantation phases, the physician can pause at any time to change implant position. Angulation of the stent lattice can be done actively or while paused. As the outer graft material approaches the wall, adjustment of the entire delivery device continues until complete coaptation of the prosthesis 10730, where it is insured that the location with respect to the renal arteries is good, along with proper angulation. As the stent graft touches the aortic wall, the physician can analyze all of the feedback devices and information to make implantation changes. At any time if the physician questions the implantation, then restart occurs to readjust the stent lattice along with a return to phase two. Further, as coaptation occurs, any other fixation devices can be utilized, for example, passive tines/barbs, a outwardly moving flex-band that presses retention device (e.g., through graft) and into aortic wall, the tissue anchor 7114, and the graft enclosures 7120. For such devices, there is no secondary action required to disengage/retract tines that are engaged. In Step 11914, the physician performs an angiogram to determine positioning of the implantation (the angiogram can be either separate or integral with the delivery system 10700), and if the positioning is not as desired (e.g., endoleak), the physician can retract the stent lattice and use the sheath 10720 to re-collapse the stent lattice using the graft material to ease the delivery sheath 1020 back over the lattice. However, if the physician determines that there is good positioning, the physician retracts the delivery sheath 10720 by pressing the upper left button rearward until at least contralateral gate is exposed. It is noted that stabilization of the ipsilateral graft material with the delivery system 10700 allows for better cannulization of the contralateral gate for a secondary prosthesis.

In Step 11916, the contralateral limb is deployed as is known in the art. However, if desired, the contralateral limb can also include the actively expanded stent lattice according to the invention. It is also desirable to perform a balloon expansion at a graft-to-graft junction if the contralateral limb utilizes a self-expanding distal stent. If the actively controllable stent lattice is used, then Steps 11900 to 11914 are repeated but for the contralateral limb. In Step 11918, the delivery sheath 10720 is retracted by pressing the upper left button rearward until ipsilateral limb is deployed. The prosthesis 10730 is, now, ready to be finally deployed.

In Step 11920, the physician actuates the lower left button rearward to unscrew the retainer screws and, thereby undock the disconnect drive blocks from the prosthesis 10730. One significant advantage of the delivery system 10700 is that there is no surge either distal or proximal when undocking occurs and finally releases the prosthesis because the entire undocking movement is merely an unscrewing of a rod from a threaded hole. Torque imposed on the stent lattice is also minimized by using counter rotating screws that result in a zero imposed torque when even in number. It is noted that, for all of the exemplary embodiment of the stent lattices that utilize the jack screws described herein, the delivery system does not impart an actuation force either on or to the stent lattices. In other words, the force for changing the configuration of the stent lattice is generated entirely within the stent lattice itself. More specifically, the forces that are used to actuate the configuration change of the stent lattice are imposed by the distal and proximal jack struts. This means that the actuation force causing expansion of the stent lattice is delivered and countered within the implant independent of the delivery tool.

The upper left button is pressed forward to extend the delivery sheath 10720 so that it connects with the distal end of nose cone 10740 while making sure that the open distal end of the delivery sheath 10720 does not catch any part of the ipsilateral distal stent or the actively controlled proximal stent. It is at this point where a manual override could be employed if the surgeon wanted to feel the re-docking of the delivery sheath 10720 to the nose cone 10740. If desired, using the lower right button pressing rearward, the physician can retract the nose cone 10740 into the distal end of the delivery sheath 10720 with the lower right button. In Step 11922, if the ipsilateral distal stent is self-expanding, the physician performs a final balloon expansion. However, if the ipsilateral distal stent utilizes the actively controllable stent lattice of the invention, Steps 11900 to 11914 are repeated but for the ipsilateral limb. A completion angiogram is performed in Step 11924 to make sure the prosthesis did not shift and that all leak possibilities have been ruled out. In an exemplary embodiment where the control system 10700 includes an integral dye system, the physician would extend the system proximal to the proximal active lattice to perform this angiogram. Finally, in Step 11926, the lower right button is pressed rearward to retract the delivery system as much as possible into the handle and, in Step 11928, the delivery system 10700 is removed from the patient.

FIG. 120 shows an exemplary embodiment of a self-expanding/forcibly-expanding lattice of an implantable stent assembly 12000 having nine lattice segments 12010 in a self-expanded native position as will be described below. In one exemplary embodiment, each of the nine lattice segments is formed with one-half of either a threaded or smooth bore 12012 for respective coordination with either a threaded or smooth portion of a jack screw 12020. In another exemplary embodiment, the nine lattice segments are formed from one integral piece of a shape memory metal (e.g., Nitinol or other super-elastic material) and with a jack screw 12020 disposed between adjacent pairs of repeating portions of the lattice and through the wall of the stent lattice. In the views shown in FIGS. 120 and 121, each jack screw 12020 is placed in a non-engaged state to allow crimp of the stent lattice for loading into a stent delivery system. In this regard, FIG. 121 illustrates the stent assembly 12000 in a contracted/crimped state for loading into the stent delivery system, an example of which is illustrated in the progression of FIGS. 217 to 212. In this non-engaged state, as the stent assembly 12000 is crimped for delivery, the proximal jack strut 12014 surrounding the non-threaded portion of each jack screw 12020 can slide thereabout with play between the two positions shown in FIGS. 120 and 121 without hindrance or bottoming out the distal drive screw coupler part 12052 while the lattice expands longitudinally when contracted by the delivery sheath of the delivery system. When the stent assembly 12000 is allowed to self-expand back to the position shown in FIG. 120, the jack screw 12020 moves into the bore of the distal jack strut 12014 until the distal drive screw coupler part 12052 hits the proximal end of the proximal jack strut 12014. Accordingly, with rotation of the jack screw 12020 in the stent-expansion direction, after the distal drive screw coupler part 12052 hits the proximal end of the proximal jack strut 12012, further lattice-expanding movement of the drive screw 12020 starts moving the proximal jack strut 12014 towards the distal jack strut 12013 to expand the stent assembly 12000.

Longitudinally, the stent assembly 12000 is provided with pairs of jack struts 12013, 12014 connected by a respective jack screw 12020 and intermediate non-moving struts 12030. In the exemplary embodiment of the stent assembly 12000 shown, there are nine pairs of jack struts 12013, 12014 and nine non-moving struts 12030. This number is merely exemplary and there can be, for example, only six of each or any other number desired. Connecting the pairs of jack struts 12013, 12014 and the non-moving struts 12030 are laterally extending arms 12040. As the stent assembly 12000 is either contracted or expanded, the arms 12040 each flex at their two endpoints, one at a respective non-moving strut 12030 and the other at a respective one of a pair of jack struts 12013, 12014. As can be seen from the configuration shown in FIG. 121, when the stent assembly 12000 is contracted (e.g., for installation into the delivery sheath), the arms 12040 move towards a longitudinal orientation. Conversely, when the stent assembly 12000 is expanded (e.g., for implantation), the arms 12040 move towards a radial orientation.

FIG. 122 shows the lattice after being allowed to return to its native position, for example, at a deployment site. Each jack screw 12020 is in an engaged state for controlled further outward expansion of the lattice. As the lattice is sized for implantation, the delivery system forcibly expands the lattice, as shown in the progression of FIGS. 123, 124, and 125. In the view of FIG. 125, the lattice is about to enter a maximum expansion state, which occurs when the proximal surface of the distal jack strut 12013 contacts the distal surface of the proximal jack strut 12014. It is noted that this exemplary embodiment does not show features of a valve sub-assembly. Valve sub-assemblies, such as shown in FIGS. 135 to 136 are envisioned to be used with this stent assembly 12000 but are not shown for reasons of clarity.

This exemplary embodiment and other exemplary embodiments of the self-expanding, forcibly expanding stent lattices described herein circumscribe cells 12310 that are comprised of either the distal jack or proximal jack part, a portion of the non-moving strut, and two arms, which together define a parallelogram (one of which is outlined in FIG. 123 with dashed lines). This shape is beneficial because it keeps the moving struts (e.g., 12013, 12014) parallel as they expand and contract, thus keeping the distal and proximal jack parts aligned with the jack screw 12020 to insure stability of the lattice. More specifically, any pitch, roll, or yaw movements of either of the jack parts (e.g., 12013, 12014) or the non-moving struts (e.g., 12030) is substantially prevented by this configuration. The configuration of adjacent cells provides significant benefits and differences from the above-mentioned scissor lattice or braided lattice structures, respectively, where mechanical pivots are present at crossings of two members or where two wires of a stent lattice or braid cross and change angles relative to one another to form a scissor when changing geometrically. In the embodiments of stent lattices described herein, no wires or members cross. Thus, without the presence of any scissoring members, the ability to sew to the stent lattice becomes possible. Further, the stent lattices are able to use all of the wall thickness for strength (there is no point where two thinner members are crossing one another). Additionally, the entire stent lattices have no points of instability and are more stable because the lattice is one continuous piece of material (with the exception of the configurations similar to FIG. 126, where the continuity is formed by fixation, such as welding or soldering).

FIG. 126 is an alternative exemplary embodiment of a portion of a self-expanding/forcibly-expanding lattice of an implantable stent assembly 12600. In the portion of the configuration shown, a separate jack screw assembly 12610 connects the two adjacent lattice segments (here the non-moving strut 12616 is shown in a vertical cross-section passing through the mid-line thereof). Separate jack tube halves 12612, 12613 are connected respectively to upper and lower jack-contact struts 12614 of the two adjacent lattice segments. To fix these tubes to the nitinol lattice, the tubes can, for example, be made of Niobium. In the exemplary embodiment shown, the external threads of the jack screw 12620 are engaged with the interior threads of the distal jack tube half 12612. A lattice-disconnect tube 12630 of the stent delivery system is engaged to cover a pair of drive screw coupler parts therein. FIG. 127 shows the lattice-disconnect tube 12630 disengaged from an exemplary embodiment of a pair of drive screw coupler parts 12752, 12754. This connected state of the pair of drive screw coupler parts 12752, 12754 is idealized because, due to the natural lateral/radial forces existing in the disconnect joint, once the lattice-disconnect tube 12630 retracts proximally past the coupling of the drive screw coupler parts 12752, 12754, the two drive screw coupler parts 12752, 12754 will naturally separate, as shown in the view of FIG. 128. In the disconnected view of FIG. 128, the proximal member of the pair of drive screw coupler parts 12752, 12754, which is part of the delivery system, is partially retracted into the central bore of the lattice-disconnect tube 12630.

FIG. 129 illustrates another exemplary embodiment of a self-expanding/forcibly-expanding lattice of an implantable stent assembly. This assembly also has nine separate lattice segments, but more or less in number is equally possible, for example, six segments. In this embodiment, a proximal disconnect block 12930 and disconnect subassemblies 12931, 12932 of a stent delivery system is an alternative to the lattice-disconnect tubes 12630 of the embodiment of FIGS. 126 to 128. Here, a proximal disconnect block 12930 is in an engaged state covering the pair of drive screw coupler parts 13052, 13054 therein. After the disconnect block 12930 is retracted in a proximal direction, all of the lattice-disconnect arms 12932 are removed from covering the pair of drive screw coupler parts 13052, 13054, thereby allowing disconnect of the lattice 12900 from the delivery system, as shown in FIG. 130. The proximal disconnect block 12930 allows all of the pairs of drive screw coupler parts 13052, 13054 to be coupled together for substantially simultaneous release.

FIGS. 131 and 132 show an alternative to the exemplary embodiment of the self-expanding/forcibly-expanding lattice of FIGS. 126 to 130. Here, the intermediate jack tubes halves 13112, 13113 for receiving one jack screw 13120 therein are connected to the adjacent lattice segments with the adjacent lattice segments 13114 not directly on opposing sides of the jack tubes 13112, 13113. The angle that the two adjacent lattice segments make is less than 180 degrees and greater than 90 degrees. In particular, the angle is between 130 degrees and 150 degrees and, more specifically, is about 140 degrees, as shown in FIG. 132.

FIG. 133 is another exemplary embodiment of a self-expanding/forcibly-expanding lattice of an implantable stent assembly 13300. In this embodiment, there are nine lattice segments but more or less is equally possible, for example, six segments. Here, the distal and proximal jack struts 13313, 13314 of the lattice are locally thicker to accommodate and connect to non-illustrated jack screw assemblies. One possible method of fabricating the stent lattice with locally thicker sections is to start with a tube of material that is at least as thick as the thickest region and to wire-EDM one of or both of the inside and outside surfaces to cut out the narrower sections and either form or leave the locally thicker sections. This applies to all of the exemplary embodiments of the stent lattice herein where locally thicker sections appear.

FIG. 134 is another exemplary embodiment of a self-expanding/forcibly-expanding lattice of an implantable stent assembly 13400. In this embodiment, there are nine lattice segments but more or less is equally possible, for example, six segments. Instead of having the non-illustrated jack screws pass entirely through the material of the lattice as shown in previous embodiments, here, the jack struts of the lattice are elongated and the elongated portions are bent-over to form tabs 13413, 13414 for connecting to non-illustrated jack screw assemblies. The tabs 13413, 13414 are shown here as bent inwards, but they can also be bent to face outwards. To operate the jacks, various ones of each of the set of longitudinal tabs are threaded or smooth.

FIGS. 135 to 137 show another exemplary embodiment of the self-expanding/forcibly-expanding lattice of an implantable valve assembly 13500. The jack assemblies are similar to the embodiment of FIGS. 120 to 125. Here, however, there are six lattice segments. The intermediate non-moving struts 13530 between the jacks 13520 form commisure connections and include through-bores 13532 for connecting the valve end points of the intermediate valve 13540 to the lattice. In this embodiment, the upper plane of the valve 13540 is in line with the upper end of the non-moving struts 13530, which are at the same plane as the upper end of the jacks 13520. The valve 13540 here is shown with three leaflets 13542 and, therefore, three commisure connections exist at three of the non-moving struts 13530. The valve assembly is shown in FIGS. 135 and 136 in an expanded position that can be commensurate with an implantation position of the valve assembly. FIG. 137, in comparison, shows the lattice of the valve assembly 13500 in a natural or pre-set, non-forcibly-expanded state. There exist some reasons for having the lattice of the valve assembly 13500 be set to a larger natural diameter than the compressed, pre-implantation size as shown in FIG. 121 or 139. For example, in such a configuration, it is desirable to have the angle of the arms of the lattice, when starting to force drive, not be shallow because it is desired to have all of the force of the screw to drive the diameter change of the stent assembly. Also, when driving the stent assembly from a natural position to a final, forcibly open position, strain is induced in the material. It is understood that, the higher the induced strain, the greater the installed strain, increasing the possibility of failure. Therefore, the closer the final position is to the natural position, the lower is the installed strain. Further, the natural position cannot be made so large because there will be too much strain to collapse the lattice for delivery. In this regard, the heat-set diameter of the stent lattices of the disclosed exemplary embodiments is optimized so that the strain imparted when moving the stent lattice from its heat-set diameter to the crimped diameter is maximized within the allowable super-elastic range of the material, therefore, minimizing the installed strain when the stent lattice is moved from its heat-set diameter to the forcibly expanded implantation diameter.

FIGS. 138 to 142 show another exemplary embodiment of the self-expanding/forcibly-expanding lattice of a stent assembly 13800. As in the above embodiments, this exemplary embodiment does not show features of a valve sub-assembly for reasons of clarity even though valve sub-assemblies, such as shown in FIGS. 135 to 136, are envisioned to be used with this stent assembly 13800. Here, the lattice of the stent assembly 13800 has six lattice segments. Instead of having the jack screws contact longitudinal bores in the wall of the lattice, pairs of jack tubes 13812, 13813 are connected (e.g., laser welded) to respective longitudinal pairs of jack connection struts 13822, 13823. This embodiment shows the jack tubes 13812, 13813 connected on the interior of the lattice but they can also be connected on the exterior, or the pairs can even be staggered on the interior and exterior in any way and in any number. The jack tubes 13812, 13813 are formed with interior threads or interior smooth bores.

After being forcibly contracted, the lattice of FIG. 138 can be further compressed within the delivery sheath of the delivery system, an orientation that is shown in FIG. 139. After delivery to the implantation site, the lattice is expanded for implementation, first naturally and then forcibly. FIGS. 140 to 142 show various expansion stages of the lattice in various perspective views with FIG. 142 showing the lattice expanded near a maximum expansion extent.

An alternative to forming interior-threaded, longitudinal through-bores in the lattice is shown in the exemplary embodiment of FIGS. 143 to 154. Here, the self-expanding/forcibly-expanding lattice of an implantable stent assembly 14300 has nine lattice segments. FIG. 143 shows the lattice in a native, self-expanded position. Both of the distal and proximal jack struts 14313, 14314 in each of the nine segments have smooth bores. The distal jack strut 14313 in each lattice segment has a proximal end formed as a first connection part 14315 shaped to receive thereat a second connection part 14330. It is this second connection part 14330 that contains the interior threads for threadingly mating with the exterior threads of the jack screw 14320. In an exemplary embodiment, the second connection part described herein can be made curved from tube-stock to fit within wall of the stent assembly when collapsed. Additionally, the drive screws and/or the second connection part can be made of materials that do not have galvanic corrosion, such as Titanium. By locking the two connection parts 14315, 14330 at least in the longitudinal direction of the lattice (for example by the opposing T-shaped tongue and grooves shown in FIG. 143), when the jack screw 14320 (longitudinally secured at the proximal side of the proximal jack strut 14314 by the distal drive screw coupler part 12052) is threaded into the second connection part 14330, a two-sided connection is formed that allows each jack assembly to function by moving the respective pair of longitudinally aligned jack struts 14313, 14314 towards or away from one another. In the exemplary embodiment, the first connection part 14315 has a T-shape and the second connection part 14330 is a nut having a bore with an interior shape corresponding to the exterior of the T-shape of the first connection part 14315. This configuration, therefore, forms a form-locking connection. A form-locking or form-fitting connection is one that connects two elements together due to the shape of the elements themselves, as opposed to a force-locking connection, which locks the elements together by force external to the elements. By creating a threaded interior bore in the second connection part 14330 that is co-axial with the smooth bores of the distal and proximal jack struts 14313, 14314, once the jack screw 14320 is threaded completely through the second connection part 14330 and enters the bore of the distal jack strut 14313, the jack screw 14320 prevents the second connection part 14330 from being removed. FIG. 153 illustrates the interior threads of the nut and shows how the jack screw 14320 prevents removal of the nut 14330 after the jack screw 14320 passes completely therethrough.

In these figures, an exemplary embodiment of commisure connector pads 14350 for each of three commisure points of the valve leaflets are provided. An exemplary form for the commisure connector pads 14350 is a rectangle with four through-bores for suturing the commisure point thereto. Outer lattice fixation paddles 14360 are provided at the ends of the non-moving struts 14316 to improve fixation of the stent assembly 14300 in the implantation site.

As can be seen by the progression from FIGS. 145 to 146, the lattice-disconnect tubes 14340 move proximally in order to disconnect the pair of drive screw coupler parts 14652, 14654. FIG. 146 shows the lattice of FIG. 143 with the connector control tubes 14340 of the delivery system in a non-engaged state after disconnection of the stent assembly 14300 by the delivery system has occurred. FIG. 149 shows the lattice expanded by the jack screw assemblies almost up to the fullest expanded extent possible, where the two jack struts 14313, 14314 of the lattice almost touch. Various other views of the stent assembly 14300 are shown in FIG. 144 (top view), FIGS. 147, 148 and 152 (enlarged views of the connection parts expanded and contracted), and FIGS. 150 and 151 (contracted stent assembly). FIG. 144 reveals that, in an exemplary embodiment of the jack struts 14652, 14654, the radial thickness 14410 is greater than a thickness 14420 of the remainder of the stent lattice, in this case, it is thicker from the interior of the lattice. If desired, it can be thicker from the exterior of the lattice.

FIG. 154 shows one exemplary embodiment of the lattice 14300' of FIG. 143 in an intermediate manufacturing step before the cylindrical stent assembly 14300 is created. For example, the lattice of the stent assembly can be laser cut from a sheet of Nitinol, wrapped around a mandrel, and welded at the two ends to form the shape of the lattice 14300 shown in FIG. 143.

FIGS. 155 to 166 illustrate another exemplary embodiment of a self-expanding/forcibly-expanding lattice of an implantable stent assembly 15500 having six lattice segments. As best seen in FIGS. 156 and 159, the jack struts 15513, 15514 have keyhole slots to accommodate the jack screws therein. This exemplary embodiment, therefore, can create the keyhole slots using a wire-EDM (electric discharge machining) process. This exemplary embodiment shows the keyhole slots open to the inside but, as described below, the keyhole slots can also be open to the outside.

The configuration of the stent assembly 15500 has similar features of the stent assembly 14300, all of which are not repeated for the sake of brevity. One feature of the stent assembly, for example, similarly has commisure connector paddles 15550 for each of three commisure points of the valve leaflets. This exemplary form for the commisure connector paddles 15550 is a waffle pattern with five through-bores and dimpled sides for suturing the commisure point thereto. The stent assembly 15500 also has some differences from the stent assembly 14300. A first difference is that outer lattice fixation pads 15560 on the non-moving struts 15516 are bent outwards to shape the lattice into a longitudinal hourglass. As particularly shown in the views of FIGS. 159 and 160, the outer lattice fixation pads 15560 each provide a beneficial location at the a distal end thereof for placing a radiopaque marker 15562.

FIG. 155 shows the stent assembly 15500 partially expanded state with each of the jack screws 15520 in a thread-engaged state for further outward expansion. As can be seen in FIG. 155, turning the jack screws 15520 so that they enter the second connection part 15530 further pulls the distal jack strut 15513 towards the proximal jack strut 15514 (because the distal drive screw coupler part 14652 is prevented from further distal longitudinal movement after hitting the proximal side of the proximal jack strut 15514). It is noted, however, that this pulling does not occur until the jack screws 15520 enter the distal jack strut 15513 to eliminate any slack that exists between the distal drive screw coupler part 14652 and the proximal most surface of the proximal jack strut 15514. When the distal drive screw coupler part 14652 finally touches the proximal end of the proximal jack strut 15514, further rotation of the jack screws 15520 cause the distal and proximal jack struts 15513, 15514 to move towards one another because the threads of the jack screws 15520 are connected with the internal threads of the second connection part 11530. As is apparent, because the stent assembly 15500 is forcibly expanded in this state, reversing the jack screws 15520 allows the stent assembly 15500 to retract radially inwards towards it natural state, which is shown, for example, in FIG. 161. FIGS. 157, 158, 160, 165, and 166 also show the stent assembly 15500 in various forcibly expanded configuration states.

However, when it is desired to forcibly contract the stent assembly 15500, further reversal of the jack screws 15520 will merely turn the screws out of the respective second connection parts 11530. To prevent this removal from occurring (because removal of the jack screws 15522 from the second connection part 15530 would allow the latter to fall off the stent lattice), each of the jack screws 15520 is provided with a back drive sleeve 15570 that is disposed fixedly on the outside of each of the jack screws 15520 at a location between the second connection part 15530 and the distal surface of the proximal jack strut 15514. To fix the back drive sleeve 15570 in place, it can be, for example, machined directly with the screw or laser welded on as secondary process. Use of the back drive sleeve 15570 to cause forcible contraction of the stent assembly 15500 can be seen in the transition from FIG. 161 to FIG. 162 to FIG. 163. In FIG. 161, the jack screws 15520 are in a position where the lattice is in the natural, self-expanded state but in a position where the distal drive screw coupler part 14652 touches the proximal-most surface of the proximal jack strut 15514. In this position an unscrewing movement of the jack screws 15520 causes no movement of the lattice until the back drive sleeve 15570 touches the distal-most surface of the proximal jack strut 15514, which is the position shown in FIG. 162. Any further reversal of the jack screws 15520 causes the distal portion of the jack screws 15520 to begin moving away from the distal jack strut 15513 but the back drive sleeve 15570 prevents any longitudinal movement of the jack screws 15520 with respect to the proximal jack strut 15514. As a result, the distal and proximal jack struts 15513, 15514 are forced apart to cause inward contraction of the stent assembly 15550. Once the stent assembly 15550 is contracted sufficiently to be loaded into the delivery sheath (indicated diagrammatically in with dashed lines 16400 in FIG. 164), any further inward contraction can be effected by forcibly loading the lattice into the delivery sheath of the delivery system for implantation. Loading the lattice into the delivery sheath can be seen in the progression from FIG. 217 to FIG. 212.

FIGS. 167 and 168 show another exemplary embodiment of a self-expanding/forcibly-expanding lattice of the implantable stent assembly of FIGS. 155 to 166. Here, the lattice also has six lattice segments but the longitudinal location of each intermediate jack screw nut to a respective one of the second connection parts 16730 is staggered longitudinally about the circumference of the lattice. This exemplary embodiment shows the staggering of the second connection parts 16730 in only two longitudinal positions (i.e., at two cross-sectional planes). However, three or more different longitudinal positions are also envisioned. FIG. 168 illustrates how the lattice is able to be collapsed even further than a configuration where all of the second connection parts 16730 are in the same radial plane (i.e., cross-sectional plane). As can be seen, the second connection parts 16730 do not hit one another during contraction. Not only does the staggered orientation reduce the impact of the second connection parts 16730 on the cross-section for available space, this configuration also reduces impact on the circumferential length where, with regard to FIG. 168, it can be seen that the second connection parts 16730 touch metal in the lattice directly adjacent the second connection parts 16730, e.g. at the lattice arms.

FIGS. 169 to 173 show a distal end of an exemplary embodiment of a delivery system containing the stent assembly 15500 of FIGS. 155 to 166, which is only shown as a stent lattice. Of course any of the stent assemblies described herein can be substituted for this stent lattice, including valve assemblies. Use of the stent assembly 15500 in this exemplary embodiment is merely for illustration purposes. The view of FIG. 169 shows the state of the lattice after the delivery sheath 11040 of the delivery system has been withdrawn to an implantation position and after the lattice has been forcibly expanded, for example, to an implantation size of the lattice.

In addition to the stent assembly 15500, distal portions of the stent delivery system are shown. First, lattice-disconnect tubes 16940 are connected to disconnect wires 770 which, in this embodiment, take the form of hollow flexible coils. Accordingly, proximal movement of the disconnect coils 770 causes movement of the lattice-disconnect tubes 16940 as shown in the progression of FIGS. 170 to 171 to 172. The disconnect coils 770 each have disposed therein a respective one of the drive wires 750 that cause rotation of each of the proximal drive screw coupler parts 14654 for expansion and contraction of the stent assembly 15500. Also shown is a distal nose cone 16920 defining therein at least a longitudinal guidewire lumen (not illustrated). Connecting the nose cone 16920 to the remainder of the delivery system is a hollow guide wire tube 16922 having a guidewire lumen coaxial with the guidewire lumen of the nose cone 16920 for a guidewire that is used to guide the delivery system to the implantation site (see, e.g., FIGS. 66 to 69). Containing the stent assembly 15500 during delivery is the delivery sheath 11040, which is shown in the retracted state in FIG. 169 for implantation of the stent assembly 15500.

FIG. 170 shows the interior of the delivery system of FIG. 169 proximal of the stent assembly to be implanted by the delivery system by the removal of the delivery sheath in this figure to a point proximal of the connector control sub-assembly 17000 of the delivery system. The connector control sub-assembly 17000 is shown fragmented in FIG. 170 for clarity. The progression of the connector control sub-assembly 17000 in FIGS. 170 to 171 to 172 illustrates how the stent assembly 15500 is actively disconnected (arrow A) from the delivery system.

In the connector control sub-assembly 17000, each of the disconnect coils 770 is grounded to a disconnect puck 17020. Accordingly, control of the stent disconnect by the delivery system is effected by retracting the disconnect puck 17020 a proximal distance sufficient to remove the lattice-disconnect tubes 16940 from covering the drive screw coupler parts 14652, 14654, which movement is illustrated in the progression of FIGS. 171 and 172. In FIG. 170, the connector control sub-assembly 17000 is in a lattice-connected state with the lattice-disconnect tubes 16940 over the drive screw coupler parts 14652, 14654. Proximal retraction of the disconnect coils 770 causes all of the lattice-disconnect tubes 16940 to move proximally into a lattice-disconnected state, shown in FIG. 171. In this figure, each of the lattice-disconnect tubes 16940 is respectively retracted proximally from each of the drive screw coupler parts 14652, 14654 an instant before all of the drive screw coupler parts 14652, 14654 disconnect from one another. It is noted that the connection of the drive screw coupler parts 14652, 14654 illustrated in FIG. 171 with the lattice-disconnect tubes 16940 disengaged from the pair of drive screw coupler parts 14652, 14654 is idealized because, due to the natural lateral/radial forces existing in the disconnect joint, once a lattice-disconnect tube 16940 retracts proximally past the coupling of these drive screw coupler parts 14652, 14654, the two drive screw coupler parts 14652, 14654 will naturally separate, as shown in the view of FIG. 172. In actuality, manufacturing tolerances and variable resistance will have the jack-screw-connector pairs disconnect at different times, even if they are microsecond from one another. FIG. 172 shows the connector control sub-assembly 17000 in a lattice-disconnected state where each of the drive screw coupler parts 14652, 14654 are disconnected from one another.

FIGS. 170 and 173 are enlarged views of various details illustrating how the disconnect coils 770 are retracted simultaneously for substantially simultaneous disconnection of the drive screw coupler parts 14652, 14654. More specifically, each of the lattice-disconnect tubes 16940 is longitudinally fixed to a respective disconnect coil 770 at the distal end of the disconnect coil 770. Two sleeves 17022, 17024 are fixed to the proximal end of each disconnect coil 770. The disconnect puck 17020 has a number of passages 17021 equal to the number of disconnect coils 770 (which also is equal to the number of jack screw assemblies). As can be seen in FIGS. 170 and 173, attachment of the proximal end of the disconnect coils 770 to the disconnect puck 17020 occurs by first placing the distal sleeve 17022 in a respective distal counterbore of one passage 17021 of the disconnect puck 17020. The passages each comprise the distal counterbore, an intermediate groove, and a proximal counterbore. At this point, the proximal end of the disconnect coil 770 and the proximal sleeve 17024 stick out from the side of the disconnect puck 17020. Then, the coil 770 is slightly stretched so that the proximal sleeve 17024 moves over the proximal corner of the disconnect puck 17020 and is allowed to move down and rest inside the proximal counterbore, shown in FIGS. 171 to 173. Even though longitudinally fixed after such a connection, the entire sub-assembly at the proximal end of the coils 770, including the distal and proximal sleeves 17022, 17024, is freely rotatable within its respective passage 17021. When torque is transmitted through the drive screw coupler parts 14652, 14654, a strong outward radial force separating the drive screw coupler parts 14652, 14654 exists. This separating force is counteracted by the sleeve 16940. To prevent drag upon the rotating drive mechanism that houses the drive screw coupler parts 14652, 14654 therein, the sleeve 16940 is allowed to spin freely within the puck passages 17021.

The disconnect puck 17020 is longitudinally slidable about the central hollow shaft of the guidewire tube 16922. Proximal of the disconnect puck 17020 but longitudinally fixed to the central guidewire tube 16922 is a control spool 17030. The control spool 17030 has puck control screws 17032 rotationally freely connected thereto but threaded in respective internally threaded bores of the disconnect puck 17020. These puck control screws 17032 are connected proximally to the disconnect drive subsystem in the delivery system handle through the delivery sheath 11040. In this way, rotation of the puck control screws 17032 allows distal and proximal movement of the disconnect puck 17020, which corresponds to distal and proximal movement of the lattice-disconnect tubes 16940. Not illustrated in FIGS. 170 to 173 but shown in FIG. 178 is an O-ring 17800 that is pierced by all of the wires passing through the control spool 17030 and is made of a polymer to provide a fluid-tight seal preventing flow of blood into the delivery sheath and/or delivery system handle.

It is noted that the position of the delivery sheath 11040 in the view of FIG. 169 covers the disconnect puck 17020 and prevents the disconnect coils 770 from coming out of the disconnect puck 17020. Accordingly, in use, the delivery sheath 11040 is retracted proximally no further than is shown in FIG. 169.

As in previous embodiments described herein, each jack assembly of the stent assembly utilizes one set of control wires, one driving wire 750 (here, rotational) and one disconnect wire 770 (here, longitudinally actuated). Also described in this exemplary embodiment are puck control screws 17032. Each of the driving wires 750 and the puck control screws 17032 extends from the connector control sub-assembly 17000 all the way distal to the control handle of the delivery system. Because the delivery sheath 11040 is flexible and is intended to move through tortuous anatomy, it is understood that all of these wires/rods will experience longitudinal forces and will move longitudinally as the delivery sheath 11040 bends. As any longitudinal force exerting on these wires/rods is undesirable, especially with the disconnect wire 770—which causes removal of the lattice-disconnect tubes 16940 and complete disconnection of the stent assembly when the lattice-disconnect tubes 16940 are moved proximally, it is important to minimize any affect that such forces would have on any of the wires/rods.

To eliminate action of such forces on the distal end of the device, the wires/rods are all grounded to the control spool 17030. As shown in FIGS. 170 to 172, and in particular FIG. 173, each of the puck control screws 17032 have puck grounding cuffs 17033 on either side of the control spool 17030 that allow rotation movement but prevent longitudinal movement. Similarly, the drive wires 750 each have drive grounding cuffs 751 on either side of the control spool 17030 that allow rotation movement but prevent longitudinal movement.

All of these control wires/rods terminate at and are fixed longitudinally to a distal part 11512 of a respective telescoping wire control column 11510. Each part of these telescoping wire control columns 11510, 11512 are rigid so that rotation of the proximal part thereof 11510 causes a corresponding rotation of the distal part 11512 and, thereby, rotation of the corresponding control wire 750, 17032. The distal part 11512 is keyed to the wire control column 11510, for example, by having an outer square rod shape slidably movable inside a corresponding interior square rod-shaped lumen of the proximal part of the wire control column 11510. In this configuration, therefore, any longitudinal force on any wire/rod will be taken up by the respective distal part 11512 moving longitudinally proximal or distal depending on the force being exerted on the respective wire/rod and virtually no longitudinal force will be imparted distal of the control spool 17030.

FIGS. 174 to 177 are photographs of an exemplary embodiment of a delivery system and stent assembly lattice similar to the configuration shown in FIGS. 167 to 168. These views show the lattice in various rotational views and in a forcibly expanded state with the back drive sleeve 15570 clearly appearing on the jack screw 15520. FIGS. 178 to 180 show additional views of the connector control sub-assembly 17000 of the delivery system. In addition to the outer delivery sheath 11040 surrounding all of the control wires/rods, also provided is a flexible multi-lumen extrusion 17810, shown in FIG. 178, which provides a separate, independent lumen for each of the driving wires 750 and the puck control screws 17032.

FIGS. 181 to 194 are photographs of various different exemplary embodiments of self-expanding/forcibly-expanding implantable heart valve assemblies. FIGS. 181 to 186 show a heart valve assembly having nine lattice segments in an expanded state and with valve leaflets in an open state. In this embodiment, the outer lattice fixation pads 15560 on the non-moving struts 15516 are bent outwards to shape the lattice into a longitudinal hourglass. The valve leaflets 18110 are connected by commisure plates 18120 to the non-moving struts 15516. The proximal ends of the drive screw coupler parts 14652 are shown in FIG. 186.

FIGS. 187 to 194 show a heart valve assembly having six lattice segments in an expanded state and with valve leaflets in an open state. The view of FIG. 188 shows only the valve leaflet sub-assembly 18800 removed from the lattice. Easily viewed in FIG. 188 is an exemplary embodiment of a commisure connector 18810 that is shown installed within the stent lattice of FIGS. 189, 190, and 208. This commisure connector 18810 allows for easier connection of a single surface valve sub-assembly 18800. When so used, the valve sub-assembly 18800 traverses approximately the dashed line shown in FIG. 208 as seen in FIGS. 189 and 190. The commisures of the various embodiments described herein are attached to the non-moving or rigid portions of the lattice, for example, at the non-moving strut or at the proximal jack strut adjacent the downstream end of the valve sub-assembly.

In the exemplary embodiment of FIGS. 190 to 192, the upper plane of the valve leaflet sub-assembly 19000 is in line with the upper end of the commisure connector paddles 15550 on the non-moving struts 15516, which are significantly longer and are not at the same plane as the upper end of the proximal jack struts 15514. Here, the plane of the upper end of the proximal jack struts 15514 is in line with the downstream end of the graft material 19010.

In an alternative, non-illustrated configuration of the self-expanding and forcibly expanding stent lattice, the commisures are fixed to the non-moving strut 19016 at a point 19020 between the outer row of arms 19040 extending away from either side of the non-moving strut 19016 and the first row of arms 19042 closer to the center of the stent lattice. In such a configuration, the loads applied by the valve leaflet sub-assembly 19000 are spread to a greater number of support areas, thereby reducing the stress and strain upon the arms 19040, 19042. In particular, in such a configuration, the forces are spread to four arms 19040, 19042, whereas in previously described configurations, the forces are born principally by the two outer-most arms 19040. One reason for this is because each arm has a mean installed strain that is generated by the forcibly expanding portion of the implantation. The same areas will experience additional strain associated with supporting the valve leaflets. In order for the stent lattice to survive long-term fatigue associated with high cycles of use, the alternating strain should be below a threshold and this process of spreading the forces to more arms allows the threshold to be maintained.

FIG. 191 shows an exemplary embodiment of a heart valve assembly connected to an exemplary embodiment of a delivery system and forcibly expanded. Here, the shape of the graft material is shown as corresponding to the shape of the upstream arms as in a saw tooth pattern.

The views of FIGS. 192 to 194 show an exemplary embodiment of how the graft and how the leaflet sub-assembly are connected to the lattice. FIGS. 193 to 194 show how the braid angle of the braided graft material 19310 closely matches the angle of the arm portions of the self-expanding/forcibly-expanding implantable heart valve. In this way, the braid is able to expand longitudinally as the sections of the frame move away from each other during collapse. Substantially simultaneously, the graft material and the stent are reducing in diameter and staying at a similar angle to reduce the stress of fixedly attaching the graft to the stent with a plurality of stitches. These figures also show one exemplary embodiment of how the graft material 19310 is stitched to the stent lattice.

One exemplary embodiment of the graft for the heart valve assemblies disclosed herein comprises nanofiber polyurethane spun into a braid-like form back and forth on a central mandrel. The view of FIG. 195 is a microscopic view of this graft as so fabricated when it is first laid down and when no stretch is being imparted; in other words, the graft is in its natural state. FIGS. 196 and 197 are close-up views that illustrate contact points between each nanofiber and show how the nanofibers adhere together. The braid angle of the graft is matched to the angle of the central arms of the stent lattice so that, as the lattice transforms, the braid goes through a matching transformation. This means that, when the graft is stretched longitudinally, it reduces in diameter, so it behaves like a braided structure. FIG. 198 shows the graft material when stretched in its length by 100%. FIG. 199 shows the graft material returning to its natural state after being stretched in FIG. 198. The braid-like form is so tightly packed, fluid does not pass through, therefore, the graft material is fluid-tight for purposes of use in blood vessels. An amount of polyurethane is added to the braid-like form of this graft material. A minimal amount is added throughout the material but a heavier amount is used at the trimmed ends of the graft where the graft, when installed on the valve assembly, might be at risk of fraying.

It is noted that the various exemplary embodiments of the graft sub-assemblies described herein show the graft material on the inside of the lattice. Placing the graft material on the outside surface of the lattice is also envisioned. In such an exemplary embodiment, the exposed drive screws are now covered and protected on one side by the graft material and, if a valve assembly is present, on the other side by the valve leaflets. Also the key-holes forming the bores for the drive screws (see, e.g., FIGS. 156 to 160 and 204 to 209) are protected by placing the graft material on the outside surfaces. An alternative to placing the graft material on the outside surfaces to protect the drive screws is a non-illustrated cover or sleeve that can be placed about the drive screws. Such a cover can be, for example, corrugated or bellows-like or smooth or any other variation.

As the lattice enlarges circumferentially, the valve leaflets, which are fixed in size, change the size of the overlap at the downstream ends of the leaflets. It may be desirable to adjust the size of this overlap. Furthermore, the leaflet length is also a factor with regard to longevity as undesirable wear can occur the more that the leaflet contacts any appreciably hard surface, including the stent lattice, the graft material, the sutures, etc. Therefore, adjustment of the leaflets to minimize or prevent such contact is desirable. With these embodiments, therefore, the leaflet size can be insured to maximize orifice area while assuring coaptation of the leaflet edges but also preventing undesirable wear.

Accordingly, FIG. 200 shows an exemplary embodiment of a device that adjusts the valve leaflet sub-assembly in the heart valve assembly. In this embodiment, the ends of the valve leaflets near the commisures are wound about a mandrel. If more overlap is desired, then the mandrel will be spun in one direction and, if less overlap is desired, the mandrel will be spun in the other direction.

FIG. 201 show another exemplary embodiment of an adjustable valve leaflet sub-assembly where each commisure has two mandrels for winding individual ends of each leaflet. In this embodiment, each mandrel of each pair of mandrels is shown as having to wind in opposing directions in order to take in the leaflets or let out the leaflets.

The view of FIGS. 202 and 203 show another exemplary embodiment of an adjustable valve leaflet sub-assembly of a heart valve assembly where a longitudinally moving adjustment shim 20300, when moved longitudinally (into or out from the view of FIG. 202), takes up more or lets out more of the valve leaflet edge to shorten or lengthen the overlap portions of the valve leaflets.

In use, the exemplary adjustable valves described herein are deployed with a minimal amount of released leaflet. This deployment configuration will likely cause some amount of central regurgitation, assuming that the valve is sized to an amount above a minimum deployed diameter. The leaflets are then released (played out) while monitoring with a transesophageal echocardiogram, for example. Once sufficient material is released to cause complete coaptation of the leaflets, the central regurgitation will cease, which can be easily confirmed with TEE Doppler evaluation.

FIG. 204 is another exemplary embodiment of a self-expanding/forcibly-expanding implantable stent assembly 20400. In contrast to previously described lattices of the stent assemblies, the distal and proximal jack struts 20412, 20414 of this embodiment have the wire-EDM jack screw bores machined from the outside surface of the stent assembly 20400. As shown in FIG. 205, the second connection part 14330 contains the interior threads for threadingly mating with the exterior threads of the jack screw 14320 and the second connection parts 14330 are staggered longitudinally about the circumference of the stent assembly 20400. As in previous exemplary embodiments, the first connection part 20615 at the distal jack strut has a T-shape and the second connection part 14330 is a nut having a cutout with an interior shape corresponding to the exterior of the T-shape of the first connection part 20615. The beneficial difference between the wire-EDM jack bores being machined from the outside surface of the stent assembly 20400 instead of the inside surface can be explained with regard to FIGS. 206, 207A, and 207B. In particular, if the cross-section of the distal jack strut 20412 was square, then, when the T-shape is formed at the proximal end for receiving the second connector part 14330 (the jack nut), there would be three spans of material connecting the proximal end to the remainder of the distal jack strut to provide three columns of support therebetween, in particular, 20610, 20612, 20614. However, the outer cross-section of the distal jack strut is not square and, instead, is trapezoidal in order to allow the circular stent assembly to be constricted to the smallest possible diameter as shown in FIG. 207. Thus, when the bore of the distal jack strut 20412 is machined from the inside surface (as shown in FIGS. 156 to 160 and 207) and the T-shape is formed at the proximal end 20615 for receiving the second connection part 14330, the first and second spans 20710, 20712 shrink to the point of disappearing, depending on the depth of the groove for receiving the tongues of the interior of the second connection part 14330. In such a case, only the third span 20714 remains, which, in such a small manufactured part, allows for the possibility of deformation of the proximal end 20615 with respect to the remainder of the distal jack strut 20412, which deformation is disadvantageous and could cause the jack screw(s) 14320 to malfunction or break. In comparison, when the jack bore is machined from the outside surface, as shown in FIG. 206, the two outer spans 20610, 20612 within the T-shape are large enough to remain because they are on the larger side of the trapezoid and, therefore, support the proximal end 20615 receiving the second connection part 14330.

FIG. 209 illustrates an exemplary embodiment of a self-expanding/forcibly-expanding implantable valve assembly 20900 utilizing the lattice of the stent assembly of FIGS. 204 to 206. Here, both the valve sub-assembly 20950 and the valve graft sub-assembly 20960 are connected using sutures 20970. Here, the upstream side of the valve sub-assembly 20950 (left in FIG. 209) is not connected at only its upstream-most end at the upstream circumference of lattice arms 20902. In addition, a suture line 20972 is created that follows two separate arms 20904 of the lattice. With this suture line 20972, pockets 20962 that might be created between the valve graft sub-assembly 20960 and the valve sub-assembly 20950 are minimized and closed off to diastole flow. This suture line 20972 can be seen in the interior of the valve sub-assembly 20950 in the views of FIGS. 210 and 211.

Also shown in FIG. 209 is a sawtooth proximal edge 20964 of the valve graft sub-assembly 20960 in addition to a sawtooth distal edge 20966. By trimming the proximal edge 20964, the possibility of obscuring either of the coronary arteries after implantation of the valve assembly 20900 is minimized. Also, having no graft material at the distal end decreases the overall amount of graft material, increasing the ability of the valve assembly to collapse and increasing the ease of recapture within the delivery sheath.

As set forth above, this application is a continuation-in-part of U.S. Pat. No. 8,252,036, U.S. patent application Ser. Nos. 12/822,291, 13/339,236, and 13/544,379, each of which have been incorporated herein. Described therein are various exemplary embodiments of aortic implants, including thoracic, abdominal, and valvular. Even though many of the exemplary embodiments of the stent lattices described herein are described as stents or valve replacements, they are equally applicable to stent grafts for treating the thoracic and abdominal aorta, including the treatment of thoracic and abdominal aortic aneurysms, whether for just the upstream end, the distal end, or both ends thereof. The specific incorporation of the exemplary stent lattices described herein into the thoracic and abdominal applications, therefore, is not repeated for the sake of brevity but is to be construed as applying to each of the embodiments described in all related and parent applications.

FIGS. 212 to 217 illustrate a process for either unsheathing and expanding a stent/valve assembly from the delivery sheath 10040, 10720, 11040 or reducing and re-sheathing the stent/valve assembly back into the delivery sheath 10040, 10720, 11040. Re-sheathing the stent/valve assembly is shown by the transition through all of these figures starting from FIG. 212 and ending at FIG. 217. Unsheathing the stent/valve assembly is shown by the transition through all of these figures in the reverse order starting from FIG. 217 and ending at FIG. 212. In these figures, the nose cone and its catheter are not illustrated for clarity.

Beginning with a re-sheathing process, FIG. 212 shows an exemplary embodiment of a valve assembly similar to the valve assemblies of FIGS. 120, 143, 169, and 191 connected to the distal end of the delivery system with the valve assembly expanded for delivering the valve assembly with the delivery system in an implantation state. As the delivery sheath 10040, 10720, 11040 is extended distally, the sheath entry device 21200 at the distal end of the delivery sheath 10040, 10720, 11040 slides upon and over the disconnect coils 770. As the delivery sheath 10040, 10720, 11040 is extended further, FIG. 213 shows the sheath entry device 21200 partially re-sheathing the lattice-disconnector tubes 12630, 14340, 16940. Continuing the re-sheathing process, FIG. 214 illustrates the valve assembly in an intermediate re-sheathing state where a proximal portion of the valve assembly, including the proximal jack struts 12012, 13314, 14314, 15514 is re-sheathed. It is noted here that the outer radial corner of the proximal end of the proximal jack struts 12013, 13314, 14314, 15514 can be chamfered in order to ease the entry of the proximal jack struts into the delivery sheath. If a wire-EDM process is used to create the keyhole bores for the drive screws as described herein, during the wire-EDM process of forming those key-holes, the outer radial corner of the proximal end of the proximal jack struts can be chamfered for the same reason. Further in the re-sheathing process, FIG. 215 shows the valve assembly re-sheathed half way across the exposed portions of the jack screws 12020, 12620, 14320, 15520. FIG. 216 shows the re-sheathing process almost complete where the distal jack struts 12013, 13313, 14313, 15513 are partially re-sheathed in the sheath entry device 21200. The re-sheathing process is complete in FIG. 217, where the valve assembly is entirely contained in the delivery sheath 10040, 10720, 11040. At this point, the entire system can be removed from the patient or repositioned and, then, unsheathing at an improved implantation site.

It is noted that the sheath entry device 21200, as shown in FIG. 217, is slightly conical with the distal end slightly larger in area than the outer circumference of the delivery sheath 10040, 10720, 11040. It is noted that this shape would be disadvantageous if in this orientation when the system is being extended up to the delivery site as providing the delivery sheath with its smallest outer circumference is most desirable. In order to minimize the outer diameter of the sheath entry device 21200, the material of the sheath entry device 21200 is selected so that the sheath entry device 21200 can be heat-shrunk or otherwise collapsed. In one exemplary process for minimizing this outer circumferential diameter, the sheath entry device 21200 is shrunk about the disconnect coils 770 as shown in FIG. 218. Thus, a maximum outer circumference of the sheath entry device 21200, even though it may be greater than 18 French, for example, can easily fit within an 18 French orifice after be so processed. FIG. 219 shows the distal end of the sheath entry device 21200 after this process is performed but without all internal components of the delivery system and FIG. 220 shows the distal end of the sheath entry device 21200 fully expanded after retraction of the implant by the delivery system as explained above.

Unique aspects of the various embodiments of the self-expanding/forcibly-expanding implantable stent/valve assemblies of the present invention include an ability to better correspond with natural geometry that is very different from prior art devices, which only expand to an ideal circular shape of an inflating balloon. FIGS. 221 to 224 show the stent assembly of FIG. 191 expanding progressively inside an irregularly shaped mock-up implantation site that is hardened so that the stent assembly does not move the mock-up from its irregular shape. As can be seen as the stent assembly expands, the mock-up implantation site does not move and the stent assembly orients itself automatically to the particular irregular interior cross-sectional shape in which it is being implanted. As clearly shown in FIG. 224, the stent assembly is implanted within the irregular-shaped implantation site with little or no room between the lattice and interior walls of the mock-up implantation site. Therefore, the invention can be used to conform to any shape, circumference, perimeter, diameter, cross-section, or other geometric configuration in two or three dimensions.

One exemplary embodiment of a process for implanting any of the stent/valve assemblies described herein is described with reference to the flow diagram FIG. 225. A handle, such as the one illustrated in FIGS. 108 to 118 and 226 to 230 includes a display 10814, 23010 and various user interface actuators 10816 and 23011 to 23017, such as buttons. The following exemplary implantation process assumes that the user interface actuators are seven in number, including a solid orange "center" button 23011, two retroflex buttons (flex 23012 and unflex 23013), expand and contract buttons 23014, 23015, and extend and retract buttons 23016, 23017. Additionally, the process flow steps shown in FIG. 225 are exemplary display screens that occur at each stage of the implantation procedure after a few preliminary steps have occurred. First, the system is opened from its dry package. The system can be pre-loaded with a stent assembly (e.g., 23 mm) at its native size and includes a stent-loading funnel. Once the device is turned on, the first screen shows the status "Ready to Collapse" and gives the user instructions on how to collapse with "Hold center button to collapse." When the button is held, the drive screws move to collapse the stent assembly and, while the collapsing occurs, the screen of the display 23010 indicates "release button to abort." The display 23010 can show, simultaneously, a progress bar indicating the progress of stent assembly collapsing. When fully collapsed by the system, the display 23010 indicates that the user should now "Manually Collapse Stent" and indicates how this is accomplished by showing "Hold center to advance funnel/sheath." Moving of the sheath starts slow then moves faster. As advancing of the sheath/funnel occurs, the display 23010 indicates "Release Button to Abort." The display 23010 simultaneously shows a progress bar indicating how much sheathing is left. When sheathed, the display shows "Sheathing Complete Remove Funnel" and the user removes the sheathing funnel from the end of the delivery sheath. The display 23010 shows that the next step can occur after the user "Hold[s the] center button to continue" and confirms that the funnel was removed. The display 23010 now indicates that the user should "Flush Stent" and to confirm this flush by "Hold[ing the] center button to continue." At this point, the "Device Ready for Patient" is displayed and the user is instructed to "Hold center button to continue."

Now the distal end of the device can be guided to the implantation site. If retroflexing is desired, then the display 23010 indicates that the Left/Right buttons show retroflexing along with a progress bar. The Up/Down buttons control sheath retraction. The display 23010 now indicates that the user should "Hold down button to commit device" and indicates that the user should "Press center button to return to previous screen" if not ready for implantation. The sheath is retracted slowly for the first half of the stent assembly with an option to reverse direction if desired. The display 23010 shows "Retracting Sheath" and gives the user the direction to "Release button to abort." If desired, the button can be held for full sheath retraction along with a displayed countdown to full retraction. The device takes up play in the drive screws and presents the stent assembly in a pre-defined position and/or a native position. For example, the stent assembly can be expanded to 15 mm in diameter and progress bars can indicate status of stent assembly along with showing diameter with a circle that is the same diameter as the stent assembly. When done, the display indicates "Sheath Fully Retracted" and the user should "Hold center button to continue."

Now, the stent assembly is ready for implantation. Both radial force and the diameter of the stent assembly can be displayed along with progress bars if desired. The diameter can be indicated with a circle that is the same diameter of the stent assembly. Any of the buttons can be used to limit the maximum radial force that is desired by the user and the display 23010 can show, with a status bar, a radial force limit indicator. The software can account for the loads required to expand the stent lattice and the friction loads of the drive system so that an accurate representation of the force being imparted to the tissue can be communicated to the user, for example, in pounds/kg. Given the time-dependent nature of tissue's reaction to load, the software can continue to apply a known target force to the tissue for a period of time after initially meeting the load. As the tissue remodels, the stent lattice will continue to expand and continue to apply the target force up to the maximum limit of the lattice's circumference. The software can track the response of the tissue and, once the rate of change of expansion declines below a threshold, it can stop expansion of the stent lattice. In an alternative embodiment, all expansion of the implant can occur synchronized with the heart's contractions to coincide with any particular portion of the sinus rhythm. Diameter control buttons 23014, 23015 are used to control the diameter, which, for this example, starts at 15 mm. Each press of a button can cause, for example, a 0.5 mm increment or decrement of the stent assembly along with showing the diameter in millimeters and/or with a circle of the same diameter. At a point where the nominal radial force detected from the implant has stabilized, the display 23010 can indicate to the user that a first angiogram or ultrasound (for example) should be carried out to see if any paravalvular leak exists. If a leak exists, the user can increase the target force level up to the maximum that the implant can take as designed and further or re-expand with the same rate of change detection repeated until paravalvular leaks are sealed or maximum expansion of the stent lattice results. If the latter occurs, the user will be notified if the radial force measured will be sufficient to prevent embolization of the implant if deployed as implanted. If not, the user will be advised or prevented from deploying the implant. When ready to implant, one of the buttons lights green (e.g., the center button 23011) to indicate that pressing that button will disconnect the implant from the delivery system. To perform the disconnect, the user holds the button for a period of time (e.g., five seconds), during which time the button flashes and the handle produced an audio indicating the automated disconnect sequence is about to begin. When first pressed, the display 21010 shows "Disconnecting" along with a countdown number for seconds to disconnect. At the end of the countdown, the automated disconnect sequence starts. One step in this sequence is to remove any wind up that has been built up in the drive screw wires. This can be done in one of two ways. A first way to perform wind up release is to reverse the drive motor with a low level of torque sufficient to remove wind up but not sufficient to create additional reverse wind up or drive the screws in reverse. Alternatively, by having known the last input torque, a look-up table can be accessed that contains the fixed number of turns that are required to remove the wind up associated with that torque. At the end of the automated disconnect sequence, the disconnect wires 770 are withdrawn from the drive screw coupler parts 14652, 14654 to complete disconnection of the implant.

When disconnected, the display shows "Disconnected" and directs the user to "Hold center button to continue." Any retroflex can be released and the user is shown that the device is "Ready to Re-Sheath" the distal parts of the delivery system into the delivery sheath and is shown that, to do so, the user must "Hold center button to re-sheath." With that button press, the display 23010 shows that "Re-Sheath" is occurring and that the user can "Release button to abort" the re-sheathing of the delivery components. When the exposed parts of the delivery system are safely located in the delivery sheath, the display indicates "Device Terminated" and, therefore, the delivery sheath is "Ready to remove from patient."

Another exemplary embodiment of a delivery system control handle is shown in FIGS. 226 to 230. The housing of the delivery system control handle 22600 is, in this exemplary embodiment, a clam-shell having top and bottom halves. The top half of the housing contains most of the electronic elements, including the electronic control circuitry, the display, and user control buttons (see FIGS. 229 and 230). The bottom half of the housing contains most of the mechanical elements. Regarding the latter, a grounding base 22610 is fixedly connected to the bottom half of the housing. This forms the ground for most of the mechanical components.

First, a retroflex support tube 22710 is secured at its proximal end to the grounding base 22610. The retroflex support tube 22710 surrounds a multilumen shaft 22630 having lumens therethrough for all control and guide wires. In this exemplary embodiment, the number of lumens is nine in total. Not illustrated is a distal retroflex knee fixedly attached to the distal end of the retroflex support tube 22710 about the multilumen shaft 22630. The knee is cylindrical in shape and has slits along one lateral side thereof. Also attached to the distal end of the knee is a distal end of a retroflex wire 22622. The proximal end of the retroflex wire 22622 is attached translatably within a retroflex trolley 22624. When the retroflex trolley 22624 translates proximally, retroflex of the distal end of the delivery system occurs. It is desirable to allow physical flexing or retroflexing of the distal end of the delivery system without use of the retroflex trolley 22624. Accordingly, the retroflex wire 22622 has a non-illustrated collar connected within a slot of the retroflex trolley 22624 that is free to move proximally but constrained to move distally within the slot. Thus, if a bend in the delivery sheath causes tension in the retroflex wire 22622, that wire is free to move proximally through the retroflex trolley 22624. Movement of the retroflex trolley 22624 upon a retroflex guide pin 22625 is caused by interaction of the retroflex trolley 22624 with rotation of a retroflex shaft 22626, for example, by a follower nut, a cam, or other similar connection that allows the retroflex trolley 22624 to translate longitudinally as the retroflex shaft 22626 rotates. Rotation of the retroflex shaft 22626 is controlled by a retroflex motor 22628.

The delivery sheath 11040 is coaxial with and surrounds the retroflex support tube 22710. The proximal end of the delivery sheath 11040 is fixed to a sheath trolley 22744, which rides along a sheath guide pin 22746 based on movement caused by rotation of a sheath drive screw 22748. Interaction of the sheath trolley 22744 occurs with rotation of a sheath drive screw 22748, for example, by a follower nut, a cam, or other similar connection that allows the sheath trolley 22744 to translate longitudinally as the sheath drive screw 22748 rotates. Rotation of the sheath drive screw 22748 is controlled by a sheath motor 22749. Because the sheath guide pin 22746 is fixed to the grounding base 22610, translation of the sheath trolley 22744 causes distal or proximal translation of the delivery sheath 11040 with respect to the control handle 22600.

It is desirable to have the entire distal delivery portion of the implant and the implant (as shown for example in FIGS. 105, 107, and 169 to 173) translate longitudinally when at the implantation site. But, it is not simply desirable to have the user control that longitudinal placement. Once the implant is near the implantation site, it would be desirable to fix the control handle 22600 with respect to the patient and mechanically extend and/or retract the implant for best positioning. However, because the drive wires 750 for turning the jack screws and the disconnect drive wires connected to the puck control screws 17032 for translating the puck 17020 and thereby the disconnect wires 770 must be rotated from within the handle, translation of those elements requires translation of at least the transmission imparting such rotation, if not also translation of the respective motors. The control handle 22600 provides such translation of both the motors and the respective transmissions. In particular, a translation ground 22800 is fixedly connected to the control handle 22600. The translation ground 22800 has a threaded bore that guides a translation drive screw 22810 therein. The translation drive screw 22810 is fixedly connected at one end to a transmission of a non-illustrated translation motor (located under a self-contained motor/transmission sub-assembly 22820. The translation motor rotates the translation drive screw 22810 when actuated and is also fixed to the control handle 22600. The motor/transmission sub-assembly 22820 is translationally associated with the translation drive screw 22810 such that the entire motor/transmission sub-assembly 22820 translates longitudinally when the translation drive screw 22810 rotates. For example, under the motor/transmission sub-assembly 22820 is a bracket attached thereto and having a threaded bore receiving therein the translation drive screw 22810 such that, when the translation drive screw 22810 rotates, the bracket with the motor/transmission sub-assembly 22820 translates. Within the motor/transmission sub-assembly 22820 are all of the motors and/or transmissions for rotating each of the, for example, six drive wires 750 for the drive screws (whether in groups or individually) and for rotating each of the, for example, two disconnect drive wires 22840, 22842. At the other end of the translation drive screw 22810 is a multilumen ground 22830 fixed to the proximal end of the multilumen shaft 22630. Like the motor/transmission sub-assembly 22820, the multilumen ground 22830 has a threaded bore shaped to fit therewithin the translation drive screw 22810. In such a configuration, any rotation of the translation drive screw 22810 simultaneously and synchronously moves the multilumen ground 22830 and the motor/transmission sub-assembly 22820 together, all the while keeping the two separated by a fixed distance. In this way, translation of the implant with respect to the control handle 22600 and the delivery sheath 11040 can be effected, for example, by the positioning buttons 23016, 23017 located on the side of the control handle. Such positioning can be analog and smooth without any particular steps or it can be programmable to move a given fixed distance every time one of these buttons 23016, 23017 is pressed.

The exemplary embodiments of the valve assemblies described herein seek to have a valve that is sized and formed for a minimum deployment diameter. This valve is secured inside the stent lattice/frame that is capable of expanding to a much larger final diameter than the internal valve. The commisures of the valve are secured to the frame with a mechanical linkage that allows the frame to expand and keep the valve at a proper size to minimize regurgitation. A lower skirt of the valve is attached to the stent through a loose connection of the variable diameter braided graft or a similar device. This configuration allows the stent frame to continue to grow and fit into a variety of native annuli that are larger than the valve carried within the device.

Even though the exemplary embodiments shown above relate primarily towards an aortic valve, these embodiments are not limited thereto. As stated before, the invention is equally applicable to pulmonary, mitral and tricuspid valves. Additionally, the invention is equally usable in any tubular anatomic structure, some embodiments of which will be disclosed herein.

Known to surgeons, physicians, and biomedical engineering and medical personnel is that, with regard to devices to be implanted in a tubular or hollow structure, whether for expanding (e.g., angioplasty), for occluding, for wall patency (e.g., stents, stent grafts), or for replacing a physical structure (e.g., replacement valve), size mismatches lead to problems. Simply put, sizing symmetrical devices to match non-ideal anatomy is an issue in medicine. Where the surgeon has no way to control the prior art devices, implantation flaws and a certain amount of para-device leaking just must be accepted. Real-time feedback (the elements of which are integrated to the platform, the delivery system, the device itself, or a combination thereof) of these flaws, imperfections, and or leaks would be beneficial for current procedures but are simply not available for, for example, balloon-installed or self-expanding devices. Significant to the embodiments disclosed and equally applicable to other tubular structures or orifices, the self-expanding and forcibly-expanding exemplary lattices described herein in contrast to the prior art has absolute controllability, allowing it to become a platform for many procedures, operations, and/or anatomies. As described herein, the various devices have actuatable geometry on all or specific locations of the device in which the self-expanding and forcibly-expanding exemplary lattice is used.

With regard to other structures of the heart, for example, the described embodiments are applicable to mitral valve replacement or repair. The mitral valve annulus is more pliable than the aortic valve annulus. It is also very close to the atrioventricular (AV) groove and the fibrous trigone (the thickened area of tissue between the aortic ring and the atrioventricular ring), which can be damaged when dealing with the mitral valve. The mitral valve also has significant sensitivity to both sizing and radial force. Undersizing of an implant causes leaks and embolization. Oversizing of the implant causes damage to the heart, not just by tearing the valve seat but also by changing the overall geometry of the left ventricle, rendering the heart less efficient for cardiac cycling. Accordingly, precise attachment and fine adjustment to the anatomy is needed, which is easily accomplished by the embodiments disclosed. Adjustability of the self-expanding and forcibly-expanding lattices of the described embodiments allows for precise and concomitant sizing and sealing, the significant issues associated with mitral valve replacement or repair. Additionally, the self-expanding and forcibly-expanding lattices described herein can be modified for mitral valve replacement to be D-shaped as an alternative to the circular shapes described herein such that a portion of the circumference is expandable (and contractable) and another portion remains constant (i.e., the flat of the D-shape). The self-expanding and forcibly-expanding lattice gives precise sizing and imparts a precise and controllable force to reduce damage and create a near-perfect seal. In mitral valve repair, modulation of the mitral valve annulus is the cornerstone of annuloplasty. In this exemplary embodiment, the device can be fixed to the mitral valve annulus directly, percutaneously, or minimal invasively, the implanted device being actuatable to change all or portions of the shape, diameter, perimeter, or overall configuration or a combination thereof to achieve proper coaptation of the native mitral valve leaflets. Other embodiments allow concomitant or independent actuation of the mitral sub-valvular apparatus. In yet other embodiments, this device can effect mitral valve repair by placement within the coronary sinus or epicardially in plane with the mitral annulus allowing for similar actuation of the native mitral annulus. Adjustability of the self-expanding and forcibly-expanding lattice, therefore, resolves both the issues of sizing and radial force. Another notable item is that the mitral valve has an axis that is very offset from the entrance vector during operation. Therefore, the device must be very steerable. The swashplate embodiments described herein, for example, aid in replacement of the mitral valve even where placement tolerance is very narrow.

Likewise, the described embodiments are applicable to tricuspid valve replacement or repair. All of the features described above for the mitral valve are equally applicable for the tricuspid valve replacement or repair and, therefore, they are not repeated for reasons of brevity. In recent times, there has been an increase in tricuspid valve disease. Significant to tricuspid valve disease is that the patients are "high-risk"; they are very sick when the disease has progressed enough for the patient to show symptoms. With regard to the tricuspid valve, it is close to the conduction region of the heart. Currently, tricuspid valve disease is repaired with a split ring so that the conduction region is not injured in any way. In comparison to the mitral valve, the axis of the tricuspid valve is ninety (90) degrees offset from the vena cava. Therefore, significant steerability is needed. The radial force that can be imparted is also limited in tricuspid valve replacement or repair. In particular, the maximum radial force that can be imparted is limited due to the proximity of the heart's conduction system. Accordingly, precise attachment and fine adjustment to the anatomy is needed, which is easily accomplished by the embodiments disclosed. The adjustability of the self-expanding and forcibly-expanding lattice of the embodiments allows for precise and concomitant sizing and sealing, the significant issues associated with tricuspid valve replacement or repair. The self-expanding and forcibly-expanding lattice gives precise sizing and imparts a precise and controllable force to reduce damage and create a near-perfect seal. Adjustability of the self-expanding and forcibly-expanding lattice, therefore, resolves both the issues of sizing and radial force. Like the mitral valve repair or replacement the swashplate embodiments, for example, can be used to aid in replacement of the tricuspid valve even where placement tolerance is very narrow.

The described embodiments are applicable also to pulmonic valve replacement or repair. The adjustability of the self-expanding and forcibly-expanding lattice of the embodiments allows is an important advantage with regard to pulmonic valves. This is because disease of the pulmonic valve is often congenital and, therefore, commonly presents in childhood. For Pulmonic Atresia, for example, the pulmonic valve becomes narrow and muscular. Therefore, not only must the surgeon replace the valve, but the surgeon must also replace some or all of tract for the pulmonic valve. The most significant problem with pulmonic valve disease is that the typical patient keeps growing after the first operation. Typically, each patient has four to six (4-6) operations during his or her life. This is because, as the patient grows, a larger and larger valve needs to be provided. Each of these surgeries has its own associated risks, but multiple surgeries just compound those risks.

In contrast to the prior art, the embodiments of the self-expanding and forcibly-expanding lattice described entirely eliminate surgeries after the first valve implantation. In particular, instead of performing open surgery on the patient for the second and subsequent surgeries, the adjustable self-expanding and forcibly-expanding lattices described herein are able to be enlarged percutaneously by simply re-docking an adjustment device to a portion of the implant's structural platform (for example, one or more jack screws) and further expanding the lattice to accommodate the growth of the patient. Not only does this save significant costs by virtually eliminating the most costly parts of the subsequent surgeries, the non-invasive expansion greatly decreases the probability of injury caused by such open surgeries.

The self-expanding and forcibly-expanding lattice embodiments described herein have been mostly cylindrical for purposes of clarity and brevity. They are not limited to this configuration, however. As shown, for example, in FIG. 155, variations to the outer shape of the self-expanding and forcibly-expanding lattices, here the lattice being hourglass-shaped, cause different and procedure-dependent improvements in the efficacy of the implant. Other shapes having geometries depending upon the implant location, including half of an hourglass, tapering, curving, and other geometries, are equally suitable for creating a seal and retention in other anatomical location. In another exemplary embodiment, an implant 23100 has a self-expanding and forcibly-expanding central lattice 23102. One or both of the open ends of the lattice 23102 (here, both ends) have a self-expanding, conical stent structure 23104, 23106 outwardly expanding away from the central lattice 23102. In the exemplary embodiment shown, all ends, including the non-moving strut 23116 and the two parts of the moving strut (the distal jack strut 23113 and the proximal jack strut 23114), extend longitudinally with respect to the implant 23100. These extended ends are curved outward to form the hourglass shape. Depending on the desired configuration of the distal and proximal ends of the implant 23100, any combination of extensions is possible. Some exemplary configurations include: both ends of only the non-moving strut 23116 extending longitudinally; only one end of the non-moving strut 23116 extending longitudinally; only the distal jack strut 23113 extending longitudinally; only the proximal jack strut 23114 extending longitudinally; and both the distal jack strut 23113 and the jack strut 23114 extending longitudinally. The illustrated exemplary embodiment also shows extensions 23123, 23124 of the distal and proximal jack struts 23113, 23114 shorter than the extension 23126 of the non-moving strut 23116. The lengths of the extensions 23123, 23124, 23126 can be the same or reversed to the configuration shown. For example, because the central lattice 23102 will shorten longitudinally when expanded, the length of the extensions 23123, 23124 of the distal and proximal jack struts 23113, 23114 can be longer than the extension 23126 of the non-moving strut 23116 so that, when circumferentially expanded to the desired size for implantation, all of the ends of the extensions 23123, 23124, 23126 are substantially aligned along a single circumferential plane perpendicular to the longitudinal axis of the implant 23100. While the surgeon may not be able to know the exact implantation diameter/perimeter/shape that would correspond to a particular geometry of the patient's implantation site, pre-surgery measurement (e.g., by trans-esophageal echocardiogram, CT scan, MRI, intra-cardiac echocardiogram, nuclear scanning, or fluoroscopic visualization) could provide the surgeon with enough information to select an implant 23100 having extensions 23123, 23124, 23126 that will be substantially aligned about a given circumference when expanded to the pre-measured geometry in the patient. Thus, before surgery, the surgeon measures the diameter of the implant desired and selects one implant 23100 from a set of differently sized implants 23100. Slightly larger or smaller expansion of the central lattice 23102 with respect to the measured diameter, therefore, only means that the ends of the extensions 23123, 23124, 23126 do not reside in the same circumferential plane. As geometry of an implantation site is irregular, it is envisioned that such an ideal configuration of ends in a single plane will be difficult to achieve even with a perfectly symmetrical device.

Between the extensions 23123, 23124, 23126 of the distal and proximal ends 23104, 23106 are intermediate arms or webs 23128 that connect adjacent pairs of extensions 23123-23126, 23124-23126 in any way desired. Here, the intermediate webs 23128 circumferentially connect adjacent pairs of extensions 23123-23126, 23124-23126 approximately at the midpoint of the extensions 23123, 23124, 23126 and at approximately the endpoints of the extensions 23123, 23124, 23126. This, however, is merely one exemplary embodiment and more or less webs 23128 can be used with any geometry, with any angle, and with any length. For example, the webs 23128 can follow the angles of the arms of the stent lattice 23102.

FIGS. 232 and 233 show, respectively, the implant 23100 before it is completely implanted in a heart valve 23201 and in a vessel 23301. In FIG. 232, the central lattice 23102 is partially expanded to start collapsing the diseased leaflets of the patient's valve 23201, but the distal and proximal ends 23104, 23106 have not yet touched the walls on either side of the valve 23201. In contrast, in FIG. 233, the central lattice 23102 is partially expanded but still not touching the walls of the diseased vessel 23301. The distal and proximal ends 23104, 23106 of the implant in FIG. 233, however, have already touched the vessel walls. In this configuration, connection of the ends to the wall of the vessel 23301 before connection of the central lattice 23102 occurs prevents shuttling of the implant 23100 while the central lattice 23102 continues to expand to the desired implantation circumference, which can be approximately equal to, smaller than, or greater than the diameter 23302 of the vessel 23301.

The ends 23104, 23106 of the central lattice 23102 or attached to the central lattice 23102 can be made of a shape-memory material such as Nitinol that is integral or connected to (e.g., fused) the central lattice 23102. These ends 23104, 23106 can also be configured in various shapes. In FIG. 231, each end 23104, 23016 is shown as being an exponentially increasing expanding cone. Alternative shapes, some described below, can include the shape of a barbell, such as the distal end 23402 of the implant 23400, or the shape of a bulb, such as the distal end 23504 of the implant 23500. The two ends of a self-expanding and forcibly-expanding implant can be identical or different, depending on the requirements of the particular implant. In each case, these extensions have a given final memory shape to suit the particular surgical procedure being conducted. When captured in the delivery sheath, as in other self-expanding memory-shape devices, the ends compress radially inward to permit loading into a delivery catheter. When allowed to release therefrom, the ends expand to the pre-defined memory shape (which can be constrained partially if the self-expanding and forcibly-expanding portion of the implant is not yet forcibly expanded to allow the self-expanding end(s) to completely self-expand.

The hourglass shape is particularly suited for various surgical applications where acute retention to prevent shuttling in the anatomy is desired. Not only is this shape beneficial for replacement of all valves of the heart, it is also advantageous in procedures treating, for example, atrial septal defects (ASD), ventricular septal defects (VSD), patent ductus arteriosis (PDA), ventricular aneurysms, patent foramen ovale (PFO), arteriovenous fistulae, paravalvular leaks, and left atrial appendage (LAA) ligation, and in performing embolization and angioplasty of vessels. Each of these procedures and conditions benefit from having self-expanding flares that establish the geometry of the anatomy and the self-expanding and forcibly-expanding central platform that precisely adjusts the waist between the flared ends. Even though an hourglass shape as described herein might be used for these procedures for various reasons, they are not described herein as being limited to and any of the implant shapes are equally applicable to any of the exemplary surgical procedures described herein.

Depending on the procedure being performed, the implant can be covered by different polymers or by a matrix or mesh of material. The covering can be semi-porous for sealing over time with cellular in-growth and/or it can have portions that are non-porous to seal immediately upon implantation or even just before implantation. A non-porous covering over the entirety is also contemplated. The covering can be external or internal or both, and can be located anywhere on the implant including the distal side, the central lattice, the proximal side, and even within the central orifice of the implant at any longitudinal position within the lumen to occlude the lumen and prevent flow through the lumen. For example, an occlusion curtain can be disposed within the cross-section of the central orifice, in particular, within the waist, dependent on the effect that is desired. It can be beneficial if the material used is distensible so that it does not corrugate or pleat but, in particular circumstances, it can be non-distensible.

An atrial septal defect (ASD) is a form of congenital heart defect that enables blood flow between two compartments of the heart—the left and right atria. Normally, the right and left atria are separated by the interatrial septum 23610. If this septum is defective or absent, then oxygen-rich blood can flow directly from the left side of the heart to mix with the oxygen-poor blood in the right side of the heart, or vice versa. Another potentially fatal consequence of an ASD is that blood clots are able to pass through the ASD and, instead of going to the lungs, where a clot might be harmless and dissolve over time, such clots travel to the brain, which can cause stroke and, in some instances, death.

During development of the fetus, the interatrial septum develops to separate the left and right atria. However, during early fetal development, a hole in the septum called the foramen ovale, naturally allows blood from the right atrium to enter the left atrium. This opening allows blood to bypass the nonfunctional fetal lungs while the fetus obtains its oxygen from the placenta. A layer of tissue called the septum primum acts as a valve over the foramen ovale during fetal development. After birth, the pressure in the right side of the heart drops as the lungs open and begin working, causing the foramen ovale to close entirely. In approximately twenty five percent (25%) of adults, the foramen ovale does not entirely seal. In these cases, any elevation of the pressure in the pulmonary circulatory system (due to pulmonary hypertension, temporarily while coughing, etc.) can cause the foramen ovale to remain open. This is known as a patent foramen ovale (PFO), a type of ASD.

One device for treating ASD currently is H-shaped. When inserted into the ASD orifice, the device expands and blocks both sides of the septum with two opposing plates, one on each side of the defect. These plates, however, are much larger than the defect. This is disadvantageous because the device places a large mass inside the atrium, decreasing atrial volume. Further, the cylindrical central connection of the two plates is not sized to fill the defect, thus, unless seal is complete across the ASD, blood can still traverse the ASD. Also disadvantageous is the fact that these plates require significant overlap to insure a seal of the defect; in other words, they are larger than the diameter of the ASD orifice.

The hourglass-shaped, self-expanding and forcibly-expanding implant of the embodiments described herein provides significant advantages over prior art devices and treatments. First, the precisely actuatable waist is able to be expanded to match the size of the defect without imposing excessive and/or uncontrollable outward force on the wall edges of the defect. Second, the implant includes an internal, central, solid mass, curtain, or plate to prevent blood crossover, this curtain is only as thin as it needs to be to last and adds no volume to either atria. The material of the curtain can be human tissue or it can be other mammalian tissue or a natural or synthetic fabric. The curtain can even be semiporous to create a natural, endothelialized wall after the implant has been in the defect for a while. The implant is flared into the hourglass shape on both sides to prevent migration. FIG. 236 illustrates a heart with an ASD and FIG. 237 illustrates this defect repaired with such a self-expanding and forcibly-expanding implant 23700. In some circumstances, the seal may breakdown and later re-adjustment and/or repositioning may be required.

Because implantation of the self-expanding and forcibly-expanding device is less invasive, it can be used more often to treat ASDs because accessing the superior vena cava is performed with an endovascular procedure and not open surgery. For example, it is believed that ASDs are one cause of migraines, due to the ASD allowing flow from the right atrium to be directed into the brain. The self-expanding and forcibly-expanding implant can treat such conditions. While VSDs occur less frequently than ASDs, VSDs can be treated in the same way as ASDs as described above.

The ductus arteriosus is a normal fetal blood vessel that closes soon after birth. Patent ductus arteriosus (PDA) is a congenital disorder in the heart wherein a neonate's ductus arteriosus fails to close after birth. In a PDA, the failure of the vessel to close results in an irregular transmission of blood between two of the most important arteries close to the heart, the aorta and the pulmonary artery. Specifically, a PDA allows a portion of the oxygenated blood from the left heart to flow back to the lungs by permitting flow from the aorta (which has higher pressure) into the pulmonary artery. The hourglass-shaped, self-expanding and forcibly-expanding device can be implanted inside the ductus arteriosus to close off the connection using a curtain within the lumen of the implant. One exemplary configuration of an internal curtain can be explained with regard to FIG. 232, 233, or 237. The inside lumen of the central lattice 23102 on one side of the jack screws 23113 (e.g., the distal side) is covered with a material that can expand along with the lattice 23102. The single sheet of material is connected to most or all of the distal struts 23113 and the non-moving struts 23116. If the material around and inside the implant is semiporous, natural ingrowth about the implant occurs, causing the implant to be completely covered and forming part of the atrial wall.

An arteriovenous fistula is an abnormal connection or passageway between an artery and a vein. It may be congenital, surgically created for hemodialysis treatments, or acquired due to pathologic process, such as trauma or erosion of an arterial aneurysm. These passageways, which may occur anywhere in the body including the brain or spinal cord, act like a short circuit diverting blood from fully circulating and delivering oxygen where it is needed. The hourglass-shaped, self-expanding and forcibly-expanding device can be implanted inside the arteriovenous fistula to close off the connection using a curtain within the lumen of the implant. The configuration illustrated in FIG. 232, 233, or 237 can form an example of a self-expanding and forcibly-expanding device that is covered about the exterior or interior and has an internal curtain within the lumen and is implanted in an arteriovenous fistula between the two vessels. If the material around and inside the implant is semiporous, natural ingrowth about the implant occurs, causing the implant to be completely covered and forming a new intermediate vessel wall.

While the cylindrical self-expanding and forcibly-expanding device can be used in vessels and other similarly shaped anatomy, in some circumstances, it may be desirable to use, instead, the hourglass-shaped, self-expanding and forcibly-expanding device. One such area includes embolization and angioplasty of vessels. Embolization is a minimally invasive treatment that occludes, or blocks, one or more blood vessels or vascular channels of malformations (abnormalities). In a catheter embolization procedure, medications or synthetic materials are placed through a catheter into a blood vessel to prevent blood flow to the area. Catheter embolization is performed, for example, to control or prevent abnormal bleeding. This includes bleeding that results from an injury, tumor, or gastrointestinal tract lesions such as ulcer or diverticular disease. Embolization is commonly the first line of treatment in gastrointestinal bleeding of any cause. Controlling bleeding into the abdomen or pelvis from injuries caused in a motor vehicle crash is especially suitable for this treatment. Catheter embolization is also performed to occlude or close off the vessels that are supplying blood to a tumor, especially when the tumor is difficult or impossible to remove, such as a brain tumor. After embolization, a tumor may shrink or it may continue to grow but more slowly, making chemotherapy or surgery a more effective option. There exist many procedures in which a surgeon intervenes at a particular anatomy to use a catheter to access a vein/artery and strategically close it. For example, in a trauma situation such as a stab of a spleen or a liver. With regard to the latter, the right lobe of the liver can survive when flow to the left lobe of the liver is occluded. Where a patient is coughing blood, embolization can be used in a pulmonary artery. In each of these situations, the hourglass-shaped, self-expanding and forcibly-expanding device can be placed as shown, for example, in FIG. 233. With an exterior or interior covering along the peripheral cylinder and an appropriately placed internal curtain closing off the central lumen of the device, when implanted, the anatomy can be securely and removably occluded.

The inventive designs can also be used in other areas, such as the left atrial appendage. In current procedures for ligating the LAA, a device referred to as the WATCHMAN® is used. There exist significant disadvantages with such a device. Prior to implantation, the surgeon needs to measure the internal volume of the LAA, which is very hard to do because the LAA is a very compliant and soft structure. Thus, presizing is difficult. The LAA is typically not under pressure during sizing. Accordingly, problems occur with finding an accurate terminal diameter of the implant when the LAA is under pressure later caused by the device. Current treatment technology comes in certain sizes, one of which needing to be selected for the surgery. The current devices are hard to install due to the volumetric and shape mismatch. If a device is too small, then a space around the device occurs after implantation, making the space(s) ripe for undesirable clotting. With insufficient volume mismatch, existing clots in the LAA can be dislodged, which is dangerous as those clots will immediately enter the aorta. On the other hand, if the sized device is too large, implantation can cause acute traumatic disruption, requiring emergency surgery or even causing death. Additionally, even if the prior art device is successfully implanted, which is shown in FIGS. 238 and 239, if that device places too much force within the LAA, it will erode the wall, ultimately causing a rupture, with the resulting negative consequences. It is known that the LAA varies substantially in thickness along the appendage and some areas are so thin that a surgeon can see right through the wall. Accordingly, ruptures are likely when implants connect with that part of the wall.

Once a surgeon implants a device to treat the LAA, it is desirable to fill the space as much as possible but to not leave a volume that allows blood to enter, to exit, and/or to clot. If one is able to close the space within the LAA and seal the orifice as well, then this could eliminate any possibility of clot dislodgement. It would be, therefore, advantageous to be able to expand a device intermittently using visulation (e.g., by continuous fluoroscopy or echocardiogram) until complete occlusion/isolation of LAA from general circulation occurs, at which time, the surgeon would stop expanding the device. However, current devices are substantially circular and only fill LAA volumetrically; they are not intended to seal the atrial-appendage junction. Thus, current devices cannot both take up the volume and seal the orifice. Additionally, current devices cannot be expanded intermittently because they are all self-expanding—they either remain contracted before removal from the delivery catheter or expand completely all at once when the delivery catheter is removed.

All of these disadvantages of the prior art are resolved by the self-expanding and forcibly-expanding devices described herein because these devices can both fill the volume of the LAA and, at the same time, create a seal at the atrial-appendage junction. FIG. 240 illustrates one exemplary embodiment of a device 24000 for treating the LAA. As before, the self-expanding and forcibly-expanding lattice 24002 forms the central portion of the device 24000. Extending distally from the distal end of the device 24000 is a bulb-shaped self-expanding extension 24004. Opposite the bulb extension 24004 is a self-expanding barbell extension 24006. Together, these two extensions 24004, 24006 work to fill the volume when the device 24000 is implanted. Sealing of the LAA occurs by placement of one or more curtains within the lumen of the device 24000. For example, if an occluding curtain is disposed within the lattice 24002 at the dashed line 24040, then, when the lattice 24002 is expanded within the atrial-appendage junction 24022 and the barbell extension is allowed to self expand at the LAA entrance, the interior of the LAA is shut off from the left atrium. Another possibility includes the curtain extending proximally into the barbell extension along the wall of the barbell extension and to the outer extremity thereof. Likewise, the curtain can extend distally into the extension 24004. If the interior catheter needs to pass through the curtain, then a valve is integral to the curtain which seals after withdrawal of the catheter or the material is self-healing to close after implantation. The curtain can also be a separately implanted device that expands into the lumen of the device to occlude the lumen after implantation of the device.

An exemplary procedure for ligating the LAA with the device 24000 starts with placing a guidewire into the left atrium 24010. The guidewire is, then, threaded into the LAA. The device 24000 is driven over the guidewire until the distal end enters the LAA cavity 24020. In its natural state, the LAA is floppy and bends from approximately ninety to approximately one-hundred and eighty degrees. The device 24000 is inserted sufficiently into the LAA cavity 24020 to place the distal bulb extension 24004 within the cavity 24020, the central lattice 24002 within the LAA orifice at the atrial-appendage junction 24022, and the barbell extension 24006 just proximal of the atrial-appendage junction 24022. In such a configuration, as shown in FIG. 240, when expanded, the device 24000 can both fill the LAA volumetrically and create a seal at the atrial-appendage junction 24022. The delivery catheter 24030 is retracted from the device 24000 to allow self-expansion of the device 24000 to a pre-set state, which, for example, can be the state shown in FIG. 240. The central lattice 24002 is set with a self-expansion diameter smaller than the diameter of the orifice at the atrial-appendage junction 24022. The distal bulb extension 24004 is partially self-expanded at this point because the lack of complete expansion of the central lattice 24002 prevents the bulb extension 24004 from self-expanding entirely. Alternatively, the bulb extension 24004 can be pre-set to be at full self-expansion when the central lattice 24002 is at its self-expanded and not-yet-forcibly-expanded state. Similarly, the proximal barbell extension 24006 is allowed to partially self-expand by being held slightly smaller due to the configuration of the central lattice 24002. Likewise, an alternative of the barbell extension 24006 can allow full self-expansion when the central lattice 24002 is at its self-expanded diameter. The surgeon, then, positions the bulb extension 24004 under visualization further into the LAA cavity 24020 until the bulb extension 24004 seats in the LAA cavity 24020. The surgeon also moves the device 24000 under visualization in a yaw direction (in the plane of FIG. 240) to have the radial plane of the barbell extension 24004 approximate and align with the plane of the atrial-appandance junction 24022. At this point, the device 24000 is stabilized within the LAA cavity 24020. Expansion of the central lattice 24002 occurs when alignment is confirmed. It is noted that the expansion of the bulb extension 20404 indexes the relationship of the adjustable central lattice 24002 to the orifice at the atrial-appendage junction 24022. As the central lattice 24002 expands, the bulb extension 24004 will expand into and fill the adjacent wall of the LAA cavity 24020 to seal off the distal end of the LAA cavity 24020 from the proximal end. The central lattice 24002, again under visualization, is expanded until the outer surface thereof contacts the orifice at the atrial-appendage junction 24022, at which time, the barbell extension 24006 has expanded outward to contact as much of the atrial-appendage junction 24022 as possible, thereby sealing the LAA cavity 24020 off from the left atrium 24010. As the barbell extension 24006 is shaped to be larger in diameter than the largest expansion diameter of the central lattice 24002, the barbell extension 24006 will contact the wall at the atrial-appendage junction 24022 to form a tight seal. Release of the device 24000 from the delivery catheter 24030 completes the operation. With such an implanted configuration, having circumferential contact at or inside the atrial-appendage junction 24022 allows endothelialization of the device at the LAA orifice 24022 to occur in a number of days.

Even though the device 24000 is shown without a covering in FIG. 240, some or all of the external and/or internal surfaces are covered to create an entirely captured volume. The device 24000 can be covered with a semiporous material to encourage ingrowth and endothelialization that entirely fills up the LAA. Alternatively, the device 24000 can be entirely covered with non-porous material or some sections can be semiporous and some can be non-porous. By combining the barbell-shaped end shown in FIG. 234 and the bulb-shaped end shown in FIG. 235, the self-expanding and forcibly-expanding device 24000 shown in FIG. 240 becomes ideal for ligating the LAA.

As mentioned above, the LAA naturally forms a curve that folds upon itself. If the LAA was pressed against the adjacent outer wall of the atrium 24012 and held there for a sufficient amount of time to seal the LAA cavity 24020 off from the left atrium 24010, the LAA would naturally close. However, the time for securing this result is measured in days. The self-expanding and forcibly-expanding device described herein can be used to carry out such a procedure. In particular, if the outside surface of the LAA and the outside surface 24012 of the atrium are accessed by surgery, the self-expanding and forcibly-expanding device can be inflated against the side 24024 of the LAA opposite the atrium, thereby pressing the LAA towards the outside surface 24012 in the direction indicated by the arrow in FIG. 240. As such, the self-expanding and forcibly-expanding device acts as a pillow that gently and slowly presses the folded appendage closed and remains there while the LAA seals off by endothelialization. Due to the floppiness of the LAA and because of the angle that the LAA naturally forms, the device easily closes up the LAA orifice 24022 in this way.

Repair of a ventricular aneurysm can also be effected using the device 24000. Ventricular aneurysms are one of the many complications that may occur after a heart attack. They usually arise from a patch of weakened tissue in a ventricular wall, which swells into a bubble filled with blood. Such an aneurysm 24100 is shown, for example, in FIG. 241. This, in turn, may block the passageways leading out of the heart, leading to severely constricted blood flow to the body. Ventricular aneurysms can be fatal. Treating such aneurysms can be done by either blocking the artery supplying the aneurysm or by closing the aneursymal sac itself as an alternative to surgery. The device 24000 can be inserted into the aneursymal sac of the aneurysm 24100 and can be expanded within the aneurysm 24100 to fill and close off the aneurysm 24100.

Another vascular procedure that can be benefited by the repositionable and controlled expansion of the stent lattices of the exemplary embodiments described herein is the area of femoral bypass surgery. When a portion of the femoral artery becomes occluded, either partially or completely, one way to provide arterial blood to the portions of the leg receiving reduced blood flow is to create a shunt around the occlusion. If performed, such a shunt would require suturing of one end to a location in the femoral artery upstream of the occlusion and suturing the other end of the shunt to a location in the femoral artery downstream of the occlusion. A stent graft having one of the stent lattices described herein at each of the ends of the graft material can be utilized to create such a shunt without the need of suturing the stent graft to the femoral artery and with other benefits as described below. With regard to FIG. 242 (depicting the arterial and venous circulation of the legs), a stent graft is prepared with the graft material having a length longer than the occlusion in the artery and sufficient to traverse from the upstream landing point to the downstream landing point in the femoral artery. A first entry point is made into the popliteal artery and the entry catheter is led up into the femoral artery just below the occlusion. The entry catheter is, then, routed out of the femoral artery either into the saphenous vein or into the subcutaneous fat of the thigh. In the former instance, the entry catheter is directed up the saphenous vein and then out thereof and into the femoral artery at a point upstream of the occlusion near the groin. In the latter instance, the entry catheter is directed through the subcutaneous fat of the thigh along the femoral artery (without accessing other vessels) and then back into the femoral artery at a point upstream of the occlusion near the groin. With a guidewire so placed, the delivery system of the various exemplary embodiments herein can be guided therealong until the distal implant is located (e.g., via fluoroscopy) at the upstream implantation site. There, the stent lattice, which is surrounded by graft material (either in the lumen or outside), is expanded to the necessary diameter (approximately between 8 and 10 mm) and is checked for perivascular leak. When seated without excessive outward pressure (which can be measured as described herein) and without leak, the upstream stent lattice is disconnected from the delivery system and upstream implantation is complete. At any time during the upstream implantation, the stent lattice can be expanded, contracted, and re-expanded and re-positioned as desired. The delivery sheath is further retracted over the graft material and the graft lumen fills with arterial blood as this retraction occurs. Again under visualization, the stent lattice at the downstream end of stent graft is positioned within the femoral artery or the upper popliteal artery just downstream of the occlusion. At any time during the downstream implantation, the stent lattice can be expanded, contracted, and re-expanded and re-positioned as desired until a beneficial orientation occurs. The downstream stent lattice is expanded to the necessary diameter and is checked for nominal pressure and no perivascular leak. When no leak is confirmed, the downstream stent lattice is disconnected from the delivery system, completing the shunt and allowing arterial flow from above the occlusion to below the occlusion.

In this exemplary embodiment, the delivery system is longer than described above at least by the distance between the two stent lattices. Further, one of the stent lattices is loaded into the delivery sheath at an intermediate point and the delivery sheath is extended over the graft material substantially without corrugation or crumpling thereof until it reaches the upstream stent lattice. Loading of the upstream stent lattice occurs similarly as described herein and the nose cone is docked at the distal end adjacent the upstream stent lattice. As the stent lattices (and graft) for this procedure are much smaller in diameter than the stent lattices described for the aorta or heart, each stent lattice does not need as many expansion devices (e.g., the jack assemblies). In particular, 1, 2, or 3 of the jack assemblies are only needed for stent lattices of 8 to 10 mm in installed diameter. Therefore, the actual number of lumens and drive wires needed for such a small stent graft may be less than the ones illustrated herein, allowing for the multilumen and delivery sheath to be made much smaller in diameter for this procedure. Accordingly, all of the control features will be similar as described herein but reduced in number with half of the control wires extending to an intermediate point within the loaded delivery sheath to the downstream stent lattice and the other half of the control wires extending to the distal end of the delivery sheath to the upstream stent lattice in a similar manner as illustrated in FIG. 169.

This exemplary embodiment not only provides controllable expansion into the fragile artery, but also eliminates the need for any suturing as the sealed upstream and downstream lattices provide the assured seal of the artery. This procedure has the added benefit of entirely eliminating any need for use of a balloon to inflate a stent portion, which inflation commonly causes injury to such arterial locations.

Many of the embodiments described above for treating one or the other of the heart valves utilize femoral or lower aorta access to implant the replacement stent valve. These procedures require a significantly long delivery system.

There are a number of other surgical procedures that access valves of the heart with entry ports that are relatively much closer to the surgical site. These procedures include, for example, direct open surgery (such as sternotomy) or through port access (indirect), such as mini-sternotomy, mini-thoracotomy, thoracoscopy, or mini-thoracoscopy. In open surgery, access to the valves is very direct, as the surgeon actually touches the repair site. When sewing in a replacement valve, such as the aortic valve, fifteen or more sutures are needed, which requires significant prowess by the surgeon to sew in such a small area. When operating with instruments in indirect procedures, significant skill is required as well.

The inventors recognize that it is equally possible to access the valves to be treated in these procedures with the systems, devices, and methods described herein. One advantage for doing so is because the distance to the implantation site is so much shorter. With a short distance, control of the handle and placement of the implant by the surgeon increases. As such, with this shorter device, the surgeon can deliver the prosthesis and implant it with one hand. Another significant benefit is that controlled expansion of the stent lattice described entirely eliminates all of the suturing, making the surgery easier and faster and negating the requirement of all surgeons to have significant technical surgical prowess. Further, as the delivery systems described herein are very small in diameter, they lend themselves to use with port access surgeries and their concomitant benefits and faster recovery times. With any of these shorter procedures, access from the incision site to the valve to be replaced also is not as curved as access through the aortic arch.

Understanding the above, a variation of the systems, devices, and methods described herein can be applied with reference to an alternative embodiment of a delivery system described with regard to FIGS. 243 to 255. FIG. 243 illustrates this alternative embodiment of a hand-held delivery system 24300 from the side of the user, where a display surface 24310 contains a display screen 24312 having all of the functions and capabilities as described herein. Also provided are control buttons 24314, 24316, and 24318 for regulating movement and deployment as set forth herein. FIGS. 244 to 250 show various views of the handle.

Internal components of the handle 24300 are visible in FIGS. 251 to 255. First, with the upper clamshell half removed, the motor and transmission assembly 25100 are visible. This assembly 25100 contains a drive screw motor 25102, a puck control motor 25104, and proximal and distal transmission covers 25106, 25108. As compared to the configuration shown in FIGS. 108 to 118, many of the components are different and many are eliminated. This is because the features used to compensate for significant curvature are no longer needed with this short embodiment. As before six throughbores 25110 are present in the distal transmission cover 25108 for receiving the control columns 25410 for the six drive wires 750 (not illustrated) and three throughbores 25112 are present for receiving the puck control columns 25420 for the three puck control screws 17032.

FIG. 252 illustrates the exterior gears 25210 of the transmission of the puck control motor 25104 proximal of the proximal transmission cover 25106. With the distal transmission cover 25108 removed in FIG. 253, the drive pinion 25310 and drive transmission gears 25312 for the six drive wires 750 are apparent. Also shown are the puck control gear 25320 and one puck transmission gear 25322 of the puck control screws 17032.

With the proximal transmission cover 25106 removed in FIG. 254, the drive control columns 25410 and the puck control columns 25420 are apparent. Also shown here are the internal transmission gears 25430 for the puck control columns 25420.

Finally, FIG. 255 shows the configuration of the puck control gear 25320 driving the two exterior puck control columns 25420.

Also, as the surgeon will be physically positioning the distal end of the delivery system (not illustrated) at the implantation site and can manually retract the sheath containing the stent lattice, most of the assembly for unsheathing the stent lattice is unnecessary. Present, instead, are catheter guides 25120 that retain the catheter in place. As compared to the previous embodiments, the delivery catheter 25130 (diagrammatically shown with a dashed line) does not need to be as flexible and, therefore, is retained by the catheter guides 25120. An exemplary embodiment of the control circuitry 25140 is shown behind the display 24312.

Based upon the above, many of the distal prosthesis delivery components described in the other exemplary embodiments are reduced in length and some become entirely unnecessary.

An exemplary process for accessing the aortic valve is described using the handle 24300. It is known that access to the aortic valve can be done in one of two ways. First, the aorta can be cross-clamped, the heart stopped, and the patient placed on bypass. The aorta is dissected and the aortic valve is visualized directly or with a scope. Alternatively, the aorta can be accessed directly (in a preferred port) or through one of the other arteries (e.g., the sub-clavians, the innominate, the brachial, or the axillary). The latter, being only a port access, does not require the patient to be on bypass. The latter is less invasive to the patient.

Because the delivery systems of the invention are sufficiently small to fit within a port access to the aorta, the inventive system can be used without bypass. Specifically, a sheath dilator accesses one of the arteries or the aorta and provides access for a guidewire. This guidewire is very short and very directly reaches the aortic valve. The system with the implant is run over the guidewire and visualized within the aortic valve. Implantation is visualized as described herein and the device is withdrawn by the surgeon.

When a replacement valve is to be implanted, the surgeon does not know with any assurance or precision the exact size of the native annulus. Presently, surgeons can determine an approximate size of the native annulus with fluoroscopy or with a CT scan, but both of these provide inexact results. As such, the surgeon can only guess what is the correct size of the implant to be used and trust that the self-expanding prior art devices will seal properly and, importantly, will not embolize.

With the systems, devices, and methods of the present invention described herein, however, exact determination of the native annulus size becomes possible. More particularly, as indicated herein, the inventive stent lattice implant is inserted into the annulus in which it is to be implanted. This stent lattice does not merely expand into the annulus as prior art self-expanding devices. Instead, as described herein, the system forcibly expands the stent lattice (e.g., the replacement valve) into the annulus.

Each of the mechanical devices used to expand the stent lattice has known properties and the system, overall, can be investigated for those characteristics. Some of the properties include current supplied to the motor and the torque of the motor. Because of the efficiencies of the screws used and due to the mechanical geometry of the stent lattice, the torque applied can be related to an outward radial force imposed by the expanding stent lattice. Each of these characteristics can be measured and/or calculated. Even further, the amount of torque required by the motors to open the stent lattice from at least the self-expanded state to the fully expanded state can be measured for one stent lattice as a baseline or it can be measured for every different stent lattice to be used.

It is known that, when unloaded and in a test-bench mode, the stent lattice to be implanted will require a certain amount of torque to expand over the entire lattice expansion range and the motors will draw a certain amount of current over that range. The required torque over the range can be measured because, with DC motors, torque relates proportionally to the amount of current needed by the motor to cause stent lattice expansion. The current, torque, or radial force curves can be recorded as a function of the stent lattice size and stored in a memory to define a characteristic or reference curve for that particular stent lattice. Then, during an actual (or simulated) implant, the current/torque can be compared to the characteristic curve and the deviation will indicate that there is force being applied to the tissue, which indicates first contact. From this, a process for remotely determining the exact size of a native annulus becomes possible. More particularly, a stent lattice is installed on the delivery system and is allowed to self-expand and then is caused to expand forcibly with the motors. The characteristics of this stent lattice are recorded and stored in the memory of the delivery system as a characteristic curve for that stent lattice. This curve is used during actual implantation (or during implantation of a simulated annulus).

Once the characteristic curve is stored for that stent lattice, the process for determining the native annulus can occur. The stent lattice is guided to the implantation annulus and is allowed to self-expand. Then, the system forcibly expands the stent lattice and compares the current drawn to the characteristic curve. The system knows exactly the diameter of the stent lattice at each moment (based upon turns of the stent expansion control rods) and, therefore, the diameter and current can both be stored as a function of time. During this time, the force of the expanding stent lattice can be calculated and stored as a function of time as well.

In addition to torque, current, and diameter as variables, utilizing data processing routines and assuming a constant current, the velocity of expansion can be calculated as well and processing of these signals can be used to detect the first substantial contact by the stent lattice within the native annulus; this is because the expansion velocity will decrease in a substantial way after first contact is made, at which time the annulus begins restricting the outward expansion of the stent lattice. Depending upon the time constant for detecting, measuring, and calculating the native annulus value based upon this first contact, the detection could lag behind the time that the stent lattice actually reaches the native annulus diameter. This is not disadvantageous because the stent lattice needs to be implanted in the annulus, not just reach the native diameter. Accordingly, the system can indicate (for example, on the display) the native annulus size and that additional expansion is needed in order to complete implantation. The maximum expansion of the stent lattice along with the maximum amount of force imparted by the stent lattice upon the native annulus can be defined and the system can be set to prevent the user from exceeding these levels during implantation. For example, if the native annulus is detected as being 20 mm in diameter, then 24 mm can be set as the maximum size for expansion.

The system also provides implantation checks to ensure implantation force within a predefined minimum. For example, if a minimum threshold of implantation force is not met and the maximum diameter of the stent lattice has not been reached, then the system will not allow disconnection to occur because there could exist a risk of lattice embolization. Conversely, if a maximum implantation force is reached but expansion of the lattice is not within an operating range for the valve leaflets, then the system will not permit disconnection. This is because even with an excellent implantation, if the leaflets will not function appropriately, implantation should not occur.

FIGS. 261 to 263 are depictions of the simultaneous display of:
- an expansion velocity v. time curve (red);
- a force v. time curve (white); and
- a stent lattice diameter v. time curve (green)

for a simulated native annulus of 19 mm, 20 mm, and 19.5 mm, respectively.

In FIG. 261, expansion of the stent lattice occurs at an 18 mm diameter at about time 21:06:14. Expansion occurs at an almost constant velocity and then starts to decrease because the model begins to resist the expansion force of the stent lattice. Then, at about 21:06:58 an implantation routine of the inventive system begins and is explained with the understanding that implantation of the stent lattice needs to create a seal at the native annulus but should not cause tissue damage. (The implantation routines for FIGS. 262 and 263 occur at about 02:34:02 and 01:16:18, respectively.) The needed input variable for preventing damage is the knowledge of the native annular diameter, which only the systems and methods described herein can provide. With this number, the surgeon can limit the expansion of the stent lattice and insure that it does not go beyond a force or size greater than pre-determined for a particular native annulus. In particular, a method for implanting a precision-actuated frame-based (PAF) stent (e.g., a replacement heart valve for any of the four valves) is now described.

The stent lattice is controllably expanded at a given velocity until the system detects contact with and application of pressure to the native annulus. At this point, the system is allowed to execute an inventive sealing routine, in which force is incrementally applied to expand and release the stent lattice, increasing the lattice diameter just a little bit each time. Therefore, as the tissue moves, pressure is applied but, then, the lattice is reduced somewhat for a short amount of time allowing the tissue to relax and to remove some pressure against the tissue. Application of this expanding force to the stent lattice is repeated to open the lattice even more but then to release it again at a larger diameter/circumference. By measuring the incremental change in diameter between each cycle, the system can determine/plot an asymptote that will be able to detect where further force is unnecessary and implantation is complete. Simply put, if a force is applied too rapidly, it can cause tissue to tear. By expanding the stent lattice in stages over time, a lower installation force can achieve an implant that comparable to a higher instant force but without damaging the tissue of the annulus. This is referred to herein as "Tissue Remodeling" and originates from the characteristic that short-time pressure on tissue allows it to spring back quickly with no deformation but even a small amount of pressure on tissue, if lasting a long time (e.g., a rubber band on a wrist), will leave a mark (e.g., an indentation) that will last a while. From this it understood that there is a time constant relating to the remodeling of the tissue because fast impartation does not leave a mark (high force/short time) but slow impartation (lower force/longer time) leaves a greater tissue remodeling "mark" or result. The time constant relates to intercellular desiccation.

After implantation, feedback parameters of the final diameter and the native annulus are used to determine absolute and percentage changes in area and diameter to give the surgeon information on satisfaction of implantation success. FIG. 264 shows what occurs on the display of FIGS. 261 to 263 when detection of the native annulus is being carried out. In the example of FIG. 264, the native annulus is 21 mm. From the start of the simulated implantation process, the stent lattice is reduced in size from just over 24 mm. Throughout the process, the green curve in the middle window is displayed. The green curve is the characteristic curve of the particular stent lattice being implanted, which was defined off-line before this implantation example. The characteristic curve is stored in memory of the system and is plotted as a function of the stent lattice diameter.

As can be seen in the four stages of reduction (starting at about 15:14:10), the velocity of reduction (shown in the bottom window in red) is substantially constant after reduction start-up. The diameter curve (yellow) shows the stent lattice being contracted down to about 18.5 mm. The stent lattice is advanced and placed in the annulus for implantation while in this contracted state. Expansion starts at approximately 15:14:45. It is noted that, as the stent lattice is contracting and expanding, the actual force (blue) applied to the stent lattice (which is related to torque/current) is plotted against the characteristic curve, which correlation can be seen from about 15:14:10 to about 15:14:43. When implantation is occurring, the force curve (blue) tracks the characteristic curve (green) until about 15:14:50, at which time, the force curve deviates from the characteristic curve.

It is at this point where the native annulus of 21 mm is reach and is detected by that deviation.

While utilization of this deviation to determine native annulus size is the first time such a measurement could be taken with reliability and accuracy and without injury to the anatomy, it is known that the structure of the implantation site is pliable and, therefore, the native annulus determined in this manner (without more) could be slightly larger than the actual annulus size. Further, the time delay between expansion and measurement, while small, does impart a lag in the annulus detection conclusion. To improve upon this measurement, various signal processing routines can be implemented using the parameters being measured by the system. For example, improvement of the measurement can occur in the following manner. First, the stent lattice can be expanded throughout its range prior to use to define a force v. diameter characteristic curve for that lattice. Then, the force v. diameter curve can be measured dynamically during implantation in the native annulus. While this is occurring, the two curves can be compared. When the native annulus is detected, that time point on the force v. diameter curve can be stored and a tangent line can be determined. This tangent line will project backward in time and will intersect the stored force v. diameter characteristic curve at a point smaller in diameter than the detected native annulus. It is this smaller diameter point where the tangent line intersects that can be considered to be a "true" native annulus (before any force is imparted on the native annulus to give a larger than "true" determination). As indicated, many signal processing routines can be used now that measurements from the device both on a test-bed and dynamically during an implantation can be obtained with the systems and methods described.

It is useful to have a single characteristic curve for every stent lattice. However, every stent lattice and delivery system is different on a micro-scale. Nonetheless, the systems and methods described can be used to determine a "single" characteristic curve of similar stent lattices based upon averages of measured curves, for example. But, if extreme accuracy is desired, every time a stent lattice is mated to a delivery device, the particular characteristic curve can be created on the fly for that particular implant and can be stored in the memory of that delivery system for use during implantation of that implant.

The systems shown in FIGS. 169 to 180 and 191 illustrate exemplary embodiments of connectivity between the drive-screw proximal ends of the stent lattice and the control subassemblies including the drive screws and the disconnect wires. If the distance between these two points is too small, then, even though the connections are coils and flexible wires, the wires will not bend easily as the system is guided around curved vessels. In contrast, if the distance is very long, then the flexible coils and wires will be very flexible and might not have enough columnar strength to push through curved vessels. Therefore, this distance is set (along with selection of the material properties of the disconnect coils and drive wires) to allow the stent to be extended out and retracted back within a curved anatomy while still having enough columnar strength to not buckle when pushed distally.

Even with these properties balanced and with excellent tracking through curved vessels, the length of each of the coil/wire subassemblies remains the same. This means that, when traversing through a curve, some of the lengths will be allowed to remain taut and some will shorten (i.e., the inside wires will be in compression and the outside wires will be in tension). Thus, the flexible coil/wire subassemblies will oppose any curving that axially aligns the cylinder of the expanded stent lattice with the cylinder of the curved anatomy in which the stent lattice is currently placed. The result is that the stent lattice is forced into an angled position in the native annulus that is not ideal.

One way to correct for this angled position is through active swashplating, for example, utilizing the exemplary systems illustrated in FIGS. 89 to 103. As can be seen in the progression of FIGS. 265 to 268, active swashplating of the subassemblies allows the partially expanded stent lattice in FIG. 265 to be rotated counter-clockwise with regard to the view of the figure (FIG. 266), to be rotated clockwise (FIG. 267), and to be implanted (FIG. 268).

Without active swashplating, for implantation of a replacement aortic valve, there will be a difference in the distance from the distal ground on the delivery sheath to each of the connection points (e.g., six) on the replacement valve's stent lattice as the delivery device is flexed around the aortic arch. This difference in path length is a function of the difference in diameter of the arch that each of the connection points pass through. The path is shorter for the inside coils/wires and longer for those on the outside of the arch. Where all of the control coils/wires are the same length, the similar lengths will cause an angled orientation.

To overcome this difference in alignment, an exemplary angular correction device 26810 is shown in FIG. 269 with the disconnection coils 26920 and the screw wires 26930 lengthened to be even more flexible than in the above embodiments. As such, the coil/wire subassemblies are free to move into an orientation that does not impart this angling force on the stent lattice. The angular correction device 26910 is grounded at the connector control sub-assembly 17000 and has a band 26912 extending distally at least until the proximal end of the stent lattice. The band 26912 has guide sleeves 26814 that laterally hold one of the coil/wire subassembly 26920/26930 therein so that this one subassembly follows the band 26912. In an exemplary embodiment, the band 26912 has guidewire sleeves 26916 on the side opposing the one subassembly to laterally hold the guidewire sleeve 26940 thereto.

With the angular correction device 26810, the subassembly 26920/26930 held to the band 26912 will follow the superior axis of the aortic arch as shown in FIG. 270, and, thereby, will cause the stent lattice to do the same. The flex of the band forces the band to the greater curvature of the arch and holds and supports the stent lattice in a position that is tangent to the end of the arch curve. This, in turn, places the lateral wall of the stent lattice on the superior side against the implantation site substantially aligned with (parallel to) the superior arch of the implantation site, which is a desirable implantation position for the stent lattice. As a result, the stent lattice is automatically placed coaxial to the axis on the native annulus, which is significant because coaxiality is the most desired orientation for limiting the depth into the left ventricular outflow tract and is required for lining up the sealing zone of the implant with the sealing area of the native annulus. An angular misalignment here can cause leaks or poor valve function. It can also contribute to lower gradients or negative impact on the hearts conduction system.

The band 26912 provides additional benefits: it supports the stent from rotating and gives the user an ability to apply longitudinal forces for precise positioning. Further, if the band 26912 is provided with forks or tines that engage the proximal end of the stent lattice, these tines can be used to rotate or translate the stent lattice as an additional measure for stent lattice repositioning.

With a parallel implantation orientation, expansion of the stent lattice (shown in FIG. 271, will cause an implantation that is virtually parallel to the implantation site. An added benefit to this configuration is that the band 26912 (along with the delivery sheath) can be pulled proximally away from the implantation site, as shown in FIG. 272, to rotate the plane of the stent lattice (here clockwise in the figure) to accommodate differing anatomy or for any other reason desired by the surgeon.

Because only one of the subassemblies is connected to the band 26912, the other loose and flexible wires are free to reposition themselves within the arch and find a natural path that allows parallel implantation within the vessel, which paths are illustrated in FIG. 271.

An exemplary embodiment of the band 26912 is a stainless steel strip that is much wider (e.g., between approximately 0.050 inches and approximately 0.2 inches) than it is thick (e.g., between approximately 0.005 inches and approximately 0.02 inches).

When the band 26912 presses the stent lattice in the implantation site, the orientation of the lateral wall of the stent lattice with respect to the implantation site will most likely be rotated too much in the clockwise direction of FIGS. 270 to 272. In order to accommodate for this possibility, in an alternative and/or additional exemplary embodiment, the band 26912 can be provided with a pre-bend just proximal of the stent lattice. In such a configuration, the stent lattice will be rotated slightly counter-clockwise in the view of these figures. Another exemplary embodiment provides an active hinge at the distal end of the band 26912 just before the proximal end of the stent lattice and having a control rod that extends back towards the delivery handle. When actuated in the proximal direction, the end of the band will rotate counter-clockwise and, thereby, move the stent lattice similarly.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for implanting a stent, which comprises:
   contracting a stent to a reduced implantation size with a delivery system having drive wires, the stent having a selectively adjustable assembly with adjustable elements operatively connected to the drive wires such that, when the adjustable elements are adjusted by the drive wires, a configuration change in at least a portion of the stent occurs;
   inserting the contracted stent into a native annulus in which the stent is to be implanted;
   rotating the drive wires with the delivery system to forcibly expand the stent;
   while rotating the drive wires, determining with the delivery system a torque applied to the drive wires;
   stopping rotation of the drive wires based upon a value of the determined torque when the stent contacts the native annulus and has a first diameter; and
   after the stent contacts the native annulus, repeatedly rotating and stopping rotation of the drive wires to incrementally expand the stent from the first diameter to a second, final diameter.

2. The method according to claim 1, which further comprises providing a user with a dynamic value of the torque and permitting the user to change the expansion and contraction of the stent.

3. The method according to claim 2, which further comprises disconnecting the stent from the delivery system to implant the stent in the native annulus.

4. The method according to claim 1, which further comprises disconnecting the stent from the delivery system to implant the stent in the native annulus.

5. The method according to claim 1, wherein the delivery system has at least one drive wire motor connected to the drive wires for rotating the drive wires and wherein the act of stopping includes:
   measuring a current required to drive the at least one drive wire motor; and
   stopping the at least one drive wire motor and thereby the rotation of the drive wires based upon a value of the current.

6. The method according to claim 5, which further comprises:
   calculating an outward radial force imposed by the expanding stent lattice on the native annulus with the value of the current; and
   stopping the at least one drive wire motor and thereby the rotation of the drive wires based upon a value of the calculated outward radial force.

7. The method according to claim 1, wherein the delivery system has at least one drive wire motor connected to the drive wires for rotating the drive wires and wherein the act of stopping includes:
   determining an outward radial force imposed by the expanding stent lattice based upon a current required to drive the at least one drive wire motor; and
   stopping the at least one drive wire motor and thereby the rotation of the drive wires based upon a value of the calculated outward radial force.

8. The method according to claim 1, wherein stopping the rotation of the drive wires as the stent incrementally expands from the first diameter to the second diameter allows the stent to contract to a plurality of intermediate diameters between the first diameter and the second diameter due to force of the native annulus pressing against the stent.

9. The method according to claim 1, wherein repeatedly rotating and stopping rotation of the drive wires includes:
   rotating the drive wires such that the stent expands from the first diameter to a third diameter which is less than the second diameter; and
   stopping rotation of the drive wires after the stent has the third diameter, whereupon the stent contracts from the third diameter to a fourth diameter which is less than the second diameter and the third diameter and greater than the first diameter due to force of the native annulus pressing against the stent.

10. The method according to claim 9, wherein repeatedly rotating and stopping rotation of the drive wires includes:
    rotating the drive wires such that the stent expands from the fourth diameter to a fifth diameter which is less than the second diameter and greater than the third diameter; and
    stopping rotation of the drive wires after the stent has the fifth diameter, whereupon the stent contracts from the fifth diameter to a sixth diameter which is less than the second diameter and the fifth diameter and greater than the fourth diameter due to force of the native annulus pressing against the stent.

11. A method for implanting a stent, which comprises:
    contracting a stent to a reduced implantation size with a delivery system having drive wires, the stent having a selectively adjustable assembly with adjustable elements operatively connected to the drive wires such that, when the adjustable elements are adjusted by the drive wires, a configuration change in at least a portion of the stent occurs;
    inserting the contracted stent into a native annulus in which the stent is to be implanted;
    rotating the drive wires with the delivery system to forcibly expand the stent;
    while rotating the drive wires, determining with the delivery system a torque applied to the drive wires;
    stopping rotation of the drive wires based upon a first value of the determined torque when the stent contacts the native annulus; and
    repeatedly rotating and stopping rotation of the drive wires based upon a second of value of the determined torque greater than the first value to incrementally expand the stent after the stent initially contacts the native annulus.

12. The method according to claim 11, which further comprises providing a user with a dynamic value of the torque and permitting the user to change the expansion and contraction of the stent.

13. The method according to claim 12, which further comprises disconnecting the stent from the delivery system to implant the stent in the native annulus.

14. The method according to claim 11, which further comprises disconnecting the stent from the delivery system to implant the stent in the native annulus.

15. The method according to claim 11, wherein the delivery system has at least one drive wire motor connected to the drive wires for rotating the drive wires and wherein the act of stopping includes:
    measuring a current required to drive the at least one drive wire motor; and
    stopping the at least one drive wire motor and thereby the rotation of the drive wires based upon a value of the current.

16. The method according to claim 15, which further comprises:
    calculating an outward radial force imposed by the expanding stent lattice on the native annulus with the value of the current; and stopping the at least one drive wire motor and thereby the rotation of the drive wires based upon a value of the calculated outward radial force.

17. The method according to claim 11, wherein the delivery system has at least one drive wire motor connected to the drive wires for rotating the drive wires, and wherein the act of stopping includes:
   determining an outward radial force imposed by the expanding stent lattice based upon a current required to drive the at least one drive wire motor; and
   stopping the at least one drive wire motor and thereby the rotation of the drive wires based upon a value of the calculated outward radial force.

18. A method for implanting a stent, which comprises:
   contracting a stent to a reduced implantation size with a delivery system having drive wires, the stent having a selectively adjustable assembly with adjustable elements operatively connected to the drive wires such that, when the adjustable elements are adjusted by the drive wires, a configuration change in at least a portion of the stent occurs;
   inserting the contracted stent into a native annulus in which the stent is to be implanted;
   moving the drive wires with the delivery system to forcibly expand the stent;
   while moving the drive wires, determining with the delivery system a torque applied to the drive wires; and
   temporarily stopping movement of the drive wires based upon a first value of the determined torque when the stent contacts the native annulus; and
   after the stent contacts the native annulus, repeatedly moving and stopping the drive wires based upon a second value of the determined torque greater than the first value to incrementally expand the stent.

19. The method according to claim 18, wherein the act of moving comprises rotating the drive wires to forcibly expand the stent into the native annulus.

20. The method according to claim 18, which further comprises providing a user with a dynamic value of the torque and permitting the user to change the expansion and contraction of the stent.

21. The method according to claim 20, which further comprises disconnecting the stent from the delivery system to implant the stent in the native annulus.

22. The method according to claim 18, which further comprises disconnecting the stent from the delivery system to implant the stent in the native annulus.

23. The method according to claim 18, wherein the delivery system has at least one drive wire motor connected to the drive wires for rotating the drive wires and wherein the act of stopping includes:
   measuring a current required to drive the at least one drive wire motor; and
   stopping the at least one drive wire motor and thereby the rotation of the drive wires based upon a value of the current.

24. The method according to claim 23, which further comprises:
   calculating an outward radial force imposed by the expanding stent lattice on the native annulus with the value of the current; and
   stopping the at least one drive wire motor and thereby the rotation of the drive wires based upon a value of the calculated outward radial force.

25. The method according to claim 18, wherein the delivery system has at least one drive wire motor connected to the drive wires for rotating the drive wires and wherein the act of stopping includes:
   determining an outward radial force imposed by the expanding stent lattice based upon a current required to drive the at least one drive wire motor; and
   stopping the at least one drive wire motor and thereby the rotation of the drive wires based upon a value of the calculated outward radial force.

* * * * *